(12) United States Patent
Ohashi et al.

(10) Patent No.: US 8,486,965 B2
(45) Date of Patent: Jul. 16, 2013

(54) PYRROLO[2,3-B]PYRIDINE DERIVATIVE AND USE THEREOF FOR TREATMENT OF CANCER

(75) Inventors: Tomohiro Ohashi, Kanagawa (JP); Zenyu Shiokawa, Kanagawa (JP); Yuta Tanaka, Kanagawa (JP); Satoshi Sasaki, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 13/391,217

(22) PCT Filed: Aug. 25, 2010

(86) PCT No.: PCT/JP2010/064410
§ 371 (c)(1),
(2), (4) Date: Apr. 27, 2012

(87) PCT Pub. No.: WO2011/024869
PCT Pub. Date: Mar. 3, 2011

(65) Prior Publication Data
US 2012/0220569 A1    Aug. 30, 2012

(30) Foreign Application Priority Data

Aug. 26, 2009 (JP) ................................ 2009-195754
Jan. 27, 2010 (JP) ................................ 2010-015643

(51) Int. Cl.
*A61K 31/44* (2006.01)

(52) U.S. Cl.
USPC ........................... 514/300; 546/113; 546/247

(58) Field of Classification Search
USPC .................................. 514/300; 546/113, 247
See application file for complete search history.

(56) References Cited

U.S. PATENT DOCUMENTS

| | | |
|---|---|---|
| 2002/0068756 A1 | 6/2002 | Labelle et al. |
| 2003/0181420 A1 | 9/2003 | Bayne et al. |
| 2003/0203909 A1 | 10/2003 | Ushio et al. |
| 2004/0259926 A1 | 12/2004 | Bruendl et al. |
| 2005/0080111 A1 | 4/2005 | Bayne et al. |
| 2007/0213323 A1 | 9/2007 | Imogai et al. |
| 2007/0232661 A1 | 10/2007 | Beachy |
| 2008/0119488 A1 | 5/2008 | Bayne et al. |
| 2008/0193423 A1 | 8/2008 | Brunton et al. |
| 2008/0194637 A1 | 8/2008 | Brunton et al. |
| 2008/0287469 A1 | 11/2008 | Diacovo et al. |
| 2009/0048286 A1 | 2/2009 | Lee et al. |
| 2009/0227561 A1 | 9/2009 | Fujii et al. |
| 2010/0056582 A1 | 3/2010 | Bayne et al. |
| 2011/0053915 A1 | 3/2011 | Ivaschenko et al. |

FOREIGN PATENT DOCUMENTS

| | | |
|---|---|---|
| WO | 01/64639 | 9/2001 |
| WO | 02/12189 | 2/2002 |
| WO | 03/059884 | 7/2003 |
| WO | 2004/108715 | 6/2004 |
| WO | 2005/033288 | 4/2005 |
| WO | 2005/081960 | 9/2005 |
| WO | 2006/030032 | 3/2006 |
| WO | 2006/089106 | 8/2006 |
| WO | 2008/057468 | 5/2008 |
| WO | 2008/057469 | 5/2008 |
| WO | 2009/077956 | 6/2009 |
| WO | 2009/107850 | 9/2009 |

OTHER PUBLICATIONS

Yang, et al., "Converse Conformational Control of Smoothened Activity by Structurally Related Small Molecules", Journal of Biological Chemistry, vol. 284, No. 31, Jul. 2009, pp. 20876-20884.

*Primary Examiner* — Douglas M Willis
(74) *Attorney, Agent, or Firm* — Hamre, Schumann, Mueller & Larson, P.C.

(57) ABSTRACT

The present invention provides a fused heterocycle derivative having a strong Smo inhibitory activity, and use thereof. Specially, the present invention relates to a compound represented by the formula

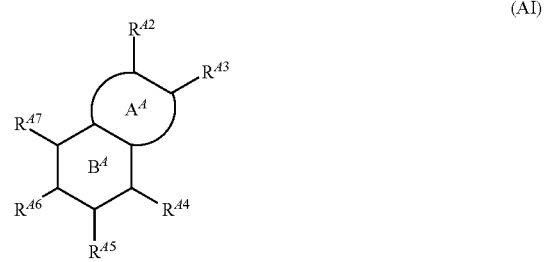

(AI)

wherein each symbol is as defined in the specification, or salt thereof, and a medicament containing the compound or a prodrug thereof, which is an Smo inhibitor or an agent for the prophylaxis or treatment of cancer.

7 Claims, No Drawings

PYRROLO[2,3-B]PYRIDINE DERIVATIVE AND USE THEREOF FOR TREATMENT OF CANCER

TECHNICAL FIELD

The present invention relates to a fused heterocycle derivative and use thereof. More particularly, the present invention relates to a compound having a strong Smo inhibitory activity and useful for the prophylaxis or treatment of cancer and the like, and use thereof.

BACKGROUND OF THE INVENTION

The study of morphogenesis during the developmental stage has been conducted based on the screening of variant using *Drosophila*. Hedgehog gene (hh) was found as one of the genes that cause morphological abnormality of *Drosophila* embryo due to mutation thereof. Hedgehog gene product (Hh) is a secretory protein, which is produced as an about 45 kDa precursor and then divided, due to autolysis, into a 20 kDa N-terminal side domain, which is a main active principle, and a 25 kDa C-terminal side domain. The 20 kDa N-terminal side domain, which is a main active principle, is modified by fatty acid on the N-terminal and cholesterol on the C-terminal thereof. The Hedgehog signal transduction system is formed by the protein group described below. Hh receptor is Patched (Ptch), which is a twelve-transmembrane-type protein. Ptch acts on Smoothened (Smo), which is a seven-transmembrane-type protein, and suppresses the function of Smo in the absence of Hh. When Hh is bound to the receptor Ptch, suppression of Smo is released and Smo is activated. The signal produced by the activation of Smo activates transcription factor Ci, which regulates the expression of the gene group involved in the morphogenesis (Curr. Opin. Genet. Dev., vol. 12, pages 503-511, 2002).

A pathway corresponding to the *Drosophila* Hedgehog signal transduction system has been confirmed also in mammals. In human, for example, three types of gene products, sonic hedgehog (Shh), indian hedgehog (Ihh) and desert hedgehog (Dhh), are known to correspond to *Drosophila* Hh, and undergo post-translational modification as in *Drosophila* Hh (Cell, vol. 103, pages 371-374, 2000). In human Shh, a 19 kDa active principle is cleaved out from a 45 kDa precursor protein by autolysis, and fatty acid is added to the N-terminal thereof, and cholesterol is added to the C-terminal thereof (J. Biol. Chem., vol. 273, pages 14037-14045, 1998). Such modification is considered to be essential for the maintenance of Shh activity and, for example, 40 times enhanced activity was achieved by the addition of palmitic acid to *Escherichia coli* recombinant human Shh free of N-terminal modification with fatty acid, and 160 times enhanced activity was achieved by the addition of myristic acid thereto (Biochemistry, vol. 40, pages 4359-4371, 2001). On the other hand, as a human gene corresponding to *Drosophila* Smo, human Smo is known, and as a human gene corresponding to *Drosophila* Ptch, 2 types of Ptch1 and Ptch2 are known. In addition, a transcription factor corresponding to *Drosophila* Ci is considered to be Gli in human, and 3 types of Gli1, Gli2 and Gli3 are known (Nature Rev. Cancer, vol. 2, pages 361-372, 2002). Shh/Ihh/Dhh are each bound to Ptch1 and activate Smo by inhibiting the bond between Ptch1 and Smo. Shh/Ihh/Dhh are also bound to Ptch2, Hip1, Gas1 and Cdo/Boc, besides Ptch1, and regulate the activation of Smo. A signal transduction from Smo induces nuclear localization of Gli1 and Gli2, and activate transcription of Gli1 (Curr. Opin. Cell Biol., vol. 19, pages 159-165, 2007).

The Hedgehog signal is involved in the morphogenesis in the developmental stages also in mammals. In human, for example, patients with Holoprosencephaly, which is a congenital developmental abnormality, showed mutation in Shh (Nat. Genet., vol. 14, pages 357-360, 1996). Moreover, a natural compound Cyclopamine derived from white hellebore known as a compound inducing Cyclopus in sheep (Am. J. Vet. Res., vol. 24, pages 1164-1175, 1963) was confirmed to inhibit Smo as action mechanism thereof (Development, vol. 125, pages 3553-3562, 1998). Furthermore, an Shh knockout mouse was prepared, and its phenotype was found to include Cyclopus, malformation of extremities (Nature, vol. 383, pages 407-413, 1996), and neural plate malformation (Cell, vol. 111, pages 63-75, 2002).

Hedgehog signal is inherently a developmental signal, which is promoted in tumor tissues and functions as a cancer cell proliferation and survival signal. Hedgehog signal is considered to function for the growth and survival of cancer cells in an autocrine mode, or function between cancer cells and cancer interstitial cells in a paracrine mode, in tumor tissues (Nat. Rev. Drug Discov., vol. 5, pages 1026-1033, 2006). In an autocrine mode, it works for the growth and maintenance of cancer cells, via transcription activation by Gli-1, by abnormal cell cycle control due to increased expression of Cyclin D and decreased expression of p21, promotion of proliferation signal by activation of EGFR pathway and the like. On the other hand, since Shh expressed in cancer cells acts on Smo in cancer interstitial cells, growth factors such as insulin-like growth factor-1, fibroblast growth factor, platelet-derived growth factor and the like are transmitted from cancer interstitial cells to cancer cells, and function for the growth and survival of cancer cells. It is also considered that promotion of VEGF, PDGF pathway and the like by Gli-1 promotes tumor angiogenesis (Clin Cancer Res., vol. 12, pages 5924-5928, 2006). As to the mechanism of promotion of Hedgehog signal, a cancer in which Hedgehog signal is promoted due to mutation of Ptch1 and a cancer which is promoted by overexpression of Shh, which is one of the ligands, have been reported (Nature Rev. Cancer, vol. 3, pages 903-911, 2003). As a cancer in which Hedgehog signal is promoted due to mutation, basal cell cancer and medulloblastoma are known, and mutation of Ptch1 observed in these cancers activates Hedgehog signal in a ligand independent manner (Am. J. Med. Gen., vol. 123A, pages 5-28, 2003). As a cancer in which Hedgehog signal is promoted by overexpression of Shh, pancreatic cancer (Nature, vol. 425, pages 846-851, 2003) and the like have been reported. In a transgenic mouse in which Shh is forcedly expressed in the pancreas, Hedgehog signal is suggested to be involved not only in the growth and maintenance of cancer, but also carcinogenic process, since a PanIN-like lesion in the initial stages of cancer progress was found in the pancreas (Nature, vol. 425, pages 851-856, 2003). Furthermore, Hedgehog signal is considered to function for the growth and survival of cancer stem cells, and play a key role in the metastasis or postoperative recurrence of tumor and the like (Trends Cell Biol., vol. 17, pages 438-447, 2007).

As the Hedgehog signal inhibitor, the following are known. Cyclopamine, which is a naturally occurring Smo inhibitory compound, has been reported to show a tumor growth suppressive effect on glioma (Development, vol. 128, pages 5201-5212, 2001) and the like. As a synthetic low-molecular-weight compound inhibiting Smo, CUR-61414 (Proc. Natl. Acad. Sci. U.S.A., vol. 100, pages 4616-4621, 2003) and SANT-1, 2, 3, 4 (Proc. Natl. Acad. Sci. U.S.A., vol. 99, pages 14071-14076, 2002) have been reported. As for the Hedgohog signal inhibitory antibody, it has been reported that administration of an anti-Shh antibody to a cancer-carrying nude mouse transplanted with colorectal cancer cell line HT-29 caused regression of cancer (WO 2004/020599).

Patent documents 1 to 5 disclose fused heterocycle compounds.

DOCUMENT LIST

Patent Document

Patent Document 1: WO 01/64639
Patent Document 2: WO 02/12189
Patent Document 3: WO 03/059884
Patent Document 4: WO 2005/081960
Patent Document 5: WO 2006/030032

SUMMARY OF THE INVENTION

Problems to be Solved by the Invention

An object of the present invention is to provide a compound having a superior Smo inhibitory activity, low toxicity and sufficiently satisfactory as a pharmaceutical product.

Means of Solving the Problems

The present inventors have conducted intensive studies in an attempt to solve the above-mentioned problems and found that a compound represented by the following formula and a salt thereof have a superior Smo inhibitory activity, which resulted in the completion of the present invention.

Accordingly, the present invention provides the following.

[1] a compound represented by the formula

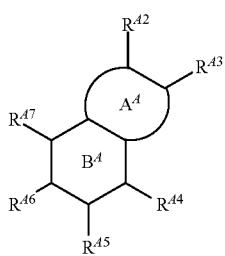

(AI)

wherein
ring $A^A$ is a 5- to 7-membered heterocycle optionally further having substituent(s);
ring $B^A$ is a 6-membered ring;
$R^{A2}$ is a carbamoyl group optionally having substituent(s);
$R^{A3}$ is a substituted hydroxy group;
$R^{A4}$ is a hydrogen atom, a halogen atom, an amino group optionally having substituent(s), a mercapto group optionally having a substituent or a thioxo group, or absent;
$R^{A5}$ is a substituted $C_{1-6}$ alkyl group, an amino group optionally having substituent(s), a cyclic group optionally having substituent(s), or a hydroxy group substituted by a cyclic group optionally having substituent(s);
$R^{A6}$ is a $C_{1-6}$ alkyl group optionally having substituent(s); and
$R^{A7}$ is a hydrogen atom, a halogen atom or a $C_{1-6}$ alkyl group, or absent,
or a salt thereof (in the present specification, sometimes to be abbreviated as "compound (AI)");

[2] the compound or salt of the above-mentioned [1], wherein the compound represented by the formula (AI) or a salt thereof is a compound represented by the following formula (AI-b)

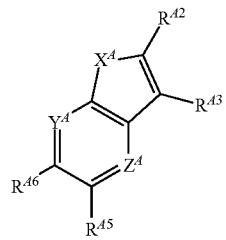

(AI-b)

wherein
$X^A$ is $NR^{A1}$ wherein $R^{A1}$ is a hydrogen atom or a $C_{1-6}$ alkyl group, a sulfur atom or an oxygen atom;
$Y^A$ is $CR^{A7}$ wherein $R^{A7}$ is a hydrogen atom, a halogen atom or a $C_{1-6}$ alkyl group, or a nitrogen atom;
$Z^A$ is $CR^{A4}$ wherein $R^{A4}$ is a hydrogen atom, a halogen atom, an amino group optionally having substituent(s) or a mercapto group optionally having a substituent, or a nitrogen atom;
$R^{A2}$ is a carbamoyl group optionally having substituent(s);
$R^{A3}$ is a substituted hydroxy group;
$R^{A5}$ is a substituted $C_{1-6}$ alkyl group, an amino group optionally having substituent(s), a cyclic group optionally having substituent(s), or a hydroxy group substituted by a cyclic group optionally having substituent(s); and
$R^{A6}$ is a $C_{1-6}$ alkyl group optionally having substituent(s), or a salt thereof;

[3] the compound or salt of the above-mentioned [2], wherein
$X^A$ is $NR^{A1}$ wherein $R^{A1}$ is methyl;
$Y^A$ is $CR^{A7}$ wherein $R^{A7}$ is a hydrogen atom, or a nitrogen atom;
$Z^A$ is $CR^{A4}$ wherein $R^{A4}$ is a hydrogen atom, or a nitrogen atom;
$R^{A2}$ is a carbamoyl group optionally having 1 or 2 substituents selected from
(1) a $C_{1-8}$ alkyl group optionally having substituent(s),
(2) a $C_{3-8}$ cycloalkyl group optionally having substituent(s), and
(3) a heterocyclic group optionally having substituent(s);
$R^{A3}$ is an optionally halogenated $C_{1-6}$ alkoxy group;
$R^{A5}$ is
(1) a substituted $C_{1-6}$ alkyl group,
(2) an amino group optionally having substituent(s),
(3) a $C_{6-10}$ aryl group optionally having substituent(s), or
(4) a heterocyclic group optionally having substituent(s); and
$R^{A6}$ is a $C_{1-6}$ alkyl group;

[4] the compound or salt of the above-mentioned [3], wherein $Y^A$ is a nitrogen atom, and $Z^A$ is $CR^{A4}$ wherein $R^{A4}$ is a hydrogen atom;

[5] 6-ethyl-N-[1-(hydroxyacetyl)piperidin-4-yl]-1-methyl-3-(1-methylethoxy)-5-[(phenylcarbonyl)amino]-1H-pyrrolo[2,3-b]pyridine-2-carboxamide or a salt thereof;

[6] 3-ethyl-N-[1-(hydroxyacetyl)piperidin-4-yl]-5-methyl-2-phenyl-7-(2,2,2-trifluoroethoxy)-5H-pyrrolo[2,3-b]pyrazine-6-carboxamide or a salt thereof;

[7] 6-ethyl-5-{[(4-fluorophenyl)carbonyl]amino}-N-[1-(hydroxyacetyl)piperidin-4-yl]-1-methyl-3-(1-methylethoxy)-1H-indole-2-carboxamide or a salt thereof;

[8] 6-ethyl-5-(4-fluorophenyl)-N-[1-(hydroxyacetyl)piperidin-4-yl]-1-methyl-3-(1-methylethoxy)-1H-pyrrolo[3,2-b]pyridine-2-carboxamide or a salt thereof;

[9] a prodrug of the compound or salt of any of the above-mentioned [1] to [8];

[10] a medicament comprising the compound or salt of any of the above-mentioned [1] to [8] or a prodrug thereof;
[11] the medicament of the above-mentioned [10], which is an Smo inhibitor;
[12] the medicament of the above-mentioned [10], which is an agent for the prophylaxis or treatment of cancer;
[13] a method for the prophylaxis or treatment of cancer in a mammal, which comprises administering an effective amount of the compound or salt of any of the above-mentioned [1] to [8] or a prodrug thereof to the mammal; and
[14] use of the compound or salt of any of the above-mentioned
[1] to [8] or a prodrug thereof for the production of an agent for the prophylaxis or treatment of cancer.

Effect of the Invention

Since the compound of the present invention has a strong Smo inhibitory action, it can provide a clinically useful agent for the prophylaxis or treatment of cancer, a cancer growth inhibitor and a cancer metastasis suppressive agent.

DETAILED DESCRIPTION OF THE INVENTION

The present invention is explained in detail in the following.

In the present specification, the "halogen atom" means a fluorine atom, a chlorine atom, a bromine atom or an iodine atom.

In the present specification, the "$C_{1-6}$ alkyl group" means, for example, methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl or the like.

In the present specification, the "$C_{2-6}$ alkenyl group" means, for example, ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl or the like.

In the present specification, the "$C_{2-6}$ alkynyl group" means, for example, ethynyl, 1-propynyl, 2-propynyl, 1-butynyl, 2-butynyl, 3-butynyl, 1-pentynyl, 2-pentynyl, 3-pentynyl, 4-pentynyl, 1,1-dimethylprop-2-yn-1-yl, 1-hexynyl, 2-hexynyl, 3-hexynyl, 4-hexynyl, 5-hexynyl or the like.

In the present specification, the "$C_{1-6}$ alkoxy group" means, for example, methoxy, ethoxy, propoxy, isopropoxy, butoxy, isobutoxy, sec-butoxy, tert-butoxy, pentoxy, isopentoxy, hexoxy or the like.

In the present specification, the "optionally halogenated $C_{1-6}$ alkoxy group" means, for example, a $C_{1-6}$ alkoxy group optionally having halogen atom(s) (preferably 1 to 5 halogen atoms, more preferably 1 to 3 halogen atoms) at substitutable position(s).

In the present specification, the "$C_{1-6}$ alkyl-carbonyl group" means, for example, acetyl, ethylcarbonyl, propylcarbonyl, isopropylcarbonyl, butylcarbonyl, isobutylcarbonyl, sec-butylcarbonyl, tert-butylcarbonyl, pentylcarbonyl, hexylcarbonyl or the like.

In the present specification, the "$C_{1-6}$ alkoxy-carbonyl group" means, for example, methoxycarbonyl, ethoxycarbonyl, propoxycarbonyl, isopropoxycarbonyl, butoxycarbonyl, isobutoxycarbonyl, tert-butoxycarbonyl or the like.

In the present specification, the "$C_{3-8}$ cycloalkyl group" means, for example, cyclopropyl, cyclobutyl, cyclopentyl, cyclohexyl, cycloheptyl, cyclooctyl or the like.

In the present specification, the "$C_{3-8}$ cycloalkane" means, for example, cyclopropane, cyclobutane, cyclopentane, cyclohexane, cycloheptane, cyclooctane or the like.

In the present specification, the "$C_{3-6}$ cycloalkane" means, for example, cyclopropane, cyclobutane, cyclopentane, cyclohexane or the like.

In the present specification, the "$C_{3-8}$ cycloalkenyl group" means, for example, cyclopropenyl (e.g., 2-cyclopropen-1-yl), cyclobutenyl (e.g., 2-cyclobuten-1-yl), cyclopentenyl (e.g., 2-cyclopenten-1-yl, 3-cyclopenten-1-yl), cyclohexenyl (e.g., 2-cyclohexen-1-yl, 3-cyclohexen-1-yl) or the like.

In the present specification, the "$C_{6-10}$ aryl group" means, for example, phenyl, 1-naphthyl, 2-naphthyl or the like.

In the present specification, the "$C_{6-10}$ arene" means, for example, benzene, naphthalene or the like.

In the present specification, the "$C_{7-13}$ aralkyl group" means, for example, benzyl, phenethyl, naphthylmethyl or the like.

In the present specification, the "$C_{6-10}$ aryl-carbonyl group" means, for example, benzoyl, 1-naphthoyl, 2-naphthoyl or the like.

In the present specification, the "heterocyclic group" means an aromatic heterocyclic group (e.g., a 5- to 12-membered aromatic heterocyclic group) or a non-aromatic heterocyclic group (e.g., a 4- to 12-membered non-aromatic heterocyclic group).

In the present specification, the "aromatic heterocyclic group" means a monocyclic aromatic heterocyclic group and a fused aromatic heterocyclic group.

Examples of the monocyclic aromatic heterocyclic group include a 5- to 7-membered (preferably 5- or 6-membered) monocyclic aromatic heterocyclic group containing, as a ring-constituting atom besides carbon atoms, 1 to 4 hetero atoms selected from an oxygen atom, a sulfur atom (optionally oxidized) and a nitrogen atom (optionally oxidized). Examples thereof include furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,2,4-triazin-3-yl, 1,2,4-triazin-6-yl) and the like.

Examples of the fused aromatic heterocyclic group include a 8- to 12-membered fused aromatic heterocyclic group, specifically, a group derived from a fused ring wherein a ring corresponding to the above-mentioned 5- to 7-membered monocyclic aromatic heterocyclic group and a $C_{6-10}$ arene are condensed; and a group derived from a fused ring wherein rings corresponding to the above-mentioned 5- to 7-membered monocyclic aromatic heterocyclic groups are condensed. Specific examples thereof include quinolyl (e.g., 2-quinolyl, 3-quinolyl, 4-quinolyl, 6-quinolyl), isoquinolyl (e.g., 3-isoquinolyl), quinazolyl (e.g., 2-quinazolyl, 4-quinazolyl), quinoxalyl (e.g., 2-quinoxalyl, 6-quinoxalyl), benzofuranyl (e.g., 2-benzofuranyl, 3-benzofuranyl), benzothienyl (e.g., 2-benzothienyl, 3-benzothienyl), benzoxazolyl (e.g., 2-benzoxazolyl), benzisoxazolyl (e.g., 3-benzisoxazolyl), benzothiazolyl (e.g., 2-benzothiazolyl), benzoisothiazolyl (e.g., 3-benzoisothiazolyl), benzimidazolyl (e.g., benzimidazol-1-yl, benzimidazol-2-yl, benzimidazol-5-yl), benzotriazolyl (e.g., 1H-1,2,3-benzotriazol-5-yl), indolyl (e.g., indol-1-yl, indol-2-yl, indol-3-yl, indol-5-yl), isoindolyl (e.g., isoindol-1-yl, isoindol-2-yl, isoindol-3-yl, isoindol-5-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), imidazopyridinyl (e.g., 1H-imidazo[4,5-b]pyridin-2-yl, 1H-imidazo[4,5-c]pyridin-2-yl, 2H-imidazo[1,2-a]pyridin-3-yl), thienopyridinyl (e.g., thieno[2,3-b]pyridin-3-yl), imidazopyrazinyl (e.g., 1H-imidazo[4,5-b]pyrazin-2-yl), pyrazolopyridinyl (e.g., 1H-pyrazolo[4,3-c]pyridin-3-yl), pyrazolothienyl (e.g., 2H-pyrazolo[3,4-b]thiophen-2-yl), pyrazolotriazinyl (e.g., pyrazolo[5,1-c][1,2,4]triazin-3-yl) and the like.

In the present specification, the "non-aromatic heterocyclic group" means a monocyclic non-aromatic heterocyclic group and a fused non-aromatic heterocyclic group.

Examples of the monocyclic non-aromatic heterocyclic group include a 4- to 7-membered (preferably 5- or 6-membered) monocyclic non-aromatic heterocyclic group containing, as a ring-constituting atom besides carbon atoms, 1 to 4 hetero atoms selected from an oxygen atom, a sulfur atom (optionally oxidized) and a nitrogen atom. Examples thereof include azetidinyl (e.g., 1-azetidinyl, 2-azetidinyl), pyrrolidinyl (e.g., 1-pyrrolidinyl, 2-pyrrolidinyl), piperidyl (e.g., piperidino, 2-piperidyl, 3-piperidyl), morpholinyl (e.g., morpholino), thiomorpholinyl (e.g., thiomorpholino), piperazinyl (e.g., 1-piperazinyl, 2-piperazinyl, 3-piperazinyl), oxazolidinyl (e.g., oxazolidin-2-yl), thiazolidinyl (e.g., thiazolidin-2-yl), imidazolidinyl (e.g., imidazolidin-2-yl, oxazolinyl (e.g., oxazolin-2-yl), thiazolinyl (e.g., thiazolin-2-yl), imidazolinyl (e.g., imidazolin-2-yl, dioxolyl (e.g., 1,3-dioxol-4-yl), dioxolanyl (e.g., 1,3-dioxolan-4-yl), dihydrooxadiazolyl (e.g., 4,5-dihydro-1,2,4-oxadiazol-3-yl), pyranyl (e.g., 2-pyranyl, 4-pyranyl), dihydropyranyl (e.g., 2,3-dihydropyran-2-yl, 2,3-dihydropyran-3-yl), tetrahydropyranyl (e.g., 2-tetrahydropyranyl, 3-s tetrahydropyranyl, 4-tetrahydropyranyl), thiopyranyl (e.g., 4-thiopyranyl), dihydrothiopyranyl (e.g., dihydrothiopyran-3-yl, dihydrothiopyran-4-yl), tetrahydrothiopyranyl (e.g., 2-tetrahydrothiopyranyl, 3-tetrahydrothiopyranyl, 4-tetrahydrothiopyranyl), 1-oxidotetrahydrothiopyranyl (e.g., 1-oxidotetrahydrothiopyran-4-yl), 1,1-dioxidotetrahydrothiopyranyl (e.g., 1,1-dioxidotetrahydrothiopyran-4-yl), tetrahydrofuryl (e.g., tetrahydrofuran-3-yl, tetrahydrofuran-2-yl), pyrazolidinyl (e.g., pyrazolidin-1-yl, pyrazolidin-3-yl), pyrazolinyl (e.g., pyrazolin-1-yl), tetrahydropyrimidinyl (e.g., tetrahydropyrimidin-1-yl), dihydrotriazolyl (e.g., 2,3-dihydro-1H-1,2,3-triazol-1-yl), tetrahydrotriazolyl (e.g., 2,3,4,5-tetrahydro-1H-1,2,3-triazol-1-yl), azepanyl (e.g., 1-azepanyl, 2-azepanyl, 3-azepanyl, 4-azepanyl), dihydropyridyl (e.g., dihydropyridin-1-yl, dihydropyridin-2-yl, dihydropyridin-3-yl, dihydropyridin-4-yl), tetrahydropyridyl (e.g., tetrahydropyridin-1-yl, tetrahydropyridin-2-yl, tetrahydropyridin-3-yl, tetrahydropyridin-4-yl) and the like.

Examples of the fused non-aromatic heterocyclic group include a 8- to 12-membered fused non-aromatic heterocyclic group, specifically, a group derived from a fused ring wherein a ring corresponding to the above-mentioned 4- to 7-membered monocyclic non-aromatic heterocyclic group and a $C_{6-10}$ arene are condensed; a group derived from a fused ring wherein rings corresponding to the above-mentioned 4- to 7-membered monocyclic non-aromatic heterocyclic groups are condensed; a group derived from a fused ring wherein a ring corresponding to the above-mentioned 4- to 7-membered monocyclic non-aromatic heterocyclic group and a ring corresponding to the above-mentioned 5- to 7-membered monocyclic aromatic heterocyclic group are condensed; and a group wherein the above-mentioned group is partially saturated. Specific examples thereof include dihydroindolyl (e.g., 2,3-dihydro-1H-indol-1-yl), dihydroisoindolyl (e.g., 1,3-dihydro-2H-isoindol-2-yl), dihydrobenzofuranyl (e.g., 2,3-dihydro-1-benzofuran-5-yl), tetrahydrobenzofuranyl (e.g., 4,5,6,7-tetrahydro-1-benzofuran-3-yl), dihydrobenzodioxinyl (e.g., 2,3-dihydro-1,4-benzodioxinyl), dihydrobenzodioxepinyl (e.g., 3,4-dihydro-2H-1,5-benzodioxepinyl), chromenyl (e.g., 4H-chromen-2-yl, 2H-chromen-3-yl), dihydrochromenyl (e.g., 3,4-dihydro-2H-chromen-2-yl), dihydroquinolinyl (e.g., 1,2-dihydroquinolin-4-yl), tetrahydroquinolinyl (e.g., 1,2,3,4-tetrahydroquinolin-4-yl), dihydroisoquinolinyl (e.g., 1,2-dihydroisoquinolin-4-yl), tetrahydroisoquinolinyl (e.g., 1,2,3,4-tetrahydroisoquinolin-4-yl), dihydrophthalazinyl (e.g., 1,4-dihydrophthalazin-4-yl), azabicyclohexyl (e.g., 2-azabicyclo[3.1.0]hexan-3-yl) and the like.

In the present specification, the "heterocycle" means an aromatic heterocycle (e.g., a 5- to 12-membered aromatic heterocycle) or a non-aromatic heterocycle (e.g., a 4- to 12-membered non-aromatic heterocycle).

In the present specification, the "aromatic heterocycle" means a monocyclic aromatic heterocycle and a fused aromatic heterocycle.

Examples of the monocyclic aromatic heterocycle include a 5- to 7-membered (preferably 5- or 6-membered) monocyclic aromatic heterocycle containing, as a ring-constituting atom besides carbon atoms, 1 to 4 hetero atoms selected from an oxygen atom, a sulfur atom (optionally oxidized) and a nitrogen atom (optionally oxidized). Examples thereof include furan, thiophene, pyridine, pyrimidine, pyridazine, pyrazine, pyrrole, imidazole, pyrazole, thiazole, isothiazole, oxazole, isoxazole, oxadiazole, thiadiazole, triazole, tetrazole, triazine and the like.

Examples of the fused aromatic heterocycle include a 8- to 12-membered fused aromatic heterocycle, specifically, a fused ring wherein the above-mentioned 5- to 7-membered monocyclic aromatic heterocycle and a $C_{6-10}$ arene are condensed; and a fused ring wherein the above-mentioned 5- to 7-membered monocyclic aromatic heterocycles are condensed. Specific examples thereof include quinoline, isoquinoline, quinazoline, quinoxaline, benzofuran, benzothiophene, benzoxazole, benzisoxazole, benzothiazole, benzoisothiazole, benzimidazole, benzotriazole, indole, isoindole, indazole, pyrrolopyrazine (e.g., 1H-pyrrolo[2,3-b]pyrazine), imidazopyridine (e.g., 2H-imidazo[1,2-a]pyridine, 1H-imidazo[4,5-b]pyridine, 1H-imidazo[4,5-c]pyridine), thienopyridine (e.g., thieno[2,3-b]pyridine), imidazopyrazine (e.g., 1H-imidazo[4,5-b]pyrazine), pyrazolopyridine (e.g., 1H-pyrazolo[4,3-c]pyridine), pyrazolothiophene (e.g., 2H-pyrazolo[3,4-b]thiophene), pyrazolotriazine (e.g., pyrazolo[5,1-c][1,2,4]triazine) and the like.

In the present specification, the "non-aromatic heterocycle" means a monocyclic non-aromatic heterocycle and a fused non-aromatic heterocycle.

Examples of the monocyclic non-aromatic heterocycle include a 4- to 7-membered (preferably 5- or 6-membered) monocyclic non-aromatic heterocycle containing, as a ring-constituting atom besides carbon atoms, 1 to 4 hetero atoms selected from an oxygen atom, a sulfur atom (optionally oxidized) and a nitrogen atom. Examples thereof include azetidine, pyrrolidine, piperidine, morpholine, thiomorpholine, piperazine, oxazolidine, thiazolidine, imidazolidine, oxazoline, thiazoline, imidazoline, dioxole, dioxolane, dihydrooxadiazole, pyran, dihydropyran, tetrahydropyran, thiopyran, dihydrothiopyran, tetrahydrothiopyran, 1-oxidotetrahydrothiopyran, 1,1-dioxidotetrahydrothiopyran, tetrahydrofuran, pyrazolidine, pyrazoline, tetrahydropyrimidine, dihydrotriazole, tetrahydrotriazole, azepane, dihydropyridine, tetrahydropyridine and the like.

Examples of the fused non-aromatic heterocycle include a 8- to 12-membered fused non-aromatic heterocycle, specifically, a fused ring wherein the above-mentioned 4- to 7-membered monocyclic non-aromatic heterocycle and a $C_{6-10}$ arene are condensed; a fused ring wherein the above-mentioned 4- to 7-membered monocyclic non-aromatic heterocycles are condensed; a fused ring wherein the above-mentioned 4- to 7-membered monocyclic non-aromatic heterocycle and the above-mentioned 5- to 7-membered monocyclic aromatic heterocycle are condensed; and a ring wherein the above-mentioned ring is partially saturated. Specific examples thereof include dihydroindole (e.g., 2,3-dihydro-1H-indole), dihydroisoindole (e.g., 1,3-dihydro-2H-isoindole), dihydrobenzofuran (e.g., 2,3-dihydro-1-benzofuran), tetrahydrobenzofuran (e.g., 4,5,6,7-tetrahydro-1-benzofuran), dihydrobenzodioxine (e.g., 2,3-dihydro-1,4-benzodioxine), dihydrobenzodioxepine (e.g., 3,4-dihydro-2H-1,5-benzodioxepine), chromene, dihydrochromene (e.g., 3,4-dihydro-2H-chromene), dihydroquinoline (e.g., 1,2-dihydroquinoline), tetrahydroquinoline (e.g., 1,2,3,4-tetrahydroquinoline), dihydroisoquinoline (e.g., 1,2-dihydroisoquinoline), tetrahydroisoquinoline (e.g., 1,2,3,4-tetrahydroisoquinoline), dihydrophthalazine (e.g., 1,4-dihydrophthalazine), azabicyclohexane (e.g., 2-azabicyclo[3.1.0]hexane) and the like.

In the present specification, the "nitrogen-containing heterocycle" means, for example, a 5- to 7-membered nitrogen-containing heterocycle containing, as a ring constituting atom besides carbon atom, at least one nitrogen atom, and optionally further containing 1 or 2 hetero atoms selected from an oxygen atom, a sulfur atom and a nitrogen atom. Preferable examples of the nitrogen-containing heterocycle include pyrrolidine, imidazolidine, pyrazolidine, piperidine, piperazine, morpholine, thiomorpholine, thiazolidine, oxazolidine and the like.

In the present specification, the "heterocyclyl-carbonyl group" means a carbonyl group substituted by the aforementioned "heterocyclic group". Specific examples of the heterocyclyl-carbonyl group include pyrrolylcarbonyl, pyrazolylcarbonyl, pyridylcarbonyl, pyrrolidinylcarbonyl, thienylcarbonyl, furylcarbonyl, thiazolylcarbonyl, oxazolylcarbonyl, piperidinocarbonyl, piperazinylcarbonyl, morpholinocarbonyl, thiomorpholinocarbonyl, tetrahydrobenzo[c]azepinylcarbonyl, tetrahydroisoquinolinylcarbonyl and the like.

In the present specification, the "$C_{3-8}$ cycloalkyl-carbonyl group" means, for example, cyclopropylcarbonyl, cyclobutylcarbonyl, cyclopentylcarbonyl, cyclohexylcarbonyl, cycloheptylcarbonyl, cyclooctylcarbonyl or the like.

In the present specification, examples of the substituent that the $C_{1-6}$ alkyl group of the "$C_{1-6}$ alkyl group optionally having substituent(s)" optionally has include substituents selected from the following Substituent A Group. While the number of the substituents is not particularly limited as long as it is a substitutable number, preferably 1 to 5, more preferably 1 to 3. When plural substituents are present, the respective substituents may be the same or different.

Substituent A Group:
(1) a halogen atom;
(2) a cyano group;
(3) a nitro group;
(4) a hydroxy group;
(5) a carboxy group;
(6) a $C_{3-8}$ cycloalkyl group optionally having 1 to 3 substituents selected from
    (a) a halogen atom,
    (b) a hydroxy group,
    (c) a $C_{1-6}$ alkyl group optionally having 1 to 3 halogen atoms,
    (d) a $C_{1-6}$ alkoxy group optionally having 1 to 3 halogen atoms, and
    (e) an oxo group;
(7) a $C_{6-10}$ aryl group optionally having 1 to 3 substituents selected from
    (a) a halogen atom,
    (b) a hydroxy group,
    (c) a $C_{1-6}$ alkyl group optionally having 1 to 3 halogen atoms, and
    (d) a $C_{1-6}$ alkoxy group optionally having 1 to 3 halogen atoms;
(8) a 5- to 12-membered (preferably 5- or 6-membered) aromatic heterocyclic group optionally having 1 to 3 substituents selected from
    (a) a halogen atom,
    (b) a hydroxy group,
    (c) a $C_{1-6}$ alkyl group optionally having 1 to 3 halogen atoms, and
    (d) a $C_{1-6}$ alkoxy group optionally having 1 to 3 halogen atoms;
(9) a 4- to 12-membered (preferably 4- to 7-membered) non-aromatic heterocyclic group optionally having 1 to 3 substituents selected from
    (a) a halogen atom,
    (b) a hydroxy group,
    (c) a $C_{1-6}$ alkyl group optionally having 1 to 3 halogen atoms,
    (d) a $C_{1-6}$ alkoxy group optionally having 1 to 3 halogen atoms,
    (e) a $C_{1-6}$ alkyl-carbonyl group optionally having 1 to 3 hydroxy, and
    (f) an oxo group;
(10) an amino group optionally having 1 or 2 substituents selected from
    (a) a $C_{1-6}$ alkyl group optionally having 1 to 3 halogen atoms,
    (b) a $C_{1-6}$ alkyl-carbonyl group optionally having 1 to 3 substituents selected from
        (i) a halogen atom,
        (ii) a hydroxy group, and
        (iii) a $C_{6-10}$ aryl group,
    (c) a $C_{1-6}$ alkoxy-carbonyl group optionally having 1 to 3 substituents selected from
        (i) a halogen atom, and
        (ii) a $C_{6-10}$ aryl group,
    (d) a $C_{1-6}$ alkylsulfonyl group (e.g., methylsulfonyl) optionally having 1 to 3 substituents selected from
        (i) a halogen atom, and
        (ii) a $C_{6-10}$ aryl group,
    (e) a $C_{6-10}$ arylsulfonyl group (e.g., phenylsulfonyl),
    (f) a carbamoyl group optionally having 1 or 2 $C_{1-6}$ alkyl groups optionally having 1 to 3 halogen atoms,
    (g) a 5- to 12-membered (preferably 5- or 6-membered) aromatic heterocyclic group optionally having 1 to 3 substituents selected from
        (i) a $C_{1-6}$ alkyl group optionally having 1 to 3 halogen atoms,
        (ii) a hydroxy group,
        (iii) a $C_{1-6}$ alkoxy group optionally having 1 to 3 halogen atoms, and (iv) a halogen atom, and
(h) a 4- to 12-membered (preferably 4- to 7-membered) non-aromatic heterocyclic group optionally having 1 to 3 substituents selected from
  (i) a $C_{1-6}$ alkyl group optionally having 1 to 3 halogen atoms,
  (ii) a hydroxy group,
  (iii) a $C_{1-6}$ alkoxy group optionally having 1 to 3 halogen atoms,
  (iv) a halogen atom, and
  (v) an oxo group;
(11) an imino group;
(12) a $C_{1-6}$ alkyl-carbonyl group optionally having 1 to 3 halogen atoms;
(13) a $C_{1-6}$ alkoxy-carbonyl group optionally having 1 to 3 substituents selected from
  (a) a halogen atom,
  (b) a $C_{1-6}$ alkoxy group,
  (c) a $C_{6-10}$ aryl group,
  (d) a 5- to 12-membered (preferably 5- or 6-membered) aromatic heterocyclic group optionally having 1 to 3 substituents selected from
    (i) a $C_{1-6}$ alkyl group optionally having 1 to 3 halogen atoms,
    (ii) a hydroxy group,
    (iii) a $C_{1-6}$ alkoxy group optionally having 1 to 3 halogen atoms, and
    (iv) a halogen atom, and
  (e) a 4- to 12-membered (preferably 4- to 7-membered) non-aromatic heterocyclic group optionally having 1 to 3 substituents selected from
    (i) a $C_{1-6}$ alkyl group optionally having 1 to 3 halogen atoms,
    (ii) a hydroxy group,
    (iii) a $C_{1-6}$ alkoxy group optionally having 1 to 3 halogen atoms,
    (iv) a halogen atom, and
    (v) an oxo group;
(14) a $C_{1-6}$ alkylsulfonyl group (e.g., methylsulfonyl, ethylsulfonyl, isopropylsulfonyl) optionally having 1 to 3 substituents selected from
  (a) a halogen atom, and
  (b) a $C_{1-6}$ alkoxy group;
(15) a $C_{6-10}$ arylsulfonyl group (e.g., phenylsulfonyl);
(16) a carbamoyl group optionally having 1 or 2 substituents selected from
  (a) a $C_{1-8}$ alkyl group optionally having 1 to 3 halogen atoms, and
  (b) a $C_{8-10}$ aryl group;
(17) a thiocarbamoyl group optionally having 1 or 2 $C_{1-6}$ alkyl groups optionally having 1 to 3 halogen atoms;
(18) a sulfamoyl group optionally having 1 or 2 $C_{1-6}$ alkyl groups optionally having 1 to 3 halogen atoms;
(19) $C_{1-6}$ alkoxy group optionally having 1 to 3 substituents selected from
  (a) a halogen atom,
  (b) a carboxy group,
  (c) a $C_{1-6}$ alkoxy group,
  (d) a $C_{1-6}$ alkoxy-carbonyl group optionally having 1 to 3 $C_{6-10}$ aryl groups,
  (e) an amino group optionally having 1 or 2 substituents selected from a $C_{1-6}$ alkyl group and a $C_{1-6}$ alkoxy-carbonyl group,
  (f) a $C_{3-8}$ cycloalkyl group,
  (g) a 5- to 12-membered (preferably 5- or 6-membered) aromatic heterocyclic group optionally having 1 to 3 substituents selected from
    (i) a halogen atom,
    (ii) a hydroxy group,
    (iii) a $C_{1-6}$ alkyl group optionally having 1 to 3 halogen atoms, and
    (iv) a $C_{1-6}$ alkoxy group optionally having 1 to 3 halogen atoms, and
  (h) a 4- to 12-membered (preferably 4- to 7-membered) non-aromatic heterocyclic group optionally having 1 to 3 substituents selected from
    (i) a halogen atom,
    (ii) a hydroxy group,
    (iii) a $C_{1-6}$ alkyl group optionally having 1 to 3 halogen atoms,
    (iv) a $C_{1-6}$ alkoxy group optionally having 1 to 3 halogen atoms, and
    (v) an oxo group;
(20) a $C_{2-6}$ alkenyloxy group (e.g., ethenyloxy) optionally having 1 to 3 halogen atoms;
(21) a $C_{3-8}$ cycloalkyloxy group (e.g., cyclopropoxy, cyclopentyloxy) optionally having 1 to 3 substituents selected from
  (a) a halogen atom, and
  (b) a $C_{1-6}$ alkoxy group;
(22) a $C_{6-10}$ aryloxy group (e.g., phenyloxy, naphthyloxy);
(23) a $C_{7-13}$ aralkyloxy group (e.g., benzyloxy);
(24) a $C_{1-6}$ alkyl-carbonyloxy group (e.g., acetyloxy, tert-butylcarbonyloxy);
(25) a $C_{6-10}$ aryl-carbonyl group optionally having 1 to 3 substituents selected from
  (a) a halogen atom, and
  (b) a $C_{1-6}$ alkyl group optionally having 1 to 3 halogen atoms;
(26) a 5- to 12-membered (preferably 5- or 6-membered) aromatic heterocyclyl-carbonyl group (e.g., thienylcarbonyl, pyrazolylcarbonyl, pyrazinylcarbonyl, isoxazolylcarbonyl, pyridylcarbonyl, thiazolylcarbonyl) optionally having 1 to 3 substituents selected from a $C_{1-6}$ alkyl group optionally having 1 to 3 halogen atoms;
(27) a 4- to 12-membered (preferably 4- to 7-membered) non-aromatic heterocyclyl-carbonyl group (e.g., pyrrolidinylcarbonyl, morpholinylcarbonyl) optionally having 1 to 3 substituents selected from a $C_{1-6}$ alkyl group optionally having 1 to 3 halogen atoms;
(28) a $C_{3-8}$ cycloalkyl-carbonyl group;
(29) a $C_{7-13}$ aralkyloxy-carbonyl group (e.g., benzyloxycarbonyl);
(30) a mercapto group;
(31) a $C_{1-6}$ alkylthio group (e.g., methylthio, ethylthio) optionally having 1 to 3 substituents selected from
  (a) a halogen atom, and
  (b) a $C_{1-6}$ alkoxy-carbonyl group;
(32) a $C_{7-13}$ aralkylthio group (e.g., benzylthio);
(33) a $C_{6-10}$ arylthio group (e.g., phenylthio, naphthylthio);
(34) a $C_{1-3}$ alkyleneoxy group (e.g., methyleneoxy, ethyleneoxy); and
(35) a $C_{1-3}$ alkylenedioxy group (e.g., methylenedioxy, ethylenedioxy).

In the present specification, examples of the substituent that the $C_{2-6}$ alkenyl group of the "$C_{2-6}$ alkenyl group optionally having substituent(s)" optionally has include substituents selected from the aforementioned Substituent A Group. While the number of the substituents is not particularly limited as long as it is a substitutable number, preferably 1 to 5, more preferably 1 to 3. When plural substituents are present, the respective substituents may be the same or different.

In the present specification, examples of the substituent that the $C_{2-6}$ alkynyl group of the "$C_{2-6}$ alkynyl group optionally having substituent(s)" optionally has include substituents selected the aforementioned Substituent A Group. While the number of the substituents is not particularly limited as long as it is a substitutable number, preferably 1 to 5, more preferably 1 to 3. When plural substituents are present, the respective substituents may be the same or different.

In the present specification, examples of the substituent that the $C_{1-6}$ alkoxy group of the "$C_{1-6}$ alkoxy group optionally having substituent(s)" optionally has include substituents selected from the aforementioned Substituent A Group. While the number of the substituents is not particularly limited as long as it is a substitutable number, preferably 1 to 5, more preferably 1 to 3. When plural substituents are present, the respective substituents may be the same or different.

In the present specification, examples of the substituent that the $C_{1-6}$ alkyl-carbonyl group of the "$C_{1-6}$ alkyl-carbonyl group optionally having substituent(s)" optionally has include substituents selected from the aforementioned Substituent A Group. While the number of the substituents is not particularly limited as long as it is a substitutable number, preferably 1 to 5, more preferably 1 to 3. When plural substituents are present, the respective substituents may be the same or different.

In the present specification, examples of the substituent that the $C_{6-10}$ aryl group of the "$C_{6-10}$ aryl group optionally having substituent(s)" optionally has include substituents selected from the following Substituent B Group. While the number of the substituents is not particularly limited as long as it is a substitutable number, preferably 1 to 5, more preferably 1 to 3. When plural substituents are present, the respective substituents may be the same or different.

Substituent B Group:
(1) the substituent selected from the aforementioned Substituent A Group;
(2) a $C_{1-6}$ alkyl group optionally having 1 to 3 substituents selected from
  (a) a halogen atom,
  (b) a hydroxy group,
  (c) a carboxy group,
  (d) a $C_{1-6}$ alkoxy group,
  (e) a $C_{1-6}$ alkoxy-carbonyl group,
  (f) an amino group optionally having 1 or 2 $C_{1-6}$ alkyl groups, and
  (g) a $C_{6-10}$ aryl-carbonyl group;
(3) a $C_{2-6}$ alkenyl group optionally having 1 to 3 substituents selected from
  (a) a halogen atom,
  (b) a hydroxy group,
  (c) a carboxy group,
  (d) a $C_{1-6}$ alkoxy group,
  (e) a $C_{1-6}$ alkoxy-carbonyl group, and
  (f) an amino group optionally having 1 or 2 $C_{1-6}$ alkyl groups; and
(4) a $C_{7-13}$ aralkyl group optionally having 1 to 3 substituents selected from
  (a) a halogen atom,
  (b) a hydroxy group,
  (c) a $C_{1-6}$ alkyl group optionally having 1 to 3 halogen atoms, and
  (d) a $C_{1-6}$ alkoxy group.

In the present specification, examples of the substituent that the $C_{3-8}$ cycloalkyl group of the "$C_{3-8}$ cycloalkyl group optionally having substituent(s)" optionally has include substituents selected from the following Substituent C Group. While the number of the substituents is not particularly limited as long as it is a substitutable number, preferably 1 to 5, more preferably 1 to 3. When plural substituents are present, the respective substituents may be the same or different.

Substituent C Group:
(1) the substituent selected from the aforementioned Substituent A Group;
(2) a $C_{1-6}$ alkyl group optionally having 1 to 3 substituents selected from
  (a) a halogen atom,
  (b) a hydroxy group,
  (c) a carboxy group,
  (d) a $C_{1-6}$ alkoxy group,
  (e) a $C_{1-6}$ alkoxy-carbonyl group,
  (f) an amino group optionally having 1 or 2 $C_{1-6}$ alkyl groups, and
  (g) a $C_{6-10}$ aryl-carbonyl group;
(3) a $C_{2-6}$ alkenyl group optionally having 1 to 3 substituents selected from
  (a) a halogen atom,
  (b) a hydroxy group,
  (c) a carboxy group,
  (d) a $C_{1-6}$ alkoxy group,
  (e) a $C_{1-6}$ alkoxy-carbonyl group, and
  (f) an amino group optionally having 1 or 2 $C_{1-6}$ alkyl groups;
(4) a $C_{7-13}$ aralkyl group optionally having 1 to 3 substituents selected from
  (a) a halogen atom,
  (b) a hydroxy group,
  (c) a $C_{1-6}$ alkyl group optionally having 1 to 3 halogen atoms,
  (d) a $C_{1-6}$ alkoxy group; and
(5) an oxo group.

In the present specification, examples of the substituent that the $C_{6-10}$ aryl-carbonyl group of the "$C_{6-10}$ aryl-carbonyl group optionally having substituent(s)" optionally has include substituents selected from the aforementioned Substituent B Group. While the number of the substituents is not particularly limited as long as it is a substitutable number, preferably 1 to 5, more preferably 1 to 3. When plural substituents are present, the respective substituents may be the same or different.

In the present specification, when the heterocyclic group of the "heterocyclic group optionally having substituent(s)" is an "aromatic heterocyclic group", examples of the substituent that the aromatic heterocyclic group optionally has include substituents selected from the aforementioned Substituent B Group. While the number of the substituents is not particularly limited as long as it is a substitutable number, preferably 1 to 5, more preferably 1 to 3. When plural substituents are present, the respective substituents may be the same or different.

In the present specification, when the heterocyclic group of the "heterocyclic group optionally having substituent(s)" is a "non-aromatic heterocyclic group", examples of the substituent that the non-aromatic heterocyclic group optionally has include substituents selected from the aforementioned Substituent C Group. While the number of the substituents is not particularly limited as long as it is a substitutable number, preferably 1 to 5, more preferably 1 to 3. When plural substituents are present, the respective substituents may be the same or different.

In the present specification, when the heterocyclyl-carbonyl group of the "heterocyclyl-carbonyl group optionally having substituent(s)" is an "aromatic heterocyclyl-carbonyl group", examples of the substituent that the aromatic heterocyclyl-carbonyl group optionally has include substituents selected from the aforementioned Substituent B Group. While the number of the substituents is not particularly limited as long as it is a substitutable number, preferably 1 to 5, more preferably 1 to 3. When plural substituents are present, the respective substituents may be the same or different.

In the present specification, when the heterocyclyl-carbonyl group of the "heterocyclyl-carbonyl group optionally having substituent(s)" is a "non-aromatic heterocyclyl-carbonyl group", examples of the substituent that the non-aromatic heterocyclyl-carbonyl group optionally has include substituents selected from the aforementioned Substituent C Group. While the number of the substituents is not particularly limited as long as it is a substitutable number, preferably 1 to 5, more preferably 1 to 3. When plural substituents are present, the respective substituents may be the same or different.

In the present specification, the "amino group optionally having substituent(s)" means, for example, an "amino group" optionally having 1 or 2 substituents selected from
(1) a $C_{1-6}$ alkyl group optionally having substituent(s);
(2) a $C_{2-6}$ alkenyl group optionally having substituent(s);
(3) a $C_{2-6}$ alkynyl group optionally having substituent(s);
(4) a $C_{1-6}$ alkoxy group optionally having substituent(s);
(5) a $C_{1-8}$ alkyl-carbonyl group optionally having substituent(s);
(6) a $C_{3-8}$ cycloalkyl group optionally having substituent(s);
(7) a $C_{6-10}$ aryl group optionally having substituent(s);
(8) a $C_{6-10}$ aryl-carbonyl group optionally having substituent(s);
(9) a heterocyclic group optionally having substituent(s);
(10) a heterocyclyl-carbonyl group optionally having substituent(s); and the like.

When the "amino group optionally having substituent(s)" is an amino group having 2 substituents, these substituents optionally form, together with the adjacent nitrogen atom, a nitrogen-containing heterocycle. Specific examples of the nitrogen-containing heterocycle include a 5- to 7-membered nitrogen-containing heterocycle. The nitrogen-containing heterocycle optionally further has substituent(s). Examples of the substituent include substituents selected from the aforementioned Substituent C Group. While the number of the substituents is not particularly limited as long as it is a substitutable number, preferably 1 to 5, more preferably 1 to 3. When plural substituents are present, the respective substituents may be the same or different.

In the present specification, the "carbamoyl group optionally having substituent(s)" means, for example, a "carbamoyl group" optionally having 1 or 2 substituents selected from
(1) a $C_{1-6}$ alkyl group optionally having substituent(s);
(2) a $C_{2-6}$ alkenyl group optionally having substituent(s);
(3) a $C_{2-6}$ alkynyl group optionally having substituent(s);
(4) a $C_{1-6}$ alkoxy group optionally having substituent(s);
(5) a $C_{1-6}$ alkyl-carbonyl group optionally having substituent(s);
(6) a $C_{3-8}$ cycloalkyl group optionally having substituent(s);
(7) a $C_{6-10}$ aryl group optionally having substituent(s);
(8) a $C_{6-10}$ aryl-carbonyl group optionally having substituent(s);
(9) a heterocyclic group optionally having substituent(s);
(10) a heterocyclyl-carbonyl group optionally having substituent(s); and the like.

When the "carbamoyl group optionally having substituent(s)" is a carbamoyl group having 2 substituents, these substituents optionally form, together with the adjacent nitrogen atom, a nitrogen-containing heterocycle. Specific examples of the nitrogen-containing heterocycle include a 5- to 7-membered nitrogen-containing heterocycle. The nitrogen-containing heterocycle optionally further has substituent(s). Examples of the substituent include substituents selected from the aforementioned Substituent C Group. While the number of the substituents is not particularly limited as long as it is a substitutable number, preferably 1 to 5, more preferably 1 to 3. When plural substituents are present, the respective substituents may be the same or different.

In the present specification, the "optionally substituted hydroxy group" means, for example, a hydroxy group optionally substituted by a substituent selected from
(1) a $C_{1-6}$ alkyl group optionally having substituent(s);
(2) a $C_{2-6}$ alkenyl group optionally having substituent(s);
(3) a $C_{2-6}$ alkynyl group optionally having substituent(s);
(4) a $C_{1-6}$ alkoxy group optionally having substituent(s);
(5) a $C_{1-6}$ alkyl-carbonyl group optionally having substituent(s);
(6) a $C_{3-8}$ cycloalkyl group optionally having substituent(s);
(7) a $C_{6-10}$ aryl group optionally having substituent(s);
(8) a $C_{6-10}$ aryl-carbonyl group optionally having substituent(s);
(9) a heterocyclic group optionally having substituent(s);
(10) a heterocyclyl-carbonyl group optionally having substituent(s); and the like.

In the present specification, the "optionally substituted mercapto group" means, for example, a mercapto group optionally substituted by a substituent selected from
(1) a $C_{1-6}$ alkyl group optionally having substituent(s);
(2) a $C_{2-6}$ alkenyl group optionally having substituent(s);
(3) a $C_{2-6}$ alkynyl group optionally having substituent(s);
(4) a $C_{1-6}$ alkoxy group optionally having substituent(s);
(5) a $C_{1-6}$ alkyl-carbonyl group optionally having substituent(s);
(6) a $C_{3-8}$ cycloalkyl group optionally having substituent(s);
(7) a $C_{6-10}$ aryl group optionally having substituent(s);
(8) a $C_{6-10}$ aryl-carbonyl group optionally having substituent(s);
(9) a heterocyclic group optionally having substituent(s);
(10) a heterocyclyl-carbonyl group optionally having substituent(s);
and the like.

In the present specification, the "cyclic group" of the "cyclic group optionally having substituent(s)" means, for example, a $C_{3-8}$ cycloalkyl group, a group derived from a fused ring wherein a $C_{3-8}$ cycloalkane and a benzene ring are condensed (e.g., indanyl, 1,2,3,4-tetrahydronaphthyl), a $C_{6-10}$ aryl group, an aromatic heterocyclic group, a non-aromatic heterocyclic group or the like.

When the "cyclic group optionally having substituent(s)" is a $C_{3-8}$ cycloalkyl group optionally having substituent(s), examples of the substituent that the $C_{3-8}$ cycloalkyl group optionally has include substituents selected from the aforementioned Substituent C Group. While the number of the substituents is not particularly limited as long as it is a substitutable number, preferably 1 to 5, more preferably 1 to 3. When plural substituents are present, the respective substituents may be the same or different.

When the "cyclic group optionally having substituent(s)" is a group derived from a fused ring wherein a $C_{3-8}$ cycloalkane and a benzene ring are condensed, which optionally has substituent(s), examples of the substituent that the fused ring group optionally has include substituents selected from the aforementioned Substituent C Group. The position of the substituent is not particularly limited as long as it is a substitutable position, and may be on the benzene ring moiety or $C_{3-8}$ cycloalkane moiety. While the number of the substituents is not particularly limited as long as it is a substitutable number, preferably 1 to 5, more preferably 1 to 3. When plural substituents are present, the respective substituents may be the same or different.

When the "cyclic group optionally having substituent(s)" is a $C_{6-10}$ aryl group optionally having substituent(s), examples of the substituent that the $C_{6-10}$ aryl group optionally has include substituents selected from the aforementioned Substituent B Group. While the number of the substituents is not particularly limited as long as it is a substitutable number, preferably 1 to 5, more preferably 1 to 3. When plural substituents are present, the respective substituents may be the same or different.

When the "cyclic group optionally having substituent(s)" is an aromatic heterocyclic group optionally having substituent(s), Examples of the substituent that the aromatic heterocyclic group optionally has include substituents selected from the aforementioned Substituent B Group. While the number of the substituents is not particularly limited as long as it is a substitutable number, preferably 1 to 5, more preferably 1 to 3. When plural substituents are present, the respective substituents may be the same or different.

When the "cyclic group optionally having substituent(s)" is a non-aromatic heterocyclic group optionally having substituent(s), examples of the substituent that the non-aromatic heterocyclic group optionally has include substituents selected from the aforementioned Substituent C Group. While the number of the substituents is not particularly limited as long as it is a substitutable number, preferably 1 to 5, more preferably 1 to 3. When plural substituents are present, the respective substituents may be the same or different.

In the formula (AI), ring $A^A$ is a 5- to 7-membered heterocycle optionally further having substituent(s).

Specifically, the formula (AI) means

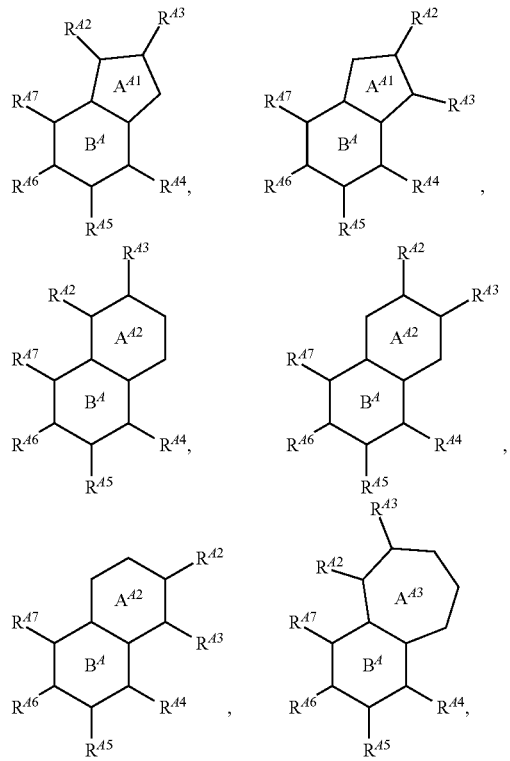

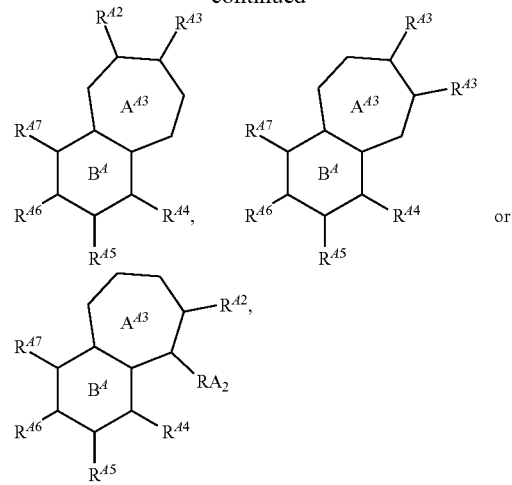

wherein ring $A^{A1}$ is a 5-membered heterocycle optionally having substituent(s), ring $A^{A2}$ is a 6-membered heterocycle optionally having substituent(s), ring $A^{A3}$ is a 7-membered heterocycle optionally having substituent(s), and the other symbols are as defined above.

Examples of the "5-membered heterocycle optionally having substituent(s)" for ring $A^{A1}$ include a 5-membered heterocycle, from among the "5- to 7-membered heterocycles optionally having substituent(s)" for ring $A^A$.

Examples of the "6-membered heterocycle optionally having substituent(s)" for ring $A^{A2}$ include a 6-membered heterocycle, from among the "5- to 7-membered heterocycles optionally having substituent(s)" for ring $A^A$.

Examples of the "7-membered heterocycle optionally having substituent(s)" for ring $A^{A3}$ include a 7-membered heterocycle, from among the "5- to 7-membered heterocycles optionally having substituent(s)" for ring $A^A$.

Examples of the "5- to 7-membered heterocycle" of the "5- to 7-membered heterocycle optionally having substituent(s)" for ring $A^A$ include a 5- to 7-membered heterocycle, from among the aforementioned heterocycles, and specific examples thereof include (1) a 5- to 7-membered (preferably 5- or 6-membered) monocyclic aromatic heterocycle, for example, furan, thiophene, pyridine, pyrimidine, pyridazine, pyrazine, pyrrole, imidazole, pyrazole, thiazole, isothiazole, oxazole, isoxazole, oxadiazole, thiadiazole, triazole, tetrazole, triazine and the like; and (2) a 5- to 7-membered (preferably 5- or 6-membered) monocyclic non-aromatic heterocycle, for example, pyrrolidine, piperidine, morpholine, thiomorpholine, piperazine, oxazolidine, thiazolidine, imidazolidine, oxazoline, thiazoline, imidazoline, dioxole, dioxolane, dihydrooxadiazole, pyran, dihydropyran, tetrahydropyran, thiopyran, dihydrothiopyran, tetrahydrothiopyran, 1-oxidotetrahydrothiopyran, 1,1-dioxidotetrahydrothiopyran, tetrahydrofuran, pyrazolidine, pyrazoline, tetrahydropyrimidine, dihydrotriazole, tetrahydrotriazole, azepane, dihydropyridine, tetrahydropyridine and the like.

The "5- to 7-membered heterocycle" of the "5- to 7-membered heterocycle optionally having substituent(s)" for ring $A^A$ is preferably a 5- or 6-membered monocyclic heterocycle, more preferably a 5-membered monocyclic aromatic heterocycle.

The "5- to 7-membered heterocycle" of the "5- to 7-membered heterocycle optionally having substituent(s)" for ring $A^4$ is more preferably pyrrole, thiophene or furan, particularly preferably pyrrole or thiophene.

The "5- to 7-membered heterocycle" of the "5- to 7-membered heterocycle optionally having substituent(s)" for ring $A^4$ optionally further has, besides the moieties $R^{A2}$ and $R^{A3}$, substituent(s) at substitutable position(s). When plural substituents are present, the respective substituents may be the same or different.

When the "5- to 7-membered heterocycle" is a "5- to 7-membered monocyclic aromatic heterocycle", examples of the substituent include substituents selected from the aforementioned Substituent B Group. When the "5- to 7-membered heterocycle" is a "5- to 7-membered monocyclic non-aromatic heterocycle", examples of the substituent include substituents selected from the aforementioned Substituent C Group.

The "5- to 7-membered heterocycle" of the "5- to 7-membered heterocycle optionally having substituent(s)" for ring $A^4$ is preferably further substituted by $C_{1-6}$ alkyl group(s).

The "5- to 7-membered heterocycle optionally having substituent(s)" for ring $A^4$ is preferably a 5- or 6-membered (preferably 5-membered) monocyclic heterocycle (preferably a monocyclic aromatic heterocycle) optionally further substituted by $C_{1-6}$ alkyl group(s).

The "5- to 7-membered heterocycle optionally having substituent(s)" for ring $A^4$ is more preferably
(1) pyrrole optionally further substituted by $C_{1-6}$ alkyl group(s) (e.g., methyl);
(2) thiophene; or
(3) furan,
particularly preferably
(1) pyrrole optionally further substituted by $C_{1-6}$ alkyl group(s) (e.g., methyl); or
(2) thiophene.

In the formula (AI), ring $B^4$ is a 6-membered ring.

Specific examples of the 6-membered ring for ring $B^4$ include
(1) benzene;
(2) cyclohexane;
(3) cyclohexadiene;
(4) a 6-membered aromatic heterocycle (e.g., pyridine, pyrimidine, pyridazine, pyrazine, triazine);
(5) a 6-membered non-aromatic heterocycle (e.g., piperidine, morpholine, thiomorpholine, piperazine, pyran, dihydropyran, tetrahydropyran, thiopyran, dihydrothiopyran, tetrahydrothiopyran, 1-oxidotetrahydrothiopyran, 1,1-dioxidotetrahydrothiopyran, tetrahydropyrimidine, dihydropyridine, tetrahydropyridine); and the like.

Regarding ring $B^4$, the atoms that $R^{A5}$ and $R^{A6}$ are each bonded to are not —N═, —S— or —O— (i.e., atoms not permitting substituent).

Ring $B^4$ is preferably (1) benzene, or (2) a 6-membered aromatic heterocycle, more preferably (1) benzene, (2) pyridine or (3) pyrazine.

In the formula (AI), the moiety represented by

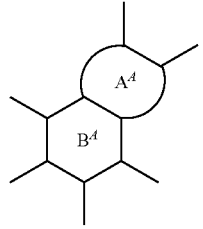

means a group derived from a bicycle formed by ring $A^4$ and ring $B^4$ having one common bond (that is, they are condensed). The bond multiplicity for ring $A^4$ and that for ring $B^4$, involved in the bicycle formation, are the same. For example, the above-mentioned moiety of the formula (AI) is represented by

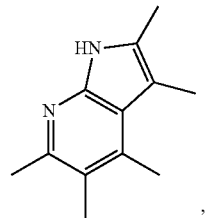

ring $A^4$ is "pyrrole", and ring $B^4$ is "pyridine".

In one preferable embodiment, the formula (AI) is preferably

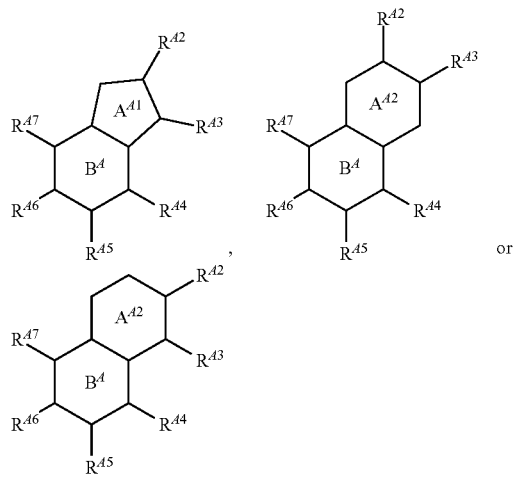

wherein each symbol is as defined above.

In another preferable embodiment, the formula (AI) is preferably

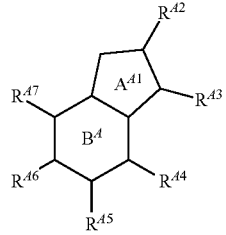

wherein each symbol is as defined above.

In another preferable embodiment, the formula (AI) is preferably the following formula (AI-a)

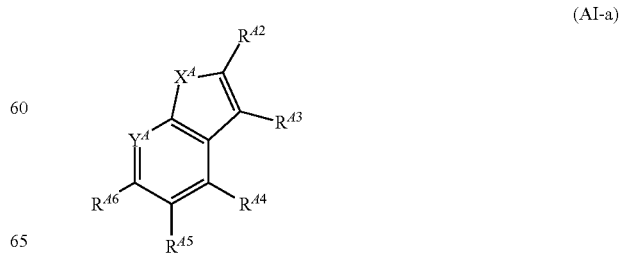

(AI-a)

wherein
X$^A$ is NR$^{A1}$ wherein R$^{A1}$ is a hydrogen atom or a C$_{1-6}$ alkyl group (e.g., methyl), a sulfur atom or an oxygen atom (preferably X$^A$ is NR$^{A1}$ (preferably R$^{A1}$ is a C$_{1-6}$ alkyl group (e.g., methyl)), or sulfur atom);
Y$^A$ is Ce wherein R$^{A7}$ is a hydrogen atom, a halogen atom or a C$_{1-6}$ alkyl group (e.g., methyl) (preferably R$^{A1}$ is a hydrogen atom), or a nitrogen atom; and
the other symbols are each as defined above.

In another preferable embodiment, the formula (AI) is preferably the following formula (AI-b)

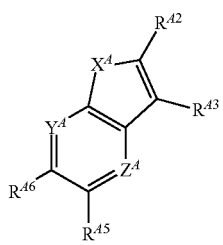

(AI-b)

wherein
X$^A$ is NR$^{A1}$ wherein R$^{A1}$ is a hydrogen atom or a C$_{1-6}$ alkyl group (e.g., methyl), a sulfur atom or an oxygen atom (preferably X$^A$ is NR$^{A1}$, and R$^{A1}$ is methyl);
Y$^A$ is CR$^{A7}$ wherein R$^{A7}$ is a hydrogen atom, a halogen atom or a C$_{1-6}$ alkyl group (preferably R$^{A7}$ is a hydrogen atom), or a nitrogen atom (preferably Y$^A$ is nitrogen atom);
Z$^A$ is CR$^{A4}$ wherein R$^{A4}$ is a hydrogen atom, a halogen atom, an amino group optionally having substituent(s), or a mercapto group optionally having a substituent (preferably R$^{A4}$ is a hydrogen atom), or a nitrogen atom (preferably Z$^A$ is CR$^{A4}$, and R$^{A4}$ is a hydrogen atom);
(preferably X$^A$ is NR$^{A1}$ wherein R$^{A1}$ is methyl, Y$^A$ is CR$^{A7}$ wherein R$^{A7}$ is a hydrogen atom, or a nitrogen atom, and Z$^A$ is CR$^{A4}$ wherein R$^{A4}$ is a hydrogen atom, or a nitrogen atom; more preferably X$^A$ is NR$^{A1}$ wherein R$^{A1}$ is methyl, Y$^A$ is a nitrogen atom, and Z$^A$ is CR$^{A4}$ wherein R$^{A4}$ is a hydrogen atom); and
the other symbols are each as defined above.

Unless particularly indicated hereinafter, the formula (AI) is interpreted to include the above-mentioned embodiments such as the formula (AI-a) and the formula (AI-b) mentioned above, and the like.

In the formula (AI), R$^{A2}$ is a carbamoyl group optionally having substituent(s).

R$^{A2}$ is preferably a carbamoyl group optionally having 1 or 2 substituents selected from
(1) a C$_{1-6}$ alkyl group optionally having substituent(s),
(2) a C$_{3-8}$ cycloalkyl group optionally having substituent(s), and
(3) a heterocyclic group optionally having substituent(s).

In one embodiment, R$^{A2}$ is more preferably a carbamoyl group having one substituent selected from
(1) a 4- to 12-membered (preferably 4- to 7-membered) non-aromatic heterocyclic group (e.g., piperidyl, tetrahydropyranyl, tetrahydrothiopyranyl, 1-oxidotetrahydrothiopyranyl, 1,1-dioxidotetrahydrothiopyranyl) optionally having 1 to 3 substituents selected from
    (a) a C$_{1-6}$ alkyl group optionally having 1 to 3 hydroxy groups, and
    (b) a C$_{1-8}$ alkyl-carbonyl group (e.g., acetyl) optionally having 1 to 3 hydroxy groups;
(2) a C$_{3-8}$ cycloalkyl group (e.g., cyclohexyl) optionally having 1 to 3 hydroxy groups; and
(3) a C$_{1-6}$ alkyl group (e.g., ethyl, propyl) having one substituent selected from
    (a) a C$_{1-6}$ alkylsulfonyl group (e.g., ethylsulfonyl) optionally having 1 to 3 C$_{1-6}$ alkoxy groups (e.g., methoxy), and
    (b) an amino group having one C$_{1-6}$ alkyl-carbonyl group (e.g., acetyl) optionally having 1 to 3 hydroxy groups.

In another embodiment, R$^{A2}$ is more preferably a carbamoyl group having one substituent selected from
(1) a 4- to 12-membered (preferably 4- to 7-membered) non-aromatic heterocyclic group (e.g., piperidyl, tetrahydropyranyl, tetrahydrothiopyranyl, 1-oxidotetrahydrothiopyranyl, 1,1-dioxidotetrahydrothiopyranyl, azepanyl) optionally having 1 to 3 substituents selected from
    (a) a C$_{1-6}$ alkyl group optionally having 1 to 3 hydroxy groups,
    (b) a C$_{1-8}$ alkyl-carbonyl group (e.g., acetyl) optionally having 1 to 3 hydroxy groups, and
    (c) an oxo group;
(2) a C$_{3-8}$ cycloalkyl group (e.g., cyclopropyl, cyclobutyl, cyclopentyl, cyclohexyl) optionally having 1 to 3 substituents selected from
    (a) a hydroxy group,
    (b) a carbamoyl group, and
    (c) a C$_{6-10}$ aryl group (e.g., phenyl); and
(3) a C$_{1-6}$ alkyl group (e.g., methyl, ethyl, propyl, isopropyl, butyl, isobutyl, sec-butyl, tert-butyl, 2,2-dimethylbutyl) having one substituent selected from
    (a) a C$_{1-6}$ alkylsulfonyl group (e.g., ethylsulfonyl) optionally having 1 to 3 C$_{1-6}$ alkoxy groups (e.g., methoxy),
    (b) an amino group optionally having 1 or 2 substituents selected from
        (i) a C$_{1-6}$ alkyl group (e.g., methyl, ethyl) optionally having 1 to 3 hydroxy groups,
        (ii) a C$_{1-6}$ alkyl-carbonyl group (e.g., acetyl) optionally having 1 to 3 hydroxy groups,
        (iii) a C$_{1-6}$ alkylsulfonyl group (e.g., methylsulfonyl) optionally having 1 to 3 halogen atoms (e.g., a fluorine atom), and
        (iv) a 5- to 12-membered (preferably 5- or 6-membered) aromatic heterocyclyl-carbonyl group (e.g., thienyl-carbonyl) optionally having 1 to 3 halogen atoms (e.g., a chlorine atom),
    (c) a hydroxy group,
    (d) a C$_{1-6}$ alkoxy group (e.g., methoxy, ethoxy) optionally having 1 to 3 hydroxy groups,
    (e) a C$_{1-6}$ alkoxy-carbonyl group (e.g., methoxycarbonyl),
    (f) a carbamoyl group,
    (g) a C$_{3-8}$ cycloalkyl group (e.g., cyclopropyl) optionally having 1 to 3 of 5- to 12-membered (preferably 5- or 6-membered) aromatic heterocyclic groups (e.g., thienyl),
    (h) a C$_{6-10}$ aryl group (e.g., phenyl) optionally having 1 to 3 substituents selected from
        (i) a halogen atom (e.g., a fluorine atom),
        (ii) a hydroxy group,
        (iii) a carbamoyl group optionally having 1 or 2 C$_{1-6}$ alkyl groups (e.g., ethyl) optionally having one hydroxy group,
        (iv) a C$_{1-3}$ alkylenedioxy group (e.g., methylenedioxy),
        (v) a sulfamoyl group, and
        (vi) a C$_{1-6}$ alkyl-carbonyl group (e.g., acetyl),
    (i) a 4- to 12-membered (preferably 4- to 7-membered) non-aromatic heterocyclic group (e.g., tetrahydrofuryl, pyrrolidinyl, oxazolidinyl, piperidyl, piperazinyl, morpholinyl) optionally having 1 to 3 substituents selected from
(i) a $C_{6-10}$ aryl group (e.g., phenyl),
(ii) a $C_{1-6}$ alkyl group (e.g., methyl),
(iii) a $C_{7-13}$ aralkyl group (e.g., benzyl), and
(iv) an oxo group, and
(j) a 5- to 12-membered (preferably 5- or 6-membered) aromatic heterocyclic group (e.g., furyl, thienyl, isoxazolyl, pyridyl, pyrazinyl, indolyl, thiazolyl) optionally having 1 to 3 $C_{1-6}$ alkyl groups (e.g., methyl).

In the formula (AI), $R^{43}$ is a substituted hydroxy group. Examples of the "substituted hydroxy group" for $R^{43}$ include a hydroxy group substituted by a substituent selected from
(1) a $C_{1-6}$ alkyl group optionally having substituent(s);
(2) a $C_{2-6}$ alkenyl group optionally having substituent(s);
(3) a $C_{2-6}$ alkynyl group optionally having substituent(s);
(4) a $C_{1-6}$ alkyl-carbonyl group optionally having substituent(s);
(5) a $C_{3-8}$ cycloalkyl group optionally having substituent(s);
(6) a $C_{6-10}$ aryl group optionally having substituent(s);
(7) a $C_{6-10}$ aryl-carbonyl group optionally having substituent(s);
(8) a heterocyclic group optionally having substituent(s);
(9) a heterocyclyl-carbonyl group optionally having substituent(s); and the like.

$R^{43}$ is preferably an optionally halogenated $C_{1-6}$ alkoxy group, more preferably a $C_{1-6}$ alkoxy group (e.g., ethoxy, isopropoxy) optionally having 1 to 3 halogen atoms (e.g., a fluorine atom).

In the formula (AI), $R^{44}$ is a hydrogen atom, a halogen atom, an amino group optionally having substituent(s), a mercapto group optionally having a substituent or a thioxo group.

$R^{44}$ is preferably hydrogen atom.

Alternatively, when the atom on ring $B^A$ that $R^{44}$ is bonded to is —N=, —S—, —O— or the like (i.e., not permitting substituent), $R^{44}$ is absent.

In the formula (AI), $R^{45}$ is a substituted $C_{1-6}$ alkyl group, an amino group optionally having substituent(s), a cyclic group optionally having substituent(s), or a hydroxy group substituted by a cyclic group optionally having substituent(s).

Examples of the "substituted $C_{1-6}$ alkyl group" for $R^{45}$ include a $C_{1-6}$ alkyl group substituted by 1 to 5 (preferably 1 to 3) substituents selected from the aforementioned Substituent A Group. When plural substituents are present, the respective substituents may be the same or different.

Examples of the "hydroxy group substituted by a cyclic group optionally having substituent(s)" for $R^{45}$ include a hydroxy group substituted by the aforementioned "cyclic group(s) optionally having substituent(s)". Of these, it is preferably (1) a hydroxy group substituted by $C_{6-10}$ aryl group(s) optionally having substituent(s), or (2) a hydroxy group substituted by 5- to 7-membered (preferably 5- or 6-membered) monocyclic aromatic heterocyclic group(s) optionally having substituent(s).

$R^{45}$ is preferably
(1) a substituted $C_{1-6}$ alkyl group,
(2) an amino group optionally having substituent(s),
(3) a $C_{6-10}$ aryl group optionally having substituent(s), or
(4) a heterocyclic group optionally having substituent(s).

In one embodiment, $R^{45}$ is more preferably
(1) a $C_{1-6}$ alkyl group (e.g., methyl, ethyl, pentyl) optionally having 1 to 3 substituents selected from
(a) a $C_{6-10}$ aryl-carbonyl group (e.g., benzoyl),
(b) a $C_{6-10}$ aryl group (e.g., phenyl) optionally having 1 to 3 substituents selected from
  (i) a halogen atom (e.g., a fluorine atom, a chlorine atom), and
  (ii) a $C_{1-6}$ alkoxy group (e.g., methoxy), and
(c) a $C_{1-6}$ alkoxy group (e.g., methoxy) optionally having 1 to 3 $C_{6-10}$ aryl groups (e.g., phenyl);
(2) an amino group optionally having one substituent selected from
(a) a $C_{1-6}$ alkyl group (e.g., methyl) optionally having 1 to 3 $C_{6-10}$ aryl groups (e.g., phenyl),
(b) a $C_{6-10}$ aryl group (e.g., phenyl) optionally having 1 to 3 substituents selected from
  (i) a halogen atom (e.g., a chlorine atom), and
  (ii) a $C_{1-6}$ alkoxy group (e.g., methoxy),
(c) a $C_{8-10}$ aryl-carbonyl group (e.g., benzoyl) optionally having 1 to 3 substituents selected from
  (i) a halogen atom (e.g., a fluorine atom, a chlorine atom), and
  (ii) a $C_{1-6}$ alkoxy group (e.g., methoxy),
(d) a 5- or 6-membered monocyclic aromatic heterocyclylcarbonyl group (e.g., pyrazolylcarbonyl, thienylcarbonyl, furylcarbonyl, thiazolylcarbonyl, oxazolylcarbonyl, pyridylcarbonyl) optionally having 1 to 3 substituents selected from
  (i) a halogen atom (e.g., a chlorine atom),
  (ii) a $C_{1-6}$ alkyl group (e.g., methyl), and
  (iii) a $C_{1-6}$ alkoxy group (e.g., methoxy),
(e) a $C_{3-8}$ cycloalkyl-carbonyl group (e.g., cyclopropylcarbonyl, cyclohexylcarbonyl), and
(f) a carbamoyl group optionally having 1 or 2 $C_{6-10}$ aryl groups (e.g., phenyl);
(3) a $C_{8-10}$ aryl group (e.g., phenyl, naphthyl) optionally having 1 to 3 substituents selected from
(a) a halogen atom (e.g., a fluorine atom, a chlorine atom),
(b) a $C_{1-6}$ alkyl group (e.g., methyl, ethyl) optionally having 1 to 3 halogen atoms (e.g., a fluorine atom), and
(c) a $C_{1-6}$ alkoxy group (e.g., methoxy, isopropoxy); or
(4) a 5- or 6-membered monocyclic aromatic heterocyclic group (e.g., pyridyl) optionally having 1 to 3 substituents selected from
(a) a halogen atom (e.g., a fluorine atom),
(b) a $C_{1-6}$ alkyl group (e.g., methyl), and
(c) a $C_{1-6}$ alkoxy group (e.g., methoxy).

In another embodiment, $R^{45}$ is more preferably
(1) a $C_{1-6}$ alkyl group (e.g., methyl, ethyl, pentyl) optionally having 1 to 3 substituents selected from
(a) a $C_{8-10}$ aryl-carbonyl group (e.g., benzoyl),
(b) a $C_{8-10}$ aryl group (e.g., phenyl) optionally having 1 to 3 substituents selected from
  (i) a halogen atom (e.g., a fluorine atom, a chlorine atom), and
  (ii) a $C_{1-6}$ alkoxy group (e.g., methoxy), and
(c) a $C_{1-6}$ alkoxy group (e.g., methoxy) optionally having 1 to 3 $C_{6-10}$ aryl groups (e.g., phenyl);
(2) an amino group optionally having one substituent selected from
(a) a $C_{1-6}$ alkyl group (e.g., methyl) optionally having 1 to 3 $C_{6-10}$ aryl groups (e.g., phenyl),
(b) a $C_{6-10}$ aryl group (e.g., phenyl) optionally having 1 to 3 substituents selected from
  (i) a halogen atom (e.g., a chlorine atom), and
  (ii) a $C_{1-6}$ alkoxy group (e.g., methoxy),
(c) a $C_{6-10}$ aryl-carbonyl group (e.g., benzoyl) optionally having 1 to 3 substituents selected from
  (i) a halogen atom (e.g., a fluorine atom, a chlorine atom), and
  (ii) a $C_{1-6}$ alkoxy group (e.g., methoxy), (d) a 5- or 6-membered monocyclic aromatic heterocyclyl-carbonyl group (e.g., pyrazolylcarbonyl, thienylcarbonyl, furylcarbonyl, thiazolylcarbonyl, oxazolylcarbonyl, pyridylcarbonyl) optionally having 1 to 3 substituents selected from
  (i) a halogen atom (e.g., a chlorine atom),
  (ii) a $C_{1-6}$ alkyl group (e.g., methyl), and
  (iii) a $C_{1-6}$ alkoxy group (e.g., methoxy),
(e) a $C_{3-8}$ cycloalkyl-carbonyl group (e.g., cyclopropylcarbonyl, cyclohexylcarbonyl), and
(f) a carbamoyl group optionally having 1 or 2 $C_{6-10}$ aryl groups (e.g., phenyl);
(3) a $C_{6-10}$ aryl group (e.g., phenyl, naphthyl) optionally having 1 to 3 substituents selected from
  (a) a halogen atom (e.g., a fluorine atom, a chlorine atom),
  (b) a $C_{1-6}$ alkyl group (e.g., methyl, ethyl) optionally having 1 to 3 halogen atoms (e.g., a fluorine atom),
  (c) a $C_{1-6}$ alkoxy group (e.g., methoxy, isopropoxy),
  (d) a hydroxy group, and
  (e) an amino group optionally having one $C_{1-6}$ alkylsulfonyl group (e.g., methylsulfonyl);
(4) a 5- or 6-membered monocyclic non-aromatic heterocyclic group (e.g., dihydropyridyl) optionally having 1 to 3 oxo groups; or
(5) a 5- or 6-membered monocyclic aromatic heterocyclic group (e.g., thienyl, pyridyl) optionally having 1 to 3 substituents selected from
  (a) a halogen atom (e.g., a fluorine atom),
  (b) a $C_{1-6}$ alkyl group (e.g., methyl), and
  (c) a $C_{1-6}$ alkoxy group (e.g., methoxy).

In the formula (AI), $R^{46}$ is a $C_{1-6}$ alkyl group optionally having substituent(s).

$R^{46}$ is preferably a $C_{1-6}$ alkyl group (e.g., methyl, ethyl).

In the formula (AI), $R^{47}$ is a hydrogen atom, a halogen atom or a $C_{1-6}$ alkyl group.

$R^{47}$ is preferably a hydrogen atom.

Alternatively, when the atom on ring $B^A$ that $R^{47}$ is bonded to is —N═, —S—, —O— or the like (i.e., not permitting substituent), $R^{47}$ is absent.

Preferable specific examples of compound (AI) include the following compounds.

Compound (AI-1)

In the formula (AI), a compound wherein
ring $A^A$ is a 5- or 6-membered (preferably 5-membered) monocyclic heterocycle (preferably a monocyclic aromatic heterocycle) optionally further substituted by $C_{1-6}$ alkyl group(s)
[preferably
(1) pyrrole optionally further substituted by $C_{1-6}$ alkyl group(s) (e.g., methyl),
(2) thiophene, or
(3) furan;
more preferably
(1) pyrrole optionally further substituted by $C_{1-6}$ alkyl group(s) (e.g., methyl), or
(2) thiophene];
  ring $B^A$ is
(1) benzene, or
(2) a 6-membered aromatic heterocycle
[preferably
(1) benzene,
(2) pyridine, or
(3) pyrazine];
  $R^{42}$ is a carbamoyl group having one substituent selected from
(1) a 4- to 12-membered (preferably 4- to 7-membered) non-aromatic heterocyclic group (e.g., piperidyl, tetrahydropyranyl, tetrahydrothiopyranyl, 1-oxidotetrahydrothiopyranyl, 1,1-dioxidotetrahydrothiopyranyl) optionally having 1 to 3 substituents selected from
  (a) a $C_{1-6}$ alkyl group optionally having 1 to 3 hydroxy groups, and
  (b) a $C_{1-6}$ alkyl-carbonyl group (e.g., acetyl) optionally having 1 to 3 hydroxy groups;
(2) a $C_{3-8}$ cycloalkyl group (e.g., cyclohexyl) optionally having 1 to 3 hydroxy groups; and
(3) a $C_{1-6}$ alkyl group (e.g., ethyl, propyl) having one substituent selected from
  (a) a $C_{1-6}$ alkylsulfonyl group (e.g., ethylsulfonyl) optionally having 1 to 3 $C_{1-6}$ alkoxy groups (e.g., methoxy), and
  (b) an amino group having one $C_{1-6}$ alkyl-carbonyl group (e.g., acetyl) optionally having 1 to 3 hydroxy groups;
$R^{43}$ is a $C_{1-6}$ alkoxy group (e.g., ethoxy, isopropoxy) optionally having 1 to 3 halogen atoms (e.g., a fluorine atom);
$R^{44}$ is a hydrogen atom, or absent;
$R^{45}$ is
(1) a $C_{1-6}$ alkyl group (e.g., methyl, ethyl, pentyl) optionally having 1 to 3 substituents selected from
  (a) a $C_{6-10}$ aryl-carbonyl group (e.g., benzoyl),
  (b) a $C_{6-10}$ aryl group (e.g., phenyl) optionally having 1 to 3 substituents selected from
    (i) a halogen atom (e.g., a fluorine atom, a chlorine atom), and
    (ii) a $C_{1-6}$ alkoxy group (e.g., methoxy), and
  (c) a $C_{1-6}$ alkoxy group (e.g., methoxy) optionally having 1 to 3 $C_{6-10}$ aryl groups (e.g., phenyl);
(2) an amino group optionally having one substituent selected from
  (a) a $C_{1-6}$ alkyl group (e.g., methyl) optionally having 1 to 3 $C_{6-10}$ aryl groups (e.g., phenyl),
  (b) a $C_{6-10}$ aryl group (e.g., phenyl) optionally having 1 to 3 substituents selected from
    (i) a halogen atom (e.g., a chlorine atom), and
    (ii) a $C_{1-6}$ alkoxy group (e.g., methoxy),
  (c) a $C_{6-10}$ aryl-carbonyl group (e.g., benzoyl) optionally having 1 to 3 substituents selected from
    (i) a halogen atom (e.g., a fluorine atom, a chlorine atom), and
    (ii) a $C_{1-6}$ alkoxy group (e.g., methoxy),
  (d) a 5- or 6-membered monocyclic aromatic heterocyclylcarbonyl group (e.g., pyrazolylcarbonyl, thienylcarbonyl, furylcarbonyl, thiazolylcarbonyl, oxazolylcarbonyl, pyridylcarbonyl) optionally having 1 to 3 substituents selected from
    (i) a halogen atom (e.g., a chlorine atom),
    (ii) a $C_{1-6}$ alkyl group (e.g., methyl), and
    (iii) a $C_{1-6}$ alkoxy group (e.g., methoxy),
  (e) a $C_{3-8}$ cycloalkyl-carbonyl group (e.g., cyclopropylcarbonyl, cyclohexylcarbonyl), and
  (f) a carbamoyl group optionally having 1 or 2 $C_{6-10}$ aryl groups (e.g., phenyl);
(3) a $C_{6-10}$ aryl group (e.g., phenyl, naphthyl) optionally having 1 to 3 substituents selected from
  (a) a halogen atom (e.g., a fluorine atom, a chlorine atom),
  (b) a $C_{1-6}$ alkyl group (e.g., methyl, ethyl) optionally having 1 to 3 halogen atoms (e.g., a fluorine atom), and
  (c) a $C_{1-6}$ alkoxy group (e.g., methoxy, isopropoxy); or
(4) a 5- or 6-membered monocyclic aromatic heterocyclic group (e.g., pyridyl) optionally having 1 to 3 substituents selected from
  (a) a halogen atom (e.g., a fluorine atom),
  (b) a $C_{1-6}$ alkyl group (e.g., methyl), and (c) a $C_{1-6}$ alkoxy group (e.g., methoxy);
$R^{46}$ is a $C_{1-6}$ alkyl group (e.g., methyl, ethyl); and
$R^{47}$ is a hydrogen atom, or absent;
or a salt thereof.

Compound (AI-2)

A compound represented by the formula (AI-a)

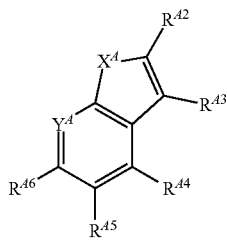
(AI-a)

wherein
$X^A$ is $NR^{A1}$, a sulfur atom or an oxygen atom (preferably $NR^{A1}$ or a sulfur atom);
$R^{A1}$ is a hydrogen atom or a $C_{1-6}$ alkyl group (e.g., methyl) (preferably a $C_{1-8}$ alkyl group (e.g., methyl));
$Y^A$ is $CR^{A7}$ or a nitrogen atom;
$R^{A7}$ is a hydrogen atom;
$R^{A2}$ is a carbamoyl group having one substituent selected from
(1) a 4- to 12-membered (preferably 4- to 7-membered) non-aromatic heterocyclic group (e.g., piperidyl, tetrahydropyranyl, tetrahydrothiopyranyl, 1-oxidotetrahydrothiopyranyl, 1,1-dioxidotetrahydrothiopyranyl) optionally having 1 to 3 substituents selected from
    (a) a $C_{1-6}$ alkyl group optionally having 1 to 3 hydroxy groups, and
    (b) a $C_{1-8}$ alkyl-carbonyl group (e.g., acetyl) optionally having 1 to 3 hydroxy groups;
(2) a $C_{3-8}$ cycloalkyl group (e.g., cyclohexyl) optionally having 1 to 3 hydroxy groups; and
(3) a $C_{1-6}$ alkyl group (e.g., ethyl, propyl) having one substituent selected from
    (a) a $C_{1-8}$ alkylsulfonyl group (e.g., ethylsulfonyl) optionally having 1 to 3 $C_{1-6}$ alkoxy groups (e.g., methoxy), and
    (b) an amino group having one $C_{1-6}$ alkyl-carbonyl group (e.g., acetyl) optionally having 1 to 3 hydroxy groups;
$R^{A3}$ is a $C_{1-6}$ alkoxy group (e.g., ethoxy, isopropoxy) optionally having 1 to 3 halogen atoms (e.g., a fluorine atom);
$R^{A4}$ is a hydrogen atom;
$R^{A5}$ is
(1) a $C_{1-6}$ alkyl group (e.g., methyl, ethyl, pentyl) optionally having 1 to 3 substituents selected from
    (a) a $C_{6-10}$ aryl-carbonyl group (e.g., benzoyl),
    (b) a $C_{6-10}$ aryl group (e.g., phenyl) optionally having 1 to 3 substituents selected from
        (i) a halogen atom (e.g., a fluorine atom, a chlorine atom), and
        (ii) a $C_{1-6}$ alkoxy group (e.g., methoxy), and
    (c) a $C_{1-6}$ alkoxy group (e.g., methoxy) optionally having 1 to 3 $C_{6-10}$ aryl groups (e.g., phenyl);
(2) an amino group optionally having one substituent selected from
    (a) a $C_{1-6}$ alkyl group (e.g., methyl) optionally having 1 to 3 $C_{6-10}$ aryl groups (e.g., phenyl),
    (b) a $C_{6-10}$ aryl group (e.g., phenyl) optionally having 1 to 3 substituents selected from
        (i) a halogen atom (e.g., a chlorine atom), and
        (ii) a $C_{1-6}$ alkoxy group (e.g., methoxy),
    (c) a $C_{6-10}$ aryl-carbonyl group (e.g., benzoyl) optionally having 1 to 3 substituents selected from
        (i) a halogen atom (e.g., a fluorine atom, a chlorine atom), and
        (ii) a $C_{1-6}$ alkoxy group (e.g., methoxy),
    (d) a 5- or 6-membered monocyclic aromatic heterocyclyl-carbonyl group (e.g., pyrazolylcarbonyl, thienylcarbonyl, furylcarbonyl, thiazolylcarbonyl, oxazolylcarbonyl, pyridylcarbonyl) optionally having 1 to 3 substituents selected from
        (i) a halogen atom (e.g., a chlorine atom),
        (ii) a $C_{1-6}$ alkyl group (e.g., methyl), and
        (iii) a $C_{1-6}$ alkoxy group (e.g., methoxy),
    (e) a $C_{3-8}$ cycloalkyl-carbonyl group (e.g., cyclopropylcarbonyl, cyclohexylcarbonyl), and
    (f) a carbamoyl group optionally having 1 or 2 $C_{6-10}$ aryl groups (e.g., phenyl);
(3) a $C_{6-10}$ aryl group (e.g., phenyl, naphthyl) optionally having 1 to 3 substituents selected from
    (a) a halogen atom (e.g., a fluorine atom, a chlorine atom),
    (b) a $C_{1-6}$ alkyl group (e.g., methyl, ethyl) optionally having 1 to 3 halogen atoms (e.g., a fluorine atom), and
    (c) a $C_{1-6}$ alkoxy group (e.g., methoxy, isopropoxy); or
(4) a 5- or 6-membered monocyclic aromatic heterocyclic group (e.g., pyridyl) optionally having 1 to 3 substituents selected from
    (a) a halogen atom (e.g., a fluorine atom),
    (b) a $C_{1-6}$ alkyl group (e.g., methyl), and
    (c) a $C_{1-6}$ alkoxy group (e.g., methoxy); and
$R^{A6}$ is a $C_{1-6}$ alkyl group (e.g., methyl, ethyl) or a salt thereof.

Compound (AI-3)

In the formula (AI), a compound wherein
ring $A^A$ is a 5- or 6-membered (preferably 5-membered) monocyclic heterocycle (preferably a monocyclic aromatic heterocycle) optionally further substituted by $C_{1-6}$ alkyl group(s) [preferably (1) pyrrole optionally further substituted by $C_{1-6}$ alkyl group(s) (e.g., methyl), (2) thiophene, or (3) furan; more preferably (1) pyrrole optionally further substituted by $C_{1-6}$ alkyl group(s) (e.g., methyl), or (2) thiophene];
ring $B^A$ is (1) benzene, or (2) a 6-membered aromatic heterocycle [preferably (1) benzene, (2) pyridine or (3) pyrazine];
$R^{A2}$ is a carbamoyl group having one substituent selected from
(1) a 4- to 12-membered (preferably 4- to 7-membered) non-aromatic heterocyclic group (e.g., piperidyl, tetrahydropyranyl, tetrahydrothiopyranyl, 1-oxidotetrahydrothiopyranyl, 1,1-dioxidotetrahydrothiopyranyl, azepanyl) optionally having 1 to 3 substituents selected from
    (a) a $C_{1-6}$ alkyl group optionally having 1 to 3 hydroxy groups,
    (b) a $C_{1-6}$ alkyl-carbonyl group (e.g., acetyl) optionally having 1 to 3 hydroxy groups, and
    (c) an oxo group;
(2) a $C_{3-8}$ cycloalkyl group (e.g., cyclopropyl, cyclobutyl, cyclopentyl, cyclohexyl) optionally having 1 to 3 substituents selected from
    (a) a hydroxy group,
    (b) a carbamoyl group, and
    (c) a $C_{6-10}$ aryl group (e.g., phenyl); and
(3) a $C_{1-6}$ alkyl group (e.g., methyl, ethyl, propyl, isopropyl, butyl, isobutyl, sec-butyl, tert-butyl, 2,2-dimethylbutyl) having one substituent selected from (a) a C$_{1-6}$ alkylsulfonyl group (e.g., ethylsulfonyl) optionally having 1 to 3 C$_{1-6}$ alkoxy groups (e.g., methoxy),
(b) an amino group optionally having 1 or 2 substituents selected from
  (i) a C$_{1-6}$ alkyl group (e.g., methyl, ethyl) optionally having 1 to 3 hydroxy groups
  (ii) a C$_{1-6}$ alkyl-carbonyl group (e.g., acetyl) optionally having 1 to 3 hydroxy groups,
  (iii) a C$_{1-6}$ alkylsulfonyl group (e.g., methylsulfonyl) optionally having 1 to 3 halogen atoms (e.g., a fluorine atom), and
  (iv) a 5- to 12-membered (preferably 5- or 6-membered) aromatic heterocyclyl-carbonyl group (e.g., thienylcarbonyl) optionally having 1 to 3 halogen atoms (e.g., a chlorine atom),
(c) a hydroxy group,
(d) a C$_{1-6}$ alkoxy group (e.g., methoxy, ethoxy) optionally having 1 to 3 hydroxy groups,
(e) a C$_{1-6}$ alkoxy-carbonyl group (e.g., methoxycarbonyl),
(f) a carbamoyl group,
(g) a C$_{3-8}$ cycloalkyl group (e.g., cyclopropyl) optionally having 1 to 3 of 5- to 12-membered (preferably 5- or 6-membered) aromatic heterocyclic groups (e.g., thienyl),
(h) a C$_{6-10}$ aryl group (e.g., phenyl) optionally having 1 to 3 substituents selected from
  (i) a halogen atom (e.g., a fluorine atom),
  (ii) a hydroxy group,
  (iii) a carbamoyl group optionally having 1 or 2 C$_{1-6}$ alkyl groups (e.g., ethyl) optionally having one hydroxy group,
  (iv) a C$_{1-3}$ alkylenedioxy group (e.g., methylenedioxy),
  (v) a sulfamoyl group, and
  (vi) a C$_{1-6}$ alkyl-carbonyl group (e.g., acetyl),
(i) a 4- to 12-membered (preferably 4- to 7-membered) non-aromatic heterocyclic group (e.g., tetrahydrofuryl, pyrrolidinyl, oxazolidinyl, piperidyl, piperazinyl, morpholinyl) optionally having 1 to 3 substituents selected from
  (i) a C$_{6-10}$ aryl group (e.g., phenyl),
  (ii) a C$_{1-6}$ alkyl group (e.g., methyl),
  (iii) a C$_{7-13}$ aralkyl group (e.g., benzyl), and
  (iv) an oxo group, and
(j) a 5- to 12-membered (preferably 5- or 6-membered) aromatic heterocyclic group (e.g., furyl, thienyl, isoxazolyl, pyridyl, pyrazinyl, indolyl, thiazolyl) optionally having 1 to 3 C$_{1-6}$ alkyl groups (e.g., methyl);
R$^{43}$ is an optionally halogenated C$_{1-6}$ alkoxy group (preferably a C$_{1-6}$ alkoxy group (e.g., ethoxy, isopropoxy) optionally having 1 to 3 halogen atoms (e.g., a fluorine atom));
R$^{44}$ is a hydrogen atom, or absent;
R$^{45}$ is
(1) a C$_{1-6}$ alkyl group (e.g., methyl, ethyl, pentyl) optionally having 1 to 3 substituents selected from
  (a) a C$_{6-10}$ aryl-carbonyl group (e.g., benzoyl),
  (b) a C$_{6-10}$ aryl group (e.g., phenyl) optionally having 1 to 3 substituents selected from
    (i) a halogen atom (e.g., a fluorine atom, a chlorine atom), and
    (ii) a C$_{1-6}$ alkoxy group (e.g., methoxy), and
  (c) a C$_{1-6}$ alkoxy group (e.g., methoxy) optionally having 1 to 3 C$_{6-10}$ aryl groups (e.g., phenyl);
(2) an amino group optionally having one substituent selected from
  (a) a C$_{1-6}$ alkyl group (e.g., methyl) optionally having 1 to 3 C$_{6-10}$ aryl groups (e.g., phenyl),
  (b) a C$_{6-10}$ aryl group (e.g., phenyl) optionally having 1 to 3 substituents selected from
    (i) a halogen atom (e.g., a chlorine atom), and
    (ii) a C$_{1-6}$ alkoxy group (e.g., methoxy),
  (c) a C$_{6-10}$ aryl-carbonyl group (e.g., benzoyl) optionally having 1 to 3 substituents selected from
    (i) a halogen atom (e.g., a fluorine atom, a chlorine atom), and
    (ii) a C$_{1-6}$ alkoxy group (e.g., methoxy),
  (d) a 5- or 6-membered monocyclic aromatic heterocyclyl-carbonyl group (e.g., pyrazolylcarbonyl, thienylcarbonyl, furylcarbonyl, thiazolylcarbonyl, oxazolylcarbonyl, pyridylcarbonyl) optionally having 1 to 3 substituents selected from
    (i) a halogen atom (e.g., a chlorine atom),
    (ii) a C$_{1-6}$ alkyl group (e.g., methyl), and
    (iii) a C$_{1-6}$ alkoxy group (e.g., methoxy),
  (e) a C$_{3-8}$ cycloalkyl-carbonyl group (e.g., cyclopropylcarbonyl, cyclohexylcarbonyl), and
  (f) a carbamoyl group optionally having 1 or 2 C$_{6-10}$ aryl groups (e.g., phenyl);
(3) a C$_{6-10}$ aryl group (e.g., phenyl, naphthyl) optionally having 1 to 3 substituents selected from
  (a) a halogen atom (e.g., a fluorine atom, a chlorine atom),
  (b) a C$_{1-6}$ alkyl group (e.g., methyl, ethyl) optionally having 1 to 3 halogen atoms (e.g., a fluorine atom),
  (c) a C$_{1-6}$ alkoxy group (e.g., methoxy, isopropoxy),
  (d) a hydroxy group, and
  (e) an amino group optionally having one C$_{1-6}$ alkylsulfonyl group (e.g., methylsulfonyl);
(4) a 5- or 6-membered monocyclic non-aromatic heterocyclic group (e.g., dihydropyridyl) optionally having 1 to 3 oxo groups; or
(5) a 5- or 6-membered monocyclic aromatic heterocyclic group (e.g., thienyl, pyridyl) optionally having 1 to 3 substituents selected from
  (a) a halogen atom (e.g., a fluorine atom),
  (b) a C$_{1-6}$ alkyl group (e.g., methyl), and
  (c) a C$_{1-6}$ alkoxy group (e.g., methoxy);
R$^{46}$ is a C$_{1-6}$ alkyl group (e.g., methyl, ethyl); and
R$^{47}$ is a hydrogen atom, or absent;
or a salt thereof.

Compound (AI-4)

A compound represented by the formula (AI-b),

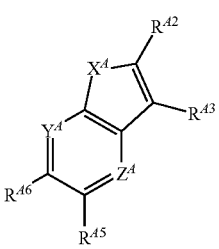

(AI-b)

wherein
X$^A$ is NR$^{A1}$ wherein R$^{A1}$ is a hydrogen atom or a C$_{1-6}$ alkyl group (e.g., methyl), a sulfur atom or an oxygen atom (preferably X$^A$ is NR$^{A1}$, and R$^{A1}$ is methyl),
Y$^A$ is CR$^{A7}$ wherein R$^{A7}$ is a hydrogen atom, a halogen atom or a C$_{1-6}$ alkyl group (preferably R$^{A7}$ is a hydrogen atom), or a nitrogen atom (preferably Y$^A$ is a nitrogen atom),
Z$^A$ is CR$^{A4}$ wherein R$^{A4}$ is a hydrogen atom, a halogen atom, an amino group optionally having substituent(s), or a mercapto group optionally having a substituent (preferably $R^{44}$ is a hydrogen atom), or a nitrogen atom (preferably $Z^A$ is $CR^{44}$, and $R^{44}$ is a hydrogen atom)
(preferably $X^A$ is $NR^{41}$ wherein $R^{41}$ is methyl, $Y^A$ is $CR^{47}$ wherein $R^{47}$ is a hydrogen atom, or a nitrogen atom, and $Z^A$ is $CR^{44}$ wherein $R^{44}$ is a hydrogen atom, or a nitrogen atom, more preferably $X^A$ is $NR^{41}$ wherein $R^{41}$ is methyl, $Y^A$ is a nitrogen atom, and $Z^A$ is $CR^{44}$ wherein $R^{44}$ is a hydrogen atom);

$R^{42}$ is a carbamoyl group optionally having 1 or 2 substituents selected from
(1) a $C_{1-6}$ alkyl group optionally having substituent(s),
(2) a $C_{3-8}$ cycloalkyl group optionally having substituent(s), and
(3) a heterocyclic group optionally having substituent(s);
$R^{43}$ is an optionally halogenated $C_{1-6}$ alkoxy group (preferably a $C_{1-6}$ alkoxy group (e.g., ethoxy, isopropoxy) optionally having 1 to 3 halogen atoms (e.g., a fluorine atom));
$R^{45}$ is
(1) a substituted $C_{1-6}$ alkyl group,
(2) an amino group optionally having substituent(s),
(3) a $C_{6-10}$ aryl group optionally having substituent(s), or
(4) a heterocyclic group optionally having substituent(s); and
$R^{46}$ is a $C_{1-6}$ alkyl group or a salt thereof.

Compound (AI-5)
A compound represented by the formula (AI-b)

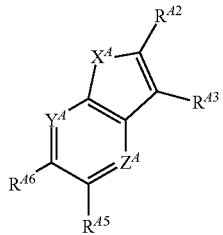

(AI-b)

wherein
$X^A$ is $NR^{41}$ wherein $R^{41}$ is methyl,
$Y^A$ is $CR^{47}$ wherein $R^{47}$ is a hydrogen atom, or a nitrogen atom (preferably a nitrogen atom),
$Z^A$ is $CR^{44}$ wherein $R^{44}$ is a hydrogen atom, or a nitrogen atom (preferably $CR^{44}$ wherein $R^{44}$ is a hydrogen atom, or a nitrogen atom),
(preferably $Y^A$ is $CR^{47}$ wherein $R^{47}$ is a hydrogen atom, or a nitrogen atom, and $Z^A$ is $CR^{44}$ wherein $R^{44}$ is a hydrogen atom, more preferably $Y^A$ is a nitrogen atom, and $Z^A$ is $CR^{44}$ wherein $R^{44}$ is a hydrogen atom);

$R^{42}$ is a carbamoyl group having one substituent selected from
(1) a 4- to 12-membered (preferably 4- to 7-membered) non-aromatic heterocyclic group (e.g., piperidyl, tetrahydropyranyl, tetrahydrothiopyranyl, 1-oxidotetrahydrothiopyranyl, 1,1-dioxidotetrahydrothiopyranyl, azepanyl) optionally having 1 to 3 substituents selected from
    (a) a $C_{1-6}$ alkyl group optionally having 1 to 3 hydroxy groups,
    (b) a $C_{1-6}$ alkyl-carbonyl group (e.g., acetyl) optionally having 1 to 3 hydroxy groups, and
    (c) an oxo group;
(2) a $C_{3-8}$ cycloalkyl group (e.g., cyclopropyl, cyclobutyl, cyclopentyl, cyclohexyl) optionally having 1 to 3 substituents selected from
    (a) a hydroxy group,
    (b) a carbamoyl group, and
    (c) a $C_{6-10}$ aryl group (e.g., phenyl); and
(3) a $C_{1-6}$ alkyl group (e.g., methyl, ethyl, propyl, isopropyl, butyl, isobutyl, sec-butyl, tert-butyl, 2,2-dimethylbutyl) having one substituent selected from
    (a) a $C_{1-8}$ alkylsulfonyl group (e.g., ethylsulfonyl) optionally having 1 to 3 $C_{1-6}$ alkoxy groups (e.g., methoxy),
    (b) an amino group optionally having 1 or 2 substituents selected from
        (i) a $C_{1-6}$ alkyl group (e.g., methyl, ethyl) optionally having 1 to 3 hydroxy groups
        (ii) a $C_{1-6}$ alkyl-carbonyl group (e.g., acetyl) optionally having 1 to 3 hydroxy groups,
        (iii) a $C_{1-6}$ alkylsulfonyl group (e.g., methylsulfonyl) optionally having 1 to 3 halogen atoms (e.g., a fluorine atom), and
        (iv) a 5- to 12-membered (preferably 5- or 6-membered) aromatic heterocyclyl-carbonyl group (e.g., thienylcarbonyl) optionally having 1 to 3 halogen atoms (e.g., a chlorine atom),
    (c) a hydroxy group,
    (d) a $C_{1-6}$ alkoxy group (e.g., methoxy, ethoxy) optionally having 1 to 3 hydroxy groups,
    (e) a $C_{1-6}$ alkoxy-carbonyl group (e.g., methoxycarbonyl),
    (f) a carbamoyl group,
    (g) a $C_{3-8}$ cycloalkyl group (e.g., cyclopropyl) optionally having 1 to 3 of 5- to 12-membered (preferably 5- or 6-membered) aromatic heterocyclic groups (e.g., thienyl),
    (h) a $C_{6-10}$ aryl group (e.g., phenyl) optionally having 1 to 3 substituents selected from
        (i) a halogen atom (e.g., a fluorine atom),
        (ii) a hydroxy group,
        (iii) a carbamoyl group optionally having 1 or 2 $C_{1-6}$ alkyl groups (e.g., ethyl) optionally having one hydroxy group,
        (iv) a $C_{1-3}$ alkylenedioxy group (e.g., methylenedioxy),
        (v) a sulfamoyl group, and
        (vi) a $C_{1-6}$ alkyl-carbonyl group (e.g., acetyl),
    (i) a 4- to 12-membered (preferably 4- to 7-membered) non-aromatic heterocyclic group (e.g., tetrahydrofuryl, pyrrolidinyl, oxazolidinyl, piperidyl, piperazinyl, morpholinyl) optionally having 1 to 3 substituents selected from
        (i) a $C_{6-10}$ aryl group (e.g., phenyl),
        (ii) a $C_{1-6}$ alkyl group (e.g., methyl),
        (iii) a $C_{7-13}$ aralkyl group (e.g., benzyl), and
        (iv) an oxo group, and
    (j) a 5- to 12-membered (preferably 5- or 6-membered) aromatic heterocyclic group (e.g., furyl, thienyl, isoxazolyl, pyridyl, pyrazinyl, indolyl, thiazolyl) optionally having 1 to 3 $C_{1-6}$ alkyl groups (e.g., methyl);

$R^{43}$ is a $C_{1-6}$ alkoxy group (e.g., ethoxy, isopropoxy) optionally having 1 to 3 halogen atoms (e.g., a fluorine atom);
$R^{45}$ is
(1) a $C_{1-6}$ alkyl group (e.g., methyl, ethyl, pentyl) optionally having 1 to 3 substituents selected from
    (a) a $C_{6-10}$ aryl-carbonyl group (e.g., benzoyl),
    (b) a $C_{6-10}$ aryl group (e.g., phenyl) optionally having 1 to 3 substituents selected from
        (i) a halogen atom (e.g., a fluorine atom, a chlorine atom), and
        (ii) a $C_{1-6}$ alkoxy group (e.g., methoxy), and
    (c) a $C_{1-6}$ alkoxy group (e.g., methoxy) optionally having 1 to 3 $C_{6-10}$ aryl groups (e.g., phenyl);

(2) an amino group optionally having one substituent selected from
- (a) a $C_{1-6}$ alkyl group (e.g., methyl) optionally having 1 to 3 $C_{6-10}$ aryl groups (e.g., phenyl),
- (b) a $C_{6-10}$ aryl group (e.g., phenyl) optionally having 1 to 3 substituents selected from
  - (i) a halogen atom (e.g., a chlorine atom), and
  - (ii) a $C_{1-6}$ alkoxy group (e.g., methoxy),
- (c) a $C_{6-10}$ aryl-carbonyl group (e.g., benzoyl) optionally having 1 to 3 substituents selected from
  - (i) a halogen atom (e.g., a fluorine atom, a chlorine atom), and
  - (ii) a $C_{1-6}$ alkoxy group (e.g., methoxy),
- (d) a 5- or 6-membered monocyclic aromatic heterocyclyl-carbonyl group (e.g., pyrazolylcarbonyl, thienylcarbonyl, furylcarbonyl, thiazolylcarbonyl, oxazolylcarbonyl, pyridylcarbonyl) optionally having 1 to 3 substituents selected from
  - (i) a halogen atom (e.g., a chlorine atom),
  - (ii) a $C_{1-6}$ alkyl group (e.g., methyl), and
  - (iii) a $C_{1-6}$ alkoxy group (e.g., methoxy),
- (e) a $C_{3-8}$ cycloalkyl-carbonyl group (e.g., cyclopropylcarbonyl, cyclohexylcarbonyl), and
- (f) a carbamoyl group optionally having 1 or 2 $C_{6-10}$ aryl groups (e.g., phenyl);

(3) a $C_{6-10}$ aryl group (e.g., phenyl, naphthyl) optionally having 1 to 3 substituents selected from
- (a) a halogen atom (e.g., a fluorine atom, a chlorine atom),
- (b) a $C_{1-6}$ alkyl group (e.g., methyl, ethyl) optionally having 1 to 3 halogen atoms (e.g., a fluorine atom),
- (c) a $C_{1-6}$ alkoxy group (e.g., methoxy, isopropoxy),
- (d) a hydroxy group, and
- (e) an amino group optionally having one $C_{1-6}$ alkylsulfonyl group (e.g., methylsulfonyl);

(4) a 5- or 6-membered monocyclic non-aromatic heterocyclic group (e.g., dihydropyridyl) optionally having 1 to 3 oxo groups; or (5) a 5- or 6-membered monocyclic aromatic heterocyclic group (e.g., thienyl, pyridyl) optionally having 1 to 3 substituents selected from
- (a) a halogen atom (e.g., a fluorine atom),
- (b) a $C_{1-6}$ alkyl group (e.g., methyl), and
- (c) a $C_{1-6}$ alkoxy group (e.g., methoxy); and $R^{46}$ is a $C_{1-6}$ alkyl group (e.g., methyl, ethyl) or a salt thereof.

Compound (AI-6)
6-ethyl-N-[1-(hydroxyacetyl)piperidin-4-yl]-1-methyl-3-(1-methylethoxy)-5-[(phenylcarbonyl)amino]-1H-pyrrolo[2,3-b]pyridine-2-carboxamide;
3-ethyl-N-[1-(hydroxyacetyl)piperidin-4-yl]-5-methyl-2-phenyl-7-(2,2,2-trifluoroethoxy)-5H-pyrrolo[2,3-b]pyrazine-6-carboxamide;
6-ethyl-5-{[(4-fluorophenyl)carbonyl]amino}-N-[1-(hydroxyacetyl)piperidin-4-yl]-1-methyl-3-(1-methylethoxy)-1H-indole-2-carboxamide; or
6-ethyl-5-(4-fluorophenyl)-N-[1-(hydroxyacetyl)piperidin-4-yl]-1-methyl-3-(1-methylethoxy)-1H-pyrrolo[3,2-b]pyridine-2-carboxamide;
or a salt thereof.

Examples of the salt in compound (AI) include metal salts, ammonium salts, salts with organic base, salts with inorganic acid, salts with organic acid, salts with basic or acidic amino acid and the like. Preferable examples of the metal salt include alkali metal salts such as sodium salt, potassium salt and the like; alkaline earth metal salts such as calcium salt, magnesium salt, barium salt and the like; an aluminum salt and the like. Preferable examples of the salt with organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with inorganic acid include salts with hydrochloric acid, hydrobromic acid, nitric acid, sulfuric acid, phosphoric acid and the like. Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salt with basic amino acid include salts with arginine, lysine, ornithine and the like, and preferable examples of the salt with acidic amino acid include salts with aspartic acid, glutamic acid and the like.

Of these, a pharmaceutically acceptable salt is preferable. For example, when a compound has an acidic functional group, examples thereof include inorganic salts such as alkali metal salts (e.g., sodium salt, potassium salt etc.), alkaline earth metal salts (e.g., calcium salt, magnesium salt etc.) and the like, ammonium salt etc., and when a compound has a basic functional group, examples thereof include salts with inorganic acids such as hydrochloric acid, hydrobromic acid, nitric acid, sulfuric acid, phosphoric acid and the like, or salts with organic acids such as acetic acid, phthalic acid, fumaric acid, oxalic acid, tartaric acid, maleic acid, citric acid, succinic acid, methanesulfonic acid, benzenesulfonic acid, p-toluenesulfonic acid and the like.

The production method of the compound of the present invention is described in the following.

In each of the following production methods, when alkylation reaction, amidation reaction (condensation reaction), esterification reaction, reduction reaction, reductive amination reaction, amination reaction, halogenation reaction, oxidation reaction and the like are performed, these reactions are performed according to methods known per se. Examples of such methods include the methods described in Organic Functional Group Preparations, 2nd edition, Academic Press, Inc. (1989), Comprehensive Organic Transformations, VCH Publishers Inc. (1989) and the like, and the like.

In the following reaction, the starting material compound or the intermediate may be in the form of a salt. Examples of the salt include those similar to the aforementioned salt of compound (AI).

The obtained compound in each step may be used in the form of the reaction mixture or as a crude product for the next step, or may be isolated from the reaction mixture according to a conventional method (e.g., separation means such as recrystallization, distillation, chromatography etc.).

In each of the above-mentioned reactions, when the starting compound has an amino group, a carboxyl group or a hydroxy group as a substituent, a protecting group generally used in peptide chemistry and the like may be introduced into these groups. By removing the protecting group as necessary after the reaction, the objective compound can be obtained. The protection and deprotection are performed according to a method known per se, for example, the method described in Protective Groups in Organic Synthesis, 3rd edition, John Wiley and Sons, Inc. (1999).

Examples of the amino-protecting group include a formyl group, a $C_{1-6}$ alkyl-carbonyl group, a $C_{1-6}$ alkoxy-carbonyl group, benzoyl group, a $C_{7-10}$ aralkyl-carbonyl group (e.g., benzylcarbonyl), a $C_{7-14}$ aralkyloxy-carbonyl group (e.g., benzyloxycarbonyl, 9-fluorenylmethoxycarbonyl), a trityl group, a phthaloyl group, an N,N-dimethylaminomethylene group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 3 substituents selected from a halogen atom, a $C_{1-6}$ alkoxy group and a nitro group.

Examples of the carboxy-protecting group include a $C_{1-6}$ alkyl group, a $C_{7-11}$ aralkyl group (e.g., benzyl), a phenyl group, a trityl group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like.

Examples of the hydroxy-protecting group include a $C_{1-6}$ alkyl group, a phenyl group, a trityl group, a $C_{7-10}$ aralkyl group (e.g., benzyl), a formyl group, a $C_{1-6}$ alkyl-carbonyl group, a benzoyl group, a $C_{7-10}$ aralkyl-carbonyl group (e.g., benzylcarbonyl), a 2-tetrahydropyranyl group, a 2-tetrahydrofuranyl group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 3 substituents selected from a halogen atom, a $C_{1-6}$ alkyl group, a $C_{1-6}$ alkoxy group and a nitro group.

The solvents indicated in generic terms, which are used in the following reactions are explained in the following.

Examples of the "alcohols" include methanol, ethanol, 1-propanol, 2-propanol, tert-butyl alcohol and the like.

Examples of the "ethers" include diethyl ether, diisopropyl ether, diphenyl ether, tetrahydrofuran, 1,4-dioxane, 1,2-dimethoxyethane and the like.

Examples of the "esters" include ethyl acetate, methyl acetate, tert-butyl acetate and the like.

Examples of the "hydrocarbons" include benzene, toluene, xylene, cyclohexane, hexane, pentane and the like.

Examples of the "amides" include N,N-dimethylformamide, N,N-dimethylacetamide, hexamethylphosphoric triamide and the like.

Examples of the "halogenated hydrocarbons" include dichloromethane, chloroform, carbon tetrachloride, 1,2-dichloroethane, tetrachloroethylene, chlorobenzene and the like.

Examples of the "nitriles" include acetonitrile, propionitrile and the like.

Examples of the "ketones" include acetone, 2-butanone and the like.

Examples of the "organic acids" include formic acid, acetic acid, propionic acid, trifluoroacetic acid, methanesulfonic acid and the like.

Examples of the "aromatic amines" include pyridine, 2,6-lutidine, quinoline and the like.

Examples of the "sulfoxides" include dimethyl sulfoxide and the like.

Compound (AI) can be produced, for example, according to the following [Method AA] or a method analogous thereto.
[AA Method]

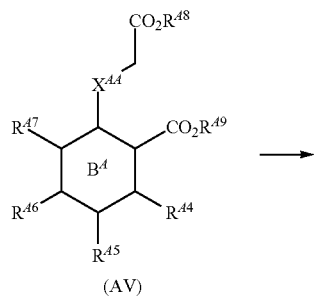

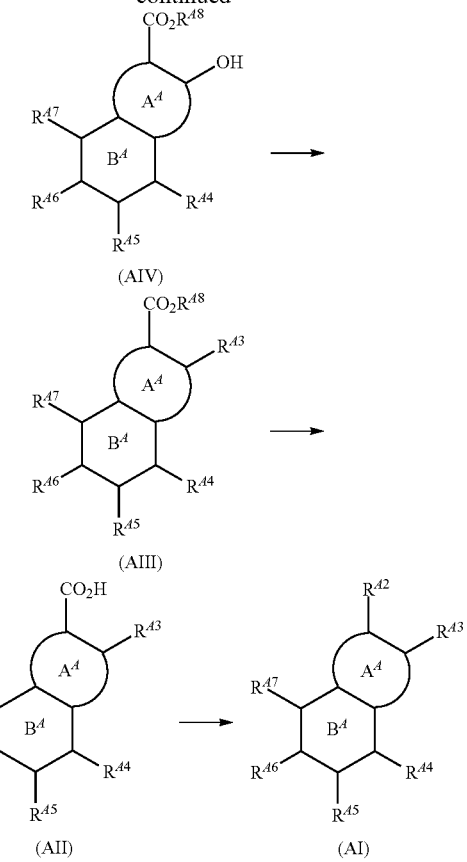

wherein $R^{A8}$ is a $C_{1-6}$ alkyl group, $R^{A9}$ is a $C_{1-6}$ alkyl group or a $C_{7-13}$ aralkyl group, $X^{AA}$ is a spacer optionally having substituent(s), and the other symbols are as defined above.

The "spacer" of the "spacer optionally having substituent(s)" for $X^{AA}$ constitutes a part of ring $A^A$, and examples thereof include (1) a straight chain $C_{1-3}$ alkylene (e.g., —$CH_2$—, —$(CH_2)_2$—, —$(CH_2)_3$—, —NH—, —S—, —O—) optionally containing hetero atom(s) (e.g., a nitrogen atom, a sulfur atom (optionally oxidized), an oxygen atom);

(2) a straight chain $C_{2-3}$ alkenylene (e.g., —CH=CH—, —CH=CH—$CH_2$—, —$CH_2$—CH=CH—, —N=CH—, —CH=N—) optionally containing hetero atom(s) (e.g., a nitrogen atom, a sulfur atom (optionally oxidized), an oxygen atom) and the like.

Examples of the substituent that the "spacer" of the "spacer optionally having substituent(s)" for $X^{AA}$ optionally has include those similar to the substituent that ring $A^A$ optionally further has.

$R^{A8}$ and $R^{A9}$ are each preferably ethyl.

The reaction from compound (AV) to compound (AIV) can be carried out using a base in a solvent that does not adversely influence the reaction.

Examples of the base include sodium methoxide, sodium ethoxide, sodium hydroxide and the like.

The amount of the base to be used is generally 2 to 5 mol, preferably 2 to 3 mol, per 1 mol of compound (AV).

Examples of the solvent that does not adversely influence the reaction include ethers, hydrocarbons, alcohols, amides, esters and the like, and ethers and amides are particularly preferable. These solvents may be used in a mixture of two or more kinds thereof in an appropriate ratio.

The reaction temperature is generally 0 to 100° C., preferably 20 to 90° C.

The reaction time is generally 0.5 to 100 hr, preferably 1 to 48 hr.

The reaction from compound (AIV) to compound (AIII) can be carried out by reacting compound (AIV) with a halide, sulfate, sulfonate or the like, which corresponds to the "substituent" of the "substituted hydroxy group" for $R^{43}$, in the presence of a base, in a solvent that does not adversely influence the reaction. The hydroxy group of compound (AIV) is converted to $R^{43}$ by the reaction.

The above-mentioned halide, sulfate, sulfonate or the like may be commercially available product, or can be produced from the corresponding starting material compound according to a method known per se.

The amount of the above-mentioned halide, sulfate, sulfonate or the like to be used is generally 1 to 3 mol, preferably 1 to 2 mol, per 1 mol of compound (AIV).

Examples of the base include sodium methoxide, sodium ethoxide, cesium carbonate, sodium carbonate, potassium carbonate, sodium hydrogen carbonate, sodium hydroxide, triethylamine, diisopropylethylamine, pyridine, 4-dimethylaminopyridine, 1,8-diazabicyclo[5.4.0]undec-7-ene (DBU) and the like.

The amount of the base to be used is generally 2 to 5 mol, preferably 2 to 3 mol, per 1 mol of compound (AIV).

Examples of the solvent that does not adversely influence the reaction include ethers, hydrocarbons, alcohols, ketones, nitriles, amides, esters and the like, and ethers and amides are particularly preferable. These solvents may be used in a mixture of two or more kinds thereof in an appropriate ratio.

The reaction temperature is generally 0 to 100° C., preferably 20 to 90° C.

The reaction time is generally 0.5 to 100 hr, preferably 1 to 48 hr.

The reaction from compound (AIII) to compound (AII) can be carried out by subjecting compound (AIII) to hydrolysis in the presence of an acid or a base, in a solvent that does not adversely influence the reaction.

When $R^{48}$ is benzyl, the reaction can also be carried out by subjecting compound (AIII) to a catalytic hydrogenation reaction in a solvent that does not adversely influence the reaction.

Examples of the acid include hydrochloric acid, sulfuric acid and the like.

Examples of the base include sodium hydroxide, potassium hydroxide, lithium hydroxide and the like.

The amount of the acid or base to be used is generally 1 to 20 mol, preferably 1 to 10 mol, per 1 mol of compound (AIII).

Examples of the catalyst used for the catalytic hydrogenation reaction include Raney-nickel; platinum oxide; palladium, ruthenium, rhodium or iridium, which is supported on activated carbon, barium sulfate, calcium carbonate or the like; and the like.

The amount of the catalyst to be used is generally 0.01 to 1 mol, preferably 0.05 to 0.5 mol, per 1 mol of compound (AIII).

Examples of the hydrogen source include hydrogen, cyclohexene, hydrazine, ammonium formate and the like.

Examples of the solvent that does not adversely influence the reaction include ethers, alcohols, hydrocarbons, ketones, nitriles, amides, esters, water and the like, and alcohols, ethers and water are particularly preferable. These solvents may be used in a mixture of two or more kinds thereof in an appropriate ratio.

The reaction temperature is generally 0 to 100° C., preferably 20 to 60° C.

The reaction time is generally 0.5 to 100 hr, preferably 1 to 48 hr.

The reaction from compound (AII) to compound (AI) can be carried out by subjecting compound (AII) and the amine compound corresponding to $R^{42}$ with a condensing agent in a solvent that does not adversely influence the reaction. Where necessary, a base such as a tertiary amine and the like may be added.

Examples of the condensing agent include carbodiimides (e.g., dicyclohexylcarbodiimide (DCCD), water-solublecarbodiimide (WSCD)), phosphates (e.g., diethyl cyanophosphonate, diethyl chlorophosphonate, diphenylphosphoryl azide), BOP reagents (e.g., 1H-benzotriazol-1-yloxytripyrrolidinophosphonium hexafluorophosphate (PyBOP)), O-(7-azabenzotriazol-1-yl) N,N,N',N'-tetramethyluronium hexafluorophosphate (HATU), 2-ethoxy-1-ethoxycarbonyl-1,2-dihydroquinoline (EEDQ), carbonyldiimidazole and the like, and WSCD and HATU are particularly preferable.

The amount of the amine compound corresponding to $R^{42}$ to be used is generally 1 to 10 mol, preferably 1 to 2 mol, per 1 mol of compound (AII).

The amount of the condensing agent to be used is generally 1 to 10 mol, preferably 1 to 2 mol, per 1 mol of compound (AII).

Examples of the solvent that does not adversely influence the reaction include ethers, hydrocarbons, ketones, nitriles, amides, esters and the like, and ethers and amides are particularly preferable. These solvents may be used in a mixture of two or more kinds thereof in an appropriate ratio.

The reaction temperature is generally 0 to 100° C., preferably 20 to 60° C.

The reaction time is generally 0.5 to 100 hr, preferably 1 to 48 hr.

The amine compound corresponding to $R^{42}$ may be commercially available product, or can be produced from the corresponding starting material compound according to a method known per se.

Alternatively, compound (AIII) can also be produced, for example, according to the following [AB Method] or a method analogous thereto.

[AB Method]

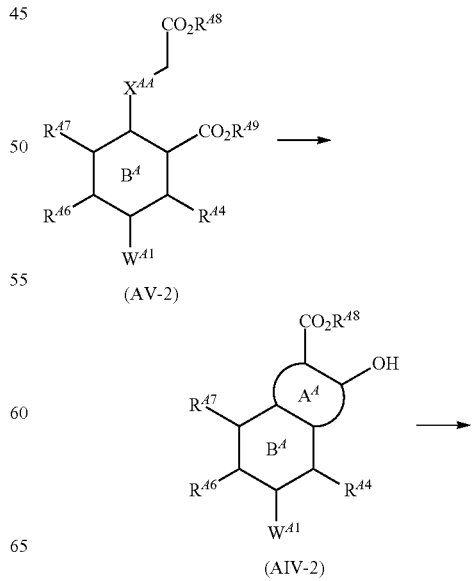

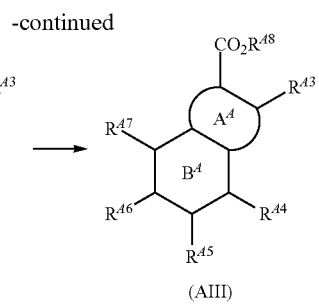

(AIII-2) → (AIII)

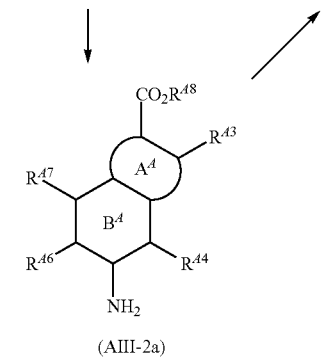

(AIII-2a)

wherein $W^{41}$ is a halogen atom or a nitro group, and the other symbols are as defined above.

The reaction from compound (AV-2) to compound (AIV-2) can be carried out according to the conversion from compound (AV) to compound (AIV) shown in [AA Method].

The reaction from compound (AIV-2) to compound (AIII-2) can be carried out according to the reaction from compound (AIV) to compound (AIII) shown in [AA Method].

The reaction from compound (AIII-2) to compound (AIII) can be carried out according to a method known per se.

Compound (AIII) wherein $R^{A5}$ is a "substituted $C_{1-6}$ alkyl group" can be obtained by subjecting compound (AIII-2) wherein $W^{41}$ is a halogen atom to a substitution reaction or coupling reaction known per se.

The amount of the carbonyl compound having hydrogen at the α-position, alkyl halide or organic metal compound to be used is generally 1 to 5 mol, preferably 1 to 2 mol, per 1 mol of compound (AIII-2).

Examples of the base include sodium hydride, sodium t-butoxide and the like.

The amount of the base to be used is generally 1 to 5 mol, preferably 1 to 3 mol, per 1 mol of compound (AIII-2).

Examples of the metal complex include a complex of palladium acetate and 2-(dicyclohexylphosphino)-2'-methylbiphenyl.

The amount of the metal complex to be used is generally 0.05 to 1 mol, preferably 0.1 to 0.5 mol, per 1 mol of compound (AIII-2).

Examples of the solvent that does not adversely influence the reaction include ethers, alcohols, hydrocarbons, ketones, nitriles, amides, esters and the like, and ethers and hydrocarbons are particularly preferable. These solvents may be used in a mixture of two or more kinds thereof in an appropriate ratio.

The reaction temperature is generally 0 to 100° C., preferably 20 to 80° C.

The reaction time is generally 0.5 to 100 hr, preferably 1 to 48 hr.

The carbonyl compound having hydrogen at the α-position, alkyl halide or organic metal compound which corresponds to the "substituted $C_{1-6}$ alkyl group" for $R^{A5}$ may be commercially available product, or can be produced from the corresponding starting material compound according to a method known per se.

Compound (AIII) wherein $R^{A5}$ is an "amino group optionally having substituent(s)" can be obtained by 1) by directly introducing a group corresponding to the "amino group optionally having substituent(s)" for $R^{A5}$ into compound (AIII-2) wherein $W^{41}$ is a halogen atom, according to a coupling reaction known per se or the like, or 2) by converting $W^{41}$ of compound (AIII-2) wherein $W^{41}$ is a halogen atom to an amino group, and then subjecting the resulting compound to acylation or reduction alkylation.

The above-mentioned 1) can be carried out, for example, by reacting compound (AIII-2) with an amine corresponding to "amino group optionally having substituent(s)" for $R^{A5}$ in the presence of a base and a metal complex, in a solvent that does not adversely influence the reaction.

The amine corresponding to "amino group optionally having substituent(s)" for $R^{A5}$ may be commercially available product, or can be produced from the corresponding starting material compound according to a method known per se.

The amount of the amine to be used is generally 1 to 5 mol, preferably 1 to 2 mol, per 1 mol of compound (AIII-2).

Examples of the base include sodium hydride, sodium t-butoxide and the like.

The amount of the base to be used is generally 1 to 5 mol, preferably 1 to 3 mol, per 1 mol of compound (AIII-2).

Examples of the metal complex include a complex of tris(dibenzylideneacetone)dipalladium(0) and (+/−)-2,2'-bis(diphenylphosphino)-1,1'-binaphthyl.

The amount of the complex to be used is generally 0.05 to 1 mol, preferably 0.1 to 0.5 mol, per 1 mol of compound (AIII-2).

Examples of the solvent that does not adversely influence the reaction include ethers, alcohols, hydrocarbons, ketones, nitriles, amides, esters and the like, and ethers and hydrocarbons are particularly preferable. These solvents may be used in a mixture of two or more kinds thereof in an appropriate ratio.

The reaction temperature is generally 0 to 100° C., preferably 20 to 80° C.

The reaction time is generally 0.5 to 100 hr, preferably 1 to 48 hr.

The above-mentioned 2) can be carried out, for example, by reacting compound (AIII-2) with benzophenonimine, subjecting the resulting compound to hydrolysis to give compound (AIII-2a) wherein $W^{41}$ is converted to an amino group, and then subjecting compound (AIII-2a) to acylation or reduction alkylation.

The reaction from compound (AIII-2) with benzophenonimine can be carried out in the presence of a base and a metal complex, in a solvent that does not adversely influence the reaction.

The amount of the benzophenonimine to be used is generally 1 to 5 mol, preferably 1 to 2 mol, per 1 mol of compound (AIII-2).

Examples of the base include cesium carbonate, potassium carbonate, sodium t-butoxide and the like.

The amount of the base to be used is generally 1 to 5 mol, preferably 1 to 3 mol, per 1 mol of compound (AIII-2).

Examples of the metal complex include a complex of tris(dibenzylideneacetone)dipalladium(0) and 4,5'-bis(diphenylphosphino)-9,9'-dimethylxanthene.

The amount of the complex to be used is generally 0.05 to 1 mol, preferably 0.1 to 0.5 mol, per 1 mol of compound (AIII-2).

Examples of the solvent that does not adversely influence the reaction include ethers, alcohols, hydrocarbons, ketones, nitriles, amides, esters and the like, and ethers and hydrocarbons are particularly preferable. These solvents may be used in a mixture of two or more kinds thereof in an appropriate ratio.

The reaction temperature is generally 0 to 100° C., preferably 20 to 80° C.

The reaction time is generally 0.5 to 100 hr, preferably 1 to 48 hr.

The hydrolysis can be carried out under an acidic condition, in a solvent that does not adversely influence the reaction.

Examples of the acid include hydrochloric acid, sulfuric acid, methanesulfonic acid and the like.

Examples of the solvent that does not adversely influence the reaction include alcohols, nitriles, amides and the like, and alcohols and amides are particularly preferable. These solvents may be used in a mixture of two or more kinds thereof in an appropriate ratio.

The reaction temperature is generally 0 to 60° C., preferably 20 to 40° C.

The reaction time is generally 0.5 to 48 hr, preferably 1 to 24 hr.

The acylation reaction can be carried out, for example, using an acid chloride corresponding to the "substituent" of the "amino group optionally having substituent(s)" for $R^{45}$ in the presence of a base, in a solvent that does not adversely influence the reaction.

The amount of the acid chloride to be used is generally 1 to 3 mol, preferably 1 to 2 mol, per 1 mol of compound (AIII-2a).

Examples of the base include sodium methoxide, sodium ethoxide, cesium carbonate, sodium carbonate, potassium carbonate, sodium hydrogen carbonate, sodium hydroxide, triethylamine, diisopropylethylamine, pyridine, 4-dimethylaminopyridine, 1,8-diazabicyclo[5.4.0]undec-7-ene (DBU) and the like, and pyridine, triethylamine and diisopropylethylamine are particularly preferable.

The amount of the base to be used is generally 1 to 5 mol, preferably 1 to 3 mol, per 1 mol of compound (AIII-2a).

Examples of the solvent that does not adversely influence the reaction include ethers, hydrocarbons, ketones, nitriles, amides, esters and the like, and ethers and amides are particularly preferable. These solvents may be used in a mixture of two or more kinds thereof in an appropriate ratio.

The reaction temperature is generally 0 to 60° C., preferably 0 to 40° C.

The reaction time is generally 0.5 to 48 hr, preferably 1 to 24 hr.

The acid chloride corresponding to the "substituent" of the "amino group optionally having substituent(s)" for $R^{45}$ may be commercially available product, or can be produced from the corresponding starting material compound according to a known method per se.

The reduction alkylation reaction can be carried out, for example, using a carbonyl compound corresponding to the "substituent" of the "amino group optionally having substituent(s)" for $R^{45}$ and a reducing agent, in the presence of an acid as necessary, in a solvent that does not adversely influence the reaction.

The amount of the carbonyl compound to be used is generally 1 to 3 mol, preferably 1 to 2 mol, per 1 mol of compound (AIII-2a).

Examples of the reducing agent include sodium borohydride, sodium triacetoxyborohydride, sodium cyanoborohydride and the like.

The amount of the reducing agent to be used is generally 1 to 5 mol, preferably 1 to 3 mol, per 1 mol of compound (AIII-2a).

Examples of the acid include hydrochloric acid, p-toluenesulfonic acid, acetic acid and the like.

The amount of the acid to be used is generally 1 to 5 mol, preferably 1 to 3 mol, per 1 mol of compound (AIII-2a).

Examples of the solvent that does not adversely influence the reaction include alcohols, ethers, hydrocarbons, nitriles, amides and the like, and alcohols, ethers and amides are particularly preferable. These solvents may be used in a mixture of two or more kinds thereof in an appropriate ratio.

The reaction temperature is generally 0 to 60° C., preferably 0 to 40° C.

The reaction time is generally 0.5 to 48 hr, preferably 1 to 24 hr.

The carbonyl compound corresponding to the "substituent" of the "amino group optionally having substituent(s)" for $R^{45}$ may be commercially available product, or can be produced from the corresponding starting material compound according to a method known per se.

Besides the above-mentioned methods, a method via compound (AIII-2) wherein $W^{41}$ is converted to azido, or a method via compound (AIII-2) wherein $W^{41}$ is converted to benzylamino are also employed.

Compound (AIII) wherein $R^{45}$ is a "cyclic group optionally having substituent(s)" can be synthesized, for example, according to a coupling reaction known per se.

The coupling reaction can be carried out, for example, by reacting compound (AIII-2) with a boric acid derivative, organic tin compound or organic zinc compound, which corresponds to the "cyclic group optionally having substituent(s)" for RA5, in the presence of a base and a metal complex, in a solvent that does not adversely influence the reaction.

The amount of the boric acid derivative, organic tin compound or organic zinc compound, which corresponds to the "cyclic group optionally having substituent(s)" for $R^{45}$ to be used is generally 1 to 5 mol, preferably 1 to 2 mol, per 1 mol of compound (AIII-2).

Examples of the base include cesium carbonate, potassium carbonate, sodium t-butoxide, diisopropylethylamine, triethylamine and the like. The amount thereof to be used is generally 3 to 20 mol, preferably 5 to 10 mol, per 1 mol of compound (AIII-2).

Examples of the metal complex include tetrakis(triphenylphosphine)palladium(0) and the like.

The amount of the metal complex to be used is generally 0.05 to 1 mol, preferably 0.1 to 0.5 mol, per 1 mol of compound (AIII-2).

Examples of the solvent that does not adversely influence the reaction include ethers, alcohols, hydrocarbons, ketones, nitriles, amides, esters and the like, and ethers and hydrocarbons are particularly preferable. These solvents may be used in a mixture of two or more kinds thereof in an appropriate ratio.

The reaction temperature is generally 0 to 160° C., preferably 20 to 140° C.

The reaction time is generally 0.5 to 100 hr, preferably 1 to 48 hr.

The boric acid derivative corresponding to the "cyclic group optionally having substituent(s)" for $R^{45}$ may be commercially available product, or can be produced from the corresponding starting material compound according to a method known per se.

The organic tin compound corresponding to the "cyclic group optionally having substituent(s)" for $R^{45}$ may be commercially available product, or can be produced from the corresponding starting material compound according to a method known per se.

The organic zinc compound corresponding to the "cyclic group optionally having substituent(s)" for $R^{45}$ may be commercially available product, or can be produced from the corresponding starting material compound according to a method known per se.

Compound (AIII) wherein $R^{45}$ is an "amino group optionally having substituent(s)" can also be obtained by reducing compound (AIII-2) wherein $W^{41}$ is a nitro group to give compound (AIII-2a) wherein $W^{41}$ is an amino group, and then subjecting compound (AIII-2a) to the above-mentioned acylation or reduction alkylation reaction.

The reduction of the nitro group can be carried out, for example, by a catalytic hydrogenation reaction in a solvent that does not adversely influence the reaction.

Examples of the catalyst used for the catalytic hydrogenation reaction include Raney-nickel; platinum oxide; palladium, ruthenium, rhodium or iridium, which is supported on activated carbon, barium sulfate, calcium carbonate or the like; and the like.

The amount of the catalyst to be used is generally 0.01 to 1 mol, preferably 0.05 to 0.5 mol, per 1 mol of compound (AIII-2).

Examples of the hydrogen source include hydrogen, cyclohexene, hydrazine, ammonium formate and the like.

Examples of the solvent that does not adversely influence the reaction include ethers, alcohols, hydrocarbons, ketones, nitriles, amides, esters, water and the like, and alcohols, ethers and water are particularly preferable. These solvents may be used in a mixture of two or more kinds thereof in an appropriate ratio.

The reaction temperature is generally 0 to 100° C., preferably 20 to 60° C.

The reaction time is generally 0.5 to 100 hr, preferably 1 to 48 hr.

The reduction of the nitro group can also be carried out by, besides the above-mentioned method, reduction using iron, reduction using zinc, or reduction using a metal hydride.

After the conversion of the nitro group to an unsubstituted amino group, the acylation or reduction alkylation reaction can be carried out according to the method mentioned above 2).

Compound (AIII) wherein $R^{45}$ is a "hydroxy group substituted by a cyclic group optionally having substituent(s)" can be obtained by reacting compound (AIII-2) wherein $W^{41}$ is a halogen atom with an alcohol or phenol corresponding to $R^{45}$ in the presence of a copper compound and a base, in a solvent that does not adversely influence the reaction.

The amount of the alcohol or phenol corresponding to $R^{45}$ to be used is generally 1 to 10 mol, preferably 1 to 5 mol, per 1 mol of compound (AIII-2).

Examples of the copper compound include copper iodide, copper bromide, copper acetate, copper oxide and the like.

The amount of the copper compound to be used is generally 1 to 3 mol, preferably 1 to 2 mol, per 1 mol of compound (AIII-2).

Examples of the base include sodium hydride, potassium carbonate, sodium carbonate, sodium hydroxide, potassium hydroxide, potassium tert-butoxide, pyridine and the like.

The amount of the base to be used is generally 1 to 5 mol, preferably 1 to 3 mol, per 1 mol of compound (AIII-2).

Examples of the solvent that does not adversely influence the reaction include ethers, alcohols, hydrocarbons, ketones, nitriles, amides, esters and the like, and nitriles, hydrocarbons and amides are particularly preferable. These solvents may be used in a mixture of two or more kinds thereof in an appropriate ratio.

The reaction temperature is generally 0 to 200° C., preferably 50 to 150° C.

The reaction time is generally 0.5 to 100 hr, preferably 1 to 48 hr.

The alcohol or phenol corresponding to $R^{45}$ may be commercially available product, or can be produced from the corresponding starting material compound according to a method known per se.

Alternatively, compound (AIII-2) can also be produced, for example, according to the following [AC Method] or a method analogous thereto.

[AC Method]

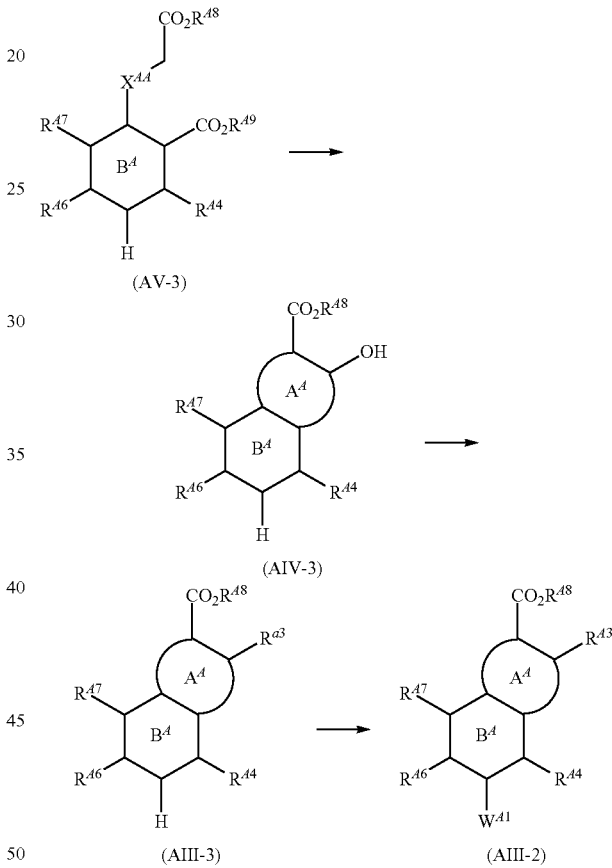

wherein each symbol is as defined above.

The reaction from compound (AV-3) to compound (AIV-3) can be carried out according to the reaction from compound (AV-2) to compound (AIV-2) shown in [AB Method].

The reaction from compound (AIV-3) to compound (AIII-3) can be carried out according to the reaction from compound (AIV-2) to compound (AIII-2) shown in [AB Method].

When $W^{41}$ is a halogen atom, the reaction from compound (AIII-3) to compound (AIII-2) can be carried out by reacting compound (AIII-3) with a halogenating reagent in a solvent that does not adversely influence the reaction or without solvent, in the presence of a base as necessary.

Examples of the halogenating reagent include N-bromosuccinimide, N-chlorosuccinimide, bromine, iodine and the like.

The amount of the halogenating reagent to be used is generally 1 to 5 mol, preferably 1 to 2 mol, per 1 mol of compound (AIII-3).

Examples of the solvent that does not adversely influence the reaction include ethers, hydrocarbons, ketones, nitriles, esters and the like, and hydrocarbons and nitriles are particularly preferable. These solvents may be used in a mixture of two or more kinds thereof in an appropriate ratio.

The reaction temperature is generally 0 to 80° C., preferably 20 to 60° C.

The reaction time is generally 0.5 to 100 hr, preferably 1 to 48 hr.

When $W^{41}$ is a nitro group, the reaction from compound (AIII-3) to compound (AIII-2) can be obtained by reacting compound (AIII-3) with fuming nitric acid-concentrated sulfuric acid or a combination of a nitrate and an acid, in a solvent that does not adversely influence the reaction or without solvent.

Examples of the nitrate include potassium nitrate, sodium nitrate and the like.

The amount of the fuming nitric acid-concentrated sulfuric acid to be used is 1 to 20 mol of fuming nitric acid –1 to 20 mol of concentrated sulfuric acid, preferably 1 to 10 mol of fuming nitric acid-1 to 10 mol of concentrated sulfuric acid, per 1 mol of compound (AIII-3).

The amount of the nitrate to be used is generally 1 to 20 mol, preferably 1 to 10 mol, per 1 mol of compound (AIII-3).

Examples of the acid include concentrated sulfuric acid, acetic acid, acetic anhydride, methanesulfonic acid and the like. These can be also used as a solvent.

Examples of the solvent that does not adversely influence the reaction include hydrocarbons, ketones, nitriles, esters and the like, and hydrocarbons and nitriles are particularly preferable. These solvents may be used in a mixture of two or more kinds thereof in an appropriate ratio.

The reaction temperature is generally –10 to 130° C., preferably 20 to 130° C.

The reaction time is generally 0.5 to 100 hr, preferably 1 to 48 hr.

Compounds (AV), (AV-2) and (AV-3) can also be produced, for example, according to the following [AD Method] or a method analogous thereto.

[AD Method]

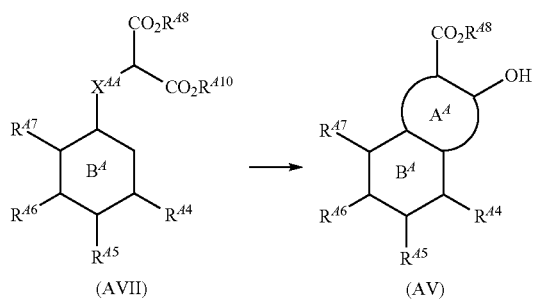

wherein $R^{410}$ is a $C_{1-6}$ alkyl group, and the other symbols are as defined above.

$R^{410}$ is preferably ethyl.

The reaction from compound (AVII) to compound (AV) can be carried out by heating compound (AVII) in a solvent that does not adversely influence the reaction, in the presence of an acid as necessary.

Examples of the acid include sulfuric acid, methanesulfonic acid, p-toluenesulfonic acid, aluminum chloride, zinc chloride, iron chloride and the like.

The amount of the acid to be used is generally 2 to 10 mol, preferably 2 to 5 mol, per 1 mol of compound (AVII).

Examples of the solvent that does not adversely influence the reaction include ethers, hydrocarbons, alcohols, amides and the like, and ethers, hydrocarbons and amides are particularly preferable. These solvents may be used in a mixture of two or more kinds thereof in an appropriate ratio.

The reaction temperature is generally 0 to 300° C., preferably 80 to 250° C.

The reaction time is generally 0.5 to 100 hr, preferably 1 to 48 hr.

Compound (AVII) can be synthesized, for example, according to the method described in Journal of Organic Chemistry, vol. 54, pages 688-693, 1989; Journal of the American Chemical Society, vol. 91, pages 6683-6689, 1969; or Tetrahydron, vol. 41, pages 479-484, 1985.

Compounds (AV), (AV-2) and (AV-3) can also be produced, for example, according to the following [AE Method] or a method analogous thereto.

[AE Method]

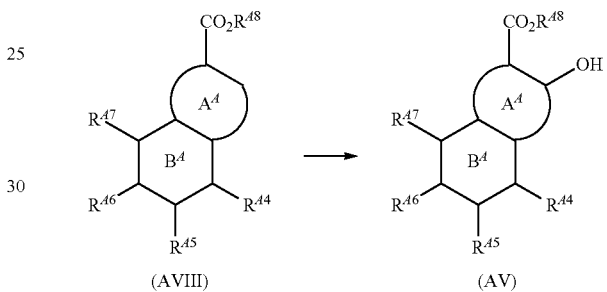

wherein each symbol is as defined above.

The reaction from compound (AVIII) to compound (AV) can be carried out by subjecting compound (AVIII) to 1) formylation, 2) the Baeyer-Villiger oxidation, and then 3) hydrolysis, in a solvent that does not adversely influence the reaction.

The formylation reaction mentioned above 1) can be carried out by reacting compound (AVIII) with the Vilsmeier reagent in a solvent that does not influence the reaction.

Examples of the Vilsmeier reagent include DMF-phosphorus oxychloride, DMF-thionyl chloride and the like.

The amount of the DMF to be used is generally 1 to 2 mol, preferably 1 to 1.5 mol, per 1 mol of compound (AVIII).

The amount of the phosphorus oxychloride or thionyl chloride to be used is generally 1 to 2 mol, preferably 1 to 1.5 mol, per 1 mol of compound (AVIII).

Examples of the solvent that does not influence the reaction include ethers, hydrocarbons, nitriles, esters and the like, and ethers and nitriles are particularly preferable. These solvents may be used in a mixture of two or more kinds thereof in an appropriate ratio.

The reaction temperature is generally 0 to 180° C., preferably 20 to 130° C.

The reaction time is generally 0.5 to 48 hr, preferably 1 to 24 hr.

Compound (AVIII) can be synthesized, for example, according to the method described in Journal of the Chemical Society, pages 884-888, 1946; Synthetic Communication, vol. 17, pages 1647-1654, 1987; or Heterocycles, vol. 27, pages 1365-1376, 1988.

The Baeyer-Villiger oxidation reaction mentioned above 2) can be carried out by reacting the compound (hereinafter to be referred to as "compound (AVIII-a)") obtained in the above-mentioned 1) with an oxidant in a solvent that does not influence the reaction.

Examples of the oxidant include m-chloroperbenzoic acid and the like.

The amount of the oxidant to be used is generally 1 to 2 mol, preferably 1 to 1.5 mol, per 1 mol of compound (AVIII-a).

Examples of the solvent that does not influence the reaction include ethers, hydrocarbons, nitriles, amides, esters and the like, and hydrocarbons and nitriles are particularly preferable. These solvents may be used in a mixture of two or more kinds thereof in an appropriate ratio.

The reaction temperature is generally 0 to 120° C., preferably 20 to 100° C.

The reaction time is generally 0.5 to 48 hr, preferably 1 to 24 hr.

The hydrolysis mentioned above 3) can be carried out by reacting the compound (hereinafter to be referred to as "compound (AVIII-b)) obtained in the above-mentioned 2) with a base, in a solvent that does not adversely influence the reaction.

Examples of the base include sodium hydroxide, potassium hydroxide, lithium hydroxide, potassium carbonate, sodium carbonate and the like, and potassium carbonate and sodium carbonate are particularly preferable.

The amount of the base to be used is generally 1 to 20 mol, preferably 1 to 10 mol, per 1 mol of compound (AVIII-b).

Examples of the solvent that does not adversely influence the reaction include ethers, alcohols, hydrocarbons, ketones, nitriles, amides, esters, water and the like, and alcohols, ethers and water are particularly preferable. These solvents may be used in a mixture of two or more kinds thereof in an appropriate ratio.

The reaction temperature is generally 0 to 100° C., preferably 20 to 60° C.

The reaction time is generally 0.5 to 100 hr, preferably 1 to 48 hr.

Compound (AIV-4), which is compound (AIV-2) wherein ring $A^A B^A$ is furo[2,3-b]pyridine, pyrrolo[2,3-b]pyridine or thieno[2,3-b]pyridine, can be produced, for example, according to the following [AF Method] or a method analogous thereto.

[AF Method]

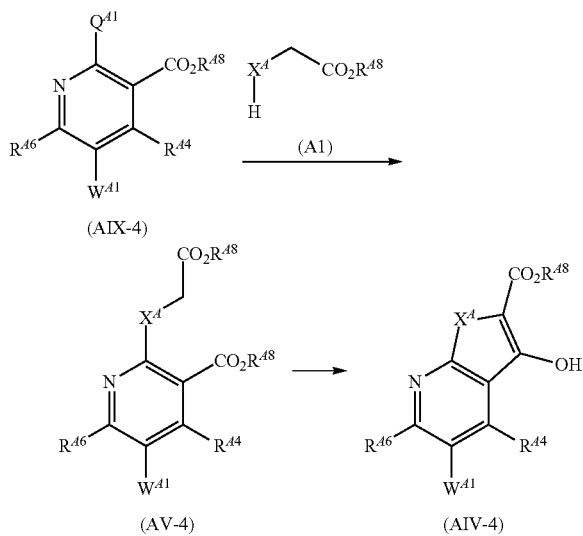

wherein $Q^{41}$ is a leaving group, and the other symbols are as defined above.

Examples of the leaving group for $Q^{41}$ include a halogen atom, a $C_{1-6}$ alkylsulfonyloxy group optionally having 1 to 3 halogen atoms (e.g., methylsulfonyloxy, ethylsulfonyloxy, trifluoromethylsulfonyloxy), a $C_{6-10}$ arylsulfonyloxy group optionally substituted by 1 to 3 $C_{1-6}$ alkyl groups (e.g., benzenesulfonyloxy, 4-toluenesulfonyloxy), a methylmercapto group, a methanesulfonyl group and the like, and a halogen atom is particularly preferable.

The reaction from compound (AIX-4) with compound (A1) can be carried out in a solvent that does not adversely influence the reaction, in the presence of a base as necessary.

The amount of compound (A1) to be used is generally 1 to 3 mol, preferably 1 to 2 mol, per 1 mol of compound (AIX-4).

Examples of the base include sodium hydride, sodium methoxide, sodium ethoxide, sodium carbonate, sodium hydrogen carbonate, sodium hydroxide, triethylamine, diisopropylethylamine, pyridine, 4-dimethylaminopyridine and the like.

The amount of the base to be used is generally 2 to 5 mol, preferably 2 to 3 mol, per 1 mol of compound (AIX-4).

Examples of the solvent that does not adversely influence the reaction include ethers, hydrocarbons, alcohols, amides, esters and the like, and ethers and amides are particularly preferable. These solvents may be used in a mixture of two or more kinds thereof in an appropriate ratio.

The reaction temperature is generally 0 to 100° C., preferably 20 to 90° C.

The reaction time is generally 0.5 to 100 hr, preferably 1 to 48 hr.

Compound (A1) may be commercially available product, or can be produced from the corresponding starting material compound according to a method known per se.

The reaction from compound (AV-4) to compound (AIV-4) can be carried out using a base in a solvent that does not adversely influence the reaction.

Examples of the base include sodium methoxide, sodium ethoxide, sodium hydroxide and the like.

The amount of the base to be used is generally 2 to 5 mol, preferably 2 to 3 mol, per 1 mol of compound (AV-4).

Examples of the solvent that does not adversely influence the reaction include ethers, hydrocarbons, alcohols, amides, esters and the like, and ethers and amides are particularly preferable. These solvents may be used in a mixture of two or more kinds thereof in an appropriate ratio.

The reaction temperature is generally 0 to 100° C., preferably 20 to 90° C.

The reaction time is generally 0.5 to 100 hr, preferably 1 to 48 hr.

Compound (AIV-4) can also be directly obtained from compound (AIX-4) without isolation of compound (AV-4).

Compound (AIX-4a), which is compound (AIX-4) wherein $R^{44}$ is a hydrogen atom, a halogen atom or an amino group optionally having substituent(s), can be produced, for example, according to the following [AG Method] or a method analogous thereto.

[AG Method]

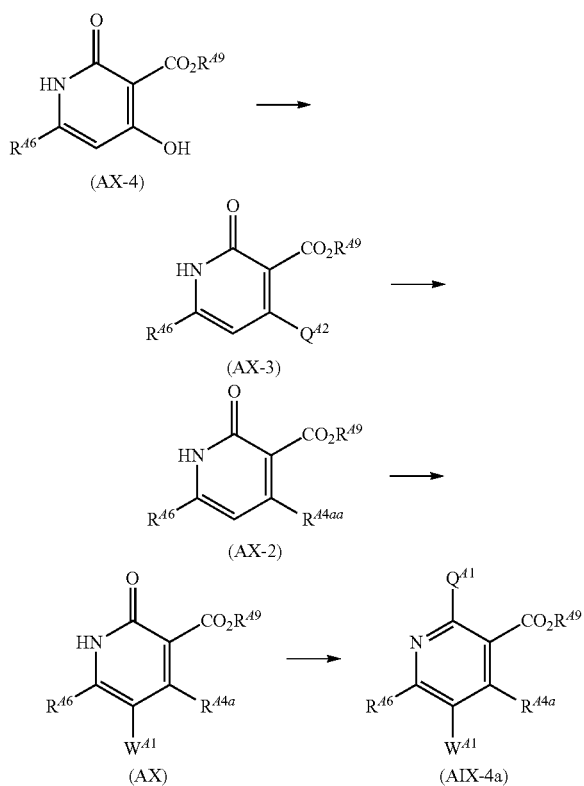

wherein is a leaving group, $R^{44a}$ is a hydrogen atom, a halogen atom or an amino group optionally having substituent(s), $R^{44aa}$ is a hydrogen atom or an amino group optionally having substituent(s), and the other symbols are as defined above.

Examples of the "leaving group" for $Q^{42}$ include those similar to the "leaving group" for $Q^{41}$, and a halogen atom is particularly preferable.

The reaction from compound (AX-4) to compound (AX-3) can be carried out using a halogenating reagent in a solvent that does not adversely influence the reaction or without solvent, in the presence of a base as necessary.

Examples of the halogenating reagent include thionyl chloride, phosphoryl chloride, phosphorus pentachloride, phosphorus tribromide and the like.

The amount of the halogenating reagent to be used is generally 1 to 20 mol, preferably 2 to 10 mol, per 1 mol of compound (AX-4).

Examples of the base include triethylamine, diisopropylethylamine, pyridine, 4-dimethylaminopyridine and the like.

The amount of the base to be used is generally 1 to 20 mol, preferably 2 to 10 mol, per 1 mol of compound (AX-4).

Examples of the solvent that does not adversely influence the reaction include ethers, hydrocarbons, alcohols, amides, esters and the like. These solvents may be used in a mixture of two or more kinds thereof in an appropriate ratio. This reaction is preferably carried out without solvent.

The reaction temperature is generally 0 to 130° C., preferably 20 to 130° C.

The reaction time is generally 0.5 to 100 hr, preferably 1 to 48 hr.

Alternatively, the reaction from compound (AX-4) to compound (AX-3) can be carried out using a sulfonylating reagent in a solvent that does not adversely influence the reaction or without solvent, in the presence of a base as necessary.

Examples of the sulfonylating reagent include trifluoromethanesulfonic anhydride, a methanesulfonyl halide optionally having 1 to 3 halogen atoms, a benzenesulfonyl halide optionally having 1 to 3 $C_{1-6}$ alkyl groups, and the like.

The amount of the sulfonylating reagent to be used is generally 1 to 2 mol, preferably 1 to 1.5 mol, per 1 mol of compound (AX-4).

Examples of the base include triethylamine, diisopropylethylamine, pyridine, 4-dimethylaminopyridine and the like.

The amount of the base to be used is generally 2 to 5 mol, preferably 2 to 3 mol, per 1 mol of compound (AX-4).

Examples of the solvent that does not adversely influence the reaction include ethers, hydrocarbons, alcohols, amides, esters and the like, and ethers and amides are particularly preferable. These solvents may be used in a mixture of two or more kinds thereof in an appropriate ratio.

The reaction temperature is generally –10 to 100° C., preferably 0 to 60° C.

The reaction time is generally 0.5 to 100 hr, preferably 1 to 48 hr.

The compound (hereinafter to be referred to as "compound (AX-2a)"), which is compound (AX-2) wherein $R^{44aa}$ is a hydrogen atom, can be obtained by subjecting compound (AX-3) to a catalytic hydrogenation reaction in a solvent that does not adversely influence the reaction.

Examples of the catalyst used for the catalytic hydrogenation reaction include Raney-nickel; platinum oxide; palladium, ruthenium, rhodium or iridium, which is supported on activated carbon, barium sulfate, calcium carbonate or the like; and the like.

The amount of the catalyst to be used is generally 0.01 to 1 mol, preferably 0.05 to 0.5 mol, per 1 mol of compound (AX-3).

Examples of the hydrogen source include hydrogen, cyclohexene, hydrazine, ammonium formate and the like.

Examples of the solvent that does not adversely influence the reaction include ethers, alcohols, hydrocarbons, ketones, nitriles, amides, esters, water and the like, and alcohols, ethers and water are particularly preferable. These solvents may be used in a mixture of two or more kinds thereof in an appropriate ratio.

The reaction temperature is generally 0 to 100° C., preferably 20 to 60° C.

The reaction time is generally 0.5 to 100 hr, preferably 1 to 48 hr.

The compound (hereinafter to be referred to as "compound (AX-2b)"), which is compound (AX-2) wherein $R^{44aa}$ is an "amino group optionally having substituent(s)", can be obtained by reacting compound (AX-3) with an amine compound corresponding to the "amino group optionally having substituent(s)" for $R^{44aa}$ in a solvent that does not adversely influence the reaction, in the presence of a base as necessary.

The amine compound corresponding to the "amino group optionally having substituent(s)" $R^{44aa}$ may be commercially available product, or can be produced from the corresponding starting material compound according to a method known per se.

The amount of the amine compound to be used is generally 1 to 20 mol, preferably 2 to 10 mol, per 1 mol of compound (AX-3).

Examples of the base include triethylamine, N, N-diisopropylethylamine, pyridine, 4-dimethylaminopyridine, potassium carbonate, cesium carbonate, sodium carbonate and the like.

The amount of the base to be used is generally 1 to 20 mol, preferably 2 to 10 mol, per 1 mol of compound (AX-3).

Examples of the solvent that does not adversely influence the reaction include ethers, nitriles, hydrocarbons, alcohols, amides, esters and the like, and ethers, nitriles, alcohols and amides are particularly preferable. These solvents may be used in a mixture of two or more kinds thereof in an appropriate ratio.

The reaction temperature is generally 0 to 130° C., preferably 20 to 130° C.

The reaction time is generally 0.5 to 100 hr, preferably 1 to 48 hr.

The reaction from compound (AX-2) to compound (AX) can be carried out according to the reaction from compound (AIII-3) to compound (AIII-2) shown in [AC Method].

The reaction from compound (AX) to compound (AIX-4a) can be carried out according to the conversion from the aforementioned compound (AX-4) to compound (AX-3) and by increasing the amount of reagents, extending the reaction time, and performing the reaction at a high temperature, where necessary.

Compound (AX-4) can be synthesized according to a method known per se (e.g., the method described in the Journal of Medicinal Chemistry, vol. 51, pages 1385-1392, 2008).

Compound (AIV-5), which is compound (AIV-3) wherein ring $A^A B^A$ is furo[2,3-b]pyridine, pyrrolo[2,3-b]pyridine or thieno[2,3-b]pyridine, and $R^{A4}$ is a hydrogen atom, a halogen atom or an amino group optionally having substituent(s), can be produced, for example, according to the following [AH Method] or a method analogous thereto.

[AH Method]

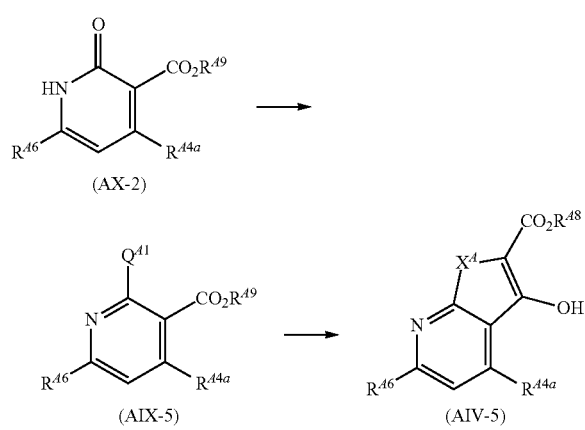

wherein each symbol is as defined above.

The reaction from compound (AX-2) to compound (AIX-5) can be carried out according to the conversion from compound (AX) to compound (AIX-4a) shown in [AG Method].

The reaction from compound (AIX-5) to compound (AIV-5) can be carried out according to [AF Method].

Compound (AIV-6), which is compound (AIV) wherein ring $A^A B^A$ is furo[2,3-b]pyrazine, pyrrolo[2,3-b]pyrazine or thieno[2,3-b]pyrazine, can be produced, for example, according to the following [AI Method] or a method analogous thereto.

[AI Method]

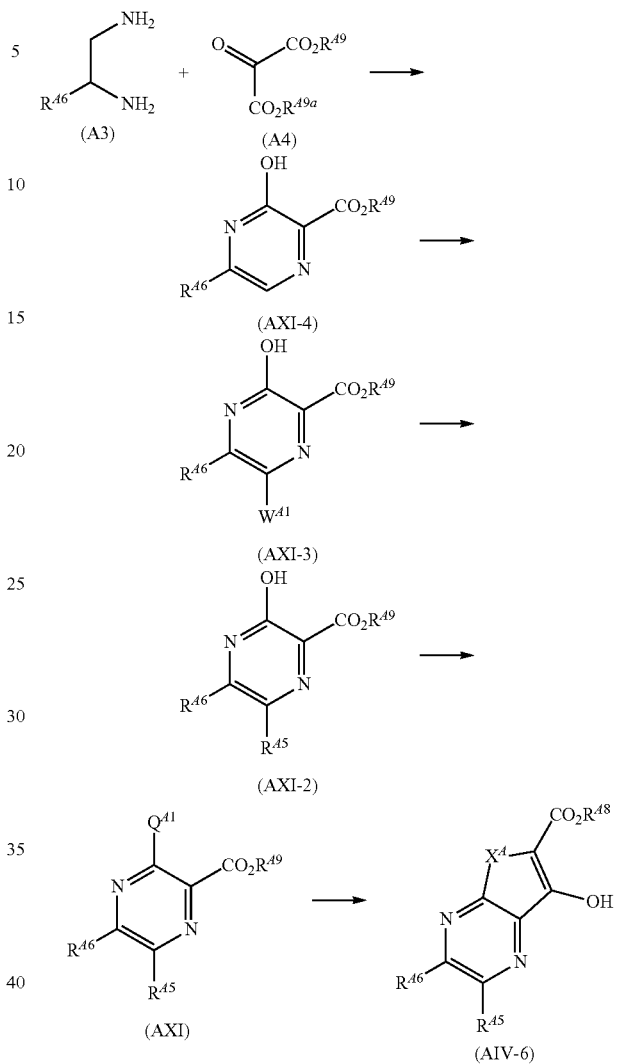

wherein $R^{A9a}$ is a $C_{1-6}$ alkyl group, and the other symbols are as defined above.

Compound (AXI-4) is obtained by reacting compound (A3) with compound (A4) in a solvent that does not adversely influence the reaction.

The amount of compound (A3) to be used is generally 1 to 2 mol, preferably 1 to 1.5 mol, per 1 mol of compound (A4).

Examples of the solvent that does not adversely influence the reaction include ethers, nitriles, hydrocarbons, alcohols, amides, esters and the like, and ethers, alcohols and amides are particularly preferable. These solvents may be used in a mixture of two or more kinds thereof in an appropriate ratio.

The reaction temperature is generally 0 to 130° C., preferably 20 to 130° C.

The reaction time is generally 0.5 to 100 hr, preferably 1 to 48 hr.

Compound (A3) may be commercially available product, or can be synthesize according to a method known per se (e.g., the method described in Tetrahydron Letter, vol. 25, pages 399-402, 1984).

Compound (A4) may be commercially available product, or can be produced from the corresponding starting material compound according to a method known per se.

The reaction from compound (AXI-4) to compound (AXI-3) can be carried out according to the reaction from compound (AIII-3) to compound (AIII-2) shown in [AC Method].

The reaction from compound (AXI-3) to compound (AXI-2) can be carried out according to the reaction from compound (AIII-2) to compound (AIII) shown in [AB Method]. In this case, the hydroxyl group of compound (AXI-3) can be protected in advance, and the resulting compound is reacted according to the reaction from compound (AIII-2) to compound (AIII) shown in [AB Method], and then deprotected to give compound (AXI-2).

The reaction from compound (AXI-2) to compound (AXI) can be carried out according to the reaction from compound (AX) to compound (AIX-4a) shown in [AG Method].

The reaction from compound (AXI-2) to compound (AIV-6) can be carried out according to [AF Method].

Compound (AIV-7), which is compound (AIV-2) wherein ring $A^A B^A$ is benzofuran, indole or benzothiophene, can be produced, for example, according to the following [AJ Method] or a method analogous thereto.

[AJ Method]

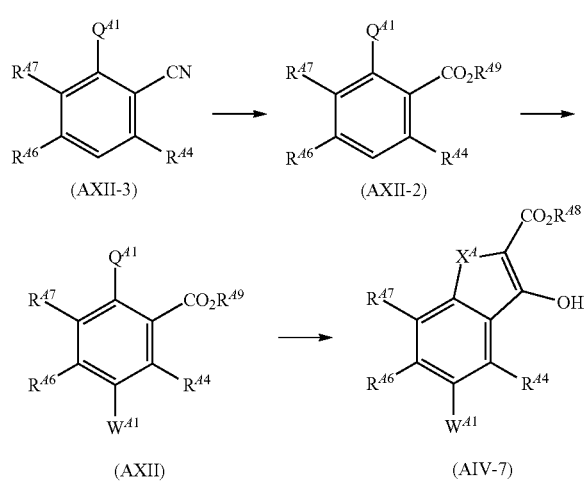

wherein each symbol is as defined above.

The reaction from compound (AXII-3) to compound (AXII-2) can be carried out by heating compound (AXII-3) in concentrated sulfuric acid-ethanol.

The reaction temperature is generally 50 to 110° C., preferably 60 to 100° C.

The reaction time is generally 0.5 to 100 hr, preferably 1 to 48 hr.

The reaction from compound (AXII-2) to compound (AXII) can be carried out according to the reaction from compound (AIII-3) to compound (AIII-2) shown in [AC Method].

The reaction from compound (AXII) to compound (AIV-7) can be carried out according to [AF Method].

Compound (AXII-3) can be synthesized according to a method known per se (e.g., the method described in the Journal of Medicinal Chemistry, vol. 15, pages 905-909, 1972).

Compound (AXII-3) wherein $R^{46}$ is methyl may be commercially available product.

Compound (AIV-8), which is compound (AIV-3) wherein ring $A^A B^A$ is furo[3,2-b]pyridine, pyrrolo[3,2-b]pyridine or thieno[3,2-b]pyridine, can be produced, for example, according to the following [AK Method] or a method analogous thereto.

[AK Method]

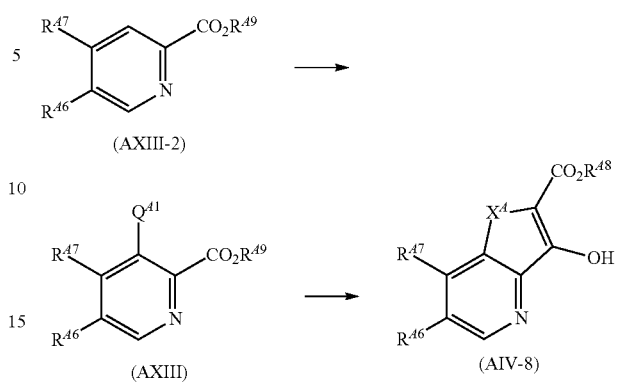

wherein each symbol is as defined above.

The reaction from compound (AXIII-2) to compound (AXIII) can be carried out, for example, using a halogenating reagent, in a solvent that does not adversely influence the reaction or without solvent, in the presence of a base as necessary.

Examples of the halogenating reagent include N-bromosuccinimide, N-chlorosuccinimide, bromine, iodine and the like.

The amount of the halogenating reagent to be used is generally 1 to 5 mol, preferably 1 to 2 mol, per 1 mol of compound (AXIII-2).

Examples of the solvent that does not adversely influence the reaction include ethers, hydrocarbons, ketones, nitriles, esters, amides and the like, and hydrocarbons, nitriles and amides are particularly preferable. These solvents may be used in a mixture of two or more kinds thereof in an appropriate ratio.

The reaction temperature is generally 0 to 80° C., preferably 20 to 60° C.

The reaction time is generally 0.5 to 100 hr, preferably 1 to 48 hr.

The reaction from compound (AXIII) to compound (AIV-8) can be carried out according to [AF Method].

Compound (AXIII-2) may be commercially available product, or can be synthesized according to a method known per se (e.g., the method described in Synthesis vol. 7, pages 584-586, 1986).

The introduction of $W^{41}$ group and conversion to $R^{44}$ group are not limited to particular steps of the above-mentioned methods, but can be carried out by any synthetically suitable step.

Compound (AXII-4), which is compound (AXII-2) wherein $R^{46}$ is ethyl, can be produced, for example, according to the following [AL Method] or a method analogous thereto.

[AL Method]

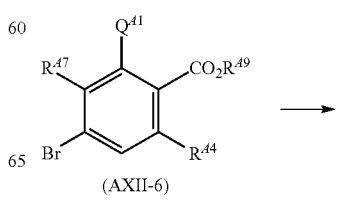

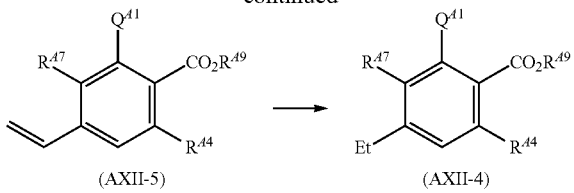

wherein each symbol is as defined above.

The reaction from compound (AXII-6) to compound (AXII-5) can be carried out by reacting compound (AXII-6) with tributyl(vinyl)tin in a solvent that does not adversely influence the reaction.

To be specific, compound (AXII-6) is reacted with tributyl (vinyl)tin and a palladium compound (e.g., tetrakis(triphenylphosphine)palladium(0), tris(dibenzylideneacetone)dipalladium(0), palladium acetate(II)), a ligand (e.g., 9,9-dimethyl-4,5-bis(diphenylphosphino)xanthene) as necessary, a base (e.g., cesium carbonate, sodium t-butoxide) as necessary.

The amount of the tributyl(vinyl)tin to be used is generally 1 to 10 mol, preferably 1 to 5 mol, per 1 mol of compound (AXII-6).

The amount of the palladium compound to be used is generally 0.01 to 1 mol, preferably 0.05 to 0.5 mol, per 1 mol of compound (AXII-6).

The amount of the ligand used as necessary is generally 0.01 to 1 mol, preferably 0.05 to 0.5 mol, per 1 mol of compound (AXII-6).

The amount of the base used as necessary is generally 1 to 5 mol, preferably 1 to 3 mol, per 1 mol of compound (AXII-6).

Examples of the solvent that does not adversely influence the reaction include ethers, hydrocarbons, alcohols, amides, esters and the like, and ethers and amides are particularly preferable. These solvents may be used in a mixture of two or more kinds thereof in an appropriate ratio.

The reaction temperature is generally 0 to 150° C., preferably 20 to 120° C.

The reaction time is generally 0.5 to 100 hr, preferably 1 to 48 hr.

The reaction from compound (AXII-5) to compound (AXII-4) can be carried out by reducing compound (AXII-5) in a solvent that does not adversely influence the reaction.

A catalytic hydrogenation reaction can be employed for the reduction. Examples of the catalyst include Raney-nickel; platinum oxide; palladium, ruthenium, rhodium or iridium, which is supported on activated carbon, barium sulfate, calcium carbonate or the like, and the like.

The amount of the catalyst to be used is generally 0.01 to 1 mol, preferably 0.05 to 0.5 mol, per 1 mol of compound (AXII-5).

Examples of the hydrogen source include hydrogen, cyclohexene, hydrazine, ammonium formate and the like.

Examples of the solvent that does not adversely influence the reaction include ethers, alcohols, hydrocarbons, ketones, nitriles, amides, esters, water and the like, and alcohols, ethers and water are particularly preferable. These solvents may be used in a mixture of two or more kinds thereof in an appropriate ratio.

The reaction temperature is generally 0 to 100° C., preferably 20 to 60° C.

The reaction time is generally 0.5 to 100 hr, preferably 1 to 48 hr.

Compound (AXII-6) may be commercially available product.

Compound (AIII-4), which is compound (AIII) wherein ring $A^4B^4$ is pyrrolo[3,2-b]pyridine, $R^{44}$ is absent, $R^{46}$ is methyl or ethyl, and $R^{47}$ is hydrogen, can be produced, for example, according to the following [AM Method] or a method analogous thereto.

[AM Method]

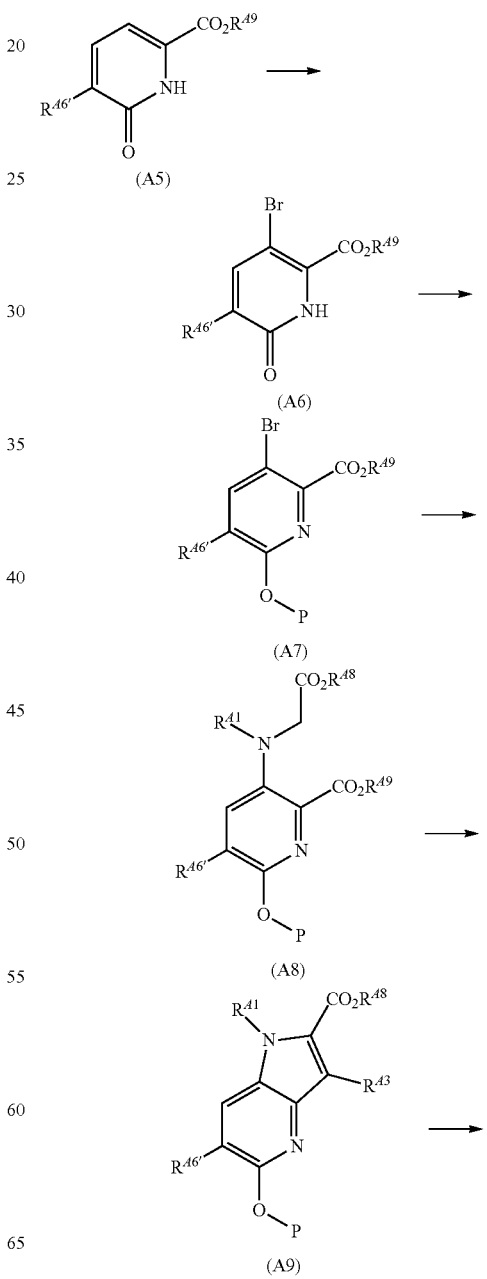

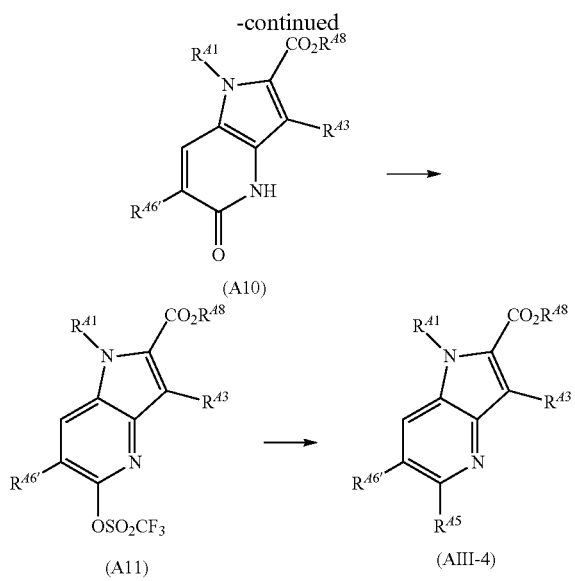

wherein P is a protecting group, $R^{46'}$ is methyl or ethyl, and the other symbols are as defined above.

The reaction from compound (A5) to compound (A6) can be carried out by reacting compound (A5) with a brominating reagent in a solvent that does not adversely influence the reaction.

Examples of the brominating reagent include bromine, N-bromosuccinimide and the like. The amount thereof to be used is generally 1 to 2 mol, preferably 1 to 1.5 mol, per 1 mol of compound (A5).

Examples of the solvent that does not adversely influence the reaction include ethers, alcohols, hydrocarbons, ketones, nitriles, amides, esters and the like, and amides are particularly preferable. These solvents may be used in a mixture of two or more kinds thereof in an appropriate ratio.

The reaction temperature is generally −10 to 50° C., preferably 0 to 40° C.

The reaction time is generally 0.5 to 48 hr, preferably 1 to 24 hr.

Examples of the protecting group for P include the aforementioned hydroxyl-protecting group, and a benzyl group is preferable. When P is a benzyl group, the reaction from compound (A6) to compound (A7) can be carried out by reacting compound (A6) with a halogenated benzyl in the presence of silver carbonate in a solvent that does not adversely influence the reaction.

The amount of the halogenated benzyl to be used is generally 1 to 5 mol, preferably 1 to 3 mol, per 1 mol of compound (A6).

The amount of the silver carbonate to be used is generally 1 to 5 mol, preferably 1 to 3 mol, per 1 mol of compound (A6).

Examples of the solvent that does not adversely influence the reaction include ethers, alcohols, hydrocarbons, ketones, nitriles, amides, esters and the like, and ethers and hydrocarbons are particularly preferable. These solvents may be used in a mixture of two or more kinds thereof in an appropriate ratio.

The reaction temperature is generally 0 to 100° C., preferably 20 to 80° C.

The reaction time is generally 0.5 to 48 hr, preferably 1 to 24 hr.

The reaction from compound (A7) to compound (A8) can be carried out according to the reaction from compound (AIX-4) to compound (AV-4) shown in [AF Method].

The reaction from compound (A8) to compound (A9) can be carried out according to the reaction from compound (AV-2) to compound (AIV-2) and the reaction from compound (AIV-2) to compound (AIII-2) shown in [AB Method].

The reaction from compound (A9) to compound (A10) can also be carried out by a catalytic hydrogenation reaction in a solvent that does not adversely influence the reaction.

Examples of the catalyst used for catalytic hydrogenation reaction include Raney-nickel; platinum oxide; palladium, ruthenium, rhodium or iridium, which is supported on activated carbon, barium sulfate, calcium carbonate or the like; and the like.

The amount of the catalyst to be used is generally 0.01 to 1 mol, preferably 0.05 to 0.5 mol, per 1 mol of compound (A9).

Examples of the hydrogen source include hydrogen, cyclohexene, hydrazine, ammonium formate and the like.

Examples of the solvent that does not adversely influence the reaction include ethers, alcohols, hydrocarbons, ketones, nitriles, amides, esters, water and the like, and alcohols, ethers and water are particularly preferable. These solvents may be used in a mixture of two or more kinds thereof in an appropriate ratio.

The reaction temperature is generally 0 to 100° C., preferably 20 to 60° C.

The reaction time is generally 0.5 to 100 hr, preferably 1 to 48 hr.

The reaction from compound (A10) to compound (A11) can be carried out using trifluoromethanesulfonic anhydride in a solvent that does not adversely influence the reaction or without solvent, in the presence of a base as necessary.

The amount of the trifluoromethanesulfonic anhydride to be used is generally 1 to 2 mol, preferably 1 to 1.5 mol, per 1 mol of compound (A10).

Examples of the base include triethylamine, diisopropylethylamine, pyridine, 4-dimethylaminopyridine and the like.

The amount of the base to be used is generally 2 to 5 mol, preferably 2 to 3 mol, per 1 mol of compound (A10).

Examples of the solvent that does not adversely influence the reaction include ethers, hydrocarbons, alcohols, amides, esters and the like, and ethers and amides are particularly preferable. These solvents may be used in a mixture of two or more kinds thereof in an appropriate ratio.

The reaction temperature is generally −10 to 100° C., preferably 0 to 60° C.

The reaction time is generally 0.5 to 100 hr, preferably 1 to 48 hr.

The reaction from compound (A11) to compound (AIII-4) can be carried out according to the reaction from compound (AIII-2) to compound (AIII) shown in [AB Method].

Compound (A5) wherein $R^{46'}$ is methyl can be synthesized according to a method known per se (e.g., the method described in Tetrahydron, vol. 12, pages 2385-2388, 2001).

Compound (A6-2), which is compound (A5) wherein $R^{46'}$ is ethyl, can be produced, for example, according to the following [AN Method] or a method analogous thereto.

[AN Method]

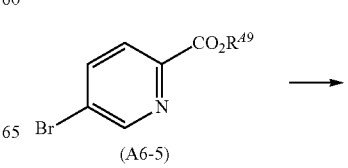

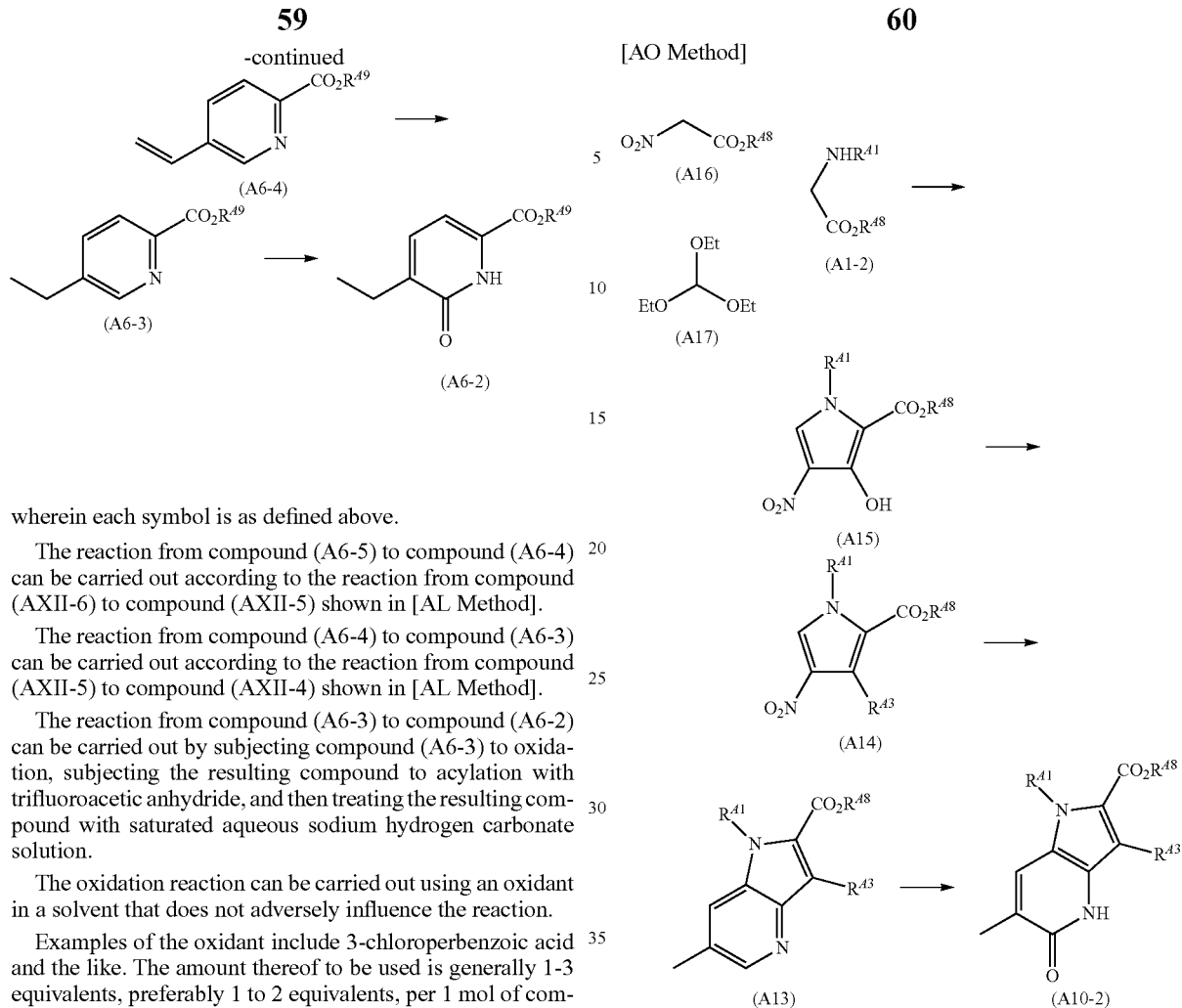

wherein each symbol is as defined above.

The reaction from compound (A6-5) to compound (A6-4) can be carried out according to the reaction from compound (AXII-6) to compound (AXII-5) shown in [AL Method].

The reaction from compound (A6-4) to compound (A6-3) can be carried out according to the reaction from compound (AXII-5) to compound (AXII-4) shown in [AL Method].

The reaction from compound (A6-3) to compound (A6-2) can be carried out by subjecting compound (A6-3) to oxidation, subjecting the resulting compound to acylation with trifluoroacetic anhydride, and then treating the resulting compound with saturated aqueous sodium hydrogen carbonate solution.

The oxidation reaction can be carried out using an oxidant in a solvent that does not adversely influence the reaction.

Examples of the oxidant include 3-chloroperbenzoic acid and the like. The amount thereof to be used is generally 1-3 equivalents, preferably 1 to 2 equivalents, per 1 mol of compound (A6-3).

The reaction temperature is generally 0 to 60° C., preferably 0 to 30° C.

The reaction time is generally 1 to 48 hr, preferably 5-30 hr.

Examples of the solvent that does not adversely influence the reaction include ethers, hydrocarbons, amides, nitriles and the like, and nitriles are particularly preferable. These solvents may be used in a mixture of two or more kinds thereof in an appropriate ratio.

The reaction with trifluoroacetic anhydride can be carried out in a solvent that does not adversely influence the reaction.

The amount of the trifluoroacetic anhydride to be used is generally 2 to 20 equivalents, preferably 5 to 10 equivalents, per 1 mol of compound (A6-3).

Examples of the solvent that does not adversely influence the reaction include ethers, hydrocarbons, nitriles, amides, esters and the like, and amides are particularly preferable. These solvents may be used in a mixture of two or more kinds thereof in an appropriate ratio.

The reaction temperature is generally 0 to 60° C., preferably 0 to 30° C.

The reaction time is generally 1 to 48 hr, preferably 5-30 hr.

Compound (A6-5) may be commercially available product.

Compound (A10-2), which is compound (A10) wherein $R^{46}$ is methyl, can be produced, for example, according to the following [AO Method] or a method analogous thereto.

wherein each symbol is as defined above.

Compound (A15) can be synthesized by heating nitroacetate (A16) and orthoformate (A17) in acetic anhydride, and then reacting the resulting compound with compound (A1-2) in the presence of a base.

The amount of orthoformate (A17) to be used is 1.5 to 3% mol per 1 mol of nitroacetate (A16). The amount of acetic anhydride to be used is 2 to 3 mol per 1 mol of nitroacetate (A16).

The reaction temperature is generally 80 to 180° C., preferably 100 to 150° C.

The reaction time is generally 1 to 48 hr, preferably 1 to 20 hr.

The amount of compound (A1-2) to be used is 0.5 to 2 mol per 1 mol of nitroacetate (A16).

Examples of the base include sodium ethoxide, and the amount thereof to be used is 1 to 10 mol per 1 mol of nitroacetate (A16).

The reaction temperature is generally 0 to 100° C., preferably 10 to 80° C.

The reaction time is generally 1 to 48 hr, preferably 1 to 10 hr.

The reaction from compound (A15) to compound (A14) can be carried out according to the reaction from compound (AIV-2) to compound (AIII-2) shown in [AB Method].

The reaction from compound (A14) to compound (A13) can be carried out by reducing the nitro group of compound (A14), and then reacting the resulting compound with 3-dimethylamino-2-methyl-2-propenal.

The reduction of the nitro group can be carried out according to the reaction from compound (AIII-2) to compound (AIII-2a) shown in [AB Method].

The reaction with 3-dimethylamino-2-methyl-2-propenal can be carried out in the presence of an acid, in a solvent that does not adversely influence the reaction, or using an acid as a solvent.

The amount of the 3-dimethylamino-2-methyl-2-propenal to be used is generally 0.5 to 2 equivalents, per 1 mol of compound (A14).

Examples of the acid include acetic acid, methanesulfonic acid, tosylic acid and the like.

Examples of the solvent that does not adversely influence the reaction include ethers, hydrocarbons, nitriles, amides, esters and the like.

The reaction temperature is generally 60 to 160° C., preferably 100 to 140° C.

The reaction time is generally 1 to 48 hr, preferably 5-30 hr.

The reaction from compound (A13) to compound (A10-2) can be carried out according to the reaction from compound (A6-3) to compound (A6-2) shown in [AN Method].

Nitroacetate (A16) and orthoformate (A17) may be commercially available product.

Compound (A1-2) may be commercially available product, or can be produced from the corresponding starting material compound according to a method known per se.

Compound (AI) can also be produced, when desired, by a combination of the above-mentioned reaction and each or two more of known hydrolysis, deprotection, acylation reaction, alkylation reaction, oxidation reaction, cyclization reaction, carbon chain extension reaction and substituent exchange reaction.

Compound (AI) can be isolated and purified by a means known per se, such as phase transfer, concentration, solvent extraction, fractionation, liquid conversion, crystallization, recrystallization, chromatography and the like. When compound (AI) is obtained as a free compound, it can be converted to a desired salt by a method known per se or a method analogous thereto. Conversely, when the compound is obtained as a salt, it can be converted to a free form or other desired salt by a method known per se or a method analogous thereto.

A compound within the scope of the present invention can also be produced by applying a means known per se to compound (AI) for introduction of substituents and conversion of functional groups. For conversion of substituents, a known conventional method can be used. For example, conversion to amino by hydrolysis of amide, conversion to carboxy by hydrolysis of ester, conversion to carbamoyl by amidation of carboxy, conversion to hydroxymethyl by reduction of carboxy, conversion to alcohol compound by reduction or alkylation of carbonyl, reductive amination of carbonyl, oximation of carbonyl, acylation, ureation, sulfonylation or alkylation of amino, substitution and amination of active halogen by amine, amination by reduction of nitro, alkylation of hydroxy, substitution and amination of hydroxy and the like. When a reactive substituent that causes non-objective reaction is present during the introduction of substituents and conversion of functional groups, a protecting group is introduced in advance as necessary into the reactive substituent by a means known per se, and the protecting group is removed by a means known per se after the objective reaction, whereby the compound within the scope of the present invention can also be produced.

Compound (AI) may be used as a prodrug. A prodrug of compound (AI) means a compound converted to compound (AI) by a reaction due to an enzyme, a gastric acid, etc. under the physiological condition in the living body, that is, a compound converted to compound (AI) by oxidation, reduction, hydrolysis, etc. due to an enzyme, a compound converted to compound (AI) by hydrolysis etc. due to gastric acid, and the like.

Examples of the prodrug of compound (AI) include a compound obtained by subjecting amino in compound (AI) to an acylation, alkylation or phosphorylation (e.g., a compound obtained by subjecting amino in compound (AI) to eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation); a compound obtained by subjecting hydroxy in compound (AI) to acylation, alkylation, phosphorylation or boration (e.g., a compound obtained by subjecting hydroxy in the compound (AI) to acetylation, palmitoylation, propanoylation, pivaloylation, succinylation, fumarylation, alanylation or dimethylaminoacethylation); a compound obtained by subjecting carboxy in compound (AI) to esterification or amidation (e.g., a compound obtained by subjecting carboxy in compound (AI) to ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation) and the like. Any one of these compounds can be produced from compound (AI) by a method known per se.

A prodrug of compound (AI) may also be a compound converted into compound (AI) under physiological conditions, such as those described in IYAKUHIN no KAIHATSU (Development of Pharmaceuticals), Vol. 7, Design of Molecules, p. 163-198, Published by HIROKAWA SHOTEN (1990).

When compound (AI) has an isomer such as optical isomer, stereoisomer, positional isomer, rotational isomer and the like, any isomer and a mixture thereof are encompassed in compound (AI). For example, when compound (AI) has an optical isomer, an optical isomer resolved from a racemate is also encompassed in compound (AI). Such isomers can be obtained as independent products by a synthesis means or a separation means (concentration, solvent extraction, column chromatography, recrystallization and the like) known per se.

Compound (AI) may be a crystal, and both a single crystal and crystal mixtures are encompassed in compound (AI). Crystals can be produced by crystallization according to crystallization methods known per se.

Compound (AI) may also be a cocrystal.

Compound (AI) may be a hydrate, a non-hydrate, a solvate or a non-solvate.

A compound labeled with an isotope (e.g., $^2H$, $^3H$, $^{14}C$, $^{35}S$, $^{125}I$ etc.) is also encompassed in compound (AI).

Compound (AI) may be a deuterium conversion.

Compound (AI) or a prodrug thereof (sometimes to be abbreviated as "the compound of the present invention" in the present specification) interacts, for example, with human Smo protein and changes the steric structure thereof, whereby formation of a complex with a protein involved in the signal transduction in the cytoplasm is inhibited and the Hedgehog signal transduction system is inhibited. Alternatively, the compound of the present invention interacts with human Smo protein and directly inhibits formation of a complex of human Smo protein with a protein involved in the Hedgehog signal transduction system in the cytoplasm, whereby the Hedgehog signal transduction system is inhibited. Alternatively, the compound of the present invention interacts with a site of an Smo protein, for example, phosphorylation site and the like, which is modified by a protein involved in the Hedgehog signal transduction system, whereby modification such as phosphorylation of Smo and the like is inhibited and the Hedgehog signal transduction system is inhibited.

Inhibition of the Hedgehog signal transduction system can be measured, for example, by quantifying a decrease in the expression level of a reporter gene connected to the downstream of the Gli binding site based on the fluorescence intensity according to the following Experimental Example 1. Alternatively, it can be measured by quantifying the expression of Gli-1 mRNA in a cell extract by quantitative PCR method and the like. A compound that inhibits Hedgehog signal targets Smo, which can be confirmed, for example, by binding fluorescence-labeled Cyclopamine and a test compound to cells expressing Smo, measuring the fluorescence level of the cell, and comparing the value with that without addition of a test compound to find a decrease.

Accordingly, the compound of the present invention is useful as an Smo inhibitor for mammals (e.g., mouse, rat, hamster, rabbit, cat, dog, bovine, sheep, monkey, human). The compound of the present invention is used as a medicament of diseases possibly influenced by Smo, for example, cancer [e.g., colorectal cancer (e.g., colorectal cancer, rectal cancer, anal cancer, familial colorectal cancer, hereditary nonpolyposis colorectal cancer, gastrointestinal stromal tumor), lung cancer (e.g., non-small cell lung cancer, small cell lung cancer, malignant mesothelioma), mesothelioma, pancreatic cancer (e.g., pancreatic duct cancer, pancreatic endocrine tumor), pharyngeal cancer, laryngeal cancer, esophageal cancer, esophagus cancer, gastric cancer (e.g., papillary adenocarcinoma, mucinous adenocarcinoma, adenosquamous cancer), duodenal cancer, small intestinal cancer, breast cancer (e.g., invasive ductal breast carcinoma, ductal cancer in situ, inflammatory breast cancer), ovarian cancer (e.g., ovarian epithelial cancer, extragonadal germ cell tumor, ovarian germ cell tumor, ovarian low malignant potential tumor), testicular tumor, prostate cancer (e.g., hormone-dependent prostate cancer, non-hormone dependent prostate cancer), liver cancer (e.g., hepatocellular carcinoma, primary liver cancer, bile duct cancer, extrahepatic bile duct cancer), thyroid cancer (e.g., medullary thyroid cancer), kidney cancer (e.g., renal cell carcinoma, renal pelvis and ureter transitional cell cancer), uterine cancer (e.g., cervical cancer, cancer of uterine body, uterine sarcoma), brain tumor (e.g., medulloblastoma, glioma, pineal astrocytoma, pilocytic astrocytoma, diffuse astrocytoma, anaplastic astrocytoma, pituitary adenoma), retinoblastoma, skin cancer (e.g., basal cell carcinoma, malignant melanoma), sarcoma (e.g., rhabdomyosarcoma, leiomyosarcoma, soft tissue sarcoma), malignant bone tumor, urinary bladder cancer, hematologic cancer (e.g., multiple myeloma, leukemia, malignant lymphoma, Hodgkin's disease, chronic myeloproliferative disorder), cancer unknown primary], a cancer growth inhibitor, a cancer metastasis inhibitor, an apoptosis promoter and the like.

Among these, the compound of the present invention is effective, for example, for brain tumor, skin cancer, lung cancer, pancreatic cancer, biliary tract cancer, prostate cancer, esophagus cancer, gastric cancer, colorectal cancer, sarcoma and breast cancer.

Especially, the compound of the present invention is effective for glioma, medulloblastoma, basal cell tumor, small cell lung cancer, pancreatic cancer, biliary tract cancer, prostate cancer, esophagus cancer, gastric cancer, colorectal cancer, rhabdomyosarcoma and breast cancer.

The compound of the present invention can be administered orally or parenterally as it is or in a mixture with a pharmacologically acceptable carrier.

The dosage form of the compound of the present invention for oral administration is, for example, tablet (including sugar-coated tablet, film-coated tablet), pill, granule, powder, capsule (including soft capsule, microcapsule), syrup, emulsion, suspension and the like, and the dosage form for parenteral administration is, for example, injection, injecting agent, instillation, suppository and the like. In addition, it is effective to make a sustained release preparation by combining the compound with a suitable base (e.g., polymer of butyric acid, polymer of glycolic acid, copolymer of butyric acid-glycolic acid, a mixture of a polymer of butyric acid and a polymer of glycolic acid, polyglycerol fatty acid ester etc.).

As a method for producing the compound of the present invention in the above-mentioned dosage form, a known production method generally used in the pertinent field can be employed. When the above-mentioned dosage form is produced, suitable amounts of additives such as excipient, binder, disintegrant, lubricant, sweetening agent, surfactant, suspending agent, emulsifier and the like, generally used in the pharmaceutical field, are appropriately added as necessary for production.

When the compound of the present invention is prepared into a tablet, for example, it can be produced by adding an excipient, a binder, a disintegrant, a lubricant and the like, and when a pill or a granule is to be prepared, it can be produced by adding an excipient, a binder, a disintegrant and the like. When a powder or a capsule is to be prepared, it can be produced by adding an excipient and the like, when a syrup is to be prepared, it can be produced by adding a sweetener and the like, and when an emulsion or a suspension is to be prepared, it can be produced by adding a suspending agent, a surfactant, an emulsifier and the like.

Examples of the excipient include lactose, sucrose, glucose, starch, sucrose, crystalline cellulose, powdered glycyrrhiza, mannitol, sodium hydrogen carbonate, calcium phosphate, calcium sulfate and the like.

Examples of the binder include 5 to 10 wt % starch liquid paste, 10 to 20 wt % gum arabic solution or gelatin solution, 1 to 5 wt % tragacanth solution, carboxymethyl cellulose solution, sodium alginate solution, glycerin and the like.

Examples of the disintegrant include starch, calcium carbonate and the like.

Examples of the lubricant include magnesium stearate, stearic acid, calcium stearate, purified talc and the like.

Examples of the sweetener include glucose, fructose, invert sugar, sorbitol, xylitol, glycerin, simple syrup and the like.

Examples of the surfactant include sodium lauryl sulfate, polysorbate 80, sorbitan monofatty acid ester, polyoxyl 40 stearate and the like.

Examples of the suspending agent include gum arabic, sodium alginate, sodium carboxymethyl cellulose, methyl cellulose, bentonite and the like.

Examples of the emulsifier include gum arabic, tragacanth, gelatin, polysorbate 80 and the like.

Furthermore, when the compound of the present invention is produced in the above-mentioned dosage form, a suitable amount of a colorant, a preservative, an aromatic, a corrigent, a stabilizer, a thickening agent and the like typically used in the field of preparation can be added on demand.

As the injection, intravenous injection as well as subcutaneous injection, intracutaneous injection, intramuscular injection, instillation and the like are mentioned, and as the sustained release preparation, an iontophoresis transdermal agent and the like are mentioned.

Such injections are prepared by methods known per se, or by dissolving, suspending or emulsifying the compound of the present invention in a sterilized aqueous or oily liquid. As an aqueous liquid for injection, physiological saline, isotonic solutions containing glucose or other auxiliary drugs (e.g., D-sorbitol, D-mannitol, sodium chloride) and the like, and they can be used in combination with suitable solubilizing agents, such as alcohols (e.g., ethanol), polyalcohols (e.g., propylene glycol, polyethylene glycol), nonionic surfactants (e.g., polysorbate 80, HCO-50) and the like. As an oily liquid, sesame oil, soybean oil and the like, which may be used in combination with solubilizing agents such as benzyl benzoate, benzyl alcohol and the like. In addition, buffers (e.g., phosphate buffer, sodium acetate buffer), soothing agents (e.g., benzalkonium chloride, procaine hydrochloride), stabilizers (e.g., human serum albumin, polyethylene glycol), preservatives (e.g., benzyl alcohol, phenol) and the like can be blended. A prepared injection is generally filled in an ampoule.

While the content of the compound of the present invention in the medicament of the present invention varies depending on the form of the pharmaceutical preparation, it is generally about 0.01 to 100 wt %, preferably about 2 to 85 wt %, more preferably about 5 to 70 wt %, relative to the entire preparation.

While the content of the additive in the medicament of the present invention varies depending on the form of the pharmaceutical preparation, it is generally about 1 to 99.9 wt %, preferably about 10 to 90 wt %, relative to the entire preparation.

The compound of the present invention is stable and low toxic, and can be used safely. While the daily dose varies depending on the condition and body weight of patients, the kind of compound, administration route and the like, in the case of, for example, oral administration to patients for the treatment of cancer, the daily dose to an adult (body weight about 60 kg), is about 1 to 1000 mg, preferably about 3 to 300 mg, more preferably about 10 to 200 mg, as an active ingredient (the compound of the present invention), which can be given in a single administration or administered in 2 or 3 portions a day.

When the compound of the present invention is administered parenterally, it is generally administered in the form of a liquid (e.g., injection). While the dose varies depending on the subject of administration, target organ, symptom, administration method and the like, it is, for example, about 0.01 mg to about 100 mg, preferably about 0.01 to about 50 mg, more preferably about 0.01 to about 20 mg, in the form of an injection, relative to 1 kg body weight, which is preferably given by intravenous injection.

The compound of the present invention can be used concurrently with other drugs. To be specific, the compound of the present invention can be used together with medicaments such as hormonal therapeutic agents, chemotherapeutic agents, immunotherapeutic agents, medicaments inhibiting the action of cell growth factors or cell growth factor receptors and the like. In the following, the drugs that can be used in combination with the compound of the present invention are abbreviated as concomitant drugs.

Examples of the "hormonal therapeutic agents" include fosfestrol, diethylstylbestrol, chlorotrianisene, medroxyprogesterone acetate, megestrol acetate, chlormadinone acetate, cyproterone acetate, danazol, allylestrenol, gestrinone, mepartricin, raloxifene, ormeloxifene, levormeloxifene, anti-estrogens (e.g., tamoxifen citrate, toremifene citrate), pill preparations, mepitiostane, testrolactone, aminoglutethimide, LH-RH agonists (e.g., goserelin acetate, buserelin, leuprorelin), droloxifene, epitiostanol, ethinylestradiol sulfonate, aromatase inhibitors (e.g., fadrozole hydrochloride, anastrozole, retrozole, exemestane, vorozole, formestane), anti-androgens (e.g., flutamide, bicartamide, nilutamide), 5α-reductase inhibitors (e.g., finasteride, epristeride), aderenal cortex hormone drugs (e.g., dexamethasone, prednisolone, betamethasone, triamcinolone), androgen synthesis inhibitors (e.g., abiraterone), retinoid and drugs that retard retinoid metabolism (e.g., liarozole), thyroid hormone, and DDS (Drug Delivery System) preparations thereof, and the like.

Examples of the "chemotherapeutic agents" include alkylating agents, antimetabolites, anticancer antibiotics, plant-derived anticancer agents, and the like.

Examples of the "alkylating agents" include nitrogen mustard, nitrogen mustard-N-oxide hydrochloride, chlorambutyl, cyclophosphamide, ifosfamide, thiotepa, carboquone, improsulfan tosylate, busulfan, nimustine hydrochloride, mitobronitol, melphalan, dacarbazine, ranimustine, sodium estramustine phosphate, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, treosulphan, trophosphamide, zinostatin stimalamer, adozelesin, cystemustine, bizelesin, DDS preparations thereof, and the like.

Examples of the "antimetabolites" include mercaptopurine, 6-mercaptopurine riboside, thioinosine, methotrexate, pemetrexed, enocitabine, cytarabine, cytarabine ocfosfate, ancitabine hydrochloride, 5-FU drugs (e.g., fluorouracil, tegafur, UFT, doxifluridine, carmofur, gallocitabine, emitefur, capecitabine), aminopterine, nelzarabine, leucovorin calcium, tabloid, butocine, calcium folinate, levofolinate calcium, cladribine, emitefur, fludarabine, gemcitabine, hydroxycarbamide, pentostatin, piritrexim, idoxuridine, mitoguazone, thiazophrine, ambamustine, bendamustine, DDS preparations thereof, and the like.

Examples of the "anticancer antibiotics" include actinomycin-D, actinomycin-C, mitomycin-C, chromomycin-A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarcomycin, carzinophilin, mitotane, zorubicin hydrochloride, mitoxantrone hydrochloride, idarubicin hydrochloride, DDS preparations thereof, and the like.

Examples of the "plant-derived anticancer agents" include etoposide, etoposide phosphate, vinblastine sulfate, vincristine sulfate, vindesine sulfate, teniposide, paclitaxel, docetaxel, vinorelbine, DDS preparations thereof, and the like.

Examples of the "immunotherapeutic agents (BRM)" include picibanil, krestin, sizofuran, lentinan, ubenimex, interferons, interleukins, macrophage colony-stimulating factor, granulocyte colony-stimulating factor, erythropoietin, lymphotoxin, BCG vaccine, *Corynebacterium parvum*, levamisole, polysaccharide K, procodazole, anti-CTLA4 antibody, and the like.

Example of the "cell growth factors" in the "medicaments inhibiting the action of cell growth factors or cell growth factor receptors" include any substances that promote cell proliferation, which are normally peptides having not more than 20,000 molecular weight that are capable of exhibiting their activity at low concentrations by binding to a receptor, including (1) EGF (epidermal growth factor) or substances possessing substantially the same activity as EGF [e.g., TGFα], (2) insulin or substances possessing substantially the same activity as insulin [e.g., insulin, IGF (insulin-like growth factor)-1, IGF-2], (3) FGF (fibroblast growth factor) or substances possessing substantially the same activity as FGF [e.g., acidic FGF, basic FGF, KGF (keratinocyte growth factor). FGF-10], and (4) other cell growth factors [e.g., CSF (colony stimulating factor), EPO (erythropoietin), IL-2 (interleukin-2), NGF (nerve growth factor), PDGF (platelet-derived growth factor), TGFβ (transforming growth factor β), HGF (hepatocyte growth factor), VEGF (vascular endothelial growth factor), heregulin, angiopoietin].

Examples of the "cell growth factor receptors" include any receptors capable of binding to the aforementioned cell growth factors, including EGF receptor, heregulin receptor (HER3, etc.), insulin receptor inhibitor, IGF receptor-1, IGF receptor-2, FGF receptor-1 or FGF receptor-2, VEGF receptor, angiopoietin receptor (Tie2 etc.), PDGF receptor, c-MET, c-Kit, Trk and the like.

Examples of the "medicaments inhibiting the action of cell growth factors or cell growth factor receptors" include EGF inhibitor, TGFα inhibitor, heregulin inhibitor, insulin inhibitor, IGF inhibitor, FGF inhibitor, KGF inhibitor, CSF inhibitor, EPO inhibitor, IL-2 inhibitor, NGF inhibitor, PDGF inhibitor, TGFβ inhibitor, HGF inhibitor, VEGF inhibitor, angiopoietin inhibitor, EGF receptor inhibitor, HER2 inhibitor, HER4 inhibitor, insulin receptor, IGF-1 receptor inhibitor, IGF-2 receptor inhibitor, FGF receptor-1 inhibitor, FGF receptor-2 inhibitor, FGF receptor-3 inhibitor, FGF receptor-4 inhibitor, VEGF receptor inhibitor, Tie-2 inhibitor, PDGF receptor inhibitor, Abl inhibitor, Raf inhibitor, FLT3 inhibitor, c-Kit inhibitor, Src inhibitor, PKC inhibitor, Trk inhibitor, Ret inhibitor, mTOR inhibitor, MEK (MEK1/2) inhibitor, MET inhibitor, Akt inhibitor, ERK inhibitor and the like. More specifically, anti-VEGF antibody (Bevacizumab etc.), anti-HER2 antibody (Trastuzumab, Pertuzumab etc.), anti-EGFR antibody (Cetuximab, Panitumumab, Matuzumab, Nimotuzumab etc.), anti-VEGFR antibody, Imatinib mesylate, Erlotinib, Gefitinib, Sorafenib, Sunitinib, Dasatinib, Lapatinib, Vatalanib, 4-(4-fluoro-2-methyl-1H-indol-5-yloxy)-6-methoxy-7-[3-(1-pyrrolidinyl)propoxy]quinazoline (AZD-2171), Lestaurtinib, Pazopanib, Canertinib, Tandutinib, 3-(4-bromo-2,6-difluorobenzyloxy)-5-[3-[4-(1-pyrrolidinyl)butyl]ureido]isothiazole-4-carboxamide (CP-547632), Axitinib, N-(3,3-dimethyl-2,3-dihydro-1H-indol-6-yl)-2-(pyridin-4-ylmethylamino)pyridine-3-carboxamide (AMG-706), Nilotinib, 6-[4-(4-ethylpiperazin-1-ylmethyl)phenyl]-N-[1(R)-phenylethyl]-7H-pyrrolo[2,3-d]pyrimidin-4-amine (AEE-788), Vandetanib, Temsirolimus, Everolimus, Sirolimus, Enzastaurin, N-[4-[4-(4-methylpiperazin-1-yl)-6-(3-methyl-1H-pyrazol-5-ylamino)pyrimidin-2-ylsulfanyl]phenyl]cyclopropanecarboxamide (VX-680), 2-[N-[3-[4-[5-[N-(3-fluorophenyl)carbamoylmethyl]-1H-pyrazol-3-ylamino]quinazolin-7-yloxy]propyl]-N-ethylamino]ethyl phosphate (AZD-1152), 4-[9-chloro-7-(2,6-difluorophenyl)-5H-pyrimido[5,4-d][2]benzazepin-2-ylamino]benzoic acid (MLN-8054), N-[2-methoxy-5-[(E)-2-(2,4,6-trimethoxyphenyl)vinylsulfonylmethyl]phenyl]glycine sodium salt (ON-1910Na), 4-[8-cyclopentyl-7(R)-ethyl-5-methyl-6-oxo-5,6,7,8-tetrahydropteridin-2-ylamino]-3-methoxy-N-(1-methylpiperidin-4-yl)benzamide (BI-2536), 2-hydroxyethyl 5-(4-bromo-2-chlorophenylamino)-4-fluoro-1-methyl-1H-benzimidazole-6-carbohydroxamate (AZD-6244), N-[2(R),3-dihydroxypropoxy]-3,4-difluoro-2-(2-fluoro-4-iodophenylamino)benzamide (PD-0325901) and the like are used.

In addition to the aforementioned drugs, cell cycle inhibitors (e.g., Aurora A inhibitors, Aurora B inhibitors, PLK inhibitors, CDK inhibitors), pro-apoptotic agents (e.g., Bcl-2 inhibitors, IAP inhibitors, Nedd-8 inhibitors), proteasome inhibitors (e.g., bortezomib), (Hedgehog signal inhibitors (e.g., Vismodegib, LDE225, IPI-926), Wnt signal inhibitors (e.g., β-catenin/TCF inhibitors, anti-Wnt antibody), Notch signal inhibitors (e.g., antti-Notch antibody, γ-secretase inhibitors), L-asparaginase, aceglatone, procarbazine hydrochloride, protoporphyrin-cobalt complex salt, mercuric hematoporphyrin-sodium, topoisomerase I inhibitors (e.g., irinotecan, topotecan), topoisomerase II inhibitors (e.g., sobuzoxane), differentiation inducers (e.g., retinoid, vitamin D), other angiogenesis inhibitors (e.g., humagillin, shark extract, COX-2 inhibitor), α-blockers (e.g., tamsulosin hydrochloride), bisphosphonic acids (e.g., pamidronate, zoledronate), thalidomide, 5-azacytidine, decitabine, antitumor antibody such as anti-CD20 antibody and the like, toxin labeled antibody and the like can also be used.

By combining the compound of the present invention and a concomitant drug, a superior effect such as
(1) the dose can be reduced as compared to single administration of the compound of the present invention or a concomitant drug,
(2) the drug to be combined with the compound of the present invention can be selected according to the condition of patients (mild case, severe case and the like),
(3) the period of treatment can be set longer,
(4) a sustained treatment effect can be designed,
(5) a synergistic effect can be afforded by a combined use of the compound of the present invention and a concomitant drug, and the like, can be achieved.

In the present specification, the compound of the present invention and a concomitant drug used in combination are referred to as the "combination agent of the present invention".

For use of the combination agent of the present invention, the administration time of the compound of the present invention and the concomitant drug is not restricted, and the compound of the present invention and the concomitant drug can be administered to an administration subject simultaneously, or may be administered at different times. The dosage of the concomitant drug may be determined according to the dose clinically set, and can be appropriately selected depending on the administration subject, administration route, disease, combination and the like.

Examples of the administration mode of the combined use of the compound of the present invention and the concomitant drug include the following methods: (1) The compound of the present invention and the concomitant drug are simultaneously produced to give a single preparation, which is then administered. (2) The compound of the present invention and the concomitant drug are separately produced to give two kinds of preparations which are administered simultaneously by the same administration route. (3) The compound of the present invention and the concomitant drug are separately produced to give two kinds of preparations which are administered by the same administration route at different times. (4) The compound of the present invention and the concomitant drug are separately produced to give two kinds of preparations which are administered simultaneously by different administration routes. (5) The compound of the present invention and the concomitant drug are separately produced to give two kinds of preparations which are administered by different administration routes at different times (e.g., the compound of the present invention and the concomitant drug are administered in this order, or in the reverse order). The dose of the concomitant drug is appropriately determined in accordance with its clinical dose, and the ratio of the compound of the present invention and the concomitant drug is appropriately determined depending on the administration subject, administration route, target disease, symptom, combination, and the like. For example, when the administration subject is human, the concomitant drug is used in 0.01 to 100 (parts by weight), relative to 1 part by weight of the compound of the present invention.

The combination agent of the present invention has low toxicity and, for example, the compound of the present invention and/or the above-mentioned concomitant drug can be mixed, according to a method known per se, with a pharmacologically acceptable carrier to give pharmaceutical compositions, such as tablets (including sugar-coated tablet, film-coated tablet), powders, granules, capsules (including soft capsule), solutions, injections, suppositories, sustained release agents and the like, which can be safely administered orally or parenterally (e.g., local, rectum, venous). An injection can be administered by intravenous, intramuscular, subcutaneous or intra-organ administration, or directly to the lesion.

As a pharmacologically acceptable carrier which may be used for preparing the combination agent of the present invention, those similar to the aforementioned pharmacologically acceptable carriers, that can be used for the production of the pharmaceutical agent of the present invention, can be mentioned. Where necessary, the aforementioned additives that can be used for the production of the pharmaceutical agent of the present invention, such as preservatives, antioxidants, colorants, sweetening agents, adsorbents, wetting agents and the like can also be appropriately used in appropriate amounts.

The compounding ratio of the compound of the present invention to the concomitant drug in the combination agent of the present invention can be appropriately set depending on the administration subject, administration route, diseases and the like.

For example, the content of the compound of the present invention in the combination agent of the present invention varies depending on the dosage form, and is usually from about 0.01 to 100% by weight, preferably from about 0.1 to 50% by weight, further preferably from about 0.5 to 20% by weight, based on the entire preparation.

The content of the concomitant drug in the combination agent of the present invention varies depending on the dosage form, and is usually from about 0.01 to 90% by weight, preferably from about 0.1 to 50% by weight, further preferably from about 0.5 to 20% by weight, based on the entire preparation.

The content of additives in the combination agent of the present invention varies depending on the dosage form, and is usually from about 1 to 99.99% by weight, preferably from about 10 to 90% by weight, based on the entire preparation.

When the compound of the present invention and the concomitant drug are separately prepared, the same content may be adopted.

These preparations can be produced by a method known per se, which is generally employed in the preparation process.

For example, the compound of the present invention and the concomitant drug can be made into an aqueous injection together with a dispersing agent (e.g., Tween 80 (manufactured by Atlas Powder, US), HCO 60 (manufactured by Nikko Chemicals), polyethylene glycol, carboxymethylcellulose, sodium alginate, hydroxypropylmethylcellulose, dextrin), a stabilizer (e.g., ascorbic acid, sodium pyrosulfite), a surfactant (e.g., Polysorbate 80, macrogol), a solubilizer (e.g., glycerin, ethanol), a buffer (e.g., phosphoric acid and alkali metal salt thereof, citric acid and alkali metal salt thereof), an isotonizing agent (e.g., sodium chloride, potassium chloride, mannitol, sorbitol, glucose), a pH adjuster (e.g., hydrochloric acid, sodium hydroxide), a preservative (e.g., ethyl paraoxybenzoate, benzoic acid, methylparaben, propylparaben, benzyl alcohol), a dissolving agent (e.g., conc. glycerin, meglumine), a solubilizing agent (e.g., propylene glycol, sucrose), a soothing agent (e.g., glucose, benzyl alcohol), and the like, or can be dissolved, suspended or emulsified in a vegetable oil such as olive oil, sesame oil, cotton seed oil, corn oil and the like or a solubilizing agent such as propylene glycol and the like and prepared into an oily injection, whereby an injection is afforded.

In addition, an excipient (e.g., lactose, sucrose, starch), a disintegrating agent (e.g., starch, calcium carbonate), a binder (e.g., starch, gum arabic, carboxymethylcellulose, polyvinylpyrrolidone, hydroxypropylcellulose), a lubricant (e.g., talc, magnesium stearate, polyethylene glycol 6000) and the like may be added to the compound of the present invention or the concomitant drug, and the mixture can be compression-molded, according to a method known per se then if desirable, the molded product can be coated by a method known per se for the purpose of masking of taste, enteric property or durability, to give a preparation for oral administration. As the coating agent, for example, hydroxypropylmethylcellulose, ethylcellulose, hydroxymethylcellulose, hydroxypropylcellulose, polyoxyethylene glycol, Tween 80, Pluronic F68, cellulose acetate phthalate, hydroxypropylmethylcellulose phthalate, hydroxymethylcellulose acetate succinate, Eudoragit (methacrylic acid acrylic acid copolymer, manufactured by Rohm, DE), pigment (e.g., iron oxide red, titanium dioxide) and the like can be used. The preparation for oral administration may be any of an immediate-release preparation and a sustained release preparation.

Moreover, the compound of the present invention and the concomitant drug can be made into an oily or aqueous solid, semisolid or liquid suppository according to a method known per se, by mixing them with an oily substrate, aqueous substrate or aqueous gel substrate. As the above-mentioned oily substrate, for example, glycerides of higher fatty acid [e.g., cacao butter, Witepsols (manufactured by Dynamit Nobel, Germany)], glycerides of medium chain fatty acid [e.g., Miglyols (manufactured by Dynamit Nobel, Germany)], or vegetable oils (e.g., sesame oil, soybean oil, cotton seed oil), and the like are mentioned. Furthermore, as the aqueous substrate, for example, polyethylene glycol, propylene glycol and the like are mentioned, and as the aqueous gel substrate, for example, natural gums, cellulose derivatives, vinyl polymers, acrylic acid polymers and the like are mentioned.

As the above-mentioned sustained release preparation, sustained release microcapsules and the like are mentioned. The sustained release microcapsule can be produced by a method known per se, for example, a method shown in the following [2].

The compound of the present invention is preferably molded into a preparation for oral administration such as a solid preparation (e.g., powder, granule, tablet, capsule) and the like, or molded into a preparation for rectal administration such as a suppository and the like. Particularly, a preparation for oral administration is preferable.

The concomitant drug can be made into the above-mentioned drug form depending on the kind of the drug.

[1] An injection of the compound of the present invention or the concomitant drug, and preparation thereof, [2] a sustained release preparation or immediate-release preparation of the compound of the present invention or the concomitant drug, and preparation thereof, [3] a sublingual, buccal or intraoral quick integrating agent of the compound of the present invention or the concomitant drug, and preparation thereof, will be described below specifically.

[1] Injection and Preparation Thereof

An injection prepared by dissolving the compound of the present invention or the concomitant drug into water is preferable. This injection may be allowed to contain a benzoate and/or salicylate.

The injection is obtained by dissolving the compound of the present invention or the concomitant drug, and if desirable, a benzoate and/or salicylate, into water.

As the above-mentioned salts of benzoic acid and salicylic acid, for example, salts of alkali metals such as sodium, potassium and the like, salts of alkaline earth metals such as calcium, magnesium and the like, ammonium salts, meglumine salts, salts with organic bases such as tromethamol and the like, etc. are listed.

The concentration of the compound of the present invention or the concomitant drug in an injection is from 0.5 to 50 w/v %, preferably from about 3 to 20 w/v %. The concentration of a benzoate or/and salicylate is from 0.5 to 50 w/v %, preferably from about 3 to 20 w/v %.

The injection of the present invention appropriately contains additives usually used in an injection, for example, a stabilizer (e.g., ascorbic acid, sodium pyrosulfite), a surfactant (e.g., Polysorbate 80, macrogol), a solubilizer (e.g., glycerin, ethanol), a buffer (e.g., phosphoric acid and alkali metal salt thereof, citric acid and alkali metal salt thereof), an isotonizing agent (e.g., sodium chloride, potassium chloride), a dispersing agent (e.g., hydroxypropylmethylcellulose, dextrin), a pH regulator (e.g., hydrochloric acid, sodium hydroxide), a preservative (e.g., ethyl parahydroxybenzoate, benzoic acid), a dissolving agent (e.g., conc. glycerin, meglumine), a solubilizing agent (e.g., propylene glycol, sucrose), a soothing agent (e.g., glucose, benzyl alcohol), and the like. These additives are generally blended in a proportion usually used in an injection.

It is advantageous that pH of an injection be controlled from pH 2 to 12, preferably from pH 2.5 to 8.0, by addition of a pH regulator.

An injection is obtained by dissolving the compound of the present invention or the concomitant drug and if desirable, a benzoate and/or a salicylate, and if necessary, the above-mentioned additives into water. These may be dissolved in any order, and can be appropriately dissolved in the same manner as in a conventional method of producing an injection.

An aqueous solution for injection may be advantageously heated, alternatively, for example, filter sterilization, high pressure heat sterilization and the like can be conducted in the same manner as for a usual injection, to provide an injection.

It may be advantageous that an aqueous solution for injection is subjected to high pressure heat sterilization at 100 to 121° C. for 5 to 30 min.

Further, a preparation endowed with an antibacterial property of a solution may also be produced so that it can be used as a preparation which is divided and administered multiple-times.

[2] Sustained Release Preparation or Immediate-Release Preparation, and Preparation Thereof A sustained release preparation is preferable which is obtained, if desirable, by coating a nucleus containing the compound of the present invention or the concomitant drug with a film agent such as a water-insoluble substance, swellable polymer and the like. For example, a sustained release preparation for oral administration of once administration per day type is preferable.

As the water-insoluble substance used in a film agent, there are listed, for example, cellulose ethers such as ethylcellulose, butylcellulose and the like, cellulose esters such as cellulose acetate, cellulose propionate and the like, polyvinyl esters such as polyvinyl acetate, polyvinyl butyrate and the like, acrylic acid/methacrylic acid copolymers, methyl methacrylate copolymers, ethoxyethyl methacrylate/cinnamoethyl methacrylate/aminoalkyl methacrylate copolymers, polyacrylic acid, polymethacrylic acid, methacrylic acid alkylamide copolymers, poly(methyl methacrylate), polymethacrylate, polymethacrylamide, aminoalkyl methacrylate copolymers, poly(methacrylic anhydride), glycidyl methacrylate copolymer, particularly, acrylic acid-based polymers such as Eudoragit (Rohm Pharma) such as Eudoragit RS-100, RL-100, RS-30D, RL-30D, RL-PO, RS-PO (ethyl acrylate/methyl methacrylate/trimethylchloride methacrylate/ethyl ammonium copolymer), Eudoragit NE-30D (methyl methacrylate/ethyl acrylate copolymer), and the like, hydrogenated oils such as hydrogenated castor oil (e.g., LUBRI WAX; Freund Corporation)), waxes such as carnauba wax, fatty acid glycerin ester, paraffin and the like, polyglycerin fatty acid esters, and the like.

As the swellable polymer, polymers having an acidic dissociating group and showing pH dependent swell are preferable, and polymers having an acidic dissociating group, which manifest small swelling in acidic regions such as in stomach and large swelling in neutral regions such as in small intestine and large intestine, are preferable.

As such a polymer having an acidic dissociating group and showing pH dependent swell, cross-linkable polyacrylic acid polymers such as, for example, Carbomer 934P, 940, 941, 974P, 980, 1342 and the like, polycarbophil, calcium polycarbophil (all of which are manufactured by BF Goodrich), Hiviswako 103, 104, 105, 304 (all are manufactured by Wako Pure Chemical Industries, Ltd.), and the like, are listed.

The film agent used in a sustained release preparation may further contain a hydrophilic substance.

As the hydrophilic substance, for example, polysaccharides which may contain a sulfate group such as pullulan, dextrin, alkali metal alginate and the like, polysaccharides having a hydroxyalkyl or carboxyalkyl such as hydroxypropylcellulose, hydroxypropylmethylcellulose, carboxymethylcellulose sodium and the like, methylcellulose, polyvinylpyrrolidone, polyvinyl alcohol, polyethylene glycol and the like.

The content of a water-insoluble substance in the film agent of a sustained release preparation is from about 30 to about 90% (w/w), preferably from about 35 to about 80% (w/w), further preferably from about 40 to about 75% (w/w), the content of a swellable polymer is from about 3 to about 30% (w/w), preferably from about 3 to about 15% (w/w). The film agent may further contain a hydrophilic substance, and in which case, the content of a hydrophilic substance in the film agent is about 50% (w/w) or less, preferably about 5 to about 40% (w/w), further preferably from about 5 to about 35% (w/w). This % (w/w) indicates % by weight based on a film agent composition which is obtained by removing a solvent (e.g., water, lower alcohols such as methanol, ethanol and the like) from a film agent solution.

The sustained release preparation is produced by preparing a nucleus containing a drugs as exemplified below, then, coating the resulted nucleus with a film agent solution prepared by heat-solving a water-insoluble substance, swellable polymer and the like or by dissolving or dispersing it in a solvent.

I. Preparation of Nucleus Containing Drug

The form of nucleus containing a drug to be coated with a film agent (hereinafter, sometimes simply referred to as nucleus) is not particularly restricted, and preferably the nucleus is formed into particles such as a granule or fine particle.

When the nucleus is composed of granules or fine particles, the average particle size thereof is preferably from about 150 to about 2000 μm, further preferably from about 500 to about 1400 μm.

Preparation of the nucleus can be effected by a usual production method. For example, a suitable excipient, binding agent, disintegrating agent, lubricant, stabilizer and the like are mixed with a drug, and the mixture is subjected to a wet extrusion granulating method, fluidized bed granulating method or the like, to prepare a nucleus.

The content of drugs in a nucleus is from about 0.5 to about 95% (w/w), preferably from about 5.0 to about 80% (w/w), further preferably from about 30 to about 70% (w/w).

As the excipient contained in the nucleus, for example, saccharides such as sucrose, lactose, mannitol, glucose and the like, starch, crystalline cellulose, calcium phosphate, corn starch and the like are used. Among them, crystalline cellulose, corn starch are preferable.

As the binding agent, for example, polyvinyl alcohol, hydroxypropylcellulose, polyethylene glycol, polyvinyl pyrrolidone, Pluronic F68, gum Arabic, gelatin, starch and the like are used. As the disintegrating agent, for example, carboxymethylcellulose calcium (ECG505), croscarmelose sodium (Ac-Di-Sol), crosslinked polyvinylpyrrolidone (Crospovidone), low substituted hydroxypropylcellulose (L-HPC) and the like are used. Among them, hydroxypropylcellulose, polyvinylpyrrolidone, lower substituted hydroxypropylcellulose are preferable. As the lubricant and coagulation inhibitor, for example, talc, magnesium stearate and inorganic salts thereof are used, and as the lubricant, polyethylene glycol and the like are used. As the stabilizer, acids such as tartaric acid, citric acid, succinic acid, fumaric acid, maleic acid and the like, are used.

A nucleus can also be prepared by, in addition to the above-mentioned productions method, for example, a rolling granulation method in which a drug or a mixture of a drug with an excipient, lubricant and the like is added portionwise onto an inert carrier particle which is the core of the nucleus while spraying a binder dissolved in a suitable solvent such as water, lower alcohol (e.g., methanol, ethanol and the like) and the like, a pan coating method, a fluidized bed coating method or a melt granulating method. As the inert carrier particle, for example, those made of sucrose, lactose, starch, crystalline cellulose or waxes can be used, and the average particle size thereof is preferably from about 100 μm to about 1500 μm.

For separating a drug contained in a nucleus and a film agent, the surface of the nucleus may be coated with a protective agent. As the protective agent, for example, the above-mentioned hydrophilic substances, water-insoluble substances and the like are used. As the protective agent, preferably polyethylene glycol, and polysaccharides having a hydroxyalkyl or carboxyalkyl are used, more preferably hydroxypropylmethylcellulose and hydroxypropylcellulose are used. The protective agent may contain, as stabilizer, acids such as tartaric acid, citric acid, succinic acid, fumaric acid, maleic acid and the like, and lubricants such as talc and the like. When the protective agent is used, the coating amount is from about 1 to about 15% (w/w), preferably from about 1 to about 10% (w/w), further preferably from about 2 to about 8% (w/w), based on the nucleus.

The protective agent can be coated by a usual coating method, and specifically, the protective agent can be coated by spray-coating the nucleus, for example, by a fluidized bed coating method, pan coating method and the like.

II. Coating of Nucleus with Film Agent

A nucleus obtained in the above-mentioned step I is coated with a film agent solution obtained by heat-solving the above-mentioned water-insoluble substance and pH-dependent swellable polymer, and a hydrophilic substance, or by dissolving or dispersing them in a solvent, to give a sustained release preparation.

As the method for coating a nucleus with a film agent solution, for example, a spray coating method and the like are listed.

The composition ratio of a water-insoluble substance, swellable polymer or hydrophilic substance in a film agent solution is appropriately selected so that the contents of these components in a coated film are the above-mentioned contents, respectively.

The coating amount of a film agent is from about 1 to about 90% (w/w), preferably from about 5 to about 50% (w/w), further preferably from about 5 to about 35% (w/w), based on a nucleus (not including coating amount of protective agent).

As the solvent in a film agent solution, water or an organic solvent can be used alone or in admixture thereof. In the case of use in admixture, the mixing ratio of water to an organic solvent (water/organic solvent: by weight) can be varied in the range from 1 to 100%, and preferably from 1 to about 30%. The organic solvent is not particularly restricted providing it dissolves a water-insoluble substance, and for example, lower alcohols such as methyl alcohol, ethyl alcohol, isopropyl alcohol, n-butyl alcohol and the like, lower alkanone such as acetone and the like, acetonitrile, chloroform, methylene chloride and the like are used. Among them, lower alcohols are preferable, and ethyl alcohol and isopropyl alcohol are particularly preferable. Water, and a mixture of water with an organic solvent are preferably used as a solvent for a film agent. In this case, if necessary, an acid such as tartaric acid, citric acid, succinic acid, fumaric acid, maleic acid and the like may also be added into a film agent solution for stabilizing the film agent solution.

An operation of coating by spray coating can be effected by a usual coating method, and specifically, it can be effected by spray-coating a film agent solution onto a nucleus by a fluidized bed coating method, pan coating method and the like. In this case, if necessary, talc, titanium oxide, magnesium stearate, calcium stearate, light anhydrous silicic acid and the like may also be added as a lubricant, and glycerin fatty acid ester, hydrogenated castor oil, triethyl citrate, cetyl alcohol, stearyl alcohol and the like may also be added as a plasticizer.

After coating with a film agent, if necessary, an antistatic agent such as talc and the like may be mixed.

The immediate-release preparation may be liquid (solution, suspension, emulsion and the like) or solid (particle, pill, tablet and the like). As the immediate-release preparation, oral administration agents and parenteral administration agents such as an injection and the like are used, and oral administration agents are preferable.

The immediate-release preparation, usually, may contain, in addition to an active component drug, also carriers, additives and excipients conventionally used in the pharmaceutical field (hereinafter, sometimes abbreviated as excipient). The excipient used is not particularly restricted providing it is an excipient ordinarily used as a preparation excipient. For example, as the excipient for an oral solid preparation, lactose, starch, corn starch, crystalline cellulose (Avicel PH101, manufactured by Asahi Kasei Corporation, and the like), powder sugar, granulated sugar, mannitol, light anhydrous silicic acid, magnesium carbonate, calcium carbonate, L-cysteine and the like are listed, and preferably corn starch and mannitol and the like are listed. These excipients can be used alone or in combination of two or more. The content of the excipient is, for example, from about 4.5 to about 99.4 w/w %, preferably from about 20 to about 98.5 w/w %, further preferably from about 30 to about 97 w/w %, based on the total amount of the immediate-release preparation.

The content of a drug in the immediate-release preparation can be appropriately selected in the range from about 0.5 to about 95w/w %, preferably from about 1 to about 60 w/w % based on the total amount of the immediate-release preparation.

When the immediate-release preparation is an oral solid preparation, it usually contains, in addition to the above-mentioned components, also an integrating agent. As this integrating agent, for example, carboxymethylcellulose calcium (ECG-505, manufactured by Gotoku Yakuhin), croscarmelose sodium (e.g., Actisol, manufactured by Asahi Kasei Corporation), crospovidone (e.g., Kollidon CL, manufactured by BASF), low substituted hydroxypropylcellulose (Shin-Etsu Chemical Co., Ltd.), carboxymethylstarch (Matsutani Kagaku K. K.), carboxymethylstarch sodium (Exprotab, manufactured by Kimura Sangyo), partially pregelatinized starch (PCS, manufactured by Asahi Kasei Corporation), and the like are used, and for example, those which disintegrate a granule by absorbing water in contact with water, causing swelling, or making a channel between an effective ingredient and an excipient constituting the nucleus, can be used. These disintegrating agents can be used alone or in combination of two or more. The amount of the disintegrating agent used is appropriately selected depending on the kind and blending amount of a drug used, design of releasing property, and the like, and for example, from about 0.05 to about 30 w/w %, preferably from about 0.5 to about 15 w/w %, based on the total amount of the immediate-release preparation.

When the immediate-release preparation is an oral solid preparation, it may further contain, in addition to the above-mentioned composition, if desired, additives conventional in solid preparations. As such an additive, there are used, for example, a binder (e.g., sucrose, gelatin, gum Arabic powder, methylcellulose, hydroxypropylcellulose, hydroxypropylmethylcellulose, carboxymethylcellulose, polyvinylpyrrolidone, pullulan, dextrin and the like), a lubricant (e.g., polyethylene glycol, magnesium stearate, talc, light anhydrous silicic acid (e.g., Aerosil (Nippon Aerosil))), a surfactant (e.g., anionic surfactants such as sodium alkylsulfate and the like, nonionic surfactants such as polyoxyethylene fatty acid ester and polyoxyethylene sorbitan fatty acid ester, polyoxyethylene castor oil derivatives and the like), a colorant (e.g., tar coloring matter, caramel, iron oxide red, titanium oxide, riboflavins), if necessary, an appetizing agent (e.g., sweetening agent, flavoring agent and the like), an adsorbent, preservative, wetting agent, antistatic agent, and the like. Further, as the stabilizer, an organic acid such as tartaric acid, citric acid, succinic acid, fumaric acid and the like may also be added.

As the above-mentioned binder, hydroxypropylcellulose, polyethylene glycol and polyvinylpyrrolidone and the like are preferably used.

The immediate-release preparation can be prepared by, based on a usual technology of producing preparations, mixing the above-mentioned components, and if necessary, further kneading the mixture, and molding it. The above-mentioned mixing is conducted by generally used methods, for example, mixing, kneading and the like. Specifically, when a immediate-release preparation is formed, for example, into a particle, it can be prepared, according to the same means as in the above-mentioned method for preparing a nucleus of a sustained release preparation, by mixing the components using a vertical granulator, universal kneader (manufactured by Hata Tekkosho), fluidized bed granulator FD-5S (manufactured by Powrex Corporation), and the like, and then, granulating the mixture by a wet extrusion granulation method, fluidized bed granulation method and the like.

Thus obtained immediate-release preparation and sustained release preparation may be themselves made into products or made into products appropriately together with preparation excipients and the like, separately, by an ordinary method, then, may be administered simultaneously or may be administered in combination at any administration interval, or they may be themselves made into one preparation for oral administration (e.g., granule, fine particle, tablet, capsule) or made into one preparation for oral administration appropriately together with preparation excipients and the like. It may also be permissible that they are made into granules or fine particles, and filled in the same capsule to be used as a preparation for oral administration.

[3] Sublingual, Buccal or Intraoral Quick Disintegrating Agent and Preparation Thereof Sublingual, buccal or intraoral quick disintegrating agents may be a solid preparation such as tablet and the like, or may be an oral mucosa membrane patch (film).

As the sublingual, buccal or intraoral quick disintegrating agent, a preparation containing the compound of the present invention or the concomitant drug and an excipient is preferable. It may contain also auxiliary agents such as a lubricant, isotonizing agent, hydrophilic carrier, water-dispersible polymer, stabilizer and the like. Further, for easy absorption and increased in vivo use efficiency, $\beta$-cyclodextrin or $\beta$cyclodextrin derivatives (e.g., hydroxypropyl-$\beta$-cyclodextrin) and the like may also be contained.

As the above-mentioned excipient, lactose, sucrose, D-mannitol, starch, crystalline cellulose, light anhydrous silicic acid and the like are listed. As the lubricant, magnesium stearate, calcium stearate, talc, colloidal silica and the like are listed, and particularly, magnesium stearate and colloidal silica are preferable. As the isotonizing agent, sodium chloride, glucose, fructose, mannitol, sorbitol, lactose, saccharose, glycerin, urea and the like are listed, and particularly, mannitol is preferable. As the hydrophilic carrier, swellable hydrophilic carriers such as crystalline cellulose, ethylcellulose, crosslinkable polyvinylpyrrolidone, light anhydrous silicic acid, silicic acid, dicalcium phosphate, calcium carbonate and the like are listed, and particularly, crystalline cellulose (e.g., microcrystalline cellulose) is preferable. As the water-dispersible polymer, gums (e.g., gum tragacanth, acacia gum, cyamoposis gum), alginates (e.g., sodium alginate), cellulose derivatives (e.g., methylcellulose, carboxymethylcellulose, hydroxymethylcellulose, hydroxypropylcellulose, hydroxypropylmethylcellulose), gelatin, water-soluble starch, polyacrylic acids (e.g., Carbomer), polymethacylic acid, polyvinyl alcohol, polyethylene glycol, polyvinylpyrrolidone, polycarbophil, ascorbic acid, palmitates and the like are listed, and hydroxypropylmethylcellulose, polyacrylic acid, alginate, gelatin, carboxymethylcellulose, polyvinylpyrrolidone, polyethylene glycol and the like are preferable. Particularly, hydroxypropylmethylcellulose is preferable. As the stabilizer, cysteine, thiosorbitol, tartaric acid, citric acid, sodium carbonate, ascorbic acid, glycine, sodium sulfite and the like are listed, and particularly, citric acid and ascorbic acid are preferable.

The sublingual, buccal or intraoral quick disintegrating agent can be produced by mixing the compound of the present invention or the concomitant drug and an excipient by a method known per se. Further, if desired, the above-mentioned auxiliary agents such as a lubricant, isotonizing agent, hydrophilic carrier, water-dispersible polymer, stabilizer, colorant, sweetening agent, preservative and the like may be mixed. The sublingual, buccal or intraoral quick disintegrating agent is obtained by mixing the above-mentioned components simultaneously or at a time interval, then subjecting the mixture to tablet-making molding under pressure. For obtaining suitable hardness, it may also be permissible that the materials are moistened by using a solvent such as water, alcohol and the like if desired before and after the tablet making process, and after the molding, the materials are dried, to obtain a product.

In the case of molding into a mucosa membrane patch (film), the compound of the present invention or the concomitant drug and the above-mentioned water-dispersible polymer (preferably hydroxypropylcellulose, hydroxypropylmethyl-cellulose), excipient and the like are dissolved in a solvent such as water and the like, and the resulted solution is cast to give a film. Further, additives such as a plasticizer, stabilizer, antioxidant, preservative, colorant, buffer, sweetening agent and the like may also be added. For imparting suitable elasticity to the film, glycols such as polyethylene glycol, propylene glycol and the like may be contained, or for enhancing adhesion of the film to an intraoral mucosa membrane lining, a bio-adhesive polymer (e.g., polycarbophil, carbopol) may also be contained. In the casting, a solution is poured on the non-adhesive surface, spread to uniform thickness (preferably about 10 to 1000 micron) by an application tool such as a doctor blade and the like, then, the solution is dried to form a film. It may be advantageous that thus formed film is dried at room temperature or under heat, and cut into a desired area.

As the preferable intraoral quick disintegrating agent, there are listed solid quick scattering dose agents composed of a network body comprising the compound of the present invention or the concomitant drug, and a water-soluble or water-diffusible carrier which is inert to the compound of the present invention or concomitant drug, are listed. This network body is obtained by sublimating a solvent from the solid composition constituted of a solution prepared by dissolving the compound of the present invention or the concomitant drug in a suitable solvent.

It is preferable that the composition of an intraoral quick disintegrating agent contains a matrix forming agent and a secondary component, in addition to the compound of the present invention or the concomitant drug.

Examples of the matrix forming agent include gelatins, dextrins, animal proteins or vegetable proteins such as soybean, wheat and psyllium seed protein and the like; rubber substances such as gum Arabic, guar gum, agar, xanthan and the like; polysaccharides; alginic acids; carboxymethylcelluloses; carageenans; dextrans; pectines; synthetic polymers such as polyvinylpyrrolidone and the like; substances derived from a gelatin-gum Arabic complex, and the like. Further, saccharides such as mannitol, dextrose, lactose, galactose, trehalose and the like; cyclic saccharides such as cyclodextrin and the like; inorganic salts such as sodium phosphate, sodium chloride and aluminum silicate and the like; amino acids having 2 to 12 carbon atoms such as glycine, L-alanine, L-aspartic acid, L-glutamic acid, L-hydroxyproline, L-isoleucine, L-leucine, L-phenylalanine and the like, are contained.

One or more of the matrix forming agents can be introduced in a solution or suspension before solidification. Such as matrix forming agent may be present in addition to a surfactant, or may be present while a surfactant being excluded. The matrix forming agents aid to maintain the compound of the present invention or the concomitant drug in the solution or suspension in diffused condition, in addition to formation of the matrix.

The composition may contain secondary components such as a preservative, antioxidant, surfactant, thickening agent, colorant, pH controlling agent, flavoring agent, sweetening agent, food taste masking agent and the like. As the suitable colorant, there are listed red, black and yellow iron oxides, and FD & C dyes such as FD & C Blue 2, FD & C Red 40 and the like manufactured by Ellis and Everard. Examples of the suitable flavoring agent include mint, raspberry, licorice, orange, lemon, grapefruit, caramel, vanilla, cherry, grape flavor and combinations thereof. Examples of the suitable pH controlling agent include citric acid, tartaric acid, phosphoric acid, hydrochloric acid and maleic acid. Examples of the suitable sweetening agent include aspartame, acesulfame K and thaumatin and the like. Examples of the suitable food taste masking agent include sodium bicarbonate, ion exchange resin, cyclodextrin-inclusion compounds, adsorbent substances and microcapsulated apomorphine.

The preparation contains the compound of the present invention or the concomitant drug in an amount usually from about 0.1 to about 50% by weight, preferably from about 0.1 to about 30% by weight, and preferable are preparations (such as the above-mentioned sublingual agent, buccal and the like) which can dissolve 90% or more of the compound of the present invention or the concomitant drug (into water) within the time range of about 1 to about 60 min, preferably of about 1 to about 15 min, more preferably of about 2 to about 5 min, and intraoral quick disintegrating preparations which are disintegrated within the range of 1 to 60 sec, preferably of 1 to 30 sec, further preferably of 1 to 10 sec, after placed in an oral cavity.

The content of the above-mentioned excipient in the whole preparation is from about 10 to about 99% by weight, preferably from about 30 to about 90% by weight. The content of $\beta$-cyclodextrin or $\beta$-cyclodextrin derivative in the whole preparation is from 0 to about 30% by weight. The content of the lubricant in the whole preparation is from about 0.01 to about 10% by weight, preferably from about 1 to about 5% by weight. The content of the isotonizing agent in the whole preparation is from about 0.1 to about 90% by weight, preferably from about 10 to about 70% by weight. The content of the hydrophilic carrier in the whole preparation is from about 0.1 to about 50% by weight, preferably from about 10 to about 30% by weight. The content of the water-dispersible polymer in the whole preparation is from about 0.1 to about 30% by weight, preferably from about 10 to about 25% by weight. The content of the stabilizer in the whole preparation is from about 0.1 to about 10% by weight, preferably from about 1 to 5% by weight. The above-mentioned preparation may further contain additives such as a colorant, sweetening agent, preservative and the like, if necessary.

The dosage of a combination agent of the present invention differs depending on the kind of a compound of the present invention, age, body weight, condition, drug form, administration method, administration period and the like, and for example, for one cancer patient (adult, body weight: about 60 kg), the combination agent is administered intravenously, at a dose of about 0.01 to about 1000 mg/kg/day, preferably about 0.01 to about 100 mg/kg/day, more preferably about 0.1 to about 100 mg/kg/day, particularly about 0.1 to about 50 mg/kg/day, especially about 1.5 to about 30 mg/kg/day, in terms of the compound of the present invention or the concomitant drug, respectively, once or several times in division a day. Of course, since the dose as described above varies depending on various conditions, amounts smaller than the above-mentioned dosage may sometimes be sufficient, further, amounts over that range sometimes have to be administered.

The amount of the concomitant drug can be set at any value unless side effects are problematical. The daily dosage in terms of the concomitant drug differs depending on the severity of the symptom, age, sex, body weight, sensitivity difference of the administration subject, administration period, interval, and nature, pharmacy, kind of the pharmaceutical preparation, kind of effective ingredient, and the like, and not particularly restricted, and the amount of a drug is, in the case of oral administration for example, usually from about 0.001 to 2000 mg, preferably from about 0.01 to 500 mg, further preferably from about 0.1 to 100 mg, per 1 kg body weight of a mammal, which is usually administered once to 4-times in division a day.

In administration of a combination agent of the present invention, the compound of the present invention may be administered after administration of the concomitant drug or the concomitant drug may be administered after administration of the compound of the present invention, though they may be administered simultaneously. When administered at a time interval, the interval differs depending on the effective ingredient to be administered, drug form and administration method, and for example, when the concomitant drug is administered first, a method in which the compound of the present invention is administered within time range of from 1 min to 3 days, preferably from 10 min to 1 day, more preferably from 15 min to 1 hr after administration of the concomitant drug is exemplified. When the compound of the present invention is administered first, a method in which the concomitant drug is administered within time range of from 1 min to 1 day, preferably from 10 min to 6 hrs, more preferably from 15 min to 1 hr after administration of the compound of the present invention is exemplified.

In a preferable administration method, for example, the concomitant drug which has been molded into an oral administration preparation is administered orally at a daily dose of about 0.001 to 200 mg/kg, and about 15 min later, the compound of the present invention which has been molded into an oral administration preparation is administered orally at a daily dose of about 0.005 to 100 mg/kg.

Furthermore, the compound of the present invention or the combination agent of the present invention can be used concurrently with a non-drug therapy. To be precise, the compound of the present invention or the combination agent of the present invention can be combined with a non-drug therapy such as (1) surgery, (2) hypertensive chemotherapy using angiotensin II etc., (3) gene therapy, (4) thermotherapy, (5) cryotherapy, (6) laser cauterization, (7) radiotherapy, and the like.

For example, by using the compound of the present invention or the combination agent of the present invention before or after an surgery and the like, or before or after a combined treatment of two or three kinds thereof, effects such as prevention of emergence of resistance, prolongation of Disease-Free Survival, suppression of cancer metastasis or recurrence, prolongation of life and the like can be afforded.

In addition, it is possible to combine a treatment with the compound of the present invention or the combination agent of the present invention with a supportive therapy [(i) administration of antibiotic (e.g., β-lactam type such as pansporin and the like, macrolide type such as clarithromycin and the like) for the complication with various infectious diseases, (ii) administration of high-calorie transfusion, amino acid preparation or general vitamin preparation for the improvement of malnutrition, (iii) administration of morphine for pain mitigation, (iv) administration of a pharmaceutical agent for ameliorating side effects such as nausea, vomiting, anorexia, diarrhea, leucopenia, thrombocytopenia, decreased hemoglobin concentration, hair loss, hepatopathy, renopathy, DIC, fever and the like and (v) administration of a pharmaceutical agent for suppressing multiple drug resistance of cancer and the like].

Preferably, the compound of the present invention or the combination agent of the present invention is administered orally (including sustained-release preparations), intravenously (including boluses, infusions and clathrates), subcutaneously and intramuscularly (including boluses, infusions and sustained-release preparations), transdermally, intratumorally or proximally before or after the above-described treatment is conducted.

As a period for administering the compound of the present invention or the combination agent of the present invention before the surgery, etc., for example, it can be administrated 1-time about 30 min to 24 hrs before the surgery, etc., or in 1 to 3 cycles about 3 months to 6 months before the surgery, etc. In this way, the surgery, etc. can be conducted easily because, for example, a cancer tissue would be reduced by administering the compound of the present invention or the combination agent of the present invention before the surgery, and the like.

As a period for administering the compound of the present invention or the combination agent of the present invention after the surgery, etc., for example, it can be administrated repeatedly per a few weeks to 3 months, about 30 min to 24 hrs after the surgery, and the like. In this way, it enhances the effect of the surgery, etc. by administering the compound of the present invention or the combination agent of the present invention after the surgery, and the like.

EXAMPLES

The present invention is explained in detail in the following by referring to Reference Examples, Examples, Formulation Examples and Experimental Examples, which are not to be construed as limitative.

In the Reference Examples and Examples, the purity of the compounds was measured under the following HPLC conditions.
measurement device: SHIMADZU Corporation LC-10 Avp system
column: CAPSEL PAK C18UG120 S-3 μm, 2.0×50 mm
solvent: Solution A; 0.1% trifluoroacetic acid-containing water,
Solution B; 0.1% trifluoroacetic acid-containing acetonitrile
gradient cycle: 0.00 min (Solution A/Solution B=90/10), 4.00 min (Solution A/Solution B=5/95), 5.50 min (Solution A/Solution B=5/95), 5.51 min (Solution A/Solution B=90/10), 8.00 min (Solution A/Solution B=90/10)
injection volume: 2 μl
flow rate: 0.5 ml/min
detection method: UV 220 nm In the Reference Examples and Examples, the purification of the compounds by preparative HPLC was performed under the following conditions.
measurement device: Gilson Company Inc., High Throughput Purification System
column: YMC CombiPrep ODS-A, S-5 μm, 50×20 mm
detection method: UV 220 nm solvent: Solution A; 0.1% trifluoroacetic acid-containing water,
Solution B; 0.1% trifluoroacetic acid-containing acetonitrile
gradient cycle: representative example 0.00 min (SOLUTION A/SOLUTION B=98/2), 1.00 min (SOLUTION A/SOLUTION B=98/2), 5.20 min (SOLUTION A/SOLUTION B=0/100), 6.40 min (SOLUTION A/SOLUTION B=0/100), 6.50 min (SOLUTION A/SOLUTION B=98/2), 6.60 min (SOLUTION A/SOLUTION B=98/2), flow rate: 25 mL/min, or,
0.00 min (SOLUTION A/SOLUTION B=90/10), 1.00 min (SOLUTION A/SOLUTION B=90/10), 4.00 min (SOLUTION A/SOLUTION B=10/95), 8.50 min (SOLUTION A/SOLUTION B=10/95), 8.60 min (SOLUTION A/SOLUTION B=90/10), 8.70 min (SOLUTION A/SOLUTION B=90/10), flow rate: 20 mL/min In the Reference Examples and Examples, mass spectrum (MS) was measured under the following conditions.
measurement device: Micromass platform II or Waters ZMD
ionization method: Atmospheric Pressure Chemical Ionization (APCI) or electron impact ionization method (Electron Spray Ionization: ESI)

In Reference Example and Example, HPLC-mass spectrum (LC-MS) was measured under the following conditions.
measurement device: Micromass ZMD, Agilent Technologies HP1100 and 1200 LC/MSD
column: CAPCELL PAK C18UG120, S-3 μm, 1.5×35 mm
solvent: SOLUTION A; 0.05% trifluoroacetic acid-containing water,
SOLUTION B; 0.04% trifluoroacetic acid-containing acetonitrile
gradient cycle: 0.00 min (SOLUTION A/SOLUTION B=90/10), 2.00 min (SOLUTION A/SOLUTION B=5/95), 2.75 min (SOLUTION A/SOLUTION B=5/95), 2.76 min (SOLUTION A/SOLUTION B=90/10), 3.45 min (SOLUTION A/SOLUTION B=90/10)
injection volume: 2 μL, flow rate: 0.5 mL/min, detection method: UV 220 nm
ionization method: electron impact ionization method (Electron Spray Ionization: ESI)

$^1$H NMR spectrum was measured using tetramethylsilane as the internal standard by AVANCE DPX-300 (300 MHz) manufactured by Bruker, AV-300M (300 MHz) manufactured by Bruker and VARIAN Mercury-300 (300 MHz), and all δ values were shown by ppm.

As the Microwave reaction apparatus, Emrys Optimizer, Biotage Japan Ltd. was used.

Unless otherwise specified, the numerical value of mixed solvent shows a volume mixing ratio of each solvent. Unless otherwise specified, % means weight %. While the room temperature (ambient temperature) in the present specification means a temperature of from about 10° C. to about 35° C., it is not particularly strictly limited.

Other abbreviations used in the specification mean the following:
s: singlet
d: doublet
t: triplet
q: quartet
m: multiplet
br: broad
J: coupling constant
Hz: hertz
CDCl$_3$: deuterated chloroform
DMSO-d$_6$: dimethyl sulfoxide-d$_6$
CD$_3$OD: deuterated methanol
$^1$H-NMR: proton nuclear magnetic resonance
DMF: N,N-dimethylformamide
THF: tetrahydrofuran
WSCD: water-soluble carbodiimide (1-ethyl-3-(3-dimethylaminopropyl)carbodiimide) hydrochloride
HOBt: 1-hydroxybenzotriazole
mCPBA: m-chloroperbenzoic acid
CDI: N,N'-carbonyldiimidazole
DMT-MM: 4-(4,6-dimethoxy-1,3,5-triazin-2-yl)-4-methylmorpholinium chloride
DPPA: diphenylphosphoryl azide
MeCN: acetonitrile
TFA: trifluoroacetic acid
Pd(PPh$_3$)$_4$: tetrakis(triphenylphosphine)palladium(0)
Pd$_2$dba$_3$: tris(dibenzylideneacetone)dipalladium(0)
PdCl$_2$(dppf).CH$_2$Cl$_2$: [1,1-bis(diphenylphosphino)ferrocene]palladium(II) chloride dichloromethane complex
Xantphos: 4,5'-bis(diphenylphosphino)-9,9'-dimethylxanthene binap: (+/−)-2,2'-bis(diphenylphosphino)-1,1'-binaphthyl
Me: methyl
Et: ethyl
HATU: O-(7-azabenzotriazol-1-yl)-N,N,N',N'-tetramethyluronium hexafluorophosphate
DIPEA: diisopropylethylamine Reference Example 1

Production of methyl(2Z)-3-amino-2-pentenoate

A mixture of methyl 3-oxovalerate (75.0 g, 576 mmol), ammonium acetate (222 g, 2.88 mol) and methanol (750 mL) was stirred at room temperature for 3 days. After concentration under reduced pressure, water (500 mL) was added to the residue and the mixture was extracted with ethyl acetate (200 mL). The extract was washed with brine, dried over magnesium sulfate, concentrated under reduced pressure, and dried to give the title compound (68.5 g, 92%) as a pale-yellow oil.
$^1$H NMR (300 MHz, DMSO-d$_6$) δ: 1.06 (3H, t, J=7.6 Hz), 2.09 (2H, q, J=7.6 Hz), 3.49 (3H, s), 4.34 (1H, s), 6.94 (1H, s), 7.72 (1H, br s).

Reference Example 2

Production of ethyl 6-ethyl-4-hydroxy-2-oxo-1,2-dihydropyridine-3-carboxylate

To a solution of the compound of Reference Example 1 (50.0 g, 387 mmol) and diethyl malonate (58.8 mL, 387 mmol) in ethanol (400 mL) was added 20% ethanol solution (133 g) of sodium ethoxide, and the mixture was stirred while evaporating ethanol at 150° C. for 15 hr. After cooling, the obtained solid was collected by filtration, washed with ethyl acetate, and dissolved in water. The insoluble material was filtered off, and the filtrate was acidified with 5N hydrochloric acid, and the precipitated solid was collected by filtration. The obtained solid was washed with water and ethyl acetate-hexane to give the title compound (36.4 g, 45%) as a white powder.
$^1$H NMR (300 MHz, DMSO-d$_6$) δ: 1.12 (3H, t, J=7.6 Hz), 1.26 (3H, t, J=7.1 Hz), 2.42 (2H, q, J=7.6 Hz), 4.25 (2H, q, J=7.0 Hz), 5.79 (1H, s), 11.37 (1H, br s), 12.57 (1H, s).

Reference Example 3

Production of ethyl 4-chloro-6-ethyl-2-oxo-1,2-dihydropyridine-3-carboxylate

A mixture of the compound of Reference Example 2 (15.0 g, 71.0 mmol) and phosphorus oxychloride (19.9 mL, 213 mmol) was stirred at 80° C. for 30 min. The mixture was concentrated under reduced pressure, and ice water was added to the residue. The precipitated solid was collected by filtration, and washed with water and ethyl acetate to give the title compound (9.80 g, 60%) as a white solid.

$^1$H NMR (300 MHz, DMSO-$d_6$) δ: 1.15 (3H, t, J=7.5 Hz), 1.26 (3H, t, J=7.0 Hz), 2.44-2.55 (2H, m), 4.25 (2H, q, J=7.1 Hz), 6.26 (1H, s), 12.28 (1H, s).

Reference Example 4

Production of ethyl 6-ethyl-2-oxo-1,2-dihydropyridine-3-carboxylate

A mixture of the compound of Reference Example 3 (32.1 g, 140 mmol), triethylamine (39 mL, 280 mmol), 10% palladium-carbon (water-containing product, 1.60 g), ethanol (180 mL) and THF (180 mL) was stirred at room temperature for 5 hr under a hydrogen atmosphere. The catalyst was filtered off, and washed with methanol, and the filtrate was concentrated under reduced pressure. To the residue was added ethyl acetate, the insoluble material was filtered off, and washed with ethyl acetate. The filtrate was washed with water containing 6N hydrochloric acid (1 ml). The aqueous layer was extracted with ethyl acetate. The combined ethyl acetate layer was washed with brine, dried over magnesium sulfate, and concentrated under reduced pressure. The obtained solid was collected by filtration, and washed with ethyl acetate-hexane to give the title compound (24.66 g, 90%) as a brown powder.

$^1$H NMR (300 MHz, CDCl$_3$) δ: 1.32 (3H, t, J=7.6 Hz), 1.38 (3H, t, J=7.2 Hz), 2.74 (2H, q, J=7.6 Hz), 4.37 (2H, q, J=7.2 Hz), 6.29 (1H, d, J=7.2 Hz), 8.18 (1H, d, J=7.6 Hz), 12.50 (1H, br s).

Reference Example 5

Production of ethyl 5-bromo-6-ethyl-2-oxo-1,2-dihydropyridine-3-carboxylate

A solution of the compound of Reference Example 4 (17.5 g, 89.7 mmol) in DMF (100 mL) was cooled to 0° C., N-bromosuccinimide (16.0 g, 89.9 mmol) was added thereto, and the mixture was stirred at room temperature for 1 hr. To the reaction mixture was added dropwise water (250 mL) at 0° C., and the mixture was stirred at room temperature for 30 min. The precipitate was collected by filtration, and washed with water to give the title compound (21.2 g, 86%) as a brown powder.

$^1$H NMR (300 MHz, DMSO-$d_6$) δ: 1.14 (3H, t, J=7.6 Hz), 1.26 (3H, t, J=7.2 Hz), 2.64 (2H, q, J=7.6 Hz), 4.20 (2H, q, J=7.2 Hz), 8.06 (1H, s), 12.42 (1H, br s).

Reference Example 6

Production of ethyl 5-bromo-2-chloro-6-ethylpyridine-3-carboxylate

A mixture of the compound of Reference Example 5 (28.0 g, 102 mmol) and phosphorus oxychloride (28 mL, 309 mmol) was stirred with heating under reflux for 12 hr. The reaction mixture was concentrated under reduced pressure, ice water (100 mL) was added to the residue at 0° C., and the mixture was extracted with ethyl acetate (100 mL×3). The extract was washed successively with saturated aqueous sodium hydrogen carbonate solution (50 mL×2) and brine, dried over anhydrous magnesium sulfate, and concentrated under reduced pressure. The residue was purified by silica gel column chromatography (eluent, hexane:ethyl acetate=99:1→9:1) to give the title compound (22.8 g, 76%) as a pale-yellow oil.

$^1$H NMR (300 MHz, DMSO-$d_6$) δ: 1.22 (3H, t, J=7.5 Hz), 1.33 (3H, t, J=7.2 Hz), 2.91 (2H, q, J=7.5 Hz), 4.34 (2H, q, J=7.2 Hz), 8.42 (1H, s).

Reference Example 7

Production of ethyl 5-bromo-6-ethyl-3-hydroxy-1-methyl-1H-pyrrolo[2,3-b]pyridine-2-carboxylate A mixture of the compound of Reference Example 6 (22.8 g, 78.0 mmol), ethyl sarcosinate hydrochloride (18.0 g, 117 mmol), triethylamine (54 mL, 387 mmol) and ethanol (200 mL) was stirred with heating under reflux for 22 hr. Then, ethyl sarcosinate hydrochloride (6.00 g, 39.1 mmol) and triethylamine (22 mL, 158 mmol) were added thereto, and the mixture was stirred with heating under reflux for 17 hr. To the reaction mixture was added water (250 mL), and the mixture was extracted with ethyl acetate (300 mL×3). The extract was washed successively with water (100 mL) and brine (100 mL), and dried over anhydrous magnesium sulfate. The insoluble material was removed by filtration, and the filtration was concentrated under reduced pressure. To the residue were added ethanol (200 mL) and a 20% ethanol solution (32.0 g, 94.0 mmol) of sodium ethoxide, and the mixture was stirred at room temperature for 1 hr. The reaction mixture was concentrated under reduced pressure, and to the residue was added water (250 mL), and the mixture was acidified with 5N hydrochloric acid (20 mL). The precipitate was collected by filtration, and washed with water to give the title compound (18.8 g, 73%) as a pale-orange solid.

$^1$H NMR (300 MHz, DMSO-$d_6$) δ: 1.27 (3H, t, J=7.6 Hz), 1.33 (3H, t, J=7.1 Hz), 2.96 (2H, q, J=7.6 Hz), 3.88 (3H, s), 4.33 (2H, q, J=7.1 Hz), 8.36 (1H, s), 9.76 (1H, br s).

Reference Example 8

Production of ethyl 5-bromo-6-ethyl-1-methyl-3-(2,2,2-trifluoroethoxy)-1H-pyrrolo[2,3-b]pyridine-2-carboxylate A solution of the compound of Reference Example 7 (1.50 g, 4.58 mmol) in DMF (20 mL) was cooled to 0° C., cesium carbonate (1.78 g, 5.46 mmol) and 2,2,2-trifluoroethyl trifluoromethanesulfonate (0.727 mL, 5.04 mmol) were added thereto, and the mixture was stirred at room temperature for 1 hr. To the mixture was added water (100 mL), and the precipitate was collected by filtration, and washed with water to give the title compound (1.80 g, 96%) as a pale-yellow powder.

$^1$H NMR (300 MHz, DMSO-$d_6$) δ: 1.22-1.41 (6H, m), 3.00 (2H, q, J=7.4 Hz), 3.96 (3H, s), 4.35 (2H, q, J=7.1 Hz), 4.86 (2H, q, J=9.1 Hz), 8.36 (1H, s).

Reference Example 9

Production of ethyl 5-amino-6-ethyl-1-methyl-3-(2,2,2-trifluoroethoxy)-1H-pyrrolo[2,3-b]pyridine-2-carboxylate To a mixture of the compound of Reference Example 8 (2.53 g, 6.18 mmol), benzophenonimine (1.5 mL, 8.94 mmol), cesium carbonate (3.98 g, 12.2 mmol) and toluene (30 mL) were added Pd$_2$dba$_3$ (389 mg, 0.425 mmol) and Xantphos (499 mg, 0.862 mmol), and the mixture was stirred at 100° C. for 22 hr under an argon atmosphere. The mixture was filtered through celite, and washed with ethyl acetate. The filtrate was washed with water (20 mL) and brine (10 mL), dried over anhydrous magnesium sulfate, and concentrated under reduced pressure. The residue was purified by silica gel column chromatography (eluent, hexane:ethyl acetate=99:1→9:1) to give crude ethyl 5-[(diphenylmethylidene)amino]-6-ethyl-1-methyl-3-(2,2,2-trifluoroethoxy)-1H-pyrrolo[2,3-b]pyridine-2-carboxylate. The obtained crude compound was dissolved in THF (20 mL), 2N hydrochloric acid (5 mL) was added thereto, and the mixture was stirred at room temperature for 1 hr. To the mixture was added aqueous sodium hydrogen carbonate solution (40 mL), and the mixture was extracted with ethyl acetate/THF=1/1 solution (50 mL×3). The extract was washed with brine (20 mL), dried over anhydrous magnesium sulfate, and concentrated under reduced pressure. The residue was purified by silica gel column chromatography (eluent, hexane:ethyl acetate=99:1→2:1) to give the title compound (1.95 g, 91%) as a yellow powder.

$^1$H NMR (300 MHz, DMSO-d$_6$) δ: 1.25 (3H, t, J=7.4 Hz), 1.34 (3H, t, J=7.1 Hz), 2.75 (2H, q, J=7.4 Hz), 3.91 (3H, s), 4.32 (2H, q, J=7.1 Hz), 4.66 (2H, q, J=9.1 Hz), 4.86 (2H, s), 7.16 (1H, s).

Reference Example 10

Production of 6-ethyl-1-methyl-5-(2-oxo-2-phenylethyl)-3-(2,2,2-trifluoroethoxy)-1H-pyrrolo[2,3-b]pyridine-2-carboxylic acid To a mixture of sodium tert-butoxide (264 mg, 2.75 mmol), palladium acetate (25.9 mg, 0.115 mmol), 2-(dicyclohexylphosphino)-2'-methylbiphenyl (86.1 mg, 0.236 mmol) and toluene (6 mL) were added a solution of the compound of Reference Example 8 (450 mg, 1.10 mmol) and acetophenone (0.256 mL, 2.20 mmol) in toluene (4 mL), and the mixture was stirred at 70° C. for 17 hr. After allowing to cool to room temperature, 1N aqueous sodium hydroxide solution (3 mL) and ethanol (5 mL) were added thereto, and the mixture was stirred at 50° C. for 2 hr. To the reaction mixture was added aqueous ammonium chloride solution (30 mL), and the mixture was extracted with ethyl acetate (20 mL×4). The extract was washed with brine (10 mL), dried over anhydrous magnesium sulfate, and concentrated under reduced pressure. The residue was purified by silica gel column chromatography (eluent, hexane:ethyl acetate=1:1→ethyl acetate→ethyl acetate:methanol=19:1) and preparative HPLC (eluent, 0.1% TFA-containing MeCN: 0.1% TFA-containing water=1:1→7:3) to give the title compound (104 mg, 22%) as a pale-yellow powder.

$^1$H NMR (300 MHz, DMSO-d$_6$) δ: 1.22 (3H, t, J=7.5 Hz), 2.70 (2H, q, J=7.5 Hz), 3.98 (3H, s), 4.63 (2H, s), 4.77 (2H, q, J=9.3 Hz), 7.51-7.63 (2H, m), 7.64-7.74 (1H, m), 7.82 (1H, s), 8.04-8.17 (2H, m), 13.35 (1H, br s).

Reference Example 11

Production of ethyl 5-(benzylamino)-6-ethyl-1-methyl-3-(2,2,2-trifluoroethoxy)-1H-pyrrolo[2,3-b]pyridine-2-carboxylate To a mixture of the compound of Reference Example 8 (297 mg, 0.725 mmol), benzylamine (0.096 mL, 0.879 mmol), sodium tert-butoxide (102 mg, 1.07 mmol), binap (70.4 mg, 0.148 mmol) and toluene (3 mL) was added Pd$_2$dba$_3$ (67.3 mg, 0.0735 mmol), and the mixture was stirred at 70° C. for 2.5 hr. To the reaction mixture was added water (5 mL), and the mixture was extracted with ethyl acetate (5 mL×4). The extract was washed with brine (5 mL), dried over anhydrous magnesium sulfate, and concentrated under reduced pressure. The residue was purified by silica gel column chromatography (eluent, hexane:ethyl acetate=49:1→4/1→ethyl acetate) to give the title compound (99.4 mg, 31%) as a pale-yellow powder.

$^1$H NMR (300 MHz, DMSO-d$_6$)-1.38 (6H, m), 2.87 (2H, q, J=7.4 Hz), 3.90 (3H, s), 4.29 (2H, q, J=7.2 Hz), 4.38 (2H, d, J=5.8 Hz), 4.54 (2H, q, J=9.1 Hz), 5.88 (1H, t, J=5.8 Hz), 6.78 (1H, s), 7.14-7.25 (1H, m), 7.25-7.35 (2H, m), 7.35-7.47 (2H, m).

Reference Example 12

Production of 5-(benzylamino)-6-ethyl-1-methyl-3-(2,2,2-trifluoroethoxy)-1H-pyrrolo[2,3-b]pyridine-2-carboxylic acid A mixture of the compound of Reference Example 11 (130 mg, 0.299 mmol), 2N aqueous sodium hydroxide solution (0.5 mL), ethanol (2 mL) and THF (1 mL) was stirred at room temperature for 21 hr. To the reaction mixture was added 1N hydrochloric acid (1.5 mL) to acidify the mixture, and the precipitate was collected by filtration, and washed with water to give the title compound (120 mg, 99%) as a yellow powder.

$^1$H NMR (300 MHz, DMSO-d$_6$) δ: 1.31 (3H, t, J=7.4 Hz), 2.87 (2H, q, J=7.4 Hz), 3.89 (3H, s), 4.37 (2H, br s), 4.52 (2H, q, J=9.1 Hz), 5.77-5.92 (1H, m), 6.76 (1H, s), 7.13-7.25 (1H, m), 7.25-7.34 (2H, m), 7.35-7.44 (2H, m), 12.98 (1H, br s).

Reference Example 13

Production of ethyl 5-[(3-chlorophenyl)amino]-6-ethyl-1-methyl-3-(2,2,2-trifluoroethoxy)-1H-pyrrolo[2,3-b]pyridine-2-carboxylate To a mixture of the compound of Reference Example 8 (349 mg, 0.853 mmol), 3-chloroaniline (0.109 mL, 1.03 mmol), cesium carbonate (410 mg, 1.26 mmol) and toluene (5 mL) were added binap (99.0 mg, 0.159 mmol) and Pd$_2$dba$_3$ (42.1 mg, 0.0460 mmol), and the mixture was stirred at 100° C. for 24 hr. The reaction mixture was filtered through celite, and washed with ethyl acetate. The filtrate was washed successively with water (5 mL) and brine (5 mL), dried over anhydrous magnesium sulfate, and concentrated under reduced pressure. The residue was purified by silica gel column chromatography (eluent, hexane:ethyl acetate=99:1→49:1) to give the title compound (367 mg, 94%) as a pale-yellow powder.

$^1$H NMR (300 MHz, DMSO-d$_6$) δ: 1.22 (3H, t, J=7.6 Hz), 1.35 (3H, t, J=7.1 Hz), 2.82 (2H, q, J=7.6 Hz), 4.00 (3H, s), 4.36 (2H, q, J=7.1 Hz), 4.79 (2H, q, J=9.1 Hz), 6.56-6.65 (2H, m), 6.65-6.73 (1H, m), 7.04-7.22 (1H, m), 7.85 (1H, s), 7.88 (1H, s).

Reference Example 14

Production of 5-[(3-chlorophenyl)amino]-6-ethyl-1-methyl-3-(2,2,2-trifluoroethoxy)-1H-pyrrolo[2,3-b]pyridine-2-carboxylic acid By a method similar to that in Reference Example 12, the title compound (317 mg, 97%) was obtained as a yellow powder from the compound of Reference Example 13 (350 mg, 0.768 mmol), 2N aqueous sodium hydroxide solution (1.5 mL) and ethanol (5 mL).

¹H NMR (300 MHz, DMSO-d₆) δ: 1.22 (3H, t, J=7.5 Hz), 2.81 (2H, q, J=7.5 Hz), 3.99 (3H, s), 4.76 (2H, q, J=9.1 Hz), 6.54-6.64 (2H, m), 6.65-6.73 (1H, m), 7.05-7.20 (1H, m), 7.79 (1H, s), 7.87 (1H, s), 13.31 (1H, br s).

Reference Example 15

Production of ethyl 6-ethyl-1-methyl-5-phenyl-3-(2, 2,2-trifluoroethoxy)-1H-pyrrolo[2,3-b]pyridine-2-carboxylate To a mixture of the compound of Reference Example 8 (203 mg, 0.496 mmol), phenylboronic acid (75.7 mg, 0.621 mmol), potassium carbonate (541 mg, 3.91 mmol), toluene (2 mL) and ethanol (2 mL) was added Pd(PPh₃)₄ (56.5 mg, 0.0489 mmol), and the mixture was stirred at 90° C. for 7 hr. To the reaction mixture was added aqueous ammonium chloride solution (5 mL), and the mixture was extracted with ethyl acetate (5 mL×3). The extract was washed with brine (5 mL), dried over anhydrous magnesium sulfate, and concentrated under reduced pressure. The residue was purified by silica gel column chromatography (eluent, hexane:ethyl acetate=99: 1→9:1) to give the title compound (171 mg, 85%) as a colorless oil.
¹H NMR (300 MHz, DMSO-d₆) δ: 1.16 (3H, t, J=7.5 Hz), 1.35 (3H, t, J=7.2 Hz), 2.80 (2H, q, J=7.5 Hz), 4.02 (3H, s), 4.36 (2H, q, J=7.2 Hz), 4.85 (2H, q, J=9.1 Hz), 7.31-7.61 (5H, m), 7.89 (1H, s).

Reference Example 16

Production of 6-ethyl-1-methyl-5-phenyl-3-(2,2,2-trifluoroethoxy)-1H-pyrrolo[2,3-b]pyridine-2-carboxylic acid By a method similar to that in Reference Example 12, the title compound (143 mg, 90%) was obtained as a white powder from the compound of Reference Example 15 (170 mg, 0.418 mmol), 2N aqueous sodium hydroxide solution (1 mL) and ethanol (3 mL).
¹H NMR (300 MHz, DMSO-d₆) δ: 1.16 (3H, t, J=7.6 Hz), 2.79 (2H, q, J=7.6 Hz), 4.02 (3H, s), 4.80 (2H, q, J=9.1 Hz), 7.30-7.59 (5H, m), 7.82 (1H, s), 13.22 (1H, br s).

Reference Example 17

Production of ethyl 6-ethyl-5-[(3-methoxyphenyl) amino]-1-methyl-3-(2,2,2-trifluoroethoxy)-1H-pyrrolo[2,3-b]pyridine-2-carboxylate By a method similar to that in Reference Example 13, the title compound (186 mg, 87%) was obtained as a brown oil from the compound of Reference Example 8 (194 mg, 0.474 mmol), 3-anisidine (0.066 mL, 0.587 mmol), cesium carbonate (250 mg, 0.768 mmol), toluene (3 mL), binap (30.2 mg, 0.0485 mmol) and Pd₂dba₃ (22.1 mg, 0.0241 mmol).
¹H NMR (300 MHz, DMSO-d₆) δ: 1.23 (3H, t, J=7.5 Hz), 1.35 (3H, t, J=7.1 Hz), 2.84 (2H, q, J=7.5 Hz), 3.65 (3H, s), 3.99 (3H, s), 4.36 (2H, q, J=7.1 Hz), 4.77 (2H, q, J=9.1 Hz), 6.18-6.35 (3H, m), 7.03 (1H, t, J=8.0 Hz), 7.57 (1H, s), 7.81 (1H, s).

Reference Example 18

Production of 6-ethyl-5-[(3-methoxyphenyl)amino]-1-methyl-3-(2,2,2-trifluoroethoxy)-1H-pyrrolo[2,3-b]pyridine-2-carboxylic acid By a method similar to that in Reference Example 12, the title compound (159 mg, 92%) was obtained as a yellow powder from the compound of Reference Example 17 (185 mg, 0.410 mmol), 2N aqueous sodium hydroxide solution (1 mL) and ethanol (3 mL).
¹H NMR (300 MHz, DMSO-d₆) δ: 1.23 (3H, t, J=7.5 Hz), 2.84 (2H, q, J=7.5 Hz), 3.65 (3H, s), 3.99 (3H, s), 4.73 (2H, q, J=9.1 Hz), 6.10-6.42 (3H, m), 7.03 (1H, t, J=8.0 Hz), 7.55 (1H, s), 7.76 (1H, s), 13.20 (1H, br s).

Reference Example 19

Production of ethyl 6-ethyl-5-(4-fluorophenyl)-1-methyl-3-(2,2,2-trifluoroethoxy)-1H-pyrrolo[2,3-b] pyridine-2-carboxylate By a method similar to that in Reference Example 15, the title compound (159 mg, 100%) was obtained as a white powder from the compound of Reference Example 8 (152 mg, 0.372 mmol), 4-fluorophenylboronic acid (62.9 mg, 0.450 mmol), potassium carbonate (413 mg, 2.99 mmol), toluene (2 mL), ethanol (2 mL) and Pd(PPh₃)₄ (20.8 mg, 0.0180 mmol).
¹H NMR (300 MHz, DMSO-d₆) δ: 1.16 (3H, t, J=7.6 Hz), 1.35 (3H, t, J=7.1 Hz), 2.78 (2H, q, J=7.6 Hz), 4.02 (3H, s), 4.36 (2H, q, J=7.1 Hz), 4.85 (2H, q, J=9.1 Hz), 7.23-7.38 (2H, m), 7.39-7.53 (2H, m), 7.89 (1H, s).

Reference Example 20

Production of 6-ethyl-5-(4-fluorophenyl)-1-methyl-3-(2,2,2-trifluoroethoxy)-1H-pyrrolo[2,3-b]pyridine-2-carboxylic acid By a method similar to that in Reference Example 12, the title compound (128 mg, 87%) was obtained as a white powder from the compound of Reference Example 19 (157 mg, 0.370 mmol), 2N aqueous sodium hydroxide solution (1 mL), ethanol (3 mL) and THF (0.5 mL).
¹H NMR (300 MHz, DMSO-d₆) δ: 1.16 (3H, t, J=7.6 Hz), 2.77 (2H, q, J=7.6 Hz), 4.01 (3H, s), 4.80 (2H, q, J=9.1 Hz), 7.25-7.38 (2H, m), 7.39-7.51 (2H, m), 7.83 (1H, s), 13.20 (1H, br s).

Reference Example 21

Production of ethyl 6-ethyl-1-methyl-5-[(phenylcarbonyl)amino]-3-(2,2,2-trifluoroethoxy)-1H-pyrrolo [2,3-b]pyridine-2-carboxylate A mixture of the compound of Reference Example 9 (135 mg, 0.391 mmol), pyridine (0.0634 mL, 0.784 mmol) and THF (3 mL) was cooled to 0° C., benzoyl chloride (0.0544 mL, 0.469 mmol) was added thereto, and the mixture was stirred at room temperature for 1.5 hr. To the reaction mixture was added water (5 mL), and the mixture was extracted with ethyl acetate (5 mL×4). The extract was dried over anhydrous magnesium sulfate, and concentrated under reduced pressure. The precipitate was collected by filtration to give the title compound (140 mg, 80%) as a white powder. The filtrate was concentrated under reduced pressure, and the residue was purified by basic silica gel column chromatography (eluent, hexane:ethyl acetate=49:1→2:1) to give the title compound (24.9 mg, 14%) as a white powder.
¹H NMR (300 MHz, DMSO-d₆) δ: 1.25 (3H, t, J=7.4 Hz), 1.36 (3H, t, J=7.1 Hz), 2.89 (2H, q, J=7.4 Hz), 4.01 (3H, s), 4.37 (2H, q, J=7.1 Hz), 4.82 (2H, q, J=9.1 Hz), 7.46-7.72 (3H, m), 7.90-8.13 (3H, m), 10.13 (1H, s).

Reference Example 22

Production of 6-ethyl-1-methyl-5-[(phenylcarbonyl)amino]-3-(2,2,2-trifluoroethoxy)-1H-pyrrolo[2,3-b]pyridine-2-carboxylic acid By a method similar to that in Reference Example 12, the title compound (75.4 mg, 95%) was obtained as a white powder from the compound of Reference Example 21 (84.5 mg, 0.188 mmol), 2N aqueous sodium hydroxide solution (0.5 mL), ethanol (2 mL) and THF (0.5 mL).

$^1$H NMR (300 MHz, DMSO-$d_6$) δ: 1.25 (3H, t, J=7.6 Hz), 2.88 (2H, q, J=7.6 Hz), 4.01 (3H, s), 4.78 (2H, q, J=9.1 Hz), 7.47-7.73 (3H, m), 7.96 (1H, s), 7.98-8.09 (2H, m), 10.12 (1H, s), 13.28 (1H, br s).

Reference Example 23

Production of ethyl 5-{[(4-chlorophenyl)carbonyl]amino}-6-ethyl-1-methyl-3-(2,2,2-trifluoroethoxy)-1H-pyrrolo[2,3-b]pyridine-2-carboxylate A mixture of the compound of Reference Example 9 (150 mg, 0.43 mmol), pyridine (69 mg, 0.87 mmol) and THF (2 mL) was cooled to 0° C., 4-chlorobenzoyl chloride (80 mg, 0.46 mmol) was added thereto, and the mixture was stirred at room temperature for 1 hr. To the reaction mixture was added water (6 mL), and the mixture was stirred at room temperature for 30 min. The precipitate was collected by filtration, washed with water, and dried under reduced pressure to give the title compound (204 mg, 98%) as a white powder.

$^1$H NMR (300 MHz, DMSO-$d_6$) δ: 1.25 (3H, t, J=7.5 Hz), 1.36 (3H, t, J=7.2 Hz), 2.87 (2H, q, J=7.5 Hz), 4.01 (3H, s), 4.36 (2H, q, J=7.2 Hz), 4.81 (2H, q, J=9.1 Hz), 7.64 (2H, d, J=8.4 Hz), 8.03-8.06 (3H, m), 10.21 (1H, s).

Reference Example 24

Production of ethyl 6-ethyl-1-methyl-5-(pyridin-3-yl)-3-(2,2,2-trifluoroethoxy)-1H-pyrrolo[2,3-b]pyridine-2-carboxylate By a method similar to that in Reference Example 15, the title compound (170 mg, 87%) was obtained as a pale-yellow solid from the compound of Reference Example 8 (200 mg, 0.48 mmol), 3-pyridylboronic acid (72 mg, 0.57 mmol), potassium carbonate (540 mg, 3.82 mmol), toluene (2 mL), ethanol (2 mL) and Pd(PPhd4 (28 mg, 0.024 mmol).

$^1$H NMR (300 MHz, DMSO-$d_6$) δ: 1.17 (3H, t, J=7.5 Hz), 1.35 (3H, t, J=7.2 Hz), 2.79 (2H, q, J=7.5 Hz), 4.03 (3H, s), 4.36 (2H, q, J=7.2 Hz), 4.87 (2H, q, J=9.0 Hz), 7.52 (1H, dd, J=7.8, 4.8 Hz), 7.89 (1H, dt, J=7.8, 2.0 Hz), 8.00 (1H, s), 8.63 (1H, s), 8.64 (1H, s).

Reference Example 25

Production of 6-ethyl-1-methyl-5-(pyridin-3-yl)-3-(2,2,2-trifluoroethoxy)-1H-pyrrolo[2,3-b]pyridine-2-carboxylic acid By a method similar to that in Reference Example 12, the title compound (130 mg, 88%) was obtained as a white solid from the compound of Reference Example 24 (160 mg, 0.39 mmol).

$^1$H NMR (300 MHz, DMSO-$d_6$) δ: 1.17 (3H, t, J=7.3 Hz), 2.78 (2H, q, J=7.3 Hz), 4.02 (3H, s), 4.82 (2H, q, J=9.0 Hz), 7.50-7.54 (1H, m), 7.87-7.92 (2H, m), 8.63 (2H, s), 13.20-13.60 (1H, br).

Reference Example 26

Production of ethyl 6-ethyl-1-methyl-5-(pyridin-4-yl)-3-(2,2,2-trifluoroethoxy)-1H-pyrrolo[2,3-b]pyridine-2-carboxylate By a method similar to that in Reference Example 15, the title compound (180 mg, 92%) was obtained as a white solid from the compound of Reference Example 8 (200 mg, 0.48 mmol), 4-pyridylboronic acid (72 mg, 0.57 mmol), potassium carbonate (540 mg, 3.82 mmol), toluene (2 mL), ethanol (2 mL) and Pd(RPh$_3$)$_4$ (28 mg, 0.024 mmol).

$^1$H NMR (300 MHz, DMSO-$d_6$) δ: 1.19 (3H, t, J=7.5 Hz), 1.35 (3H, t, J=7.2 Hz), 2.83 (2H, q, J=7.5 Hz), 4.02 (3H, s), 4.36 (2H, q, J=7.2 Hz), 4.87 (2H, q, J=9.1 Hz), 7.48 (2H, dd, J=4.2, 1.5 Hz), 7.99 (1H, s), 8.68 (2H, dd, J=4.2, 1.5 Hz).

Reference Example 27

Production of 6-ethyl-1-methyl-5-(pyridin-4-yl)-3-(2,2,2-trifluoroethoxy)-1H-pyrrolo[2,3-b]pyridine-2-carboxylic acid By a method similar to that in Reference Example 12, the title compound (110 mg, 69%) was obtained as a white solid from the compound of Reference Example 26 (170 mg, 0.39 mmol).

$^1$H NMR (300 MHz, DMSO-$d_6$) δ: 1.19 (3H, t, J=7.4 Hz), 2.78 (2H, q, J=7.4 Hz), 4.02 (3H, s), 4.82 (2H, q, J=9.1 Hz), 7.48 (2H, d, J=6.0 Hz), 7.92 (1H, s), 8.68 (2H, d, J=5.4 Hz), 13.37 (1H, br s).

Reference Example 28

Production of ethyl 6-ethyl-5-(3-fluorophenyl)-1-methyl-3-(2,2,2-trifluoroethoxy)-1H-pyrrolo[2,3-b]pyridine-2-carboxylate By a method similar to that in Reference Example 15, the title compound (180 mg, 88%) was obtained as a white solid from the compound of Reference Example 8 (200 mg, 0.48 mmol), 3-fluorophenylboronic acid (82 mg, 0.57 mmol), potassium carbonate (540 mg, 3.82 mmol), toluene (2 mL), ethanol (2 mL) and Pd(PPh$_3$)$_4$ (28 mg, 0.024 mmol).

$^1$H NMR (300 MHz, DMSO-$d_6$) δ: 1.18 (3H, t, J=7.5 Hz), 1.35 (3H, t, J=7.1 Hz), 2.80 (2H, q, J=7.5 Hz), 4.02 (3H, s), 4.36 (2H, q, J=7.1 Hz), 4.86 (2H, q, J=9.1 Hz), 7.24-7.32 (3H, m), 7.49-7.57 (1H, m), 7.94 (1H, s).

Reference Example 29

Production of 6-ethyl-5-(3-fluorophenyl)-1-methyl-3-(2,2,2-trifluoroethoxy)-1H-pyrrolo[2,3-b]pyridine-2-carboxylic acid By a method similar to that in Reference Example 12, the title compound (154 mg, 100%) was obtained as a white solid from the compound of Reference Example 28 (160 mg, 0.38 mmol).

¹H NMR (300 MHz, DMSO-d₆) δ: 1.18 (3H, t, J=7.4 Hz), 2.80 (2H, q, J=7.4 Hz), 4.02 (3H, s), 4.81 (2H, q, J=9.1 Hz), 7.24-7.30 (3H, m), 7.53 (1H, q, J=6.3 Hz), 7.87 (1H, s), 13.32 (1H, br s).

Reference Example 30

Production of ethyl 6-ethyl-5-(2-methoxyphenyl)-1-methyl-3-(2,2,2-trifluoroethoxy)-1H-pyrrolo[2,3-b]pyridine-2-carboxylate By a method similar to that in Reference Example 15, the title compound (190 mg, 91%) was obtained as a white solid from the compound of Reference Example 8 (200 mg, 0.48 mmol), 2-methoxyphenylboronic acid (89 mg, 0.57 mmol), potassium carbonate (540 mg, 3.82 mmol), toluene (2 mL), ethanol (2 mL) and Pd(PPh₃)₄ (28 mg, 0.024 mmol).
¹H NMR (300 MHz, DMSO-d₆) δ: 1.12 (3H, t, J=7.4 Hz), 1.35 (3H, t, J=7.2 Hz), 2.58-2.65 (2H, m), 3.71 (3H, s), 4.02 (3H, s), 4.36 (2H, q, J=7.1 Hz), 4.82 (2H, q, J=9.0 Hz), 7.03-7.14 (2H, m), 7.21 (1H, dd, J=7.5, 1.8 Hz), 7.42 (1H, td, J=8.0, 2.1 Hz), 7.79 (1H, s).

Reference Example 31

Production of 6-ethyl-5-(2-methoxyphenyl)-1-methyl-3-(2,2,2-trifluoroethoxy)-1H-pyrrolo[2,3-b]pyridine-2-carboxylic acid By a method similar to that in Reference Example 12, the title compound (154 mg, 90%) was obtained as a white solid from the compound of Reference Example 30 (180 mg, 0.41 mmol).
¹H NMR (300 MHz, DMSO-d₆) δ: 1.12 (3H, t, J=7.4 Hz), 2.55-2.70 (2H, m), 3.71 (3H, s), 4.01 (3H, s), 4.78 (2H, q, J=9.1 Hz), 7.03-7.14 (2H, m), 7.20 (1H, dd, J=7.5, 1.8 Hz), 7.39-7.45 (1H, m), 7.72 (1H, s), 13.27 (1H, br s).

Reference Example 32

Production of ethyl 6-ethyl-5-(3-methoxyphenyl)-1-methyl-3-(2,2,2-trifluoroethoxy)-1H-pyrrolo[2,3-b]pyridine-2-carboxylate By a method similar to that in Reference Example 15, the title compound (190 mg, 91%) was obtained as a white solid from the compound of Reference Example 8 (200 mg, 0.48 mmol), 3-methoxyphenylboronic acid (89 mg, 0.57 mmol), potassium carbonate (540 mg, 3.82 mmol), toluene (2 mL), ethanol (2 mL) and Pd(PPh₃)₄ (28 mg, 0.024 mmol).
¹H NMR (300 MHz, DMSO-d₆) δ: 1.18 (3H, t, J=7.4 Hz), 1.35 (3H, t, J=7.1 Hz), 2.80 (2H, q, J=7.5 Hz), 3.80 (3H, s), 4.02 (3H, s), 4.36 (2H, q, J=7.1 Hz), 4.85 (2H, q, J=9.1 Hz), 6.95-7.01 (3H, m), 7.40 (1H, t, J=8.0 Hz), 7.89 (1H, s).

Reference Example 33

Production of 6-ethyl-5-(3-methoxyphenyl)-1-methyl-3-(2,2,2-trifluoroethoxy)-1H-pyrrolo[2,3-b]pyridine-2-carboxylic acid By a method similar to that in Reference Example 12, the title compound (160 mg, 89%) was obtained as a white solid from the compound of Reference Example 32 (190 mg, 0.44 mmol).

¹H NMR (300 MHz, DMSO-d₆) δ: 1.17 (3H, t, J=7.4 Hz), 2.80 (2H, q, J=7.4 Hz), 3.82 (3H, s), 4.02 (3H, s), 4.79 (2H, q, J=9.1 Hz), 6.94-7.01 (3H, m), 7.39 (1H, t, J=8.0 Hz), 7.83 (1H, s), 13.31 (1H, br s).

Reference Example 34

Production of ethyl 6-ethyl-5-(4-methoxyphenyl)-1-methyl-3-(2,2,2-trifluoroethoxy)-1H-pyrrolo[2,3-b]pyridine-2-carboxylate By a method similar to that in Reference Example 15, the title compound (200 mg, 95%) was obtained as a white solid from the compound of Reference Example 8 (200 mg, 0.48 mmol), 4-methoxyphenylboronic acid (89 mg, 0.57 mmol), potassium carbonate (540 mg, 3.82 mmol), toluene (2 mL), ethanol (2 mL) and Pd(PPh₃)₄ (28 mg, 0.024 mmol).
¹H NMR (300 MHz, DMSO-d₆) δ: 1.16 (3H, t, J=7.4 Hz), 1.35 (3H, t, J=7.2 Hz), 2.80 (2H, q, J=7.5 Hz), 3.82 (3H, s), 4.01 (3H, s), 4.36 (2H, q, J=7.1 Hz), 4.84 (2H, q, J=9.0 Hz), 7.05 (2H, d, J=8.7 Hz), 7.32 (2H, d, J=8.7 Hz), 7.84 (1H, s).

Reference Example 35

Production of 6-ethyl-5-(4-methoxyphenyl)-1-methyl-3-(2,2,2-trifluoroethoxy)-1H-pyrrolo[2,3-b]pyridine-2-carboxylic acid By a method similar to that in Reference Example 12, the title compound (150 mg, 83%) was obtained as a white solid from the compound of Reference Example 34 (190 mg, 0.44 mmol).
¹H NMR (300 MHz, DMSO-d₆) δ: 1.16 (3H, t, J=7.4 Hz), 2.80 (2H, q, J=7.4 Hz), 3.82 (3H, s), 4.01 (3H, s), 4.79 (2H, q, J=9.1 Hz), 6.97-7.05 (2H, m), 7.31 (2H, dd, J=6.9, 2.1 Hz), 7.78 (1H, s), 13.24 (1H, br s).

Reference Example 36

Production of ethyl 5-(4-chlorophenyl)-6-ethyl-1-methyl-3-(2,2,2-trifluoroethoxy)-1H-pyrrolo[2,3-b]pyridine-2-carboxylate By a method similar to that in Reference Example 15, the title compound (200 mg, 95%) was obtained as a white solid from the compound of Reference Example 8 (200 mg, 0.48 mmol), 4-chlorophenylboronic acid (92 mg, 0.57 mmol), potassium carbonate (540 mg, 3.82 mmol), toluene (2 mL), ethanol (2 mL) and Pd(PPh₃)₄ (28 mg, 0.024 mmol).
¹H NMR (300 MHz, DMSO-d₆) δ: 1.17 (3H, t, J=7.4 Hz), 1.35 (3H, t, J=7.2 Hz), 2.79 (2H, q, J=7.4 Hz), 4.02 (3H, s), 4.36 (2H, q, J=7.1 Hz), 4.85 (2H, q, J=9.1 Hz), 7.42-7.47 (2H, m), 7.53-7.56 (2H, m), 7.91 (1H, s).

Reference Example 37

Production of 5-(4-chlorophenyl)-6-ethyl-1-methyl-3-(2,2,2-trifluoroethoxy)-1H-pyrrolo[2,3-b]pyridine-2-carboxylic acid By a method similar to that in Reference Example 12, the title compound (156 mg, 88%) was obtained as a white powder from the compound of Reference Example 36 (190 mg, 0.43 mmol).

¹H NMR (300 MHz, DMSO-d₆) δ: 1.17 (3H, t, J=7.4 Hz), 2.78 (2H, q, J=7.4 Hz), 4.02 (3H, s), 4.80 (2H, q, J=9.1 Hz), 7.44 (2H, dd, J=6.3, 1.8 Hz), 7.54 (2H, dd, J=6.3, 1.8 Hz), 7.84 (1H, s), 13.33 (1H, br s).

Reference Example 38

Production of ethyl 6-ethyl-1-methyl-5-[4-(1-methylethoxy)phenyl]-3-(2,2,2-trifluoroethoxy)-1H-pyrrolo[2,3-b]pyridine-2-carboxylate By a method similar to that in Reference Example 15, the title compound (230 mg, 100%) was obtained as a white solid from the compound of Reference Example 8 (200 mg, 0.48 mmol), 4-(isopropoxy)phenylboronic acid (106 mg, 0.59 mmol), potassium carbonate (540 mg, 3.82 mmol), toluene (2 mL), ethanol (2 mL) and Pd(PPh₃)₄ (28 mg, 0.024 mmol).

¹H NMR (300 MHz, DMSO-d₆) δ: 1.17 (3H, t, J=7.4 Hz), 1.27-1.37 (9H, m), 2.80 (2H, q, J=7.4 Hz), 4.01 (3H, s), 4.35 (2H, q, J=7.1 Hz), 4.60-4.70 (1H, m), 4.84 (2H, q, J=9.1 Hz), 7.00 (2H, dd, J=6.6, 2.1 Hz), 7.29 (2H, dd, J=6.6, 2.1 Hz), 7.85 (1H, s).

Reference Example 39

Production of 6-ethyl-1-methyl-5-[4-(1-methylethoxy)phenyl]-3-(2,2,2-trifluoroethoxy)-1H-pyrrolo[2,3-b]pyridine-2-carboxylic acid By a method similar to that in Reference Example 12, the title compound (168 mg, 82%) was obtained as a white powder from the compound of Reference Example 38 (220 mg, 0.47 mmol).

¹H NMR (300 MHz, DMSO-d₆) δ: 1.17 (3H, t, J=7.5 Hz), 1.27-1.32 (6H, m), 2.80 (2H, q, J=7.5 Hz), 4.01 (3H, s), 4.63-4.71 (1H, m), 4.79 (2H, q, J=9.1 Hz), 6.99-7.02 (2H, m), 7.26-7.30 (2H, m), 7.78 (1H, s), 13.29 (1H, br s).

Reference Example 40

Production of ethyl 6-ethyl-1-methyl-3-(2,2,2-trifluoroethoxy)-5-[4-(trifluoromethyl)phenyl]-1H-pyrrolo[2,3-b]pyridine-2-carboxylate By a method similar to that in Reference Example 15, the title compound (210 mg, 92%) was obtained as a white solid from the compound of Reference Example 8 (200 mg, 0.48 mmol), 4-(trifluoromethyl)phenylboronic acid (111 mg, 0.59 mmol), potassium carbonate (540 mg, 3.82 mmol), toluene (2 mL), ethanol (2 mL) and Pd(PPh₃)₄ (28 mg, 0.024 mmol).

¹H NMR (300 MHz, DMSO-d₆) δ: 1.18 (3H, t, J=7.4 Hz), 1.35 (3H, t, J=7.2 Hz), 2.79 (2H, q, J=7.4 Hz), 4.03 (3H, s), 4.36 (2H, q, J=7.2 Hz), 4.87 (2H, q, J=9.1 Hz), 7.67 (2H, d, J=7.8 Hz), 7.85 (2H, d, J=7.8 Hz), 7.98 (1H, s).

Reference Example 41

Production of 6-ethyl-1-methyl-3-(2,2,2-trifluoroethoxy)-5-[4-(trifluoromethyl)phenyl]-1H-pyrrolo[2,3-b]pyridine-2-carboxylic acid By a method similar to that in Reference Example 12, the title compound (181 mg, 97%) was obtained as a white powder from the compound of Reference Example 40 (200 mg, 0.42 mmol).

¹H NMR (300 MHz, DMSO-d₆) δ: 1.18 (3H, t, J=7.4 Hz), 2.79 (2H, q, J=7.4 Hz), 4.03 (3H, s), 4.81 (2H, q, J=9.1 Hz), 7.66 (2H, d, J=7.8 Hz), 7.84-7.91 (3H, m), 13.35 (1H, br s).

Reference Example 42

Production of ethyl 6-ethyl-5-(4-ethylphenyl)-1-methyl-3-(2,2,2-trifluoroethoxy)-1H-pyrrolo[2,3-b]pyridine-2-carboxylate By a method similar to that in Reference Example 15, the title compound (200 mg, 96%) was obtained as a colorless oil from the compound of Reference Example 8 (200 mg, 0.48 mmol), 4-ethylphenylboronic acid (88 mg, 0.58 mmol), potassium carbonate (540 mg, 3.82 mmol), toluene (2 mL), ethanol (2 mL) and Pd(PPh₃)₄ (28 mg, 0.024 mmol).

¹H NMR (300 MHz, DMSO-d₆) δ: 1.09-1.27 (6H, m), 1.35 (3H, t, J=7.1 Hz), 2.68 (2H, q, J=7.5 Hz), 2.80 (2H, q, J=7.5 Hz), 4.02 (3H, s), 4.36 (2H, q, J=7.1 Hz), 4.84 (2H, q, J=9.1 Hz), 7.31 (4H, s), 7.86 (1H, s).

Reference Example 43

Production of 6-ethyl-5-(4-ethylphenyl)-1-methyl-3-(2,2,2-trifluoroethoxy)-1H-pyrrolo[2,3-b]pyridine-2-carboxylic acid By a method similar to that in Reference Example 12, the title compound (151 mg, 84%) was obtained as a white powder from the compound of Reference Example 42 (190 mg, 0.44 mmol).

¹H NMR (300 MHz, DMSO-d₆) δ: 1.14-1.27 (6H, m), 2.68 (2H, q, J=7.5 Hz), 2.79 (2H, q, J=7.5 Hz), 4.01 (3H, s), 4.80 (2H, q, J=9.1 Hz), 7.31 (4H, s), 7.80 (1H, s), 13.30 (1H, br s).

Reference Example 44

Production of 5-{[(4-chlorophenyl)carbonyl]amino}-6-ethyl-1-methyl-3-(2,2,2-trifluoroethoxy)-1H-pyrrolo[2,3-b]pyridine-2-carboxylic acid By a method similar to that in Reference Example 12, the title compound (169 mg, 95%) was obtained as a white powder from the compound of Reference Example 23 (190 mg, 0.39 mmol).

¹H NMR (300 MHz, DMSO-d₆) δ: 1.25 (3H, t, J=7.5 Hz), 2.87 (2H, q, J=7.5 Hz), 4.01 (3H, s), 4.78 (2H, q, J=9.1 Hz), 7.64 (2H, d, J=8.4 Hz), 7.97 (1H, s), 8.04 (2H, d, J=8.4 Hz), 10.20 (1H, s), 13.37 (1H, br s).

Reference Example 45

Production of ethyl 6-ethyl-5-{[(4-methoxyphenyl)carbonyl]amino}-1-methyl-3-(2,2,2-trifluoroethoxy)-1H-pyrrolo[2,3-b]pyridine-2-carboxylate By a method similar to that in Reference Example 23, the title compound (198 mg, 96%) was obtained as a white powder from the compound of Reference Example 9 (150 mg, 0.43 mmol) and 4-methoxybenzoyl chloride (78 mg, 0.46 mmol).

¹H NMR (300 MHz, DMSO-d₆) δ: 1.24 (3H, t, J=7.5 Hz), 1.36 (3H, t, J=7.1 Hz), 2.87 (2H, q, J=7.5 Hz), 3.85 (3H, s), 4.01 (3H, s), 4.36 (2H, q, J=7.1 Hz), 4.81 (2H, q, J=9.1 Hz), 7.08 (2H, d, J=9.0 Hz), 8.00-8.02 (3H, m), 9.98 (1H, s).

Reference Example 46

Production of 6-ethyl-5-{[(4-methoxyphenyl)carbonyl]amino}-1-methyl-3-(2,2,2-trifluoroethoxy)-1H-pyrrolo[2,3-b]pyridine-2-carboxylic acid By a method similar to that in Reference Example 12, the title compound (164 mg, 91%) was obtained as a white powder from the compound of Reference Example 45 (190 mg, 0.39 mmol).

$^1$H NMR (300 MHz, DMSO-$d_6$) δ: 1.24 (3H, t, J=7.5 Hz), 2.86 (2H, q, J=7.5 Hz), 3.85 (3H, s), 4.00 (3H, s), 4.77 (2H, q, J=9.1 Hz), 7.08 (2H, d, J=9.0 Hz), 7.94 (1H, s), 8.01 (2H, d, J=9.0 Hz), 9.97 (1H, s), 13.35 (1H, br s).

Reference Example 47

Production of ethyl 5-[(cyclopropylcarbonyl)amino]-6-ethyl-1-methyl-3-(2,2,2-trifluoroethoxy)-1H-pyrrolo[2,3-b]pyridine-2-carboxylate By a method similar to that in Reference Example 23, the title compound (166 mg, 93%) was obtained as a white powder from the compound of Reference Example 9 (150 mg, 0.43 mmol) and cyclopropanecarbonyl chloride (48 mg, 0.46 mmol).

$^1$H NMR (300 MHz, DMSO-$d_6$) δ: 0.81 (4H, d, J=6.0 Hz), 1.24 (3H, t, J=7.5 Hz), 1.35 (3H, t, J=7.2 Hz), 1.90 (1H, t, J=6.3 Hz), 2.85 (2H, q, J=7.5 Hz), 3.97 (3H, s), 4.35 (2H, q, J=7.2 Hz), 4.78 (2H, q, J=9.1 Hz), 7.99 (1H, s), 9.76% (1H, s).

Reference Example 48

Production of 5-[(cyclopropylcarbonyl)amino]-6-ethyl-1-methyl-3-(2,2,2-trifluoroethoxy)-1H-pyrrolo[2,3-b]pyridine-2-carboxylic acid By a method similar to that in Reference Example 12, the title compound (132 mg, 95%) was obtained as a white powder from the compound of Reference Example 47 (150 mg, 0.36 mmol).

$^1$H NMR (300 MHz, DMSO-$d_6$) δ: 0.81 (4H, d, J=5.7 Hz), 1.24 (3H, t, J=7.4 Hz), 1.85-1.93 (1H, m), 2.85 (2H, q, J=7.4 Hz), 3.97 (3H, s), 4.74 (2H, q, J=9.0 Hz), 7.94 (1H, s), 9.75 (1H, s), 13.20-13.40 (1H, br).

Reference Example 49

Production of ethyl 5-[(cyclohexylcarbonyl)amino]-6-ethyl-1-methyl-3-(2,2,2-trifluoroethoxy)-1H-pyrrolo[2,3-b]pyridine-2-carboxylate By a method similar to that in Reference Example 23, the title compound (179 mg, 91%) was obtained as a white powder from the compound of Reference Example 9 (150 mg, 0.43 mmol) and cyclohexanecarbonyl chloride (67 mg, 0.46 mmol).

$^1$H NMR (300 MHz, DMSO-$d_6$) δ: 1.19-1.46 (11H, m), 1.66 (1H, d, J=10.2 Hz), 1.76-1.89 (4H, m), 2.38-2.49 (1H, m), 2.81 (2H, q, J=7.5 Hz), 3.97 (3H, s), 4.35 (2H, q, J=7.1 Hz), 4.78 (2H, q, J=9.0 Hz), 7.91 (1H, s), 9.41 (1H, s).

Reference Example 50

Production of 5-[(cyclohexylcarbonyl)amino]-6-ethyl-1-methyl-3-(2,2,2-trifluoroethoxy)-1H-pyrrolo[2,3-b]pyridine-2-carboxylic acid By a method similar to that in Reference Example 12, the title compound (143 mg, 96%) was obtained as a white powder from the compound of Reference Example 49 (160 mg, 0.35 mmol).

$^1$H NMR (300 MHz, DMSO-$d_6$) δ: 1.19-1.50 (7H, m), 1.66 (1H, J=9.6 Hz), 1.75-1.89 (4H, m), 2.39-2.51 (2H, m), 2.81 (2H, q, J=7.5 Hz), 3.97 (3H, s), 4.75 (2H, q, J=9.1 Hz), 7.86 (1H, s), 9.39 (1H, s), 13.20-13.50 (1H, br).

Reference Example 51

Production of ethyl 6-ethyl-1-methyl-5-[(pyridin-2-ylcarbonyl)amino]-3-(2,2,2-trifluoroethoxy)-1H-pyrrolo[2,3-b]pyridine-2-carboxylate By a method similar to that in Reference Example 23, the title compound (126 mg, 96%) was obtained as a white solid from the compound of Reference Example 9 (100 mg, 0.29 mmol), pyridine (69 mg, 0.87 mmol) and picolinoyl chloride hydrochloride (54 mg, 0.30 mmol).

$^1$H NMR (300 MHz, DMSO-$d_6$) δ: 1.28 (3H, t, J=7.4 Hz), 1.37 (3H, t, J=7.2 Hz), 2.93 (2H, q, J=7.4 Hz), 4.01 (3H, s), 4.37 (2H, q, J=7.2 Hz), 4.80 (2H, q, J=9.0 Hz), 7.69-7.74 (1H, m), 8.07-8.12 (1H, m), 8.18 (1H, d, J=7.5 Hz), 8.30 (1H, s), 8.78 (1H, d, J=4.2 Hz), 10.51 (1H, s).

Reference Example 52

Production of 6-ethyl-1-methyl-5-[(pyridin-2-ylcarbonyl)amino]-3-(2,2,2-trifluoroethoxy)-1H-pyrrolo[2,3-b]pyridine-2-carboxylic acid By a method similar to that in Reference Example 12, the title compound (91 mg, 90%) was obtained as a white powder from the compound of Reference Example 51 (110 mg, 0.24 mmol).

$^1$H NMR (300 MHz, DMSO-$d_6$) δ: 1.28 (3H, t, J=7.5 Hz), 2.93 (2H, q, J=7.5 Hz), 4.00 (3H, s), 4.77 (2H, q, J=9.1 Hz), 7.69-7.73 (1H, m), 8.06-8.12 (1H, m), 8.18 (1H, d, J=7.8 Hz), 8.26 (1H, s), 8.77 (1H, dd, J=4.2, 1.2 Hz), 10.41 (1H, s), 13.37 (1H, br s).

Reference Example 53

Production of ethyl 6-ethyl-1-methyl-5-(4-methylphenyl)-3-(2,2,2-trifluoroethoxy)-1H-pyrrolo[2,3-b]pyridine-2-carboxylate By a method similar to that in Reference Example 15, the title compound (150 mg, 74%) was obtained as a white solid from the compound of Reference Example 8 (200 mg, 0.48 mmol), 4-methylphenylboronic acid (80 mg, 0.58 mmol), potassium carbonate (540 mg, 3.82 mmol), toluene (2 mL), ethanol (2 mL) and Pd(PPh$_3$)$_4$ (28 mg, 0.024 mmol).

$^1$H NMR (300 MHz, DMSO-$d_6$) δ: 1.16 (3H, t, J=7.5 Hz), 1.35 (3H, t, J=7.1 Hz), 2.38 (3H, s), 2.79 (2H, q, J=7.5 Hz), 4.01 (3H, s), 4.36 (2H, q, J=7.1 Hz), 4.84 (2H, q, J=9.0 Hz), 7.29 (4H, s), 7.84 (1H, s).

Reference Example 54

Production of 6-ethyl-1-methyl-5-(4-methylphenyl)-3-(2,2,2-trifluoroethoxy)-1H-pyrrolo[2,3-b]pyridine-2-carboxylic acid By a method similar to that in Reference Example 12, the title compound (136 mg, 100%) was obtained as a pale-yellow solid from the compound of Reference Example 53 (140 mg, 0.33 mmol).

$^1$H NMR (300 MHz, DMSO-$d_6$) δ: 1.16 (3H, t, J=7.5 Hz), 2.38 (3H, s), 2.79 (2H, q, J=7.5 Hz), 4.01 (3H, s), 4.79 (2H, q, J=9.1 Hz), 7.28 (4H, s), 7.78 (1H, s), 13.30 (1H, br s).

Reference Example 55

Production of ethyl 6-ethyl-1-methyl-5-(naphthalen-2-yl)-3-(2,2,2-trifluoroethoxy)-1H-pyrrolo[2,3-b]pyridine-2-carboxylate By a method similar to that in Reference Example 15, the title compound (90 mg, 41%) was obtained as a white solid from the compound of Reference Example 8 (200 mg, 0.48 mmol), 2-naphthaleneboronic acid (101 mg, 0.58 mmol), potassium carbonate (540 mg, 3.82 mmol), toluene (2 mL), ethanol (2 mL) and Pd(PPh$_3$)$_4$ (28 mg, 0.024 mmol).

$^1$H NMR (300 MHz, DMSO-$d_6$) δ: 1.18 (3H, t, J=7.4 Hz), 1.36 (3H, t, J=7.1 Hz), 2.85 (2H, q, J=7.4 Hz), 4.05 (3H, s), 4.37 (2H, q, J=7.1 Hz), 4.86 (2H, q, J=9.1 Hz), 7.55-7.59 (3H, m), 7.95-8.04 (5H, m).

Reference Example 56

Production of 6-ethyl-1-methyl-5-(naphthalen-2-yl)-3-(2,2,2-trifluoroethoxy)-1H-pyrrolo[2,3-b]pyridine-2-carboxylic acid By a method similar to that in Reference Example 12, the title compound (65 mg, 84%) was obtained as a pale-yellow solid from the compound of Reference Example 55 (80 mg, 0.18 mmol).

$^1$H NMR (300 MHz, DMSO-$d_6$) δ: 1.18 (3H, t, J=7.5 Hz), 2.85 (2H, q, J=7.5 Hz), 4.05 (3H, s), 4.82 (2H, q, J=9.0 Hz), 7.55-7.59 (3H, m), 7.94-8.04 (5H, m), 13.33 (1H, br s).

Reference Example 57

Production of ethyl 4-chloro-6-methyl-2-oxo-1,2-dihydropyridine-3-carboxylate

A mixture of ethyl 4-hydroxy-6-methyl-2-oxo-1,2-dihydropyridine-3-carboxylate (3.00 g, 15.2 mmol), phosphorus oxychloride (7.75 mL), n-butyltriethylammonium chloride (13.8 g, 60.8 mmol) and acetonitrile (60 mL) was stirred at 40° C. for 30 min, and then for 30 min under refluxing conditions. After cooling, the reaction mixture was concentrated under reduced pressure, and water was added to the residue. The mixture was extracted with ethyl acetate. The extract was washed with brine, dried over magnesium sulfate, and concentrated under reduced pressure. The residue was washed with a mixed solvent of ethyl acetate-hexane, and dried under reduced pressure to give the title compound (1.45 g, 44%) as a white powder.

$^1$H NMR (300 MHz, DMSO-$d_6$) δ: 1.26 (3H, t, J=7.0 Hz), 2.20 (3H, s), 4.25 (2H, q, J=7.0 Hz), 6.26 (1H, s), 12.29 (1H, s).

Reference Example 58

Production of ethyl 6-methyl-2-oxo-1,2-dihydro-pyridine-3-carboxylate

By a method similar to that in Reference Example 4, the title compound (5.6 g, 67%) was obtained as a beige powder from the compound of Reference Example 57 (10.0 g, 46.3 mmol).

$^1$H NMR (300 MHz, DMSO-$d_6$) δ: 1.24 (3H, t, J=7.1 Hz), 2.23 (3H, s), 4.17 (2H, q, J=7.1 Hz), 6.09 (1H, d, J=7.2 Hz), 7.97 (1H, d, J=7.2 Hz), 12.07 (1H, br s).

Reference Example 59

Production of ethyl 5-bromo-6-methyl-2-oxo-1,2-dihydropyridine-3-carboxylate

By a method similar to that in Reference Example 5, the title compound (2.94 g, 66%) was obtained as a pale-yellow powder from the compound of Reference Example 58 (3.11 g, 17.16 mmol).

$^1$H NMR (300 MHz, DMSO-$d_6$) δ: 1.24 (3H, t, J=7.1 Hz), 2.33 (3H, s), 4.20 (2H, q, J=7.1 Hz), 8.06 (1H, s), 12.40-12.60 (1H, br).

Reference Example 60

Production of ethyl 5-bromo-2-chloro-6-methylpyridine-3-carboxylate

By a method similar to that in Reference Example 6, the title compound (1.92 g, 90%) was obtained as a pale-brown oil from the compound of Reference Example 59 (2.00 g, 7.69 mmol).

$^1$H NMR (300 MHz, DMSO-$d_6$) δ: 1.33 (3H, t, J=7.2 Hz), 2.61 (3H, s), 4.34 (2H, q, J=7.1 Hz), 8.41 (1H, s).

Reference Example 61

Production of ethyl 5-bromo-3-hydroxy-1,6-dimethyl-1H-pyrrolo[2,3-b]pyridine-2-carboxylate By a method similar to that in Reference Example 7, the title compound (777 mg, 69%) was obtained as a beige powder from the compound of Reference Example 60 (1.0 g, 3.59 mmol).

$^1$H NMR (300 MHz, DMSO-$d_6$) δ: 1.33 (3H, t, J=7.1 Hz), 2.65 (3H, s), 3.88 (3H, s), 4.33 (2H, q, J=7.1 Hz), 8.35 (1H, s), 9.70 (1H, br s).

Reference Example 62

Production of ethyl 5-bromo-1,6-dimethyl-3-(2,2,2-trifluoroethoxy)-1H-pyrrolo[2,3-b]pyridine-2-carboxylate By a method similar to that in Reference Example 8, the title compound (846 mg, 96%) was obtained as a beige powder from the compound of Reference Example 61 (700 mg, 2.24 mmol).

$^1$H NMR (300 MHz, DMSO-d$_6$) δ: 1.34 (3H, t, J=7.1 Hz), 2.69 (3H, s), 3.95 (3H, s), 4.35 (2H, q, J=7.1 Hz), 4.85 (2H, q, J=9.1 Hz), 8.36 (1H, s).

Reference Example 63

Production of ethyl 5-amino-1,6-dimethyl-3-(2,2,2-trifluoroethoxy)-1H-pyrrolo[2,3-b]pyridine-2-carboxylate By a method similar to that in Reference Example 9, the title compound (0.32 g, 55%) was obtained as a yellow solid from the compound of Reference Example 62 (700 mg, 1.77 mmol).
$^1$H NMR (300 MHz, DMSO-d$_6$) δ: 1.34 (3H, t, J=7.1 Hz), 2.42 (3H, s), 3.89 (3H, s), 4.33 (2H, q, J=7.1 Hz), 4.66 (2H, q, J=9.1 Hz), 4.83 (2H, br s), 7.16 (1H, s).

Reference Example 64

Production of ethyl 5-{[(4-fluorophenyl)carbonyl]amino}-1,6-dimethyl-3-(2,2,2-trifluoroethoxy)-1H-pyrrolo[2,3-b]pyridine-2-carboxylate By a method similar to that in Reference Example 21, the title compound (209 mg, 100%) was obtained as a pale-yellow powder from the compound of Reference Example 63 (150 mg, 0.45 mmol) and 4-fluorobenzoyl chloride (79 mg, 0.50 mmol).
$^1$H NMR (300 MHz, DMSO-d$_6$) δ: 1.36 (3H, t, J=7.1 Hz), 2.55 (3H, s), 4.00 (3H, s), 4.37 (2H, q, J=7.1 Hz), 4.81 (2H, q, J=9.1 Hz), 7.36-7.42 (2H, m), 8.05-8.13 (3H, m), 10.13 (1H, s).

Reference Example 65

Production of 5-{[(4-fluorophenyl)carbonyl]amino}-1,6-dimethyl-3-(2,2,2-trifluoroethoxy)-1H-pyrrolo[2,3-b]pyridine-2-carboxylic acid By a method similar to that in Reference Example 12, the title compound (160 mg, 94%) was obtained as a white powder from the compound of Reference Example 64 (180 mg, 0.40 mmol), 2N aqueous sodium hydroxide solution (1 mL), ethanol (3 mL) and THF (0.5 mL).
$^1$H NMR (300 MHz, DMSO-d$_6$) δ: 2.54 (3H, s), 3.99 (3H, s), 4.77 (2H, q, J=9.1 Hz), 7.36-7.42 (2H, m), 7.99 (1H, s), 8.08-8.12 (2H, m), 10.11 (1H, s), 13.32 (1H, br s).

Reference Example 66

Production of ethyl 1,6-dimethyl-5-[(phenylcarbonyl)amino]-3-(2,2,2-trifluoroethoxy)-1H-pyrrolo[2,3-b]pyridine-2-carboxylate By a method similar to that in Reference Example 21, the title compound (181 mg, 92%) was obtained as a pale-yellow powder from the compound of Reference Example 63 (150 mg, 0.45 mmol) and benzoyl chloride (70 mg, 0.50 mmol). $^1$H NMR (300 MHz, DMSO-d$_6$) δ: 1.37 (3H, t, J=7.1 Hz), 2.56 (3H, s), 4.00 (3H, s), 4.37 (2H, q, J=7.1 Hz), 4.81 (2H, q, J=9.1 Hz), 7.53-7.62 (3H, m), 8.02-8.05 (3H, m), 10.11 (1H, s).

Reference Example 67

Production of 1,6-dimethyl-5-[(phenylcarbonyl)amino]-3-(2,2,2-trifluoroethoxy)-1H-pyrrolo[2,3-b]pyridine-2-carboxylic acid By a method similar to that in Reference Example 12, the title compound (140 mg, 93%) was obtained as a white powder from the compound of Reference Example 66 (160 mg, 0.37 mmol).
$^1$H NMR (300 MHz, DMSO-d$_6$) δ: 2.55 (3H, s), 3.99 (3H, s), 4.77 (2H, q, J=9.1 Hz), 7.23-7.62 (3H, m), 7.99-8.04 (3H, m), 10.09 (1H, s), 13.32 (1H, br s).

Reference Example 68

Production of ethyl 6-ethyl-5-[(furan-2-ylcarbonyl)amino]-1-methyl-3-(2,2,2-trifluoroethoxy)-1H-pyrrolo[2,3-b]pyridine-2-carboxylate By a method similar to that in Reference Example 21, the title compound (176 mg, 93%) was obtained as a pale-brown powder from the compound of Reference Example 9 (150 mg, 0.45 mmol) and 2-furoyl chloride (62 mg, 0.48 mmol).
$^1$H NMR (300 MHz, DMSO-d$_6$) δ: 1.25 (3H, t, J=7.5 Hz), 1.36 (3H, t, J=7.2 Hz), 2.86 (2H, q, J=7.5 Hz), 4.01 (3H, s), 4.37 (2H, q, J=7.1 Hz), 4.80 (2H, q, J=9.1 Hz), 6.72 (1H, q, J=1.7 Hz), 7.31 (1H, d, J=3.3 Hz), 7.95 (1H, q, J=0.8 Hz), 8.00 (1H, s), 10.01 (1H, s).

Reference Example 69

Production of 6-ethyl-5-[(furan-2-ylcarbonyl)amino]-1-methyl-3-(2,2,2-trifluoroethoxy)-1H-pyrrolo[2,3-b]pyridine-2-carboxylic acid By a method similar to that in Reference Example 12, the title compound (141 mg, 95%) was obtained as a white powder from the compound of Reference Example 68 (160 mg, 0.36 mmol).
$^1$H NMR (300 MHz, DMSO-d$_6$) δ: 1.24 (3H, t, J=7.5 Hz), 2.85 (2H, q, J=7.5 Hz), 4.00 (3H, s), 4.76 (2H, q, J=9.1 Hz), 6.71 (1H, q, J=1.8 Hz), 7.31 (1H, d, J=3.0 Hz), 7.94 (2H, s), 10.00 (1H, s), 13.32 (1H, br s).

Reference Example 70

Production of ethyl 6-ethyl-1-methyl-5-[(1,3-thiazol-5-ylcarbonyl)amino]-3-(2,2,2-trifluoroethoxy)-1H-pyrrolo[2,3-b]pyridine-2-carboxylate To a solution of thiazole-5-carboxylic acid (53 mg, 0.41 mmol) in THF (2 mL) were added oxalyl chloride (53 mg, 0.41 mmol) and DMF (1 drop), and the mixture was stirred at room temperature for 1 hr. The reaction mixture was concentrated, and the residue was dissolved in THF (1 mL) and the solution was added to a solution of the compound of Reference Example 9 (130 mg, 0.38 mmol) and pyridine (60 mg, 0.75 mmol) in THF (2 ml) under ice-cooling. After stirring at room temperature for 1 hr, a half amount of THF was evaporated, and the mixture was diluted with water (8 mL). After stirring at room temperature for 30 min, the precipitate was collected by filtration, washed with water, and dried under reduced pressure to give the title compound (153 mg, 82%) as a white powder.
$^1$H NMR (300 MHz, DMSO-d$_6$) δ: 1.26 (3H, t, J=7.5 Hz), 1.36 (3H, t, J=7.1 Hz), 2.87 (2H, q, J=7.5 Hz), 4.01 (3H, s), 4.37 (2H, q, J=7.1 Hz), 4.81 (2H, q, J=9.0 Hz), 8.04 (1H, s), 8.70 (1H, s), 9.32 (1H, s), 10.34 (1H, s).

Reference Example 71

Production of 6-ethyl-1-methyl-5-[(1,3-thiazol-5-ylcarbonyl)amino]-3-(2,2,2-trifluoroethoxy)-1H-pyrrolo[2,3-b]pyridine-2-carboxylic acid By a method similar to that in Reference Example 12, the title compound (114 mg, 95%) was obtained as a white powder from the compound of Reference Example 70 (130 mg, 0.28 mmol).
$^1$H NMR (300 MHz, DMSO-$d_6$) δ: 1.26 (3H, t, J=7.4 Hz), 2.87 (2H, q, J=7.5 Hz), 4.00 (3H, s), 4.77 (2H, q, J=9.1 Hz), 7.98 (1H, s), 8.70 (1H, s), 9.32 (1H, s), 10.33 (1H, s), 13.33 (1H, br s).

Reference Example 72

Production of ethyl 6-ethyl-5-(2-fluorophenyl)-1-methyl-3-(2,2,2-trifluoroethoxy)-1H-pyrrolo[2,3-b]pyridine-2-carboxylate By a method similar to that in Reference Example 15, the title compound (112 mg, 68%) was obtained as a colorless oil from the compound of Reference Example 8 (159 mg, 0.389 mmol), o-fluorophenylboronic acid (67.4 mg, 0.482 mmol), potassium carbonate (432 mg, 3.12 mmol), toluene (2 mL), ethanol (2 mL) and Pd(PPh$_3$)$_4$ (21.8 mg, 0.0189 mmol).
$^1$H NMR (300 MHz, DMSO-$d_6$) δ: 1.15 (3H, t, J=7.5 Hz), 1.35 (3H, t, J=7.1 Hz), 2.68 (2H, q, J=7.5 Hz), 4.03 (3H, s), 4.36 (2H, q, J=7.1 Hz), 4.85 (2H, q, J=9.0 Hz), 7.24-7.63 (4H, m), 7.96 (1H, s).

Reference Example 73

Production of 6-ethyl-5-(2-fluorophenyl)-1-methyl-3-(2,2,2-trifluoroethoxy)-1H-pyrrolo[2,3-b]pyridine-2-carboxylic acid By a method similar to that in Reference Example 12, the title compound (89.8 mg, 87%) was obtained as a white powder from the compound of Reference Example 72 (111 mg, 0.262 mmol), 2N aqueous sodium hydroxide solution (0.5 mL) and ethanol (3 mL).
$^1$H NMR (300 MHz, DMSO-$d_6$) δ: 1.15 (3H, t, J=7.5 Hz), 2.68 (2H, q, J=7.5 Hz), 4.02 (3H, s), 4.80 (2H, q, J=9.1 Hz), 7.22-7.65 (4H, m), 7.88 (1H, s), 13.26 (1H, br s).

Reference Example 74

Production of ethyl 6-ethyl-1-methyl-5-(phenylamino)-3-(2,2,2-trifluoroethoxy)-1H-pyrrolo[2,3-b]pyridine-2-carboxylate By a method similar to that in Reference Example 13, the title compound (125 mg, 80%) was obtained as a yellow powder from the compound of Reference Example 8 (151 mg, 0.370 mmol), aniline (0.040 mL, 0.439 mmol), cesium carbonate (192 mg, 0.590 mmol), toluene (2 mL), binap (23.0 mg, 0.0369 mmol) and Pd$_2$dba$_3$ (17.7 mg, 0.0193 mmol).
$^1$H NMR (300 MHz, DMSO-$d_6$) δ: 1.23 (3H, t, J=7.5 Hz), 1.35 (3H, t, J=7.1 Hz), 2.84 (2H, q, J=7.5 Hz), 3.99 (3H, s), 4.36 (2H, q, J=7.1 Hz), 4.76 (2H, q, J=9.2 Hz), 6.61-6.77 (3H, m), 7.14 (2H, t, J=7.9 Hz), 7.54 (1H, s), 7.80 (1H, s).

Reference Example 75

Production of 6-ethyl-1-methyl-5-(phenylamino)-3-(2,2,2-trifluoroethoxy)-1H-pyrrolo[2,3-b]pyridine-2-carboxylic acid By a method similar to that in Reference Example 12, the title compound (109 mg, 94%) was obtained as a yellow powder from the compound of Reference Example 74 (124 mg, 0.294 mmol), 2N aqueous sodium hydroxide solution (0.5 mL) and ethanol (3 mL).
$^1$H NMR (300 MHz, DMSO-$d_6$) δ: 1.23 (3H, t, J=7.5 Hz), 2.84 (2H, q, J=7.5 Hz), 3.99 (3H, s), 4.73 (2H, q, J=9.3 Hz), 6.58-6.81 (3H, m), 7.13 (2H, t, J=7.9 Hz), 7.53 (1H, s), 7.75 (1H, s), 13.28 (1H, br s).

Reference Example 76

Production of ethyl 6-ethyl-5-{[(2-fluorophenyl)carbonyl]amino}-1-methyl-3-(2,2,2-trifluoroethoxy)-1H-pyrrolo[2,3-b]pyridine-2-carboxylate By a method similar to that in Reference Example 21, the title compound (108 mg, 88%) was obtained as a white powder from the compound of Reference Example 9 (90.0 mg, 0.261 mmol), pyridine (0.0400 mL, 0.495 mmol) and THF (2 mL), 2-fluorobenzoyl chloride (0.0326 mL, 0.271 mmol).
$^1$H NMR (300 MHz, DMSO-$d_6$) δ: 1.28 (3H, t, J=7.5 Hz), 1.36 (3H, t, J=7.1 Hz), 2.93 (2H, q, J=7.5 Hz), 4.01 (3H, s), 4.37 (2H, q, J=7.1 Hz), 4.82 (2H, q, J=9.0 Hz), 7.30-7.45 (2H, m), 7.55-7.68 (1H, m), 7.78 (1H, td, J=7.6, 1.7 Hz), 8.10 (1H, s), 10.07 (1H, s).

Reference Example 77

Production of 6-ethyl-5-{[(2-fluorophenyl)carbonyl]amino}-1-methyl-3-(2,2,2-trifluoroethoxy)-1H-pyrrolo[2,3-b]pyridine-2-carboxylic acid By a method similar to that in Reference Example 12, the title compound (97.5 mg, 97%) was obtained as a white powder from the compound of Reference Example 76 (107 mg, 0.229 mmol), 2N aqueous sodium hydroxide solution (0.5 mL), ethanol (2 mL) and THF (0.5 mL).
$^1$H NMR (300 MHz, DMSO-$d_6$) δ: 1.28 (3H, t, J=7.5 Hz), 2.92 (2H, q, J=7.5 Hz), 4.00 (3H, s), 4.78 (2H, q, J=9.1 Hz), 7.30-7.46 (2H, m), 7.55-7.68 (1H, m), 7.78 (1H, td, J=7.5, 1.6 Hz), 8.04 (1H, s), 10.05 (1H, s), 13.38 (1H, br s).

Reference Example 78

Production of ethyl 6-ethyl-5-{[(4-fluorophenyl)carbonyl]amino}-1-methyl-3-(2,2,2-trifluoroethoxy)-1H-pyrrolo[2,3-b]pyridine-2-carboxylate By a method similar to that in Reference Example 21, the title compound (98.9 mg, 82%) was obtained as a white powder from the compound of Reference Example 9 (88.6 mg, 0.257 mmol), pyridine (0.0400 mL, 0.495 mmol), THF (2 mL) and 4-fluorobenzoyl chloride (0.0322 mL, 0.272 mmol).
$^1$H NMR (300 MHz, DMSO-$d_6$) δ: 1.25 (3H, t, J=7.6 Hz), 1.36 (3H, t, J=7.2 Hz), 2.87 (2H, q, J=7.6 Hz), 4.01 (3H, s), 4.37 (2H, q, J=7.2 Hz), 4.81 (2H, q, J=9.1 Hz), 7.33-7.46 (2H, m), 8.02 (1H, s), 8.05-8.15 (2H, m), 10.16 (1H, s).

Reference Example 79

Production of 6-ethyl-5-{[(4-fluorophenyl)carbonyl]amino}-1-methyl-3-(2,2,2-trifluoroethoxy)-1H-pyrrolo[2,3-b]pyridine-2-carboxylic acid By a method similar to that in Reference Example 12, the title compound (89.5 mg, 97%) was obtained as a white powder from the compound of Reference Example 78 (98.0 mg, 0.210 mmol), 2N aqueous sodium hydroxide solution (0.5 mL), ethanol (2 mL) and THF (0.5 mL).
$^1$H NMR (300 MHz, DMSO-$d_6$) δ: 1.25 (3H, t, J=7.5 Hz), 2.87 (2H, q, J=7.5 Hz), 4.00 (3H, s), 4.78 (2H, q, J=9.1 Hz), 7.28-7.49 (2H, m), 7.95 (1H, s), 8.00-8.21 (2H, m), 10.14 (1H, s), 13.36 (1H, br s).

Reference Example 80

Production of ethyl 6-ethyl-1-methyl-5-[(thiophen-2-ylcarbonyl)amino]-3-(2,2,2-trifluoroethoxy)-1H-pyrrolo[2,3-b]pyridine-2-carboxylate By a method similar to that in Reference Example 23, the title compound (178 mg, 91%) was obtained as a white powder from the compound of Reference Example 9 (149 mg, 0.431 mmol), pyridine (0.0526 mL, 0.650 mmol), THF (3 mL) and thiophene-2-carbonyl chloride (0.0506 mL, 0.476 mmol).
$^1$H NMR (300 MHz, DMSO-$d_6$) δ: 1.25 (3H, t, J=7.6 Hz), 1.36 (3H, t, J=7.1 Hz), 2.87 (2H, q, J=7.6 Hz), 4.01 (3H, s), 4.36 (2H, q, J=7.1 Hz), 4.82 (2H, q, J=9.1 Hz), 7.25 (1H, dd, J=5.0, 3.9 Hz), 7.87 (1H, dd, J=5.0, 1.0 Hz), 7.98-8.05 (2H, m), 10.15 (1H, s).

Reference Example 81

Production of 6-ethyl-1-methyl-5-[(thiophen-2-ylcarbonyl)amino]-3-(2,2,2-trifluoroethoxy)-1H-pyrrolo[2,3-b]pyridine-2-carboxylic acid By a method similar to that in Reference Example 12, the title compound (162 mg, 99%) was obtained as a white powder from the compound of Reference Example 80 (175 mg, 0.384 mmol), 2N aqueous sodium hydroxide solution (0.5 mL), ethanol (2 mL) and THF (1 mL).
$^1$H NMR (300 MHz, DMSO-$d_6$) δ: 1.25 (3H, t, J=7.6 Hz), 2.87 (2H, q, J=7.6 Hz), 4.00 (3H, s), 4.78 (2H, q, J=9.2 Hz), 7.25 (1H, dd, J=5.0, 3.8 Hz), 7.87 (1H, dd, J=5.0, 0.8 Hz), 7.95 (1H, s), 8.01 (1H, d, J=3.2 Hz), 10.14 (1H, s), 13.37 (1H, br s).

Reference Example 82

Production of ethyl 6-ethyl-5-{[(3-fluorophenyl)carbonyl]amino}-1-methyl-3-(2,2,2-trifluoroethoxy)-1H-pyrrolo[2,3-b]pyridine-2-carboxylate By a method similar to that in Reference Example 23, the title compound (192 mg, 96%) was obtained as a white powder from the compound of Reference Example 9 (148 mg, 0.429 mmol), pyridine (0.0526 mL, 0.650 mmol), THF (2 mL) and 3-fluorobenzoyl chloride (0.058 mL, 0.477 mmol).
$^1$H NMR (300 MHz, DMSO-$d_6$) δ: 1.25 (3H, t, J=7.5 Hz), 1.36 (3H, t, J=7.1 Hz), 2.88 (2H, q, J=7.5 Hz), 4.01 (3H, s), 4.37 (2H, q, J=7.1 Hz), 4.82 (2H, q, J=9.1 Hz), 7.48 (1H, td, J=8.5, 2.2 Hz), 7.62 (1H, td, J=7.8, 5.9 Hz), 7.77-7.85 (1H, m), 7.88 (1H, d, J=7.8 Hz), 8.03 (1H, s), 10.22 (1H, s).

Reference Example 83

Production of 6-ethyl-5-{[(3-fluorophenyl)carbonyl]amino}-1-methyl-3-(2,2,2-trifluoroethoxy)-1H-pyrrolo[2,3-b]pyridine-2-carboxylic acid By a method similar to that in Reference Example 12, the title compound (171 mg, 96%) was obtained as a white powder from the compound of Reference Example 82 (190 mg, 0.407 mmol), 2N aqueous sodium hydroxide solution (1 mL), ethanol (2 mL) and THF (1 mL).
$^1$H NMR (300 MHz, DMSO-$d_6$) δ: 1.25 (3H, t, J=7.5 Hz), 2.87 (2H, q, J=7.5 Hz), 4.01 (3H, s), 4.78 (2H, q, J=9.2 Hz), 7.48 (1H, td, J=8.6, 2.5 Hz), 7.56-7.68 (1H, m), 7.77-7.85 (1H, m), 7.88 (1H, d, J=7.7 Hz), 7.97 (1H, s), 10.21 (1H, s), 13.37 (1H, br s).

Reference Example 84

Production of ethyl 5-bromo-6-ethyl-1-methyl-3-(1-methylethoxy)-1H-pyrrolo[2,3-b]pyridine-2-carboxylate A mixture of the compound of Reference Example 7 (2.00 g, 6.11 mmol), acetone (40 mL), potassium carbonate (1.19 g, 8.61 mmol) and diisopropyl sulfate (1.1 mL, 6.64 mmol) was stirred for 4 hr with heating under reflux. To the reaction mixture was added water (100 mL), and the precipitate was collected by filtration, washed with water, and dried under reduced pressure to give the title compound (2.18 g, 97%) as a yellow powder.
$^1$H NMR (300 MHz, DMSO-$d_6$) δ: 1.24-1.32 (9H, m), 1.35 (3H, t, J=7.1 Hz), 2.99 (2H, q, J=7.4 Hz), 3.94 (3H, s), 4.34 (2H, q, J=7.1 Hz), 4.44-4.57 (1H, m), 8.30 (1H, s).

Reference Example 85

Production of ethyl 5-amino-6-ethyl-1-methyl-3-(1-methylethoxy)-1H-pyrrolo[2,3-b]pyridine-2-carboxylate By a method similar to that in Reference Example 9, the title compound (613 mg, 93%) was obtained as an orange powder from the compound of Reference Example 84 (799 mg, 2.16 mmol), benzophenonimine (0.546 mL, 3.25 mmol), cesium carbonate (1.39 g, 4.27 mmol), toluene (10 mL), Pd$_2$dba$_3$ (98.3 mg, 0.107 mmol), Xantphos (128 mg, 0.221 mmol), THF (8 mL), and 2N hydrochloric acid (2 mL).
$^1$H NMR (300 MHz, DMSO-$d_6$) δ: 1.21-1.29 (9H, m), 1.33 (3H, t, J=7.2 Hz), 2.73 (2H, q, J=7.4 Hz), 3.88 (3H, s), 4.29 (2H, q, J=7.2 Hz), 4.33-4.44 (1H, m), 4.74 (2H, s), 7.17 (1H, s).

Reference Example 86

Production of ethyl 6-ethyl-5-{[(4-fluorophenyl)carbonyl]amino}-1-methyl-3-(1-methylethoxy)-1H-pyrrolo[2,3-b]pyridine-2-carboxylate By a method similar to that in Reference Example 23, the title compound (188 mg, 89%) was obtained as a white powder from the compound of Reference Example 85 (150 mg, 0.492 mmol), pyridine (0.0596 mL, 0.737 mmol), THF (2 mL), and 4-fluorobenzoyl chloride (0.0638 mL, 0.539 mmol).

$^1$H NMR (300 MHz, DMSO-$d_6$) δ: 1.20-1.32 (9H, m), 1.36 (3H, t, J=7.1 Hz), 2.86 (2H, q, J=7.4 Hz), 3.98 (3H, s), 4.34 (2H, q, J=7.1 Hz), 4.44-4.58 (1H, m), 7.39 (2H, t, J=8.9 Hz), 7.98 (1H, s), 8.02-8.16 (2H, m), 10.11 (1H, s).

Reference Example 87

Production of 6-ethyl-5-{[(4-fluorophenyl)carbonyl]amino}-1-methyl-3-(1-methylethoxy)-1H-pyrrolo[2,3-b]pyridine-2-carboxylic acid By a method similar to that in Reference Example 12, the title compound (165 mg, 96%) was obtained as a white powder from the compound of Reference Example 86 (184 mg, 0.430 mmol), 2N aqueous sodium hydroxide solution (0.5 mL) and ethanol (2 mL).

$^1$H NMR (300 MHz, DMSO-$d_6$) δ: 1.25 (3H, t, J=7.6 Hz), 1.27 (6H, d, J=6.0 Hz), 2.85 (2H, q, J=7.6 Hz), 3.98 (3H, s), 4.41-4.60 (1H, m), 7.39 (2H, t, J=8.8 Hz), 7.94 (1H, s), 8.02-8.18 (2H, m), 10.09 (1H, s), 12.87 (1H, br s).

Reference Example 88

Production of ethyl 6-ethyl-1-methyl-3-(1-methylethoxy)-5-[(phenylcarbonyl)amino]-1H-pyrrolo[2,3-b]pyridine-2-carboxylate By a method similar to that in Reference Example 23, the title compound (183 mg, 92%) was obtained as a white powder from the compound of Reference Example 85 (149 mg, 0.487 mmol), pyridine (0.0596 mL, 0.737 mmol), THF (2 mL), and benzoyl chloride (0.0628 mL, 0.541 mmol).

$^1$H NMR (300 MHz, DMSO-$d_6$) δ: 1.19-1.32 (9H, m), 1.36 (3H, t, J=7.2 Hz), 2.87 (2H, q, J=7.4 Hz), 3.99 (3H, s), 4.34 (2H, q, J=7.2 Hz), 4.44-4.58 (1H, m), 7.48-7.69 (3H, m), 7.98 (1H, s), 7.99-8.08 (2H, m), 10.08 (1H, s).

Reference Example 89

Production of 6-ethyl-1-methyl-3-(1-methylethoxy)-5-[(phenylcarbonyl)amino]-1H-pyrrolo[2,3-b]pyridine-2-carboxylic acid By a method similar to that in Reference Example 12, the title compound (163 mg, 97%) was obtained as a white powder from the compound of Example 88 (180 mg, 0.440 mmol), 2N aqueous sodium hydroxide solution (0.5 mL) and ethanol (2 mL).

$^1$H NMR (300 MHz, DMSO-$d_6$) δ: 1.25 (3H, t, J=7.5 Hz), 1.27 (6H, d, J=6.2 Hz), 2.86 (2H, q, J=7.5 Hz), 3.98 (3H, s), 4.44-4.57 (1H, m), 7.49-7.67 (3H, m), 7.94 (1H, s), 7.98-8.07 (2H, m), 10.07 (1H, s), 12.92 (1H, br s).

Reference Example 90

Production of ethyl 6-ethyl-1-methyl-5-(4,4,5,5-tetramethyl-1,3,2-dioxaborolan-2-yl)-3-(2,2,2-trifluoroethoxy)-1H-pyrrolo[2,3-b]pyridine-2-carboxylate To a mixture of the compound of Reference Example 8 (403 mg, 0.985 mmol), bis(pinacolato)diboron (447 mg, 1.76 mmol), potassium acetate (246 mg, 2.50 mmol) and DMF (5 mL) was added PdCl$_2$(dppf).CH$_2$Cl$_2$ (81.2 mg, 0.0994 mmol), and the mixture was stirred at 100° C. for 14 hr under an argon atmosphere. The reaction mixture was filtered through celite, and washed with ethyl acetate. The filtrate was washed successively with water (10 mL) and brine (10 mL), dried over anhydrous magnesium sulfate, and concentrated under reduced pressure. The residue was purified by silica gel column chromatography (eluent, hexane:ethyl acetate=99:1→9:1) to give the title compound (296 mg, 66%) as a white powder.

$^1$H NMR (300 MHz, DMSO-$d_6$) δ: 1.23 (3H, t, J=7.6 Hz), 1.29-1.40 (15H, m), 3.11 (2H, q, J=7.6 Hz), 3.98 (3H, s), 4.36 (2H, q, J=7.1 Hz), 4.83 (2H, q, J=9.1 Hz), 8.31 (1H, s).

Reference Example 91

Production of ethyl 6-ethyl-5-(3-methoxyphenoxy)-1-methyl-3-(2,2,2-trifluoroethoxy)-1H-pyrrolo[2,3-b]pyridine-2-carboxylate A mixture of the compound of Reference Example 90 (260 mg, 0.570 mmol), 3-methoxyphenol (0.188 mL, 1.71 mmol), copper(II) acetate (125 mg, 0.689 mmol), pyridine (0.070 mL, 0.865 mmol) and DMF (4 mL) was stirred at 100° C. for 1 hr. The reaction mixture was filtered through celite, and washed with ethyl acetate. The filtrate was washed successively with water (10 ml) and brine (5 mL), dried over anhydrous magnesium sulfate, and concentrated under reduced pressure. The residue was purified by silica gel column chromatography (eluent, hexane→hexane:ethyl acetate=9:1) to give the title compound (103 mg, 400) as a white powder.

$^1$H NMR (300 MHz, DMSO-$d_6$) δ: 1.23 (3H, t, J=7.5 Hz), 1.34 (3H, t, J=7.1 Hz), 2.79 (2H, q, J=7.5 Hz), 3.72 (3H, s), 4.00 (3H, s), 4.36 (2H, q, J=7.1 Hz), 4.79 (2H, q, J=9.1 Hz), 6.43 (1H, dd, J=8.0, 2.1 Hz), 6.52 (1H, t, J=2.1 Hz), 6.68 (1H, dd, J=8.0, 2.1 Hz), 7.24 (1H, t, J=8.0 Hz), 7.74 (1H, s).

Reference Example 92

Production of 6-ethyl-5-(3-methoxyphenoxy)-1-methyl-3-(2,2,2-trifluoroethoxy)-1H-pyrrolo[2,3-b]pyridine-2-carboxylic acid By a method similar to that in Reference Example 12, the title compound (79.2 mg, 84%) was obtained as a white powder from the compound of Reference Example 91 (101 mg, 0.223 mmol), 2N aqueous sodium hydroxide solution (0.3 mL) and ethanol (2 mL).

$^1$H NMR (300 MHz, DMSO-$d_6$) δ: 1.23 (3H, t, J=7.6 Hz), 2.78 (2H, q, J=7.6 Hz), 3.72 (3H, s), 4.00 (3H, s), 4.75 (2H, q, J=9.2 Hz), 6.42 (1H, dd, J=8.2, 2.4 Hz), 6.52 (1H, t, J=2.4 Hz), 6.67 (1H, dd, J=8.2, 2.4 Hz), 7.24 (1H, t, J=8.2 Hz), 7.66 (1H, s), 13.37 (1H, br s).

Reference Example 93

Production of ethyl 5-amino-6-ethyl-1-methyl-3-(2,2,2-trifluoroethoxy)-1H-pyrrolo[2,3-b]pyridine-2-carboxylate hydrochloride To a mixture of the compound of Reference Example 8 (1.37 g, 3.35 mmol), benzophenonimine (0.812 mL, 4.84 mmol), cesium carbonate (2.42 g, 7.43 mmol) and toluene (20 mL) were added Pd$_2$dba$_3$ (147 mg, 0.161 mmol) and Xantphos (181 mg, 0.312 mmol), and the mixture was stirred at 100° C. for 15 hr under an argon atmosphere. The mixture was filtered through celite, and washed with ethyl acetate. The filtrate was washed with brine (10 mL), dried over anhydrous magnesium sulfate, and concentrated under reduced pressure.

The residue was purified by silica gel column chromatography (eluent, hexane:ethyl acetate=99:1→9:1) to give crude ethyl 5-[(diphenylmethylidene)amino]-6-ethyl-1-methyl-3-(2,2,2-trifluoroethoxy)-1H-pyrrolo[2,3-b]pyridine-2-carboxylate. The obtained crude compound was dissolved in THF (20 mL), 2N hydrochloric acid (2 mL) was added thereto, and the mixture was stirred at room temperature for 1 hr. Diethyl ether (40 ml) was added to the mixture, and the resulting precipitate was collected by filtration, and washed with diethyl ether to give the title compound (1.15 g, 90%) as a white powder.

$^1$H NMR (300 MHz, DMSO-$d_6$) δ: 1.32 (3H, t, J=7.4 Hz), 1.36 (3H, t, J=7.1 Hz), 2.93 (2H, q, J=7.4 Hz), 3.99 (3H, s), 4.37 (2H, q, J=7.1 Hz), 4.77 (2H, q, J=9.1 Hz), 7.96 (1H, s), 9.49 (3H, br s).

Reference Example 94

Production of ethyl 6-ethyl-1-methyl-5-[(thiophen-3-ylcarbonyl)amino]-3-(2,2,2-trifluoroethoxy)-1H-pyrrolo[2,3-b]pyridine-2-carboxylate By a method similar to that in Reference Example 23, the title compound (149 mg, 97%) was obtained as a white powder from the compound of Reference Example 93 (129 mg, 0.338 mmol), thiophene-3-carbonyl chloride (0.0655 mL, 0.447 mmol), pyridine (0.070 mmol, 0.865 mmol) and THF (3 mL).

$^1$H NMR (300 MHz, DMSO-$d_6$) δ: 1.25 (3H, t, J=7.6 Hz), 1.36 (3H, t, J=7.1 Hz), 2.87 (2H, q, J=7.6 Hz), 4.01 (3H, s), 4.36 (2H, q, J=7.1 Hz), 4.81 (2H, q, J=9.0 Hz), 7.65 (1H, dd, J=5.1, 1.2 Hz), 7.68 (1H, dd, J=5.1, 2.8 Hz), 8.00 (1H, s), 8.36 (1H, d, J=1.2 Hz), 9.96 (1H, s).

Reference Example 95

Production of 6-ethyl-1-methyl-5-[(thiophen-3-ylcarbonyl)amino]-3-(2,2,2-trifluoroethoxy)-1H-pyrrolo[2,3-b]pyridine-2-carboxylic acid By a method similar to that in Reference Example 12, the title compound (135 mg, 98%) was obtained as a white powder from the compound of Reference Example 94 (147 mg, 0.323 mmol), 2N aqueous sodium hydroxide solution (0.5 mL), ethanol (2 mL) and THF (0.5 mL).

$^1$H NMR (300 MHz, DMSO-$d_6$) δ: 1.24 (3H, t, J=7.5 Hz), 2.86 (2H, q, J=7.5 Hz), 4.00 (3H, s), 4.78 (2H, q, J=9.1 Hz), 7.65 (1H, dd, J=5.1, 1.2 Hz), 7.68 (1H, dd, J=5.1, 2.8 Hz), 7.93 (1H, s), 8.35 (1H, d, J=1.2 Hz), 9.95 (1H, s), 13.37 (1H, br s).

Reference Example 96

Production of ethyl 6-ethyl-1-methyl-3-(1-methylethoxy)-5-[(thiophen-2-ylcarbonyl)amino]-1H-pyrrolo[2,3-b]pyridine-2-carboxylate By a method similar to that in Reference Example 23, the title compound (149 mg, 91%) was obtained as a pale-orange powder from the compound of Reference Example 85 (120 mg, 0.393 mmol), pyridine (0.048 mL, 0.593 mmol), THF (2 mL) and thiophene-2-carbonyl chloride (0.046 mL, 0.433 mmol). $^1$H NMR (300 MHz, DMSO-$d_6$) δ: 1.20-1.32 (9H, m), 1.36 (3H, t, J=7.2 Hz), 2.86 (2H, q, J=7.5 Hz), 3.98 (3H, s), 4.34 (2H, q, J=7.2 Hz), 4.43-4.57 (1H, m), 7.25 (1H, dd, J=4.8, 3.9 Hz), 7.87 (1H, d, J=4.8 Hz), 7.96 (1H, s), 8.00 (1H, d, J=3.9 Hz), 10.10 (1H, s).

Reference Example 97

Production of 6-ethyl-1-methyl-3-(1-methylethoxy)-5-[(thiophen-2-ylcarbonyl)amino]-1H-pyrrolo[2,3-b]pyridine-2-carboxylic acid By a method similar to that in Reference Example 12, the title compound (127 mg, 92%) was obtained as a white powder from the compound of Reference Example 96 (147 mg, 0.354 mmol), 2N aqueous sodium hydroxide solution (0.5 mL), ethanol (2 mL) and THF (0.25 mL).

$^1$H NMR (300 MHz, DMSO-$d_6$) δ: 1.24 (3H, t, J=7.5 Hz), 1.27 (6H, d, J=6.0 Hz), 2.85 (2H, q, J=7.5 Hz), 3.98 (3H, s), 4.40-4.61 (1H, m), 7.24 (1H, dd, J=5.0, 4.0 Hz), 7.86 (1H, dd, J=5.0, 0.8 Hz), 7.93 (1H, s), 8.01 (1H, d, J=4.0 Hz), 10.09 (1H, s), 12.93 (1H, br s).

Reference Example 98

Production of ethyl 5-{[(1,3-dimethyl-1H-pyrazol-5-yl)carbonyl]amino}-6-ethyl-1-methyl-3-(2,2,2-trifluoroethoxy)-1H-pyrrolo[2,3-b]pyridine-2-carboxylate To a solution of 1,3-dimethyl-1H-pyrazole-5-carboxylic acid (72.6 mg, 0.518 mmol) in THF (1 mL) were added DMF (0.01 mL) and oxalyl chloride (0.0904 mL, 1.05 mmol), and the mixture was stirred at room temperature for 3 hr. The reaction mixture was concentrated under reduced pressure, and the residue was dissolved in THF (1 mL). This solution was added dropwise to a mixture of the compound of Reference Example 9 (119 mg, 0.348 mmol), pyridine (0.0422 mL, 0.522 mmol) and THF (2 mL), and the mixture was stirred at room temperature for 3 hr. To the reaction mixture was added water (15 mL), and the precipitate was collected by filtration, and washed with water to give the title compound (153 mg, 95%) as a pale-orange powder.

$^1$H NMR (300 MHz, DMSO-$d_6$) δ: 1.24 (3H, t, J=7.5 Hz), 1.36 (3H, t, J=7.1 Hz), 2.22 (3H, s), 2.86 (2H, q, J=7.5 Hz), 4.00 (6H, s), 4.36 (2H, q, J=7.1 Hz), 4.81 (2H, q, J=9.1 Hz), 6.87 (1H, s), 8.00 (1H, s), 10.00 (1H, s).

Reference Example 99

Production of 5-{[(1,3-dimethyl-1H-pyrazol-5-yl)carbonyl]amino}-6-ethyl-1-methyl-3-(2,2,2-trifluoroethoxy)-1H-pyrrolo[2,3-b]pyridine-2-carboxylic acid By a method similar to that in Reference Example 12, the title compound (136 mg, 96%) was obtained as a pale-orange powder from the compound of Reference Example 98 (152 mg, 0.324 mmol), 2N aqueous sodium hydroxide solution (0.5 mL), ethanol (2 mL) and THF (0.5 mL).

$^1$H NMR (300 MHz, DMSO-$d_6$) δ: 1.24 (3H, t, J=7.5 Hz), 2.21 (3H, s), 2.85 (2H, q, J=7.5 Hz), 4.00 (3H, s), 4.00 (3H, s), 4.78 (2H, q, J=9.1 Hz), 6.87 (1H, s), 7.93 (1H, s), 9.99 (1H, s), 13.38 (1H, br s).

Reference Example 100

Production of ethyl 5-{[(5-chlorothiophen-2-yl)carbonyl]amino}-6-ethyl-1-methyl-3-(1-methylethoxy)-1H-pyrrolo[2,3-b]pyridine-2-carboxylate By a method similar to that in Reference Example 98, the title compound (189 mg, 94%) was obtained as a white powder from 5-chlorothiophene-2-carboxylic acid (93.8 mg, 0.577 mmol), oxalyl chloride (0.0648 mL, 0.756 mmol), the compound of Reference Example 85 (136 mg, 0.445 mmol) and pyridine (0.072 mL, 0.890 mmol).

$^1$H NMR (300 MHz, DMSO-d$_6$) δ: 1.20-1.31 (9H, m), 1.36 (3H, t, J=7.1 Hz), 2.84 (2H, q, J=7.6 Hz), 3.98 (3H, s), 4.34 (2H, q, J=7.1 Hz), 4.43-4.58 (1H, m), 7.29 (1H, d, J=4.0 Hz), 7.89 (1H, d, J=4.0 Hz), 7.97 (1H, s), 10.19 (1H, s).

Reference Example 101

Production of 5-{[(5-chlorothiophen-2-yl)carbonyl]amino}-6-ethyl-1-methyl-3-(1-methylethoxy)-1H-pyrrolo[2,3-b]pyridine-2-carboxylic acid By a method similar to that in Reference Example 12, the title compound (163 mg, 93%) was obtained as a pale-orange powder from the compound of Reference Example 100 (186 mg, 0.324 mmol), 2N aqueous sodium hydroxide solution (0.5 mL), ethanol (2 mL) and THF (0.5 mL).

$^1$H NMR (300 MHz, DMSO-d$_6$) δ: 1.24 (3H, t, J=7.5 Hz), 1.27 (6H, d, J=6.2 Hz), 2.83 (2H, q, J=7.5 Hz), 3.97 (3H, s), 4.42-4.58 (1H, m), 7.29 (1H, d, J=4.0 Hz), 7.89 (1H, d, J=4.0 Hz), 7.94 (1H, s), 10.19 (1H, s), 12.92 (1H, br s).

Reference Example 102

Production of ethyl 6-ethyl-1-methyl-3-(1-methylethoxy)-5-[(thiophen-3-ylcarbonyl)amino]-1H-pyrrolo[2,3-b]pyridine-2-carboxylate By a method similar to that in Reference Example 23, the title compound (121 mg, 88%) was obtained as a white powder from the compound of Reference Example 85 (101 mg, 0.332 mmol), thiophene-3-carbonyl chloride (0.0546 mL, 0.372 mmol), pyridine (0.040 mL, 0.495 mmol) and THF (2 mL).

$^1$H NMR (300 MHz, DMSO-d$_6$) δ: 1.18-1.32 (9H, m), 1.36 (3H, t, J=7.2 Hz), 2.85 (2H, q, J=7.4 Hz), 3.98 (3H, s), 4.34 (2H, q, J=7.2 Hz), 4.43-4.61 (1H, m), 7.58-7.74 (2H, m), 7.95 (1H, s), 8.34 (1H, d, J=1.3 Hz), 9.91 (1H, s).

Reference Example 103

Production of 6-ethyl-1-methyl-3-(1-methylethoxy)-5-[(thiophen-3-ylcarbonyl)amino]-1H-pyrrolo[2,3-b]pyridine-2-carboxylic acid By a method similar to that in Reference Example 12, the title compound (107 mg, 96%) was obtained as a white powder from the compound of Reference Example 102 (120 mg, 0.289 mmol), 2N aqueous sodium hydroxide solution (0.5 mL) and ethanol (2 mL).

$^1$H NMR (300 MHz, DMSO-d$_6$) δ: 1.24 (3H, t, J=7.5 Hz), 1.27 (6H, d, J=6.0 Hz), 2.85 (2H, q, J=7.5 Hz), 3.98 (3H, s), 4.39-4.59 (1H, m), 7.58-7.75 (2H, m), 7.91 (1H, s), 8.27-8.42 (1H, m), 9.91 (1H, s), 12.89 (1H, br s).

Reference Example 104

Production of ethyl 6-ethyl-5-{[(4-methoxythiophen-3-yl)carbonyl]amino}-1-methyl-3-(1-methylethoxy)-1H-pyrrolo[2,3-b]pyridine-2-carboxylate By a method similar to that in Reference Example 98, the title compound (114 mg, 78%) was obtained as a white powder from 4-methoxythiophene-3-carboxylic acid (65.4 mg, 0.413 mmol), oxalyl chloride (0.0478 mL, 0.558 mmol), the compound of Reference Example 85 (100 mg, 0.327 mmol) and pyridine (0.053 mL, 0.655 mmol).

$^1$H NMR (300 MHz, DMSO-d$_6$) δ: 1.26-1.40 (12H, m), 2.91 (2H, q, J=7.4 Hz), 3.97 (3H, s), 4.00 (3H, s), 4.34 (2H, q, J=7.1 Hz), 4.41-4.56 (1H, m), 6.92 (1H, d, J=3.6 Hz), 8.23 (1H, d, J=3.6 Hz), 8.50 (1H, s), 9.48 (1H, s).

Reference Example 105

Production of 6-ethyl-5-{[(4-methoxythiophen-3-yl)carbonyl]amino}-1-methyl-3-(1-methylethoxy)-1H-pyrrolo[2,3-b]pyridine-2-carboxylic acid By a method similar to that in Reference Example 12, the title compound (105 mg, 100%) was obtained as a white powder from the compound of Reference Example 104 (112 mg, 0.251 mmol), 2N aqueous sodium hydroxide solution (0.5 mL), ethanol (2 mL) and THF (0.1 mL).

$^1$H NMR (300 MHz, DMSO-d$_6$) δ: 1.28 (6H, d, J=6.2 Hz), 1.30 (3H, t, J=7.6 Hz), 2.90 (2H, q, J=7.6 Hz), 3.96 (3H, s), 4.00 (3H, s), 4.38-4.59 (1H, m), 6.92 (1H, d, J=3.5 Hz), 8.23 (1H, d, J=3.5 Hz), 8.47 (1H, s), 9.47 (1H, s), 12.92 (1H, br s).

Reference Example 106

Production of ethyl 5-{[(3-chlorothiophen-2-yl)carbonyl]amino}-6-ethyl-1-methyl-3-(1-methylethoxy)-1H-pyrrolo[2,3-b]pyridine-2-carboxylate By a method similar to that in Reference Example 98, the title compound (114 mg, 78%) was obtained as a pale-yellow powder from 3-chlorothiophene-2-carboxylic acid (79.0 mg, 0.486 mmol), oxalyl chloride (0.0506 mmol, 0.590 mmol), the compound of Reference Example 85 (99.4 mg, 0.326 mmol) and pyridine (0.053 mL, 0.655 mmol).

$^1$H NMR (300 MHz, DMSO-d$_6$) δ: 1.21-1.32 (9H, m), 1.36 (3H, t, J=7.2 Hz), 2.90 (2H, q, J=7.4 Hz), 3.98 (3H, s), 4.34 (2H, q, J=7.2 Hz), 4.43-4.57 (1H, m), 7.24 (1H, d, J=5.3 Hz), 7.94 (1H, d, J=5.3 Hz), 8.08 (1H, s), 9.79 (1H, s).

Reference Example 107

Production of 5-{[(3-chlorothiophen-2-yl)carbonyl]amino}-6-ethyl-1-methyl-3-(1-methylethoxy)-1H-pyrrolo[2,3-b]pyridine-2-carboxylic acid By a method similar to that in Reference Example 12, the title compound (101 mg, 96%) was obtained as a pale-yellow powder from the compound of Reference Example 106 (112 mg, 0.249 mmol), 2N aqueous sodium hydroxide solution (0.5 ethanol (2 mL) and THF (0.5 mL).

$^1$H NMR (300 MHz, DMSO-d$_6$) δ: 1.28 (3H, t, J=7.6 Hz), 1.27 (6H, d, J=6.0 Hz), 2.90 (2H, q, J=7.6 Hz), 3.97 (3H, s), 4.40-4.61 (1H, m), 7.24 (1H, d, J=5.3 Hz), 7.93 (1H, d, J=5.3 Hz), 8.04 (1H, s), 9.78 (1H, s), 12.95 (1H, br s).

Reference Example 108

Production of 2-({3-[(tert-butoxycarbonyl)amino]propyl}amino)-2-oxoethyl acetate To a solution of tert-butyl N-(3-aminopropyl)carbamate (1.00 g, 5.74 mmol) in THF (10 mL) were added triethylamine (1.6 mL, 11.5 mmol) and acetoxyacetyl chloride (0.678 mL, 6.31 mmol) at 0° C., and the mixture was stirred at room temperature for 2 hr. To the reaction mixture was added water (30 mL), and the mixture was extracted with ethyl acetate (20 mL×3). The organic layers were combined and washed with brine (10 mL), dried over anhydrous magnesium sulfate, and concentrated under reduced pressure. The residue was purified by silica gel column chromatography (eluent, hexane:ethyl acetate=4:1→1:4) to give the title compound (1.35 g, 86%) as a colorless oil.

$^1$H NMR (300 MHz, DMSO-$d_6$) δ: 1.37 (9H, s), 1.42-1.57 (2H, m), 2.09 (3H, s), 2.83-2.98 (2H, m), 2.99-3.13 (2H, m), 4.41 (2H, s), 6.78 (1H, t, J=5.8 Hz), 7.95 (1H, t, J=5.8 Hz).

Reference Example 109

Production of N-(3-aminopropyl)-2-hydroxyacetamide hydrochloride

To a solution of the compound of Reference Example 108 (1.20 g, 4.37 mmol) in ethanol (12 mL) was added 5N hydrochloric acid (5 mL), and the mixture was stirred at 60° C. for 1 day. The reaction mixture was concentrated under reduced pressure, and the residue was azeotropically distilled with ethanol (10 mL×3). The precipitate was collected by filtration, and dried to give the title compound (614 mg, 83%) as a white powder.

$^1$H NMR (300 MHz, DMSO-$d_6$) δ: 1.60-1.81 (2H, m), 2.76 (2H, t, J=7.4 Hz), 3.17 (2H, q, J=6.5 Hz), 3.80 (2H, d, J=5.8 Hz), 5.56 (1H, t, J=5.8 Hz), 7.71-8.18 (4H, m).

Reference Example 110

Production of ethyl 3-hydroxy-5-methylpyrazine-2-carboxylate

To a solution of propane-1,2-diamine (5.7 mL, 66.4 mmol) in ethanol (100 mL) was added dropwise diethyl ketomalonate (10 mL, 65.6 mmol) at 0° C., and the mixture was stirred at room temperature for 2 hr, and then stirred for 1 day with heating under reflux. The reaction mixture was concentrated under reduced pressure, and the residue was dissolved in a small amount of ethanol, and the solution was passed through silica gel (150 g, eluent, hexane:ethyl acetate=1:1→ethyl acetate). The eluate was concentrated under reduced pressure, and the precipitate was collected by filtration, and washed with diisopropyl ether to give the title compound (2.27 g, 19%) as a pale-orange powder. The filtrate was concentrated under reduced pressure, and the residue was purified by silica gel column chromatography (eluent, hexane:ethyl acetate=1:1→ethyl acetate) to give the title compound (726 mg, 6.1%) as a pale-yellow powder.

$^1$H NMR (300 MHz, DMSO-$d_6$) δ: 1.27 (3H, t, J=7.1 Hz), 2.24 (3H, s), 4.26 (2H, q, J=7.1 Hz), 7.35 (1H, br s), 12.80 (1H, br s).

Reference Example 111

Production of ethyl 6-bromo-3-hydroxy-5-methylpyrazine-2-carboxylate

To a solution of the compound of Reference Example 110 (1.01 g, 5.54 mmol) in DMF (10 mL) was added N-bromosuccinimide (1.03 g, 5.79 mmol) at 0° C., and the mixture was stirred at room temperature for 1 hr. To the reaction mixture was added water (30 mL), and the mixture was extracted with ethyl acetate (30 mL×4). The extract was washed with brine (10 mL), dried over anhydrous magnesium sulfate, and concentrated under reduced pressure. The precipitate was collected by filtration to give the title compound (1.04 g, 72%) as a white powder. The filtrate was concentrated under reduced pressure, and the residue was purified by silica gel column chromatography (eluent, hexane:ethyl acetate=99:1→4:1) to give the title compound (201 mg, 14%) as a white powder.

$^1$H NMR (300 MHz, DMSO-$d_6$) δ: 1.29 (3H, t, J=7.1 Hz), 2.45 (3H, s), 4.30 (2H, q, J=7.1 Hz), 12.80 (1H, br s).

Reference Example 112

Production of ethyl 3-hydroxy-5-methyl-6-phenylpyrazine-2-carboxylate

To a mixture of the compound of Reference Example 111 (1.20 g, 4.60 mmol), phenylboronic acid (835 mg, 6.84 mmol), toluene (30 mL) and ethanol (40 mL) were added potassium carbonate (3.15 g, 22.8 mmol) and Pd(PPh$_3$)$_4$ (268 mg, 0.232 mmol), and the mixture was stirred at 80° C. for 1 hr under an argon atmosphere. Ethanol was evaporated under reduced pressure, and to the residue was added aqueous ammonium chloride solution (50 mL). The mixture was filtered through celite, and the organic layer was washed with brine (10 mL), dried over anhydrous magnesium sulfate, and concentrated under reduced pressure. The residue was purified by silica gel column chromatography (eluent, hexane:ethyl acetate=19:1→1:2) to give the title compound (1.10 g, 93%) as a yellow powder.

$^1$H NMR (300 MHz, DMSO-$d_6$) δ: 1.28 (3H, t, J=7.2 Hz), 2.34 (3H, s), 4.29 (2H, q, J=7.2 Hz), 7.27-7.59 (5H, m), 12.88 (1H, br s).

Reference Example 113

Production of ethyl 3-chloro-5-methyl-6-phenylpyrazine-2-carboxylate

By a method similar to that in Reference Example 6, the title compound (623 mg, 53%) was obtained as a yellow oil from the compound of Reference Example 112 (1.10 g, 4.26 mmol) and phosphorus oxychloride (1.2 mL, 13.2 mmol).

$^1$H NMR (300 MHz, DMSO-$d_6$) δ: 1.33 (3H, t, J=7.1 Hz), 2.60 (3H, s), 4.41 (2H, q, J=7.1 Hz), 7.47-7.60 (3H, m), 7.60-7.73 (2H, m).

Reference Example 114

Production of ethyl 7-hydroxy-3,5-dimethyl-2-phenyl-5H-pyrrolo[2,3-b]pyrazine-6-carboxylate A mixture of the compound of Reference Example 113 (620 mg, 2.24 mmol), ethyl sarcosinate hydrochloride (598 mg, 3.89 mmol), triethylamine (3.5 mL, 25.1 mmol) and ethanol (5 mL) was stirred for 20.5 hr with heating under reflux. Then, ethyl sarcosinate hydrochloride (200 mg, 1.30 mmol) and triethylamine (1.5 mL, 10.8 mmol) were added thereto, and the mixture was stirred overnight with heating under reflux. The reaction mixture was cooled to room temperature, an ethanol solution (20%, 2.55 g, 7.49 mmol) of sodium ethoxide was added thereto, and the mixture was stirred at 60° C. for 3 hr. Ethanol was evaporated under reduced pressure, and to the residue was added water (20 mL), and the mixture was acidified with 1N hydrochloric acid. The mixture was extracted with ethyl acetate (15 mL×3) and the organic layer was washed with brine (10 mL), dried over anhydrous magnesium sulfate and concentrated under reduced pressure. The precipitate was collected by filtration and dried to give the title compound (225 mg, 32%) as a brown powder. The filtrate was concentrated under reduced pressure, and the residue was purified by silica gel column chromatography (eluent, hexane:ethyl acetate=99:1→2:1) to give the title compound (218 mg, 31%) as a yellow powder.
$^1$H NMR (300 MHz, DMSO-$d_6$) δ: 1.35 (3H, t, J=7.2 Hz), 2.60 (3H, s), 3.93 (3H, s), 4.37 (2H, q, J=7.2 Hz), 7.36-7.69 (5H, m), 9.88 (1H, s).

Reference Example 115

Production of ethyl 3,5-dimethyl-2-phenyl-7-(2,2,2-trifluoroethoxy)-5H-pyrrolo[2,3-b]pyrazine-6-carboxylate To a solution of the compound of Reference Example (223 mg, 0.716 mmol) 114 in DMF (2 mL) were added cesium carbonate (371 mg, 1.14 mmol) and 2,2,2-trifluoroethyl trifluoromethanesulfonate (0.134 mL, 0.931 mmol), and the mixture was stirred at room temperature for 2 hr. To the reaction mixture was added aqueous ammonium chloride solution (5 mL), and the mixture was extracted with ethyl acetate (5 mL×4). The extract was dried over anhydrous magnesium sulfate, and concentrated under reduced pressure. The residue was purified by silica gel column chromatography (hexane:ethyl acetate=99:1→9:1) to give the title compound (263 mg, 93%) as a pale-yellow powder.
$^1$H NMR (300 MHz, DMSO-$d_6$) δ: 1.34 (3H, t, J=7.1 Hz), 2.65 (3H, s), 4.00 (3H, s), 4.36 (2H, q, J=7.1 Hz), 5.23 (2H, q, J=8.9 Hz), 7.43-7.61 (3H, m), 7.61-7.73 (2H, m).

Reference Example 116

Production of 3,5-dimethyl-2-phenyl-7-(2,2,2-trifluoroethoxy)-5H-pyrrolo[2,3-b]pyrazine-6-carboxylic acid By a method similar to that in Reference Example 12, the title compound (234 mg, 96%) was obtained as a white powder from the compound of Reference Example 115 (262 mg, 0.665 mmol), 2N aqueous sodium hydroxide solution (1 mL), ethanol (3 ml) and THF (1 mL).
$^1$H NMR (300 MHz, DMSO-$d_6$) δ: 2.65 (3H, s), 3.99 (3H, s), 5.22 (2H, q, J=9.1 Hz), 7.37-7.60 (3H, m), 7.60-7.71 (2H, m), 13.41 (1H, br s).

Reference Example 117

Production of ethyl 6-ethyl-5-(6-fluoropyridin-3-yl)-1-methyl-3-(2,2,2-trifluoroethoxy)-1H-pyrrolo[2,3-b]pyridine-2-carboxylate By a method similar to that in Reference Example 15, the title compound (198 mg, 97%) was obtained as a white solid from the compound of Reference Example 8 (200 mg, 0.489 mmol), 2-fluoropyridine-5-boronic acid (82.6 mg, 0.587 mmol), potassium carbonate (540 mg, 3.91 mmol), toluene (2.0 mL), ethanol (2.0 mL) and Pd(PPh$_3$)$_4$ (28.3 mg, 24.5 μmol).
$^1$H NMR (300 MHz, DMSO-$d_6$) δ: 1.18 (3H, t, J=7.4 Hz), 1.35 (3H, t, J=7.1 Hz), 2.78 (2H, q, J=7.4 Hz), 4.02 (3H, s), 4.36 (2H, q, J=7.1 Hz), 4.87 (2H, q, J=8.9 Hz), 7.32 (1H, dd, J=8.5, 2.6 Hz), 8.02 (1H, s), 8.05-8.14 (1H, m), 8.29-8.32 (1H, m).

Reference Example 118

Production of 6-ethyl-5-(6-fluoropyridin-3-yl)-1-methyl-3-(2,2,2-trifluoroethoxy)-1H-pyrrolo[2,3-b]pyridine-2-carboxylic acid By a method similar to that in Reference Example 12, the title compound (155 mg, 85%) was obtained as a white solid from the compound of Reference Example 117 (195 mg, 0.458 mmol), 8N aqueous sodium hydroxide solution (0.195 mL) and ethanol (9.8 mL).
$^1$H NMR (300 MHz, DMSO-$d_6$) δ: 1.18 (3H, t, J=7.4 Hz), 2.77 (2H, q, J=7.4 Hz), 4.02 (3H, s), 4.82 (2H, q, J=9.1 Hz), 7.32 (1H, dd, J=8.4, 2.7 Hz), 7.95 (1H, s), 8.08 (1H, td, J=8.2, 2.6 Hz), 8.29 (1H, d, J=2.6 Hz), 13.34 (1H, br s).

Reference Example 119

Production of ethyl 6-ethyl-5-(6-methoxypyridin-3-yl)-1-methyl-3-(2,2,2-trifluoroethoxy)-1H-pyrrolo[2,3-b]pyridine-2-carboxylate By a method similar to that in Reference Example 15, the title compound (220 mg, 100%) was obtained as a white solid from the compound of Reference Example 8 (200 mg, 0.489 mmol), 2-methoxy-5-(4,4,5,5-tetramethyl-1,3,2-dioxaborolan-2-yl)pyridine (139 mg, 0.587 mmol), potassium carbonate (540 mg, 3.91 mmol), toluene (2.0 mL), ethanol (2.0 mL) and Pd(PPh$_3$)$_4$ (28.3 mg, 24.5 μmol).
$^1$H NMR (300 MHz, DMSO-$d_6$) δ: 1.18 (3H, t, J=7.5 Hz), 1.35 (3H, t, J=7.1 Hz), 2.79 (2H, q, J=7.5 Hz), 3.92 (3H, s), 4.02 (3H, s), 4.36 (2H, q, J=7.1 Hz), 4.86 (2H, q, J=8.9 Hz), 6.94 (1H, d, J=8.5 Hz), 7.79 (1H, dd, J=8.5, 2.6 Hz), 7.94 (1H, s), 8.20 (1H, d, J=2.6 Hz).

Reference Example 120

Production of 6-ethyl-5-(6-methoxypyridin-3-yl)-1-methyl-3-(2,2,2-trifluoroethoxy)-1H-pyrrolo[2,3-b]pyridine-2-carboxylic acid By a method similar to that in Reference Example 12, the title compound (185 mg, 94%) was obtained as a white solid from the compound of Reference Example 119 (210 mg, 0.480 mmol), 8N aqueous sodium hydroxide solution (0.210 mL) and ethanol (10.5 mL).
$^1$H NMR (300 MHz, DMSO-$d_6$) δ: 1.17 (3H, t, J=7.5 Hz), 2.78 (2H, q, J=7.5 Hz), 3.91 (3H, s), 4.01 (3H, s), 4.81 (2H, q, J=9.1 Hz), 6.93 (1H, d, J=8.5 Hz), 7.78 (1H, dd, J=8.5, 2.6 Hz), 7.85 (1H, s), 8.19 (1H, d, J=2.6 Hz), 13.32 (1H, br s).

Reference Example 121

Production of ethyl 5-[(2-chlorophenyl)amino]-6-ethyl-1-methyl-3-(2,2,2-trifluoroethoxy)-1H-pyrrolo[2,3-b]pyridine-2-carboxylate By a method similar to that in Reference Example 13, the title compound (340 mg, 87%) was obtained as a yellow solid from the compound of Reference Example 8 (350 mg, 0.855 mmol), 2-chloroaniline (0.122 mL, 1.03 mmol), cesium carbonate (446 mg, 1.37 mmol), toluene (7.0 mL), binap (53.2 mg, 85.5 μmol) and Pd$_2$dba$_3$ (39.1 mg, 42.8 μmol).
$^1$H NMR (300 MHz, DMSO-$d_6$) δ: 1.21 (3H, t, J=7.5 Hz), 1.35 (3H, t, J=7.1 Hz), 2.77 (2H, q, J=7.5 Hz), 4.01 (3H, s), 4.36 (2H, q, J=7.1 Hz), 4.79 (2H, q, J=9.1 Hz), 6.32 (1H, dd, J=7.9, 1.3 Hz), 6.72 (1H, td, J=7.9, 1.3 Hz), 6.97-7.09 (1H, m), 7.34 (1H, s), 7.37 (1H, dd, J=7.9, 1.3 Hz), 7.83 (1H, s).

Reference Example 122

Production of 5-[(2-chlorophenyl)amino]-6-ethyl-1-methyl-3-(2,2,2-trifluoroethoxy)-1H-pyrrolo[2,3-b]pyridine-2-carboxylic acid By a method similar to that in Reference Example 12, the title compound (205 mg, 72%) was obtained as a yellow solid from the compound of Reference Example 121 (302 mg, 0.662 mmol), 8N aqueous sodium hydroxide solution (0.302 mL) and ethanol (6.0 mL).
$^1$H NMR (300 MHz, DMSO-$d_6$) δ: 1.21 (3H, t, J=7.5 Hz), 2.76 (2H, q, J=7.5 Hz), 4.00 (3H, s), 4.75 (2H, q, J=9.1 Hz), 6.31 (1H, dd, J=7.9, 1.3 Hz), 6.72 (1H, td, J=7.9, 1.3 Hz), 6.98-7.09 (1H, m), 7.33 (1H, s), 7.36 (1H, dd, J=7.9, 1.3 Hz), 7.76 (1H, s), 13.32 (1H, br s).

Reference Example 123

Production of ethyl 5-[(4-chlorophenyl)amino]-6-ethyl-1-methyl-3-(2,2,2-trifluoroethoxy)-1H-pyrrolo[2,3-b]pyridine-2-carboxylate By a method similar to that in Reference Example 13, the title compound (381 mg, 98%) was obtained as a yellow solid from the compound of Reference Example 8 (350 mg, 0.855 mmol), 4-chloroaniline (147 mg, 1.03 mmol), cesium carbonate (446 mg, 1.37 mmol), toluene (7.0 mL), binap (53.2 mg, 85.5 µmol) and Pd$_2$dba$_3$ (39.1 mg, 42.8 µmol).
$^1$H NMR (300 MHz, DMSO-$d_6$) δ: 1.22 (3H, t, J=7.5 Hz), 1.35 (3H, t, J=7.1 Hz), 2.82 (2H, q, J=7.5 Hz), 3.99 (3H, s), 4.35 (2H, q, J=7.1 Hz), 4.79 (2H, q, J=9.1 Hz), 6.63-6.71 (2H, m), 7.11-7.19 (2H, m), 7.75 (1H, s), 7.81 (1H, s).

Reference Example 124

Production of 5-[(4-chlorophenyl)amino]-6-ethyl-1-methyl-3-(2,2,2-trifluoroethoxy)-1H-pyrrolo[2,3-b]pyridine-2-carboxylic acid By a method similar to that in Reference Example 12, the title compound (194 mg, 98%) was obtained as a yellow solid from the compound of Reference Example 123 (210 mg, 0.461 mmol), 8N aqueous sodium hydroxide solution (0.210 mL) and ethanol (4.2 mL).
$^1$H NMR (300 MHz, DMSO-$d_6$) δ: 1.22 (3H, t, J=7.5 Hz), 2.80 (2H, q, J=7.5 Hz), 3.98 (3H, s), 4.75 (2H, q, J=9.1 Hz), 6.59-6.70 (2H, m), 7.06-7.22 (2H, m), 7.66-7.78 (2H, m), 13.40 (1H, br s).

Reference Example 125

Production of ethyl 6-ethyl-5-[(2-methoxyphenyl)amino]-1-methyl-3-(2,2,2-trifluoroethoxy)-1H-pyrrolo[2,3-b]pyridine-2-carboxylate By a method similar to that in Reference Example 13, the title compound (388 mg, 100%) was obtained as a yellow solid from the compound of Reference Example 8 (350 mg, 0.855 mmol), 2-methoxyaniline (0.116 mL, 1.03 mmol), cesium carbonate (446 mg, 1.37 mmol), toluene (7.0 mL), binap (53.2 mg, 85.5 µmol) and Pd$_2$dba$_3$ (39.1 mg, 42.8 µmol).
$^1$H NMR (300 MHz, DMSO-$d_6$) δ: 1.22 (3H, t, J=7.5 Hz), 1.35 (3H, t, J=7.1 Hz), 2.81 (2H, q, J=7.5 Hz), 3.85 (3H, s), 3.99 (3H, s), 4.35 (2H, q, J=7.1 Hz), 4.75 (2H, q, J=9.1 Hz), 6.34-6.40 (1H, m), 6.69-6.75 (2H, m), 6.84 (1H, s), 6.94-7.00 (1H, m), 7.71 (1H, s).

Reference Example 126

Production of 6-ethyl-5-[(2-methoxyphenyl)amino]-1-methyl-3-(2,2,2-trifluoroethoxy)-1H-pyrrolo[2,3-b]pyridine-2-carboxylic acid By a method similar to that in Reference Example 12, the title compound (163 mg, 92%) was obtained as a yellow solid from the compound of Reference Example 125 (190 mg, 0.421 mmol), 8N aqueous sodium hydroxide solution (0.190 mL) and ethanol (3.8 mL).
$^1$H NMR (300 MHz, DMSO-$d_6$) δ: 1.22 (3H, t, J=7.5 Hz), 2.80 (2H, q, J=7.5 Hz), 3.85 (3H, s), 3.99 (3H, s), 4.72 (2H, q, J=9.1 Hz), 6.31-6.41 (1H, m), 6.65-6.78 (2H, m), 6.83 (1H, s), 6.91-7.02 (1H, m), 7.67 (1H, s), 13.27 (1H, br s).

Reference Example 127

Production of ethyl 6-ethyl-5-[(4-methoxyphenyl)amino]-1-methyl-3-(2,2,2-trifluoroethoxy)-1H-pyrrolo[2,3-b]pyridine-2-carboxylate By a method similar to that in Reference Example 13, the title compound (381 mg, 99%) was obtained as a yellow solid from the compound of Reference Example 8 (350 mg, 0.855 mmol), 4-methoxyaniline (127 mg, 1.03 mmol), cesium carbonate (446 mg, 1.37 mmol), toluene (7.0 mL), binap (53.2 mg, 85.5 µmol) and Pd$_2$dba$_3$ (39.1 mg, 42.8 µmol).
$^1$H NMR (300 MHz, DMSO-$d_6$) δ: 1.25 (3H, t, J=7.4 Hz), 1.34 (3H, t, J=7.1 Hz), 2.85 (2H, q, J=7.4 Hz), 3.69 (3H, s), 3.98 (3H, s), 4.35 (2H, q, J=7.1 Hz), 4.71 (2H, q, J=9.1 Hz), 6.69-6.87 (4H, m), 7.18 (1H, s), 7.62 (1H, s).

Reference Example 128

Production of 6-ethyl-5-[(4-methoxyphenyl)amino]-1-methyl-3-(2,2,2-trifluoroethoxy)-1H-pyrrolo[2,3-b]pyridine-2-carboxylic acid By a method similar to that in Reference Example 12, the title compound (179 mg, 100%) was obtained as a white solid from the compound of Reference Example 127 (185 mg, 0.410 mmol), 8N aqueous sodium hydroxide solution (0.185 mL) and ethanol (3.7 mL).
$^1$H NMR (300 MHz, DMSO-$d_6$) δ: 1.25 (3H, t, J=7.5 Hz), 2.85 (2H, q, J=7.5 Hz), 3.68 (3H, s), 3.97 (3H, s), 4.69 (2H, q, J=9.2 Hz), 6.71-6.87 (4H, m), 7.17 (1H, s), 7.59 (1H, s), 13.23 (1H, br s).

Reference Example 129

Production of ethyl 6-ethyl-1-methyl-5-[(phenylcarbamoyl)amino]-3-(2,2,2-trifluoroethoxy)-1H-pyrrolo[2,3-b]pyridine-2-carboxylate To a solution of the compound of Reference Example 9 (150 mg, 0.434 mmol) in DMF (3.0 mL) was added phenyl isocyanate (56.4 µL, 0.521 mmol), and the mixture was stirred at room temperature for 4 hr. To the reaction mixture was added dropwise water (50 mL), and the precipitate was collected by filtration, and washed with ethyl acetate to give the title compound (181 mg, 90%) as a white powder.
$^1$H NMR (300 MHz, DMSO-$d_6$) δ: 1.30 (3H, t, J=7.4 Hz), 1.36 (3H, t, J=7.1 Hz), 2.90 (2H, q, J=7.4 Hz), 3.98 (3H, s), 4.36 (2H, q, J=7.1 Hz), 4.77 (2H, q, J=9.1 Hz), 6.88-7.06 (1H, m), 7.22-7.35 (2H, m), 7.42-7.53 (2H, m), 8.10 (1H, s), 8.30 (1H, s), 9.02 (1H, s).

Reference Example 130

Production of 6-ethyl-1-methyl-5-[(phenylcarbamoyl)amino]-3-(2,2,2-trifluoroethoxy)-1H-pyrrolo[2,3-b]pyridine-2-carboxylic acid By a method similar to that in Reference Example 12, the title compound (152 mg, 89%) was obtained as a white solid from the compound of Reference Example 129 (181 mg, 0.390 mmol), 8N aqueous sodium hydroxide solution (0.362 mL) and ethanol (3.6 mL).
$^1$H NMR (300 MHz, DMSO-$d_6$) δ: 1.30 (3H, t, J=7.5 Hz), 2.89 (2H, q, J=7.4 Hz), 3.97 (3H, s), 4.74 (2H, q, J=9.2 Hz), 6.91-7.02 (1H, m), 7.21-7.34 (2H, m), 7.43-7.55 (2H, m), 8.11 (1H, s), 8.25 (1H, s), 9.03 (1H, s), 13.32 (1H, br s).

Reference Example 131

Production of ethyl 5-bromo-3-ethoxy-6-ethyl-1-methyl-1H-pyrrolo[2,3-b]pyridine-2-carboxylate To a solution of the compound of Reference Example 7 (2.00 g, 6.11 mmol) in acetone (40 mL) were added potassium carbonate (1.69 g, 12.2 mmol) and diethyl sulfate (1.20 mL, 9.17 mmol), and the mixture was stirred for 3 hr with heating under reflux. The reaction mixture was cooled to 0° C., water (50 mL) was added thereto, and the precipitate was collected by filtration, and washed with water to give the title compound (2.04 g, 94%) as a yellow solid.
$^1$H NMR (300 MHz, DMSO-$d_6$) δ: 1.24-1.38 (9H, m), 2.98 (2H, q, J=7.6 Hz), 3.93 (3H, s), 4.23 (2H, q, J=7.0 Hz), 4.33 (2H, q, J=7.2 Hz), 8.39 (1H, s).

Reference Example 132

Production of ethyl 5-amino-3-ethoxy-6-ethyl-1-methyl-1H-pyrrolo[2,3-b]pyridine-2-carboxylate By a method similar to that in Reference Example 9, the title compound (231 mg, 35%) was obtained as a yellow solid from the compound of Reference Example 131 (800 mg, 2.25 mmol), benzophenonimine (567 μL, 3.38 mmol), cesium carbonate (1.47 g, 4.50 mmol), Pd$_2$dba$_3$ (103 mg, 0.113 mmol), Xantphos (169 mg, 0.293 mmol) and toluene (16 mL).
$^1$H NMR (300 MHz, DMSO-$d_6$) δ: 1.25 (3H, t, J=7.5 Hz), 1.28-1.37 (6H, m), 2.74 (2H, q, J=7.5 Hz), 3.87 (3H, s), 4.12 (2H, q, J=7.0 Hz), 4.29 (2H, q, J=7.1 Hz), 4.74 (2H, s), 7.21 (1H, s).

Reference Example 133

Production of ethyl 3-ethoxy-6-ethyl-5-{[(4-fluorophenyl)carbonyl]amino}-1-methyl-1H-pyrrolo[2,3-b]pyridine-2-carboxylate By a method similar to that in Reference Example 23, the title compound (205 mg, 96%) was obtained as a white solid from the compound of Reference Example 132 (150 mg, 0.515 mmol), pyridine (62.5 μL, 0.773 mmol) and 4-fluorobenzoyl chloride (74.2 μL, 0.618 mmol).
$^1$H NMR (300 MHz, DMSO-$d_6$) δ: 1.25 (3H, t, J=7.5 Hz), 1.30-1.40 (6H, m), 2.86 (2H, q, J=7.5 Hz), 3.98 (3H, s), 4.23 (2H, q, J=7.0 Hz), 4.34 (2H, q, J=7.0 Hz), 7.34-7.45 (2H, m), 8.01-8.17 (3H, m), 10.11 (1H, s).

Reference Example 134

Production of 3-ethoxy-6-ethyl-5-{[(4-fluorophenyl)carbonyl]amino}-1-methyl-1H-pyrrolo[2,3-b]pyridine-2-carboxylic acid By a method similar to that in Reference Example 12, the title compound (191 mg, 100%) was obtained as a white solid from the compound of Reference Example 133 (205 mg, 0.496 mmol), 2N aqueous sodium hydroxide solution (0.410 mL) and ethanol (4.1 mL).
$^1$H NMR (300 MHz, DMSO-$d_6$) δ: 1.24 (3H, t, J=7.5 Hz), 1.31 (3H, t, J=7.0 Hz), 2.85 (2H, q, J=7.5 Hz), 3.97 (3H, s), 4.23 (2H, q, J=7.0 Hz), 7.19-7.70 (2H, m), 7.90-8.28 (3H, m), 10.11 (1H, s), 12.89 (1H, br s).

Reference Example 135

Production of ethyl 3-ethoxy-6-ethyl-1-methyl-5-[(phenylcarbonyl)amino]-1H-pyrrolo[2,3-b]pyridine-2-carboxylate By a method similar to that in Reference Example 23, the title compound (101 mg, 93%) was obtained as a white solid from the compound of Reference Example 132 (80.0 mg, 0.275 mmol), pyridine (33.4 μL, 0.413 mmol) and benzoyl chloride (38.3 μL, 0.330 mmol).
$^1$H NMR (300 MHz, DMSO-$d_6$) δ: 1.25 (3H, t, J=7.5 Hz), 1.30-1.41 (6H, m), 2.87 (2H, q, J=7.5 Hz), 3.98 (3H, s), 4.23 (2H, q, J=7.0 Hz), 4.34 (2H, q, J=7.0 Hz), 7.50-7.67 (3H, m), 7.96-8.11 (3H, m), 10.09 (1H, s).

Reference Example 136

Production of 3-ethoxy-6-ethyl-1-methyl-5-[(phenylcarbonyl)amino]-1H-pyrrolo[2,3-b]pyridine-2-carboxylic acid By a method similar to that in Reference Example 12, the title compound (87.1 mg, 93%) was obtained as a white powder from the compound of Reference Example 135 (101 mg, 0.255 mmol), 2N aqueous sodium hydroxide solution (0.202 mL) and ethanol (2.0 mL).
$^1$H NMR (300 MHz, DMSO-$d_6$) δ: 1.25 (3H, t, J=7.5 Hz), 1.31 (3H, t, J=7.0 Hz), 2.86 (2H, q, J=7.5 Hz), 3.97 (3H, s), 4.23 (2H, q, J=7.0 Hz), 7.48-7.67 (3H, m), 7.97-8.08 (3H, m), 10.08 (1H, s), 12.87 (1H, br s).

Reference Example 137

Production of ethyl 6-ethyl-5-[(furan-3-ylcarbonyl)amino]-1-methyl-3-(2,2,2-trifluoroethoxy)-1H-pyrrolo[2,3-b]pyridine-2-carboxylate By a method similar to that in Reference Example 98, the title compound (140 mg, 92%) was obtained as a pale-yellow powder from the compound of Reference Example 9 (120 mg, 0.348 mmol), furan-3-carboxylic acid (58.5 mg, 0.522 mmol), oxalyl chloride (61.1 μL, 0.696 mmol) and THF (2 mL).

¹H NMR (300 MHz, DMSO-d₆) δ: 1.24 (3H, t, J=7.5 Hz), 1.36 (3H, t, J=7.1 Hz), 2.86 (2H, q, J=7.5 Hz), 4.00 (3H, s), 4.36 (2H, q, J=7.1 Hz), 4.81 (2H, q, J=9.0 Hz), 7.01 (1H, s), 7.82 (1H, t, J=1.5 Hz), 7.98 (1H, s), 8.38 (1H, s), 9.85 (1H, s).

Reference Example 138

Production of 6-ethyl-5-[(furan-3-ylcarbonyl)amino]-1-methyl-3-(2,2,2-trifluoroethoxy)-1H-pyrrolo[2,3-b]pyridine-2-carboxylic acid By a method similar to that in Reference Example 12, the title compound (125 mg, 95%) was obtained as a pale-yellow powder from the compound of Reference Example 137 (140 mg, 0.319 mmol), 2N aqueous sodium hydroxide solution (0.420 mL) and ethanol (2.8 mL).

¹H NMR (300 MHz, DMSO-d₆) δ: 1.24 (3H, t, J=7.5 Hz), 2.85 (2H, q, J=7.5 Hz), 4.00 (3H, s), 4.78 (2H, q, J=9.1 Hz), 7.01 (1H, s), 7.80-7.84 (1H, m), 7.91 (1H, s), 8.38 (1H, s), 9.83 (1H, s), 13.37 (1H, br s).

Reference Example 139

Production of ethyl 6-ethyl-1-methyl-5-[(1,3-oxazol-4-ylcarbonyl)amino]-3-(2,2,2-trifluoroethoxy)-1H-pyrrolo[2,3-b]pyridine-2-carboxylate By a method similar to that in Reference Example 98, the title compound (153 mg, 100%) was obtained as a pale-yellow solid from the compound of Reference Example 9 (120 mg, 0.348% mmol), 1,3-oxazole-4-carboxylic acid (59.0 mg, 0.522 mmol), oxalyl chloride (61.1 μL, 0.696 mmol) and THF (2 mL).

¹H NMR (300 MHz, DMSO-d₆) δ: 1.25 (3H, t, J=7.5 Hz), 1.36 (3H, t, J=7.1 Hz), 2.87 (2H, q, J=7.5 Hz), 4.00 (3H, s), 4.36 (2H, q, J=7.1 Hz), 4.80 (2H, q, J=9.1 Hz), 8.07 (1H, s), 8.64 (1H, s), 8.81 (1H, s), 9.99 (1H, s).

Reference Example 140

Production of 6-ethyl-1-methyl-5-[(1,3-oxazol-4-ylcarbonyl)amino]-3-(2,2,2-trifluoroethoxy)-1H-pyrrolo[2,3-b]pyridine-2-carboxylic acid By a method similar to that in Reference Example 12, the title compound (131 mg, 92%) was obtained as a white solid from the compound of Reference Example 139 (153 mg, 0.347 mmol), 2N aqueous sodium hydroxide solution (0.459 mL) and ethanol (3.1 mL).

¹H NMR (300 MHz, DMSO-d₆) δ: 1.24 (3H, t, J=7.5 Hz), 2.86 (2H, q, J=7.5 Hz), 3.99 (3H, s), 4.76 (2H, q, J=9.1 Hz), 8.01 (1H, s), 8.64 (1H, s), 8.81 (1H, s), 9.98 (1H, s), 13.39 (1H, br s).

Reference Example 141

Production of ethyl 6-ethyl-1-methyl-5-[(1,3-thiazol-4-ylcarbonyl)amino]-3-(2,2,2-trifluoroethoxy)-1H-pyrrolo[2,3-b]pyridine-2-carboxylate By a method similar to that in Reference Example 98, the title compound (150 mg, 94%) was obtained as a pale-yellow solid from the compound of Reference Example 9 (120 mg, 0.348 mmol), 1,3-thiazole-4-carboxylic acid (67.4 mg, 0.522 mmol), oxalyl chloride (61.1 μL, 0.696 mmol) and THF (2 mL).

¹H NMR (300 MHz, DMSO-d₆) δ: 1.26 (3H, t, J=7.5 Hz), 1.36 (3H, t, J=7.1 Hz), 2.90 (2H, q, J=7.5 Hz), 4.00 (3H, s), 4.37 (2H, q, J=7.1 Hz), 4.80 (2H, q, J=9.1 Hz), 8.16 (1H, s), 8.51 (1H, d, J=2.0 Hz), 9.30 (1H, d, J=2.0 Hz), 10.15 (1H, s).

Reference Example 142

Production of 6-ethyl-1-methyl-5-[(1,3-thiazol-4-ylcarbonyl)amino]-3-(2,2,2-trifluoroethoxy)-1H-pyrrolo[2,3-b]pyridine-2-carboxylic acid By a method similar to that in Reference Example 12, the title compound (129 mg, 91%) was obtained as a pale-yellow solid from the compound of Reference Example 141 (150 mg, 0.329 mmol), 2N aqueous sodium hydroxide solution (0.450 mL) and ethanol (3.0 mL).

¹H NMR (300 MHz, DMSO-d₆) δ: 1.26 (3H, t, J=7.5 Hz), 2.89 (2H, q, J=7.5 Hz), 4.00 (3H, s), 4.77 (2H, q, J=9.1 Hz), 8.10 (1H, s), 8.51 (1H, d, J=1.9 Hz), 9.30 (1H, d, J=1.9 Hz), 10.12 (1H, s), 13.38 (1H, br s).

Reference Example 143

Production of ethyl 5-bromo-6-ethyl-3-hydroxythieno[2,3-b]pyridine-2-carboxylate A mixture of the compound of Reference Example 6 (1.65 g, 5.64 mmol), ethyl mercaptoacetate (1.23 mL, 11.3 mmol), 20% ethanol solution (4.84 mL, 14.2 mmol) of sodium ethoxide and ethanol (33 mL) was stirred at room temperature for 2 days. The reaction mixture was concentrated under reduced pressure, and to the residue was added water (50 mL), and the mixture was acidified with 5N hydrochloric acid. The precipitate was collected by filtration, and washed with water to give the title compound (1.74 g, 94%) as a pale-yellow solid.

¹H NMR (300 MHz, DMSO-d₆) δ: 1.23-1.35 (6H, m), 3.02 (2H, q, J=7.5 Hz), 4.33 (2H, q, J=7.1 Hz), 8.54 (1H, s), 11.03 (1H, s).

Reference Example 144

Production of ethyl 5-bromo-6-ethyl-3-(2,2,2-trifluoroethoxy)thieno[2,3-b]pyridine-2-carboxylate By a method similar to that in Reference Example 8, the title compound (1.64 g, 88%) was obtained as a pale-orange solid from the compound of Reference Example 143 (1.50 g, 4.54 mmol), cesium carbonate (1.78 g, 5.45 mmol), 2,2,2-trifluoroethyl trifluoromethanesulfonate (0.721 mL, 5.00 mmol) and DMF (15 mL).

¹H NMR (300 MHz, DMSO-d₆) δ: 1.25-1.38 (6H, m), 3.05 (2H, q, J=7.5 Hz), 4.36 (2H, q, J=7.1 Hz), 5.05 (2H, q, J=9.1 Hz), 8.36 (1H, s).

Reference Example 145

Production of ethyl 5-amino-6-ethyl-3-(2,2,2-trifluoroethoxy)thieno[2,3-b]pyridine-2-carboxylate By a method similar to that in Reference Example 9, the title compound (558 mg, 83%) was obtained as a pale-yellow powder from the compound of Reference Example 144 (800 mg, 1.94 mmol), benzophenonimine (489 μL, 2.91 mmol), cesium carbonate (1.26 g, 3.88 mmol), Pd₂dba₃ (88.8 mg, 97.0 μmol), Xantphos (151 mg, 0.252 mmol) and toluene (16 mL).

$^1$H NMR (300 MHz, DMSO-d$_6$) δ: 1.23 (3H, t, J=7.4 Hz), 1.32 (3H, t, J=7.1 Hz), 2.76 (2H, q, J=7.4 Hz), 4.32 (2H, q, J=7.1 Hz), 4.93 (2H, q, J=9.0 Hz), 5.46 (2H, s), 7.27 (1H, s).

Reference Example 146

Production of ethyl 6-ethyl-5-{[(4-fluorophenyl)carbonyl]amino}3-(2,2,2-trifluoroethoxy)thieno[2,3-b]pyridine-2-carboxylate By a method similar to that in Reference Example 23, the title compound (203 mg, 100%) was obtained as a white solid from the compound of Reference Example 145 (150 mg, 0.431 mmol), pyridine (52.3 μL, 0.647 mmol) and 4-fluorobenzoyl chloride (62.1 μL, 0.517 mmol).
$^1$H NMR (300 MHz, DMSO-d$_6$) δ: 1.25 (3H, t, J=7.5 Hz), 1.35 (3H, t, J=7.1 Hz), 2.95 (2H, q, J=7.5 Hz), 4.37 (2H, q, J=7.1 Hz), 5.04 (2H, q, J=8.9 Hz), 7.34-7.50 (2H, m), 8.05-8.15 (2H, m), 8.17 (1H, s), 10.30 (1H, s).

Reference Example 147

Production of 6-ethyl-5-{[(4-fluorophenyl)carbonyl]amino}-3-(2,2,2-trifluoroethoxy)thieno[2,3-b]pyridine-2-carboxylic acid By a method similar to that in Reference Example 12, the title compound (170 mg, 90%) was obtained as a pale-yellow solid from the compound of Reference Example 146 (200 mg, 0.425 mmol), 2N aqueous sodium hydroxide solution (0.400 mL) and ethanol (4.0 mL).
$^1$H NMR (300 MHz, DMSO-d$_6$) δ: 1.25 (3H, t, J=7.5 Hz), 2.95 (2H, q, J=7.5 Hz), 5.04 (2H, q, J=9.1 Hz), 7.03-7.53 (2H, m), 7.98-8.21 (3H, m), 10.28 (1H, s), 13.84 (1H, br s).

Reference Example 148

Production of ethyl 2-chloro-4-methylbenzoate

A mixture of 2-chloro-4-methylbenzonitrile (5.5 g, 36.28 mmol), conc. sulfuric acid (30 mL) and ethanol (30 mL) was heated under reflux for 22 hr. The reaction mixture was ice-cooled, and neutralized with 8N aqueous sodium hydroxide solution, and ethanol was evaporated. The residue was extracted with ethyl acetate, and the extract was washed with brine, dried over magnesium sulfate and concentrated under reduced pressure. The residue was diluted with ethyl acetate-hexane (1:10, 120 mL). The insoluble material was filtered off, and the filtrate was under reduced pressure and concentrated to give the title compound (3.23 g, 45%) as a pale-brown liquid.
$^1$H NMR (300 MHz, DMSO-d$_6$) δ: 1.31 (3H, t, J=7.1 Hz), 2.35 (3H, s), 4.30 (2H, q, J=7.1 Hz), 7.26 (1H, d, J=7.8 Hz), 7.41 (1H, s), 7.71 (1H, d, J=7.8 Hz).

Reference Example 149

Production of ethyl 2-chloro-4-methyl-5-nitrobenzoate

To a solution of the compound of Reference Example 148 (3.1 g, 15.61 mmol) in conc. sulfuric acid (10 mL) was added a solution of sodium nitrate (1.33 g, 15.61 mmol) in sulfuric acid (10 mL) under ice-cooling, and the mixture was stirred for 30 min. The reaction mixture was added to water (300 mL), and the mixture was extracted with ethyl acetate. The extract was washed with saturated aqueous sodium hydrogen carbonate and brine, dried over magnesium sulfate and concentrated under reduced pressure. The residue was purified by silica gel column chromatography (eluent, hexane:ethyl acetate=1:10) to give the title compound (2.84 g, 75%) as a pale-yellow solid.
$^1$H NMR (300 MHz, DMSO-d$_6$) δ: 1.34 (3H, t, J=7.2 Hz), 2.58 (3H, s), 4.36 (2H, q, J=7.1 Hz), 7.83 (1H, s), 8.42 (1H, s).

Reference Example 150

Production of ethyl 3-hydroxy-6-methyl-5-nitro-1-benzothiophene-2-carboxylate

A 20% ethanol solution (0.7 g, 2.05 mmol) of sodium ethoxide was diluted with ethanol (3 mL), ethyl mercaptoacetate (148 mg, 1.23 mmol) was added thereto, and the mixture was stirred at room temperature for 5 min. The compound of Reference Example 149 (200 mg, 0.82 mmol) was added to this mixture, and the mixture was stirred at room temperature for 16 hr. To the reaction mixture was added 1N hydrochloric acid (2.5 mL), and the precipitate was collected by filtration and washed with water and dried under reduced pressure to give the title compound (168 mg, 73%) as a pale-yellow powder.
$^1$H NMR (300 MHz, DMSO-d$_6$) δ: 1.32 (3H, t, J=7.1 Hz), 2.63 (3H, s), 4.33 (2H, q, J=7.1 Hz), 8.06 (1H, s), 8.59 (1H, s), 10.80-11.20 (1H, br).

Reference Example 151

Production of ethyl 6-methyl-5-nitro-3-(2,2,2-trifluoroethoxy)-1-benzothiophene-2-carboxylate By a method similar to that in Reference Example 8, the title compound (190 mg, 92%) was obtained as a white solid from the compound of Reference Example 150 (160 mg, 0.57 mmol).
$^1$H NMR (300 MHz, DMSO-d$_6$) δ: 1.35 (3H, t, J=7.2 Hz), 2.64 (3H, s), 4.37 (2H, q, J=7.2 Hz), 5.06 (2H, q, J=9.1 Hz), 8.18 (1H, s), 8.37 (1H, s).

Reference Example 152

Production of ethyl 5-amino-6-methyl-3-(2,2,2-trifluoroethoxy)-1-benzothiophene-2-carboxylate A mixture of the compound of Reference Example 151 (140 mg, 0.39 mmol) and 10% palladium-carbon (50% in water, 28 mg) in THF (2 mL)-ethanol (6 mL) was stirred for 3 hr under a hydrogen atmosphere. The catalyst was filtered off, and the filtrate was concentrated under reduced pressure to give the title compound (130 mg, 100%) as a beige solid.
$^1$H NMR (300 MHz, DMSO-d$_6$) δ: 1.31 (3H, t, J=7.2 Hz), 2.20 (3H, s), 4.30 (2H, q, J=7.2 Hz), 4.88 (2H, q, J=9.1 Hz), 5.17 (2H, s), 7.01 (1H, s), 7.51 (1H, s).

Reference Example 153

Production of ethyl 6-methyl-5-[(phenylcarbonyl)amino]-3-(2,2,2-trifluoroethoxy)-1-benzothiophene-2-carboxylate By a method similar to that in Reference Example 21, the title compound (150 mg, 88%) was obtained as a beige solid from the compound of Reference Example 152 (130 mg, 0.39 mmol) and benzoyl chloride (60 mg, 0.43 mmol).

¹H NMR (300 MHz, DMSO-d₆) δ: 1.34 (3H, t, J=7.1 Hz), 2.40 (3H, s), 4.35 (2H, q, J=7.1 Hz), 4.99 (2H, q, J=9.0 Hz), 7.52-7.62 (3H, m), 7.85 (1H, s), 7.92 (1H, s), 8.00-8.03 (2H, m), 10.05 (1H, s).

Reference Example 154

Production of 6-methyl-5-[(phenylcarbonyl)amino]-3-(2,2,2-trifluoroethoxy)-1-benzothiophene-2-carboxylic acid By a method similar to that in Reference Example 12, the title compound (82 mg, 87%) was obtained as a beige powder from the compound of Reference Example 153 (100 mg, 0.23 mmol).

¹H NMR (300 MHz, DMSO-d₆) δ: 2.39 (3H, s), 5.00 (2H, q, J=9.1 Hz), 7.52-7.64 (3H, m), 7.82 (1H, s), 7.90 (1H, s), 8.00-8.03 (2H, m), 10.04 (1H, s), 13.40-13.70 (1H, br).

Reference Example 155

Production of ethyl 3-hydroxy-1,6-dimethyl-5-nitro-1H-indole-2-carboxylate

A mixture of the compound of Reference Example 149 (200 mg, 0.82 mmol), ethyl sarcosinate hydrochloride (504 mg, 3.28 mmol) and triethylamine (498 mg, 4.92 mmol) in ethanol (3 mL) was heated under reflux for 42 hr. After cooling, the reaction mixture was partitioned between diluted hydrochloric acid and ethyl acetate, and the organic phase was washed with brine, dried over magnesium sulfate, and concentrated under reduced pressure. The residue was purified by silica gel column chromatography (eluent, hexane:ethyl acetate=3:1) to give the title compound (150 mg, 66%) as a yellow solid.

¹H NMR (300 MHz, DMSO-d₆) δ: 1.33 (3H, t, J=7.2 Hz), 2.65 (3H, s), 3.88 (3H, s), 4.33 (2H, q, J=7.2 Hz), 7.53 (1H, s), 8.61 (1H, s), 9.80-10.00 (1H, br).

Reference Example 156

Production of ethyl 1,6-dimethyl-5-nitro-3-(2,2,2-trifluoroethoxy)-1H-indole-2-carboxylate By a method similar to that in Reference Example 8, the title compound (140 mg, 78%) was obtained as a yellow solid from the compound of Reference Example 155 (140 mg, 0.50 mmol).

¹H NMR (300 MHz, DMSO-d₆) δ: 1.36 (3H, t, J=7.1 Hz), 2.65 (3H, s), 3.97 (3H, s), 4.37 (2H, q, J=7.1 Hz), 4.84 (2H, q, J=9.1 Hz), 7.71 (1H, s), 8.39 (1H, s).

Reference Example 157

Production of ethyl 5-amino-1,6-dimethyl-3-(2,2,2-trifluoroethoxy)-1H-indole-2-carboxylate By a method similar to that in Reference Example 152, the title compound (110 mg, 93%) was obtained as a yellow solid from the compound of Reference Example 156 (130 mg, 0.36 mmol).

¹H NMR (300 MHz, DMSO-d₆) δ: 1.33 (3H, t, J=7.1 Hz), 2.23 (3H, s), 3.83 (3H, s), 4.31 (2H, q, J=7.1 Hz), 4.61 (2H, q, J=9.1 Hz), 4.79 (2H, br s), 6.79 (1H, s), 7.21 (1H, s).

Reference Example 158

Production of ethyl 1,6-dimethyl-5-[(phenylcarbonyl)amino]-3-(2,2,2-trifluoroethoxy)-1H-indole-2-carboxylate By a method similar to that in Reference Example 21, the title compound (145 mg, 100%) was obtained as a beige powder from the compound of Reference Example 157 (110 mg, 0.33 mmol) and benzoyl chloride (51 mg, 0.37 mmol).

¹H NMR (300 MHz, DMSO-d₆) δ: 1.36 (3H, t, J=7.1 Hz), 2.38 (3H, s), 3.94 (3H, s), 4.36 (2H, q, J=7.1 Hz), 4.73 (2H, q, J=9.0 Hz), 7.52-7.60 (5H, m), 8.02 (2H, d, J=6.9 Hz), 9.92 (1H, s).

Reference Example 159

Production of 1,6-dimethyl-5-[(phenylcarbonyl)amino]-3-(2,2,2-trifluoroethoxy)-1H-indole-2-carboxylic acid By a method similar to that in Reference Example 12, the title compound (88 mg, 68%) was obtained as a beige powder from the compound of Reference Example 158 (140 mg, 0.32 mmol).

¹H NMR (300 MHz, DMSO-d₆) δ: 2.37 (3H, s), 3.94 (3H, s), 4.71 (2H, q, J=9.1 Hz), 7.49-7.63 (5H, m), 8.02 (2H, d, J=6.9 Hz), 9.91 (1H, s), 13.10-13.20 (1H, br).

Reference Example 160

Production of ethyl 6-ethyl-1-methyl-5-[(1,3-thiazol-2-ylcarbonyl)amino]-3-(2,2,2-trifluoroethoxy)-1H-pyrrolo[2,3-b]pyridine-2-carboxylate By a method similar to that in Reference Example 23, the title compound (164 mg, 92%) was obtained as a beige powder from the compound of Reference Example 93 (150 mg, 0.39 mmol), 1,3-thiazole-2-carbonyl chloride (64 mg, 0.43 mmol), pyridine (93 mg, 1.18 mmol) and THF (3 mL).

¹H NMR (300 MHz, DMSO-d₆) δ: 1.26 (3H, t, J=7.5 Hz), 1.36 (3H, t, J=7.1 Hz), 2.90 (2H, q, J=7.5 Hz), 4.01 (3H, s), 4.37 (2H, q, J=7.1 Hz), 4.80 (2H, q, J=9.0 Hz), 8.11-8.15 (3H, m), 10.49 (1H, s).

Reference Example 161

Production of 6-ethyl-1-methyl-5-[(1,3-thiazol-2-ylcarbonyl)amino]-3-(2,2,2-trifluoroethoxy)-1H-pyrrolo[2,3-b]pyridine-2-carboxylic acid By a method similar to that in Reference Example 12, the title compound (75 mg, 80%) was obtained as a beige powder from the compound of Reference Example 160 (100 mg, 0.22 mmol), 2N aqueous sodium hydroxide solution (1 mL), ethanol (3 mL) and THF (0.5 mL).

¹H NMR (300 MHz, DMSO-d₆) δ: 1.26 (3H, t, J=7.5 Hz), 2.89 (2H, q, J=7.5 Hz), 4.00 (3H, s), 4.76 (2H, q, J=9.1 Hz), 8.06 (1H, s), 8.11-8.15 (2H, m), 10.47 (1H, s), 13.00-13.50 (1H, br).

Reference Example 162

Production of ethyl 2-chloro-4-ethenylbenzoate

A mixture of ethyl 4-bromo-2-chlorobenzoate (1.00 g, 3.79 mmol), tributyl(vinyl)tin (2.41 g, 7.59 mmol) and tetrakis(triphenylphosphine)palladium (0) (439 mg, 0.38 mmol) in DMF (15 mL) was stirred at 100° C. for 1 hr. After cooling, the mixture was diluted with water (150 mL), and extracted twice with ethyl acetate. The extracts were combined, washed with brine, dried over magnesium sulfate, and concentrated under reduced pressure. The residue was purified by silica gel column chromatography (eluent, hexane:ethyl acetate=20:1) to give the title compound (820 mg, 100%) as a colorless oil.

$^1$H NMR (300 MHz, DMSO-$d_6$) δ: 1.32 (3H, t, J=7.1 Hz), 4.32 (2H, q, J=7.1 Hz), 5.48 (1H, d, J=11.1 Hz), 6.06 (1H, d, J=17.7 Hz), 6.78 (1H, dd, J=17.7, 11.1 Hz), 7.57 (1H, dd, J=8.1, 1.5 Hz), 7.70 (1H, d, J=1.5 Hz), 7.79 (1H, d, J=8.1 Hz).

Reference Example 163

Production of ethyl 2-chloro-4-ethylbenzoate

A mixture of the compound of Reference Example 162 (7.70 g, 36.55 mmol) and 5% hydroxide barium on palladium (1.5 g) in ethyl acetate (150 mL) was stirred at room temperature for 8 hr under a hydrogen atmosphere. The catalyst was filtered off, and the filtrate was concentrated under reduced pressure to give the title compound (7.61 g, 98%) as a pale-yellow liquid.

$^1$H NMR (300 MHz, CDCl$_3$) δ: 1.24 (3H, t, J=7.5 Hz), 1.40 (3H, t, J=7.2 Hz), 2.65 (2H, q, J=7.5 Hz), 4.38 (2H, q, J=7.2 Hz), 7.13 (1H, dd, J=8.1, 1.2 Hz), 7.28 (1H, d, J=1.2 Hz), 7.76 (1H, d, J=8.1 Hz).

Reference Example 164

Production of ethyl 2-chloro-4-ethyl-5-nitrobenzoate

By a method similar to that in Reference Example 149, the title compound (2.56 g, 70%) was obtained as a pale-yellow solid from the compound of Reference Example 163 (3.0 g, 14.11 mmol).

$^1$H NMR (300 MHz, DMSO-$d_6$) δ: 1.22 (3H, t, J=7.5 Hz), 1.34 (3H, t, J=7.1 Hz), 2.88 (2H, q, J=7.5 Hz), 4.36 (2H, q, J=7.1 Hz), 7.82 (1H, s), 8.38 (1H, s).

Reference Example 165

Production of ethyl 6-ethyl-3-hydroxy-1-methyl-5-nitro-1H-indole-2-carboxylate

By a method similar to that in Reference Example 155, the title compound (557 mg, 41%) was obtained as a yellow solid from the compound of Reference Example 164 (1.2 g, 4.66 mmol).

$^1$H NMR (300 MHz, DMSO-$d_6$) δ: 1.25 (3H, t, J=7.5 Hz), 1.33 (3H, t, J=7.1 Hz), 2.99 (2H, q, J=7.5 Hz), 3.90 (3H, s), 4.33 (2H, q, J=7.1 Hz), 7.53 (1H, s), 8.57 (1H, s), 9.92 (1H, br s).

Reference Example 166

Production of ethyl 6-ethyl-1-methyl-3-(1-methylethoxy)-5-nitro-1H-indole-2-carboxylate A mixture of the compound of Reference Example 165 (350 mg, 1.20 mmol), diisopropyl sulfate (240 mg, 1.32 mmol) and potassium carbonate (331 mg, 2.39 mmol) in acetone (10 mL) was heated under reflux for 20 hr. After cooling, the reaction mixture was diluted with saturated aqueous sodium hydrogen carbonate, and the mixture was extracted with ethyl acetate. The extract was washed with brine, dried over magnesium sulfate, and concentrated under reduced pressure. The residue was purified by silica gel column chromatography (eluent, hexane:ethyl acetate=5:1) to give the title compound (366 mg, 91%) as a yellow solid.

$^1$H NMR (300 MHz, DMSO-$d_6$) δ: 1.23-1.30 (9H, m), 1.36 (3H, t, J=7.1 Hz), 2.98 (2H, q, J=7.4 Hz), 3.96 (3H, s), 4.35 (2H, q, J=7.1 Hz), 4.48-4.54 (1H, m), 7.66 (1H, s), 9.29 (1H, s).

Reference Example 167

Production of ethyl 5-amino-6-ethyl-1-methyl-3-(1-methylethoxy)-1H-indole-2-carboxylate By a method similar to that in Reference Example 152, the title compound (250 mg, 78%) was obtained as a pale-brown oil from the compound of Reference Example 166 (350 mg, 1.05 mmol).

$^1$H NMR (300 MHz, DMSO-$d_6$) δ: 1.18-1.35 (12H, m), 2.58 (2H, q, J=7.4 Hz), 3.81 (3H, s), 4.24-4.40 (3H, m), 4.56 (2H, br s), 6.78 (1H, s), 7.10 (1H, s).

Reference Example 168

Production of ethyl 6-ethyl-1-methyl-3-(1-methylethoxy)-5-[(phenylcarbonyl)amino]-1H-indole-2-carboxylate By a method similar to that in Reference Example 21, the title compound (140 mg, 88%) was obtained as a colorless powder from the compound of Reference Example 167 (120 mg, 0.39 mmol) and benzoyl chloride (61 mg, 0.43 mmol).

$^1$H NMR (300 MHz, DMSO-$d_6$) δ: 1.20 (3H, t, J=7.5 Hz), 1.27 (6H, d, J=6.3 Hz), 1.36 (3H, t, J=7.1 Hz), 2.73 (2H, q, J=7.5 Hz), 3.93 (3H, s), 4.33 (2H, q, J=7.1 Hz), 4.41-4.49 (1H, m), 7.43 (1H, s), 7.52-7.64 (4H, m), 8.01 (2H, d, J=6.9 Hz), 9.93 (1H, s).

Reference Example 169

Production of 6-ethyl-1-methyl-3-(1-methylethoxy)-5-[(phenylcarbonyl)amino]-1H-indole-2-carboxylic acid By a method similar to that in Reference Example 12, the title compound (105 mg, 86%) was obtained as a white powder from the compound of Reference Example 168 (130 mg, 0.32 mmol). $^1$H NMR (300 MHz, DMSO-$d_6$) δ: 1.20 (3H, t, J=7.5 Hz), 1.26 (6H, d, J=6.0 Hz), 2.72 (2H, q, J=7.5 Hz), 3.92 (3H, s), 4.35-4.50 (1H, m), 7.41 (1H, s), 7.49-7.60 (4H, m), 8.00 (2H, d, J=7.2 Hz), 9.91 (1H, s), 12.70-12.90 (1H, br).

Reference Example 170

Production of ethyl 6-ethyl-3-hydroxy-5-nitro-1-benzothiophene-2-carboxylate

By a method similar to that in Reference Example 150, the title compound (1.10 g, 80%) was obtained as a yellow solid from the compound of Reference Example 164 (1.2 g, 4.66 mmol).

¹H NMR (300 MHz, DMSO-d₆) δ: 1.23-1.34 (6H, m), 2.94 (2H, q, J=7.4 Hz), 4.32 (2H, q, J=7.1 Hz), 8.08 (1H, s), 8.52 (1H, s), 10.80-11.30 (1H, br).

Reference Example 171

Production of ethyl 6-ethyl-5-nitro-3-(2,2,2-trifluoroethoxy)-1-benzothiophene-2-carboxylate By a method similar to that in Reference Example 8, the title compound (240 mg, 94%) was obtained as a white solid from the compound of Reference Example 170 (200 mg, 0.68 mmol).
¹H NMR (300 MHz, DMSO-d₆) δ: 1.27 (3H, t, J=7.5 Hz), 1.35 (3H, t, J=7.1 Hz) 2.95 (2H, q, J=7.5 Hz), 4.37 (2H, q, J=7.1 Hz), 5.07 (2H, q, J=9.0 Hz), 8.23 (1H, s), 8.32 (1H, s).

Reference Example 172

Production of ethyl 5-amino-6-ethyl-3-(2,2,2-trifluoroethoxy)-1-benzothiophene-2-carboxylate By a method similar to that in Reference Example 152, the title compound (210 mg, 99%) was obtained as a pale-yellow solid from the compound of Reference Example 171 (230 mg, 0.61 mmol).
¹H NMR (300 MHz, DMSO-d₆) δ: 1.19 (3H, t, J=7.5 Hz), 1.31 (3H, t, J=7.1 Hz) 2.57 (2H, q, J=7.5 Hz), 4.30 (2H, q, J=7.1 Hz), 4.89 (2H, q, J=9.1 Hz), 5.22 (2H, s), 7.00 (1H, s), 7.50 (1H, s).

Reference Example 173

Production of ethyl 6-ethyl-5-[(phenylcarbonyl)amino]-3-(2,2,2-trifluoroethoxy)-1-benzothiophene-2-carboxylate By a method similar to that in Reference Example 21, the title compound (125 mg, 95%) was obtained as a beige powder from the compound of Reference Example 172 (100 mg, 0.29 mmol) and benzoyl chloride (45 mg, 0.32 mmol).
¹H NMR (300 MHz, DMSO-d₆) δ: 1.20 (3H, t, J=7.5. Hz), 1.35 (3H, t, J=7.1 Hz) 2.77 (2H, q, J=7.5 Hz), 4.35 (2H, q, J=7.1 Hz), 5.01 (2H, q, J=9.0 Hz), 7.53-7.63 (3H, m), 7.78 (1H, s), 7.96 (1H, s), 8.00-8.03 (2H, m), 10.12 (1H, s).

Reference Example 174

Production of 6-ethyl-5-[(phenylcarbonyl)amino]-3-(2,2,2-trifluoroethoxy)-1-benzothiophene-2-carboxylic acid By a method similar to that in Reference Example 12, the title compound (86 mg, 92%) was obtained as a beige solid from the compound of Reference Example 173 (100 mg, 0.22 mmol).
¹H NMR (300 MHz, DMSO-d₆) δ: 1.20 (3H, t, J=7.5 Hz), 2.76 (2H, q, J=7.5 Hz), 5.01 (2H, q, J=9.1 Hz), 7.53-7.65 (3H, m), 7.75 (1H, s), 7.93 (1H, s), 8.01 (2H, d, J=6.9 Hz), 10.11 (1H, s), 13.50-13.80 (1H, br).

Reference Example 175

Production of ethyl 6-ethyl-5-[(thiophen-3-ylcarbonyl)amino]-3-(2,2,2-trifluoroethoxy)-1-benzothiophene-2-carboxylate By a method similar to that in Reference Example 21, the title compound (121 mg, 91%) was obtained as a beige powder from the compound of Reference Example 172 (100 mg, 0.29 mmol) and 3-thiophenecarbonyl chloride (46 mg, 0.32 mmol).
¹H NMR (300 MHz, DMSO-d₆) δ: 1.19 (3H, t, J=7.5 Hz), 1.34 (3H, t, J=7.1 Hz) 2.76 (2H, q, J=7.5 Hz), 4.35 (2H, q, J=7.1 Hz), 5.00 (2H, q, J=9.0 Hz), 7.64-7.70 (2H, m), 7.75 (1H, s), 7.95 (1H, s), 8.36-8.37 (1H, m), 9.93 (1H, s).

Reference Example 176

Production of 6-ethyl-5-[(thiophen-3-ylcarbonyl)amino]-3-(2,2,2-trifluoroethoxy)-1-benzothiophene-2-carboxylic acid By a method similar to that in Reference Example 12, the title compound (78 mg, 83%) was obtained as a beige solid from the compound of Reference Example 175 (100 mg, 0.22 mmol).
¹H NMR (300 MHz, DMSO-d₆) δ: 1.19 (3H, t, J=7.5 Hz), 2.75 (2H, q, J=7.5 Hz), 5.01 (2H, q, J=9.1 Hz), 7.64-7.72 (3H, m), 7.92 (1H, s), 8.36 (1H, q, J=1.2 Hz), 9.92 (1H, s), 13.50-13.80 (1H, br).

Reference Example 177

Production of ethyl 6-ethyl-3-(1-methylethoxy)-5-nitro-1-benzothiophene-2-carboxylate By a method similar to that in Reference Example 84, the title compound (720 mg, 90%) was obtained as a pale-yellow solid from the compound of Reference Example 170 (700 mg, 2.37 mmol).
¹H NMR (300 MHz, DMSO-d₆) δ: 1.26 (3H, t, J=7.5 Hz), 1.32-1.38 (9H, m) 2.93 (2H, q, J=7.5 Hz), 4.34 (2H, q, J=7.1 Hz), 4.80-4.88 (1H, m), 8.16 (1H, s), 8.35 (1H, s).

Reference Example 178

Production of ethyl 5-amino-6-ethyl-3-(1-methylethoxy)-1-benzothiophene-2-carboxylate By a method similar to that in Reference Example 152, the title compound (690 mg, 100%) was obtained as an orange solid from the compound of Reference Example 177 (720 mg, 2.13 mmol).
¹H NMR (300 MHz, DMSO-d₆) δ: 1.21 (3H, t, J=7.5 Hz), 1.29-1.36 (9H, m) 2.59 (2H, q, J=7.5 Hz), 4.28 (2H, q, J=7.1 Hz), 4.67-4.75 (1H, m), 5.50-6.30 (2H, br), 7.15 (1H, s), 7.51 (1H, s).

Reference Example 179

Production of ethyl 6-ethyl-3-(1-methylethoxy)-5-[(phenylcarbonyl)amino]-1-benzothiophene-2-carboxylate By a method similar to that in Reference Example 21, the title compound (100 mg, 81%) was obtained as a pale-orange solid from the compound of Reference Example 178 (100 mg, 0.30 mmol) and benzoyl chloride (46 mg, 0.33 mmol).
¹H NMR (300 MHz, DMSO-d₆) δ: 1.20 (3H, t, J=7.5 Hz), 1.30-1.36 (9H, m) 2.76 (2H, q, J=7.5 Hz), 4.32 (2H, q, J=7.0

Hz), 4.75-4.82 (1H, m), 7.48-7.65 (3H, m), 7.81 (1H, s), 7.89 (1H, s), 8.01 (2H, d, J=6.9 Hz), 10.06 (1H, s).

Reference Example 180

Production of 6-ethyl-3-(1-methylethoxy)-5-[(phenylcarbonyl)amino]-1-benzothiophene-2-carboxylic acid By a method similar to that in Reference Example 12, the title compound (57 mg, 68%) was obtained as a beige solid from the compound of Reference Example 179 (90 mg, 0.22 mmol).
$^1$H NMR (300 MHz, DMSO-d$_6$) δ: 1.20 (3H, t, J=7.5 Hz), 1.30 (6H, d, J=6.0 Hz), 2.76 (2H, q, J=7.5 Hz), 4.75-4.85 (1H, m), 7.53-7.62 (3H, m), 7.78 (1H, s), 7.86 (1H, s), 8.01 (2H, d, J=6.9 Hz), 10.05 (1H, s), 13.10-13.30 (1H, br).

Reference Example 181

Production of ethyl 6-ethyl-3-(1-methylethoxy)-5-[(thiophen-3-ylcarbonyl)amino]-1-benzothiophene-2-carboxylate By a method similar to that in Reference Example 21, the title compound (91 mg, 73%) was obtained as a pale-orange solid from the compound of Reference Example 178 (100 mg, 0.30 mmol) and 3-thiophenecarbonyl chloride (48 mg, 0.33 mmol).
$^1$H NMR (300 MHz, DMSO-d$_6$) δ: 1.19 (3H, t, J=7.5 Hz), 1.30-1.36 (9H, m) 2.75 (2H, q, J=7.5 Hz), 4.32 (2H, q, J=7.1 Hz), 4.75-4.81 (1H, m), 7.64-7.69 (2H, m), 7.78 (1H, s), 7.88 (1H, s), 8.35 (1H, t, J=1.5 Hz), 9.88 (1H, s).

Reference Example 182

Production of 6-ethyl-3-(1-methylethoxy)-5-[(thiophen-3-ylcarbonyl)amino]-1-benzothiophene-2-carboxylic acid By a method similar to that in Reference Example 12, the title compound (65 mg, 83%) was obtained as a beige powder from the compound of Reference Example 181 (85 mg, 0.20 mmol).
$^1$H NMR (300 MHz, DMSO-d$_6$) δ: 1.19 (3H, t, J=7.5 Hz), 1.29 (6H, d, J=6.0 Hz), 2.74 (2H, q, J=7.5 Hz), 4.75-4.85 (1H, m), 7.64-7.68 (2H, m), 7.74 (1H, s), 7.85 (1H, s), 8.35 (1H, s), 9.87 (1H, s), 13.10-13.30 (1H, br).

Reference Example 183

Production of ethyl 6-ethyl-3-(1-methylethoxy)-5-[(thiophen-2-ylcarbonyl)amino]-1-benzothiophene-2-carboxylate By a method similar to that in Reference Example 21, the title compound (217 mg, 87%) was obtained as a beige solid from the compound of Reference Example 178 (200 mg, 0.60 mmol) and 2-thiophenecarbonyl chloride (96 mg, 0.66 mmol).
$^1$H NMR (300 MHz, DMSO-d$_6$) δ: 1.20 (3H, t, J=7.5 Hz), 1.28-1.36 (9H, m) 2.75 (2H, q, J=7.5 Hz), 4.32 (2H, q, J=7.0 Hz), 4.76-4.82 (1H, m), 7.24 (1H, dd, J=5.1, 3.9 Hz), 7.77 (1H, s), 7.86-7.89 (2H, m), 8.01 (1H, d, J=3.9 Hz), 10.07 (1H, s).

Reference Example 184

Production of 6-ethyl-3-(1-methylethoxy)-5-[(thiophen-2-ylcarbonyl)amino]-1-benzothiophene-2-carboxylic acid By a method similar to that in Reference Example 12, the title compound (144 mg, 77%) was obtained as a beige powder from the compound of Reference Example 183 (200 mg, 0.48 mmol).
$^1$H NMR (300 MHz, DMSO-d$_6$) δ: 1.19 (3H, t, J=7.5 Hz), 1.29 (6H, d, J=6.3 Hz), 2.74 (2H, q, J=7.5 Hz), 4.75-4.88 (1H, m), 7.23-7.26 (1H, m), 7.74 (1H, s), 7.86-7.88 (2H, m), 8.01 (1H, d, J=3.0 Hz), 10.06 (1H, s), 13.10-13.40 (1H, br).

Reference Example 185

Production of ethyl 6-ethyl-5-{[(4-fluorophenyl)carbonyl]amino}-3-(1-methylethoxy)-1-benzothiophene-2-carboxylate By a method similar to that in Reference Example 21, the title compound (220 mg, 85%) was obtained as a pale-orange solid from the compound of Reference Example 178 (200 mg, 0.60 mmol) and 4-fluorobenzoyl chloride (104 mg, 0.66 mmol).
$^1$H NMR (300 MHz, DMSO-d$_6$) δ: 1.20 (3H, t, J=7.5 Hz), 1.29-1.36 (9H, m) 2.75 (2H, q, J=7.5 Hz), 4.32 (2H, q, J=7.0 Hz), 4.75-4.82 (1H, m), 7.39 (2H, t, J=8.9 Hz), 7.80 (1H, s), 7.89 (1H, s), 8.09 (2H, dd, J=8.7, 5.7 Hz), 10.08 (1H, s).

Reference Example 186

Production of 6-ethyl-5-{[(4-fluorophenyl)carbonyl]amino}-3-(1-methylethoxy)-1-benzothiophene-2-carboxylic acid By a method similar to that in Reference Example 12, the title compound (69 mg, 75%) was obtained as a beige powder from the compound of Reference Example 185 (100 mg, 0.23 mmol).
$^1$H NMR (300 MHz, DMSO-d$_6$) δ: 1.19 (3H, t, J=7.5 Hz), 1.29 (6H, d, J=6.3 Hz), 2.74 (2H, q, J=7.5 Hz), 4.79-4.87 (1H, m), 7.39 (2H, t, J=8.9 Hz), 7.76 (1H, s), 7.86 (1H, s), 8.06-8.11 (2H, m), 10.07 (1H, s), 13.10-13.30 (1H, br).

Reference Example 187

Production of ethyl 5-bromo-1,6-dimethyl-3-(1-methylethoxy)-1H-pyrrolo[2,3-b]pyridine-2-carboxylate By a method similar to that in Reference Example 84, the title compound (1.18 g, 100%) was obtained as a yellow powder from the compound of Reference Example 61 (1.0 g, 3.19 mmol).
$^1$H NMR (300 MHz, DMSO-d$_6$) δ: 1.27 (6H, d, J=6.3 Hz), 1.36 (3H, t, J=7.1 Hz), 2.68 (3H, s), 3.93 (3H, s), 4.33 (2H, q, J=7.1 Hz), 4.47-4.55 (1H, m), 8.30 (1H, s).

Reference Example 188

Production of ethyl 5-[(diphenylmethylidene)amino]-1,6-dimethyl-3-(1-methylethoxy)-1H-pyrrolo[2,3-b]pyridine-2-carboxylate To a mixture of the compound of Reference Example 187 (600 mg, 1.69 mmol), benzophenonimine (0.4 mL), cesium carbonate (1.10 g, 3.38 mmol) and toluene (20 mL) were added Pd$_2$dba$_3$ (77 mg, 0.08 mmol) and Xantphos (98 mg, 0.17 mmol), and the mixture was stirred at 100° C. for 18 hr under an argon atmosphere. The mixture was filtered through celite, and washed with ethyl acetate. The filtrate was washed with water (20 mL) and brine (10 mL), dried over anhydrous magnesium sulfate, and concentrated under reduced pressure. The residue was purified by silica gel column chromatography (eluent, hexane/ethyl acetate=5/1), and recrystallized from ethyl acetate-diisopropyl ether-hexane to give the title compound (454 mg, 59%) as yellow crystals.

$^1$H NMR (300 MHz, DMSO-d$_6$) δ: 1.06 (6H, d, J=6.3 Hz), 1.30 (3H, t, J=7.2 Hz), 2.50 (3H, s), 3.88 (3H, s), 4.10-4.16 (1H, m), 4.27 (2H, q, J=7.2 Hz), 6.97 (1H, s), 7.17-7.20 (2H, m), 7.27-7.33 (3H, m), 7.47-7.56 (3H, m), 7.73-7.76 (2H, m).

Reference Example 189

Production of ethyl 5-amino-1,6-dimethyl-3-(1-methylethoxy)-1H-pyrrolo[2,3-b]pyridine-2-carboxylate A mixture of the compound of Reference Example 188 (400 mg, 0.88 mmol) and 2N hydrochloric acid (1.5 mL) in THF (6 mL) was stirred at room temperature for 1 hr. To the mixture was added aqueous sodium hydrogen carbonate solution, and the mixture was extracted three times with ethyl acetate. The extracts were combined and washed with brine, dried over anhydrous magnesium sulfate, and concentrated under reduced pressure. The residue was purified by silica gel column chromatography (eluent, hexane/ethyl acetate=4/1-1/1) to give the title compound (250 mg, 98%) as a yellow solid. $^1$H NMR (300 MHz, DMSO-d$_6$) δ: 1.26 (6H, d, J=6.0 Hz), 1.33 (3H, t, J=7.2 Hz), 2.40 (3H, s), 3.86 (3H, s), 4.29 (2H, q, J=7.2 Hz), 4.33-4.41 (1H, m), 4.74 (2H, s), 7.17 (1H, s).

Reference Example 190

Production of ethyl 1,6-dimethyl-3-(1-methylethoxy)-5-[(phenylcarbonyl)amino]-1H-pyrrolo[2,3-b]pyridine-2-carboxylate A mixture of the compound of Reference Example 189 (120 mg, 0.41 mmol), pyridine (65 mg, 0.82 mmol) and THF (2 mL) was cooled to 0° C., benzoyl chloride (64 mg, 0.45 mmol) was added thereto, and the mixture was stirred at 0° C. for 30 min. To the reaction mixture was added water (6 mL), and the mixture was stirred at room temperature for 30 min. The precipitate was collected by filtration, washed with water, and dried under reduced pressure to give the title compound (128 mg, 79%) as a white powder.

$^1$H NMR (300 MHz, DMSO-d$_6$) δ: 1.29 (6H, d, J=6.0 Hz), 1.36 (3H, t, J=7.1 Hz), 2.54 (3H, s), 3.97 (3H, s), 4.34 (2H, q, J=7.1 Hz), 4.47-4.53 (1H, m), 7.53-7.62 (3H, m), 8.01-8.04 (3H, m), 10.08 (1H, s).

Reference Example 191

Production of 1,6-dimethyl-3-(1-methylethoxy)-5-[(phenylcarbonyl)amino]-1H-pyrrolo[2,3-b]pyridine-2-carboxylic acid By a method similar to that in Reference Example 12, the title compound (87 mg, 79%) was obtained as a white powder from the compound of Reference Example 190 (120 mg, 0.30 mmol), 2N aqueous sodium hydroxide solution (1 mL), ethanol (3 mL) and THF (0.5 mL).

$^1$H NMR (300 MHz, DMSO-d$_6$) δ: 1.27 (6H, d, J=6.3 Hz), 2.53 (3H, s), 3.96 (3H, s), 4.46-4.54 (1H, m), 7.52-7.64 (3H, m), 7.97 (1H, s), 8.02 (2H, d, J=6.9 Hz), 10.06 (1H, s), 12.92 (1H, br s).

Reference Example 192

Production of ethyl 5-{[(4-fluorophenyl)carbonyl]amino}-1,6-dimethyl-3-(1-methylethoxy)-1H-pyrrolo[2,3-b]pyridine-2-carboxylate A mixture of the compound of Reference Example 189 (120 mg, 0.41 mmol), pyridine (65 mg, 0.82 mmol) and THF (2 mL) was cooled to 0° C., 4-fluorobenzoyl chloride (72 mg, 0.45 mmol) was added thereto, and the mixture was stirred at 0° C. for 30 min. To the reaction mixture was added water (8 mL), and the mixture was stirred at room temperature for 30 min. The precipitate was collected by filtration, washed with water, and dried under reduced pressure to give the title compound (146 mg, 86%) as a white powder.

$^1$H NMR (300 MHz, DMSO-d$_6$) δ: 1.28 (6H, d, J=6.3 Hz), 1.36 (3H, t, J=7.1 Hz), 2.53 (3H, s), 3.96 (3H, s), 4.34 (2H, q, J=7.1 Hz), 4.46-4.53 (1H, m), 7.39 (2H, d, J=8.9 Hz), 8.00 (1H, s), 8.07-8.12 (2H, m), 10.11 (1H, s).

Reference Example 193

Production of 5-{[(4-fluorophenyl)carbonyl]amino}-1,6-dimethyl-3-(1-methylethoxy)-1H-pyrrolo[2,3-b]pyridine-2-carboxylic acid By a method similar to that in Reference Example 12, the title compound (80 mg, 61%) was obtained as a white powder from the compound of Reference Example 192 (140 mg, 0.34 mmol), 2N aqueous sodium hydroxide solution (1 mL), ethanol (3 mL) and THF (0.5 mL).

$^1$H NMR (300 MHz, DMSO-d$_6$) δ: 1.27 (6H, d, J=6.0 Hz), 2.52 (3H, s), 3.96 (3H, s), 4.47-4.52 (1H, m), 7.39 (2H, t, J=8.9 Hz), 7.97 (1H, s), 8.07-8.12 (2H, m), 10.09 (1H, s), 12.92 (1H, br s).

Reference Example 194

Production of ethyl 6-ethyl-5-{[(4-fluorophenyl)carbonyl]amino}-1-methyl-3-(1-methylethoxy)-1H-indole-2-carboxylate By a method similar to that in Reference Example 21, the title compound (196 mg, 94%) was obtained as a beige powder from the compound of Reference Example 167 (150 mg, 0.49 mmol) and 4-fluorobenzoyl chloride (86 mg, 0.54 mmol).

$^1$H NMR (300 MHz, DMSO-d$_6$) δ: 1.20 (3H, t, J=7.5 Hz), 1.27 (6H, d, J=6.0 Hz), 1.36 (3H, t, J=7.1 Hz), 2.71 (2H, q, J=7.5 Hz), 3.93 (3H, s), 4.33 (2H, q, J=7.1 Hz), 4.42-4.47 (1H, m), 7.37 (2H, t, J=8.9 Hz), 7.43 (1H, s), 7.51 (1H, s), 8.06-8.10 (2H, m), 9.95 (1H, s).

Reference Example 195

Production of 6-ethyl-5-{[(4-fluorophenyl)carbonyl]amino}-1-methyl-3-(1-methylethoxy)-1H-indole-2-carboxylic acid By a method similar to that in Reference Example 12, the title compound (164 mg, 91%) was obtained as a pale-beige powder from the compound of Reference Example 194 (190 mg, 0.45 mmol).

¹H NMR (300 MHz, DMSO-d₆) δ: 1.19 (3H, t, J=7.5 Hz), 1.26 (6H, d, J=6.3 Hz), 2.71 (2H, q, J=7.5 Hz), 3.92 (3H, s), 4.41-4.49 (1H, m), 7.34-7.41 (3H, m), 7.49 (1H, s), 8.05-8.10 (2H, m), 9.93 (1H, s), 12.60-12.70 (1H, br).

Reference Example 196

Production of ethyl 5-{[(4-chlorophenyl)carbonyl]amino}-6-ethyl-1-methyl-3-(1-methylethoxy)-1H-indole-2-carboxylate By a method similar to that in Reference Example 21, the title compound (207 mg, 95%) was obtained as a beige powder from the compound of Reference Example 167 (150 mg, 0.49 mmol) and 4-chlorobenzoyl chloride (95 mg, 0.54 mmol).
¹H NMR (300 MHz, DMSO-d₆) δ: 1.19 (3H, t, J=7.5 Hz), 1.27 (6H, d, J=6.0 Hz), 1.35 (3H, t, J=7.1 Hz), 2.71 (2H, q, J=7.5 Hz), 3.92 (3H, s), 4.33 (2H, q, J=7.1 Hz), 4.42-4.47 (1H, m), 7.43 (1H, s), 7.51 (1H, s), 7.61 (2H, d, J=8.4 Hz), 8.03 (2H, d, J=8.4 Hz), 10.00 (1H, s).

Reference Example 197

Production of 5-{[(4-chlorophenyl)carbonyl]amino}-6-ethyl-1-methyl-3-(1-methylethoxy)-1H-indole-2-carboxylic acid By a method similar to that in Reference Example 12, the title compound (162 mg, 87%) was obtained as a white powder from the compound of Reference Example 196 (200 mg, 0.45 mmol).
¹H NMR (300 MHz, DMSO-d₆) δ: 1.19 (3H, t, J=7.5 Hz), 1.26 (6H, d, J=6.0 Hz), 2.71 (2H, q, J=7.5 Hz), 3.92 (3H, s), 4.42-4.48 (1H, m), 7.41 (1H, s), 7.49 (1H, s), 7.62 (2H, d, J=8.4 Hz), 8.03 (2H, d, J=8.4 Hz), 9.99 (1H, s), 12.70-12.90 (1H, br).

Reference Example 198

Production of ethyl 6-ethyl-1-methyl-5-nitro-3-(2,2,2-trifluoroethoxy)-1H-indole-2-carboxylate By a method similar to that in Reference Example 8, the title compound (190 mg, 100%) was obtained as a yellow solid from the compound of Reference Example 165 (150 mg, 0.51 mmol).
¹H NMR (300 MHz, DMSO-d₆) δ: 1.26 (3H, t, J=7.5 Hz), 1.35 (3H, t, J=7.1 Hz) 2.98 (2H, q, J=7.5 Hz), 3.99 (3H, s), 4.36 (2H, q, J=7.1 Hz), 4.85 (2H, q, J=9.1 Hz), 7.72 (1H, s), 8.34 (1H, s).

Reference Example 199

Production of ethyl 5-amino-6-ethyl-1-methyl-3-(2,2,2-trifluoroethoxy)-1H-indole-2-carboxylate By a method similar to that in Reference Example 152, the title compound (160 mg, 97%) was obtained as a pale-brown solid from the compound of Reference Example 198 (180 mg, 0.48 mmol).
¹H NMR (300 MHz, DMSO-d₆) δ: 1.21 (3H, t, J=7.4 Hz), 1.33 (3H, t, J=7.1 Hz), 2.59 (2H, q, J=7.4 Hz), 3.84 (3H, s), 4.31 (2H, q, J=7.1 Hz), 4.61 (2H, q, J=9.3 Hz), 4.67 (2H, s), 6.77 (1H, s), 7.16 (1H, s).

Reference Example 200

Production of ethyl 6-ethyl-1-methyl-5-[(phenylcarbonyl)amino]-3-(2,2,2-trifluoroethoxy)-1H-indole-2-carboxylate By a method similar to that in Reference Example 21, the title compound (89 mg, 86%) was obtained as a beige powder from the compound of Reference Example 199 (80 mg, 0.23 mmol) and benzoyl chloride (36 mg, 0.26 mmol).
¹H NMR (300 MHz, DMSO-d₆) δ: 1.20 (3H, t, J=7.4 Hz), 1.36 (3H, t, J=7.1 Hz), 2.74 (2H, q, J=7.4 Hz), 3.96 (3H, s), 4.36 (2H, q, J=7.1 Hz), 4.74 (2H, q, J=9.0 Hz), 7.49-7.61 (5H, m), 8.01 (2H, d, J=7.2 Hz), 9.97 (1H, s).

Reference Example 201

Production of 6-ethyl-1-methyl-5-[(phenylcarbonyl)amino]-3-(2,2,2-trifluoroethoxy)-1H-indole-2-carboxylic acid By a method similar to that in Reference Example 12, the title compound (72 mg, 95%) was obtained as a white powder from the compound of Reference Example 200 (80 mg, 0.18 mmol).
¹H NMR (300 MHz, DMSO-d₆) δ: 1.20 (3H, t, J=7.5 Hz), 2.73 (2H, q, J=7.5 Hz), 3.96 (3H, s), 4.72 (2H, q, J=9.1 Hz), 7.46-7.60 (5H, m), 8.01 (2H, d, J=6.9 Hz), 9.96 (1H, s), 13.20-13.40 (1H, br).

Reference Example 202

Production of ethyl 6-ethyl-1-methyl-5-[(thiophen-3-ylcarbonyl)amino]-3-(2,2,2-trifluoroethoxy)-1H-indole-2-carboxylate By a method similar to that in Reference Example 21, the title compound (89 mg, 85%) was obtained as a beige powder from the compound of Reference Example 199 (80 mg, 0.23 mmol) and 3-thiophenecarbonyl chloride (37 mg, 0.26 mmol).
¹H NMR (300 MHz, DMSO-d₆) δ: 1.19 (3H, t, J=7.5 Hz), 1.36 (3H, t, J=7.1 Hz), 2.72 (2H, q, J=7.5 Hz), 3.96 (3H, s), 4.35 (2H, q, J=7.1 Hz), 4.74 (2H, q, J=9.1 Hz), 7.49 (1H, s), 7.52 (1H, s), 7.66-7.68 (2H, m), 8.33 (1H, s), 9.80 (1H, s).

Reference Example 203

Production of 6-ethyl-1-methyl-5-[(thiophen-3-ylcarbonyl)amino]-3-(2,2,2-trifluoroethoxy)-1H-indole-2-carboxylic acid By a method similar to that in Reference Example 12, the title compound (67 mg, 87%) was obtained as a white powder from the compound of Reference Example 202 (80 mg, 0.18 mmol).
¹H NMR (300 MHz, DMSO-d₆) δ: 1.19 (3H, t, J=7.5 Hz), 2.72 (2H, q, J=7.5 Hz), 3.95 (3H, s), 4.71 (2H, q, J=9.2 Hz), 7.46 (1H, s), 7.48 (1H, s), 7.65 (1H, s), 7.66 (1H, s), 8.33 (1H, s), 9.79 (1H, s), 13.20-13.40 (1H, br).

Reference Example 204

Production of ethyl 6-ethyl-1-methyl-3-(1-methylethoxy)-5-[(thiophen-3-ylcarbonyl)amino]-1H-indole-2-carboxylate By a method similar to that in Reference Example 21, the title compound (135 mg, 84%) was obtained as a white powder from the compound of Reference Example 167 (120 mg, 0.39 mmol) and 3-thiophenecarbonyl chloride (64 mg, 0.43 mmol).

$^1$H NMR (300 MHz, DMSO-d$_6$) δ: 1.19 (3H, t, J=7.5 Hz), 1.27 (6H, d, J=6.3 Hz), 1.35 (3H, t, J=7.2 Hz), 2.71 (2H, q, J=7.5 Hz), 3.92 (3H, s), 4.32 (2H, q, J=7.2 Hz), 4.40-4.47 (1H, m), 7.43 (1H, s), 7.48 (1H, s), 7.65-7.67 (2H, m), 8.32 (1H, s), 9.76 (1H, s).

Reference Example 205

Production of 6-ethyl-1-methyl-3-(1-methylethoxy)-5-[(thiophen-3-ylcarbonyl)amino]-1H-indole-2-carboxylic acid By a method similar to that in Reference Example 12, the title compound (101 mg, 90%) was obtained as a white powder from the compound of Reference Example 204 (120 mg, 0.29 mmol).

$^1$H NMR (300 MHz, DMSO-d$_6$) δ: 1.19 (3H, t, J=7.5 Hz), 1.26 (6H, d, J=6.3 Hz), 2.71 (2H, q, J=7.5 Hz), 3.92 (3H, s), 4.40-4.47 (1H, m), 7.40 (1H, s), 7.46 (1H, s), 7.65 (2H, s), 8.32 (1H, s), 9.74 (1H, s), 12.74 (1H, br s).

Reference Example 206

Production of ethyl 3,5-dimethyl-7-(1-methylethoxy)-2-phenyl-5H-pyrrolo[2,3-b]pyrazine-6-carboxylate By a method similar to that in Reference Example 84, the title compound (184 mg, quantitatively) was obtained as a yellow powder from the compound of Reference Example 114 (161 mg, 0.518 mmol), diisopropyl sulfate (104 μL, 0.627 mmol) and potassium carbonate (106 mg, 0.768 mmol).

$^1$H NMR (300 MHz, DMSO-d$_6$) δ: 1.30 (6H, d, J=6.0 Hz), 1.36 (3H, t, J=7.1 Hz), 2.63 (3H, s), 3.97 (3H, s), 4.35 (2H, q, J=7.1 Hz), 5.12-5.29 (1H, m), 7.40-7.58 (3H, m), 7.58-7.69 (2H, m).

Reference Example 207

Production of 3,5-dimethyl-7-(1-methylethoxy)-2-phenyl-5H-pyrrolo[2,3-b]pyrazine-6-carboxylic acid By a method similar to that in Reference Example 12, the title compound (154 mg, 93%) was obtained as a yellow powder from the compound of Reference Example 206 (180 mg, 0.509 mmol) and 2N aqueous sodium hydroxide solution (1 mL).

$^1$H NMR (300 MHz, DMSO-d$_6$) δ: 1.29 (6H, d, J=6.2 Hz), 2.63 (3H, s), 3.96 (3H, s), 5.13-5.35 (1H, m), 7.39-7.57 (3H, m), 7.57-7.71 (2H, m), 13.04 (1H, br s).

Reference Example 208

Production of ethyl 5-ethyl-3-hydroxypyrazine-2-carboxylate

To a suspension of butane-1,2-diamine hydrochloride (6.40 g, 39.7 mmol) in ethanol (60 mL) was added diisopropylethylamine (14 mL, 80.4 mmol), and the mixture was stirred at room temperature for 10 min. To this solution was added dropwise diethyl ketomalonate (6 mL, 39.3 mmol) at 0° C., and the mixture was stirred at room temperature for 1.5 hr with heating under reflux for 20 hr. The reaction mixture was concentrated under reduced pressure, and the residue was dissolved in a small amount of ethanol. The solution was passed through silica gel (100 g, eluent, hexane:ethyl acetate=1:1→ethyl acetate). The eluate was concentrated under reduced pressure, and the residue was purified by silica gel column chromatography (eluent, hexane:ethyl acetate=2:1→ethyl acetate) to give the title compound (1.94 g, 25%) as a pale-yellow powder.

$^1$H NMR (300 MHz, DMSO-d$_6$) δ: 1.19 (3H, t, J=7.6 Hz), 1.27 (3H, t, J=7.2 Hz), 2.53-2.62 (2H, m), 4.26 (2H, q, J=7.2 Hz), 7.42 (1H, br s), 12.68 (1H, br s).

Reference Example 209

Production of ethyl 5-ethyl-3-hydroxy-6-phenylpyrazine-2-carboxylate

To a solution of the compound of Reference Example 208 (0.90 g, 4.59 mmol) in DMF (10 mL) was added N-bromosuccinimide (0.86 g, 4.83 mmol), and the mixture was stirred at room temperature for 3 hr. To the reaction mixture was added water (30 mL), and the mixture was extracted with ethyl acetate (20 mL×3). The organic layers were combined and washed with brine (10 mL), dried over anhydrous magnesium sulfate and concentrated under reduced pressure. The residue was purified by silica gel column chromatography (eluent, hexane:ethyl acetate=99:1→4:1) to give crude ethyl 6-bromo-5-ethyl-3-hydroxypyrazine-2-carboxylate. The obtained compound was dissolved in a mixed solvent of toluene (10 mL)/DMF (10 mL), and phenylboronic acid (679 mg, 5.57 mmol), potassium carbonate (3.09 g, 22.4 mmol) and Pd(PPh$_3$)$_4$ (260 mg, 0.225 mmol) were added thereto, and the mixture was stirred under an argon atmosphere at 100° C. for 1 hr. To the reaction mixture was added ethyl acetate (10 mL), and the mixture was filtered through celite to remove an insoluble material. The filtrate was concentrated under reduced pressure, and the residue was purified by silica gel column chromatography (eluent, hexane:ethyl acetate=49:1→2:1) to give the title compound (720 mg, 58%) as a yellow powder.

$^1$H NMR (300 MHz, DMSO-d$_6$) δ: 1.15 (3H, t, J=7.6 Hz), 1.27 (3H, t, J=7.2 Hz), 2.53-2.71 (2H, m), 4.29 (2H, q, J=7.2 Hz), 7.25-7.55 (5H, m), 13.01 (1H, br s).

Reference Example 210

Production of ethyl 3-chloro-5-ethyl-6-phenylpyrazine-2-carboxylate

By a method similar to that in Reference Example 6, the title compound (107 mg, 14%) was obtained as a pale-yellow oil from the compound of Reference Example 209 (716 mg, 2.63 mmol) and phosphorus oxychloride (716 μL, 7.90 mmol).

$^1$H NMR (300 MHz, DMSO-d$_6$) δ: 1.18 (3H, t, J=7.5 Hz), 1.33 (3H, t, J=7.1 Hz), 2.88 (2H, q, J=7.5 Hz), 4.41 (2H, q, J=7.1 Hz), 7.46-7.66 (5H, m).

Reference Example 211

Production of ethyl 3-ethyl-7-hydroxy-5-methyl-2-phenyl-5H-pyrrolo[2,3-b]pyrazine-6-carboxylate A mixture of the compound of Reference Example 210 (106 mg, 0.365 mmol), ethyl sarcosinate hydrochloride (101 mg, 0.660 mmol), triethylamine (1 mL) and ethanol (2 mL) was stirred for 14 hr with heating under reflux. Then, ethyl sarcosinate hydrochloride (100 mg, 0.651 mmol) and triethylamine (1 mL) were added thereto, and the mixture was stirred with heating under reflux for 9 hr. Water was added to the reaction mixture, and the mixture was extracted with ethyl acetate (10 mL×3). The organic layers were combined and dried over anhydrous magnesium sulfate, and concentrated under reduced pressure. The residue was dissolved in ethanol (1 mL), an ethanol solution (20%, 372 mg, 1.09 mmol) of sodium ethoxide was added thereto, and the mixture was stirred at room temperature for 1 hr. The reaction mixture was acidified with 1N hydrochloric acid, and extracted with ethyl acetate (10 mL×3). The organic layers were combined, dried over anhydrous magnesium sulfate, and concentrated under reduced pressure. The residue was purified by silica gel column chromatography (eluent, hexane:ethyl acetate=19:1→1:2) to give the title compound (102 mg, 86%) as a pale-yellow powder.

$^1$H NMR (300 MHz, DMSO-d$_6$) δ: 1.20 (3H, t, J=7.5 Hz), 1.35 (3H, t, J=7.1 Hz), 2.87 (2H, q, J=7.5 Hz), 3.95 (3H, s), 4.36 (2H, q, J=7.1 Hz), 7.38-7.64 (5H, m), 9.94 (1H, br s).

Reference Example 212

Production of ethyl 3-ethyl-5-methyl-2-phenyl-7-(2,2,2-trifluoroethoxy)-5H-pyrrolo[2,3-b]pyrazine-6-carboxylate By a method similar to that in Reference Example 8, the title compound (102 mg, 82%) was obtained as a pale-yellow powder from the compound of Reference Example 211 (100 mg, 0.307 mmol), cesium carbonate (164 mg, 0.505 mmol) and 2,2,2-trifluoroethyl trifluoromethanesulfonate (57.6 μL, 0.400 mmol).

$^1$H NMR (300 MHz, DMSO-d$_6$) δ: 1.22 (3H, t, J=7.5 Hz), 1.35 (3H, t, J=7.2 Hz), 2.93 (2H, q, J=7.5 Hz), 4.02 (3H, s), 4.37 (2H, q, J=7.2 Hz), 5.21 (2H, q, J=8.9 Hz), 7.44-7.64 (5H, m).

Reference Example 213

Production of 3-ethyl-5-methyl-2-phenyl-7-(2,2,2-trifluoroethoxy)-5H-pyrrolo[2,3-b]pyrazine-6-carboxylic acid By a method similar to that in Reference Example 12, the title compound (90.6 mg, 97%) was obtained as a pale-yellow powder from the compound of Reference Example 212 (100 mg, 0.245 mmol).

$^1$H NMR (300 MHz, DMSO-d$_6$) δ: 1.22 (3H, t, J=7.5 Hz), 2.93 (2H, q, J=7.5 Hz), 4.01 (3H, s), 5.20 (2H, q, J=8.9 Hz), 7.39-7.68 (5H, m), 13.42 (1H, br s).

Reference Example 214

Production of ethyl 3-(benzyloxy)-6-bromo-5-methylpyrazine-2-carboxylate

To a solution of the compound of Reference Example 111 (1.23 g, 4.71 mmol) in toluene (20 mL) were added silver carbonate (1.80 g, 6.53 mmol) and benzyl bromide (672 μL, 5.65 mmol) at 0° C., and the mixture was stirred at room temperature for 8 hr. The insoluble material was filtered through celite, and the filtrate was concentrated under reduced pressure. The residue was purified by silica gel column chromatography (eluent, hexane:ethyl acetate=99:1→4:1) to give the title compound (1.29 g, 78%) as a white powder.

$^1$H NMR (300 MHz, DMSO-d$_6$) δ: 1.28 (3H, t, J=7.1 Hz), 2.60 (3H, s), 4.33 (2H, q, J=7.1 Hz), 5.46 (2H, s), 7.29-7.46 (3H, m), 7.46-7.55 (2H, m).

Reference Example 215

Production of ethyl 6-amino-3-(benzyloxy)-5-methylpyrazine-2-carboxylate

By a reaction similar to that in Reference Example 9, the title compound (603 mg, 59%) was obtained as a pale-yellow powder from the compound of Reference Example 214 (1.26 g, 3.59 mmol), benzophenonimine (860 μL, 5.12 mmol), cesium carbonate (2.23 g, 6.84 mmol), Pd$_2$dba$_3$ (156 mg, 0.170 mmol), Xantphos (204 mg, 0.352 mmol) and 2N hydrochloric acid (5 mL).

$^1$H NMR (300 MHz, DMSO-d$_6$) δ: 1.26 (3H, t, J=7.1 Hz), 2.32 (3H, s), 4.26 (2H, q, J=7.1 Hz), 5.31 (2H, s), 5.98 (2H, s), 7.21-7.53 (5H, m).

Reference Example 216

Production of ethyl 3-(benzyloxy)-5-methyl-6-[(phenylcarbonyl)amino]pyrazine-2-carboxylate By a method similar to that in Reference Example 21, the title compound (352 mg, quantitatively) was obtained as a pale-yellow powder from the compound of Reference Example 215 (251 mg, 0.873 mmol), benzoyl chloride (152 μL, 1.31 mmol) and pyridine (141 μL, 1.74 mmol).

$^1$H NMR (300 MHz, DMSO-d$_6$) δ: 1.28 (3H, t, J=7.1 Hz), 2.43 (3H, s), 4.33 (2H, q, J=7.1 Hz), 5.51 (2H, s), 7.27-7.71 (8H, m), 7.97-8.12 (2H, m), 10.85 (1H, s).

Reference Example 217

Production of ethyl 3-hydroxy-5-methyl-6-[(phenylcarbonyl)amino]pyrazine-2-carboxylate To a solution of the compound of Reference Example 216 (350 mg, 0.894 mmol) in ethanol (5 mL) was added 10% palladium-carbon (water-containing product, 36.3 mg), and the mixture was stirred for 1.5 hr under a hydrogen atmosphere. The catalyst was filtered through celite, and the filtrate was concentrated under reduced pressure. The residue was purified by silica gel column chromatography (eluent, hexane:ethyl acetate=4:1→1:4) to give the title compound (207 mg, 77%) as a pale-yellow powder.

$^1$H NMR (300 MHz, DMSO-d$_6$) δ: 1.28 (3H, t, J=7.2 Hz), 2.25 (3H, s), 4.29 (2H, q, J=7.2 Hz), 7.42-7.71 (3H, m), 7.91-8.09 (2H, m), 10.51 (1H, br s), 12.78 (1H, br s).

Reference Example 218

Production of ethyl 5-methyl-6-[(phenylcarbonyl)amino]-3-{[(trifluoromethyl)sulfonyl]oxy}pyrazine-2-carboxylate To a solution of the compound of Reference Example 217 (162 mg, 0.539 mmol) in pyridine (2 mL) was added dropwise trifluoromethanesulfonic anhydride (134 μL, 0.796 mmol) at 0° C., and the mixture was stirred at 0° C. for 1.5 hr. Trifluoromethanesulfonic anhydride (40 μL, 0.238 mmol) was added again, and the mixture was stirred at 0° C. for 1 hr. To the reaction mixture was added water (10 mL), and the mixture was extracted with ethyl acetate (15 mL×2). The organic layers were combined, dried over anhydrous magnesium sulfate, and concentrated under reduced pressure. The residue was purified by silica gel column chromatography (eluent, hexane:ethyl acetate=19:1→1:1) to give the title compound (222 mg, 95%) as a pale-yellow oil.

$^1$H NMR (300 MHz, DMSO-d$_6$) δ: 1.34 (3H, t, J=7.1 Hz), 2.39-2.59 (3H, m), 4.43 (2H, q, J=7.1 Hz), 7.49-7.73 (3H, m), 7.98-8.15 (2H, m), 11.49 (1H, s).

Reference Example 219

Production of ethyl 7-hydroxy-3,5-dimethyl-2-[(phenylcarbonyl)amino]-5H-pyrrolo[2,3-b]pyrazine-6-carboxylate By a method similar to that in Reference Example 7, the title compound (129 mg, 72%) was obtained as a pale-yellow powder from the compound of Reference Example 218 (220 mg, 0.507 mmol), ethyl sarcosinate hydrochloride (111 mg, 0.724 mmol), triethylamine (704 μL, 5.05 mmol), and an ethanol solution (20%, 653 mg, 1.92 mmol) of sodium ethoxide.

$^1$H NMR (300 MHz, DMSO-d$_6$) δ: 1.35 (3H, t, J=7.2 Hz), 2.55 (3H, s), 3.93 (3H, s), 4.37 (2H, q, J=7.2 Hz), 7.48-7.73 (3H, m), 7.97-8.11 (2H, m), 9.86 (1H, s), 10.77 (1H, s).

Reference Example 220

Production of ethyl 3,5-dimethyl-2-[(phenylcarbonyl)amino]-7-(2,2,2-trifluoroethoxy)-5H-pyrrolo[2,3-b]pyrazine-6-carboxylate By a method similar to that in Reference Example 8, the title compound (154 mg, 89%) was obtained as a pale-yellow powder from the compound of Reference Example 219 (140 mg, 0.396 mmol), cesium carbonate (205 mg, 0.630 mmol) and 2,2,2-trifluoroethyl trifluoromethanesulfonate (74.2 μL, 0.515 mmol).

$^1$H NMR (300 MHz, DMSO-d$_6$) δ: 1.34 (3H, t, J=7.2 Hz), 2.57 (3H, s), 4.00 (3H, s), 4.37 (2H, q, J=7.2 Hz), 5.12 (2H, q, J=8.9 Hz), 7.50-7.70 (3H, m), 7.97-8.10 (2H, m), 10.90 (1H, s).

Reference Example 221

Production of 3,5-dimethyl-2-[(phenylcarbonyl)amino]-7-(2,2,2-trifluoroethoxy)-5H-pyrrolo[2,3-b]pyrazine-6-carboxylic acid By a reaction similar to that in Reference Example 12, the title compound (139 mg, 98%) was obtained as a yellow powder from the compound of Reference Example 220 (152 mg, 0.349 mmol).

$^1$H NMR (300 MHz, DMSO-d$_6$) δ: 2.56 (3H, s), 3.99 (3H, s), 5.10 (2H, q, J=9.0 Hz), 7.47-7.73 (3H, m), 7.97-8.12 (2H, m), 10.88 (1H, s), 13.48 (1H, br s).

Reference Example 222

Production of ethyl 6-bromo-5-ethyl-3-hydroxypyrazine-2-carboxylate

By a method similar to that in Reference Example 5, the title compound (4.45 g, 85%) was obtained as a white powder from the compound of Reference Example 208 (3.75 g, 19.1 mmol) and N-bromosuccinimide (3.43 g, 19.3 mmol).

$^1$H NMR (300 MHz, DMSO-d$_6$) δ: 1.21 (3H, t, J=7.6 Hz), 1.29 (3H, t, J=7.1 Hz), 2.77 (2H, q, J=7.6 Hz), 4.31 (2H, q, J=7.1 Hz), 12.67 (1H, br s).

Reference Example 223

Production of ethyl 5-ethyl-6-(4-fluorophenyl)-3-hydroxypyrazine-2-carboxylate

By a method similar to that in Reference Example 15, the title compound (395 mg, 94%) was obtained as a pale-yellow powder from the compound of Reference Example 222 (398 mg, 1.45 mmol), p-fluorophenylboronic acid (241 mg, 1.72 mmol), Pd(PPh$_3$)$_4$ (87.5 mg, 0.0757 mmol) and potassium carbonate (1.02 g, 7.38 mmol).

$^1$H NMR (300 MHz, DMSO-d$_6$) δ: 1.14 (3H, t, J=7.5 Hz), 1.27 (3H, t, J=7.1 Hz), 2.46-2.66 (2H, m), 4.29 (2H, q, J=7.1 Hz), 7.18-7.38 (2H, m), 7.38-7.57 (2H, m), 12.95 (1H, br s).

Reference Example 224

Production of ethyl 5-ethyl-6-(4-fluorophenyl)-3-{[(trifluoromethyl)sulfonyl]oxy}pyrazine-2-carboxylate By a method similar to that in Reference Example 218, the title compound (534 mg, 94%) was obtained as a colorless oil from the compound of Reference Example 223 (393 mg, 1.35 mmol) and trifluoromethanesulfonic anhydride (342 μL, 2.03 mmol).

$^1$H NMR (300 MHz, DMSO-d$_6$) δ: 1.18 (3H, t, J=7.4 Hz), 1.34 (3H, t, J=7.2 Hz), 2.95 (2H, q, J=7.4 Hz), 4.44 (2H, q, J=7.2 Hz), 7.34-7.46 (2H, m), 7.65-7.80 (2H, m).

Reference Example 225

Production of ethyl 3-ethyl-2-(4-fluorophenyl)-7-hydroxy-5-methyl-5H-pyrrolo[2,3-b]pyrazine-6-carboxylate By a method similar to that in Reference Example 7, the title compound (359 mg, 83%) was obtained as a yellow powder from the compound of Reference Example 224 (532 mg, 1.26 mmol), ethyl sarcosinate hydrochloride (251 mg, 1.63 mmol), triethylamine (1.75 mL, 12.6 mmol), and an ethanol solution (20%, 562 mg, 1.65 mmol) of sodium ethoxide.

$^1$H NMR (300 MHz, DMSO-d$_6$) δ: 1.20 (3H, t, J=7.5 Hz), 1.35 (3H, t, J=7.1 Hz), 2.86 (2H, q, J=7.5 Hz), 3.95 (3H, s), 4.37 (2H, q, J=7.1 Hz), 7.25-7.40 (2H, m), 7.53-7.68 (2H, m), 9.94 (1H, br s).

Reference Example 226

Production of ethyl 3-ethyl-2-(4-fluorophenyl)-5-methyl-7-(2,2,2-trifluoroethoxy)-5H-pyrrolo[2,3-b]pyrazine-6-carboxylate By a method similar to that in Reference Example 8, the title compound (169 mg, 97%) was obtained as a pale-orange powder from the compound of Reference Example 225 (140 mg, 0.407 mmol) and 2,2,2-trifluoroethyl trifluoromethanesulfonate (75.6 μL, 0.524 mmol).

$^1$H NMR (300 MHz, DMSO-d$_6$) δ: 1.22 (3H, t, J=7.5 Hz), 1.35 (3H, t, J=7.2 Hz), 2.93 (2H, q, J=7.5 Hz), 4.01 (3H, s), 4.37 (2H, q, J=7.2 Hz), 5.21 (2H, q, J=8.9 Hz), 7.27-7.43 (2H, m), 7.60-7.73 (2H, m).

Reference Example 227

Production of 3-ethyl-2-(4-fluorophenyl)-5-methyl-7-(2,2,2-trifluoroethoxy)-5H-pyrrolo[2,3-b]pyrazine-6-carboxylic acid By a method similar to that in Reference Example 12, the title compound (147 mg, 94%) was obtained as a pale-orange powder from the compound of Reference Example 226 (167 mg, 0.393 mmol) and 1N aqueous sodium hydroxide solution (0.8 mL).
$^1$H NMR (300 MHz, DMSO-$d_6$) δ: 1.22 (3H, t, J=7.5 Hz), 2.92 (2H, q, J=7.5 Hz), 4.01 (3H, s), 5.19 (2H, q, J=8.9 Hz), 7.23-7.48 (2H, m), 7.56-7.74 (2H, m), 13.37 (1H, br s).

Reference Example 228

Production of 3-ethyl-2-(4-fluorophenyl)-5-methyl-7-(1-methylethoxy)-5H-pyrrolo[2,3-b]pyrazine-6-carboxylic acid A mixture of the compound of Reference Example 225 (150 mg, 0.436 mmol), diisopropyl sulfate (94 μL, 0.567 mmol), potassium carbonate (97.7 mg, 0.707 mmol) and acetone (4 mL) was stirred for 20 hr with heating under reflux. Then, diisopropyl sulfate (94 μL, 0.567 mmol) and potassium carbonate (100 mg, 0.724 mmol) were added thereto, and the mixture was stirred with heating under reflux for 1 day. To the reaction mixture was added water (15 mL), and the mixture was extracted with ethyl acetate (15 mL×3). The organic layers were combined, dried over anhydrous magnesium sulfate, and concentrated under reduced pressure. The residue was purified by silica gel column chromatography (eluent, hexane:ethyl acetate=49:1→2:1) to give crude ethyl 3-ethyl-2-(4-fluorophenyl)-5-methyl-7-(1-methylethoxy)-5H-pyrrolo[2,3-b]pyrazine-6-carboxylate. The obtained compound was dissolved in a mixed solvent of ethanol (3 mL)/THF (1 mL), 1N aqueous sodium hydroxide solution (1.5 mL) was added thereto, and the mixture was stirred at room temperature for 2 days. The reaction mixture was acidified with 2N hydrochloric acid, and diluted with water (10 mL). The resulting solid was collected by filtration, washed with water, and dried to give the title compound (139 mg, 89%) as a yellow powder.
$^1$H NMR (300 MHz, DMSO-$d_6$) δ: 1.22 (3H, t, J=7.5 Hz), 1.28 (6H, d, J=6.2 Hz), 2.90 (2H, q, J=7.5 Hz), 3.98 (3H, s), 5.10-5.31 (1H, m), 7.26-7.43 (2H, m), 7.54-7.70 (2H, m), 13.07 (1H, br s).

Reference Example 229

Production of ethyl 3-(benzyloxy)-6-bromo-5-ethylpyrazine-2-carboxylate

By a method similar to that in Reference Example 214, the title compound (908 mg, 91%) was obtained as a colorless oil from the compound of Reference Example 222 (750 mg, 2.73 mmol), benzyl bromide (390 μL, 3.28 mmol) and silver carbonate (1.05 g, 3.81 mmol).
$^1$H NMR (300 MHz, DMSO-$d_6$) δ: 1.25 (3H, t, J=7.5 Hz), 1.29 (3H, t, J=7.1 Hz), 2.89 (2H, q, J=7.5 Hz), 4.33 (2H, q, J=7.1 Hz), 5.50 (2H, s), 7.28-7.44 (3H, m), 7.44-7.56 (2H, m).

Reference Example 230

Production of ethyl 6-amino-3-(benzyloxy)-5-ethylpyrazine-2-carboxylate

By a method similar to that in Reference Example 9, the title compound (441 mg, 59%) was obtained as a brown powder from the compound of Reference Example 229 (906 mg, 2.48 mmol), benzophenonimine (624 μL, 3.72 mmol), $Pd_2dba_3$ (228 mg, 0.249 mmol), Xantphos (294 mg, 0.508 mmol), cesium carbonate (1.62 g, 4.97 mmol) and 2N hydrochloric acid (3 mL).
$^1$H NMR (300 MHz, DMSO-$d_6$) δ: 1.18 (3H, t, J=7.4 Hz), 1.26 (3H, t, J=7.1 Hz), 2.62 (2H, q, J=7.4 Hz), 4.26 (2H, q, J=7.1 Hz), 5.35 (2H, s), 5.97 (2H, s), 7.23-7.41 (3H, m), 7.41-7.50 (2H, m).

Reference Example 231

Production of ethyl 3-(benzyloxy)-5-ethyl-6-[(phenylcarbonyl)amino]pyrazine-2-carboxylate By a method similar to that in Reference Example 21, the title compound (312 mg, 93%) was obtained as an orange oil from the compound of Reference Example 230 (250 mg, 0.828 mmol), benzoyl chloride (106 μL, 0.913 mmol) and pyridine (100 μL, 1.24 mmol).
$^1$H NMR (300 MHz, DMSO-$d_6$) δ: 1.22 (3H, t, J=7.5 Hz), 1.28 (3H, t, J=7.1 Hz), 2.73 (2H, q, J=7.5 Hz), 4.33 (2H, q, J=7.1 Hz), 5.55 (2H, s), 7.28-7.47 (3H, m), 7.47-7.71 (5H, m), 7.95-8.09 (2H, m), 10.76 (1H, s).

Reference Example 232

Production of ethyl 5-ethyl-3-hydroxy-6-[(phenylcarbonyl)amino]pyrazine-2-carboxylate By a method similar to that in Reference Example 217, the title compound (185 mg, 77%) was obtained as a pale-yellow powder from the compound of Reference Example 231 (310 mg, 0.765 mmol) and 10% palladium-carbon (water-containing product, 32.7 mg).
$^1$H NMR (300 MHz, DMSO-$d_6$) δ: 1.17 (3H, t, J=7.5 Hz), 1.28 (3H, t, J=7.2 Hz), 2.53-2.70 (2H, m), 4.30 (2H, q, J=7.2 Hz), 7.48-7.68 (3H, m), 7.90-8.07 (2H, m), 10.46 (1H, br s), 12.60 (1H, br s).

Reference Example 233

Production of ethyl 5-ethyl-6-[(phenylcarbonyl)amino]-3-{[(trifluoromethyl)sulfonyl]oxy}pyrazine-2-carboxylate By a method similar to that in Reference Example 218, the title compound (244 mg, 94%) was obtained as a yellow oil from the compound of Reference Example 232 (183 mg, 0.580 mmol) and trifluoromethanesulfonic anhydride (147 μL, 0.871 mmol).
$^1$H NMR (300 MHz, DMSO-$d_6$) δ: 1.21 (3H, t, J=7.3 Hz), 1.34 (3H, t, J=7.1 Hz), 2.83 (2H, q, J=7.3 Hz), 4.43 (2H, q, J=7.1 Hz), 7.49-7.74 (3H, m), 7.99-8.10 (2H, m), 11.42 (1H, s).

Reference Example 234

Production of ethyl 3-ethyl-7-hydroxy-5-methyl-2-[(phenylcarbonyl)amino]-5H-pyrrolo[2,3-b]pyrazine-6-carboxylate By a method similar to that in Reference Example 7, the title compound (159 mg, 80%) was obtained as a pale-yellow powder from the compound of Reference Example 233 (242 mg, 0.541 mmol), ethyl sarcosinate hydrochloride (102 mg, 0.665 mmol), triethylamine (378 μL, 2.71 mmol) and an ethanol solution (20%, 562 mg, 1.65 mmol) of sodium ethoxide.

$^1$H NMR (300 MHz, DMSO-$d_6$) δ: 1.28 (3H, t, J=7.6 Hz), 1.35 (3H, t, J=7.2 Hz), 2.88 (2H, q, J=7.6 Hz), 3.95 (3H, s), 4.37 (2H, q, J=7.2 Hz), 7.45-7.72 (3H, m), 7.94-8.12 (2H, m), 9.91 (1H, br s), 10.72 (1H, s).

Reference Example 235

Production of ethyl 3-ethyl-5-methyl-2-[(phenylcarbonyl)amino]-7-(2,2,2-trifluoroethoxy)-5H-pyrrolo[2,3-b]pyrazine-6-carboxylate By a method similar to that in Reference Example 8, the title compound (53.2 mg, 74%) was obtained as a pale-yellow powder from the compound of Reference Example 234 (59.2 mg, 0.161 mmol), 2,2,2-trifluoroethyl trifluoromethanesulfonate (28 μL, 0.166 mmol) and cesium carbonate (72.0 mg, 0.220 mmol).

$^1$H NMR (300 MHz, DMSO-$d_6$) δ: 1.29 (3H, t, J=7.5 Hz), 1.35 (3H, t, J=7.1 Hz), 2.90 (2H, q, J=7.5 Hz), 4.02 (3H, s), 4.37 (2H, q, J=7.1 Hz), 5.12 (2H, q, J=8.9 Hz), 7.48-7.72 (3H, m), 7.97-8.09 (2H, m), 10.84 (1H, s).

Reference Example 236

Production of 3-ethyl-5-methyl-2-[(phenylcarbonyl)amino]-7-(2,2,2-trifluoroethoxy)-5H-pyrrolo[2,3-b]pyrazine-6-carboxylic acid By a method similar to that in Reference Example 12, the title compound (99.6 mg, 99%) was obtained as a pale-yellow powder from the compound of Reference Example 235 (107 mg, 0.238 mmol) and 1N aqueous sodium hydroxide solution (0.5 mL).

$^1$H NMR (300 MHz, DMSO-$d_6$) δ: 1.29 (3H, t, J=7.4 Hz), 2.89 (2H, q, J=7.4 Hz), 4.01 (3H, s), 5.10 (2H, q, J=8.9 Hz), 7.45-7.72 (3H, m), 7.96-8.10 (2H, m), 10.82 (1H, s), 13.47 (1H, br s).

Reference Example 237

Production of ethyl 6-bromo-5-ethyl-3-{[(trifluoromethyl)sulfonyl]oxy}pyrazine-2-carboxylate By a method similar to that in Reference Example 218, the title compound (1.41 g, 47%) was obtained as a pink oil from the compound of Reference Example 222 (2.01 g, 7.31 mmol) and trifluoromethanesulfonic anhydride (1.35 mL, 8.02 mmol).

$^1$H NMR (300 MHz, DMSO-$d_6$) δ: 1.23 (3H, t, J=7.4 Hz), 1.35 (3H, t, J=7.1 Hz), 3.02 (2H, q, J=7.4 Hz), 4.43 (2H, q, J=7.1 Hz).

Reference Example 238

Production of ethyl 2-bromo-3-ethyl-7-hydroxy-5-methyl-5H-pyrrolo[2,3-b]pyrazine-6-carboxylate A mixture of the compound of Reference Example 237 (1.53 g, 3.76 mmol), ethyl sarcosinate hydrochloride (607 mg, 3.95 mmol), triethylamine (2.6 mL, 18.7 mmol) and ethanol (20 mL) was stirred at room temperature for 2 hr. ethyl sarcosinate hydrochloride (51.4 mg, 0.335 mmol) was added thereto, and the mixture was further stirred for 1 hr. To the reaction mixture was added water (30 mL), and the mixture was extracted with ethyl acetate (30 mL×3). The organic layers were combined, washed with brine (10 mL), dried over anhydrous magnesium sulfate, and concentrated under reduced pressure. The residue was dissolved in THF (20 mL), potassium tert-butoxide (840 mg, 7.49 mmol) was added thereto, and the mixture was stirred at 0° C. for 1 hr. The reaction mixture was acidified with 1N hydrochloric acid, and extracted with ethyl acetate (30 mL×3). The organic layers were combined, washed with brine (10 mL), dried over anhydrous magnesium sulfate, and concentrated under reduced pressure. The precipitate was collected by filtration, and dried to give the title compound (978 mg, 79%) as a yellow powder.

$^1$H NMR (300 MHz, DMSO-$d_6$) δ: 1.26-1.39 (6H, m), 3.01 (2H, q, J=7.5 Hz), 3.91 (3H, s), 4.35 (2H, q, J=7.0 Hz), 10.14 (1H, br s).

Reference Example 239

Production of ethyl 2-bromo-3-ethyl-5-methyl-7-(1-methylethoxy)-5H-pyrrolo[2,3-b]pyrazine-6-carboxylate A mixture of the compound of Reference Example 238 (99.8% mg, 0.304 mmol), diisopropyl sulfate (60.6 μL, 0.366 mmol), potassium carbonate (64.1 mg, 0.464 mmol) and 2-butanone (3 ml) was stirred at 80° C. for 17 hr. Then, diisopropyl sulfate (40 μL, 0.241 mmol) and DMF (1 mL) were added thereto, and the mixture was stirred at 80° C. for 7 hr. To the reaction mixture was added water (10 mL), and the mixture was extracted with ethyl acetate (10 mL×4). The organic layers were combined, dried over anhydrous magnesium sulfate, and concentrated under reduced pressure. The residue was purified by silica gel column chromatography (eluent, hexane:ethyl acetate=99:1→2:1) to give the title compound (90.1 mg, 80%) as a pale-yellow powder.

$^1$H NMR (300 MHz, DMSO-$d_6$) δ: 1.27-1.34 (9H, m), 1.35 (3H, t, J=7.1 Hz), 3.02 (2H, q, J=7.4 Hz), 3.94 (3H, s), 4.35 (2H, q, J=7.1 Hz), 4.95-5.11 (1H, m).

Reference Example 240

Production of ethyl 2-(4-chlorophenyl)-3-ethyl-5-methyl-7-(1-methylethoxy)-5H-pyrrolo[2,3-b]pyrazine-6-carboxylate By a method similar to that in Reference Example 15, the title compound (94.7 mg, 86%) was obtained as a yellow powder from the compound of Reference Example 239 (102 mg, 0.275 mmol), p-chlorophenylboronic acid (53.5 mg, 0.342 mmol), Pd(PPh$_3$)$_4$ (16.2 mg, 0.0140 mmol) and potassium carbonate (199 mg, 1.44 mmol).

$^1$H NMR (300 MHz, DMSO-$d_6$) δ: 1.22 (3H, t, J=7.5 Hz), 1.30 (6H, d, J=6.2 Hz), 1.36 (3H, t, J=7.2 Hz), 2.91 (2H, q, J=7.5 Hz), 3.99 (3H, s), 4.35 (2H, q, J=7.2 Hz), 5.10-5.25 (1H, m), 7.53-7.67 (4H, m).

Reference Example 241

Production of 2-(4-chlorophenyl)-3-ethyl-5-methyl-7-(1-methylethoxy)-5H-pyrrolo[2,3-b]pyrazine-6-carboxylic acid By a method similar to that in Reference Example 12, the title compound (83.4 mg, 96%) was obtained as a yellow powder from the compound of Reference Example 240 (93.0 mg, 0.231 mmol), and 1N aqueous sodium hydroxide solution (0.5 mL).

¹H NMR (300 MHz, DMSO-d₆) δ: 1.22 (3H, t, J=7.5 Hz), 1.28 (6H, d, J=6.0 Hz), 2.90 (2H, q, J=7.5 Hz), 3.98 (3H, s), 5.11-5.28 (1H, m), 7.51-7.66 (4H, m), 13.09 (1H, br s).

Reference Example 242

Production of ethyl 2-amino-3-ethyl-5-methyl-7-(1-methylethoxy)-5H-pyrrolo[2,3-b]pyrazine-6-carboxylate To a mixture of the compound of Reference Example 239 (300 mg, 0.810 mmol), benzophenonimine (200 μL, 1.19 mmol), cesium carbonate (545 mg, 1.67 mmol) and toluene (5 mL) were added Xantphos (48.8 mg, 0.0843 mmol) and Pd₂dba₃ (36.5 mg, 0.0399 mmol), and the mixture was stirred at 100° C. for 30 hr. Benzophenonimine (200 μL, 1.19 mmol), Pd₂dba₃ (49.2 mg, 0.0537 mmol), and Xantphos (48.8 mg, 0.0843 mmol) were added thereto, and the mixture was stirred at 100° C. for 16 hr. Then, benzophenonimine (200 μL, 1.19 mmol), Pd₂dba₃ (36.5 mg, 0.0399 mmol) and Xantphos (47.2 mg, 0.0816 mmol) were added thereto, and the mixture was stirred at 100° C. for 4 hr. The reaction mixture was filtered through celite, and washed with ethyl acetate. The filtrate was washed successively with water (10 mL) and brine (10 mL), dried over anhydrous magnesium sulfate, and concentrated under reduced pressure. The residue was dissolved in a mixed solvent of THF (5 mL)/ethanol (1 mL), 2N hydrochloric acid (1.5 mL) was added thereto, and the mixture was stirred at room temperature for 1 hr. The reaction mixture was neutralized with aqueous sodium hydrogen carbonate solution, and extracted with ethyl acetate (10 mL×3). The organic layers were combined, dried over anhydrous magnesium sulfate, and concentrated under reduced pressure. The residue was purified by silica gel column chromatography (eluent, hexane:ethyl acetate=99:1→1:2) to give the title compound (181 mg, 73%) as a brown powder.

¹H NMR (300 MHz, DMSO-d₆) δ: 1.20-1.29 (9H, m), 1.32 (3H, t, J=7.2 Hz), 2.74 (2H, q, J=7.4 Hz), 3.86 (3H, s), 4.28 (2H, q, J=7.2 Hz), 4.89-5.09 (1H, m), 6.03 (2H, s).

Reference Example 243

Production of ethyl 3-ethyl-2-{[(4-fluorophenyl)carbonyl]amino}-5-methyl-7-(1-methylethoxy)-5H-pyrrolo[2,3-b]pyrazine-6-carboxylate To a solution of the compound of Reference Example 242 (87.0 mg, 0.284 mmol) in THF (2 mL) were added pyridine (59 μL, 0.729 mmol) and p-fluorobenzoyl chloride (52.4 μL, 0.437 mmol), and the mixture was stirred at room temperature for 1.5 hr. p-fluorobenzoyl chloride (26.2 μL, 0.219 mmol) was added thereto, and the mixture was stirred at room temperature for 1.5 hr. Then, p-fluorobenzoyl chloride (52.4 μL, 0.437 mmol) and pyridine (30 μL, 0.371 mmol) were added thereto, and the mixture was stirred at room temperature for 1.5 hr. To the reaction mixture was added aqueous sodium hydrogen carbonate solution (10 mL), and the mixture was extracted with ethyl acetate (10 mL×3). The organic layers were combined, dried over anhydrous magnesium sulfate, and concentrated under reduced pressure. The residue was purified by silica gel column chromatography (eluent, hexane:ethyl acetate=49:1→1:1) to give the title compound (114 mg, 93%) as a pale-yellow powder.

¹H NMR (300 MHz, DMSO-d₆) δ: 1.28 (3H, t, J=7.5 Hz), 1.28 (6H, d, J=6.2 Hz), 1.36 (3H, t, J=7.1 Hz), 2.87 (2H, q, J=7.5 Hz), 3.99 (3H, s), 4.35 (2H, q, J=7.1 Hz), 5.00-5.15 (1H, m), 7.33-7.46 (2H, m), 8.05-8.17 (2H, m), 10.80 (1H, s).

Reference Example 244

Production of 3-ethyl-2-{[(4-fluorophenyl)carbonyl]amino}-5-methyl-7-(1-methylethoxy)-5H-pyrrolo[2,3-b]pyrazine-6-carboxylic acid By a method similar to that in Reference Example 12, the title compound (96.3 mg, 88%) was obtained as a yellow powder from the compound of Reference Example 243 (112 mg, 0.261 mmol) and 1N aqueous sodium hydroxide solution (0.7 mL).

¹H NMR (300 MHz, DMSO-d₆) δ: 1.19-1.34 (9H, m), 2.86 (2H, q, J=7.5 Hz), 3.98 (3H, s), 5.03-5.18 (1H, m), 7.32-7.47 (2H, m), 8.02-8.18 (2H, m), 10.78 (1H, s), 13.10 (1H, br s).

Reference Example 245

Production of ethyl 3-ethyl-5-methyl-7-(1-methylethoxy)-2-[(phenylcarbonyl)amino]-5H-pyrrolo[2,3-b]pyrazine-6-carboxylate To a solution of the compound of Reference Example 242 (87.4 mg, 0.285 mmol) in THF (2 mL) were added pyridine (59 μL, 0.729 mmol) and benzoyl chloride (50.8 μL, 0.438 mmol), and the mixture was stirred at room temperature for 1.5 hr. Benzoyl chloride (25.4 μL, 0.212 mmol) was added thereto, and the mixture was stirred at room temperature for 1.5 hr. Then, benzoyl chloride (50.8 μL, 0.438 mmol) and pyridine (30 μL, 0.371 mmol) were added thereto, and the mixture was stirred at room temperature for 1.5 hr. To the reaction mixture was added aqueous sodium hydrogen carbonate solution (10 mL), and the mixture was extracted with ethyl acetate (10 mL×3). The organic layers were combined, dried over anhydrous magnesium sulfate, and concentrated under reduced pressure. The residue was purified by silica gel column chromatography (eluent, hexane:ethyl acetate=49:1→1:1) to give the title compound (114 mg, 98%) as a yellow powder.

¹H NMR (300 MHz, DMSO-d₆) δ: 1.28 (3H, t, J=7.6 Hz), 1.28 (6H, d, J=6.2 Hz), 1.36 (3H, t, J=7.1 Hz), 2.88 (2H, q, J=7.6 Hz), 3.99 (3H, s), 4.35 (2H, q, J=7.1 Hz), 5.00-5.16 (1H, m), 7.47-7.71 (3H, m), 7.97-8.10 (2H, m), 10.77 (1H, s).

Reference Example 246

Production of 3-ethyl-5-methyl-7-(1-methylethoxy)-2-[(phenylcarbonyl)amino]-5H-pyrrolo[2,3-b]pyrazine-6-carboxylic acid By a method similar to that in Reference Example 12, the title compound (92.5 mg, 89%) was obtained as a yellow powder from the compound of Reference Example 245 (112 mg, 0.273 mmol) and 1N aqueous sodium hydroxide solution (0.7 mL).

¹H NMR (300 MHz, DMSO-d₆) δ: 1.17-1.38 (9H, m), 2.87 (2H, q, J=7.4 Hz), 3.99 (3H, s), 5.01-5.20 (1H, m), 7.46-7.72 (3H, m), 7.94-8.14 (2H, m), 10.75 (1H, s), 13.09 (1H, br s).

Reference Example 247

Production of ethyl 3,5-dimethyl-7-(1-methylethoxy)-2-[(phenylcarbonyl)amino]-5H-pyrrolo[2,3-b]pyrazine-6-carboxylate By a method similar to that in Reference Example 84, the title compound (103 mg, 77%) was obtained as a yellow powder from the compound of Reference Example 219 (119 mg, 0.334 mmol), diisopropyl sulfate (84 μL, 0.507 mmol) and potassium carbonate (94.8 mg, 0.686 mmol).

$^1$H NMR (300 MHz, DMSO-d$_6$) δ: 1.28 (6H, d, J=6.0 Hz), 1.36 (3H, t, J=7.2 Hz), 2.55 (3H, s), 3.97 (3H, s), 4.35 (2H, q, J=7.2 Hz), 4.99-5.18 (1H, m), 7.48-7.70 (3H, m), 7.98-8.12 (2H, m), 10.82 (1H, s).

Reference Example 248

Production of 3,5-dimethyl-7-(1-methylethoxy)-2-[(phenylcarbonyl)amino]-5H-pyrrolo[2,3-b]pyrazine-6-carboxylic acid By a method similar to that in Reference Example 12, the title compound (86.0 mg, 93%) was obtained as a yellow powder from the compound of Reference Example 247 (100 mg, 0.252 mmol) and 1N aqueous sodium hydroxide solution (0.5 mL).

$^1$H NMR (300 MHz, DMSO-d$_6$) δ: 1.27 (6H, d, J=6.2 Hz), 2.54 (3H, s), 3.97 (3H, s), 5.07-5.20 (1H, m), 7.45-7.72 (3H, m), 7.95-8.13 (2H, m), 10.80 (1H, s), 13.04 (1H, br s).

Reference Example 249

Production of ethyl 3,5-dimethyl-7-(1-methylethoxy)-2-[methyl(phenylcarbonyl)amino]-5H-pyrrolo[2,3-b]pyrazine-6-carboxylate To a mixture of the compound of Reference Example 247 (75.0 mg, 0.189 mmol), methyl iodide (23.6 μL, 0.379 mmol) and DMF (3 mL) was added sodium hydride (60%, 16.2 mg, 0.405 mmol) at 0° C., and the mixture was stirred at room temperature for 30 min. To the reaction mixture was added aqueous ammonium chloride solution (10 mL), and the mixture was extracted with ethyl acetate (10 mL×3). The organic layers were combined, dried over anhydrous magnesium sulfate, and concentrated under reduced pressure. The residue was purified by silica gel column chromatography (eluent, hexane:ethyl acetate=49:1→1:1) to give the title compound (71.4 mg, 92%) as an orange oil.

$^1$H NMR (300 MHz, DMSO-d$_6$) δ: 0.95-1.27 (6H, m), 1.32 (3H, t, J=7.1 Hz), 2.57 (3H, s), 3.35 (3H, s), 3.88 (3H, s), 4.20-4.41 (2H, m), 4.66-4.90 (1H, m), 7.03-7.37 (5H, m).

Reference Example 250

Production of 3,5-dimethyl-7-(1-methylethoxy)-2-[methyl(phenylcarbonyl)amino]-5H-pyrrolo[2,3-b]pyrazine-6-carboxylic acid By a method similar to that in Reference Example 12, the title compound (67.5 mg, 91%) was obtained as an orange powder from the compound of Reference Example 249 (80.0 mg, 0.195 mmol) and 1N aqueous sodium hydroxide solution (0.7 mL).

$^1$H NMR (300 MHz, DMSO-d$_6$) δ: 0.98-1.32 (6H, m), 2.56 (3H, s), 3.34 (3H, s), 3.87 (3H, s), 4.73-4.90 (1H, m), 7.00-7.37 (5H, m), 13.13 (1H, br s).

Reference Example 251

Production of diethyl 3-ethyl-5-hydroxypyrazine-2,6-dicarboxylate

A mixture of the compound of Reference Example 222 (1.50 g, 5.45 mmol), dichlorobis(triphenylphosphine)palladium(II) (769 mg, 1.10 mmol), 1,1'-bis(diphenylphosphino)ferrocene (1.21 g, 2.18 mmol), triethylamine (2.3 mL, 16.5 mmol), ethanol (15 mL) and DMF (15 mL) was stirred at 80° C. for 7 hr under a carbon monoxide atmosphere. The reaction mixture was filtered through celite, and washed with ethyl acetate. The filtrate was washed successively with 1N hydrochloric acid (20 mL) and brine (10 mL), dried over anhydrous magnesium sulfate, and concentrated under reduced pressure. The residue was purified by silica gel column chromatography (eluent, hexane:ethyl acetate=19:1→1:1→ethyl acetate) to give the title compound (1.09 g, 75%) as a pale-yellow powder.

$^1$H NMR (300 MHz, DMSO-d$_6$) δ: 1.19 (3H, t, J=7.6 Hz), 1.28 (3H, t, J=7.2 Hz), 1.28 (3H, t, J=7.2 Hz), 2.89 (2H, q, J=7.6 Hz), 4.27 (2H, q, J=7.0 Hz), 4.30 (2H, q, J=7.0 Hz), 13.26 (1H, br s).

Reference Example 252

Production of 6-benzyl 2-ethyl 3-ethyl-5-methyl-7-(1-methylethoxy)-5H-pyrrolo[2,3-b]pyrazine-2,6-dicarboxylate A solution of the compound of Reference Example 251 (1.10 g, 4.10 mmol) in ethyl acetate (20 mL) was cooled to 0° C., triethylamine (860 μL, 6.17 mmol) and methanesulfonyl chloride (350 μL, 4.52 mmol) were added thereto, and the mixture was stirred at 0° C. for 20 min. To the reaction mixture was added water (50 mL), and the mixture was extracted with ethyl acetate (20 mL×2). The organic layers were combined, washed with brine (10 mL), dried over anhydrous magnesium sulfate, and concentrated under reduced pressure. The residue was dissolved in THF (20 mL), triethylamine (860 μL, 6.17 mmol) and benzyl sarcosinate hydrochloride (982 mg, 4.55 mmol) were added thereto, and the mixture was stirred at room temperature for 4 hr. Then, benzyl sarcosinate hydrochloride (192 mg, 0.892 mmol) and triethylamine (860 μL, 6.17 mmol) were added thereto, and the mixture was stirred at room temperature for 30 min. To the reaction mixture was added water (30 mL), and the mixture was extracted with ethyl acetate (20 mL×3). The organic layers were combined, dried over anhydrous magnesium sulfate, and concentrated under reduced pressure. The residue was dissolved in THF (20 mL) and the solution was cooled to 0° C., potassium tert-butoxide (941 mg, 8.39 mmol) was added thereto, and the mixture was stirred at room temperature for 1.5 hr. The reaction mixture was acidified with 1N hydrochloric acid, and extracted with ethyl acetate (20 mL×3). The organic layers were combined, washed with brine (10 mL), dried over anhydrous magnesium sulfate, and concentrated under reduced pressure. The residue was purified by silica gel column chromatography (eluent, hexane:ethyl acetate=99:1→2:1) to give crude 2-ethyl 6-benzyl 3-ethyl-7-hydroxy-5-methyl-5H-pyrrolo[2,3-b]pyrazine-2,6-dicarboxylate. To the obtained compound were added diisopropyl sulfate (680 μL, 4.10 mmol), potassium carbonate (847 mg, 6.13 mmol) and 2-butanone (20 mL)/DMF (3 mL), and the mixture was stirred at 80° C. for 6 hr. To the reaction mixture was added water (60 mL), and the mixture was extracted with ethyl acetate (50 mL×3). The organic layers were combined, washed with brine (20 mL), dried over anhydrous magnesium sulfate, and concentrated under reduced pressure. The residue was purified by silica gel column chromatography (eluent, hexane:ethyl acetate=99:1→4:1) to give the title compound (479 mg, 27%) as a yellow powder.

$^1$H NMR (300 MHz, DMSO-d$_6$) δ: 1.24 (6H, d, J=6.0 Hz), 1.26-1.41 (6H, m), 3.10 (2H, q, J=7.4 Hz), 3.97 (3H, s), 4.39 (2H, q, J=7.2 Hz), 5.23-5.37 (1H, m), 5.40 (2H, s), 7.32-7.48 (3H, m), 7.50-7.60 (2H, m).

Reference Example 253

Production of 2-(ethoxycarbonyl)-3-ethyl-5-methyl-7-(1-methylethoxy)-5H-pyrrolo[2,3-b]pyrazine-6-carboxylic acid To a solution of the compound of Reference Example 252 (440 mg, 1.06 mmol) in a mixed solvent of ethanol (10 mL)/THF (2 mL) was added 10% palladium-carbon (water-containing product, 52.2 mg), and the mixture was stirred under a hydrogen atmosphere at room temperature for 1 hr. To the reaction mixture was added THF to dissolve the precipitate, and filtered through celite. The filtrate was concentrated under reduced pressure, and the precipitate was collected by filtration to give the title compound (263 mg, 76%) as a yellow powder. The filtrate was concentrated under reduced pressure, and the precipitate was collected by filtration to give the title compound (36.0 mg, 10%) as a yellow powder.

$^1$H NMR (300 MHz, DMSO-d$_6$) δ: 1.25-1.32 (9H, m), 1.35 (3H, t, J=7.2 Hz), 3.10 (2H, q, J=7.4 Hz), 3.95 (3H, s), 4.39 (2H, q, J=7.2 Hz), 5.07-5.28 (1H, m), 13.26 (1H, br s).

Reference Example 254

Production of 3-ethyl-6-{[1-(hydroxyacetyl)piperidin-4-yl]carbamoyl}-5-methyl-7-(1-methylethoxy)-5H-pyrrolo[2,3-b]pyrazine-2-carboxylic acid To a solution of the compound (277 mg, 0.583 mmol) of Reference Example 329 in a mixed solvent of ethanol (5 mL)/THF (1.5 mL) was added 1N aqueous sodium hydroxide solution (3 mL), and the mixture was stirred at room temperature for 2.5 hr. The reaction mixture was acidified with 2N hydrochloric acid, and extracted with ethyl acetate (15 mL×3). The organic layers were combined, dried over anhydrous magnesium sulfate, and concentrated under reduced pressure. The precipitate was collected by filtration to give the title compound (186 mg, 71%) as a yellow powder.

$^1$H NMR (300 MHz, DMSO-d$_6$) δ: 1.29 (3H, t, J=7.5 Hz), 1.35 (6H, d, J=6.0 Hz), 1.38-1.64 (2H, m), 1.85-2.00 (2H, m), 2.84-3.01 (1H, m), 3.06-3.22 (3H, m), 3.61-3.77 (1H, m), 3.98 (3H, s), 4.02-4.16 (3H, m), 4.17-4.32 (1H, m), 4.52 (1H, t, J=5.4 Hz), 5.31-5.46 (1H, m), 7.96 (1H, d, J=7.7 Hz), 13.27 (1H, br s).

Reference Example 255

Production of ethyl 5-bromopyridine-2-carboxylate

A mixture of 5-bromopyridine-2-carboxylic acid (35.0 g, 173 mmol), sulfuric acid (12.0 mL) and ethanol (300 mL) was stirred at 75° C. for 2 hr. After cooling to 0° C., the mixture was neutralized with sodium hydrogen carbonate and diluted with water (150 mL). Ethanol was evaporated under reduced pressure, and the residue was extracted with ethyl acetate (300 mL). The extract was washed with brine, dried over magnesium sulfate, and concentrated under reduced pressure. The obtained solid was collected by filtration, washed with hexane, and dried to give the title compound (34.5 g, 86%) as a white solid.

$^1$H NMR (300 MHz, DMSO-d$_6$) δ: 1.33 (3H, t, J=7.1 Hz), 4.35 (2H, q, J=7.1 Hz), 7.99 (1H, d, J=8.3 Hz), 8.27 (1H, dd, J=2.3, 8.3 Hz), 8.86 (1H, d, J=2.3 Hz).

Reference Example 256

Production of ethyl 5-ethenylpyridine-2-carboxylate

A mixture of the compound of Reference Example 255 (20.0 g, 86.9 mmol), tributylvinyltin (28.1 mL, 95.6 mmol), Pd(PPh$_3$)$_4$ (2.01 g, 1.74 mmol) and DMF (100 mL) was stirred at 100° C. for 2 hr under an argon atmosphere. To the reaction mixture was added water (200 mL), and the mixture was extracted with ethyl acetate (400 mL). The extract was washed with brine (200 mL), and dried over anhydrous sodium sulfate. The insoluble material was removed by filtration, and the solution was concentrated under reduced pressure. The residue was purified by silica gel column chromatography (eluent, hexane:ethyl acetate=98:2→20:80) to give the title compound (16.5 g, 100%) as a pale-yellow oil.

$^1$H NMR (300 MHz, DMSO-d$_6$) δ: 1.33 (3H, t, J=7.1 Hz), 4.34 (2H, q, J=7.1 Hz), 5.56 (1H, d, J=11.1 Hz), 6.14 (1H, d, J=17.8 Hz), 6.87 (1H, dd, J=11.1, 17.8 Hz), 8.00-8.06 (1H, m), 8.07-8.16 (1H, m), 8.80 (1H, d, J=1.9 Hz).

Reference Example 257

Production of ethyl 5-ethylpyridine-2-carboxylate

A mixture of the compound of Reference Example 256 (7.71 g, 43.5 mmol), 10% palladium-carbon (water-containing product, 1.54 g) and ethanol (77 mL) was stirred at room temperature for 3 hr under a hydrogen atmosphere. The catalyst was filtered off, washed with ethanol, and the filtrate was concentrated under reduced pressure to give the title compound (7.92 g, 100%) as a pale-yellow oil.

$^1$H NMR (300 MHz, DMSO-d$_6$) δ: 1.22 (3H, t, J=7.6 Hz), 1.33 (3H, t, J=7.1 Hz), 2.71 (2H, q, J=7.6 Hz), 4.33 (2H, q, J=7.1 Hz), 7.83 (1H, dd, J=2.2, 8.0 Hz), 7.98 (1H, d, J=8.0 Hz), 8.58 (1H, d, J=2.2 Hz).

Reference Example 258

Production of 5-ethylpyridine-2-carboxylate ethyl 1-oxide

A mixture of the compound of Reference Example 257 (1.28 g, 7.14 mmol), 3-chloroperbenzoic acid (2.84 g, 10.7 mmol) and acetonitrile (13 mL) was stirred at room temperature for 20 hr. The reaction mixture was concentrated to a half amount under reduced pressure, the residue was diluted with ethyl acetate (50 mL), and the mixture was washed with saturated aqueous sodium hydrogen carbonate solution (100 mL) and brine (50 mL), and dried over anhydrous sodium sulfate. The insoluble material was removed by filtration, and the filtrate was concentrated under reduced pressure. The residue was purified by silica gel column chromatography (eluent, hexane:ethyl acetate=90:10→0:100) to give the title compound (1.15 g, 83%) as a yellow oil.

$^1$H NMR (300 MHz, DMSO-d$_6$) δ: 1.17 (3H, t, J=7.6 Hz), 1.29 (3H, t, J=7.1 Hz), 2.60 (2H, q, J=7.6 Hz), 4.32 (2H, q, J=7.1 Hz), 7.30 (1H, dd, J=8.1, 0.8 Hz), 7.61 (1H, d, J=8.1 Hz), 8.22-8.27 (1H, m).

Reference Example 259

Production of ethyl 5-ethyl-6-oxo-1,6-dihydropyridine-2-carboxylate

A mixture of the compound of Reference Example 258 (1.15 g, 5.89 mmol), trifluoroacetic anhydride (8.19 mL, 58.9 mmol) and DMF (12 mL) was stirred at room temperature for 12 hr under an argon atmosphere. The reaction mixture was concentrated under reduced pressure, the residue was diluted with water (50 mL), and the solution was extracted with ethyl acetate (100 mL). The extract was washed with brine (50 mL), and dried over anhydrous sodium sulfate. The insoluble material was removed by filtration, and the filtrate was concentrated under reduced pressure. The residue was purified by silica gel column chromatography (eluent, hexane:ethyl acetate=95:5→50:50) to give the title compound (1.10 g, 96%) as a yellow oil.
$^1$H NMR (300 MHz, DMSO-$d_6$) δ: 1.11 (3H, t, J=7.5 Hz), 1.30 (3H, t, J=7.1 Hz), 2.41-2.49 (2H, m), 4.29 (2H, q, J=7.1 Hz), 6.99 (1H, d, J=7.0 Hz), 7.41 (1H, d, J=7.0 Hz), 11.53 (1H, br s).

Reference Example 260

Production of ethyl 3-bromo-5-ethyl-6-oxo-1,6-dihydropyridine-2-carboxylate

By a method similar to that in Reference Example 5, the title compound (1.21 g, 79%) was obtained as a white solid from the compound of Reference Example 259 (1.10 g, 5.63 mmol), N-bromosuccinimide (1.30 g, 7.33 mmol) and DMF (11 mL).
$^1$H NMR (300 MHz, DMSO-$d_6$) δ: 1.12 (3H, t, J=7.5 Hz), 1.30 (3H, t, J=7.1 Hz), 2.45-2.54 (2H, m), 4.32 (2H, q, J=7.1 Hz), 7.71 (1H, s), 11.77 (1H, br s).

Reference Example 261

Production of ethyl 6-(benzyloxy)-3-bromo-5-ethylpyridine-2-carboxylate

A mixture of the compound of Reference Example 260 (17.1% g, 62.3 mmol), silver carbonate (29.2 g, 106 mmol), benzyl bromide (14.8 mL, 125 mmol) and toluene (342 mL) was stirred at 40° C. for 2 hr. The insoluble material was removed by filtration, and the filtrate was concentrated under reduced pressure. The residue was purified by silica gel column chromatography (eluent, hexane:ethyl acetate=100:0→94:6) to give the title compound (22.4 g, 99%) as a yellow oil.
$^1$H NMR (300 MHz, DMSO-$d_6$) δ: 1.14 (3H, t, J=7.4 Hz), 1.34 (3H, t, J=7.0 Hz), 2.60 (2H, q, J=7.4 Hz), 4.36 (2H, q, J=7.0 Hz), 5.35 (2H, s), 7.31-7.43 (3H, m), 7.45-7.53 (2H, m), 7.92 (1H, s).

Reference Example 262

Production of ethyl 3-amino-6-(benzyloxy)-5-ethylpyridine-2-carboxylate

By a method similar to that in Reference Example 9, the title compound (17.8 g, 98%) was obtained as a yellow oil from the compound of Reference Example 261 (22.0 g, 60.4 mmol), benzophenonimine (12.2 mL, 72.5 mmol), cesium carbonate (39.4 g, 121 mmol), Pd$_2$dba$_3$ (2.77 g, 3.02 mmol), Xantphos (4.54 g, 7.85 mmol) and toluene (220 mL).
$^1$H NMR (300 MHz, DMSO-$d_6$) δ: 1.12 (3H, t, J=7.5 Hz), 1.33 (3H, t, J=7.1 Hz), 2.45-2.58 (2H, m), 4.27 (2H, q, J=7.1 Hz), 5.26 (2H, s), 6.33 (2H, s), 7.08 (1H, s), 7.27-7.40 (3H, m), 7.48-7.57 (2H, m).

Reference Example 263

Production of ethyl 6-(benzyloxy)-5-ethyl-3-(methylamino)pyridine-2-carboxylate

A mixture of the compound of Reference Example 262 (771 mg, 2.57 mmol), di-t-butyl carbonate (1.77 mL, 7.71 mmol) and t-butyl alcohol (7.7 mL) was stirred at 90° C. for 18 hr. The reaction mixture was concentrated under reduced pressure, DMF (10 mL), cesium carbonate (2.93 g, 9.00 mmol) and iodomethane (0.480 mL, 7.71 mmol) were added thereto, and the mixture was stirred at room temperature for 4 hr stirred for. The reaction mixture was diluted with water (50 mL), and extracted with ethyl acetate (100 mL). The extract was washed with brine (50 mL), and dried over anhydrous sodium sulfate. The insoluble material was removed by filtration, and the filtrate was concentrated under reduced pressure. To the obtained residue was added 4N hydrochloric acid/ethyl acetate (5.4 mL), and the mixture was stirred at 0° C. for 2 hr. The reaction mixture was diluted with saturated aqueous sodium hydrogen carbonate solution (50 mL), and extracted with ethyl acetate (100 mL). The extract was washed with brine (50 mL), and dried over anhydrous sodium sulfate. The insoluble material was removed by filtration, and the filtrate was concentrated under reduced pressure. The residue was purified by silica gel column chromatography (eluent, hexane:ethyl acetate=98:2→94:6) to give the title compound (705 mg, 87%) as a yellow oil.
$^1$H NMR (300 MHz, DMSO-$d_6$) δ: 1.16 (3H, t, J=7.4 Hz), 1.34 (3H, t, J=7.0 Hz), 2.59 (2H, q, J=7.4 Hz), 2.85 (3H, d, J=4.9 Hz), 4.28 (2H, q, J=7.0 Hz), 5.28 (2H, s), 7.13 (1H, s), 7.17-7.41 (4H, m), 7.48-7.56 (2H, m).

Reference Example 264

Production of ethyl 6-(benzyloxy)-3-[(2-ethoxy-2-oxoethyl)(methyl)amino]-5-ethylpyridine-2-carboxylate A mixture of the compound of Reference Example 263 (705 mg, 2.24 mmol), diisopropylethylamine (2.35 mL, 13.5 mmol), ethyl bromoacetate (1.49 mL, 13.5 mmol) and DMF (14 mL) was stirred at 110° C. for 24 hr. The reaction mixture was diluted with water (50 mL), and extracted with ethyl acetate (100 mL). The extract was washed with brine (50 mL), and dried over anhydrous sodium sulfate. The insoluble material was removed by filtration, and the filtrate was concentrated under reduced pressure. The residue was purified by silica gel column chromatography (eluent, hexane:ethyl acetate=100:0→80:20) to give the title compound (711 mg, 79%) as a yellow oil.
$^1$H NMR (300 MHz, DMSO-$d_6$) δ: 1.09-1.21 (6H, m), 1.30 (3H, t, J=7.1 Hz), 2.57 (2H, q, J=7.4 Hz), 2.81 (3H, s), 3.88 (2H, s), 4.07 (2H, q, J=7.1 Hz), 4.28 (2H, q, J=7.1 Hz), 5.28 (2H, s), 7.26-7.42 (3H, m), 7.42-7.51 (3H, m).

Reference Example 265

Production of ethyl 5-(benzyloxy)-6-ethyl-3-hydroxy-1-methyl-1H-pyrrolo[3,2-b]pyridine-2-carboxylate A mixture of the compound of Reference Example 264 (711 mg, 1.78 mmol), 20% ethanol solution (1.42 mL) of sodium ethoxide and ethanol (14 mL) was stirred at room temperature for 1 hr. The reaction mixture was concentrated under reduced pressure, and the residue was acidified with 1N hydrochloric acid, and the mixture was extracted with ethyl acetate (100 mL). The extract was washed with brine (50 mL), and dried over anhydrous sodium sulfate. The insoluble material was removed by filtration, and the filtrate was concentrated under reduced pressure. The precipitate was collected by filtration, and washed with diisopropyl ether to give the title compound (485 mg, 77%) as a pale-orange powder.

$^1$H NMR (300 MHz, DMSO-$d_6$) δ: 1.22 (3H, t, J=7.4 Hz), 1.34 (3H, t, J=7.1 Hz), 2.69 (2H, q, J=7.4 Hz), 3.84 (3H, s), 4.35 (2H, q, J=7.1 Hz), 5.44 (2H, s), 7.27-7.44 (3H, m), 7.46-7.56 (2H, m), 7.78 (1H, s), 8.84 (1H, s).

Reference Example 266

Production of ethyl 5-(benzyloxy)-6-ethyl-1-methyl-3-(2,2,2-trifluoroethoxy)-1H-pyrrolo[3,2-b]pyridine-2-carboxylate By a method similar to that in Reference Example 8, the title compound (580 mg, 97%) was obtained as a pale-orange powder from the compound of Reference Example 265 (485 mg, 1.37 mmol), cesium carbonate (534 g, 1.64 mmol), 2,2,2-trifluoroethyl trifluoromethanesulfonate (0.217 mL, 1.51 mmol) and DMF (4.9 mL).

$^1$H NMR (300 MHz, DMSO-$d_6$) δ: 1.23 (3H, t, J=7.4 Hz), 1.30 (3H, t, J=7.1 Hz), 2.71 (2H, q, J=7.4 Hz), 3.90 (3H, s), 4.29 (2H, q, J=7.1 Hz), 5.07 (2H, q, J=9.1 Hz), 5.44 (2H, s), 7.25-7.41 (3H, m), 7.43-7.51 (2H, m), 7.88 (1H, s).

Reference Example 267

Production of 5-(benzyloxy)-6-ethyl-1-methyl-3-(2,2,2-trifluoroethoxy)-1H-pyrrolo[3,2-b]pyridine-2-carboxylic acid By a method similar to that in Reference Example 12, the title compound (103 mg, 74%) was obtained as a white powder from the compound of Reference Example 266 (150 mg, 0.344 mmol), 8N aqueous sodium hydroxide solution (0.300 mL) and ethanol (3.0 mL).

$^1$H NMR (300 MHz, DMSO-$d_6$) δ: 1.23 (3H, t, J=7.4 Hz), 2.71 (2H, q, J=7.4 Hz), 3.89 (3H, s), 5.05 (2H, q, J=9.1 Hz), 5.43 (2H, s), 7.23-7.42 (3H, m), 7.42-7.52 (2H, m), 7.84 (1H, s), 12.86 (1H, br s).

Reference Example 268

Production of ethyl 6-ethyl-1-methyl-5-oxo-3-(2,2,2-trifluoroethoxy)-4,5-dihydro-1H-pyrrolo[3,2-b]pyridine-2-carboxylate A mixture of the compound of Reference Example 266 (428 mg, 0.981 mmol), 10% palladium-carbon (water-containing product, 128 mg), ethanol (8.7 mL) and THF (4.3 mL) was stirred at room temperature for 1 hr under a hydrogen atmosphere. The catalyst was filtered off, washed with ethanol, and the filtrate was concentrated under reduced pressure. The obtained solid was collected by filtration, washed with ethyl acetate-hexane to give the title compound (330 mg, 97%) as a white solid.

$^1$H NMR (300 MHz, DMSO-$d_6$) δ: 1.15 (3H, t, J=7.5 Hz), 1.29 (3H, t, J=7.1 Hz), 2.45-2.55 (2H, m), 3.87 (3H, s), 4.27 (2H, q, J=7.1 Hz), 4.62 (2H, q, J=9.1 Hz), 7.74 (1H, s), 11.66 (1H, br s).

Reference Example 269

Production of ethyl 6-ethyl-1-methyl-3-(2,2,2-trifluoroethoxy)-5-{[(trifluoromethyl)sulfonyl]oxy}-1H-pyrrolo[3,2-b]pyridine-2-carboxylate To a solution (9.9 mL) of the compound of Reference Example 268 (330 mg, 0.953 mmol) in pyridine was added trifluoromethanesulfonic anhydride (0.384 mL, 2.28 mmol) at 0° C., and the mixture was stirred under a nitrogen atmosphere at 60° C. for 16 hr. The reaction mixture was concentrated under reduced pressure, and the residue was diluted with saturated aqueous sodium hydrogen carbonate solution (50 mL), and the mixture was extracted with ethyl acetate (100 mL). The extract was washed with brine (50 mL), and dried over anhydrous sodium sulfate. The insoluble material was removed by filtration, and the filtrate was concentrated under reduced pressure. The precipitate was collected by filtration, washed with hexane to give the title compound (418 mg, 92%) as a pale-yellow powder.

$^1$H NMR (300 MHz, DMSO-$d_6$) δ: 1.24-1.39 (6H, m), 2.79 (2H, q, J=7.6 Hz), 3.99 (3H, s), 4.36 (2H, q, J=7.2 Hz), 5.05 (2H, q, J=8.9 Hz), 8.35 (1H, s).

Reference Example 270

Production of ethyl 5-amino-6-ethyl-1-methyl-3-(2,2,2-trifluoroethoxy)-1H-pyrrolo[3,2-b]pyridine-2-carboxylate By a method similar to that in Reference Example 9, the title compound (141 mg, 90%) was obtained as a white powder from the compound of Reference Example 269 (218 mg, 0.456 mmol), benzophenonimine (0.0918 mL, 0.549 mmol), cesium carbonate (297 mg, 0.912 mmol), Pd$_2$dba$_3$ (20.9 mg, 0.0228 mmol), Xantphos (34.3 mg, 0.0593 mmol) and toluene (2.2 mL).

$^1$H NMR (300 MHz, DMSO-$d_6$) δ: 1.20 (3H, t, J=7.5 Hz), 1.29 (3H, t, J=7.1 Hz), 2.51-2.61 (2H, m), 3.83 (3H, s), 4.26 (2H, q, J=7.1 Hz), 5.10 (2H, q, J=9.1 Hz), 5.75 (2H, s), 7.55 (1H, s).

Reference Example 271

Production of 6-ethyl-1-methyl-5-[(phenylcarbonyl)amino]-3-(2,2,2-trifluoroethoxy)-1H-pyrrolo[3,2-b]pyridine-2-carboxylic acid A mixture of the compound of Reference Example 270 (141' mg, 0.408 mmol), pyridine (0.0858 mL, 1.06 mmol), benzoyl chloride (0.104 mL, 0.898 mmol) and THF (1.4 mL) was stirred at 50° C. for 2 hr. The reaction mixture was diluted with water (30 mL), and the mixture was extracted with ethyl acetate (50 mL). The extract was washed with brine (30 mL), and dried over anhydrous sodium sulfate. The insoluble material was removed by filtration, and the filtrate was concentrated under reduced pressure. To the residue were added ethanol (3.7 mL) and 8N aqueous sodium hydroxide solution (0.366 mL), and the mixture was stirred at 50° C. for 1 hr. The reaction mixture was concentrated under reduced pressure, and the residue was diluted with water (20 mL), and the mixture was acidified with 1N hydrochloric acid. The precipitate was collected by filtration, and washed with water, and dried to give the title compound (152 mg, 88%) as a white solid.

$^1$H NMR (300 MHz, DMSO-d$_6$) δ: 1.23 (3H, t, J=7.5 Hz), 2.71 (2H, q, J=7.5 Hz), 3.97 (3H, s), 5.10 (2H, q, J=9.1 Hz), 7.49-7.65 (3H, m), 7.97-8.06 (3H, m), 10.56 (1H, s), 13.17 (1H, br s).

Reference Example 272

Production of ethyl 6-ethyl-1-methyl-5-phenyl-3-(2,2,2-trifluoroethoxy)-1H-pyrrolo[3,2-b]pyridine-2-carboxylate By a method similar to that in Reference Example 15, the title compound (161 mg, 95%) was obtained as a yellow oil from the compound of Reference Example 269 (200 mg, 0.418 mmol), phenylboronic acid (61.2 mg, 0.502 mmol), potassium carbonate (462 mg, 3.34 mmol), toluene (2.0 mL), ethanol (2.0 mL) and Pd(PPh$_3$)$_4$ (24.2 mg, 20.9 μmol).
$^1$H NMR (300 MHz, DMSO-d$_6$) δ: 1.11 (3H, t, J=7.6 Hz), 1.33 (3H, t, J=7.2 Hz), 2.74 (2H, q, J=7.6 Hz), 3.97 (3H, s), 4.34 (2H, q, J=7.2 Hz), 5.22 (2H, q, J=9.0 Hz), 7.38-7.55 (5H, m), 8.03 (1H, s).

Reference Example 273

Production of 6-ethyl-1-methyl-5-phenyl-3-(2,2,2-trifluoroethoxy)-1H-pyrrolo[3,2-b]pyridine-2-carboxylic acid By a method similar to that in Reference Example 12, the title compound (123 mg, 82%) was obtained as a pale-yellow solid from the compound of Reference Example 272 (161 mg, 0.396 mmol), 8N aqueous sodium hydroxide solution (0.322 mL) and ethanol (3.2 mL).
$^1$H NMR (300 MHz, DMSO-d$_6$) δ: 1.11 (3H, t, J=7.4 Hz), 2.73 (2H, q, J=7.4 Hz), 3.96 (3H, s), 5.18 (2H, q, J=9.1 Hz), 7.36-7.55 (5H, m), 7.97 (1H, s), 13.08 (1H, br s).

Reference Example 274

Production of ethyl 5-(benzyloxy)-3-ethoxy-6-ethyl-1-methyl-1H-pyrrolo[3,2-b]pyridine-2-carboxylate By a method similar to that in Reference Example 131, the title compound (488 mg, 91%) was obtained as a yellow oil from the compound of Reference Example 265 (500 mg, 1.41 mmol), potassium carbonate (390 mg, 2.82 mmol), diethyl sulfate (0.240 mL, 1.83 mmol) and acetone (10 mL).
$^1$H NMR (300 MHz, DMSO-d$_6$) δ: 1.23 (3H, t, J=7.5 Hz), 1.26-1.36 (6H, m), 2.70 (2H, q, J=7.5 Hz), 3.87 (3H, s), 4.29 (2H, q, J=7.1 Hz), 4.46 (2H, q, J=7.1 Hz), 5.42 (2H, s), 7.26-7.42 (3H, m), 7.44-7.52 (2H, m), 7.82 (1H, s).

Reference Example 275

Production of ethyl 3-ethoxy-6-ethyl-1-methyl-5-oxo-4,5-dihydro-1H-pyrrolo[3,2-b]pyridine-2-carboxylate By a method similar to that in Reference Example 268, the title compound (316 mg, 85%) was obtained as a pale-yellow solid from the compound of Reference Example 274 (488 mg, 1.28% mmol), 10% palladium-carbon (water-containing product, 97.6 mg), ethanol (9.8 mL) and THF (4.8 mL).
$^1$H NMR (300 MHz, DMSO-d$_6$) δ: 1.14 (3H, t, J=7.5 Hz), 1.24-1.35 (6H, m), 2.43-2.49 (2H, m), 3.85 (3H, s), 3.97 (2H, q, J=7.0 Hz), 4.26 (2H, q, J=7.0 Hz), 7.70 (1H, s), 11.61 (1H, br s).

Reference Example 276

Production of ethyl 3-ethoxy-6-ethyl-1-methyl-5-{[(trifluoromethyl)sulfonyl]oxy}-1H-pyrrolo[3,2-b]pyridine-2-carboxylate By a method similar to that in Reference Example 269, the title compound (451 mg, 98%) was obtained as a pale-yellow solid from the compound of Reference Example 275 (316 mg, 1.08 mmol), trifluoromethanesulfonic anhydride (0.364 mL, 2.16 mmol) and pyridine (6.3 mL).
$^1$H NMR (300 MHz, DMSO-d$_6$) δ: 1.24-1.38 (9, m), 2.78 (2H, q, J=7.6 Hz), 3.95 (3H, s), 4.34 (2H, q, J=7.2 Hz), 4.45 (2H, q, J=7.0 Hz), 8.28 (1H, s).

Reference Example 277

Production of ethyl 5-amino-3-ethoxy-6-ethyl-1-methyl-1H-pyrrolo[3,2-b]pyridine-2-carboxylate By a method similar to that in Reference Example 9, the title compound (151 mg, 87%) was obtained as a yellow solid from the compound of Reference Example 276 (251 mg, 0.591 mmol), benzophenonimine (0.119 mL, 0.710 mmol), cesium carbonate (385 mg, 1.18 mmol), Pd$_2$dba$_3$ (27.1 mg, 0.0296 mmol), Xantphos (44.5 mg, 0.0768 mmol) and toluene (2.5 mL).
$^1$H NMR (300 MHz, DMSO-d$_6$) δ: 1.20 (3H, t, J=7.4 Hz), 1.24-1.36 (6H, m), 2.52-2.61 (2H, m), 3.81 (3H, s), 4.19-4.41 (4H, m), 5.54-5.69 (2H, m), 7.50 (1H, s).

Reference Example 278

Production of ethyl 3-ethoxy-6-ethyl-1-methyl-5-[(phenylcarbonyl)amino]-1H-pyrrolo[3,2-b]pyridine-2-carboxylate By a method similar to that in Reference Example 23, the title compound (148 mg, 72%) was obtained as a white solid from the compound of Reference Example 277 (151 mg, 0.518 mmol), pyridine (168 μL, 2.08 mmol), benzoyl chloride (181 μL, 0.777 mmol) and THF (1.5 mL).
$^1$H NMR (300 MHz, DMSO-d$_6$) δ: 1.23 (3H, t, J=7.5 Hz), 1.27-1.39 (6H, m), 2.70 (2H, q, J=7.5 Hz), 3.94 (3H, s), 4.33 (2H, q, J=7.1 Hz), 4.43 (2H, q, J=7.1 Hz), 7.46-7.66 (3H, m), 7.96 (1H, s), 7.98-8.06 (2H, m), 10.54 (1H, s).

Reference Example 279

Production of 3-ethoxy-6-ethyl-1-methyl-5-[(phenylcarbonyl)amino]-1H-pyrrolo[3,2-b]pyridine-2-carboxylic acid By a method similar to that in Reference Example 12, the title compound (109 mg, 79%) was obtained as a yellow solid from the compound of Reference Example 278 (148 mg, 0.374 mmol), 8N aqueous sodium hydroxide solution (0.296 mL) and ethanol (3.0 mL).
$^1$H NMR (300 MHz, DMSO-d$_6$) δ: 1.18-1.33 (6H, m), 2.69 (2H, q, J=7.5 Hz), 3.94 (3H, s), 4.45 (2H, q, J=7.1 Hz), 7.46-7.65 (3H, m), 7.93 (1H, s), 7.97-8.07 (2H, m), 10.52 (1H, s), 12.88 (1H, br s).

Reference Example 280

Production of ethyl 5-(benzyloxy)-6-ethyl-1-methyl-3-(1-methylethoxy)-1H-pyrrolo[3,2-b]pyridine-2-carboxylate By a method similar to that in Reference Example 84, the title compound (5.03 mg, 90%) was obtained as a yellow oil from the compound of Reference Example 265 (5.00 g, 14.1 mmol), acetone (50 mL), potassium carbonate (3.90 g, 28.2 mmol) and diisopropyl sulfate (3.03 mL, 18.3 mmol).

$^1$H NMR (300 MHz, DMSO-$d_6$) δ: 1.19-1.28 (9H, m), 1.32 (3H, t, J=7.1 Hz), 2.70 (2H, q, J=7.4 Hz), 3.87 (3H, s), 4.28 (2H, q, J=7.1 Hz), 4.94-5.09 (1H, m), 5.42 (2H, s), 7.24-7.42 (3H, m), 7.43-7.50 (2H, m), 7.81 (1H, s).

Reference Example 281

Production of ethyl 6-ethyl-1-methyl-3-(1-methylethoxy)-5-oxo-4,5-dihydro-1H-pyrrolo[3,2-b]pyridine-2-carboxylate By a method similar to that in Reference Example 268, the title compound (3.31 mg, 94%) was obtained as a white powder from the compound of Reference Example 280 (4.56 g, 11.5 mmol), 10% palladium-carbon (water-containing product, 456 mg), ethanol (91 mL) and THF (46 mL).

$^1$H NMR (300 MHz, DMSO-$d_6$) δ: 1.15 (3H, t, J=7.5 Hz), 1.22 (6H, d, J=6.2 Hz), 1.31 (3H, t, J=7.1 Hz), 2.42-2.49 (2H, m), 3.85 (3H, s), 4.20-4.43 (3H, m), 7.70 (1H, s), 11.47 (1H, br s).

Reference Example 282

Production of ethyl 6-ethyl-1-methyl-3-(1-methylethoxy)-5-{[(trifluoromethyl)sulfonyl]oxy}-1H-pyrrolo[3,2-b]pyridine-2-carboxylate By a method similar to that in Reference Example 269, the title compound (4.03 g, 90%) was obtained as a pale-yellow powder from the compound of Reference Example 281 (3.11 g, 10.2 mmol), trifluoromethanesulfonic anhydride (3.42 mL, 20.3 mmol) and pyridine (62 mL).

$^1$H NMR (300 MHz, DMSO-$d_6$) δ: 1.23-1.32 (9H, m), 1.35 (3H, t, J=7.1 Hz), 2.78 (2H, q, J=7.6 Hz), 3.96 (3H, s), 4.34 (2H, q, J=7.1 Hz), 4.93 (1H, spt, J=6.1 Hz), 8.27 (1H, s).

Reference Example 283

Production of ethyl 5-amino-6-ethyl-1-methyl-3-(1-methylethoxy)-1H-pyrrolo[3,2-b]pyridine-2-carboxylate By a method similar to that in Reference Example 9, the title compound (935 mg, 90%) was obtained as a pale-orange powder from the compound of Reference Example 282 (1.50 g, 3.42 mmol), benzophenonimine (0.689 mL, 4.11 mmol), cesium carbonate (2.23 g, 6.84 mmol), Pd$_2$dba$_3$ (157 mg, 0.171 mmol). Xantphos (257 mg, 0.445 mmol) and toluene (15 mL).

$^1$H NMR (300 MHz, DMSO-$d_6$) δ: 1.17-1.26 (9H, m), 1.31 (3H, t, J=7.1 Hz), 2.51-2.60 (2H, m), 3.80 (3H, s), 4.26 (2H, q, J=7.1 Hz), 5.03 (1H, spt, J=6.1 Hz), 5.57 (2H, s), 7.49 (1H, s).

Reference Example 284

Production of ethyl 6-ethyl-1-methyl-3-(1-methylethoxy)-5-[(phenylcarbonyl)amino]-1H-pyrrolo[3,2-b]pyridine-2-carboxylate By a method similar to that in Reference Example 23, the title compound (191 mg, 79%) was obtained as a white solid from the compound of Reference Example 283 (180 mg, 0.589 mmol), pyridine (191 μL, 2.36 mmol), benzoyl chloride (206 μL, 1.77 mmol) and THF (1.8 mL).

$^1$H NMR (300 MHz, DMSO-$d_6$) δ: 1.20-1.28 (9H, m), 1.35 (3H, t, J=7.1 Hz), 2.70 (2H, q, J=7.5 Hz), 3.94 (3H, s), 4.32 (2H, q, J=7.1 Hz), 5.02-5.17 (1H, m), 7.48-7.65 (3H, m), 7.95 (1H, s), 7.98-8.06 (2H, m), 10.53 (1H, s).

Reference Example 285

Production of 6-ethyl-1-methyl-3-(1-methylethoxy)-5-[(phenylcarbonyl)amino]-1H-pyrrolo[3,2-b]pyridine-2-carboxylic acid By a method similar to that in Reference Example 12, the title compound (166 mg, 93%) was obtained as a pale-yellow solid from the compound of Reference Example 284 (191 mg, 0.466 mmol), 8N aqueous sodium hydroxide solution (0.382 mL) and ethanol (3.8 mL).

$^1$H NMR (300 MHz, DMSO-$d_6$) δ: 1.16-1.31 (9H, m), 2.69 (2H, q, J=7.4 Hz), 3.94 (3H, s), 5.02-5.19 (1H, m), 7.46-7.65 (3H, m), 7.93 (1H, s), 7.97-8.08 (2H, m), 10.51 (1H, s), 12.80 (1H, br s).

Reference Example 286

Production of ethyl 6-ethyl-1-methyl-3-(1-methylethoxy)-5-phenyl-1H-pyrrolo[3,2-b]pyridine-2-carboxylate By a method similar to that in Reference Example 15, the title compound (144 mg, 94%) was obtained as a white solid from the compound of Reference Example 282 (183 mg, 0.418 mmol), phenylboronic acid (61.2 mg, 0.502 mmol), potassium carbonate (462 mg, 3.34 mmol), toluene (2.0 mL), ethanol (2.0 mL) and Pd(PPh$d_4$ (24.2 mg, 20.9 μmol).

$^1$H NMR (300 MHz, DMSO-$d_6$) δ: 1.11 (3H, t, J=7.6 Hz), 1.26 (6H, d, J=6.0 Hz), 1.35 (3H, t, J=7.1 Hz), 2.74 (2H, q, J=7.6 Hz), 3.93 (3H, s), 4.32 (2H, q, J=7.1 Hz), 5.12-5.25 (1H, m), 7.34-7.55 (5H, m), 7.95 (1H, s).

Reference Example 287

Production of 6-ethyl-1-methyl-3-(1-methylethoxy)-5-phenyl-1H-pyrrolo[3,2-b]pyridine-2-carboxylic acid By a method similar to that in Reference Example 12, the title compound (125 mg, 94%) was obtained as a white powder from the compound of Reference Example 286 (144 mg, 0.393 mmol), 8N aqueous sodium hydroxide solution (0.288 mL) and ethanol (2.9 mL).

$^1$H NMR (300 MHz, DMSO-$d_6$) δ: 1.11 (3H, t, J=7.5 Hz), 1.25 (6H, d, J=6.2 Hz), 2.72 (2H, q, J=7.5 Hz), 3.93 (3H, s), 5.11-5.30 (1H, m), 7.33-7.56 (5H, m), 7.92 (1H, s), 12.76 (1H, br s).

Reference Example 288

Production of ethyl 6-ethyl-5-(4-fluorophenyl)-1-methyl-3-(1-methylethoxy)-1H-pyrrolo[3,2-b]pyridine-2-carboxylate By a method similar to that in Reference Example 15, the title compound (161 mg, 100%) was obtained as a white solid from the compound of Reference Example 282 (183 mg, 0.418% mmol), 4-fluorophenylboronic acid (70.2 mg, 0.502 mmol), potassium carbonate (462 mg, 3.34 mmol), toluene (2.0 mL), ethanol (2.0 mL) and Pd(PPh$_3$)$_4$ (24.2 mg, 20.9 mmol).

$^1$H NMR (300 MHz, DMSO-d$_6$) δ: 1.12 (3H, t, J=7.5 Hz), 1.26 (6H, d, J=6.0 Hz), 1.35 (3H, t, J=7.1 Hz), 2.72 (2H, q, J=7.5 Hz), 3.93 (3H, s), 4.32 (2H, q, J=7.1 Hz), 5.08-5.27 (1H, m), 7.24-7.37 (2H, m), 7.47-7.58 (2H, m), 7.95 (1H, s).

Reference Example 289

Production of 6-ethyl-5-(4-fluorophenyl)-1-methyl-3-(1-methylethoxy)-1H-pyrrolo[3,2-b]pyridine-2-carboxylic acid By a method similar to that in Reference Example 12, the title compound (137 mg, 92%) was obtained as a white powder from the compound of Reference Example 288 (161 mg, 0.419 mmol), and 8N aqueous sodium hydroxide solution (0.322 mL) and ethanol (3.2 mL).

$^1$H NMR (300 MHz, DMSO-d$_6$) δ: 1.11 (3H, t, J=7.5 Hz), 1.25 (6H, d, J=6.2 Hz), 2.72 (2H, q, J=7.5 Hz), 3.93 (3H, s), 5.12-5.26 (1H, m), 7.24-7.35 (2H, m), 7.48-7.58 (2H, m), 7.93 (1H, s), 12.78 (1H, br s).

Reference Example 290

Production of ethyl 6-ethyl-1-methyl-3-(1-methylethoxy)-5-[(thiophen-2-ylcarbonyl)amino]-1H-pyrrolo[3,2-b]pyridine-2-carboxylate By a method similar to that in Reference Example 23, the title compound (203 mg, 83%) was obtained as a white powder from the compound of Reference Example 283 (180 mg, 0.589 mmol), pyridine (238 μL, 2.94 mmol), 2-thiophenecarbonyl chloride (252 μL, 2.36 mmol) and THF (3.6 mL).

$^1$H NMR (300 MHz, DMSO-d$_6$) δ: 1.19-1.30 (9H, m), 1.35 (3H, t, J=7.2 Hz), 2.69 (2H, q, J=7.6 Hz), 3.94 (3H, s), 4.32 (2H, q, J=7.2 Hz), 5.03-5.20 (1H, m), 7.23 (1H, dd, J=4.9, 3.8 Hz), 7.84-7.90 (1H, m), 7.96 (1H, s), 7.99-8.05 (1H, m), 10.58 (1H, s).

Reference Example 291

Production of 6-ethyl-1-methyl-3-(1-methylethoxy)-5-[(thiophen-2-ylcarbonyl)amino]-1H-pyrrolo[3,2-b]pyridine-2-carboxylic acid By a method similar to that in Reference Example 12, the title compound (188 mg, 99%) was obtained as a pale-yellow solid from the compound of Reference Example 290 (203 mg, 0.489 mmol), 8N aqueous sodium hydroxide solution (0.406 mL) and ethanol (4.1 mL).

$^1$H NMR (300 MHz, DMSO-d$_6$) δ: 1.17-1.30 (9H, m), 2.68 (2H, q, J=7.5 Hz), 3.93 (3H, s), 5.04-5.21 (1H, m), 7.23 (1H, dd, J=4.9, 3.7 Hz), 7.86 (1H, d, J=4.9 Hz), 7.93 (1H, s), 8.02 (1H, d, J=3.7 Hz), 10.56 (1H, s), 12.83 (1H, br s).

Reference Example 292

Production of ethyl 6-ethyl-5-[(3-methoxyphenyl)amino]-1-methyl-3-(1-methylethoxy)-1H-pyrrolo[3,2-b]pyridine-2-carboxylate By a method similar to that in Reference Example 13, the title compound (160 mg, 93%) was obtained as a pale-yellow powder from the compound of Reference Example 282 (183 mg, 0.418 mmol), 3-methoxyaniline (56.4 μL, 0.502 mmol), cesium carbonate (218 mg, 0.669 mmol), toluene (3.6 mL), binap (26.0 mg, 41.8 μmol) and Pd$_2$dba$_3$ (19.1 mg, 20.9 μmol).

$^1$H NMR (300 MHz, DMSO-d$_6$) δ: 1.23-1.36 (12H, m), 2.81 (2H, q, J=7.2 Hz), 3.74 (3H, s), 3.87 (3H, s), 4.28 (2H, q, J=7.2 Hz), 5.04-5.20 (1H, m), 6.47 (1H, dd, J=8.0, 2.4 Hz), 7.13 (1H, t, J=8.0 Hz), 7.33-7.41 (1H, m), 7.52-7.57 (1H, m), 7.71 (1H, s), 7.83 (1H, s).

Reference Example 293

Production of 6-ethyl-5-[(3-methoxyphenyl)amino]-1-methyl-3-(1-methylethoxy)-1H-pyrrolo[3,2-b]pyridine-2-carboxylic acid By a method similar to that in Reference Example 12, the title compound (107 mg, 72%) was obtained as a pale-yellow powder from the compound of Reference Example 292 (160 mg, 0.389 mmol), 8N aqueous sodium hydroxide solution (0.320 mL) and ethanol (3.2 mL).

$^1$H NMR (300 MHz, DMSO-d$_6$) δ: 1.21-1.34 (9H, m), 2.81 (2H, q, J=7.4 Hz), 3.74 (3H, s), 3.87 (3H, s), 5.10-5.24 (1H, m), 6.46 (1H, dd, J=8.0, 2.4 Hz), 7.13 (1H, t, J=8.0 Hz), 7.33-7.41 (1H, m), 7.49-7.56 (1H, m), 7.69 (1H, s), 7.81 (1H, s), 12.41 (1H, br s).

Reference Example 294

Production of ethyl 6-ethyl-1-methyl-3-(1-methylethoxy)-5-[4-(trifluoromethyl)phenyl]-1H-pyrrolo[3,2-b]pyridine-2-carboxylate By a method similar to that in Reference Example 15, the title compound (140 mg, 94%) was obtained as a white solid from the compound of Reference Example 282 (150 mg, 0.342 mmol), 4-(trifluoromethyl)phenylboronic acid (78.0 mg, 0.411 mmol), potassium carbonate (378 mg, 2.74 mmol), toluene (1.5 mL), ethanol (1.5 mL) and Pd(PPh$_3$)$_4$ (19.8 mg, 17.1 μmol).

$^1$H NMR (300 MHz, DMSO-d$_6$) δ: 1.13 (3H, t, J=7.5 Hz), 1.27 (6H, d, J=6.0 Hz), 1.35 (3H, t, J=7.1 Hz), 2.73 (2H, q, J=7.5 Hz), 3.95 (3H, s), 4.34 (2H, q, J=7.1 Hz), 5.10-5.24 (1H, m), 7.69-7.77 (2H, m), 7.80-7.89 (2H, m), 8.01 (1H, s).

Reference Example 295

Production of 6-ethyl-1-methyl-3-(1-methylethoxy)-5-[4-(trifluoromethyl)phenyl]-1H-pyrrolo[3,2-b]pyridine-2-carboxylic acid By a method similar to that in Reference Example 12, the title compound (124 mg, 95%) was obtained as a white powder from the compound of Reference Example 294 (140 mg, 0.322 mmol), 8N aqueous sodium hydroxide solution (0.280 mL) and ethanol (2.8 mL).

¹H NMR (300 MHz, DMSO-d₆) δ: 1.13 (3H, t, J=7.5 Hz), 1.25 (6H, d, J=6.0 Hz), 2.73 (2H, q, J=7.5 Hz), 3.94 (3H, s), 5.10-5.25 (1H, m), 7.69-7.77 (2H, m), 7.80-7.89 (2H, m), 7.97 (1H, s), 12.84 (1H, br s).

Reference Example 296

Production of ethyl 3-hydroxy-1-methyl-4-nitro-1H-pyrrole-2-carboxylate

A mixture of nitroethyl acetate (1.80 g, 13.5 mmol), triethyl orthoformate (4.50 mL, 27.0 mmol) and acetic anhydride (3.57 mL, 37.8 mmol) was stirred at 120° C. for 1 hr, and then at 130° C. for 1 hr, and then at 140° C. for 2 hr. The reaction mixture was concentrated under reduced pressure, and ethanol (25 mL), ethyl sarcosinate hydrochloride (2.03 g, 13.2 mmol) and triethylamine (1.83 mL, 13.2 mmol) were added thereto. After stirring at room temperature for 30 min, a 20% ethanol solution (6.7 mL) of sodium ethoxide was added thereto, and the mixture was further stirred at 70° C. for 2 hr. The reaction mixture was concentrated under reduced pressure, the residue was acidified with 1N hydrochloric acid (100 mL), and the mixture was extracted with ethyl acetate (100 mL). The extract was washed with brine (50 mL), and dried over anhydrous sodium sulfate. The insoluble material was removed by filtration, and the filtrate was concentrated under reduced pressure. The residue was purified by silica gel column chromatography (eluent, hexane:ethyl acetate=98:2→70:30) to give the title compound (981 mg, 35%) as a yellow solid.

¹H NMR (300 MHz, DMSO-d₆) δ: 1.28 (3H, t, J=7.1 Hz), 3.81 (3H, s), 4.27 (2H, q, J=7.1 Hz), 8.06 (1H, s), 9.59 (1H, s).

Reference Example 297

Production of ethyl 1-methyl-4-nitro-3-(2,2,2-trifluoroethoxy)-1H-pyrrole-2-carboxylate By a method similar to that in Reference Example 8, the title compound (505 mg, 37%) was obtained as a white solid from the compound of Reference Example 296 (981 mg, 4.58 mmol), cesium carbonate (1.79 g, 5.50 mmol), 2,2,2-trifluoroethyl trifluoromethanesulfonate (0.726 mL, 5.04 mmol) and DMF (9.8 mL).

¹H NMR (300 MHz, DMSO-d₆) δ: 1.29 (3H, t, J=7.1 Hz), 3.86 (3H, s), 4.27 (2H, q, J=7.1 Hz), 4.67 (2H, q, J=9.1 Hz), 8.21 (1H, s).

Reference Example 298

Production of ethyl 1,6-dimethyl-3-(2,2,2-trifluoroethoxy)-1H-pyrrolo[3,2-b]pyridine-2-carboxylate A mixture of the compound of Reference Example 297 (505 mg, 1.70 mmol), 10% palladium-carbon (water-containing product, 101 mg), ethanol (5.0 mL) and THF (5.0 mL) was stirred at room temperature for 2 hr under a hydrogen atmosphere. The catalyst was filtered off, and washed with ethanol, and the filtrate was concentrated under reduced pressure. To the residue were added acetic acid (14 mL) and 3-dimethylamino-2-methyl-2-propenal (0.230 mL, 1.17 mmol), and the mixture was stirred with heating under reflux for 24 hr. The reaction mixture was concentrated under reduced pressure, the residue was diluted with saturated aqueous sodium hydrogen carbonate solution (50 mL), and the mixture was extracted with ethyl acetate (100 mL). The extract was washed with brine (50 mL), and dried over anhydrous sodium sulfate. The insoluble material was removed by filtration, and the filtrate was concentrated under reduced pressure. The residue was purified by silica gel column chromatography (eluent, hexane:ethyl acetate=98:2→80:20) to give the title compound (231 mg, 43%) as a pale-yellow solid.

¹H NMR (300 MHz, DMSO-d₆) δ: 1.32 (3H, t, J=7.1 Hz), 2.45 (3H, s), 3.90 (3H, s), 4.32 (2H, q, J=7.1 Hz), 5.22 (2H, q, J=9.1 Hz), 7.89 (1H, s), 8.34 (1H, d, J=1.5 Hz).

Reference Example 299

Production of ethyl 1,6-dimethyl-5-oxo-3-(2,2,2-trifluoroethoxy)-4,5-dihydro-1H-pyrrolo[3,2-b]pyridine-2-carboxylate A mixture of the compound of Reference Example 298 (231 mg, 0.730 mmol), 3-chloroperoxybenzoic acid (291 mg, 1.10 mmol) and acetonitrile (4.6 mL) was stirred at room temperature for 20 hr. The reaction mixture was concentrated to a half amount under reduced pressure, and the residue was diluted with ethyl acetate (150 mL). The mixture was washed with saturated aqueous sodium hydrogen carbonate solution (50 mL) and brine (50 mL), and dried over anhydrous sodium sulfate. The insoluble material was removed by filtration, and the filtrate was concentrated under reduced pressure. To the residue were added DMF (2.4 mL) and trifluoroacetic anhydride (0.508 mL, 3.66 mmol), and the mixture was stirred at room temperature for 1 hr. The reaction mixture was concentrated under reduced pressure, and the residue was diluted with saturated aqueous sodium hydrogen carbonate solution (50 mL), and the mixture was extracted with ethyl acetate (100 mL). The extract was washed with brine (50 mL), and dried over anhydrous sodium sulfate. The insoluble material was removed by filtration, and the filtrate was concentrated under reduced pressure. The precipitate was collected by filtration, and washed with diisopropyl ether to give the title compound (125 mg, 51%) as a pale-yellow powder.

¹H NMR (300 MHz, DMSO-d₆) δ: 1.29 (3H, t, J=7.2 Hz), 2.09 (3H, s), 3.85 (3H, s), 4.27 (2H, q, J=7.2 Hz), 4.51-4.72 (2H, m), 7.82 (1H, d, J=0.9 Hz), 11.69 (1H, br s).

Reference Example 300

Production of ethyl 1,6-dimethyl-3-(2,2,2-trifluoroethoxy)-5-{[(trifluoromethyl)sulfonyl]oxy}-1H-pyrrolo[3,2-b]pyridine-2-carboxylate By a method similar to that in Reference Example 269, the title compound (171 mg, 98%) was obtained as a yellow solid from the compound of Reference Example 299 (125 mg, 0.376 mmol), trifluoromethanesulfonic anhydride (0.127 mL, 0.752 mmol) and pyridine (2.5 mL).

¹H NMR (300 MHz, DMSO-d₆) δ: 1.33 (3H, t, J=7.1 Hz), 2.45 (3H, s), 3.97 (3H, s), 4.35 (2H, q, J=7.1 Hz), 5.05 (2H, q, J=9.0 Hz), 8.37 (1H, s).

Reference Example 301

Production of ethyl 1,6-dimethyl-5-phenyl-3-(2,2,2-trifluoroethoxy)-1H-pyrrolo[3,2-b]pyridine-2-carboxylate By a method similar to that in Reference Example 15, the title compound (136 mg, 94%) was obtained as a pale-yellow powder from the compound of Reference Example 300 (171 mg, 0.368 mmol), phenylboronic acid (53.9 mg, 0.442 mmol), potassium carbonate (407 mg, 2.94 mmol), toluene (1.7 mL), ethanol (1.7 mL) and Pd(PPh$_3$)$_4$ (21.3 mg, 18.4 mmol).

$^1$H NMR (300 MHz, DMSO-d$_6$) δ: 1.33 (3H, t, J=7.1 Hz), 2.43 (3H, s), 3.94 (3H, s), 4.33 (2H, q, J=7.1 Hz), 5.24 (2H, q, J=9.0 Hz), 7.40-7.53 (3H, m), 7.54-7.61 (2H, m), 8.02 (1H, s).

Reference Example 302

Production of 1,6-dimethyl-5-phenyl-3-(2,2,2-trifluoroethoxy)-1H-pyrrolo[3,2-b]pyridine-2-carboxylic acid By a method similar to that in Reference Example 12, the title compound (126 mg, 100%) was obtained as a pale-yellow solid from the compound of Reference Example 301 (136 mg, 0.347 mmol), 8N aqueous sodium hydroxide solution (0.272 mL) and ethanol (2.7 mL).

$^1$H NMR (300 MHz, DMSO-d$_6$) δ: 2.42 (3H, s), 3.94 (3H, s), 5.22 (2H, q, J=9.2 Hz), 7.39-7.53 (3H, m), 7.53-7.60 (2H, m), 7.98 (1H, s), 13.11 (1H, br s).

Reference Example 303

Production of ethyl 6-ethyl-1-methyl-3-(1-methylethoxy)-5-(thiophen-2-yl)-1H-pyrrolo[3,2-b]pyridine-2-carboxylate By a method similar to that in Reference Example 15, the title compound (120 mg, 94%) was obtained as a white powder from the compound of Reference Example 282 (150 mg, 0.342 mmol), 2-thiopheneboronic acid (52.6 mg, 0.411 mmol), potassium carbonate (378 mg, 2.74 mmol), toluene (1.5 mL), ethanol (1.5 mL) and Pd(PPh$_3$)$_4$ (19.8 mg, 17.1 µmol).

$^1$H NMR (300 MHz, DMSO-d$_6$) δ: 1.25-1.39 (12H, m), 3.02 (2H, q, J=7.4 Hz), 3.91 (3H, s), 4.32 (2H, q, J=7.1 Hz), 5.21-5.35 (1H, m), 7.16 (1H, dd, J=5.0, 3.6 Hz), 7.47 (1H, d, J=3.6 Hz), 7.60 (1H, d, J=5.0 Hz), 7.92 (1H, s).

Reference Example 304

Production of 6-ethyl-1-methyl-3-(1-methylethoxy)-5-(thiophen-2-yl)-1H-pyrrolo[3,2-b]pyridine-2-carboxylic acid By a method similar to that in Reference Example 12, the title compound (90.7 mg, 82%) was obtained as a pale-yellow solid from the compound of Reference Example 303 (120 mg, 0.322 mmol), 8N aqueous sodium hydroxide solution (0.240 mL) and ethanol (2.4 mL).

$^1$H NMR (300 MHz, DMSO-d$_6$) δ: 1.24-1.37 (9H, m), 3.01 (2H, q, J=7.6 Hz), 3.91 (3H, s), 5.23-5.37 (1H, m), 7.15 (1H, dd, J=5.0, 3.8 Hz), 7.46 (1H, d, J=3.8 Hz), 7.59 (1H, d, J=5.0 Hz), 7.89 (1H, s), 12.77 (1H, br s).

Reference Example 305

Production of ethyl 6-ethyl-1-methyl-3-(1-methylethoxy)-5-(2-oxopyridine-1(2H)-yl)-1H-pyrrolo[3,2-b]pyridine-2-carboxylate A mixture of the compound of Reference Example 283 (200 mg, 0.655 mmol), 2H-pyran-2-one (0.524 mL, 6.55 mmol) and acetic acid (4.0 mL) was stirred at 180° C. for 3 hr under microwave irradiation. The reaction mixture was concentrated under reduced pressure, and the residue was diluted with saturated aqueous sodium hydrogen carbonate solution (30 mL). The mixture was extracted with ethyl acetate (50 mL). The extract was washed with brine (30 mL), and dried over anhydrous sodium sulfate. The insoluble material was removed by filtration, and the filtrate was concentrated under reduced pressure. The residue was purified by silica gel column chromatography (eluent, hexane:ethyl acetate=98:2→50:50) to give the title compound (135 mg, 54%) as a pale-yellow powder.

$^1$H NMR (300 MHz, DMSO-d$_6$) δ: 1.14 (3H, t, J=7.5 Hz), 1.26 (6H, d, J=6.0 Hz), 1.35 (3H, t, J=7.1 Hz), 2.52-2.58 (2H, m), 3.97 (3H, s), 4.34 (2H, q, J=7.1 Hz), 4.94-5.06 (1H, m), 6.37 (1H, t, J=6.3 Hz), 6.50 (1H, d, J=9.3 Hz), 7.54-7.69 (2H, m), 8.08 (1H, s).

Reference Example 306

Production of 6-ethyl-1-methyl-3-(1-methylethoxy)-5-(2-oxopyridine-1(2H)-yl)-1H-pyrrolo[3,2-b]pyridine-2-carboxylic acid By a method similar to that in Reference Example 12, the title compound (35.3 mg, 28%) was obtained as a white powder from the compound of Reference Example 305 (135 mg, 0.352 mmol), 8N aqueous sodium hydroxide solution (0.270 mL) and ethanol (2.7 mL).

$^1$H NMR (300 MHz, DMSO-d$_6$) δ: 1.13 (3H, t, J=7.5 Hz), 1.24 (6H, d, J=6.2 Hz), 2.51-2.59 (2H, m), 3.97 (3H, s), 4.92-5.07 (1H, m), 6.31-6.41 (1H, m), 6.50 (1H, d, J=9.1 Hz), 7.52-7.70 (2H, m), 8.04 (1H, s), 12.97 (1H, br s).

Reference Example 307

Production of ethyl 6-ethyl-5-(2-fluorophenyl)-1-methyl-3-(1-methylethoxy)-1H-pyrrolo[3,2-b]pyridine-2-carboxylate By a method similar to that in Reference Example 15, the title compound (128 mg, 98%) was obtained as a white powder from the compound of Reference Example 282 (150 mg, 0.342 mmol), 2-fluorophenylboronic acid (57.5 mg, 0.411 mmol), potassium carbonate (378 mg, 2.74 mmol), toluene (1.5 mL), ethanol (1.5 mL) and Pd(PPh$_3$)$_4$ (19.8 mg, 17.1 µmol).

$^1$H NMR (300 MHz, DMSO-d$_6$) δ: 1.08 (3H, t, J=7.5 Hz), 1.25 (6H, d, J=6.0 Hz), 1.35 (3H, t, J=7.1 Hz), 2.57 (2H, q, J=7.5 Hz), 3.94 (3H, s), 4.33 (2H, q, J=7.1 Hz), 5.05-5.19 (1H, m), 7.27-7.37 (2H, m), 7.38-7.56 (2H, m), 7.97 (1H, s).

Reference Example 308

Production of 6-ethyl-5-(2-fluorophenyl)-1-methyl-3-(1-methylethoxy)-1H-pyrrolo[3,2-b]pyridine-2-carboxylic acid By a method similar to that in Reference Example 12, the title compound (107 mg, 90%) was obtained as a white powder from the compound of Reference Example 307 (128 mg, 0.333 mmol), 8N aqueous sodium hydroxide solution (0.256 mL) and ethanol (2.6 mL).

$^1$H NMR (300 MHz, DMSO-d$_6$) δ: 1.08 (3H, t, J=7.5 Hz), 1.24 (6H, d, J=6.0 Hz), 2.57 (2H, q, J=7.5 Hz), 3.94 (3H, s), 5.05-5.20 (1H, m), 7.26-7.37 (2H, m), 7.37-7.57 (2H, m), 7.94 (1H, s), 12.81 (1H, br s).

Reference Example 309

Production of ethyl 6-ethyl-5-(2-methoxyphenyl)-1-methyl-3-(1-methylethoxy)-1H-pyrrolo[3,2-b]pyridine-2-carboxylate By a method similar to that in Reference Example 15, the title compound (136 mg, 100%) was obtained as a white powder from the compound of Reference Example 282 (150 mg, 0.342 mmol), 2-methoxyphenylboronic acid (62.5 mg, 0.411 mmol), potassium carbonate (378 mg, 2.74 mmol), toluene (1.5 mL), ethanol (1.5 mL) and Pd(PPh$_3$)$_4$ (19.8 mg, 17.1 μmol).

$^1$H NMR (300 MHz, DMSO-d$_6$) δ: 1.05 (3H, t, J=7.5 Hz), 1.24 (6H, d, J=6.0 Hz), 1.35 (3H, t, J=7.1 Hz), 2.37-2.48 (2H, m), 3.69 (3H, s), 3.93 (3H, s), 4.32 (2H, q, J=7.1 Hz), 5.05-5.18 (1H, m), 7.00-7.14 (2H, m), 7.15-7.22 (1H, m), 7.37-7.46 (1H, m), 7.85 (1H, s).

Reference Example 310

Production of 6-ethyl-5-(2-methoxyphenyl)-1-methyl-3-(1-methylethoxy)-1H-pyrrolo[3,2-b]pyridine-2-carboxylic acid By a method similar to that in Reference Example 12, the title compound (119 mg, 94%) was obtained as a pale-yellow oil from the compound of Reference Example 309 (136 mg, 0.343 mmol), 8N aqueous sodium hydroxide solution (0.272 mL) and ethanol (2.7 mL).

$^1$H NMR (300 MHz, DMSO-d$_6$) δ: 1.04 (3H, t, J=7.5 Hz), 1.23 (6H, d, J=6.0 Hz), 2.38-2.50 (2H, m), 3.69 (3H, s), 3.92 (3H, s), 5.05-5.21 (1H, m), 7.00-7.14 (2H, m), 7.14-7.23 (1H, m), 7.36-7.47 (1H, m), 7.82 (1H, s), 12.70 (1H, br s).

Reference Example 311

Production of ethyl 6-ethyl-5-(2-hydroxyphenyl)-1-methyl-3-(1-methylethoxy)-1H-pyrrolo[3,2-b]pyridine-2-carboxylate By a method similar to that in Reference Example 15, the title compound (131 mg, 100%) was obtained as a white powder from the compound of Reference Example 282 (150 mg, 0.342 mmol), 2-(4,4,5,5-tetramethyl-1,3,2-dioxaborolan-2-yl)phenol (90.4 mg, 0.411 mmol), potassium carbonate (378 mg, 2.74 mmol), toluene (1.5 mL), ethanol (1.5 mL) and Pd(PPh$_3$)$_4$ (19.8 mg, 17.1 μmol).

$^1$H NMR (300 MHz, DMSO-d$_6$) δ: 1.07 (3H, t, J=7.5 Hz), 1.24 (6H, d, J=6.0 Hz), 1.35 (3H, t, J=7.1 Hz), 2.60 (2H, q, J=7.5 Hz), 3.93 (3H, s), 4.32 (2H, q, J=7.1 Hz), 5.07-5.20 (1H, m), 6.84-6.96 (2H, m), 7.09-7.16 (1H, m), 7.18-7.27 (1H, m), 7.85 (1H, s), 9.53 (1H, s).

Reference Example 312

Production of 6-ethyl-5-(2-hydroxyphenyl)-1-methyl-3-(1-methylethoxy)-1H-pyrrolo[3,2-b]pyridine-2-carboxylic acid By a method similar to that in Reference Example 12, the title compound (118 mg, 98%) was obtained as a yellow powder from the compound of Reference Example 311 (131 mg, 0.343 mmol), 8N aqueous sodium hydroxide solution (0.262 mL) and ethanol (2.6 mL).

$^1$H NMR (300 MHz, DMSO-d$_6$) δ: 1.07 (3H, t, J=7.5 Hz), 1.24 (6H, d, J=6.0 Hz), 2.60 (2H, q, J=7.5 Hz), 3.93 (3H, s), 5.09-5.22 (1H, m), 6.84-6.95 (2H, m), 7.10-7.17 (1H, m), 7.18-7.27 (1H, m), 7.83 (1H, s), 9.50 (1H, br s), 12.64 (1H, br s).

Reference Example 313

Production of ethyl 6-ethyl-1-methyl-3-(1-methylethoxy)-5-{2-[(methylsulfonyl)amino]phenyl}-1H-pyrrolo[3,2-b]pyridine-2-carboxylate By a method similar to that in Reference Example 15, the title compound (155 mg, 99%) was obtained as a white solid from the compound of Reference Example 282 (150 mg, 0.342 mmol), N-[2-(4,4,5,5-tetramethyl-1,3,2-dioxaborolan-2-yl)phenyl]methanesulfonamide (122 mg, 0.411 mmol), potassium carbonate (378 mg, 2.74 mmol), toluene (1.5 mL), ethanol (1.5 mL) and Pd(PPh$_3$)$_4$ (19.8 mg, 17.1 μmol).

$^1$H NMR (300 MHz, DMSO-d$_6$) δ: 1.09 (3H, t, J=7.5 Hz), 1.23 (6H, d, J=6.0 Hz), 1.35 (3H, t, J=7.1 Hz), 2.58 (2H, q, J=7.5 Hz), 2.88 (3H, s), 3.95 (3H, s), 4.33 (2H, q, J=7.1 Hz), 5.00-5.13 (1H, m), 7.17-7.36 (2H, m), 7.38-7.48 (1H, m), 7.49-7.58 (1H, m), 7.98 (1H, s), 8.77 (1H, br s).

Reference Example 314

Production of 6-ethyl-1-methyl-3-(1-methylethoxy)-5-{2-[(methylsulfonyl)amino]phenyl}-1H-pyrrolo[3,2-b]pyridine-2-carboxylic acid By a method similar to that in Reference Example 12, the title compound (140 mg, 96%) was obtained as a white powder from the compound of Reference Example 313 (155 mg, 0.337 mmol), 8N aqueous sodium hydroxide solution (0.310 mL) and ethanol (3.1 mL).

$^1$H NMR (300 MHz, DMSO-d$_6$) δ: 1.10 (3H, t, J=7.5 Hz), 1.23 (6H, d, J=6.2 Hz), 2.58 (2H, q, J=7.5 Hz), 2.89 (3H, s), 3.96 (3H, s), 5.00-5.15 (1H, m), 7.22-7.37 (2H, m), 7.39-7.49 (1H, m), 7.51-7.59 (1H, m), 7.97 (1H, s), 8.75 (1H, s), 12.83 (1H, br s).

Reference Example 315

Production of ethyl 6-ethyl-5-[2-fluoro-4-(trifluoromethyl)phenyl]-1-methyl-3-(1-methylethoxy)-1H-pyrrolo[3,2-b]pyridine-2-carboxylate By a method similar to that in Reference Example 15, the title compound (149 mg, 96%) was obtained as a pale-yellow powder from the compound of Reference Example 282 (150 mg, 0.342 mmol), 2-fluoro-4-(trifluoromethyl)phenylboronic acid (85.5 mg, 0.342 mmol), potassium carbonate (378 mg, 2.74 mmol), toluene (1.5 mL), ethanol (1.5 mL) and Pd(PPh$_3$)$_4$ (19.8 mg, 17.1 μmol).

$^1$H NMR (300 MHz, DMSO-d$_6$) δ: 1.10 (3H, t, J=7.5 Hz), 1.25 (6H, d, J=6.2 Hz), 1.35 (3H, t, J=7.2 Hz), 2.58 (2H, q, J=7.5 Hz), 3.95 (3H, s), 4.34 (2H, q, J=7.2 Hz), 5.03-5.17 (1H, m), 7.65-7.77 (2H, m), 7.83 (1H, d, J=9.8 Hz), 8.03 (1H, s).

Reference Example 316

Production of 6-ethyl-5-[2-fluoro-4-(trifluoromethyl)phenyl]-1-methyl-3-(1-methylethoxy)-1H-pyrrolo[3,2-b]pyridine-2-carboxylic acid By a method similar to that in Reference Example 12, the title compound (140 mg, 100%) was obtained as a white powder from the compound of Reference Example 315 (149 mg, 0.329 mmol), 8N aqueous sodium hydroxide solution (0.298 mL) and ethanol (4.5 mL).

$^1$H NMR (300 MHz, DMSO-$d_6$) δ: 1.10 (3H, t, J=7.5 Hz), 1.24 (6H, d, J=6.0 Hz), 2.57 (2H, q, J=7.5 Hz), 3.95 (3H, s), 5.03-5.17 (1H, m), 7.64-7.76 (2H, m), 7.83 (1H, d, J=9.6 Hz), 7.99 (1H, s), 12.91 (1H, br s).

Reference Example 317

Production of ethyl 6-ethyl-5-{[(4-fluorophenyl)carbonyl]amino}-1-methyl-3-(1-methylethoxy)-1H-pyrrolo[3,2-b]pyridine-2-carboxylate By a method similar to that in Reference Example 23, the title compound (155 mg, 74%) was obtained as a white powder from the compound of Reference Example 283 (150 mg, 0.491 mmol), pyridine (119 μL, 1.47 mmol), 4-fluorobenzoyl chloride (118 μL, 0.982 mmol) and THF (1.5 mL).

$^1$H NMR (300 MHz, DMSO-$d_6$) δ: 1.19-1.27 (9H, m), 1.35 (3H, t, J=7.1 Hz), 2.69 (2H, q, J=7.5 Hz), 3.94 (3H, s), 4.32 (2H, q, J=7.1 Hz), 5.01-5.14 (1H, m), 7.31-7.42 (2H, m), 7.95 (1H, s), 8.02-8.13 (2H, m), 10.56 (1H, s).

Reference Example 318

Production of 6-ethyl-5-{[(4-fluorophenyl)carbonyl]amino}-1-methyl-3-(1-methylethoxy)-1H-pyrrolo[3,2-b]pyridine-2-carboxylic acid By a method similar to that in Reference Example 12, the title compound (109 mg, 75%) was obtained as a white powder from the compound of Reference Example 317 (155 mg, 0.363 mmol), 8N aqueous sodium hydroxide solution (0.310 mL) and ethanol (4.7 mL).

$^1$H NMR (300 MHz, DMSO-$d_6$) δ: 1.16-1.30 (9H, m), 2.68 (2H, q, J=7.6 Hz), 3.93 (3H, s), 5.02-5.16 (1H, m), 7.30-7.43 (2H, m), 7.92 (1H, s), 8.02-8.15 (2H, m), 10.53 (1H, s), 12.81 (1H, br s).

Reference Example 319

Production of ethyl 2,4-dichloro-6-ethylpyridine-3-carboxylate

A mixture of the compound of Reference Example 2 (500 mg, 2.18 mmol) and phosphorus oxychloride (20 mL) was heated under reflux for 8.5 hr. After cooling, the mixture was concentrated under reduced pressure, and the residue was poured into ice water. The obtained mixture was extracted with ethyl acetate, and the extract was washed successively with saturated aqueous sodium hydrogen carbonate and brine, dried over magnesium sulfate, and concentrated under reduced pressure. The residue was purified by silica gel column chromatography (eluent, hexane:ethyl acetate=90:10→50:50) to give the title compound (406 mg, 75%) as a pale-yellow liquid.

$^1$H NMR (300 MHz, CDCl$_3$) δ: 1.30 (3H, t, J=7.6 Hz), 1.42 (3H, t, J=7.2 Hz), 2.80 (2H, q, J=7.6 Hz), 4.47 (2H, 7.2 Hz), 7.18 (1H, s).

Reference Example 320

Production of ethyl 4-(benzyloxy)-2-chloro-6-ethylpyridine-3-carboxylate

To a solution of benzyl alcohol (3.2 mL, 31 mmol) in THF (50 mL) was added sodium hydride (60% in oil, 1.2 g, 31 mmol) by small portions under ice-cooling, and the mixture was stirred at 0° C. for 30 min. A solution of the compound of Reference Example 319 (7.3 g, 30 mmol) in THF (23 mL) was added dropwise to the reaction mixture under ice-cooling, and the mixture was stirred at room temperature for 15 hr. To the reaction mixture was added water under ice-cooling, and the mixture was extracted twice with ethyl acetate. The extract was washed with brine, dried over magnesium sulfate, and concentrated under reduced pressure. The residue was purified by silica gel column chromatography (eluent, hexane:ethyl acetate=95:5→60:40) to give the title compound (5.9 g, 62%) as a colorless oil.

$^1$H NMR (300 MHz, CDCl$_3$) δ: 1.18-1.29 (3H, m), 1.30-1.39 (3H, m), 2.59-2.85 (2H, m), 4.40 (2H, q, J=7.2 Hz), 5.10-5.22 (2H, m), 6.69 (1H, s), 7.28-7.45 (5H, m).

Reference Example 321

Production of ethyl 5-bromo-2-chloro-6-ethyl-4-hydroxypyridine-3-carboxylate

To a solution of the compound of Reference Example 320 (5.9 g, 18 mmol) in acetic acid (30 mL) was added dropwise a solution of bromine (1.1 mL, 22 mmol) in acetic acid (25 mL), and the mixture was stirred at room temperature for 16 hr. The reaction mixture was stirred at 65° C. for 3 hr, and then at 70° C. for 3 hr. The reaction mixture was concentrated under reduced pressure, and the residue was dissolved in ethyl acetate, and the solution was washed with water and brine. The aqueous layer was extracted with ethyl acetate. The combined organic layer was dried over magnesium sulfate, and concentrated under reduced pressure. The residue was purified by silica gel column chromatography (eluent, hexane:ethyl acetate=98:2→87:13), and purified again by silica gel column chromatography (eluent, hexane:ethyl acetate=98:2→87:13) to give the title compound (3.6 g, 63%) as a pale-brown oil.

$^1$H NMR (300 MHz, CDCl$_3$) δ: 1.28 (3H, t, J=7.6 Hz), 1.47 (3H, t, J=7.2 Hz), 2.96 (2H, q, J=7.5 Hz), 4.51 (2H, q, J=7.2 Hz), 12.75 (1H, br s).

Reference Example 322

Production of ethyl 5-bromo-2-chloro-4-[(2,2-dimethylpropanoyl)oxy]-6-ethylpyridine-3-carboxylate To a solution of the compound of Reference Example 321 (3.6 g, 12 mmol) and triethylamine (3.2 mL, 23 mmol) in THF (35 mL) was added dropwise under ice-cooling 2,2-dimethylpropanoyl chloride (1.7 mL, 14 mmol), and the mixture was stirred at room temperature for 13.5 hr. To the reaction mixture was added saturated aqueous sodium hydrogen carbonate, and the mixture was extracted twice with ethyl acetate. The extract was washed with brine, dried over magnesium sulfate, and concentrated under reduced pressure. The residue was purified by silica gel column chromatography (eluent, hexane:ethyl acetate=98:2→90:10) to give the title compound (4.5 g, 100%) as a pale-yellow oil.

$^1$H NMR (300 MHz, CDCl$_3$) δ: 1.24-1.33 (3H, m), 1.34-1.43 (12H, m), 3.00 (2H, q, J=7.6 Hz), 4.38 (2H, q, J=7.2 Hz).

Reference Example 323

Production of ethyl 5-bromo-4-[(2,2-dimethylpropanoyl)oxy]-2-[(2-ethoxy-2-oxoethyl)(methyl)amino]-6-ethylpyridine-3-carboxylate A solution of the compound of Reference Example 322 (4.4 g, 11 mmol), ethyl sarcosinate hydrochloride (2.6 g, 17 mmol) and triethylamine (4.6 mL, 33 mmol) in DMF (44 mL) was stirred at 80° C. for 15 hr. After allowing to cool to room temperature, to the reaction mixture was added water, and the mixture was extracted twice with ethyl acetate. The extract was washed with brine, dried over magnesium sulfate, and concentrated under reduced pressure. The residue was purified by silica gel column chromatography (eluent, hexane:ethyl acetate=95:5→80:20) to give the title compound (1.6 g, 30%) as a pale-a brown oil.

$^1$H NMR (300 MHz, CDCl$_3$) δ: 1.12-1.31 (6H, m), 1.31-1.41 (12H, m), 2.80 (2H, q, J=7.6 Hz), 3.05 (3H, s), 4.07-4.24 (4H, m), 4.31 (2H, q, J=7.2 Hz).

Reference Example 324

Production of ethyl 5-bromo-4-[(2,2-dimethylpropanoyl)oxy]-6-ethyl-3-hydroxy-1-methyl-1H-pyrrolo[2,3-b]pyridine-2-carboxylate A solution of the compound of Reference Example 323 (525 mg, 1.1 mmol) and potassium tert-butoxide (249 mg, 2.2 mmol) in ethanol (10 mL) was stirred at room temperature for 1 hr. The reaction mixture was neutralized with acetic acid, and stirred under ice-cooling for 1 hr. The precipitated solid was collected by filtration. The solid was washed with water, and dried under reduced pressure to give the title compound (410 mg, 86%) as a white powder.

$^1$H NMR (300 MHz, CDCl$_3$) δ: 1.27-1.46 (15H, m), 2.99 (2H, q, J=7.4 Hz), 4.07 (3H, s), 4.38 (2H, q, J=7.2 Hz), 6.36 (1H, s).

Reference Example 325

Production of ethyl 5-bromo-4-[(2,2-dimethylpropanoyl)oxy]-6-ethyl-1-methyl-3-(2,2,2-trifluoroethoxy)-1H-pyrrolo[2,3-b]pyridine-2-carboxylate To a solution of the compound of Reference Example 324 (400 mg, 0.94 mmol) and cesium carbonate (335 mg, 1.0 mmol) in DMF (4.0 mL) was added under ice-cooling 2,2,2-trifluoroethyl trifluoromethanesulfonate (0.16 mL, 1.1 mmol), and the mixture was stirred at room temperature for 19.5 hr. To the reaction mixture were added saturated aqueous sodium hydrogen carbonate and water, and the mixture was extracted twice with ethyl acetate. The extract was washed with brine, dried over magnesium sulfate, and concentrated under reduced pressure. The residue was purified by silica gel column chromatography (eluent, hexane:ethyl acetate=98:2→90:10) to give the title compound (463 mg, 97%) as a white powder.

$^1$H NMR (300 MHz, CDCl$_3$) δ: 1.28-1.47 (15H, m), 3.08 (2H, q, J=7.4 Hz), 4.10 (3H, s), 4.41 (2H, q, J=7.0 Hz), 4.54 (2H, q, J=8.2 Hz).

Reference Example 326

Production of ethyl 5-bromo-6-ethyl-4-hydroxy-1-methyl-3-(2,2,2-trifluoroethoxy)-1H-pyrrolo[2,3-b]pyridine-2-carboxylate A solution of the compound of Reference Example 325 (663 mg, 1.3 mmol) and 20% ethanol solution (886 mg, 2.6 mmol) of sodium ethoxide in ethanol (20 mL) was stirred at room temperature for 64 hr. The reaction mixture was neutralized with 1N hydrochloric acid, diluted with water, and stirred at 0° C. for 20 min. The precipitated solid was collected by filtration, and washed with water, and dried under reduced pressure to give the title compound (480 mg, 87%) as a pale-yellow powder.

$^1$H NMR (300 MHz, CDCl$_3$) δ: 1.29-1.37 (3H, m), 1.46 (3H, t, J=7.2 Hz), 3.06 (2H, q, J=7.4 Hz), 3.96 (3H, s), 4.49 (2H, q, J=7.2 Hz), 4.88 (2H, q, J=8.3 Hz), 9.41 (1H, br s).

Reference Example 327

Production of ethyl 5-bromo-6-ethyl-4-methoxy-1-methyl-3-(2,2,2-trifluoroethoxy)-1H-pyrrolo[2,3-b]pyridine-2-carboxylate A solution of the compound of Reference Example 326 (295 mg, 0.69 mmol), dimethyl sulfate (0.13 ml, 1.4 mmol) and potassium carbonate (192 mg, 1.4 mmol) in acetone (6.0 mL) was heated under reflux for 14 hr. After allowing to cool to room temperature, the reaction mixture was diluted with water, and the precipitated solid was collected by filtration, washed with water, and dried under reduced pressure to give the title compound (285 mg, 93%) as a pale-yellow powder.

$^1$H NMR (300 MHz, CDCl$_3$) δ: 1.35 (3H, t, J=7.4 Hz), 1.46 (3H, t, J=7.2 Hz), 3.08 (2H, q, J=7.4 Hz), 3.94 (3H, s), 4.06 (3H, s), 4.45 (2H, q, J=7.2 Hz), 4.67 (2H, q, J=8.3 Hz).

Reference Example 328

Production of 6-ethyl-5-(4-fluorophenyl)-4-methoxy-1-methyl-3-(2,2,2-trifluoroethoxy)-1H-pyrrolo[2,3-b]pyridine-2-carboxylic acid A mixture of the compound of Reference Example 327 (225 mg, 0.51 mmol), (4-fluorophenyl)boronic acid (108 mg, 0.77 mmol) tetrakis(triphenylphosphine)palladium(0) (59 mg, 0.051 mmol), 2N aqueous sodium carbonate solution (2.0 mL) and DME (2.5 mL) was stirred at 80° C. for 3 hr. Tetrakis(triphenylphosphine)palladium(0) (30 mg, 0.026 mmol) was added thereto, and the mixture was stirred at 80° C. for 3.5 hr. After allowing to cool to room temperature, to the reaction mixture was added brine, and the mixture was extracted twice with ethyl acetate. The extract was dried over magnesium sulfate, concentrated under reduced pressure, and the residue was purified by silica gel column chromatography (eluent, hexane:ethyl acetate=98:2→90:10). The obtained compound was dissolved in a mixed solvent of ethanol (4.0 mL) and THF (2.0 mL), 8N aqueous sodium hydroxide solution (0.40 mL) was added thereto, and the mixture was stirred at room temperature for 2 hr. The reaction mixture was neutralized with acetic acid, diluted with water, and stirred at 0° C. for 20 min. The precipitated solid was collected by filtration, washed with water, and dried under reduced pressure to give the title compound (143 mg, 66%) as a pale-yellow powder.

$^1$H NMR (300 MHz, CDCl$_3$) δ: 1.19 (3H, t, J=7.5 Hz), 2.68 (2H, q, J=7.4 Hz), 4.05-4.22 (8H, m), 7.12-7.22 (2H, m), 7.22-7.32 (2H, m).

Reference Example 329

Production of ethyl 3-ethyl-6-{[1-(hydroxyacetyl)piperidin-4-yl]carbamoyl}-5-methyl-7-(1-methylethoxy)-5H-pyrrolo[2,3-b]pyrazine-2-carboxylate By a method similar to that in Example 1, the title compound (342 mg, 81%) was obtained as yellow crystals from the compound of Reference Example 253 (297 mg, 0.886 mmol), 2-(4-aminopiperidin-1-yl)-2-oxoethanol hydrochloride (216 mg, 1.11 mmol), HOBt (183 mg, 1.35 mmol), WSCD (247 mg, 1.29 mmol) and triethylamine (230 μL, 1.65 mmol).

$^1$H NMR (300 MHz, DMSO-$d_6$) δ: 1.29 (3H, t, J=7.5 Hz), 1.32-1.38 (9H, m), 1.38-1.64 (2H, m), 1.85-2.00 (2H, m), 2.82-3.00 (1H, m), 3.02-3.23 (3H, m), 3.60-3.77 (1H, m), 3.98 (3H, s), 4.02-4.17 (3H, m), 4.18-4.31 (1H, m), 4.39 (2H, q, J=7.0 Hz), 4.53 (1H, t, J=5.4 Hz), 5.22-5.36 (1H, m), 7.97 (1H, d, J=7.7 Hz).

Reference Example 330

Production of ethyl 5-amino-6-ethyl-1-methyl-3-(1-methylethoxy)-1H-pyrrolo[2,3-b]pyridine-2-carboxylate To a mixture of the compound of Reference Example 84 (799 mg, 2.16 mmol), benzophenonimine (0.546 mL, 3.25 mmol), cesium carbonate (1.39 g, 4.27 mmol) and toluene (10 mL) were added Pd$_2$dba$_3$ (98.3 mg, 0.107 mmol) and Xantphos (128 mg, 0.221 mmol), and the mixture was stirred at 100° C. for 20 hr under an argon atmosphere. The reaction mixture was filtered through celite, and washed with ethyl acetate. The filtrate was washed with water (10 mL) and brine (10 mL), dried over anhydrous magnesium sulfate, and concentrated under reduced pressure. The residue was separated by silica gel column chromatography (eluent, hexane:ethyl acetate=99:1→9:1) to give crude ethyl 5-[(diphenylmethylidene)amino]-6-ethyl-1-methyl-3-(1-methylethoxy)-1H-pyrrolo[2,3-b]pyridine-2-carboxylate. To a solution of the obtained compound in THF (8 mL) was added 2N hydrochloric acid (2 mL), and the mixture was stirred at room temperature for 1.5 hr. The reaction mixture was diluted with ethyl acetate (20 mL), and aqueous sodium hydrogen carbonate solution (10 mL) was added thereto. The organic layer was separated, and the aqueous layer was extracted with ethyl acetate (20 mL×3). The organic layers were combined, washed with brine (10 mL), dried over anhydrous magnesium sulfate, and concentrated under reduced pressure. The residue was purified by silica gel column chromatography (eluent, hexane:ethyl acetate=99:1→2:1) to give the title compound (613 mg, 93%) as an orange powder.

$^1$H NMR (300 MHz, DMSO-$d_6$) δ: 1.21-1.29 (9H, m), 1.33 (3H, t, J=7.2 Hz), 2.73 (2H, q, J=7.4 Hz), 3.88 (3H, s), 4.29 (2H, q, J=7.2 Hz), 4.33-4.44 (1H, m), 4.74 (2H, s), 7.17 (1H, s).

Reference Example 331

Production of ethyl 6-ethyl-1-methyl-3-(1-methylethoxy)-5-[(phenylcarbonyl)amino]-1H-pyrrolo[2,3-b]pyridine-2-carboxylate To a mixture of the compound of Reference Example 330 (149 mg, 0.487 mmol), pyridine (0.0596 mL, 0.737 mmol) and THF (2 mL) was added benzoyl chloride (0.0628 mL, 0.541 mmol), and the mixture was stirred at room temperature for 30 min. To the reaction mixture was added water (5 mL), and the mixture was extracted with ethyl acetate (10 mL×2). The organic layers were combined, washed with brine (5 mL), dried over anhydrous magnesium sulfate, and concentrated under reduced pressure. The precipitate was collected by filtration, and washed with diisopropyl ether to give the title compound (183 mg, 92%) as a white powder.

$^1$H NMR (300 MHz, DMSO-$d_6$) δ: 1.19-1.32 (9H, m), 1.36 (3H, t, J=7.2 Hz), 2.87 (2H, q, J=7.4 Hz), 3.99 (3H, s), 4.34 (2H, q, J=7.2 Hz), 4.44-4.58 (1H, m), 7.48-7.69 (3H, m), 7.98 (1H, s), 7.99-8.08 (2H, m), 10.08 (1H, s).

Reference Example 332

Production of 6-ethyl-1-methyl-3-(1-methylethoxy)-5-[(phenylcarbonyl)amino]-1H-pyrrolo[2,3-b]pyridine-2-carboxylic acid To a solution of the compound of Reference Example 331 (180 mg, 0.440 mmol) in ethanol (2 mL) was added 2N aqueous sodium hydroxide solution (0.5 mL), and the mixture was stirred at room temperature for 60 hr. The reaction mixture was acidified with 2N hydrochloric acid and diluted with water (10 mL). The precipitate was collected by filtration, and washed with water to give the title compound (163 mg, 97%) as a white powder.

$^1$H NMR (300 MHz, DMSO-$d_6$) δ: 1.25 (3H, t, J=7.5 Hz), 1.27 (6H, d, J=6.2 Hz), 2.86 (2H, q, J=7.5 Hz), 3.98 (3H, s), 4.44-4.57 (1H, m), 7.49-7.67 (3H, m), 7.94 (1H, s), 7.98-8.07 (2H, m), 10.07 (1H, s), 12.92 (1H, br s).

Example 1

Production of 6-ethyl-N-[1-(hydroxyacetyl)piperidin-4-yl]-1-methyl-5-(pyridin-3-yl)-3-(2,2,2-trifluoroethoxy)-1H-pyrrolo[2,3-b]pyridine-2-carboxamide

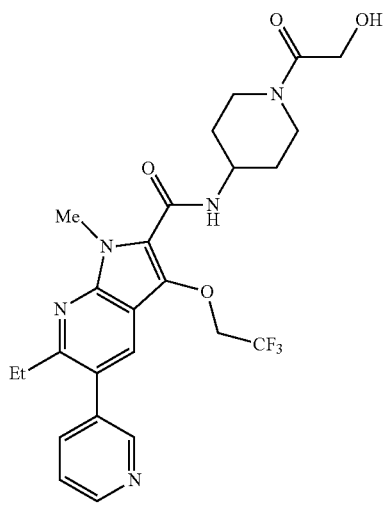 [SMILES: CCc1nc2c(cc1-c1cccnc1)c(OCC(F)(F)F)c(C(=O)NC1CCN(C(=O)CO)CC1)n2C]

A mixture of the compound of Reference Example 25 (130 mg, 0.34 mmol), 2-(4-aminopiperidin-1-yl)-2-oxoethanol hydrochloride (87 mg, 0.45 mmol), HOBt (69 mg, 0.51 mmol), WSCD (92 mg, 0.48 mmol) and triethylamine (69 mg, 0.69 mmol) in DMF (2 mL) was stirred at room temperature for 16 hr. To the reaction mixture was added 1N aqueous sodium hydroxide solution (0.5 mL), and the mixture was stirred for 30 min. The mixture was diluted with ethyl acetate, washed successively with saturated aqueous sodium hydrogen carbonate and brine, dried over magnesium sulfate, and concentrated under reduced pressure. The residue was purified by amino silica gel column chromatography (eluent, ethyl acetate) and recrystallized from diethyl ether-hexane to give the title compound (89 mg, 50%) as white crystals.

$^1$H NMR (300 MHz, DMSO-$d_6$) δ 1.17 (3H, t, J=7.5 Hz), 1.30-1.55 (2H, m), 1.92 (2H, d, J=12.9 Hz), 2.70-2.90 (3H, m), 3.12 (1H, t, J=11.7 Hz), 3.70 (1H, d, J=15.0 Hz), 3.97

(3H, s), 4.02-4.20 (3H, m), 4.28 (1H, d, J=12.6 Hz), 4.54 (1H, t, J=5.6 Hz), 5.01 (2H, q, J=9.0 Hz), 7.50-7.54 (1H, m), 7.81 (1H, d, J=7.8 Hz), 7.87-7.91 (1H, m), 8.12 (1H, s), 8.62-8.65 (2H, m).

Example 2

Production of 5-(benzylamino)-6-ethyl-N-[1-(hydroxyacetyl)piperidin-4-yl]-1-methyl-3-(2,2,2-trifluoroethoxy)-1H-pyrrolo[2,3-b]pyridine-2-carboxamide

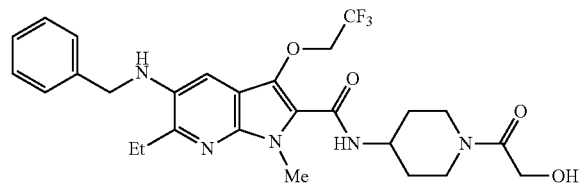 [SMILES: CCc1nc2c(cc1NCc1ccccc1)c(OCC(F)(F)F)c(C(=O)NC1CCN(C(=O)CO)CC1)n2C]

By a method similar to that in Example 1, the title compound (89.2 mg, 57%) was obtained as pale-yellow crystals from the compound of Reference Example 12 (116 mg, 0.285 mmol), 2-(4-aminopiperidin-1-yl)-2-oxoethanol hydrochloride (71.8 mg, 0.369 mmol), HOBt (60.1 mg, 0.445 mmol), WSCD (84.9 mg, 0.443 mmol), triethylamine (0.080 mL, 0.574 mmol) and DMF (1.5 mL).

$^1$H NMR (300 MHz, DMSO-d$_6$) δ: 1.21-1.48 (2H, m), 1.29 (3H, t, J=7.4 Hz), 1.79-1.97 (2H, m), 2.75-2.91 (1H, m), 2.85 (2H, q, J=7.4 Hz), 3.00-3.17 (1H, m), 3.59-3.75 (1H, m), 3.84 (3H, s), 3.94-4.16 (1H, m), 4.08 (2H, t, J=5.5 Hz), 4.18-4.32 (1H, m), 4.40 (2H, d, J=5.9 Hz), 4.52 (1H, t, J=5.5 Hz), 4.69 (2H, q, J=9.0 Hz), 5.73 (1H, t, J=5.9 Hz), 6.92 (1H, s), 7.13-7.24 (1H, m), 7.24-7.36 (2H, m), 7.35-7.48 (2H, m), 7.58 (1H, d, J=7.6 Hz).

Example 3

Production of 5-[(3-chlorophenyl)amino]-6-ethyl-N-[1-(hydroxyacetyl)piperidin-4-yl]-1-methyl-3-(2,2,2-trifluoroethoxy)-1H-pyrrolo[2,3-b]pyridine-2-carboxamide

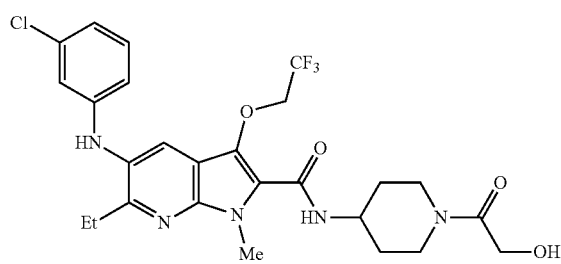 [SMILES: CCc1nc2c(cc1Nc1cccc(Cl)c1)c(OCC(F)(F)F)c(C(=O)NC1CCN(C(=O)CO)CC1)n2C]

By a method similar to that in Example 1, the title compound (108 mg, 48%) was obtained as a pale-yellow non-crystalline solid from the compound of Reference Example 14 (169 mg, 0.391 mmol), 2-(4-aminopiperidin-1-yl)-2-oxoethanol hydrochloride (99.3 mg, 0.510 mmol), HOBt (82.0 mg, 0.607 mmol), WSCD (118 mg, 0.614 mmol), triethylamine (0.110 mL, 0.789 mmol) and DMF (2 mL).

$^1$H NMR (300 MHz, DMSO-d$_6$) δ: 1.21 (3H, t, J=7.5 Hz), 1.28-1.55 (2H, m), 1.83-1.99 (2H, m), 2.70-2.93 (1H, m), 2.80 (2H, q, J=7.5 Hz), 3.01-3.21 (1H, m), 3.62-3.77 (1H, m), 3.92 (3H, s), 3.99-4.18 (3H, m), 4.20-4.36 (1H, m), 4.54 (1H, t, J=5.4 Hz), 4.92 (2H, q, J=8.9 Hz), 6.52-6.60 (2H, m), 6.62-6.70 (1H, m), 7.07-7.17 (1H, m), 7.79-7.90 (2H, m), 8.00 (1H, s).

Example 4

Production of 6-ethyl-N-[1-(hydroxyacetyl)piperidin-4-yl]-1-methyl-5-phenyl-3-(2,2,2-trifluoroethoxy)-1H-pyrrolo[2,3-b]pyridine-2-carboxamide

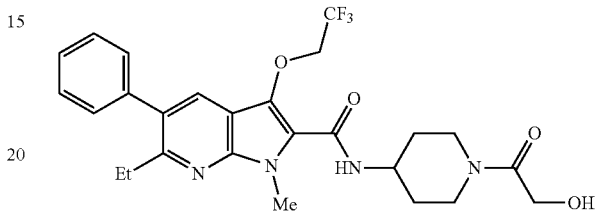

By a method similar to that in Example 1, the title compound (134 mg, 76%) was obtained as white crystals from the compound of Reference Example 16 (129 mg, 0.341 mmol), 2-(4-s aminopiperidin-1-yl)-2-oxoethanol hydrochloride (73.1 mg, 0.378 mmol), HOBt (71.2 mg, 0.527 mmol), WSCD (131 mg, 0.681 mmol), triethylamine (0.105 mL, 0.753 mmol) and DMF (2 mL).

$^1$H NMR (300 MHz, DMSO-d$_6$) δ: 1.16 (3H, t, J=7.4 Hz), 1.26-1.57 (2H, m), 1.84-2.02 (2H, m), 2.71-2.92 (1H, m), 2.79 (2H, q, J=7.4 Hz), 3.04-3.21 (1H, m), 3.62-3.80 (1H, m), 3.96 (3H, s), 4.02-4.20 (1H, m), 4.10 (2H, t, J=5.8 Hz), 4.22-4.37 (1H, m), 4.54 (1H, t, J=5.8 Hz), 5.00 (2H, q, J=8.9 Hz), 7.33-7.58 (5H, m), 7.80 (1H, d, J=7.7 Hz), 8.01 (1H, s).

Example 5

Production of 6-ethyl-N-[1-(hydroxyacetyl)piperidin-4-yl]-5-[(3-methoxyphenyl)amino]-1-methyl-3-(2,2,2-trifluoroethoxy)-1H-pyrrolo[2,3-b]pyridine-2-carboxamide

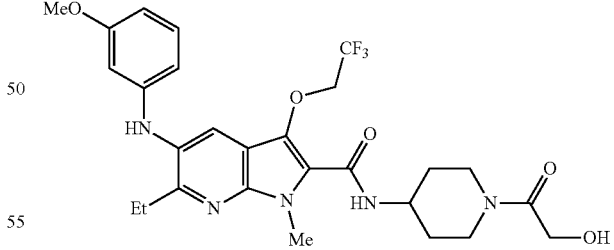

By a method similar to that in Example 1, the title compound (130 mg, 62%) was obtained as a pale-orange non-crystalline solid from the compound of Reference Example 18 (158 mg, 0.373 mmol), 2-(4-aminopiperidin-1-yl)-2-oxoethanol hydrochloride (86.5 mg, 0.444 mmol), HOBt (69.0 mg, 0.511 mmol), WSCD (96.8 mg, 0.505 mmol), triethylamine (0.104 mL, 0.746 mmol) and DMF (2.5 mL).

$^1$H NMR (300 MHz, DMSO-d$_6$) δ: 1.21 (3H, t, J=7.5 Hz), 1.29-1.55 (2H, m), 1.84-1.99 (2H, m), 2.82 (2H, q, J=7.5 Hz), 2.81-2.93 (1H, m), 3.02-3.19 (1H, m), 3.64 (3H, s), 3.65-3.76

(1H, m), 3.92 (3H, s), 4.00-4.14 (1H, m), 4.10 (2H, t, J=5.8 Hz), 4.21-4.36 (1H, m), 4.52 (1H, t, J=5.8 Hz), 4.90 (2H, q, J=9.1 Hz), 6.15-6.31 (3H, m), 7.01 (1H, t, J=8.0 Hz), 7.53 (1H, s), 7.82 (1H, d, J=7.9 Hz), 7.94 (1H, s).

Example 6

Production of 6-ethyl-5-(4-fluorophenyl)-N-[1-(hydroxyacetyl)piperidin-4-yl]-1-methyl-3-(2,2,2-trifluoroethoxy)-1H-pyrrolo[2,3-b]pyridine-2-carboxamide

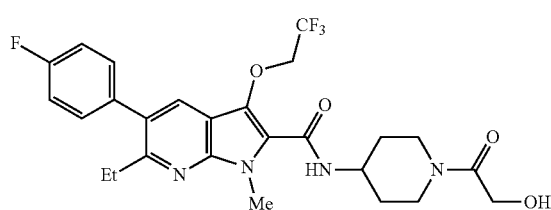 [SMILES: CCc1nc2c(cc1-c1ccc(F)cc1)c(OCC(F)(F)F)c(C(=O)NC1CCN(C(=O)CO)CC1)n2C]

By a method similar to that in Example 1, the title compound (116 mg, 68%) was obtained as white crystals from the compound of Reference Example 20 (126 mg, 0.318 mmol), 2-(4-aminopiperidin-1-yl)-2-oxoethanol hydrochloride (77.7 mg, 0.399 mmol), HOBt (62.9 mg, 0.466 mmol), WSCD (84.4 mg, 0.440 mmol), triethylamine (0.0886 mL, 0.636 mmol) and DMF (2 mL).

$^1$H NMR (300 MHz, DMSO-d$_6$) δ: 1.16 (3H, t, J=7.6 Hz), 1.26-1.56 (2H, m), 1.84-2.00 (2H, m), 2.77 (2H, q, J=7.6 Hz), 2.77-2.94 (1H, m), 3.03-3.21 (1H, m), 3.63-3.78 (1H, m), 3.96 (3H, s), 4.01-4.16 (1H, m), 4.10 (2H, t, J=5.6 Hz), 4.20-4.37 (1H, m), 4.53 (1H, t, J=5.6 Hz), 5.00 (2H, q, J=8.9 Hz), 7.23-7.39 (2H, m), 7.39-7.54 (2H, m), 7.79 (1H, d, J=7.6 Hz), 8.01 (1H, s).

Example 7

Production of 6-ethyl-N-[1-(hydroxyacetyl)piperidin-4-yl]-1-methyl-5-[(phenylcarbonyl)amino]-3-(2,2,2-trifluoroethoxy)-1H-pyrrolo[2,3-b]pyridine-2-carboxamide

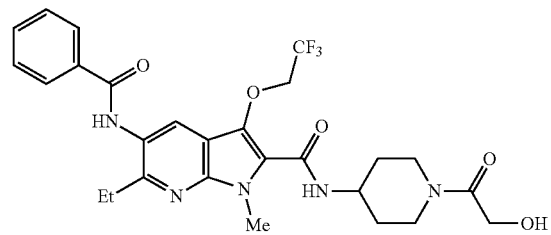 [SMILES: CCc1nc2c(cc1NC(=O)c1ccccc1)c(OCC(F)(F)F)c(C(=O)NC1CCN(C(=O)CO)CC1)n2C]

By a method similar to that in Example 1, the title compound (52.4 mg, 53%) was obtained as white crystals from the compound of Reference Example 22 (74.0 mg, 0.176 mmol), 2-(4-aminopiperidin-1-yl)-2-oxoethanol hydrochloride (44.3 mg, 0.228 mmol), HOBt (38.1 mg, 0.282 mmol), WSCD (47.4 mg, 0.247 mmol), triethylamine (0.0490 mL, 0.352 mmol) and DMF (1.5 mL).

$^1$H NMR (300 MHz, DMSO-d$_6$) δ: 1.24 (3H, t, J=7.5 Hz), 1.32-1.55 (2H, m), 1.84-1.99 (2H, m), 2.79-2.92 (1H, m), 2.86 (2H, q, J=7.5 Hz), 3.02-3.19 (1H, m), 3.63-3.78 (1H, m), 3.94 (3H, s), 4.00-4.18 (1H, m), 4.10 (2H, t, J=5.6 Hz), 4.21-4.37 (1H, m), 4.53 (1H, t, J=5.6 Hz), 4.94 (2H, q, J=8.8 Hz), 7.46-7.71 (3H, m), 7.86 (1H, d, J=7.6 Hz), 8.03 (2H, d, J=6.8 Hz), 8.13 (1H, s), 10.11 (1H, s).

Example 8

Production of 6-ethyl-5-(2-fluorophenyl)-N-[1-(hydroxyacetyl)piperidin-4-yl]-1-methyl-3-(2,2,2-trifluoroethoxy)-1H-pyrrolo[2,3-b]pyridine-2-carboxamide

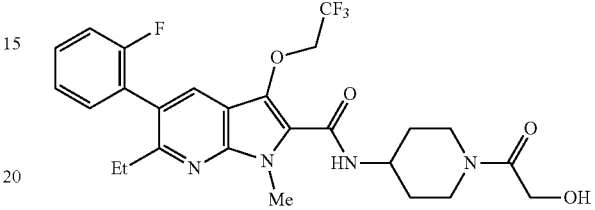

By a method similar to that in Example 1, the title compound (47.5 mg, 39%) was obtained as a white non-crystalline solid from the compound of Reference Example 73 (89.0 mg, 0.225 mmol), 2-(4-aminopiperidin-1-yl)-2-oxoethanol hydrochloride (52.4 mg, 0.269 mmol), HOBt (51.4 mg, 0.380 mmol), WSCD (80.4 mg, 0.419 mmol), triethylamine (0.0626 mL, 0.449 mmol) and DMF (1.5 mL).

$^1$H NMR (300 MHz, DMSO-d$_6$) δ: 1.14 (3H, t, J=7.3 Hz), 1.26-1.55 (2H, m), 1.83-2.01 (2H, m), 2.67 (2H, q, J=7.3 Hz), 2.78-2.94 (1H, m), 3.04-3.19 (1H, m), 3.63-3.78 (1H, m), 3.96 (3H, s), 4.02-4.18 (1H, m), 4.10 (2H, t, J=5.6 Hz), 4.22-4.35 (1H, m), 4.53 (1H, t, J=5.6 Hz), 4.99 (2H, q, J=9.0 Hz), 7.25-7.57 (4H, m), 7.81 (1H, d, J=7.7 Hz), 8.08 (1H, s).

Example 9

Production of 6-ethyl-N-[1-(hydroxyacetyl)piperidin-4-yl]-1-methyl-5-(2-oxo-2-phenylethyl)-3-(2,2,2-trifluoroethoxy)-1H-pyrrolo[2,3-b]pyridine-2-carboxamide

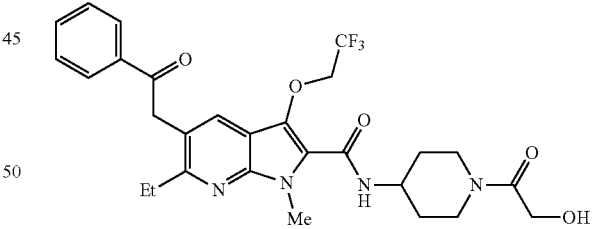

By a method similar to that in Example 1, the title compound (62.4 mg, 47%) was obtained as white crystals from the compound of Reference Example 10 (100 mg, 0.238 mmol), 2-(4-aminopiperidin-1-yl)-2-oxoethanol hydrochloride (61.3 mg, 0.315 mmol), HOBt (50.7 mg, 0.375 mmol), WSCD (67.6 mg, 0.353 mmol), triethylamine (0.0670 mL, 0.481 mmol) and DMF (1.5 mL).

$^1$H NMR (300 MHz, DMSO-d$_6$) δ: 1.22 (3H, t, J=7.3 Hz), 1.28-1.58 (2H, m), 1.82-2.02 (2H, m), 2.70 (2H, q, J=7.3 Hz), 2.78-2.94 (1H, m), 3.02-3.21 (1H, m), 3.60-3.78 (1H, m), 3.93 (3H, s), 4.00-4.19 (3H, m), 4.20-4.36 (1H, m), 4.53 (1H, t, J=5.4 Hz), 4.63 (2H, s), 4.91 (2H, q, J=8.9 Hz), 7.52-7.64 (2H, m), 7.64-7.74 (1H, m), 7.79 (1H, d, J=7.7 Hz), 8.03 (1H, s), 8.11 (2H, d, J=7.4 Hz).

Example 10

Production of 6-ethyl-N-[1-(hydroxyacetyl)piperidin-4-yl]-1-methyl-5-(pyridin-4-yl)-3-(2,2,2-trifluoroethoxy)-1H-pyrrolo[2,3-b]pyridine-2-carboxamide

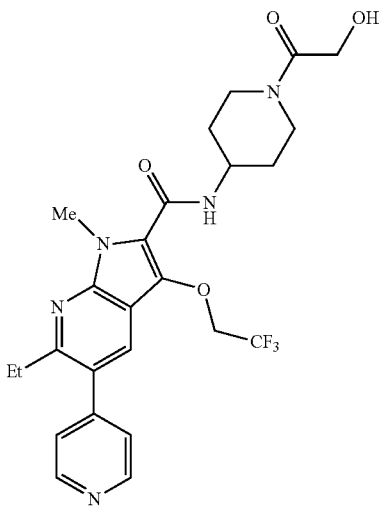 [SMILES: CCc1nc2c(cc1-c1ccncc1)c(OCC(F)(F)F)c(C(=O)NC1CCN(C(=O)CO)CC1)n2C]

By a method similar to that in Example 1, the title compound (116 mg, 86%) was obtained as white crystals from the compound of Reference Example 27 (100 mg, 0.26 mmol).

$^1$H NMR (300 MHz, DMSO-$d_6$) δ 1.18 (3H, t, J=7.5 Hz), 1.30-1.55 (2H, m), 1.92 (2H, d, J=13.2 Hz), 2.78-2.89 (3H, m), 3.11 (1H, t, J=12.9 Hz), 3.70 (1H, d, J=12.6 Hz), 3.96 (3H, s), 4.04-4.26 (3H, m), 4.28 (1H, d, J=13.8 Hz), 4.54 (1H, t, J=5.9 Hz), 5.01 (2H, q, J=9.0 Hz), 7.49 (2H, dd, J=4.5, 1.5 Hz), 7.83 (1H, d, J=7.8 Hz), 8.12 (1H, s), 8.67 (2H, dd, J=4.2, 1.5 Hz).

Example 11

Production of 6-ethyl-5-(3-fluorophenyl)-N-[1-(hydroxyacetyl)piperidin-4-yl]-1-methyl-3-(2,2,2-trifluoroethoxy)-1H-pyrrolo[2,3-b]pyridine-2-carboxamide

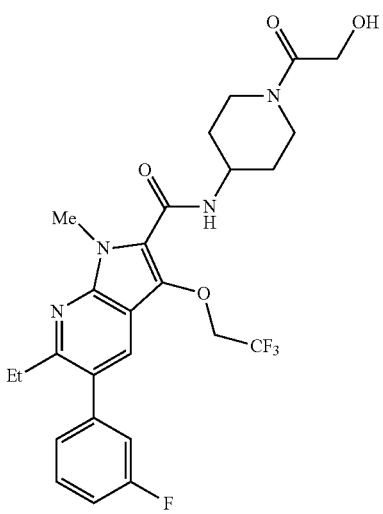 [SMILES: CCc1nc2c(cc1-c1cccc(F)c1)c(OCC(F)(F)F)c(C(=O)NC1CCN(C(=O)CO)CC1)n2C]

By a method similar to that in Example 1, the title compound (149 mg, 79%) was obtained as white crystals from the compound of Reference Example 29 (140 mg, 0.35 mmol).

$^1$H NMR (300 MHz, DMSO-$d_6$) δ 1.17 (3H, t, J=7.4 Hz), 1.29-1.50 (2H, m), 1.92 (2H, d, J=12.9 Hz), 2.73-2.89 (3H, m), 3.11 (1H, t, J=12.2 Hz), 3.70 (1H, d, J=13.5 Hz), 3.96 (3H, s), 4.03-4.12 (3H, m), 4.28 (1H, d, J=12.6 Hz), 4.54 (1H, t, J=5.4 Hz), 5.01 (2H, q, J=9.0 Hz), 7.23-7.32 (3H, m), 7.49-7.57 (1H, m), 7.80 (1H, d, J=7.8 Hz), 8.06 (1H, s).

Example 12

Production of 6-ethyl-N-[1-(hydroxyacetyl)piperidin-4-yl]-5-(2-methoxyphenyl)-1-methyl-3-(2,2,2-trifluoroethoxy)-1H-pyrrolo[2,3-b]pyridine-2-carboxamide

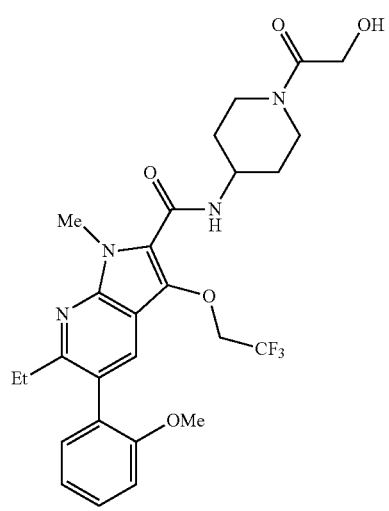 [SMILES: CCc1nc2c(cc1-c1ccccc1OC)c(OCC(F)(F)F)c(C(=O)NC1CCN(C(=O)CO)CC1)n2C]

A mixture of the compound of Reference Example 31 (140 mg, 0.34 mmol), 2-(4-aminopiperidin-1-yl)-2-oxoethanol hydrochloride (87 mg, 0.45 mmol), HOBt (65 mg, 0.48 mmol), WSCD (92 mg, 0.48 mmol) and triethylamine (69 mg, 0.69 mmol) in DMF (2 mL) was stirred at room temperature for 3 hr. The reaction mixture was diluted with saturated aqueous sodium hydrogen carbonate, and extracted twice with ethyl acetate. The extracts were combined, washed with brine, dried over magnesium sulfate, and concentrated under reduced pressure. The residue was purified by amino silica gel column chromatography (eluent, ethyl acetate) to give the title compound (170 mg, 81%) as a white non-crystalline solid.

$^1$H NMR (300 MHz, DMSO-$d_6$) δ 1.11 (3H, t, J=7.5 Hz), 1.30-1.55 (2H, m), 1.92 (2H, d, J=9.9 Hz), 2.55-2.65 (2H, m), 2.86 (1H, t, J=11.3 Hz), 3.12 (1H, t, J=12.9 Hz), 3.71 (4H, s), 3.96 (3H, s), 4.04-4.12 (3H, m), 4.27 (1H, d, J=12.0 Hz), 4.50 (1H, t, J=5.4 Hz), 4.96 (2H, q, J=9.0 Hz), 7.03-7.13 (2H, m), 7.21 (1H, dd, J=7.2, 1.5 Hz), 7.38-7.44 (1H, m), 7.72 (1H, d, J=7.5 Hz), 7.91 (1H, s).

Example 13

Production of 6-ethyl-N-[1-(hydroxyacetyl)piperidin-4-yl]-5-(3-methoxyphenyl)-1-methyl-3-(2,2,2-trifluoroethoxy)-1H-pyrrolo[2,3-b]pyridine-2-carboxamide

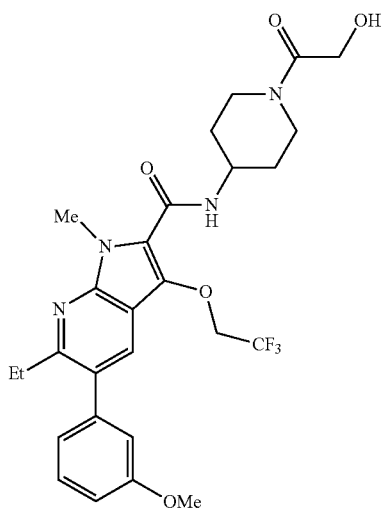 [SMILES: CCc1nc2c(cc1-c1cccc(OC)c1)c(OCC(F)(F)F)c(C(=O)NC1CCN(C(=O)CO)CC1)n2C]

By a method similar to that in Example 12, the title compound (160 mg, 86%) was obtained as a pale-yellow non-crystalline solid from the compound of Reference Example 33 (140 mg, 0.34 mmol).

$^1$H NMR (300 MHz, DMSO-$d_6$) δ 1.18 (3H, t, J=7.5 Hz), 1.30-1.55 (2H, m), 1.93 (2H, d, J=12.6 Hz), 2.77-2.90 (3H, m), 3.12 (1H, t, J=11.4 Hz), 3.70 (1H, d, J=10.8 Hz), 3.81 (3H, s), 3.97 (3H, s), 4.03-4.20 (3H, m), 4.28 (1H, d, J=12.3 Hz), 4.50 (1H, t, J=5.4 Hz), 5.00 (2H, q, J=8.9 Hz), 6.96-7.01 (3H, m), 7.39 (1H, t, J=8.0 Hz), 7.76 (1H, d, J=7.8 Hz), 8.01 (1H, s).

Example 14

Production of 6-ethyl-N-[1-(hydroxyacetyl)piperidin-4-yl]-5-(4-methoxyphenyl)-1-methyl-3-(2,2,2-trifluoroethoxy)-1H-pyrrolo[2,3-b]pyridine-2-carboxamide

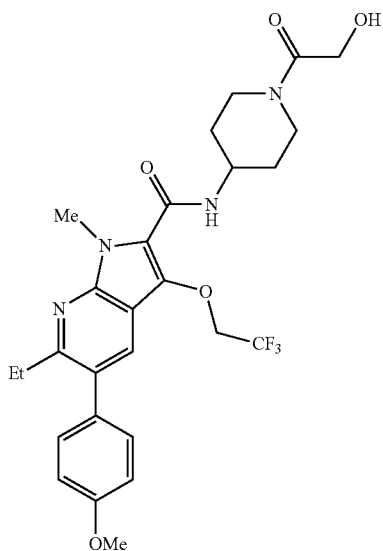 [SMILES: CCc1nc2c(cc1-c1ccc(OC)cc1)c(OCC(F)(F)F)c(C(=O)NC1CCN(C(=O)CO)CC1)n2C]

By a method similar to that in Example 12, the title compound (160 mg, 86%) was obtained as a white non-crystalline solid from the compound of Reference Example 35 (140 mg, 0.34 mmol).

$^1$H NMR (300 MHz, DMSO-$d_6$) δ 1.16 (3H, t, J=7.5 Hz), 1.30-1.55 (2H, m), 1.93 (2H, d, J=10.2 Hz), 2.75-2.90 (3H, m), 3.12 (1H, t, J=12.6 Hz), 3.71 (1H, d, J=10.2 Hz), 3.82 (3H, s), 3.95 (3H, s), 4.00-4.12 (3H, m), 4.27 (1H, d, J=11.7 Hz), 4.50 (1H, t, J=5.4 Hz), 4.98 (2H, q, J=8.9 Hz), 7.03 (2H, d, J=8.7 Hz), 7.32 (2H, d, J=8.7 Hz), 7.75 (1H, d, J=7.8 Hz), 7.95 (1H, s).

Example 15

Production of 6-ethyl-N-[1-(hydroxyacetyl)piperidin-4-yl]-1-methyl-5-(pyridin-2-yl)-3-(2,2,2-trifluoroethoxy)-1H-pyrrolo[2,3-b]pyridine-2-carboxamide

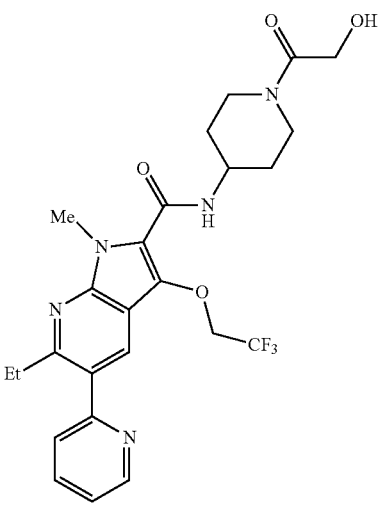 [SMILES: CCc1nc2c(cc1-c1ccccn1)c(OCC(F)(F)F)c(C(=O)NC1CCN(C(=O)CO)CC1)n2C]

A mixture of the compound of Reference Example 8 (200 mg, 0.48 mmol), 2-(tributyltin)pyridine (200 μL, 0.57 mmol) and Pd(PPh$_3$)$_4$ (28 mg, 0.024 mmol) in toluene (2 mL) was stirred at 90° C. for 2 days. After cooling, the reaction mixture was partitioned between saturated aqueous sodium hydrogen carbonate and ethyl acetate, and the organic layer was washed with brine, dried over magnesium sulfate, and concentrated under reduced pressure. The residue was purified by silica gel chromatography (eluent; ethyl acetate/hexane=⅓) to give 6-ethyl-1-methyl-5-(pyridin-2-yl)-3-(2,2,2-trifluoroethoxy)-1H-pyrrolo[2,3-b]pyridine-2-carboxylate ethyl (80 mg) as a brown solid.

A solution (0.5 mL) of this compound (80 mg) and 2N aqueous sodium hydroxide in a mixed solvent of THF (0.2 mL)-ethanol (1.5 mL) was stirred at room temperature for 2 hr. The reaction mixture was neutralized with 1N hydrochloric acid, and concentrated under reduced pressure. The residue was washed with water, and dried under reduced pressure to give 6-ethyl-1-methyl-5-(pyridin-2-yl)-3-(2,2,2-trifluoroethoxy)-1H-pyrrolo[2,3-b]pyridine-2-carboxylic acid (60 mg) as a white solid.

A mixture of this white solid (60 mg), 2-(4-aminopiperidin-1-yl)-2-oxoethanol hydrochloride (46 mg, 0.24 mmol), HOBt (37 mg, 0.27 mmol), WSCD (52 mg, 0.27 mmol) and triethylamine (40 mg, 0.40 mmol) in DMF (2 mL) was stirred at room temperature for 2 hr. The reaction mixture was diluted with saturated aqueous sodium hydrogen carbonate, and the mixture was extracted with ethyl acetate. The extract was washed with brine, dried over magnesium sulfate, and concentrated under reduced pressure. The residue was purified by amino silica gel chromatography (eluent; ethyl acetate) to give the title compound (25 mg, 10%) as a white non-crystalline solid.

$^1$H NMR (300 MHz, DMSO-d$_6$) δ 1.16 (3H, t, J=7.5 Hz), 1.30-1.55 (2H, m), 1.93 (2H, d, J=10.2 Hz), 2.75-2.90 (3H, m), 3.12 (1H, t, J=12.6 Hz), 3.71 (1H, d, J=10.2 Hz), 3.95 (3H, s), 4.00-4.12 (3H, m), 4.27 (1H, d, J=11.7 Hz), 4.50 (1H, t, J=5.4 Hz), 4.98 (2H, q, J=8.9 Hz), 7.03 (2H, d, J=8.7 Hz), 7.32 (2H, d, J=8.7 Hz), 7.75 (1H, d, J=7.8 Hz), 7.95 (1H, s).

recrystallized from ethyl acetate to give the title compound (112 mg, 53%) as white crystals.

$^1$H NMR (300 MHz, DMSO-d$_6$) δ: 1.17 (3H, t, J=7.4 Hz), 1.36-1.53 (2H, m), 1.86-1.98 (2H, m), 2.78 (2H, q, J=7.4 Hz), 2.82-2.93 (1H, m), 3.04-3.19 (1H, m), 3.64-3.78 (1H, m), 3.96 (3H, s), 4.02-4.16 (3H, m), 4.22-4.33 (1H, m), 4.53 (1H, t, J=5.4 Hz), 5.01 (2H, q, J=9.0 Hz), 7.32 (1H, dd, J=8.4, 2.7 Hz), 7.81 (1H, d, J=7.6 Hz), 8.04-8.15 (2H, m), 8.31 (1H, d, J=2.7 Hz).

Example 16

Production of 6-ethyl-5-(6-fluoropyridin-3-yl)-N-[1-(hydroxyacetyl)piperidin-4-yl]-1-methyl-3-(2,2,2-trifluoroethoxy)-1H-pyrrolo[2,3-b]pyridine-2-carboxamide

Example 17

Production of 6-ethyl-N-[1-(hydroxyacetyl)piperidin-4-yl]-5-(6-methoxypyridin-3-yl)-1-methyl-3-(2,2,2-trifluoroethoxy)-1H-pyrrolo[2,3-b]pyridine-2-carboxamide

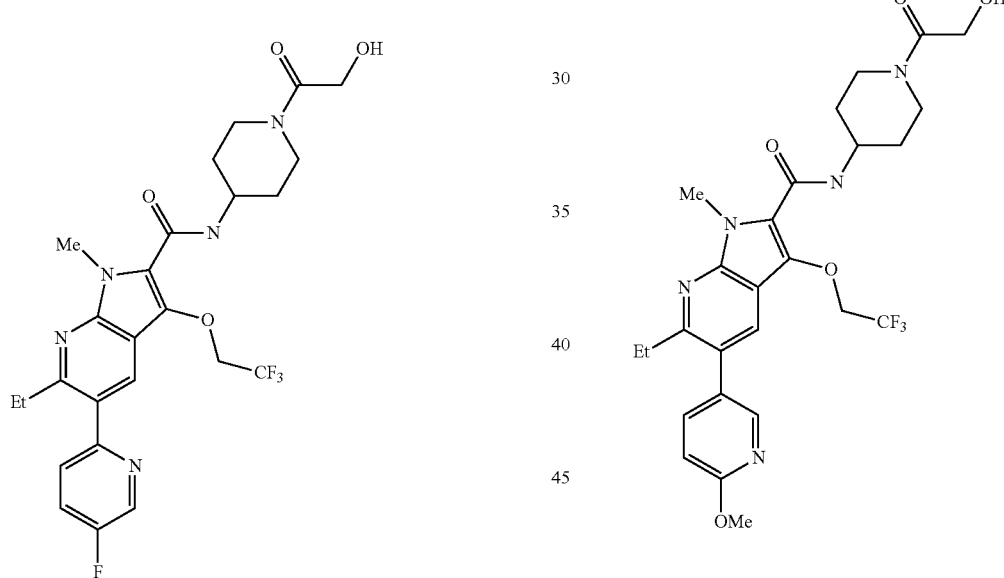

A mixture of the compound of Reference Example 118 (155 mg, 0.390 mmol), 2-(4-aminopiperidin-1-yl)-2-oxoethanol hydrochloride (91.1 mg, 0.468 mmol), HOBt (79.1 mg, 0.585 mmol), WSCD (112 mg, 0.585 mmol), triethylamine (0.162 mL, 1.17 mmol) and DMF (3.1 mL) was stirred at room temperature for 24 hr. The reaction mixture was diluted with water, and extracted twice with ethyl acetate. The extracts were combined, washed with water and brine, dried over sodium sulfate, and concentrated under reduced pressure. The residue was purified by amino silica gel chromatography (eluent; ethyl acetate) and the obtained solid was By a method similar to that in Example 16, the title compound (147 mg, 59%) was obtained as a pale-yellow non-crystalline solid from the compound of Reference Example 120 (185 mg, 0.452 mmol), 2-(4-aminopiperidin-1-yl)-2-oxoethanol hydrochloride (106 mg, 0.542 mmol), HOBt (91.6 mg, 0.678 mmol), WSCD (130 mg, 0.678 mmol), triethylamine (0.188 mL, 1.36 mmol) and DMF (3.7 mL).

$^1$H NMR (300 MHz, DMSO-d$_6$) δ: 1.17 (3H, t, J=7.4 Hz), 1.27-1.54 (2H, m), 1.86-1.98 (2H, m), 2.74-2.93 (3H, m), 3.04-3.19 (1H, m), 3.63-3.77 (1H, m), 3.91 (3H, s), 3.96 (3H, s), 4.01-4.17 (3H, m), 4.22-4.35 (1H, m), 4.53 (1H, t, J=5.5 Hz), 5.01 (2H, q, J=8.9 Hz), 6.93 (1H, d, J=8.5 Hz), 7.73-7.84 (2H, m), 8.06 (1H, s), 8.21 (1H, d, J=2.3 Hz).

Example 18

Production of 5-[(2-chlorophenyl)amino]-6-ethyl-N-[1-(hydroxyacetyl)piperidin-4-yl]-1-methyl-3-(2,2,2-trifluoroethoxy)-1H-pyrrolo[2,3-b]pyridine-2-carboxamide

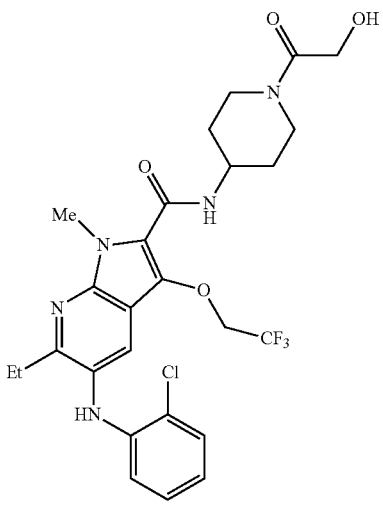 [SMILES: CCc1nc2c(cc1Nc1ccccc1Cl)c(OCC(F)(F)F)c(C(=O)NC1CCN(C(=O)CO)CC1)n2C]

By a method similar to that in Example 16, the title compound (117 mg, 43%) was obtained as a white powder from the compound of Reference Example 122 (203 mg, 0.475 mmol), 2-(4-aminopiperidin-1-yl)-2-oxoethanol hydrochloride (111 mg, 0.570 mmol), HOBt (96.3 mg, 0.713 mmol), WSCD (137 mg, 0.713 mmol), triethylamine (0.197 mL, 1.43 mmol) and DMF (4.1 mL).

$^1$H NMR (300 MHz, DMSO-$d_6$) δ: 1.20 (3H, t, J=7.5 Hz), 1.30-1.54 (2H, m), 1.84-1.98 (2H, m), 2.67-2.94 (3H, m), 3.05-3.20 (1H, m), 3.62-3.78 (1H, m), 3.94 (3H, s), 4.01-4.18 (3H, m), 4.22-4.35 (1H, m), 4.53 (1H, t, J=5.4 Hz), 4.92 (2H, q, J=8.9 Hz), 6.22-6.30 (1H, m), 6.64-6.73 (1H, m), 6.97-7.07 (1H, m), 7.29 (1H, s), 7.35 (1H, dd, J=7.8, 1.2 Hz), 7.83 (1H, d, J=7.6 Hz), 8.00 (1H, s).

Example 19

Production of 5-[(4-chlorophenyl)amino]-6-ethyl-N-[1-(hydroxyacetyl)piperidin-4-yl]-1-methyl-3-(2,2,2-trifluoroethoxy)-1H-pyrrolo[2,3-b]pyridine-2-carboxamide

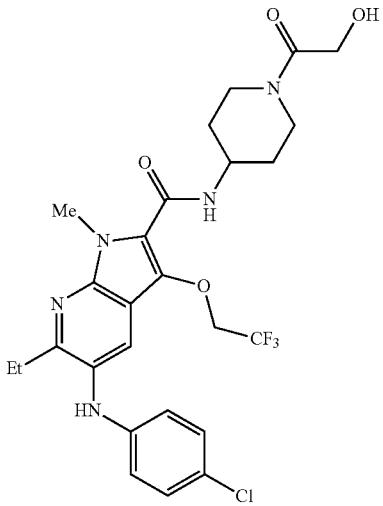 [SMILES: CCc1nc2c(cc1Nc1ccc(Cl)cc1)c(OCC(F)(F)F)c(C(=O)NC1CCN(C(=O)CO)CC1)n2C]

By a method similar to that in Example 16, the title compound (158 mg, 63%) was obtained as a pale-yellow non-crystalline solid from the compound of Reference Example 124 (190 mg, 0.444 mmol), 2-(4-aminopiperidin-1-yl)-2-oxoethanol hydrochloride (104 mg, 0.533 mmol), HOBt (90.0 mg, 0.666 mmol), WSCD (127 mg, 0.666 mmol), triethylamine (0.184 mL, 1.33 mmol) and DMF (3.8 mL).

$^1$H NMR (300 MHz, DMSO-$d_6$) δ: 1.20 (3H, t, J=7.5 Hz), 1.28-1.53 (2H, m), 1.85-1.97 (2H, m), 2.74-2.91 (3H, m), 3.02-3.19 (1H, m), 3.62-3.75 (1H, m), 3.92 (3H, s), 4.01-4.17 (3H, m), 4.21-4.34 (1H, m), 4.53 (1H, t, J=5.4 Hz), 4.91 (2H, q, J=9.1 Hz), 6.58-6.67 (2H, m), 7.09-7.18 (2H, m), 7.72 (1H, s), 7.81 (1H, d, J=7.6 Hz), 7.95 (1H, s).

Example 20

Production of 6-ethyl-N-[1-(hydroxyacetyl)piperidin-4-yl]-1-methyl-5-(phenylamino)-3-(2,2,2-trifluoroethoxy)-1H-pyrrolo[2,3-b]pyridine-2-carboxamide

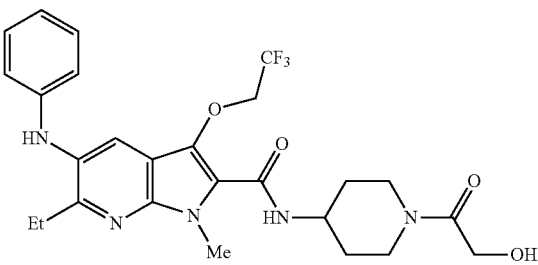 [SMILES: CCc1nc2c(cc1Nc1ccccc1)c(OCC(F)(F)F)c(C(=O)NC1CCN(C(=O)CO)CC1)n2C]

By a method similar to that in Example 1, the title compound (87.0 mg, 60%) was obtained as pale-yellow crystals from the compound of Reference Example 75 (107 mg, 0.272 mmol), 2-(4-aminopiperidin-1-yl)-2-oxoethanol hydrochloride (63.4 mg, 0.326 mmol), HOBt (57.6 mg, 0.426 mmol), WSCD (76.8 mg, 0.401 mmol), triethylamine (0.0758 mL, 0.544 mmol) and DMF (1.5 mL).

$^1$H NMR (300 MHz, DMSO-$d_6$) δ: 1.21 (3H, t, J=7.6 Hz), 1.28-1.54 (2H, m), 1.84-1.98 (2H, m), 2.82 (2H, q, J=7.6 Hz), 2.79-2.93 (1H, m), 3.03-3.19 (1H, m), 3.63-3.77 (1H, m), 3.92 (3H, s), 3.99-4.17 (1H, m), 4.10 (2H, t, J=5.6 Hz), 4.21-4.35 (1H, m), 4.53 (1H, t, J=5.6 Hz), 4.89 (2H, q, J=9.1 Hz), 6.60-6.70 (3H, m), 7.06-7.17 (2H, m), 7.52 (1H, s), 7.82 (1H, d, J=7.7 Hz), 7.93 (1H, s).

Example 21

Production of 6-ethyl-N-[1-(hydroxyacetyl)piperidin-4-yl]-5-[(2-methoxyphenyl)amino]-1-methyl-3-(2,2,2-trifluoroethoxy)-1H-pyrrolo[2,3-b]pyridine-2-carboxamide

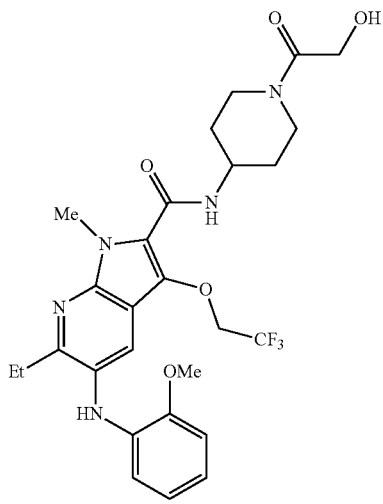 [SMILES: CCc1nc2c(cc1Nc1ccccc1OC)c(OCC(F)(F)F)c(C(=O)NC1CCN(C(=O)CO)CC1)n2C]

By a method similar to that in Example 16, the title compound (160 mg, 75%) was obtained as a pale-yellow non-crystalline solid from the compound of Reference Example 126 (160 mg, 0.378 mmol), 2-(4-aminopiperidin-1-yl)-2-oxoethanol hydrochloride (86.3 mg, 0.454 mmol), HOBt (76.6 mg, 0.567 mmol), WSCD (109 mg, 0.567 mmol), triethylamine (0.157 mL, 1.13 mmol) and DMF (3.2 mL).

$^1$H NMR (300 MHz, DMSO-$d_6$) δ: 1.20 (3H, t, J=7.5 Hz), 1.29-1.52 (2H, m), 1.84-1.97 (2H, m), 2.72-2.93 (3H, m), 3.03-3.18 (1H, m), 3.64-3.78 (1H, m), 3.86 (3H, s), 3.92 (3H, s), 4.02-4.15 (3H, m), 4.20-4.34 (1H, m), 4.53 (1H, t, J=5.5 Hz), 4.89 (2H, q, J=8.9 Hz), 6.24-6.32 (1H, m), 6.63-6.73 (2H, m), 6.78 (1H, s), 6.89-7.01 (1H, m), 7.80 (1H, d, J=7.7 Hz), 7.89 (1H, s).

Example 22

Production of 6-ethyl-5-{[(2-fluorophenyl)carbonyl]amino}-N-[1-(hydroxyacetyl)piperidin-4-yl]-1-methyl-3-(2,2,2-trifluoroethoxy)-1H-pyrrolo[2,3-b]pyridine-2-carboxamide

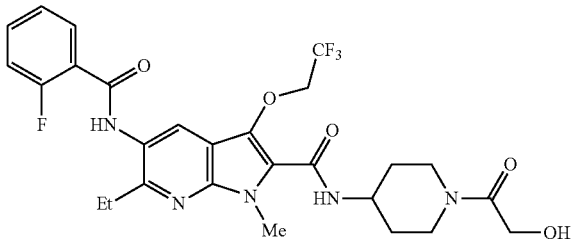 [SMILES: CCc1nc2c(cc1NC(=O)c1ccccc1F)c(OCC(F)(F)F)c(C(=O)NC1CCN(C(=O)CO)CC1)n2C]

By a method similar to that in Example 1, the title compound (92.7 mg, 73%) was obtained as white crystals from the compound of Reference Example 77 (96.0 mg, 0.219 mmol), 2-(4-aminopiperidin-1-yl)-2-oxoethanol hydrochloride (53.7 mg, 0.276 mmol), HOBt (48.0 mg, 0.355 mmol), WSCD (64.6 mg, 0.337 mmol), triethylamine (0.0610 mL, 0.438 mmol) and DMF (1.5 mL).

$^1$H NMR (300 MHz, DMSO-$d_6$) δ: 1.27 (3H, t, J=7.5 Hz), 1.32-1.55 (2H, m), 1.84-1.98 (2H, m), 2.78-2.93 (2H, m), 2.90 (2H, q, J=7.5 Hz), 3.03-3.20 (1H, m), 3.63-3.78 (1H, m), 3.93 (3H, s), 4.00-4.19 (1H, m), 4.10 (2H, t, J=5.6 Hz), 4.22-4.36 (1H, m), 4.53 (1H, t, J=5.6 Hz), 4.94 (2H, q, J=8.9 Hz), 7.31-7.44 (2H, m), 7.56-7.67 (1H, m), 7.77 (1H, td, J=7.5, 1.7 Hz), 7.88 (1H, d, J=7.7 Hz), 8.18 (1H, s), 10.04 (1H, s).

Example 23

Production of 6-ethyl-N-[1-(hydroxyacetyl)piperidin-4-yl]-5-[(4-methoxyphenyl)amino]-1-methyl-3-(2,2,2-trifluoroethoxy)-1H-pyrrolo[2,3-b]pyridine-2-carboxamide

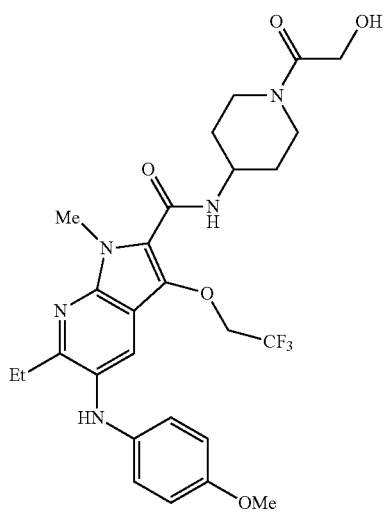 [SMILES: CCc1nc2c(cc1Nc1ccc(OC)cc1)c(OCC(F)(F)F)c(C(=O)NC1CCN(C(=O)CO)CC1)n2C]

By a method similar to that in Example 16, the title compound (171 mg, 75%) was obtained as a pale-yellow non-crystalline solid from the compound of Reference Example 128 (172 mg, 0.406 mmol), 2-(4-aminopiperidin-1-yl)-2-oxoethanol hydrochloride (93.4 mg, 0.480 mmol), HOBt (81.0 mg, 0.600 mmol), WSCD (115 mg, 0.600 mmol), triethylamine (0.169 mL, 1.22 mmol) and DMF (3.4 mL).

$^1$H NMR (300 MHz, DMSO-$d_6$) δ: 1.22 (3H, t, J=7.5 Hz), 1.29-1.52 (2H, m), 1.83-1.97 (2H, m), 2.77-2.91 (3H, m), 3.02-3.18 (1H, m), 3.63-3.75 (4H, m), 3.90 (3H, s), 4.00-4.16 (3H, m), 4.21-4.34 (1H, m), 4.52 (1H, t, J=5.5 Hz), 4.85 (2H, q, J=8.9 Hz), 6.67-6.74 (2H, m), 6.74-6.81 (2H, m), 7.15 (1H, s), 7.72-7.89 (2H, m).

Example 24

Production of 6-ethyl-5-{[(4-fluorophenyl)carbonyl]amino}-N-[1-(hydroxyacetyl)piperidin-4-yl]-1-methyl-3-(2,2,2-trifluoroethoxy)-1H-pyrrolo[2,3-b]pyridine-2-carboxamide

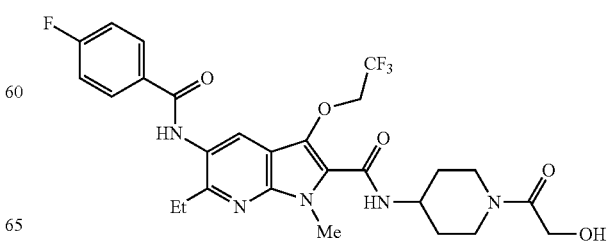

By a method similar to that in Example 1, the title compound (66.3 mg, 57%) was obtained as white crystals from the compound of Reference Example 79 (88.0 mg, 0.200 mmol), 2-(4-aminopiperidin-1-yl)-2-oxoethanol hydrochloride (47.4 mg, 0.244 mmol), HOBt (41.2 mg, 0.305 mmol), WSCD (57.3 mg, 0.299 mmol), triethylamine (0.0560 mL, 0.402 mmol) and DMF (1.5 mL).

$^1$H NMR (300 MHz, DMSO-$d_6$) δ: 1.24 (3H, t, J=7.5 Hz), 1.29-1.55 (2H, m), 1.85-1.99 (2H, m), 2.78-2.92 (1H, m), 2.85 (2H, q, J=7.5 Hz), 3.03-3.20 (1H, m), 3.63-3.79 (1H, m), 3.93 (3H, s), 4.01-4.18 (1H, m), 4.10 (2H, t, J=5.6 Hz), 4.22-4.37 (1H, m), 4.53 (1H, t, J=5.6 Hz), 4.94 (2H, q, J=9.0 Hz), 7.31-7.48 (2H, m), 7.86 (1H, d, J=7.7 Hz), 8.02-8.18 (3H, m), 10.14 (1H, s).

brine, dried over magnesium sulfate, and concentrated under reduced pressure. The residue was purified by amino silica gel column chromatography (eluent, ethyl acetate) and recrystallized from diethyl ether-hexane to give the title compound (146 mg, 78%) as white crystals.

$^1$H NMR (300 MHz, DMSO-$d_6$) δ 1.16 (3H, t, J=7.4 Hz), 1.30-1.55 (2H, m), 1.92 (2H, dd, J=12.3, 2.7 Hz), 2.74-2.89 (3H, m), 3.11 (1H, t, J=11.9 Hz), 3.70 (1H, d, J=12.0 Hz), 3.90 (3H, s), 4.00-4.15 (3H, m), 4.28 (1H, d, J=13.8 Hz), 4.53 (1H, t, J=5.4 Hz), 4.99 (2H, q, J=9.0 Hz), 7.44-7.47 (2H, m), 7.52-7.56 (2H, m), 7.80 (1H, d, J=7.5 Hz), 8.03 (1H, s).

Example 25

Production of 5-(4-chlorophenyl)-6-ethyl-N-[1-(hydroxyacetyl)piperidin-4-yl]-1-methyl-3-(2,2,2-trifluoroethoxy)-1H-pyrrolo[2,3-b]pyridine-2-carboxamide Example 26

Production of 6-ethyl-N-[1-(hydroxyacetyl)piperidin-4-yl]-1-methyl-5-[4-(1-methylethoxy)phenyl]-3-(2,2,2-trifluoroethoxy)-1H-pyrrolo[2,3-b]pyridine-2-carboxamide

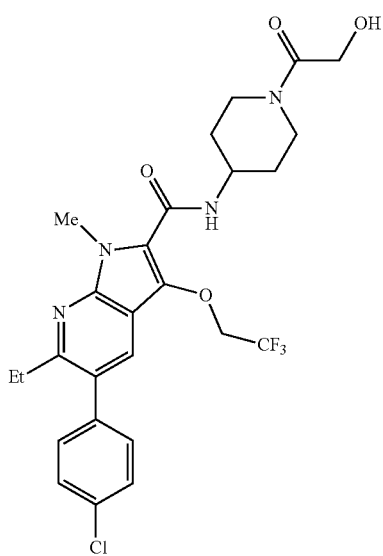 [SMILES: CCc1nc2c(cc1-c1ccc(Cl)cc1)c(OCC(F)(F)F)c(C(=O)NC1CCN(C(=O)CO)CC1)n2C]

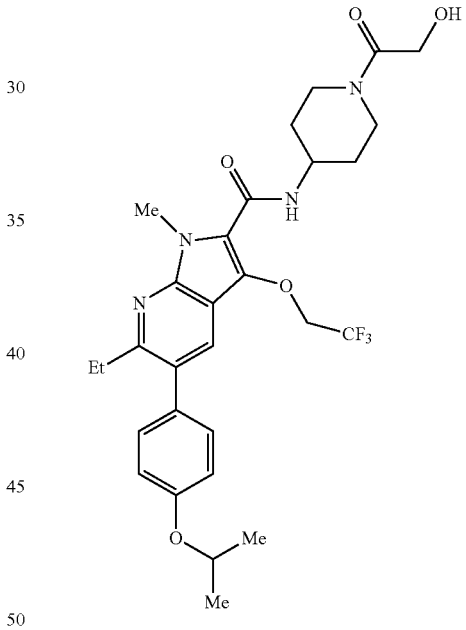

A mixture of the compound of Reference Example 37 (140 mg, 0.34 mmol), 2-(4-aminopiperidin-1-yl)-2-oxoethanol hydrochloride (79 mg, 0.41 mmol), HOBt (60 mg, 0.44 mmol), WSCD (85 mg, 0.44 mmol) and triethylamine (69 mg, 0.67 mmol) in DMF (2 mL) was stirred at room temperature for 16 hr. The reaction mixture was diluted with saturated aqueous sodium hydrogen carbonate, and extracted twice with ethyl acetate. The extracts were combined, washed with By a method similar to that in Example 25, the title compound (154 mg, 79%) was obtained as white crystals from the compound of Reference Example 39 (150 mg, 0.34 mmol).

$^1$H NMR (300 MHz, DMSO-$d_6$) δ 1.16 (3H, t, J=7.5 Hz), 1.25-1.55 (8H, m), 1.92 (2H, d, J=10.5 Hz), 2.76-2.89 (3H, m), 3.11 (1H, t, J=11.6 Hz), 3.70 (1H, d, J=12.9 Hz), 3.95 (3H, s), 4.00-4.12 (3H, m), 4.28 (1H, d, J=14.4 Hz), 4.53 (1H, t, J=5.4 Hz), 4.63-4.71 (1H, m), 4.99 (2H, q, J=9.0 Hz), 7.00 (2H, d, J=8.7 Hz), 7.30 (2H, d, J=8.7 Hz), 7.77 (1H, d, J=7.8 Hz), 7.97 (1H, s).

Example 27

Production of 6-ethyl-N-[1-(hydroxyacetyl)piperidin-4-yl]-1-methyl-3-(2,2,2-trifluoroethoxy)-5-[4-(trifluoromethyl)phenyl]-1H-pyrrolo[2,3-b]pyridine-2-carboxamide

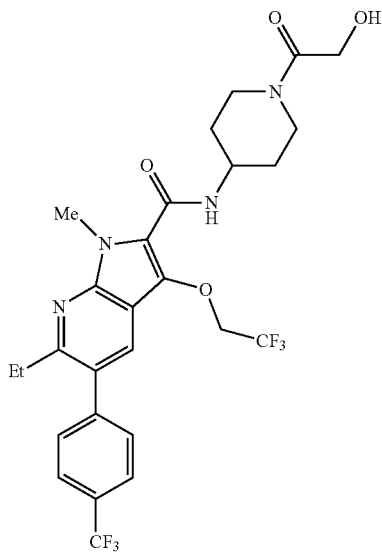 [SMILES: CCc1nc2c(cc1-c1ccc(C(F)(F)F)cc1)c(OCC(F)(F)F)c(C(=O)NC1CCN(C(=O)CO)CC1)n2C]

By a method similar to that in Example 12, the title compound (94 mg, 47%) was obtained as a white non-crystalline solid from the compound of Reference Example 41 (150 mg, 0.34 mmol).

$^1$H NMR (300 MHz, DMSO-$d_6$) δ 1.17 (3H, t, J=7.5 Hz), 1.30-1.55 (2H, m), 1.92 (2H, d, J=9.9 Hz), 2.73-2.89 (3H, m), 3.11 (1H, t, J=12.3 Hz), 3.70 (1H, d, J=13.2 Hz), 3.97 (3H, s), 4.04-4.15 (3H, m), 4.28 (1H, d, J=12.9 Hz), 4.53 (1H, br s), 5.01 (2H, q, J=9.0 Hz), 7.67 (2H, d, J=7.8 Hz), 7.80-7.86 (3H, m), 8.09 (1H, s).

Example 28

Production of 6-ethyl-5-(4-ethylphenyl)-N-[1-(hydroxyacetyl)piperidin-4-yl]-1-methyl-3-(2,2,2-trifluoroethoxy)-1H-pyrrolo[2,3-b]pyridine-2-carboxamide

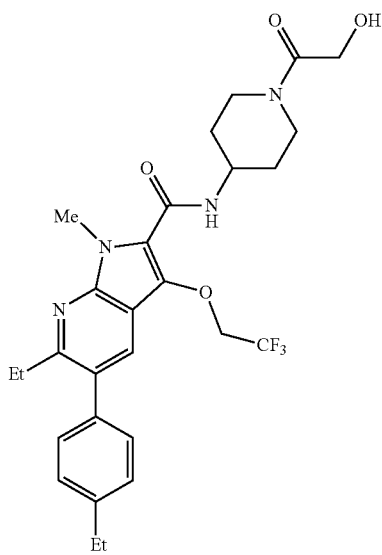

By a method similar to that in Example 25, the title compound (148 mg, 80%) was obtained as white crystals from the compound of Reference Example 43 (140 mg, 0.34 mmol).

$^1$H NMR (300 MHz, DMSO-$d_6$) δ 1.19 (3H, t, J=7.5 Hz), 1.24 (3H, t, J=7.5 Hz), 1.30-1.55 (2H, m), 1.92 (2H, d, J=12.6 Hz), 2.68 (2H, q, J=7.6 Hz), 2.75-2.89 (3H, m), 3.11 (1H, t, J=11.7 Hz), 3.70 (1H, d, J=11.1 Hz), 3.96 (3H, s), 4.02-4.15 (3H, m), 4.28 (1H, d, J=12.9 Hz), 4.53 (1H, t, J=5.4 Hz), 4.99 (2H, q, J=9.0 Hz), 7.32 (4H, s), 7.78 (1H, d, J=7.5 Hz), 7.99 (1H, s).

Example 29

Production of 6-ethyl-N-[1-(hydroxyacetyl)piperidin-4-yl]-1-methyl-5-[(thiophen-2-ylcarbonyl)amino]-3-(2,2,2-trifluoroethoxy)-1H-pyrrolo[2,3-b]pyridine-2-carboxamide

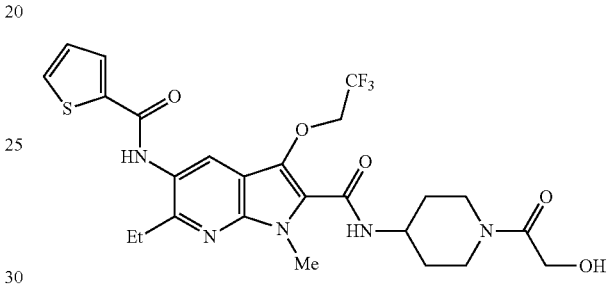

By a method similar to that in Example 1, the title compound (150 mg, 71%) was obtained as white crystals from the compound of Reference Example 81 (160 mg, 0.374 mmol), 2-(4-aminopiperidin-1-yl)-2-oxoethanol hydrochloride (86.1 mg, 0.442 mmol), HOBt (80.7 mg, 0.597 mmol), WSCD (104 mg, 0.545 mmol), triethylamine (0.0104 mL, 0.746 mmol) and DMF (2 mL).

$^1$H NMR (300 MHz, DMSO-$d_6$) δ: 1.24 (3H, t, J=7.5 Hz), 1.29-1.56 (2H, m), 1.83-1.97 (2H, m), 2.77-2.93 (1H, m), 2.85 (2H, q, J=7.5 Hz), 3.03-3.19 (1H, m), 3.63-3.77 (1H, m), 3.93 (3H, s), 4.00-4.18 (1H, m), 4.10 (2H, t, J=5.6 Hz), 4.21-4.36 (1H, m), 4.53 (1H, t, J=5.6 Hz), 4.94 (2H, q, J=9.0 Hz), 7.25 (1H, dd, J=4.8, 3.9 Hz), 7.87 (2H, d, J=6.2 Hz), 8.02 (1H, d, J=3.4 Hz), 8.13 (1H, s), 10.14 (1H, s).

Example 30

Production of 6-ethyl-5-{[(3-fluorophenyl)carbonyl]amino}-N-[1-(hydroxyacetyl)piperidin-4-yl]-1-methyl-3-(2,2,2-trifluoroethoxy)-1H-pyrrolo[2,3-b]pyridine-2-carboxamide

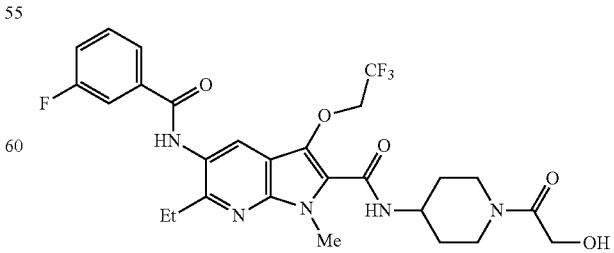

By a method similar to that in Example 1, the title compound (164 mg, 73%) was obtained as white crystals from the compound of Reference Example 83 (170 mg, 0.387 mmol), 2-(4-aminopiperidin-1-yl)-2-oxoethanol hydrochloride (88.8 mg, 0.456 mmol), HOBt (77.4 mg, 0.573 mmol), WSCD (112 mg, 0.586 mmol), triethylamine (0.0780 mL, 0.560 mmol) and DMF (3 mL).

$^1$H NMR (300 MHz, DMSO-d$_6$) δ: 1.24 (3H, t, J=7.5 Hz), 1.29-1.55 (2H, m), 1.84-2.01 (2H, m), 2.77-2.92 (1H, m), 2.85 (2H, q, J=7.5 Hz), 3.03-3.20 (1H, m), 3.63-3.78 (1H, m), 3.94 (3H, s), 4.01-4.20 (1H, m), 4.10 (2H, t, J=5.7 Hz), 4.21-4.37 (1H, m), 4.53 (1H, t, J=5.7 Hz), 4.94 (2H, q, J=8.9 Hz), 7.43-7.53 (1H, m), 7.62 (1H, td, J=7.9, 6.0 Hz), 7.77-7.85 (1H, m), 7.85-7.93 (2H, m), 8.14 (1H, s), 10.21 (1H, s).

Example 31

Production of 6-ethyl-N-[1-(hydroxyacetyl)piperidin-4-yl]-1-methyl-5-[(phenylcarbamoyl)amino]-3-(2,2,2-trifluoroethoxy)-1H-pyrrolo[2,3-b]pyridine-2-carboxamide

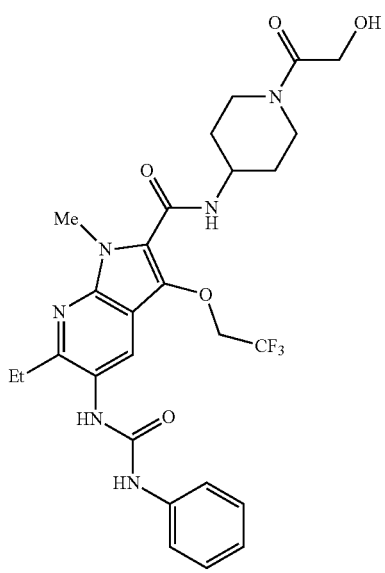 [SMILES: CCc1nc2c(cc1NC(=O)Nc1ccccc1)c(OCC(F)(F)F)c(C(=O)NC1CCN(C(=O)CO)CC1)n2C]

By a method similar to that in Example 16, the title compound (137 mg, 68%) was obtained as a white powder from compound of Reference Example 130 (152 mg, 0.348 mmol), 2-(4-aminopiperidin-1-yl)-2-oxoethanol hydrochloride (81.4 mg, 0.418 mmol), HOBt (70.5 mg, 0.522 mmol), WSCD (100 mg, 0.522 mmol), triethylamine (0.145 mL, 1.04 mmol) and DMF (3.0 mL).

$^1$H NMR (300 MHz, DMSO-d$_6$) δ: 1.28 (3H, t, J=7.5 Hz), 1.33-1.55 (2H, m), 1.84-2.00 (2H, m), 2.81-2.95 (3H, m), 3.02-3.19 (1H, m), 3.61-3.79 (1H, m), 3.90 (3H, s), 4.00-4.18 (3H, m), 4.21-4.36 (1H, m), 4.53 (1H, t, J=5.5 Hz), 4.89 (2H, q, J=8.9 Hz), 6.92-7.02 (1H, m), 7.23-7.33 (2H, m), 7.43-7.52 (2H, m), 7.85 (1H, d, J=7.7 Hz), 8.06 (1H, s), 8.31 (1H, s), 8.96 (1H, s).

Example 32

Production of 5-{[(4-chlorophenyl)carbonyl]amino}-6-ethyl-N-[1-(hydroxyacetyl)piperidin-4-yl]-1-methyl-3-(2,2,2-trifluoroethoxy)-1H-pyrrolo[2,3-b]pyridine-2-carboxamide

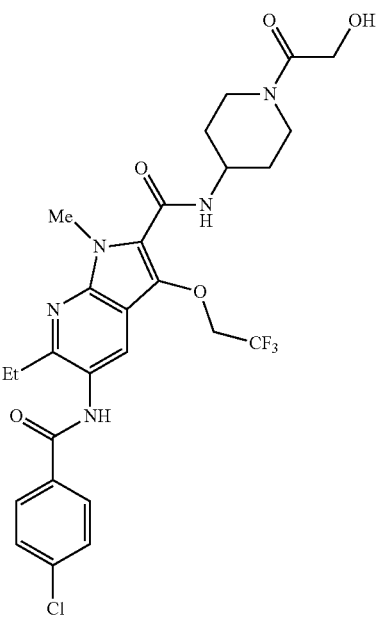 [SMILES: CCc1nc2c(cc1NC(=O)c1ccc(Cl)cc1)c(OCC(F)(F)F)c(C(=O)NC1CCN(C(=O)CO)CC1)n2C]

By a method similar to that in Example 25, the title compound (130 mg, 66%) was obtained as white crystals from the compound of Reference Example 44 (150 mg, 0.33 mmol).

$^1$H NMR (300 MHz, DMSO-d$_6$) δ 1.24 (3H, t, J=7.5 Hz), 1.30-1.50 (2H, m), 1.92 (2H, d, J=10.2 Hz), 2.84 (3H, q, J=7.5 Hz), 3.11 (1H, t, J=11.9 Hz), 3.71 (1H, d, J=14.4 Hz), 3.93 (3H, s), 4.02-4.15 (3H, m), 4.29 (1H, d, J=12.0 Hz), 4.53 (1H, t, J=5.4 Hz), 4.94 (2H, q, J=8.9 Hz), 7.64 (2H, d, J=8.4 Hz), 7.86 (1H, d, J=7.5 Hz), 8.04 (2H, d, J=8.4 Hz), 8.13 (1H, s), 10.20 (1H, s).

Example 33

Production of 6-ethyl-5-{[(4-fluorophenyl)carbonyl]amino}-N-[1-(hydroxyacetyl)piperidin-4-yl]-1-methyl-3-(1-methylethoxy)-1H-pyrrolo[2,3-b]pyridine-2-carboxamide

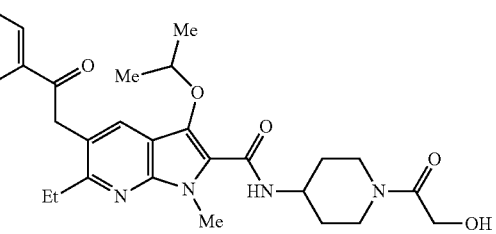

By a method similar to that in Example 1, the title compound (92.1 mg, 42%) was obtained as white crystals from the compound of Reference Example 87 (163 mg, 0.408 mmol), 2-(4-aminopiperidin-1-yl)-2-oxoethanol hydrochloride (93.9 mg, 0.482 mmol), HOBt (78.7 mg, 0.582 mmol), WSCD (111 mg, 0.577 mmol), triethylamine (0.114 mL, 0.816 mmol) and DMF (3 mL).

$^{1}$H NMR (300 MHz, DMSO-d$_{6}$) δ: 1.24 (3H, t, J=7.5 Hz), 1.31 (6H, d, J=6.0 Hz), 1.35-1.63 (2H, m), 1.85-1.99 (2H, m), 2.84 (2H, q, J=7.5 Hz), 2.81-2.94 (1H, m), 3.04-3.22 (1H, m), 3.63-3.76 (1H, m), 3.99 (3H, s), 4.03-4.18 (1H, m), 4.11 (2H, t, J=5.6 Hz), 4.22-4.36 (1H, m), 4.52 (1H, t, J=5.6 Hz), 4.61-4.77 (1H, m), 7.39 (2H, t, J=8.9 Hz), 7.85 (1H, d, J=7.9 Hz), 8.02 (1H, s), 8.09 (2H, dd, J=8.7, 5.5 Hz), 10.10 (1H, s).

Example 34

Production of 6-ethyl-N-[1-(hydroxyacetyl)piperidin-4-yl]-5-{[(4-methoxyphenyl)carbonyl]amino}-1-methyl-3-(2,2,2-trifluoroethoxy)-1H-pyrrolo[2,3-b]pyridine-2-carboxamide

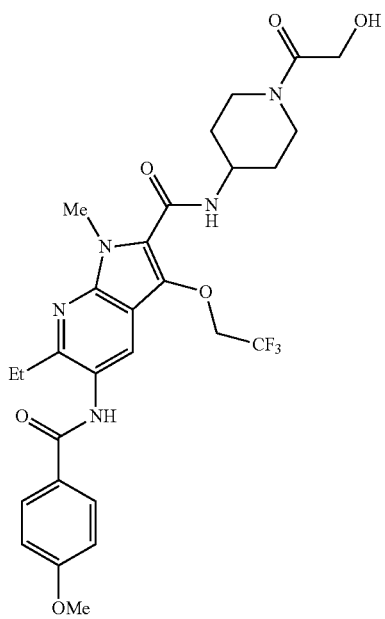 [SMILES: CCc1nc2c(cc1NC(=O)c1ccc(OC)cc1)c(OCC(F)(F)F)c(C(=O)NC1CCN(C(=O)CO)CC1)n2C]

By a method similar to that in Example 25, the title compound (82 mg, 42%) was obtained as pale-yellow crystals from the compound of Reference Example 46 (150 mg, 0.33 mmol).

$^{1}$H NMR (300 MHz, DMSO-d$_{6}$) δ 1.24 (3H, t, J=7.5 Hz), 1.30-1.55 (2H, m), 1.93 (2H, d, J=10.2 Hz), 2.85 (3H, q, J=7.5 Hz), 3.12 (1H, t, J=11.9 Hz), 3.70 (1H, d, J=13.5 Hz), 3.85 (3H, s), 3.94 (3H, s), 4.00-4.15 (3H, m), 4.29 (1H, d, J=13.2 Hz), 4.54 (1H, t, J=5.4 Hz), 4.94 (2H, q, J=9.0 Hz), 7.08 (2H, d, J=9.0 Hz), 7.86 (1H, d, J=7.8 Hz), 8.01 (2H, d, J=9.0 Hz), 8.11 (1H, s), 9.96 (1H, s).

Example 35

Production of 5-[(cyclopropylcarbonyl)amino]-6-ethyl-N-[1-(hydroxyacetyl)piperidin-4-yl]-1-methyl-3-(2,2,2-trifluoroethoxy)-1H-pyrrolo[2,3-b]pyridine-2-carboxamide

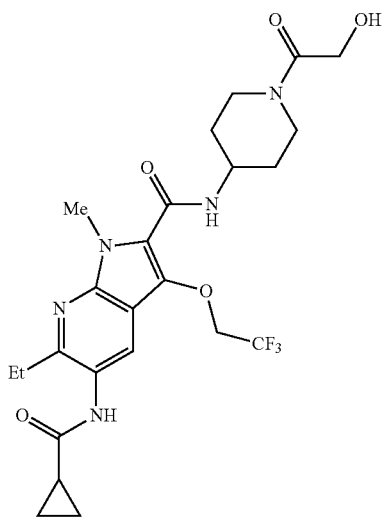 [SMILES: CCc1nc2c(cc1NC(=O)C1CC1)c(OCC(F)(F)F)c(C(=O)NC1CCN(C(=O)CO)CC1)n2C]

By a method similar to that in Example 25, the title compound (113 mg, 69%) was obtained as white crystals from the compound of Reference Example 48 (120 mg, 0.31 mmol).

$^{1}$H NMR (300 MHz, DMSO-d$_{6}$) δ 0.80 (4H, d, J=6.0 Hz), 1.23 (3H, t, J=7.5 Hz), 1.30-1.50 (2H, m), 1.86-1.99 (3H, m), 2.79-2.88 (3H, m), 3.10 (1H, t, J=11.7 Hz), 3.69 (1H, d, J=13.2 Hz), 3.90 (3H, s), 4.00-4.12 (3H, m), 4.27 (1H, d, J=12.9 Hz), 4.53 (1H, t, J=5.4 Hz), 4.90 (2H, q, J=8.9 Hz), 7.84 (1H, d, J=7.8 Hz), 8.06 (1H, s), 9.75 (1H, s).

Example 36

Production of 5-[(cyclohexylcarbonyl)amino]-6-ethyl-N-[1-(hydroxyacetyl)piperidin-4-yl]-1-methyl-3-(2,2,2-trifluoroethoxy)-1H-pyrrolo[2,3-b]pyridine-2-carboxamide

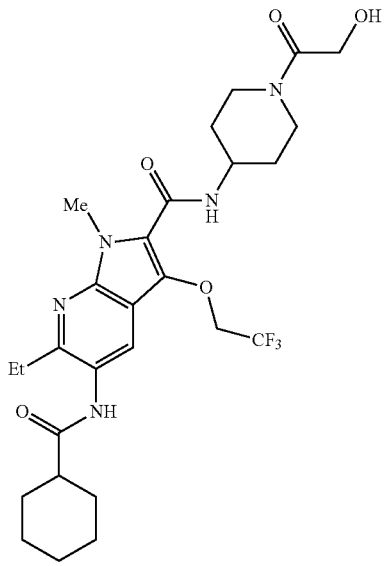 [SMILES: CCc1nc2c(cc1NC(=O)C1CCCCC1)c(OCC(F)(F)F)c(C(=O)NC1CCN(C(=O)CO)CC1)n2C]

By a method similar to that in Example 25, the title compound (123 mg, 72%) was obtained as white crystals from the compound of Reference Example 50 (130 mg, 0.30 mmol).

$^1$H NMR (300 MHz, DMSO-$d_6$) δ 1.20-1.51 (11H, m), 1.77 (1H, d, J=12.0 Hz), 1.85-1.99 (5H, m), 2.37-2.41 (1H, m), 2.75-2.87 (3H, m), 3.10 (1H, t, J=12.2 Hz), 3.70 (1H, d, J=12.9 Hz), 3.90 (3H, s), 4.00-4.12 (3H, m), 4.28 (1H, d, J=12.3 Hz), 4.53 (1H, t, J=5.4 Hz), 4.90 (2H, q, J=9.0 Hz), 7.85 (1H, d, J=7.5 Hz), 7.99 (1H, s), 9.38 (1H, s).

$^1$H NMR (300 MHz, DMSO-$d_6$) δ: 1.19-1.39 (7H, m), 1.78-1.97 (4H, m), 2.86 (2H, q, J=7.3 Hz), 3.35-3.50 (1H, m), 3.66-3.84 (1H, m), 3.93 (3H, s), 4.58 (1H, d, J=4.3 Hz), 4.95 (2H, q, J=9.0 Hz), 7.50-7.73 (4H, m), 7.98-8.07 (2H, m), 8.13 (1H, s), 10.11 (1H, s).

Example 38

Production of 6-ethyl-1-methyl-5-[(phenylcarbonyl)amino]-N-(tetrahydro-2H-thiopyran-4-yl)-3-(2,2,2-trifluoroethoxy)-1H-pyrrolo[2,3-b]pyridine-2-carboxamide Example 37

Production of 6-ethyl-N-(trans-4-hydroxycyclohexyl)-1-methyl-5-[(phenylcarbonyl)amino]-3-(2,2,2-trifluoroethoxy)-1H-pyrrolo[2,3-b]pyridine-2-carboxamide

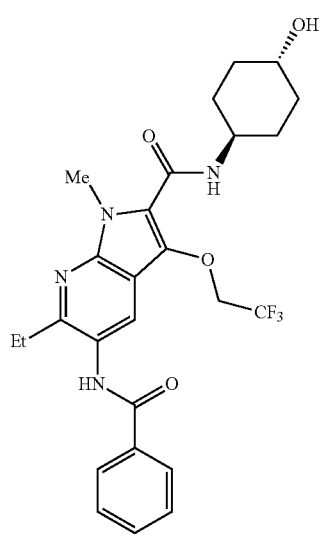 [SMILES: CCc1nc2c(cc1NC(=O)c1ccccc1)c(OCC(F)(F)F)c(C(=O)N[C@H]1CC[C@H](O)CC1)n2C]

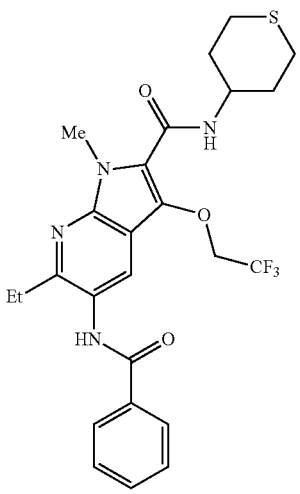 [SMILES: CCc1nc2c(cc1NC(=O)c1ccccc1)c(OCC(F)(F)F)c(C(=O)NC1CCSCC1)n2C]

By a method similar to that in Example 16, the title compound (96.5 mg, 60%) was obtained as a white powder from the compound of Reference Example 22 (130 mg, 0.309 mmol), trans-4-aminocyclohexanol (42.6 mg, 0.370 mmol), HOBt (62.7 mg, 0.464 mmol), WSCD (88.9 mg, 0.4664 mmol), triethylamine (0.128 mL, 0.927 mmol) and DMF (2.6 mL).

By a method similar to that in Example 16, the title compound (150 mg, 71%) was obtained as a white powder from the compound of Reference Example 22 (170 mg, 0.403 mmol), 4-amino-tetrahydrothiopyran (56.7 mg, 0.484 mmol), HOBt (81.8 mg, 0.605 mmol), WSCD (116 mg, 0.605 mmol), triethylamine (0.167 mL, 1.21 mmol) and DMF (3.4 mL).

$^1$H NMR (300 MHz, DMSO-$d_6$) δ: 1.24 (3H, t, J=7.5 Hz), 1.52-1.71 (2H, m), 2.11-2.24 (2H, m), 2.56-2.93 (6H, m), 3.80-3.98 (4H, m), 4.96 (2H, q, J=8.9 Hz), 7.50-7.67 (3H, m), 7.86 (1H, d, J=7.9 Hz), 7.98-8.08 (2H, m), 8.14 (1H, s), 10.12 (1H, s).

Example 39

Production of 3-ethoxy-6-ethyl-5-{[(4-fluorophenyl)carbonyl]amino}-N-[1-(hydroxyacetyl)piperidin-4-yl]-1-methyl-1H-pyrrolo[2,3-b]pyridine-2-carboxamide

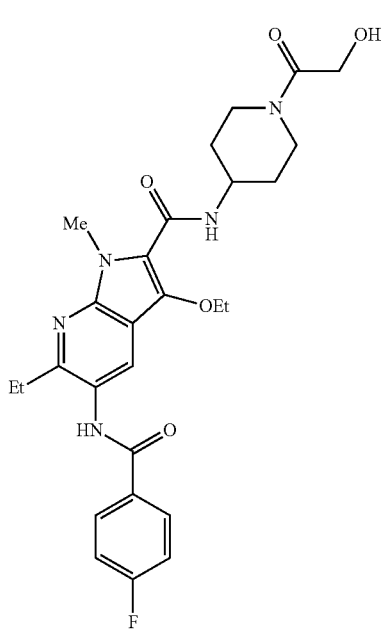 [SMILES: CCOc1c(C(=O)NC2CCN(C(=O)CO)CC2)n(C)c2nc(CC)c(NC(=O)c3ccc(F)cc3)cc12]

By a method similar to that in Example 16, the title compound (189 mg, 73%) was obtained as a white powder from the compound of Reference Example 134 (191 mg, 0.496 mmol), 2-(4-aminopiperidin-1-yl)-2-oxoethanol hydrochloride (116 mg, 0.595 mmol), HOBt (101 mg, 0.744 mmol), WSCD (143 mg, 0.744 mmol), triethylamine (0.206 mL, 1.49 mmol) and DMF (3.8 mL).

$^1$H NMR (300 MHz, DMSO-$d_6$) δ: 1.24 (3H, t, J=7.5 Hz), 1.36 (3H, t, J=7.0 Hz), 1.39-1.59 (2H, m), 1.86-1.98 (2H, m), 2.77-2.98 (3H, m), 3.06-3.21 (1H, m), 3.61-3.74 (1 m), 3.99 (3H, s), 4.02-4.17 (3H, m), 4.18-4.30 (1H, m), 4.36 (2H, q, J=7.0 Hz), 4.52 (1H, t, J=5.5 Hz), 7.33-7.44 (2H, m), 7.84 (1H, d, J=7.7 Hz), 8.04-8.15 (3H, m), 10.10 (1H, s).

Example 40

Production of N-(1,1-dioxidotetrahydro-2H-thiopyran-4-yl)-6-ethyl-1-methyl-5-[(phenylcarbonyl)amino]-3-(2,2,2-trifluoroethoxy)-1H-pyrrolo[2,3-b]pyridine-2-carboxamide

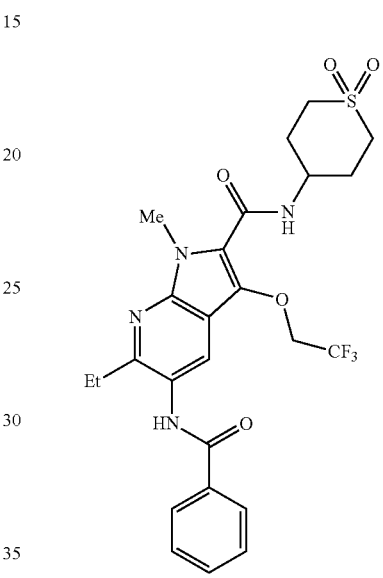

A mixture of the compound of Example 38 (130 mg, 0.250 mmol), 3-chloroperbenzoic acid (58.1 mg, 0.337 mmol) and ethyl acetate (13.0 mL) was stirred at 0° C. for 2.5 hr. To the reaction mixture was added saturated aqueous sodium hydrogen carbonate solution (30 mL), and the mixture was extracted with ethyl acetate. The extract was washed with brine, dried over sodium sulfate, and concentrated under reduced pressure. The residue was purified by silica gel chromatography (eluent; ethyl acetate/hexane=10/90-0/100) to give the title compound (36.9 mg, 27%) as a white powder.

$^1$H NMR (300 MHz, DMSO-$d_6$) δ: 1.24 (3H, t, J=7.5 Hz), 2.00-2.13 (2H, m), 2.14-2.29 (2H, m), 2.86 (2H, q, J=7.4 Hz), 3.07-3.19 (2H, m), 3.33-3.42 (2H, m), 3.91 (3H, s), 4.16-4.33 (1H, m), 4.93 (2H, q, J=8.9 Hz), 7.50-7.66 (3H, m), 7.99-8.06 (2H, m), 8.08 (1H, d, J=8.1 Hz), 8.13 (1H, s), 10.12 (1H, s).

Example 41

Production of 6-ethyl-1-methyl-N-(1-oxidotetrahydro-2H-thiopyran-4-yl)-5-[(phenylcarbonyl)amino]-3-(2,2,2-trifluoroethoxy)-1H-pyrrolo[2,3-b]pyridine-2-carboxamide

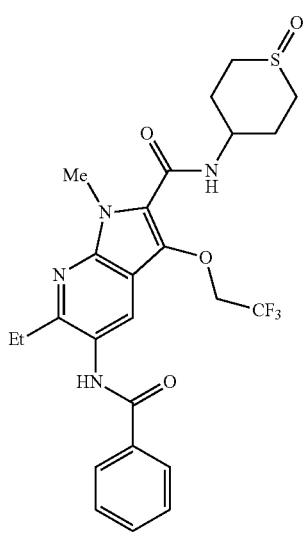 [SMILES: CCc1nc2c(cc1NC(=O)c1ccccc1)c(OCC(F)(F)F)c(C(=O)NC1CCS(=O)CC1)n2C]

A mixture of the compound of Example 38 (130 mg, 0.250 mmol), 3-chloroperbenzoic acid (58.1 mg, 0.337 mmol) and ethyl acetate (13.0 mL) was stirred at 0° C. for 2.5 hr. To the reaction mixture was added saturated aqueous sodium hydrogen carbonate solution (30 mL), and the mixture was extracted with ethyl acetate. The extract was washed with brine, dried over sodium sulfate, and concentrated under reduced pressure. The residue was purified by silica gel chromatography (eluent; ethyl acetate/hexane=10/90-0/100) to give the title compound (20.1 mg, 150) as a white powder.

$^1$H NMR (300 MHz, DMSO-d$_6$) δ: 1.25 (3H, t, J=7.5 Hz), 1.65-1.95 (2H, m), 2.08-2.34 (2H, m), 2.71-3.04 (5H, m), 3.09-3.23 (1H, m), 3.87-3.97 (3H, m), 3.97-4.22 (1H, m), 4.83-5.07 (2H, m), 7.50-7.67 (3H, m), 7.93-8.08 (3H, m), 8.10-8.20 (1H, m), 10.12 (1H, s).

Example 42

Production of 6-ethyl-N-[1-(hydroxyacetyl)piperidin-4-yl]-1-methyl-5-[(pyridin-2-ylcarbonyl)amino]-3-(2,2,2-trifluoroethoxy)-1H-pyrrolo[2,3-b]pyridine-2-carboxamide

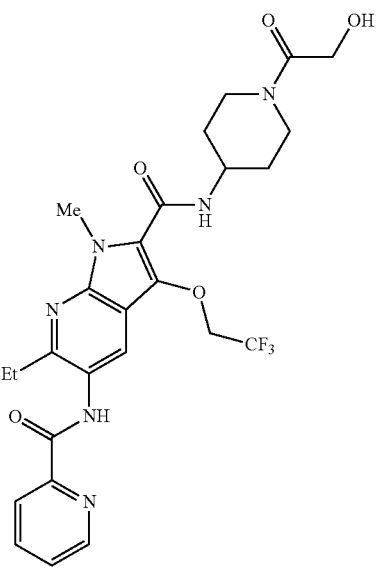 [SMILES: CCc1nc2c(cc1NC(=O)c1ccccn1)c(OCC(F)(F)F)c(C(=O)NC1CCN(C(=O)CO)CC1)n2C]

By a method similar to that in Example 25, the title compound (85 mg, 79%) was obtained as white crystals from the compound of Reference Example 52 (80 mg, 0.19 mmol).

$^1$H NMR (300 MHz, DMSO-d$_6$) δ 1.26 (3H, t, J=7.5 Hz), 1.30-1.55 (2H, m), 1.93 (2H, d, J=9.9 Hz), 2.81-2.94 (3H, m), 3.11 (1H, t, J=12.5 Hz), 3.71 (1H, d, J=13.5 Hz), 3.93 (3H, s), 4.00-4.15 (3H, m), 4.28 (1H, d, J=13.8 Hz), 4.54 (1H, t, J=5.4 Hz), 4.92 (2H, q, J=8.9 Hz), 7.68-7.73 (1H, m), 7.88 (1H, d, J=7.8 Hz), 8.09 (1H, td, J=7.5, 1.8 Hz), 8.17 (1H, d, J=7.8 Hz), 8.34 (1H, s), 8.77 (1H, d, J=4.8 Hz), 10.47 (1H, s).

Example 43

Production of 6-ethyl-N-[1-(hydroxyacetyl)piperidin-4-yl]-1-methyl-5-(4-methylphenyl)-3-(2,2,2-trifluoroethoxy)-1H-pyrrolo[2,3-b]pyridine-2-carboxamide

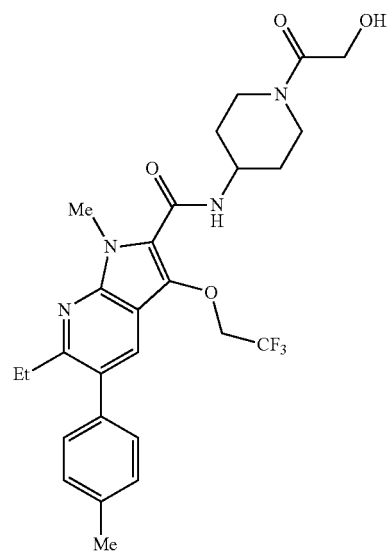 [SMILES: CCc1nc2c(cc1-c1ccc(C)cc1)c(OCC(F)(F)F)c(C(=O)NC1CCN(C(=O)CO)CC1)n2C]

By a method similar to that in Example 25, the title compound (96 mg, 55%) was obtained as white crystals from the compound of Reference Example 54 (130 mg, 0.33 mmol).

¹H NMR (300 MHz, DMSO-d₆) δ 1.15 (3H, t, J=7.5 Hz), 1.25-1.55 (2H, m), 1.92 (2H, d, J=10.2 Hz), 2.38 (3H, s), 2.75-2.89 (3H, m), 3.11 (1H, t, J=12.0 Hz), 3.70 (1H, d, J=12.6 Hz), 3.95 (3H, s), 4.00-4.20 (3H, m), 4.28 (1H, d, J=13.5 Hz), 4.53 (1H, t, J=5.4 Hz), 4.99 (2H, q, J=9.0 Hz), 7.29 (4H, s), 7.79 (1H, d, J=7.8 Hz), 7.97 (1H, s).

Example 44

Production of 6-ethyl-N-[1-(hydroxyacetyl)piperidin-4-yl]-1-methyl-5-(naphthalen-2-yl)-3-(2,2,2-trifluoroethoxy)-1H-pyrrolo[2,3-b]pyridine-2-carboxamide

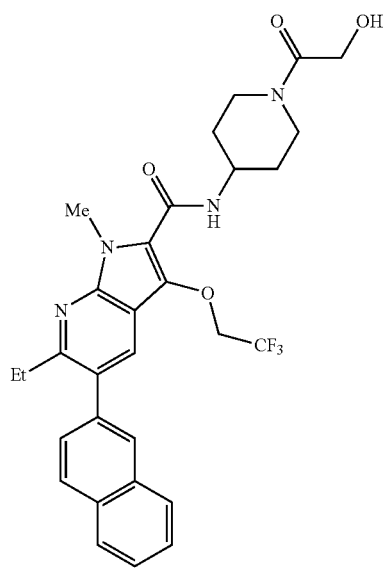 [SMILES: CCc1nc2c(cc1-c1ccc3ccccc3c1)c(OCC(F)(F)F)c(C(=O)NC1CCN(C(=O)CO)CC1)n2C]

By a method similar to that in Example 25, the title compound (58 mg, 73%) was obtained as white crystals from the compound of Reference Example 56 (60 mg, 0.14 mmol).

¹H NMR (300 MHz, DMSO-d₆) δ 1.17 (3H, t, J=7.4 Hz), 1.25-1.55 (2H, m), 1.93 (2H, d, J=10.8 Hz), 2.84 (3H, q, J=7.4 Hz), 3.12 (1H, t, J=12.3 Hz), 3.70 (1H, d, J=12.3 Hz), 3.90 (3H, s), 4.00-4.15 (3H, m), 4.29 (1H, d, J=12.9 Hz), 4.54 (1H, t, J=5.4 Hz), 5.01 (2H, q, J=8.9 Hz), 7.50-7.51 (3H, m), 7.81 (1H, d, J=7.8 Hz), 7.95-8.03 (4H, m), 8.13 (1H, s).

Example 45

Production of 3-ethoxy-6-ethyl-N-[1-(hydroxyacetyl)piperidin-4-yl]-1-methyl-5-[(phenylcarbonyl)amino]-1H-pyrrolo[2,3-b]pyridine-2-carboxamide

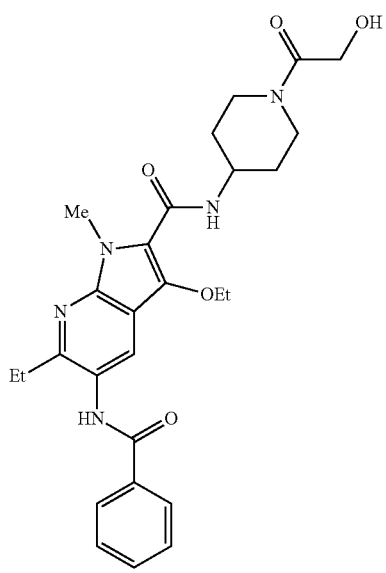 [SMILES: CCOc1c(C(=O)NC2CCN(C(=O)CO)CC2)n(C)c2nc(CC)c(NC(=O)c3ccccc3)cc12]

By a method similar to that in Example 16, the title compound (92.3 mg, 77%) was obtained as a white powder from the compound of Reference Example 136 (87.1 mg, 0.237 mmol), 2-(4-aminopiperidin-1-yl)-2-oxoethanol hydrochloride (55.4 mg, 0.284 mmol), HOBt (48.1 mg, 0.356 mmol), WSCD (68.1 mg, 0.356 mmol), triethylamine (98.5 μL, 0.711 mmol) and DMF (1.7 mL).

¹H NMR (300 MHz, DMSO-d₆) δ: 1.24 (3H, t, J=7.5 Hz), 1.36 (3H, t, J=7.0 Hz), 1.39-1.60 (2H, m), 1.87-1.98 (2H, m), 2.79-2.98 (3H, m), 3.06-3.21 (1H, m), 3.61-3.76 (1H, m), 3.99 (3H, s), 4.04-4.17 (3H, m), 4.18-4.30 (1H, m), 4.36 (2H, q, J=7.0 Hz), 4.52 (1H, t, J=5.5 Hz), 7.50-7.66 (3H, m), 7.84 (1H, d, J=7.7 Hz), 7.98-8.06 (2H, m), 8.09 (1H, s), 10.08 (1H, s).

Example 46

Production of 6-ethyl-N-[1-(hydroxyacetyl)piperidin-4-yl]-1-methyl-3-(1-methylethoxy)-5-[(phenylcarbonyl)amino]-1H-pyrrolo[2,3-b]pyridine-2-carboxamide

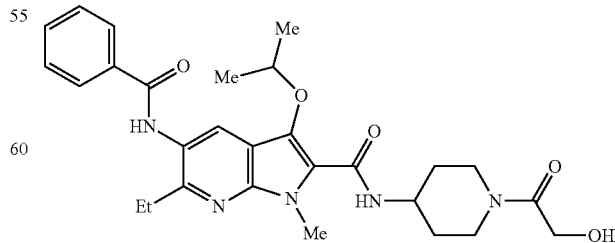

By a method similar to that in Example 1, the title compound (155 mg, 71%) was obtained as white crystals from the compound of Reference Example 89 (161 mg, 0.422 mmol), 2-(4-aminopiperidin-1-yl)-2-oxoethanol hydrochloride (97.2 mg, 0.499 mmol), HOBt (81.5 mg, 0.603 mmol), WSCD (137 mg, 0.715 mmol), triethylamine (0.118 mL, 0.844 mmol) and DMF (3 mL).

$^1$H NMR (300 MHz, DMSO-d$_6$) δ: 1.25 (3H, t, J=7.6 Hz), 1.31 (6H, d, J=6.0 Hz), 1.34-1.61 (2H, m), 1.86-1.98 (2H, m), 2.78-2.95 (1H, m), 2.85 (2H, q, J=7.6 Hz), 3.05-3.21 (1H, m), 3.62-3.77 (1H, m), 3.99 (3H, s), 4.03-4.18 (1H, m), 4.11 (2H, t, J=5.7 Hz), 4.22-4.35 (1H, m), 4.52 (1H, t, J=5.7 Hz), 4.63-4.76 (1H, m), 7.49-7.66 (3H, m), 7.85 (1H, d, J=7.7 Hz), 7.96-8.07 (3H, m), 10.07 (1H, s).

Example 47

Production of N-[1-(hydroxyacetyl)piperidin-4-yl]-1,6-dimethyl-5-[(phenylcarbonyl)amino]-3-(2,2,2-trifluoroethoxy)-1H-pyrrolo[2,3-b]pyridine-2-carboxamide

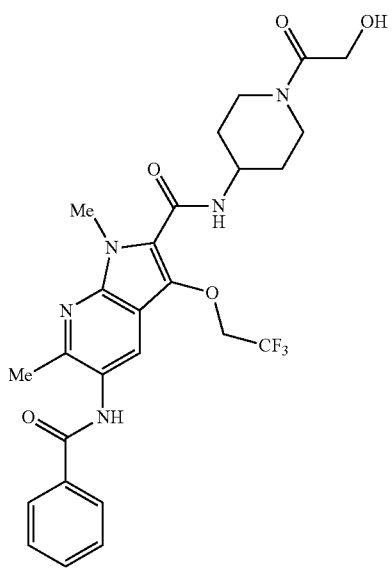 [SMILES: Cc1nc2c(cc1NC(=O)c1ccccc1)c(OCC(F)(F)F)c(C(=O)NC1CCN(C(=O)CO)CC1)n2C]

By a method similar to that in Example 25, the title compound (126 mg, 72%) was obtained as white crystals from the compound of Reference Example 67 (130 mg, 0.32 mmol).

$^1$H NMR (300 MHz, DMSO-d$_6$) δ 1.30-1.60 (2H, m), 1.93 (2H, d, J=12.6 Hz), 2.54 (3H, s), 2.86 (1H, t, J=12.6 Hz), 3.12 (1H, t, J=12.8 Hz), 3.71 (1H, d, J=13.2 Hz), 3.93 (3H, s), 4.03-4.20 (3H, m), 4.28 (1H, d, J=12.9 Hz), 4.50 (1H, t, J=5.4 Hz), 4.93 (2H, q, J=8.9 Hz), 7.53-7.65 (3H, m), 7.86 (1H, d, J=7.8 Hz), 8.03 (2H, d, J=7.2 Hz), 8.15 (1H, s), 10.09 (1H, s).

Example 48

Production of 5-{[(4-fluorophenyl)carbonyl]amino}-N-[1-(hydroxyacetyl)piperidin-4-yl]-1,6-dimethyl-3-(2,2,2-trifluoroethoxy)-1H-pyrrolo[2,3-b]pyridine-2-carboxamide

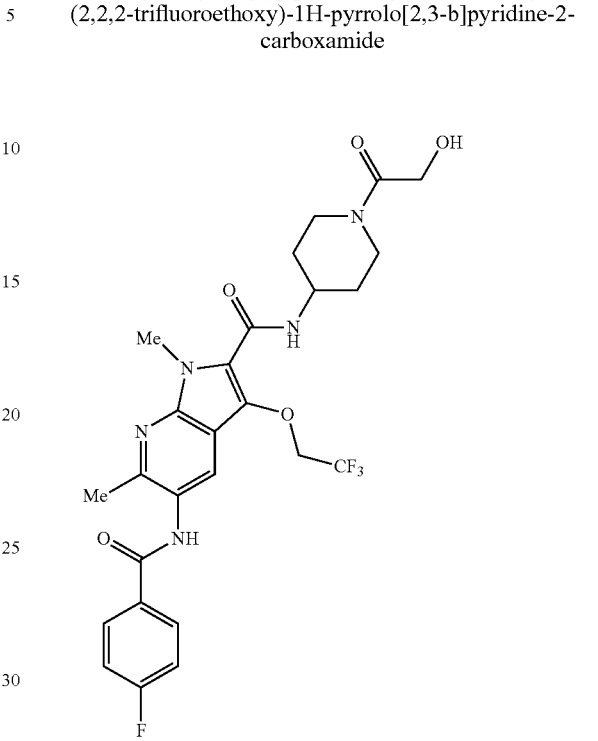

By a method similar to that in Example 25, the title compound (147 mg, 79%) was obtained as white crystals from the compound of Reference Example 65 (140 mg, 0.33 mmol).

$^1$H NMR (300 MHz, DMSO-d$_6$) δ 1.30-1.60 (2H, m), 1.93 (2H, d, J=10.5 Hz), 2.52 (3H, s), 2.86 (1H, t, J=11.0 Hz), 3.12 (1H, t, J=12.3 Hz), 3.70 (1H, d, J=12.0 Hz), 3.92 (3H, s), 4.00-4.20 (3H, m), 4.28 (1H, d, J=12.3 Hz), 4.50 (1H, t, J=5.4 Hz), 4.92 (2H, q, J=8.9 Hz), 7.39 (2H, t, J=8.9 Hz), 7.85 (1H, d, J=7.5 Hz), 8.08-8.13 (3H, m), 10.11 (1H, s).

Example 49

Production of 6-ethyl-N-[1-(hydroxyacetyl)piperidin-4-yl]-5-(3-methoxyphenoxy)-1-methyl-3-(2,2,2-trifluoroethoxy)-1H-pyrrolo[2,3-b]pyridine-2-carboxamide

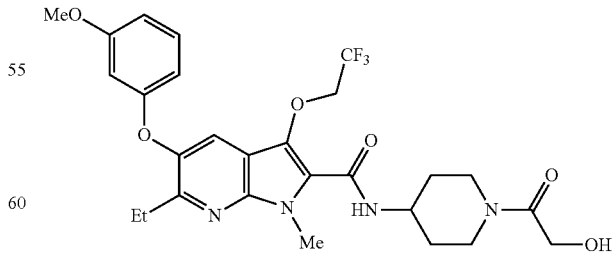

By a method similar to that in Example 1, the title compound (45.1 mg, 44%) was obtained as a white non-crystalline solid from the compound of Reference Example 92 (77.7 mg, 0.183 mmol), 2-(4-aminopiperidin-1-yl)-2-oxoethanol hydrochloride (44.6 mg, 0.229 mmol), HOBt (40.6 mg, 0.300 mmol), WSCD (54.2 mg, 0.283 mmol), triethylamine (0.0506 mL, 0.363 mmol) and DMF (1 mL).

$^1$H NMR (300 MHz, DMSO-$d_6$) δ: 1.21 (3H, t, J=7.5 Hz), 1.26-1.54 (2H, m), 1.83-1.97 (2H, m), 2.75 (2H, q, J=7.5 Hz), 2.79-2.94 (1H, m), 3.02-3.19 (1H, m), 3.62-3.77 (1H, m), 3.72 (3H, s), 3.93 (3H, s), 4.00-4.19 (1H, m), 4.10 (2H, t, J=5.6 Hz), 4.20-4.35 (1H, m), 4.53 (1H, t, J=5.6 Hz), 4.92 (2H, q, J=8.9 Hz), 6.38 (1H, dd, J=8.2, 2.3 Hz), 6.47 (1H, t, J=2.3 Hz), 6.65 (1H, dd, J=8.2, 2.3 Hz), 7.23 (1H, t, J=8.2 Hz), 7.86 (1H, d, J=7.7 Hz), 7.95 (1H, s).

Example 50

Production of 6-ethyl-N-[1-(hydroxyacetyl)piperidin-4-yl]-1-methyl-5-[(thiophen-3-ylcarbonyl)amino]-3-(2,2,2-trifluoroethoxy)-1H-pyrrolo[2,3-b]pyridine-2-carboxamide

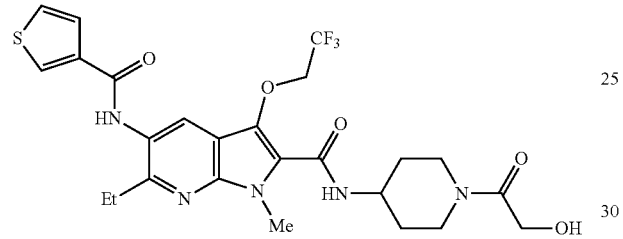

By a method similar to that in Example 1, the title compound (115 mg, 65%) was obtained as white crystals from the compound of Reference Example 95 (133 mg, 0.311 mmol), 2-(4-aminopiperidin-1-yl)-2-oxoethanol hydrochloride (71.0 mg, 0.365 mmol), HOBt (64.6 mg, 0.478 mmol), WSCD (82.9 mg, 0.432 mmol), triethylamine (0.0868 mL, 0.623 mmol) and DMF (2 mL).

$^1$H NMR (300 MHz, DMSO-$d_6$) δ: 1.24 (3H, t, J=7.6 Hz), 1.29-1.56 (2H, m), 1.85-1.97 (2H, m), 2.85 (2H, q, J=7.6 Hz), 2.78-2.92 (1H, m), 3.04-3.18 (1H, m), 3.64-3.77 (1H, m), 3.93 (3H, s), 4.02-4.18 (1H, m), 4.10 (2H, t, J=5.6 Hz), 4.22-4.36 (1H, m), 4.53 (1H, t, J=5.6 Hz), 4.94 (2H, q, J=8.9 Hz), 7.59-7.74 (2H, m), 7.86 (1H, d, J=7.7 Hz), 8.11 (1H, s), 8.29-8.39 (1H, m), 9.95 (1H, s).

Example 51

Production of 6-ethyl-N-[1-(hydroxyacetyl)piperidin-4-yl]-1-methyl-3-(1-methylethoxy)-5-[(thiophen-2-ylcarbonyl)amino]-1H-pyrrolo[2,3-b]pyridine-2-carboxamide

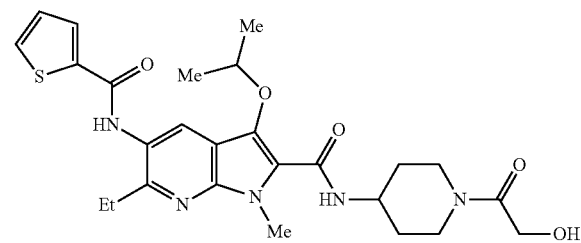 [SMILES: CCc1nc2c(cc1NC(=O)c1cccs1)c(OC(C)C)c(C(=O)NC1CCN(C(=O)CO)CC1)n2C]

By a method similar to that in Example 1, the title compound (105 mg, 62%) was obtained as white crystals from the compound of Reference Example 97 (125 mg, 0.323 mmol), 2-(4-aminopiperidin-1-yl)-2-oxoethanol hydrochloride (74.2 mg, 0.381 mmol), HOBt (66.9 mg, 0.495 mmol), WSCD (104 mg, 0.543 mmol), triethylamine (0.0900 mL, 0.646 mmol) and DMF (2 mL).

$^1$H NMR (300 MHz, DMSO-$d_6$) δ: 1.24 (3H, t, J=7.6 Hz), 1.31 (6H, d, J=6.0 Hz), 1.34-1.62 (2H, m), 1.86-2.01 (2H, m), 2.84 (2H, q, J=7.6 Hz), 2.79-2.97 (1H, m), 3.05-3.20 (1H, m), 3.61-3.78 (1H, m), 3.99 (3H, s), 4.02-4.19 (1H, m), 4.11 (2H, t, J=5.7 Hz), 4.22-4.36 (1H, m), 4.52 (1H, t, J=5.7 Hz), 4.62-4.75 (1H, m), 7.24 (1H, dd, J=4.8, 3.9 Hz), 7.81-7.90 (2H, m), 7.97-8.04 (2H, m), 10.10 (1H, s).

Example 52

Production of 6-ethyl-5-[(furan-2-ylcarbonyl)amino]-N-[1-(hydroxyacetyl)piperidin-4-yl]-1-methyl-3-(2,2,2-trifluoroethoxy)-1H-pyrrolo[2,3-b]pyridine-2-carboxamide

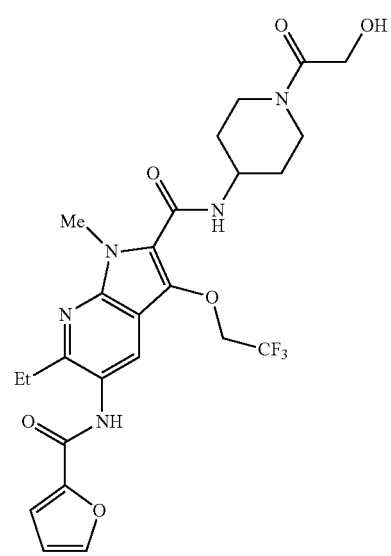 [SMILES: CCc1nc2c(cc1NC(=O)c1ccco1)c(OCC(F)(F)F)c(C(=O)NC1CCN(C(=O)CO)CC1)n2C]

By a method similar to that in Example 25, the title compound (137 mg, 78%) was obtained as white crystals from the compound of Reference Example 69 (130 mg, 0.32 mmol).

$^1$H NMR (300 MHz, DMSO-$d_6$) δ 1.23 (3H, t, J=7.5 Hz), 1.30-1.50 (2H, m), 1.92 (2H, d, J=12.6 Hz), 2.83 (3H, q, J=7.4 Hz), 3.12 (1H, t, J=10.4 Hz), 3.71 (1H, d, J=9.6 Hz), 3.93 (3H, s), 4.05-4.15 (3H, m), 4.28 (1H, d, J=11.7 Hz), 4.49 (1H, t, J=5.4 Hz), 4.92 (2H, q, J=8.9 Hz), 6.71 (1H, q, J=1.7 Hz), 7.30 (1H, d, J=3.3 Hz), 7.82 (1H, d, J=7.8 Hz), 7.94 (1H, q, J=0.8 Hz), 8.10 (1H, s), 9.99 (1H, s).

Example 53

Production of 6-ethyl-N-[1-(hydroxyacetyl)piperidin-4-yl]-1-methyl-5-[(1,3-thiazol-5-ylcarbonyl)amino]-3-(2,2,2-trifluoroethoxy)-1H-pyrrolo[2,3-b]pyridine-2-carboxamide

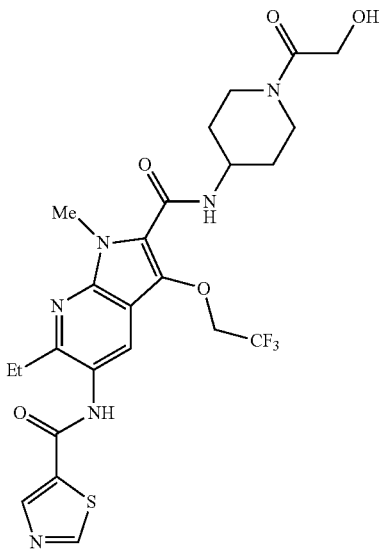 [SMILES: CCc1nc2c(cc1NC(=O)c1cncs1)c(OCC(F)(F)F)c(C(=O)NC1CCN(C(=O)CO)CC1)n2C]

By a method similar to that in Example 25, the title compound (98 mg, 75%) was obtained as white crystals from the compound of Reference Example 71 (100 mg, 0.23 mmol).

$^1$H NMR (300 MHz, DMSO-$d_6$) δ 1.25 (3H, t, J=7.5 Hz), 1.30-1.60 (2H, m), 1.92 (2H, d, J=9.0 Hz), 2.85 (3H, q, J=7.5 Hz), 3.12 (1H, t, J=10.2 Hz), 3.72 (1H, d, J=10.5 Hz), 3.93 (3H, s), 4.05-4.15 (3H, m), 4.28 (1H, d, J=10.5 Hz), 4.50 (1H, t, J=5.4 Hz), 4.93 (2H, q, J=8.9 Hz), 7.84 (1H, d, J=7.5 Hz), 8.15 (1H, s), 8.70 (1H, s), 9.32 (1H, s), 10.33 (1H, s).

Example 54

Production of 6-ethyl-5-[(furan-3-ylcarbonyl)amino]-N-[1-(hydroxyacetyl)piperidin-4-yl]-1-methyl-3-(2,2,2-trifluoroethoxy)-1H-pyrrolo[2,3-b]pyridine-2-carboxamide

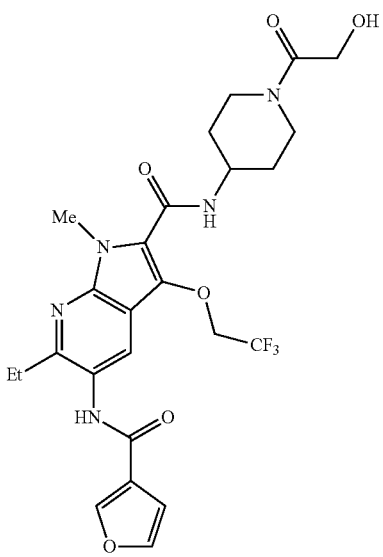 [SMILES: CCc1nc2c(cc1NC(=O)c1ccoc1)c(OCC(F)(F)F)c(C(=O)NC1CCN(C(=O)CO)CC1)n2C]

By a method similar to that in Example 16, the title compound (119 mg, 71%) was obtained as a white powder from the compound of Reference Example 138 (125 mg, 0.304 mmol), 2-(4-aminopiperidin-1-yl)-2-oxoethanol hydrochloride (71.0 mg, 0.365 mmol), HOBt (61.6 mg, 0.456 mmol), WSCD (87.4 mg, 0.456 mmol), triethylamine (0.126 mL, 0.912 mmol) and DMF (2.5 mL).

$^1$H NMR (300 MHz, DMSO-$d_6$) δ: 1.23 (3H, t, J=7.5 Hz), 1.29-1.55 (2H, m), 1.85-1.97 (2H, m), 2.77-2.93 (3H, m), 3.04-3.20 (1H, m), 3.62-3.79 (1H, m), 3.93 (3H, s), 4.00-4.19 (3H, m), 4.21-4.36 (1H, m), 4.53 (1H, t, J=5.4 Hz), 4.94 (2H, q, J=8.9 Hz), 7.01 (1H, s), 7.80-7.83 (1H, m), 7.86 (1H, d, J=7.7 Hz), 8.09 (1H, s), 8.37 (1H, s), 9.83 (1H, s).

Example 55

Production of 6-ethyl-N-[1-(hydroxyacetyl)piperidin-4-yl]-1-methyl-5-[(1,3-oxazol-4-ylcarbonyl)amino]-3-(2,2,2-trifluoroethoxy)-1H-pyrrolo[2,3-b]pyridine-2-carboxamide

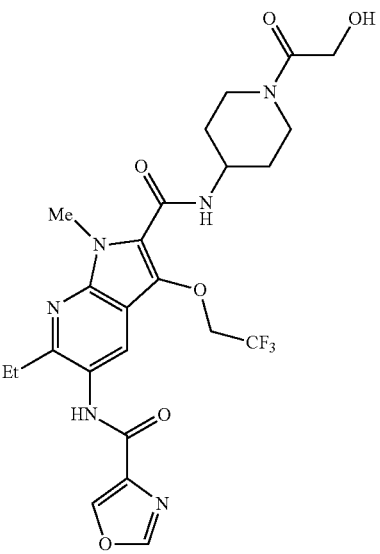 [SMILES: CCc1nc2c(cc1NC(=O)c1cocn1)c(OCC(F)(F)F)c(C(=O)NC1CCN(C(=O)CO)CC1)n2C]

By a method similar to that in Example 16, the title compound (89.3 mg, 51%) was obtained as a pale-yellow powder from the compound of Reference Example 140 (131 mg, 0.318 mmol), 2-(4-aminopiperidin-1-yl)-2-oxoethanol hydrochloride (74.3 mg, 0.382 mmol), HOBt (64.5 mg, 0.477 mmol), WSCD (91.4 mg, 0.477 mmol), triethylamine (0.132 mL, 0.954 mmol) and DMF (2.6 mL).

$^1$H NMR (300 MHz, DMSO-$d_6$) δ: 1.23 (3H, t, J=7.5 Hz), 1.29-1.55 (2H, m), 1.85-1.98 (2H, m), 2.76-2.92 (3H, m), 3.03-3.18 (1H, m), 3.62-3.80 (1H, m), 3.92 (3H, s), 4.01-4.19 (3H, m), 4.21-4.36 (1H, m), 4.53 (1H, t, J=5.4 Hz), 4.92 (2H, q, J=8.9 Hz), 7.85 (1H, d, J=7.6 Hz), 8.15 (1H, s), 8.63 (1H, s), 8.80 (1H, s), 9.98 (1H, s).

Example 56

Production of 6-ethyl-N-[1-(hydroxyacetyl)piperidin-4-yl]-1-methyl-5-[(1,3-thiazol-4-ylcarbonyl)amino]-3-(2,2,2-trifluoroethoxy)-1H-pyrrolo[2,3-b]pyridine-2-carboxamide

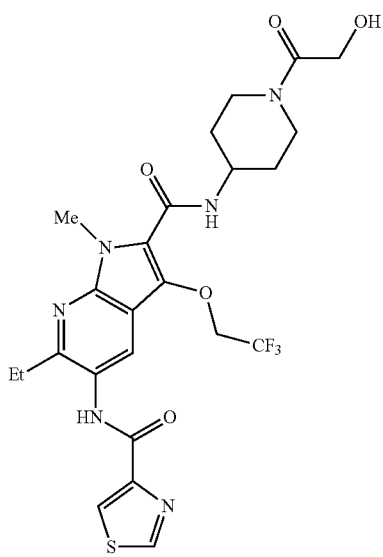

By a method similar to that in Example 16, the title compound (85.3 mg, 50%) was obtained as a white powder from the compound of Reference Example 142 (129 mg, 0.301 mmol), 2-(4-aminopiperidin-1-yl)-2-oxoethanol hydrochloride (70.3 mg, 0.361 mmol), HOBt (61.1 mg, 0.452 mmol), WSCD (86.6 mg, 0.452 mmol), triethylamine (0.125 mL, 0.903 mmol) and DMF (2.6 mL).

$^1$H NMR (300 MHz, DMSO-$d_6$) δ: 1.24 (3H, t, J=7.5 Hz), 1.30-1.55 (2H, m), 1.85-1.97 (2H, m), 2.79-2.93 (3H, m), 3.04-3.19 (1H, m), 3.63-3.77 (1H, m), 3.93 (3H, s), 4.01-4.17 (3H, m), 4.21-4.36 (1H, m), 4.53 (1H, t, J=5.4 Hz), 4.92 (2H, q, J=9.1 Hz), 7.86 (1H, d, J=7.7 Hz), 8.23 (1H, s), 8.50 (1H, d, J=2.1 Hz), 9.30 (1H, d, J=2.1 Hz), 10.13 (1H, s).

Example 57

Production of 5-{[(1,3-dimethyl-1H-pyrazol-5-yl)carbonyl]amino}-6-ethyl-N-[1-(hydroxyacetyl)piperidin-4-yl]-1-methyl-3-(2,2,2-trifluoroethoxy)-1H-pyrrolo[2,3-b]pyridine-2-carboxamide

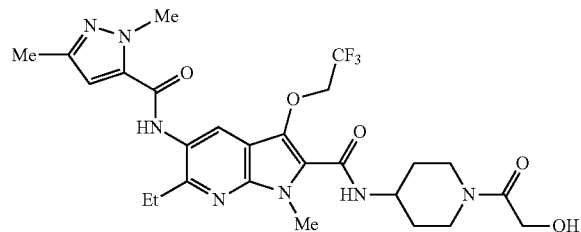 [SMILES: CCc1nc2c(cc1NC(=O)c1cc(C)nn1C)c(OCC(F)(F)F)c(C(=O)NC1CCN(C(=O)CO)CC1)n2C]

By a method similar to that in Example 1, the title compound (127 mg, 72%) was obtained as white crystals from the compound of Reference Example 99 (134 mg, 0.305 mmol), 2-(4-aminopiperidin-1-yl)-2-oxoethanol hydrochloride (69.8 mg, 0.359 mmol), HOBt (59.8 mg, 0.443 mmol), WSCD (83.6 mg, 0.436 mmol), triethylamine (0.0850 mL, 0.610 mmol) and DMF (2 mL).

$^1$H NMR (300 MHz, DMSO-$d_6$) δ: 1.23 (3H, t, J=7.5 Hz), 1.28-1.59 (2H, m), 1.83-1.97 (2H, m), 2.21 (3H, s), 2.77-2.93 (1H, m), 2.83 (2H, q, J=7.5 Hz), 3.02-3.20 (1H, m), 3.62-3.79 (1H, m), 3.93 (3H, s), 4.01 (3H, s), 4.05-4.19 (1H, m), 4.10 (2H, t, J=5.6 Hz), 4.20-4.38 (1H, m), 4.53 (1H, t, J=5.6 Hz), 4.94 (2H, q, J=8.9 Hz), 6.87 (1H, s), 7.87 (1H, d, J=7.7 Hz), 8.11 (1H, s), 9.98 (1H, s).

Example 58

Production of 6-ethyl-5-{[(4-fluorophenyl)carbonyl]amino}-N-[1-(hydroxyacetyl)piperidin-4-yl]-3-(2,2,2-trifluoroethoxy)thieno[2,3-b]pyridine-2-carboxamide

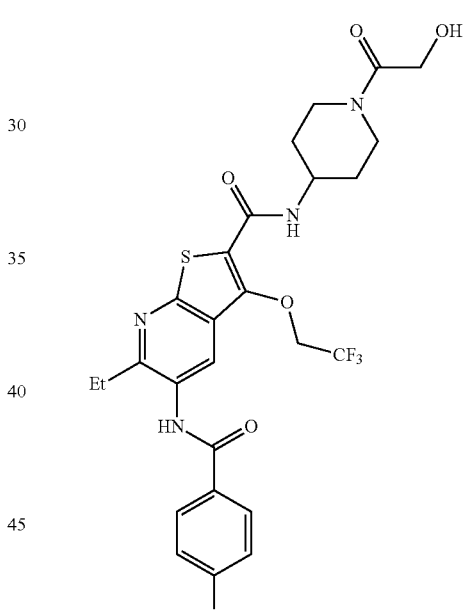

By a method similar to that in Example 16, the title compound (109 mg, 47%) was obtained as a white powder from the compound of Reference Example 147 (170 mg, 0.402 mmol), 2-(4-aminopiperidin-1-yl)-2-oxoethanol hydrochloride (94.0 mg, 0.483 mmol), HOBt (81.5 mg, 0.603 mmol), WSCD (116 mg, 0.603 mmol), triethylamine (0.167 mL, 1.21 mmol) and DMF (3.4 mL).

$^1$H NMR (300 MHz, DMSO-$d_6$) δ: 1.24 (3H, t, J=7.5 Hz), 1.30-1.57 (2H, m), 1.84-1.98 (2H, m), 2.73-2.86 (1H, m), 2.92 (2H, q, J=7.4 Hz), 3.02-3.17 (1H, m), 3.65-3.77 (1H, m), 3.98-4.16 (3H, m), 4.26-4.40 (1H, m), 4.53 (1H, t, J=5.4 Hz), 5.09 (2H, q, J=9.0 Hz), 7.36-7.47 (2H, m), 7.84 (1H, d, J=7.7 Hz), 8.05-8.17 (2H, m), 8.28 (1H, s) 10.29 (1H, s).

Example 59

Production of 5-{[(5-chlorothiophen-2-yl)carbonyl]amino}-6-ethyl-N-[1-(hydroxyacetyl)piperidin-4-yl]-1-methyl-3-(1-methylethoxy)-1H-pyrrolo[2,3-b]pyridine-2-carboxamide

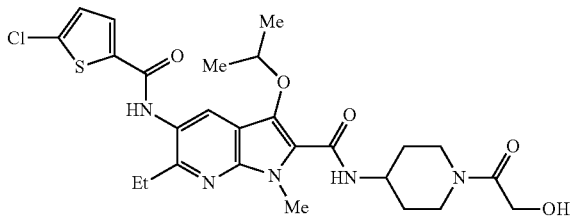 [SMILES: CCc1nc2c(cc1NC(=O)c1ccc(Cl)s1)c(OC(C)C)c(C(=O)NC1CCN(C(=O)CO)CC1)n2C]

By a method similar to that in Example 1, the title compound (117 mg, 55%) was obtained as a white non-crystalline solid from the compound of Reference Example 101 (160 mg, 0.379 mmol), 2-(4-aminopiperidin-1-yl)-2-oxoethanol hydrochloride (84.2 mg, 0.433 mmol), HOBt (71.2 mg, 0.527 mmol), WSCD (108 mg, 0.564 mmol), triethylamine (0.106 mL, 0.759 mmol) and DMF (2 mL).

$^1$H NMR (300 MHz, DMSO-$d_6$) δ: 1.23 (3H, t, J=7.5 Hz), 1.30 (6H, d, J=6.0 Hz), 1.34-1.61 (2H, m), 1.84-1.98 (2H, m), 2.82 (2H, q, J=7.5 Hz), 2.79-2.96 (1H, m), 3.03-3.22 (1H, m), 3.61-3.77 (1H, m), 3.98 (3H, s), 4.02-4.19 (3H, m), 4.20-4.35 (1H, m), 4.52 (1H, t, J=5.4 Hz), 4.60-4.75 (1H, m), 7.29 (1H, d, J=4.0 Hz), 7.85 (1H, d, J=7.7 Hz), 7.89 (1H, d, J=4.0 Hz), 8.02 (1H, s), 10.19 (1H, s).

Example 60

Production of 6-ethyl-N-{2-[(2-methoxyethyl)sulfonyl]ethyl}-1-methyl-3-(1-methylethoxy)-5-[(phenylcarbonyl)amino]-1H-pyrrolo[2,3-b]pyridine-2-carboxamide

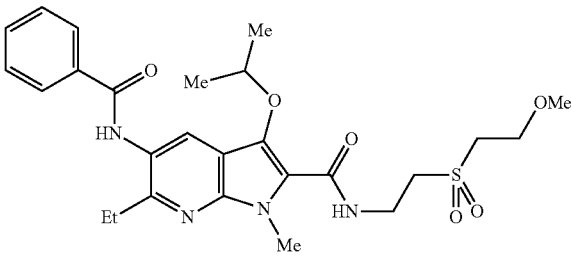 [SMILES: CCc1nc2c(cc1NC(=O)c1ccccc1)c(OC(C)C)c(C(=O)NCCS(=O)(=O)CCOC)n2C]

By a method similar to that in Example 1, the title compound. (133 mg, 87%) was obtained as white crystals from the compound of Reference Example 89 (109 mg, 0.286 mmol), 2-[(2-methoxyethyl)sulfonyl]ethanamine hydrochloride (70.5 mg, 0.346 mmol), HOBt (65.8 mg, 0.487 mmol), WSCD (87.8 mg, 0.458 mmol), triethylamine (0.0800 mL, 0.574 mmol) and DMF (1.5 mL).

$^1$H NMR (300 MHz, DMSO-$d_6$) δ: 1.25 (3H, t, J=7.5 Hz), 1.34 (6H, d, J=6.0 Hz), 2.85 (2H, q, J=7.5 Hz), 3.28 (3H, s), 3.41 (2H, t, J=6.5 Hz), 3.44-3.52 (2H, m), 3.69-3.76 (2H, m), 3.81 (2H, q, J=6.2 Hz), 4.01 (3H, s), 4.63-4.83 (1H, m), 7.45-7.74 (3H, m), 7.96-8.09 (3H, m), 8.16 (1H, t, J=5.9 Hz), 10.08 (1H, s).

Example 61

Production of 6-ethyl-N-[1-(hydroxyacetyl)piperidin-4-yl]-1-methyl-3-(1-methylethoxy)-5-[(thiophen-3-ylcarbonyl)amino]-1H-pyrrolo[2,3-b]pyridine-2-carboxamide

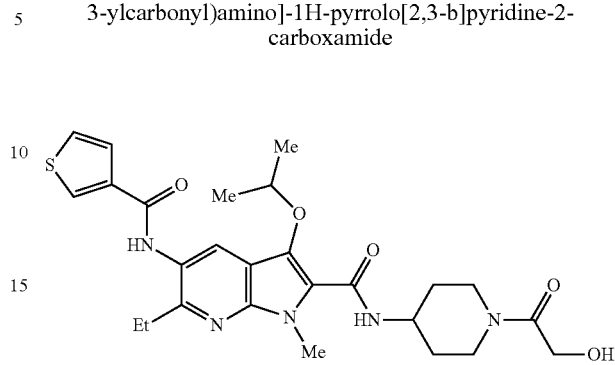

By a method similar to that in Example 1, the title compound (73.2 mg, 51%) was obtained as white crystals from the compound of Reference Example 103 (105 mg, 0.271 mmol), 2-(4-aminopiperidin-1-yl)-2-oxoethanol hydrochloride (62.1 mg, 0.319 mmol), HOBt (64.0 mg, 0.474 mmol), WSCD (75.0 mg, 0.391 mmol), triethylamine (0.0756 mL, 0.542 mmol) and DMF (1.5 mL).

$^1$H NMR (300 MHz, DMSO-$d_6$) δ: 1.24 (3H, t, J=7.5 Hz), 1.31 (6H, d, J=6.0 Hz), 1.35-1.60 (2H, m), 1.85-2.01 (2H, m), 2.84 (2H, q, J=7.5 Hz), 2.91 (1H, m), 3.04-3.21 (1H, m), 3.62-3.78 (1H, m), 3.99 (3H, s), 4.01-4.20 (1H, m), 4.11 (2H, t, J=5.6 Hz), 4.21-4.35 (1H, m), 4.52 (1H, t, J=5.6 Hz), 4.61-4.75 (1H, m), 7.60-7.73 (2H, m), 7.85 (1H, d, J=7.7 Hz), 8.00 (1H, s), 8.34 (1H, d, J=1.5 Hz), 9.91 (1H, s).

Example 62

Production of 6-ethyl-N-[1-(hydroxyacetyl)piperidin-4-yl]-5-{[(4-methoxythiophene-3-yl)carbonyl]amino}-1-methyl-3-(1-methylethoxy)-1H-pyrrolo[2,3-b]pyridine-2-carboxamide

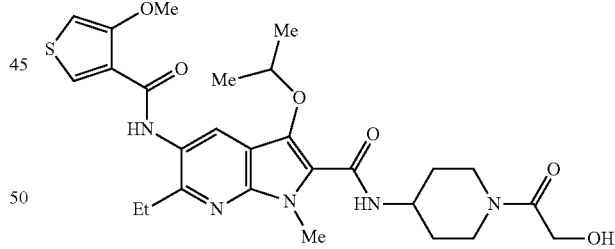

By a method similar to that in Example 1, the title compound (92.9 mg, 68%) was obtained as white crystals from the compound of Reference Example 105 (103 mg, 0.247 mmol), 2-(4-aminopiperidin-1-yl)-2-oxoethanol hydrochloride (58.3 mg, 0.300 mmol), HOBt (52.4 mg, 0.388 mmol), WSCD (79.3 mg, 0.412 mmol), triethylamine (0.0688 mL, 0.494 mmol) and DMF (1.5 mL).

$^1$H NMR (300 MHz, DMSO-$d_6$) δ: 1.23-1.35 (9H, m), 1.36-1.63 (2H, m), 1.84-2.01 (2H, m), 2.77-2.98 (3H, m), 3.04-3.21 (1H, m), 3.61-3.78 (1H, m), 3.97 (3H, s), 3.99 (3H, s), 4.03-4.20 (1H, m), 4.11 (2H, t, J=5.7 Hz), 4.21-4.37 (1H, m), 4.52 (1H, t, J=5.7 Hz), 4.58-4.72 (1H, m), 6.91 (1H, d, J=3.6 Hz), 7.85 (1H, d, J=7.9 Hz), 8.23 (1H, d, J=3.4 Hz), 8.51 (1H, s), 9.46 (1H, s).

Example 63

Production of 5-{[(3-chlorothiophen-2-yl)carbonyl]amino}-6-ethyl-N-[1-(hydroxyacetyl)piperidin-4-yl]-1-methyl-3-(1-methylethoxy)-1H-pyrrolo[2,3-b]pyridine-2-carboxamide

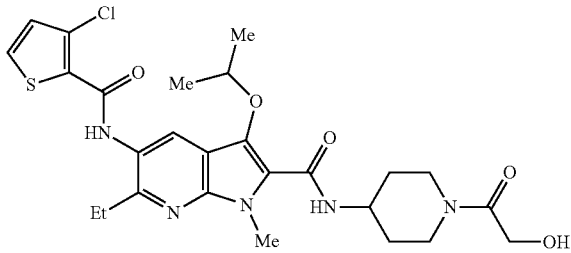 [SMILES: CCc1nc2c(cc1NC(=O)c1sccc1Cl)c(OC(C)C)c(C(=O)NC1CCN(C(=O)CO)CC1)n2C]

By a method similar to that in Example 1, the title compound (88.6 mg, 67%) was obtained as white crystals from the compound of Reference Example 107 (100 mg, 0.237 mmol), 2-(4-aminopiperidin-1-yl)-2-oxoethanol hydrochloride (58.0 mg, 0.298 mmol), HOBt (48.8 mg, 0.361 mmol), WSCD (82.3 mg, 0.429 mmol), triethylamine (0.0660 mL, 0.474 mmol) and DMF (1.5 mL).

$^1$H NMR (300 MHz, DMSO-$d_6$) δ: 1.27 (3H, t, J=7.5 Hz), 1.31 (6H, d, J=6.0 Hz), 1.35-1.62 (2H, m), 1.86-1.98 (2H, m), 2.79-2.94 (1H, m), 2.88 (2H, q, J=7.5 Hz), 3.04-3.21 (1H, m), 3.60-3.79 (1H, m), 3.98 (3H, s), 4.01-4.21 (1H, m), 4.11 (2H, t, J=5.8 Hz), 4.22-4.37 (1H, m), 4.52 (1H, t, J=5.8 Hz), 4.59-4.75 (1H, m), 7.24 (1H, d, J=5.1 Hz), 7.86 (1H, d, J=7.7 Hz), 7.93 (1H, d, J=5.3 Hz), 8.12 (1H, s), 9.78 (1H, s).

Example 64

Production of 6-ethyl-N-{2-[(hydroxyacetyl)amino]ethyl}-1-methyl-3-(1-methylethoxy)-5-[(phenylcarbonyl)amino]-1H-pyrrolo[2,3-b]pyridine-2-carboxamide

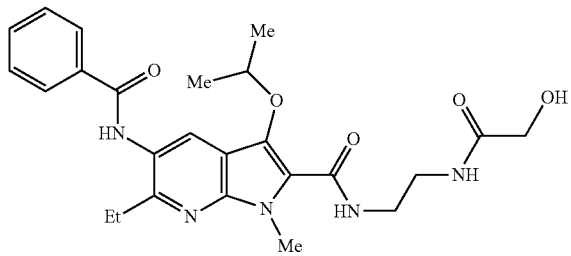 [SMILES: CCc1nc2c(cc1NC(=O)c1ccccc1)c(OC(C)C)c(C(=O)NCCNC(=O)CO)n2C]

By a method similar to that in Example 1, the title compound (76.9 mg, 62%) was obtained as white crystals from the compound of Reference Example 89 (99.0 mg, 0.237 mmol), N-(2-aminoethyl)-2-hydroxyacetamide hydrochloride (54.5 mg, 0.353 mmol), HOBt (62.1 mg, 0.460 mmol), WSCD (88.9 mg, 0.464 mmol), triethylamine (0.0730 mL, 0.524 mmol) and DMF (1.5 mL).

$^1$H NMR (300 MHz, DMSO-$d_6$) δ: 1.25 (3H, t, J=7.5 Hz), 1.31 (6H, d, J=6.2 Hz), 2.85 (2H, q, J=7.5 Hz), 3.27-3.40 (2H, m), 3.47 (2H, q, J=5.7 Hz), 3.82 (2H, d, J=5.5 Hz), 3.99 (3H, s), 4.56-4.72 (1H, m), 5.50 (1H, t, J=5.7 Hz), 7.47-7.68 (3H, m), 7.85-8.11 (5H, m), 10.07 (1H, s).

Example 65

Production of 6-ethyl-N-{3-[(hydroxyacetyl)amino]propyl}-1-methyl-3-(1-methylethoxy)-5-[(phenylcarbonyl)amino]-1H-pyrrolo[2,3-b]pyridine-2-carboxamide

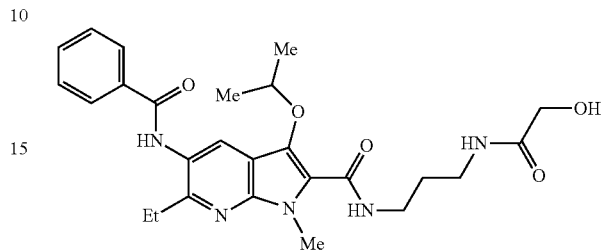

By a method similar to that in Example 1, the title compound (92.8 mg, 64%) was obtained as white crystals from the compound of Reference Example 89 (112 mg, 0.292 mmol), the compound of Reference Example 109 (62.3 mg, 0.369 mmol), HOBt (59.0 mg, 0.437 mmol), WSCD (81.2 mg, 0.424 mmol), triethylamine (0.0804 mL, 0.577 mmol) and DMF (1.5 mL).

$^1$H NMR (300 MHz, DMSO-$d_6$) δ: 1.24 (3H, t, J=7.5 Hz), 1.33 (6H, d, J=6.2 Hz), 1.60-1.76 (2H, m), 2.85 (2H, q, J=7.5 Hz), 3.22 (2H, q, J=6.3 Hz), 3.27-3.40 (2H, m), 3.81 (2H, d, J=5.1 Hz), 3.99 (3H, s), 4.59-4.75 (1H, m), 5.51 (1H, t, J=5.4 Hz), 7.47-7.70 (3H, m), 7.82-8.09 (5H, m), 10.07 (1H, s).

Example 66

Production of N-[1-(hydroxyacetyl)piperidin-4-yl]-3,5-dimethyl-2-phenyl-7-(2,2,2-trifluoroethoxy)-5H-pyrrolo[2,3-b]pyrazine-6-carboxamide

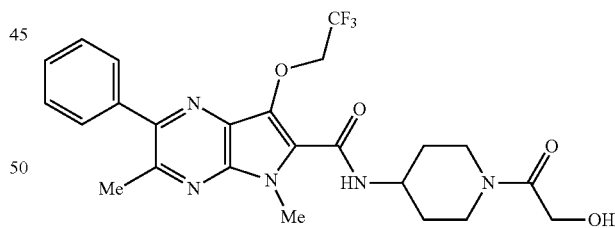

By a method similar to that in Example 1, the title compound (174 mg, 64%) was obtained as pale-yellow crystals from the compound of Reference Example 116 (202 mg, 0.552 mmol), 2-(4-aminopiperidin-1-yl)-2-oxoethanol hydrochloride (137 mg, 0.704 mmol), HOBt (109 mg, 0.804 mmol), WSCD (154 mg, 0.801 mmol), triethylamine (0.154 mL, 1.10 mmol) and DMF (3mL).

$^1$H NMR (300 MHz, DMSO-$d_6$) δ: 1.28-1.58 (2H, m), 1.82-1.98 (2H, m), 2.65 (3H, s), 2.81-2.99 (1H, m), 3.04-3.22 (1H, m), 3.61-3.79 (1H, m), 3.95 (3H, s), 4.01-4.17 (3H, m), 4.18-4.33 (1H, m), 4.54 (1H, t, J=5.3 Hz), 5.29 (2H, q, J=8.9 Hz), 7.42-7.59 (3H, m), 7.61-7.70 (2H, m), 7.92 (1H, d, J=7.7 Hz).

Example 67

Production of N-[1-(hydroxyacetyl)piperidin-4-yl]-1,6-dimethyl-5-[(phenylcarbonyl)amino]-3-(2,2,2-trifluoroethoxy)-1H-indole-2-carboxamide

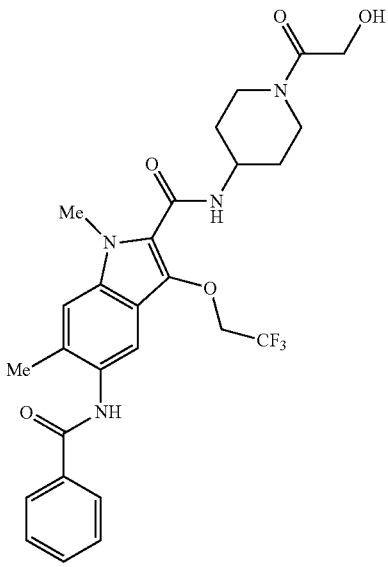 [SMILES: Cc1cc2c(cc1NC(=O)c1ccccc1)c(OCC(F)(F)F)c(C(=O)NC1CCN(C(=O)CO)CC1)n2C]

By a method similar to that in Example 1, the title compound (88 mg, 81%) was obtained as white crystals from the compound of Reference Example 159 (80 mg, 0.20 mmol).

$^1$H NMR (300 MHz, DMSO-$d_6$) δ: 1.35-1.55 (2H, m), 1.93 (2H, d, J=9.9 Hz), 2.36 (3H, s), 2.84 (1H, t, J=11.7 Hz), 3.11 (1H, t, J=12.9 Hz), 3.72 (1H, d, J=13.2 Hz), 3.87 (3H, s), 4.00-4.20 (3H, m), 4.30 (1H, d, J=11.7 Hz), 4.50 (1H, t, J=5.4 Hz), 4.84 (2H, q, J=9.0 Hz), 7.46-7.66 (5H, m), 7.81 (1H, d, J=7.5 Hz), 8.02 (2H, d, J=6.9 Hz), 9.91 (1H, s).

Example 68

Production of N-[1-(hydroxyacetyl)piperidin-4-yl]-6-methyl-5-[(phenylcarbonyl)amino]-3-(2,2,2-trifluoroethoxy)-1-benzothiophene-2-carboxamide

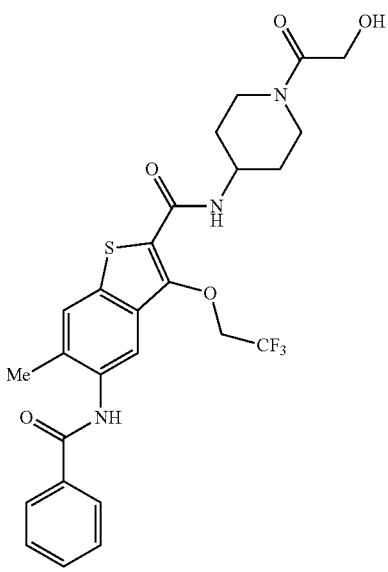 [SMILES: Cc1cc2sc(C(=O)NC3CCN(C(=O)CO)CC3)c(OCC(F)(F)F)c2cc1NC(=O)c1ccccc1]

By a method similar to that in Example 1, the title compound (87 mg, 93%) was obtained as white crystals from the compound of Reference Example 154 (70 mg, 0.17 mmol).

$^1$H NMR (300 MHz, DMSO-$d_6$) δ: 1.35-1.55 (2H, m), 1.92 (2H, J=9.9 Hz), 2.38 (3H, s), 2.80 (1H, t, J=12.0 Hz), 3.09 (1H, t, J=11.6 Hz), 3.73 (1H, d, J=12.3 Hz), 4.00-4.12 (3H, m), 4.33 (1H, d, J=10.5 Hz), 4.50 (1H, t, J=5.4 Hz), 5.00 (2H, q, J=8.9 Hz), 7.53-7.65 (3H, m), 7.82 (1H, d, J=7.8 Hz), 7.90 (2H, d, J=8.4 Hz), 8.01-8.04 (2H, m), 10.05 (1H, s).

Example 69

Production of 6-ethyl-N-[1-(hydroxyacetyl)piperidin-4-yl]-1-methyl-5-[(1,3-thiazol-2-ylcarbonyl)amino]-3-(2,2,2-trifluoroethoxy)-1H-pyrrolo[2,3-b]pyridine-2-carboxamide

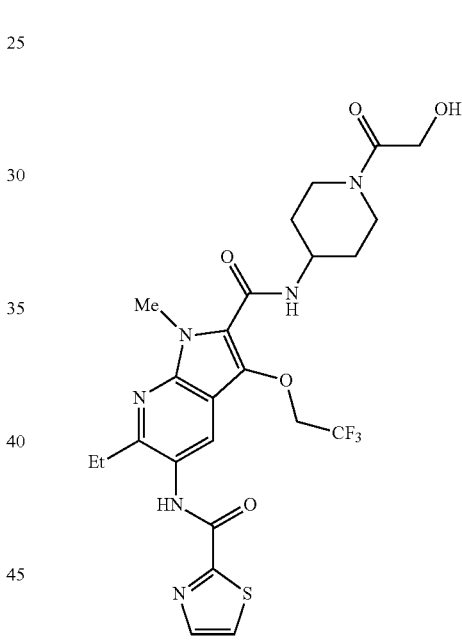

By a method similar to that in Example 1, the title compound (56 mg, 70%) was obtained as white crystals from the compound of Reference Example 161 (60 mg, 0.14 mmol), 2-(4-aminopiperidin-1-yl)-2-oxoethanol hydrochloride (33 mg, 0.17 mmol), HOBt (25 mg, 0.18 mmol), WSCD (35 mg, 0.18 mmol), triethylamine (28 mg, 0.28 mmol), DMF (2 mL).

$^1$H NMR (300 MHz, DMSO-$d_6$) δ: 1.24 (3H, t, J=7.5 Hz), 1.30-1.55 (2H, m), 1.93 (2H, d, J=12.9, 2.7 Hz), 2.87 (3H, q, J=7.5 Hz), 3.12 (1H, t, J=12.9 Hz), 3.71 (1H, d, J=9.3 Hz), 3.93 (3H, s), 4.00-4.20 (3H, m), 4.28 (1H, d, J=10.8 Hz), 4.49 (1H, t, J=5.4 Hz), 4.93 (2H, q, J=8.9 Hz), 7.83 (1H, d, J=7.5 Hz), 8.13-8.15 (2H, m), 8.20 (1H, s), 10.47 (1H, s).

Example 70

Production of 6-ethyl-N-[1-(hydroxyacetyl)piperidin-4-yl]-1-methyl-3-(1-methylethoxy)-5-[(phenylcarbonyl)amino]-1H-pyrrolo[2,3-b]pyridine-2-carboxamide

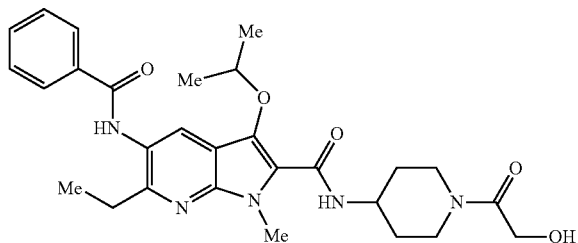 [SMILES: CCc1nc2c(cc1NC(=O)c1ccccc1)c(OC(C)C)c(C(=O)NC1CCN(C(=O)CO)CC1)n2C]

A mixture of the compound of Reference Example 332 (161 mg, 0.422 mmol), 2-(4-aminopiperidin-1-yl)-2-oxoethanol hydrochloride (97.2 mg, 0.499 mmol), HOBt (81.5 mg, 0.603 mmol), WSCD (137 mg, 0.715 mmol) and triethylamine (0.118 mL, 0.844 mmol) in DMF (3 mL) was stirred at room temperature for 15 hr. To the reaction mixture was added water (5 mL), and the mixture was extracted with ethyl acetate (5 mL×3). The organic layers were combined, dried over anhydrous magnesium sulfate, and concentrated under reduced pressure. The residue was purified by amino silica gel column chromatography (eluent, hexane:ethyl acetate=2:1→ethyl acetate) and crystallized from hexane/diisopropyl ether to give the title compound (155 mg, 71%) as white crystals.

$^1$H NMR (300 MHz, DMSO-$d_6$) δ: 1.25 (3H, t, J=7.6 Hz), 1.31 (6H, d, J=6.0 Hz), 1.34-1.61 (2H, m), 1.86-1.98 (2H, m), 2.78-2.95 (1H, m), 2.85 (2H, q, J=7.6 Hz), 3.05-3.21 (1H, m), 3.62-3.77 (2H, m), 3.99 (3H, s), 4.03-4.18 (1H, m), 4.11 (2H, t, J=5.7 Hz), 4.22-4.35 (1H, m), 4.52 (1H, t, J=5.7 Hz), 4.63-4.76 (1H, m), 7.49-7.66 (3H, m), 7.85 (1H, d, J=7.7 Hz), 7.96-8.07 (3H, m), 10.07 (1H, s).

Example 71

Production of 6-ethyl-N-[1-(hydroxyacetyl)piperidin-4-yl]-1-methyl-3-(1-methylethoxy)-5-[(phenylcarbonyl)amino]-1H-indole-2-carboxamide

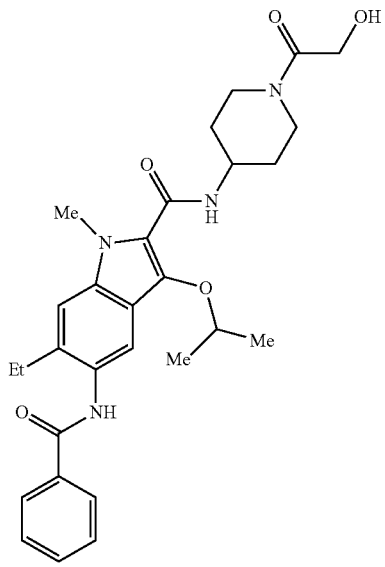 [SMILES: CCc1cc2c(cc1NC(=O)c1ccccc1)c(OC(C)C)c(C(=O)NC1CCN(C(=O)CO)CC1)n2C]

A mixture of the compound of Reference Example 169 (90 mg, 0.24 mmol), 2-(4-aminopiperidin-1-yl)-2-oxoethanol hydrochloride (55 mg, 0.28 mmol), HOBt (42 mg, 0.31 mmol), WSCD (59 mg, 0.31 mmol) and triethylamine (48 mg, 0.47 mmol) in DMF (2 mL) was stirred at room temperature for 20 hr. The reaction mixture was diluted with saturated aqueous sodium hydrogen carbonate, and extracted twice with ethyl acetate. The extracts were combined and washed with brine, dried over magnesium sulfate, and concentrated under reduced pressure. The residue was purified by amino silica gel column chromatography (eluent, ethyl acetate) and recrystallized from ethyl acetate/hexane to give the title compound (97 mg, 78%) as white crystals.

$^1$H NMR (300 MHz, DMSO-$d_6$) δ: 1.20 (3H, t, J=7.5 Hz), 1.30 (6H, d, J=6.3 Hz), 1.36-1.60 (2H, m), 1.93 (2H, d, J=10.8 Hz), 2.71 (2H, q, J=7.5 Hz), 2.84 (1H, t, J=11.6 Hz), 3.12 (1H, t, J=11.6 Hz), 3.70 (1H, d, J=12.9 Hz), 3.95 (3H, s), 4.02-4.13 (3H, m), 4.30 (1H, d, J=12.9 Hz), 4.51 (1H, t, J=5.3 Hz), 4.53-4.66 (1H, m), 7.41 (1H, s), 7.51-7.62 (4H, m), 7.82 (1H, d, J=7.8 Hz), 8.01 (2H, d, J=7.2 Hz), 9.91 (1H, s).

Example 72

Production of N-cyclopentyl-6-ethyl-1-methyl-3-(1-methylethoxy)-5-[(phenylcarbonyl)amino]-1H-pyrrolo[2,3-b]pyridine-2-carboxamide

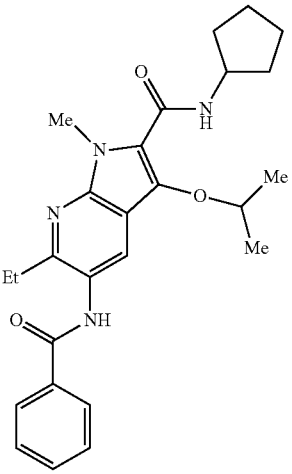 [SMILES: CCc1nc2c(cc1NC(=O)c1ccccc1)c(OC(C)C)c(C(=O)NC1CCCC1)n2C]

To a 0.24M-DMF solution (500 μL, 120 μmol) of cyclopentylamine was added a 0.16M-DMF solution (500 μL, 80 μmol) of the compound of Reference Example 89, and a solution (500 μL) of HOBt (120 μmol), WSCD (120 μmol) and triethylamine (160 μmol) in DMF was added thereto. The reaction mixture was stirred at room temperature overnight. The mixture was extracted with ethyl acetate (3 mL) and 2% aqueous sodium bicarbonate solution (2 mL), and the organic layer was collected by upper layer phase Septube (manufactured by Wako Pure Chemical Industries, Ltd.). Ethyl acetate was evaporated by blowing nitrogen and the residue was dissolved in acetonitrile (1000 μL) and the solution was purified by preparative HPLC (acetonitrile-10 mM ammonium carbonate-containing aqueous solvent) to give the title compound.

yield: 23.6 mg

LC-MS analysis: purity 100%

MS (ESI+): 449.3 (M+H)

Example 73-Example 120

By a method similar to that in Example 72, the compounds shown in Table 1 were obtained from the compound of Reference Example 89 and the corresponding amine.

TABLE 1

| Ex. No. | structure | yield (mg) | purity (%) | MS (ESI+) |
|---|---|---|---|---|
| 73 | 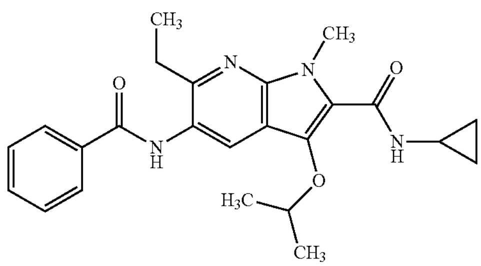 [SMILES: CCc1nc2c(cc1NC(=O)c1ccccc1)c(OC(C)C)c(C(=O)NC1CC1)n2C] | 37.8 | 100 | 421.3 |
| 74 | 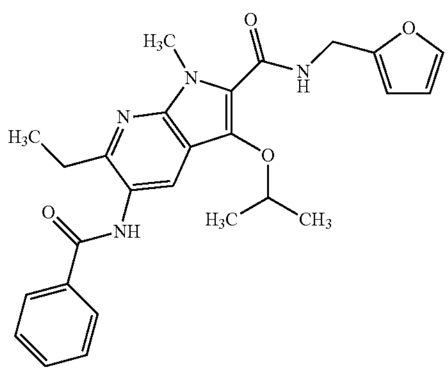 [SMILES: CCc1nc2c(cc1NC(=O)c1ccccc1)c(OC(C)C)c(C(=O)NCc1ccco1)n2C] | 57.1 | 100 | 461.2 |
| 75 | 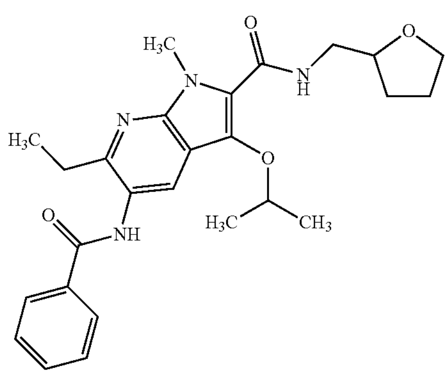 [SMILES: CCc1nc2c(cc1NC(=O)c1ccccc1)c(OC(C)C)c(C(=O)NCC1CCCO1)n2C] | 47.8 | 100 | 465.3 |
| 76 | 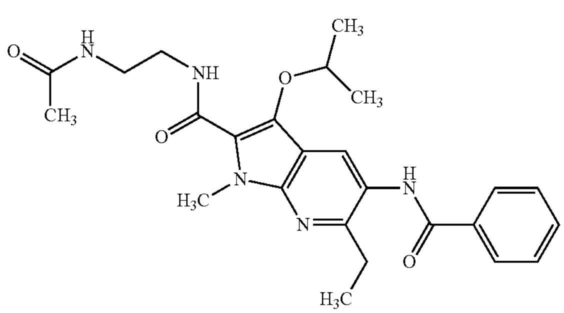 [SMILES: CCc1nc2c(cc1NC(=O)c1ccccc1)c(OC(C)C)c(C(=O)NCCNC(C)=O)n2C] | 35.7 | 100 | 466.2 |

TABLE 1-continued

| Ex. No. | structure | yield (mg) | purity (%) | MS (ESI+) |
|---|---|---|---|---|
| 77 | 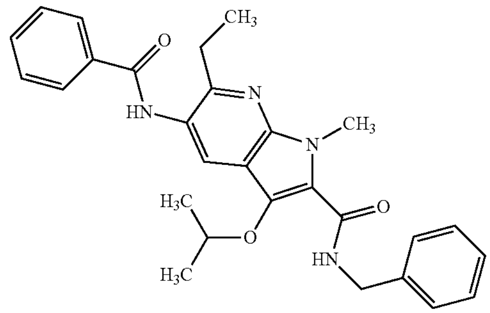 [SMILES: CCc1nc2c(cc1NC(=O)c1ccccc1)c(OC(C)C)c(C(=O)NCc1ccccc1)n2C] | 54.6 | 100 | 471.2 |
| 78 | 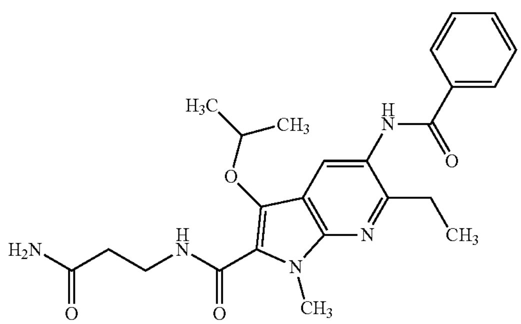 [SMILES: CCc1nc2c(cc1NC(=O)c1ccccc1)c(OC(C)C)c(C(=O)NCCC(N)=O)n2C] | 41.2 | 100 | 452.2 |
| 79 | 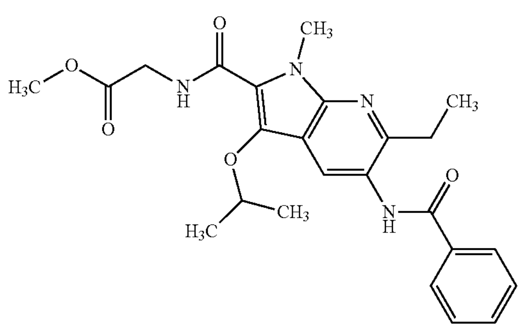 [SMILES: CCc1nc2c(cc1NC(=O)c1ccccc1)c(OC(C)C)c(C(=O)NCC(=O)OC)n2C] | 49.1 | 100 | 453.2 |
| 80 | 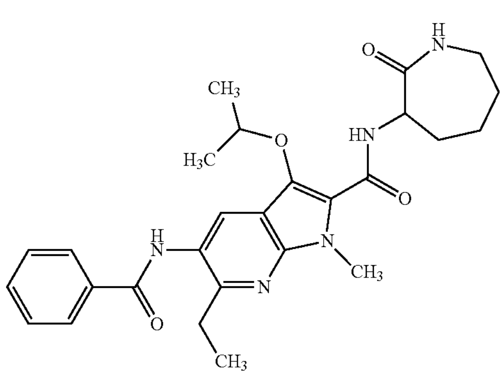 [SMILES: CCc1nc2c(cc1NC(=O)c1ccccc1)c(OC(C)C)c(C(=O)NC1CCCCNC1=O)n2C] | 48.2 | 100 | 492.3 |

TABLE 1-continued

| Ex. No. | structure | yield (mg) | purity (%) | MS (ESI+) |
|---|---|---|---|---|
| 81 | 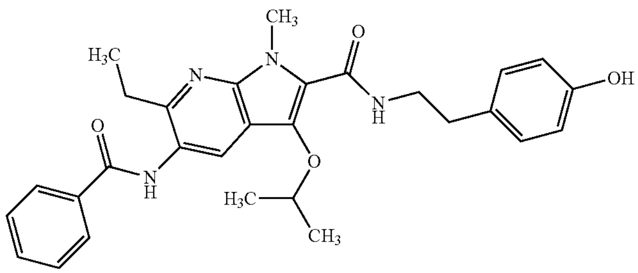 [SMILES: CCc1nc2c(cc1NC(=O)c1ccccc1)c(OC(C)C)c(C(=O)NCCc1ccc(O)cc1)n2C] | 44.7 | 100 | 501.2 |
| 82 | 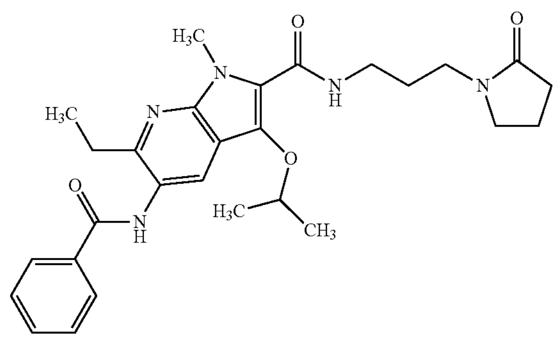 [SMILES: CCc1nc2c(cc1NC(=O)c1ccccc1)c(OC(C)C)c(C(=O)NCCCN1CCCC1=O)n2C] | 43.3 | 100 | 506.3 |
| 83 | 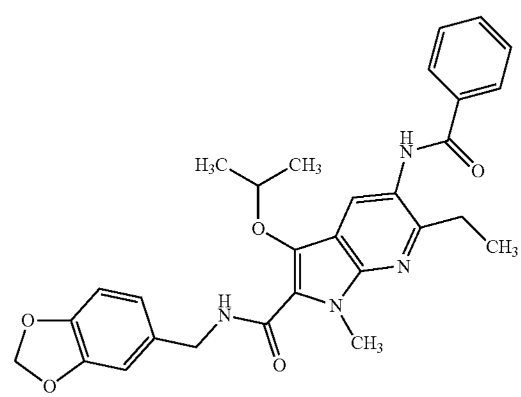 [SMILES: CCc1nc2c(cc1NC(=O)c1ccccc1)c(OC(C)C)c(C(=O)NCc1ccc3c(c1)OCO3)n2C] | 52.7 | 100 | 515.2 |
| 84 | 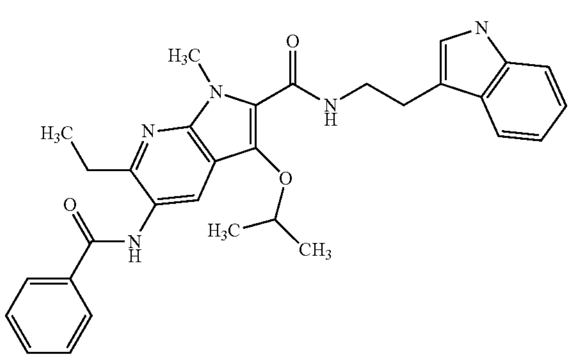 [SMILES: CCc1nc2c(cc1NC(=O)c1ccccc1)c(OC(C)C)c(C(=O)NCCc1c[nH]c3ccccc13)n2C] | 41.3 | 100 | 524.3 |

TABLE 1-continued
| Ex. No. | structure | yield (mg) | purity (%) | MS (ESI+) |
|---|---|---|---|---|
| 85 | 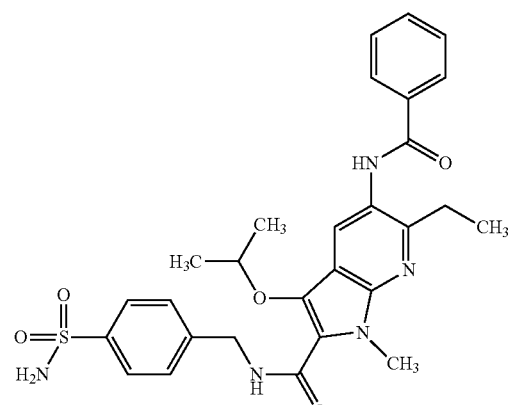 | 39.7 | 100 | 550.3 |
| 86 | 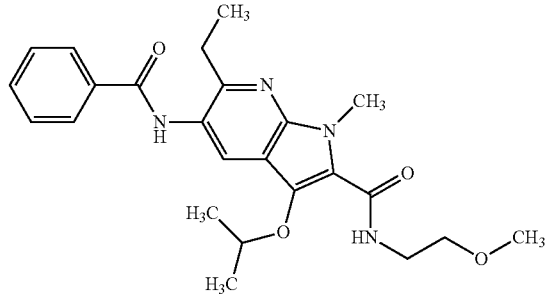 [SMILES: CCc1nc2c(cc1NC(=O)c1ccccc1)c(OC(C)C)c(C(=O)NCCOC)n2C] | 31.2 | 98 | 439.2 |
| 87 | 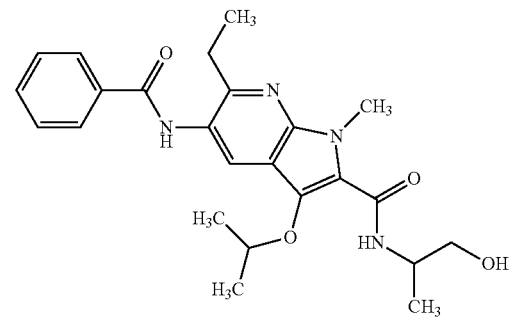 [SMILES: CCc1nc2c(cc1NC(=O)c1ccccc1)c(OC(C)C)c(C(=O)NC(C)CO)n2C] | 44.5 | 100 | 439.2 |
| 88 | 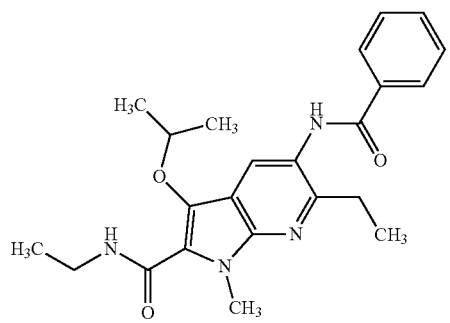 [SMILES: CCNC(=O)c1c(OC(C)C)c2cc(NC(=O)c3ccccc3)c(CC)nc2n1C] | 46.5 | 100 | 409.2 |

TABLE 1-continued

| Ex. No. | structure | yield (mg) | purity (%) | MS (ESI+) |
|---|---|---|---|---|
| 89 | 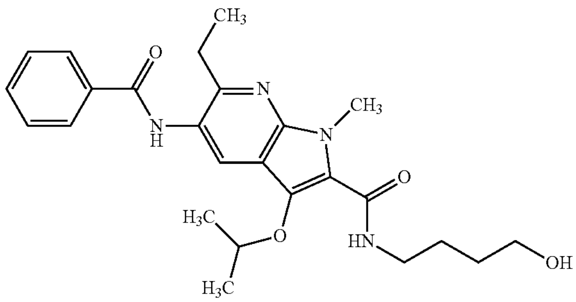 [SMILES: CCc1nc2c(cc1NC(=O)c1ccccc1)c(OC(C)C)c(C(=O)NCCCCO)n2C] | 44.2 | 100 | 453.2 |
| 90 | 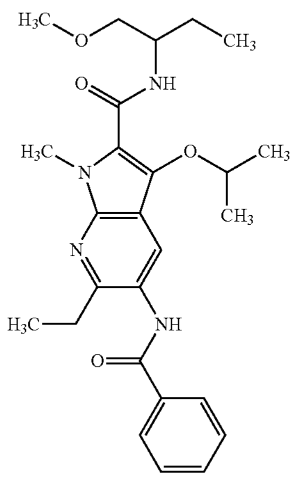 [SMILES: CCc1nc2c(cc1NC(=O)c1ccccc1)c(OC(C)C)c(C(=O)NC(CC)COC)n2C] | 34.9 | 100 | 467.3 |
| 91 | 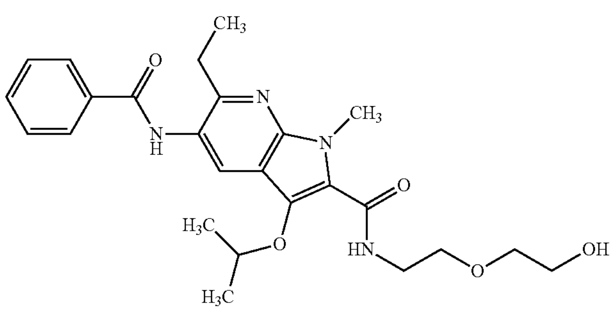 [SMILES: CCc1nc2c(cc1NC(=O)c1ccccc1)c(OC(C)C)c(C(=O)NCCOCCO)n2C] | 40.6 | 100 | 469.2 |
| 92 | 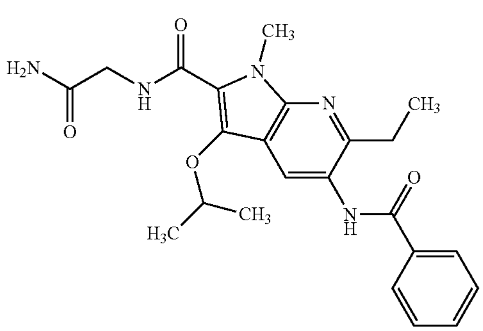 [SMILES: CCc1nc2c(cc1NC(=O)c1ccccc1)c(OC(C)C)c(C(=O)NCC(N)=O)n2C] | 30.9 | 100 | 438.2 |

TABLE 1-continued

| Ex. No. | structure | yield (mg) | purity (%) | MS (ESI+) |
|---|---|---|---|---|
| 93 | 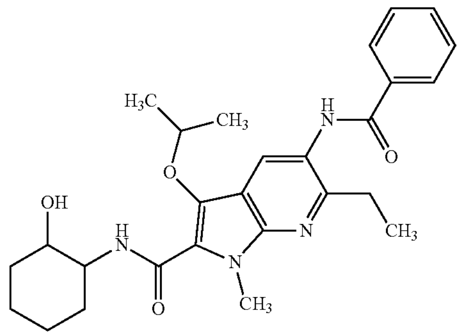 [SMILES: CCc1nc2c(cc1NC(=O)c1ccccc1)c(OC(C)C)c(C(=O)NC1CCCCC1O)n2C] | 40.1 | 100 | 479.2 |
| 94 | 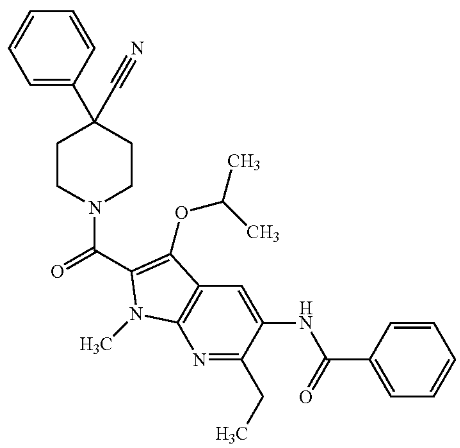 [SMILES: CCc1nc2c(cc1NC(=O)c1ccccc1)c(OC(C)C)c(C(=O)N1CCC(C#N)(c3ccccc3)CC1)n2C] | 51.1 | 100 | 550.3 |
| 95 | 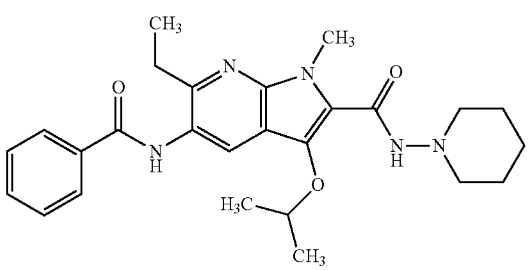 [SMILES: CCc1nc2c(cc1NC(=O)c1ccccc1)c(OC(C)C)c(C(=O)NN1CCCCC1)n2C] | 26.5 | 100 | 464.3 |
| 96 | 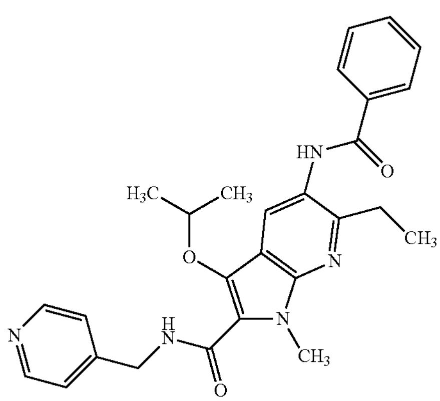 [SMILES: CCc1nc2c(cc1NC(=O)c1ccccc1)c(OC(C)C)c(C(=O)NCc1ccncc1)n2C] | 53.2 | 100 | 472.2 |

TABLE 1-continued

| Ex. No. | structure | yield (mg) | purity (%) | MS (ESI+) |
|---|---|---|---|---|
| 97 | 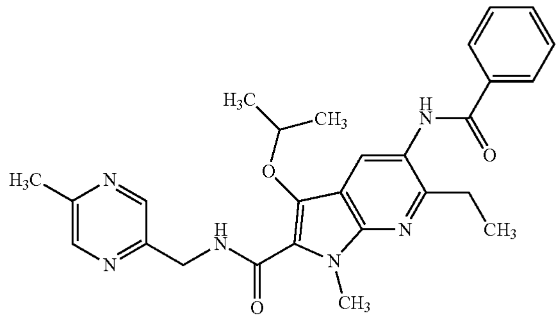 [SMILES: CCc1nc2c(cc1NC(=O)c1ccccc1)c(OC(C)C)c(C(=O)NCc1cnc(C)cn1)n2C] | 54.1 | 100 | 487.3 |
| 98 | 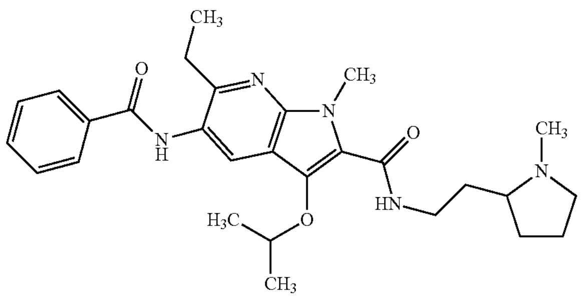 [SMILES: CCc1nc2c(cc1NC(=O)c1ccccc1)c(OC(C)C)c(C(=O)NCCC1CCCN1C)n2C] | 79.7 | 100 | 492.3 |
| 99 | 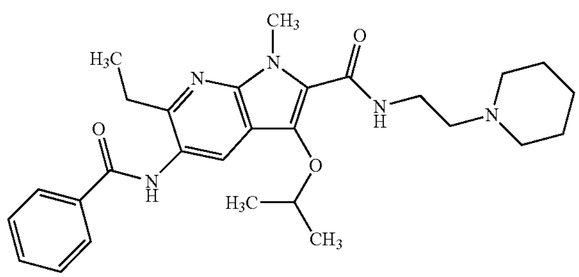 [SMILES: CCc1nc2c(cc1NC(=O)c1ccccc1)c(OC(C)C)c(C(=O)NCCN1CCCCC1)n2C] | 84 | 100 | 492.3 |
| 100 | 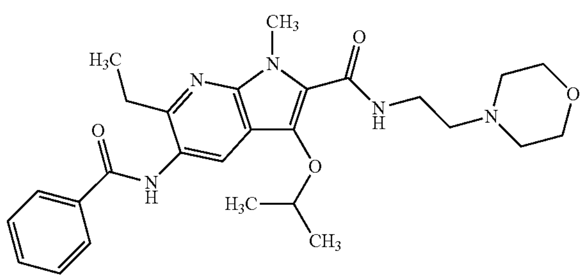 [SMILES: CCc1nc2c(cc1NC(=O)c1ccccc1)c(OC(C)C)c(C(=O)NCCN1CCOCC1)n2C] | 51.3 | 100 | 494.3 |
| 101 | 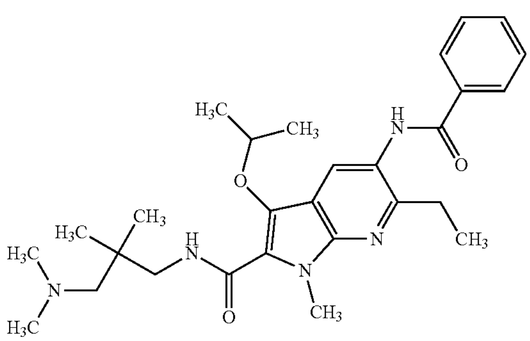 [SMILES: CCc1nc2c(cc1NC(=O)c1ccccc1)c(OC(C)C)c(C(=O)NCC(C)(C)CN(C)C)n2C] | 16.2 | 100 | 494.3 |

TABLE 1-continued

| Ex. No. | structure | yield (mg) | purity (%) | MS (ESI+) |
| --- | --- | --- | --- | --- |
| 102 | 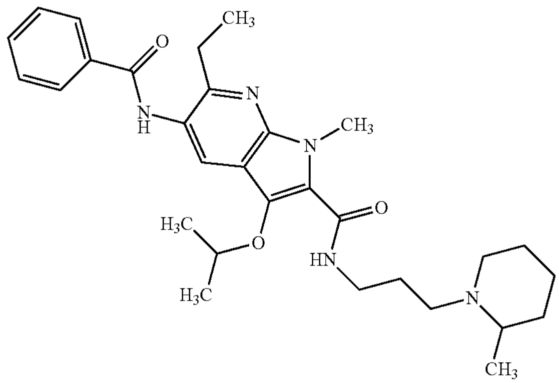 [SMILES: CCc1nc2c(cc1NC(=O)c1ccccc1)c(OC(C)C)c(C(=O)NCCCN1CCCCC1C)n2C] | 55.2 | 100 | 520.4 |
| 103 | 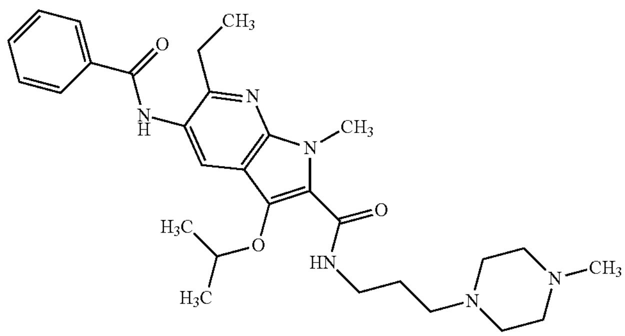 [SMILES: CCc1nc2c(cc1NC(=O)c1ccccc1)c(OC(C)C)c(C(=O)NCCCN1CCN(C)CC1)n2C] | 51.3 | 99 | 521.4 |
| 104 | 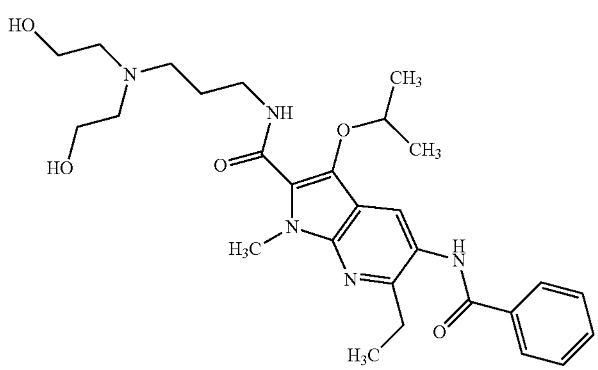 [SMILES: CCc1nc2c(cc1NC(=O)c1ccccc1)c(OC(C)C)c(C(=O)NCCCN(CCO)CCO)n2C] | 40.9 | 100 | 526.3 |
| 105 | 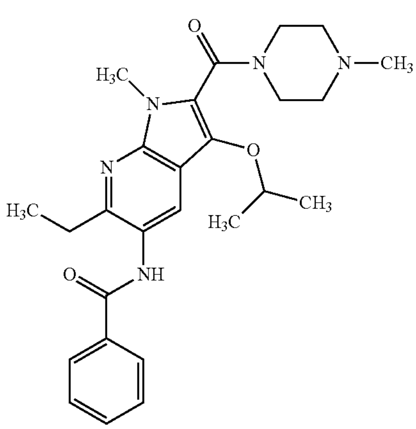 [SMILES: CCc1nc2c(cc1NC(=O)c1ccccc1)c(OC(C)C)c(C(=O)N1CCN(C)CC1)n2C] | 54.8 | 100 | 464.3 |

TABLE 1-continued

| Ex. No. | structure | yield (mg) | purity (%) | MS (ESI+) |
|---|---|---|---|---|
| 106 | 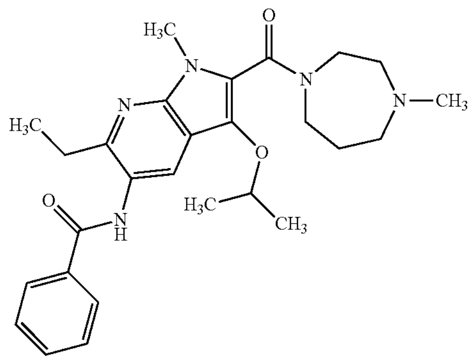 [SMILES: CCc1nc2c(cc1NC(=O)c1ccccc1)c(OC(C)C)c(C(=O)N1CCCN(C)CC1)n2C] | 47.5 | 100 | 478.3 |
| 107 | 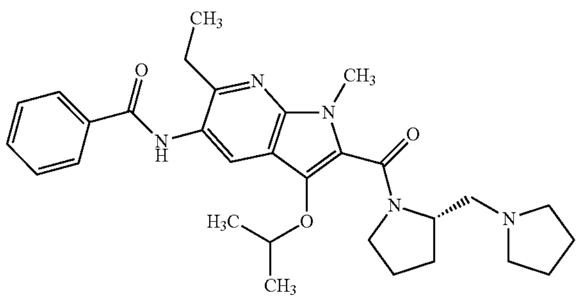 [SMILES: CCc1nc2c(cc1NC(=O)c1ccccc1)c(OC(C)C)c(C(=O)N1CCC[C@H]1CN1CCCC1)n2C] | 44 | 100 | 518.4 |
| 108 | 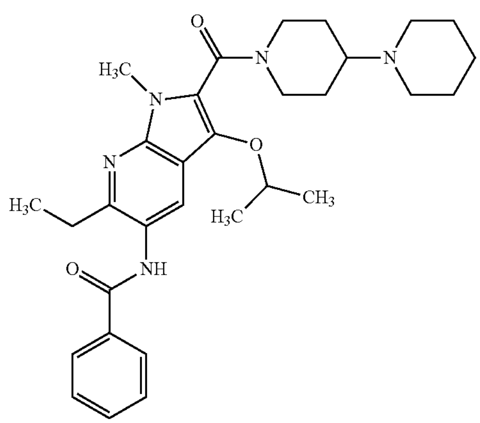 [SMILES: CCc1nc2c(cc1NC(=O)c1ccccc1)c(OC(C)C)c(C(=O)N1CCC(N3CCCCC3)CC1)n2C] | 45.7 | 100 | 532.3 |
| 109 | 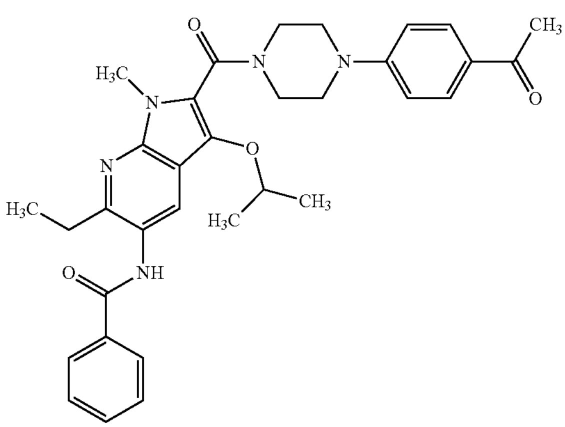 [SMILES: CCc1nc2c(cc1NC(=O)c1ccccc1)c(OC(C)C)c(C(=O)N1CCN(c3ccc(C(C)=O)cc3)CC1)n2C] | 58.3 | 100 | 568.3 |

TABLE 1-continued

| Ex. No. | structure | yield (mg) | purity (%) | MS (ESI+) |
|---|---|---|---|---|
| 110 | 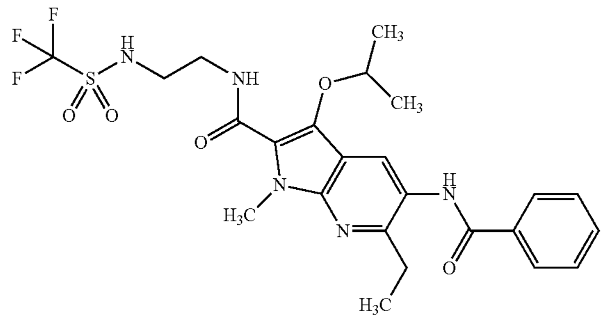 [SMILES: CCc1nc2c(cc1NC(=O)c1ccccc1)c(OC(C)C)c(C(=O)NCCNS(=O)(=O)C(F)(F)F)n2C] | 43 | 100 | 556.2 |
| 111 | 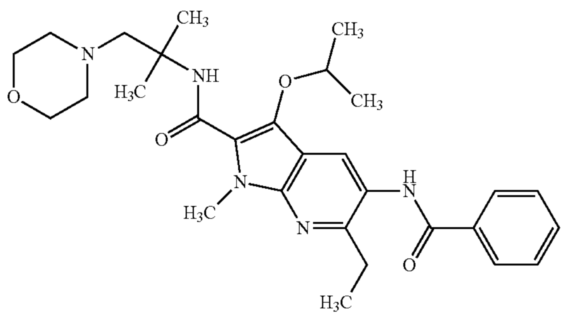 [SMILES: CCc1nc2c(cc1NC(=O)c1ccccc1)c(OC(C)C)c(C(=O)NC(C)(C)CN1CCOCC1)n2C] | 57.9 | 100 | 522.3 |
| 112 | 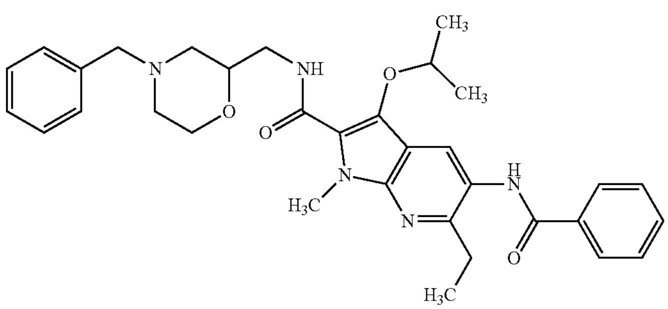 [SMILES: CCc1nc2c(cc1NC(=O)c1ccccc1)c(OC(C)C)c(C(=O)NCC1CN(Cc3ccccc3)CCO1)n2C] | 48.1 | 100 | 570.3 |
| 113 | 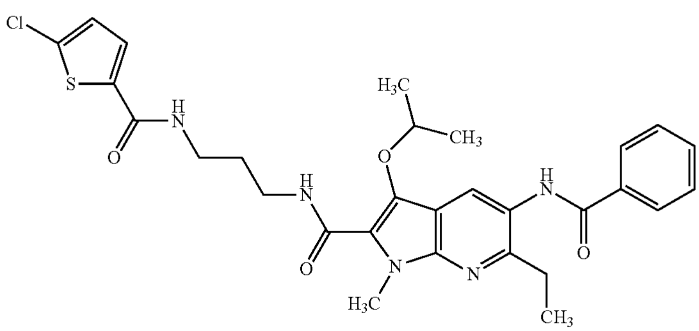 [SMILES: CCc1nc2c(cc1NC(=O)c1ccccc1)c(OC(C)C)c(C(=O)NCCCNC(=O)c1ccc(Cl)s1)n2C] | 47.2 | 100 | 582.2 |

TABLE 1-continued

| Ex. No. | structure | yield (mg) | purity (%) | MS (ESI+) |
|---|---|---|---|---|
| 114 | 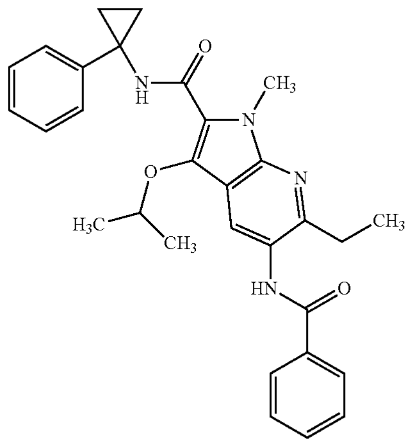 [SMILES: CCc1nc2c(cc1NC(=O)c1ccccc1)c(OC(C)C)c(C(=O)NC1(c3ccccc3)CC1)n2C] | 3 | 100 | 497.3 |
| 115 | 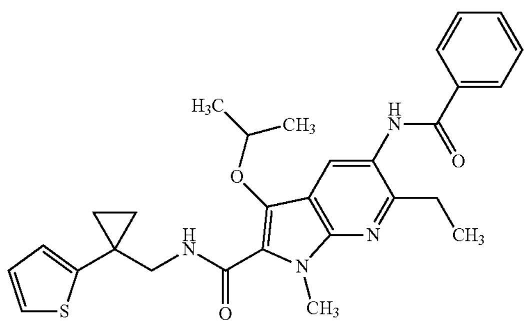 [SMILES: CCc1nc2c(cc1NC(=O)c1ccccc1)c(OC(C)C)c(C(=O)NCC1(c3cccs3)CC1)n2C] | 54.8 | 100 | 517.3 |
| 116 | 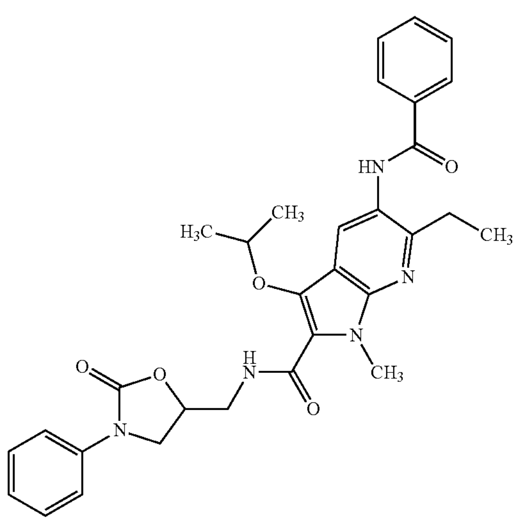 [SMILES: CCc1nc2c(cc1NC(=O)c1ccccc1)c(OC(C)C)c(C(=O)NCC1CN(c3ccccc3)C(=O)O1)n2C] | 54 | 100 | 556.2 |

TABLE 1-continued

| Ex. No. | structure | yield (mg) | purity (%) | MS (ESI+) |
|---|---|---|---|---|
| 117 | 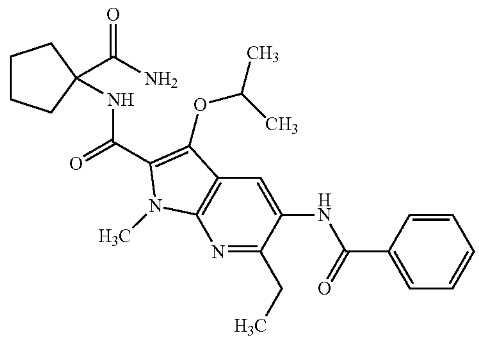 [SMILES: CCc1nc2c(cc1NC(=O)c1ccccc1)c(OC(C)C)c(C(=O)NC1(C(N)=O)CCCC1)n2C] | 50 | 100 | 492.2 |
| 118 | 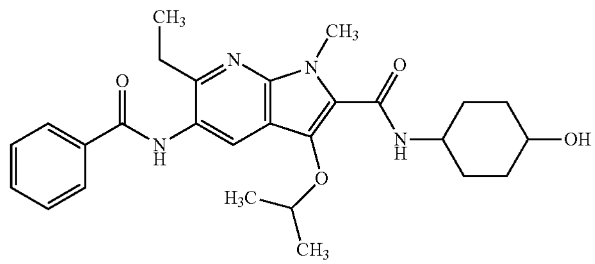 [SMILES: CCc1nc2c(cc1NC(=O)c1ccccc1)c(OC(C)C)c(C(=O)NC1CCC(O)CC1)n2C] | 29.3 | 100 | 479.3 |
| 119 | 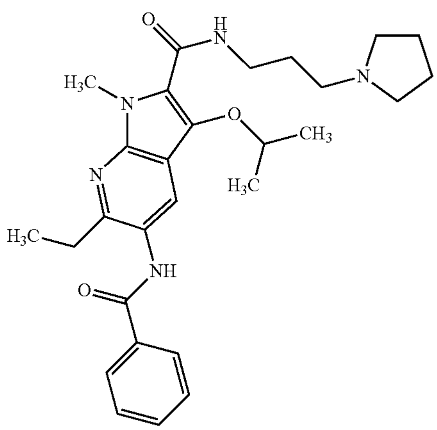 [SMILES: CCc1nc2c(cc1NC(=O)c1ccccc1)c(OC(C)C)c(C(=O)NCCCN1CCCC1)n2C] | 36.4 | 97 | 492.3 |
| 120 | 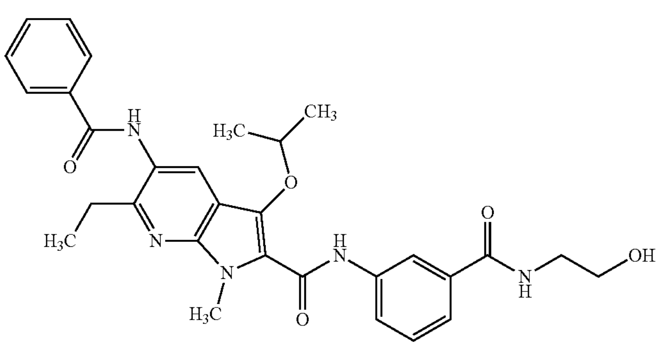 [SMILES: CCc1nc2c(cc1NC(=O)c1ccccc1)c(OC(C)C)c(C(=O)Nc1cccc(C(=O)NCCO)c1)n2C] | 6.8 | 100 | 544.2 |

Example 121

Production of 6-ethyl-N-(2-fluorophenyl)-1-methyl-3-(1-methylethoxy)-5-[(phenylcarbonyl)amino]-1H-pyrrolo[2,3-b]pyridine-2-carboxamide

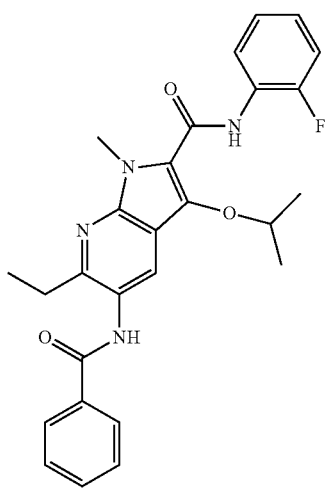 [SMILES: CCc1nc2c(cc1NC(=O)c1ccccc1)c(OC(C)C)c(C(=O)Nc1ccccc1F)n2C]

To a 0.24M-DMF solution (500 μL, 120 μmol) of 2-fluoroaniline was added a 0.16M-DMF solution (500 μL, 80 μmol) of the compound of Reference Example 89, and a solution (500 μL) of HATU (160 μmol) and diisopropylethylamine (160 μmol) in DMF was added thereto. The reaction mixture was stirred at 70° C. overnight. The mixture was extracted with ethyl acetate (3 mL) and 2% aqueous sodium bicarbonate solution (2 mL), and the organic layer was collected by upper layer Phase Septube (manufactured by Wako Pure Chemical Industries, Ltd.). Ethyl acetate was evaporated by blowing nitrogen and the residue was dissolved in acetonitrile (1000 μL) and the solution was purified by preparative HPLC (acetonitrile-10 mM ammonium carbonate-containing aqueous solvent) to give the title compound.

yield: 22.5 mg

LC-MS analysis: purity 100%

MS (ESI+): 475.2 (M+H)

Example 122-Example 125

By a method similar to that in Example 121, the compounds shown in Table 2 were obtained from the compound of Reference Example 89 and the corresponding amine.

TABLE 2

| Ex. No. | structure | yield (mg) | purity (%) | MS (ESI+) |
|---|---|---|---|---|
| 122 | 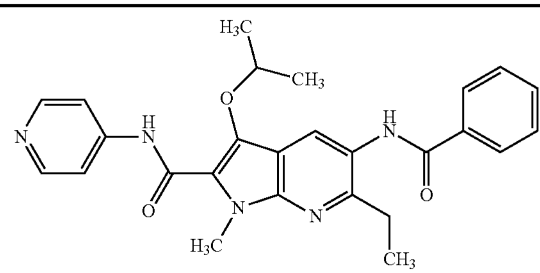 | 43.9 | 100 | 458.2 |
| 123 | 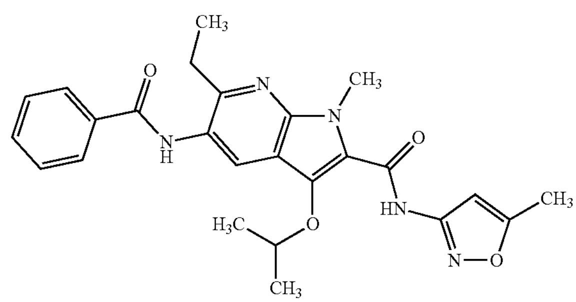 [SMILES: CCc1nc2c(cc1NC(=O)c1ccccc1)c(OC(C)C)c(C(=O)Nc1cc(C)on1)n2C] | 7.2 | 100 | 462.2 |
| 124 | 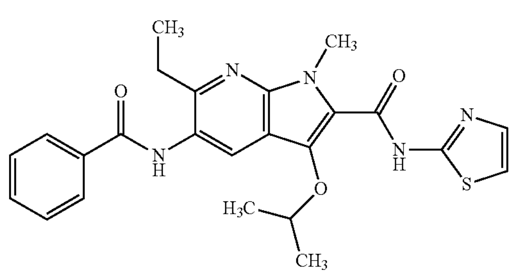 [SMILES: CCc1nc2c(cc1NC(=O)c1ccccc1)c(OC(C)C)c(C(=O)Nc1nccs1)n2C] | 35.6 | 97 | 464.1 |

TABLE 2-continued

| Ex. No. | structure | yield (mg) | purity (%) | MS (ESI+) |
|---|---|---|---|---|
| 125 | 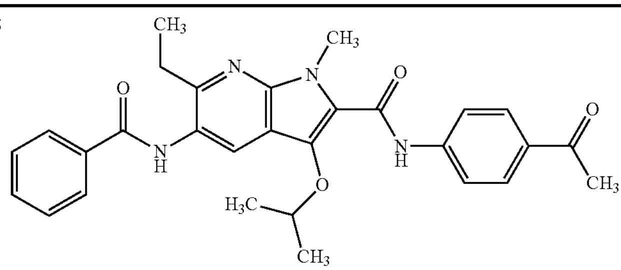 | 40.3 | 100 | 499.2 |

Example 127

Production of 6-ethyl-N-[1-(hydroxyacetyl)piperidin-4-yl]-1-methyl-5-[(phenylcarbonyl)amino]-3-(2,2,2-trifluoroethoxy)-1H-pyrrolo[3,2-b]pyridine-2-carboxamide

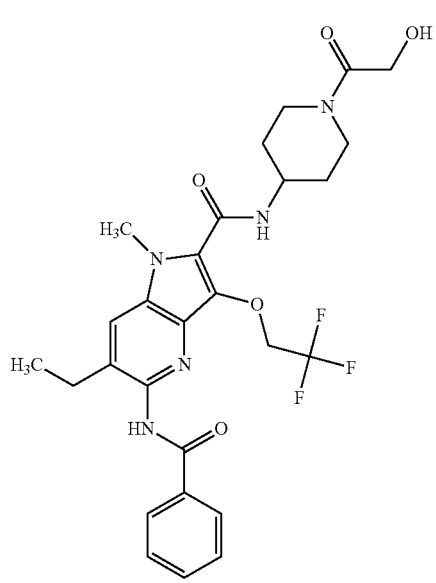 [SMILES: CCc1cc2c(nc1NC(=O)c1ccccc1)c(OCC(F)(F)F)c(C(=O)NC1CCN(C(=O)CO)CC1)n2C]

By a method similar to that in Example 16, the title compound (93.4 mg, 46%) was obtained as a white non-crystalline solid from the compound of Reference Example 271 (152 mg, 0.361 mmol), 2-(4-aminopiperidin-1-yl)-2-oxoethanol hydrochloride (84.3 mg, 0.433 mmol), HOBt (73.2 mg, 0.542 mmol), WSCD (104 mg, 0.542 mmol), triethylamine (0.150 mL, 1.08 mmol) and DMF (3.0 mL).

$^1$H NMR (300 MHz, DMSO-d$_6$) δ: 1.23 (3H, t, J=7.5 Hz), 1.31-1.53 (2H, m), 1.84-1.96 (2H, m), 2.71 (2H, q, J=7.5 Hz), 2.80-2.96 (1H, m), 3.04-3.20 (1H, m), 3.62-3.77 (1H, m), 3.94 (3H, s), 4.02-4.16 (3H, m), 4.19-4.30 (1H, m), 4.54 (1H, t, J=5.5 Hz), 5.23 (2H, q, J=8.9 Hz), 7.47-7.65 (3H, m), 7.80 (1H, d, J=7.7 Hz), 7.95-8.05 (3H, m), 10.52 (1H, s).

Example 128

Production of 6-ethyl-N-[1-(hydroxyacetyl)piperidin-4-yl]-1-methyl-5-phenyl-3-(2,2,2-trifluoroethoxy)-1H-pyrrolo[3,2-b]pyridine-2-carboxamide

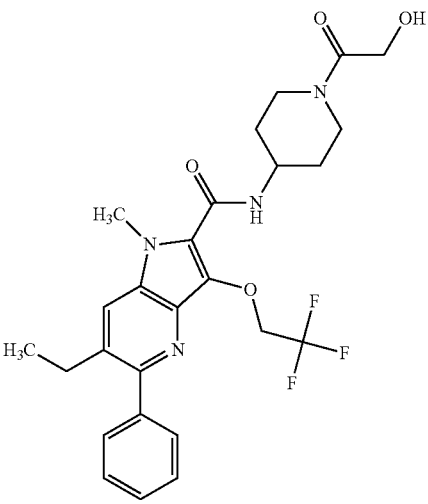 [SMILES: CCc1cc2c(nc1-c1ccccc1)c(OCC(F)(F)F)c(C(=O)NC1CCN(C(=O)CO)CC1)n2C]

By a method similar to that in Example 16, the title compound (72.3 mg, 43%) was obtained as a white powder from the compound of Reference Example 273 (123 mg, 0.325 mmol), 2-(4-aminopiperidin-1-yl)-2-oxoethanol hydrochloride (75.9 mg, 0.390 mmol), HOBt (65.9 mg, 0.488 mmol), WSCD (93.5 mg, 0.488 mmol), triethylamine (0.135 mL, 0.975 mmol) and DMF (2.5 mL).

$^1$H NMR (300 MHz, DMSO-d$_6$) δ: 1.11 (3H, t, J=7.5 Hz), 1.29-1.56 (2H, m), 1.84-1.97 (2H, m), 2.74 (2H, q, J=7.5 Hz), 2.82-2.97 (1H, m), 3.05-3.21 (1H, m), 3.61-3.75 (1H, m), 3.95 (3H, s), 4.01-4.17 (3H, m), 4.18-4.30 (1H, m), 4.54 (1H, t, J=5.5 Hz), 5.32 (2H, q, J=9.2 Hz), 7.39-7.55 (5H, m), 7.78 (1H, d, J=7.6 Hz), 7.98 (1H, s).

Example 129

Production of 3-ethoxy-6-ethyl-N-[1-(hydroxy-acetyl)piperidin-4-yl]-1-methyl-5-[(phenylcarbonyl)amino]-1H-pyrrolo[3,2-b]pyridine-2-carboxamide

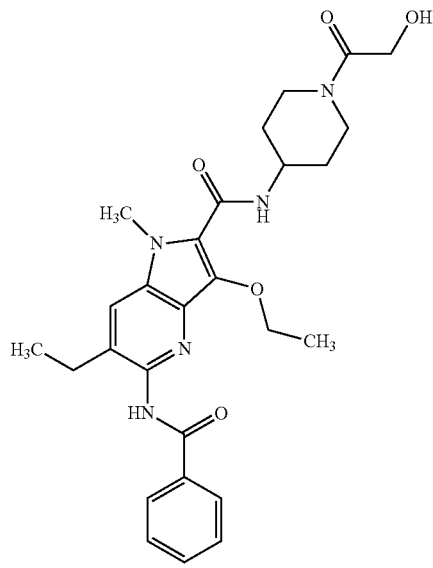 [SMILES: CCOc1c(C(=O)NC2CCN(C(=O)CO)CC2)n(C)c2cc(CC)c(NC(=O)c3ccccc3)nc12]

By a method similar to that in Example 16, the title compound (105 mg, 70%) was obtained as a white powder from the compound of Reference Example 279 (109 mg, 0.297 mmol), 2-(4-aminopiperidin-1-yl)-2-oxoethanol hydrochloride (69.4 mg, 0.356 mmol), HOBt (60.3 mg, 0.446 mmol), WSCD (85.4 mg, 0.446 mmol), triethylamine (0.0969 mL, 0.891 mmol) and DMF (2.2 mL).

$^1$H NMR (300 MHz, DMSO-$d_6$) δ: 1.22 (3H, t, J=7.7 Hz), 1.32 (3H, t, J=7.1 Hz), 1.37-1.61 (2H, m), 1.85-1.98 (2H, m), 2.69 (2H, q, J=7.7 Hz), 2.84-2.99 (1H, m), 3.07-3.22 (1H, m), 3.60-3.74 (1H, m), 3.98 (3H, s), 4.03-4.16 (3H, m), 4.16-4.30 (1H, m), 4.52 (1H, t, J=5.4 Hz), 4.60 (2H, q, J=7.1 Hz), 7.48-7.65 (3H, m), 7.89 (1H, d, J=7.9 Hz), 7.93 (1H, s), 7.97-8.06 (2H, m), 10.50 (1H, s).

Example 130

Production of 6-ethyl-N-[1-(hydroxyacetyl)piperidin-4-yl]-1-methyl-3-(1-methylethoxy)-5-[(phenylcarbonyl)amino]-1H-pyrrolo[3,2-b]pyridine-2-carboxamide

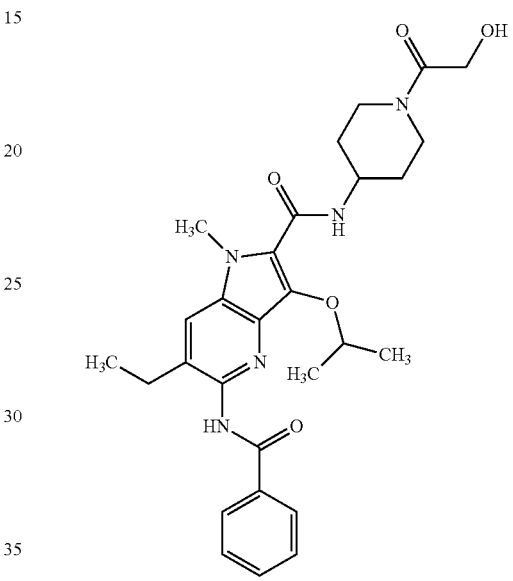

By a method similar to that in Example 16, the title compound (169 mg, 74%) was obtained as a white powder from the compound of Reference Example 285 (166 mg, 0.435 mmol), 2-(4-aminopiperidin-1-yl)-2-oxoethanol hydrochloride (102 mg, 0.522 mmol), HOBt (88.2 mg, 0.653 mmol), WSCD (125 mg, 0.653 mmol), triethylamine (0.141 mL, 1.31 mmol) and DMF (3.3 mL).

$^1$H NMR (300 MHz, DMSO-$d_6$) δ: 1.23 (3H, t, J=7.6 Hz), 1.26-1.31 (6H, m), 1.33-1.60 (2H, m), 1.87-1.99 (2H, m), 2.69 (2H, q, J=7.6 Hz), 2.83-2.98 (1H, m), 3.07-3.22 (1H, m), 3.60-3.74 (1H, m), 4.00 (3H, s), 4.03-4.18 (3H, m), 4.19-4.32 (1H, m), 4.52 (1H, t, J=5.4 Hz), 5.30-5.44 (1H, m), 7.48-7.64 (3H, m), 7.88 (1H, d, J=7.6 Hz), 7.94 (1H, s), 7.97-8.05 (2H, m), 10.50 (1H, s).

Example 131

Production of 6-ethyl-N-[1-(hydroxyacetyl)piperidin-4-yl]-1-methyl-3-(1-methylethoxy)-5-phenyl-1H-pyrrolo[3,2-b]pyridine-2-carboxamide

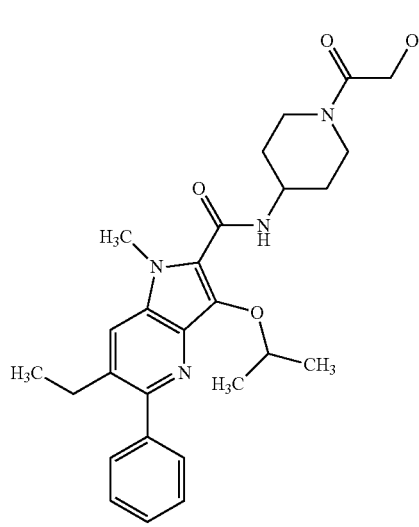

By a method similar to that in Example 16, the title compound (129 mg, 73%) was obtained as a white powder from the compound of Reference Example 287 (125 mg, 0.369 mmol), 2-(4-aminopiperidin-1-yl)-2-oxoethanol hydrochloride (86.3 mg, 0.443 mmol), HOBt (74.9 mg, 0.554 mmol), WSCD (106 mg, 0.554 mmol), triethylamine (0.154 mL, 1.11 mmol) and DMF (2.5 mL).

$^1$H NMR (300 MHz, DMSO-$d_6$) δ: 1.11 (3H, t, J=7.6 Hz), 1.30 (6H, d, J=6.0 Hz), 1.34-1.59 (2H, m), 1.88-1.99 (2H, m), 2.72 (2H, q, J=7.5 Hz), 2.84-3.00 (1H, m), 3.08-3.22 (1H, m), 3.61-3.73 (1H, m), 4.00 (3H, s), 4.02-4.16 (3H, m), 4.16-4.30 (1H, m), 4.53 (1H, t, J=5.1 Hz), 5.40-5.54 (1H, m), 7.38-7.52 (5H, m), 7.86-7.97 (2H, m).

Example 132

Production of 6-ethyl-5-(4-fluorophenyl)-N-[1-(hydroxyacetyl)piperidin-4-yl]-1-methyl-3-(1-methylethoxy)-1H-pyrrolo[3,2-b]pyridine-2-carboxamide

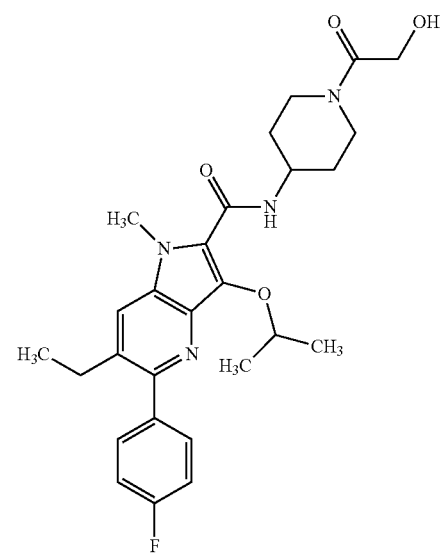 [SMILES: CCc1cc2c(nc1-c1ccc(F)cc1)c(OC(C)C)c(C(=O)NC1CCN(C(=O)CO)CC1)n2C]

By a method similar to that in Example 16, the title compound (157 mg, 82%) was obtained as a white powder from the compound of Reference Example 289 (137 mg, 0.384 mmol), 2-(4-aminopiperidin-1-yl)-2-oxoethanol hydrochloride (89.7 mg, 0.461 mmol), HOBt (77.8 mg, 0.576 mmol), WSCD (110 mg, 0.576 mmol), triethylamine (0.159 mL, 1.15 mmol) and DMF (2.7 mL).

$^1$H NMR (300 MHz, DMSO-$d_6$) δ: 1.12 (3H, t, J=7.5 Hz), 1.30 (6H, d, J=6.0 Hz), 1.34-1.59 (2H, m), 1.87-1.99 (2H, m), 2.72 (2H, q, J=7.5 Hz), 2.85-3.00 (1H, m), 3.06-3.22 (1H, m), 3.61-3.74 (1H, m), 4.00 (3H, s), 4.02-4.17 (3H, m), 4.16-4.30 (1H, m), 4.53 (1H, t, J=5.4 Hz), 5.38-5.52 (1H, m), 7.24-7.35 (2H, m), 7.48-7.59 (2H, m), 7.85-7.97 (2H, m).

Example 133

Production of 6-ethyl-N-[1-(hydroxyacetyl)piperidin-4-yl]-1-methyl-3-(1-methylethoxy)-5-[(thiophen-2-ylcarbonyl)amino]-1H-pyrrolo[3,2-b]pyridine-2-carboxamide

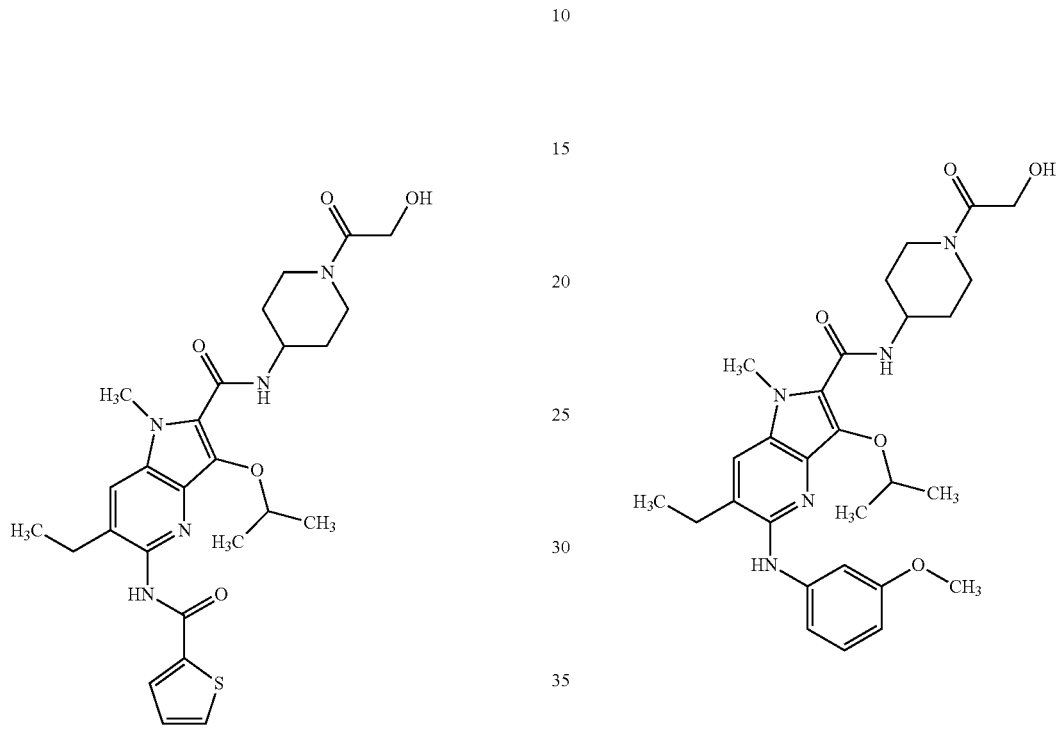

By a method similar to that in Example 16, the title compound (182 mg, 71%) was obtained as a white powder from the compound of Reference Example 291 (188 mg, 0.485 mmol), 2-(4-aminopiperidin-1-yl)-2-oxoethanol hydrochloride (113 mg, 0.582 mmol), HOBt (98.3 mg, 0.728 mmol), WSCD (140 mg, 0.728 mmol), triethylamine (0.201 mL, 1.46 mmol) and DMF (3.8 mL).

$^1$H NMR (300 MHz, DMSO-$d_6$) δ: 1.22 (3H, t, J=7.5 Hz), 1.30 (6H, d, J=6.0 Hz), 1.34-1.60 (2H, m), 1.87-1.98 (2H, m), 2.68 (2H, q, J=7.5 Hz), 2.82-2.98 (1H, m), 3.06-3.22 (1H, m), 3.62-3.74 (1H, m), 3.99 (3H, s), 4.03-4.16 (3H, m), 4.19-4.31 (1H, m), 4.52 (1H, t, J=5.4 Hz), 5.32-5.46 (1H, m), 7.23 (1H, dd, J=4.9, 3.8 Hz), 7.84-7.92 (2H, m), 7.94 (1H, s), 7.99-8.04 (1H, m), 10.55 (1H, s).

Example 134

Production of 6-ethyl-N-[1-(hydroxyacetyl)piperidin-4-yl]-5-[(3-methoxyphenyl)amino]-1-methyl-3-(1-methylethoxy)-1H-pyrrolo[3,2-b]pyridine-2-carboxamide

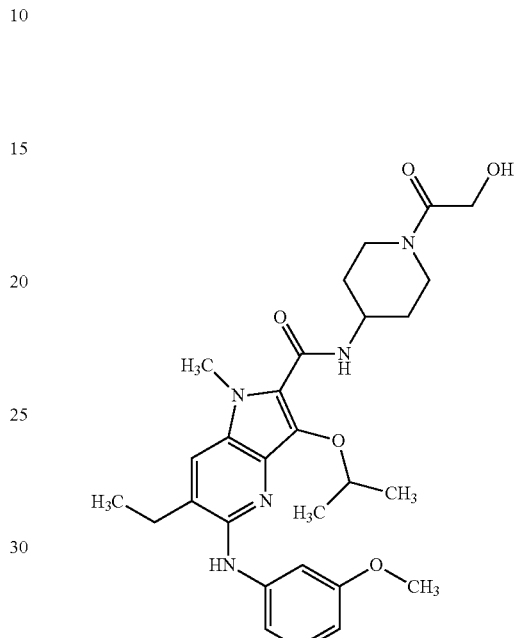

By a method similar to that in Example 16, the title compound (122 mg, 84%) was obtained as a white powder from the compound of Reference Example 293 (107 mg, 0.279 mmol), 2-(4-aminopiperidin-1-yl)-2-oxoethanol hydrochloride (65.2 mg, 0.335 mmol), HOBt (56.6 mg, 0.419 mmol), WSCD (80.2 mg, 0.419 mmol), triethylamine (0.116 mL, 0.837 mmol) and DMF (2.1 mL).

$^1$H NMR (300 MHz, DMSO-$d_6$) δ: 1.26 (3H, t, J=7.4 Hz), 1.32 (6H, d, J=6.0 Hz), 1.35-1.56 (2H, m), 1.86-1.98 (2H, m), 2.80 (2H, q, J=7.4 Hz), 2.86-2.99 (1H, m), 3.08-3.21 (1H, m), 3.61-3.71 (1H, m), 3.74 (3H, s), 3.94 (3H, s), 4.00-4.15 (3H, m), 4.15-4.28 (1H, m), 4.52 (1H, t, J=5.4 Hz), 5.40-5.53 (1H, m), 6.46 (1H, dd, J=7.9, 2.1 Hz), 7.13 (1H, t, J=7.9 Hz), 7.28-7.36 (1H, m), 7.44-7.50 (1H, m), 7.69 (1H, s), 7.76-7.86 (2H, m).

Example 135

Production of 6-ethyl-N-[1-(hydroxyacetyl)piperidin-4-yl]-1-methyl-3-(1-methylethoxy)-5-[4-(trifluoromethyl)phenyl]-1H-pyrrolo[3,2-b]pyridine-2-carboxamide

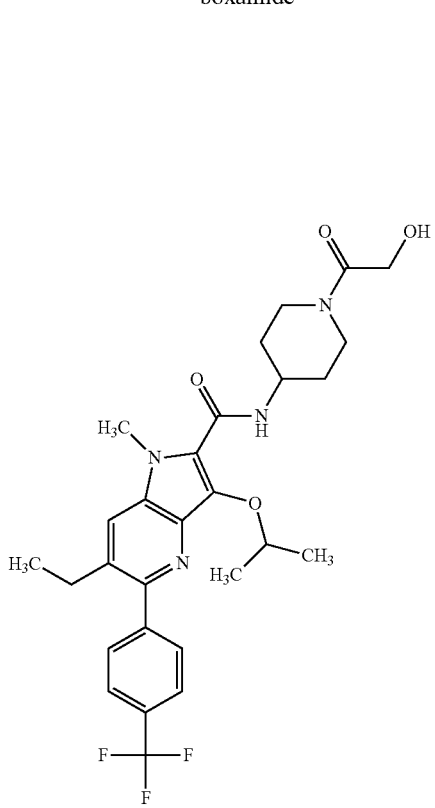

By a method similar to that in Example 16, the title compound (115 mg, 69%) was obtained as a white powder from the compound of Reference Example 295 (124 mg, 0.305 mmol), 2-(4-aminopiperidin-1-yl)-2-oxoethanol hydrochloride (71.3 mg, 0.366 mmol), HOBt (61.8 mg, 0.458 mmol), WSCD (87.7 mg, 0.458 mmol), triethylamine (0.127 mL, 0.915 mmol) and DMF (2.5 mL).

$^1$H NMR (300 MHz, DMSO-$d_6$) δ: 1.13 (3H, t, J=7.5 Hz), 1.30 (6H, d, J=6.0 Hz), 1.34-1.60 (2H, m), 1.87-1.98 (2H, m), 2.73 (2H, q, J=7.5 Hz), 2.85-3.00 (1H, m), 3.08-3.23 (1H, m), 3.62-3.74 (1H, m), 4.01 (3H, s), 4.03-4.16 (3H, m), 4.17-4.30 (1H, m), 4.52 (1H, t, J=4.9 Hz), 5.37-5.52 (1 m), 7.69-7.77 (2H, m), 7.79-7.87 (2H, m), 7.90 (1H, d, J=7.7 Hz), 7.98 (1H, s).

Example 136

Production of N-[1-(hydroxyacetyl)piperidin-4-yl]-1,6-dimethyl-5-phenyl-3-(2,2,2-trifluoroethoxy)-1H-pyrrolo[3,2-b]pyridine-2-carboxamide

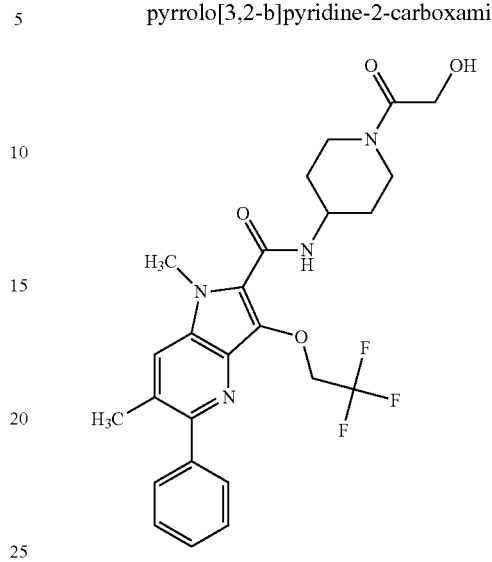

By a method similar to that in Example 16, the title compound (102 mg, 59%) was obtained as a white powder from the compound of Reference Example 302 (126 mg, 0.346 mmol), 2-(4-aminopiperidin-1-yl)-2-oxoethanol hydrochloride (80.8 mg, 0.415 mmol), HOBt (70.1 mg, 0.519 mmol), WSCD (99.5 mg, 0.519 mmol), triethylamine (0.144 mL, 1.04 mmol) and DMF (2.5 mL).

$^1$H NMR (300 MHz, DMSO-$d_6$) δ: 1.28-1.57 (2H, m), 1.84-1.97 (2H, m), 2.43 (3H, s), 2.82-2.98 (1H, m), 3.06-3.20 (1H, m), 3.62-3.76 (1H, m), 3.93 (3H, s), 4.01-4.17 (3H, m), 4.18-4.30 (1H, m), 4.54 (1H, t, J=5.3 Hz), 5.35 (2H, q, J=9.0 Hz), 7.38-7.53 (3H, m), 7.54-7.62 (2H, m), 7.78 (1H, d, J=7.7 Hz), 7.97 (1H, s).

Example 137

Production of 6-ethyl-N-[1-(hydroxyacetyl)piperidin-4-yl]-1-methyl-3-(1-methylethoxy)-5-(thiophen-2-yl)-1H-pyrrolo[3,2-b]pyridine-2-carboxamide

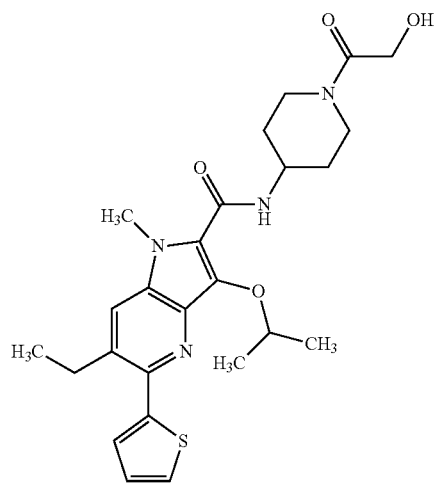 [SMILES: CCc1cc2c(nc1-c1cccs1)c(OC(C)C)c(C(=O)NC1CCN(C(=O)CO)CC1)n2C]

By a method similar to that in Example 16, the title compound (95.3 mg, 75%) was obtained as a white powder from the compound of Reference Example 304 (90.7 mg, 0.263 mmol), 2-(4-aminopiperidin-1-yl)-2-oxoethanol hydrochloride (61.5 mg, 0.316 mmol), HOBt (53.4 mg, 0.395 mmol), WSCD (75.6 mg, 0.395 mmol), triethylamine (0.109 mL, 0.789 mmol) and DMF (1.8 mL).

$^1$H NMR (300 MHz, DMSO-$d_6$) δ: 1.29 (3H, t, J=7.4 Hz), 1.34-1.61 (8H, m), 1.87-2.00 (2H, m), 2.86-3.07 (3H, m), 3.08-3.23 (1H, m), 3.60-3.74 (1H, m), 3.98 (3H, s), 4.02-4.16 (3H, m), 4.16-4.29 (1H, m), 4.52 (1H, t, J=5.4 Hz), 5.48-5.60 (1H, m), 7.15 (1H, dd, J=5.0, 3.6 Hz), 7.46 (1H, d, J=3.6 Hz), 7.59 (1H, d, J=5.0 Hz), 7.84-7.93 (2H, m).

Example 138

Production of 6-ethyl-N-[1-(hydroxyacetyl)piperidin-4-yl]-1-methyl-3-(1-methylethoxy)-5-(2-oxopyridine-1(2H)-yl)-1H-pyrrolo[3,2-b]pyridine-2-carboxamide

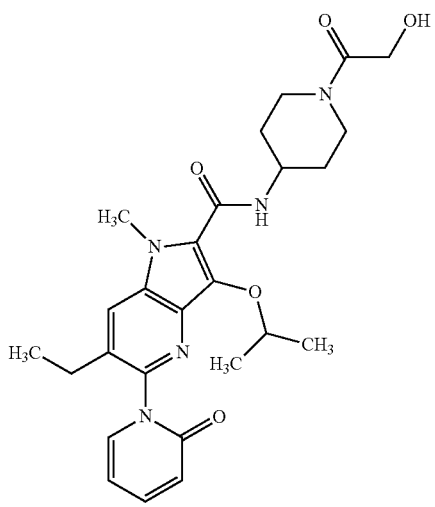 [SMILES: CCc1cc2c(nc1-n1ccccc1=O)c(OC(C)C)c(C(=O)NC1CCN(C(=O)CO)CC1)n2C]

By a method similar to that in Example 16, the title compound (34.8 mg, 82%) was obtained as a white powder from the compound of Reference Example 306 (30.5 mg, 0.0858 mmol), 2-(4-aminopiperidin-1-yl)-2-oxoethanol hydrochloride (20.0 mg, 0.103 mmol), HOBt (17.4 mg, 0.129 mmol), WSCD (24.7 mg, 0.129 mmol), triethylamine (35.6 μL, 0.257 mmol) and DMF (0.61 mL).

$^1$H NMR (300 MHz, DMSO-$d_6$) δ: 1.13 (3H, t, J=7.6 Hz), 1.29 (6H, d, J=6.2 Hz), 1.35-1.60 (2H, m), 1.87-1.98 (2H, m), 2.50-2.59 (2H, m), 2.84-2.98 (1H, m), 3.07-3.22 (1H, m), 3.61-3.74 (1H, m), 3.98-4.16 (6H, m), 4.19-4.31 (1H, m), 4.52 (1H, t, J=5.0 Hz), 5.19-5.31 (1H, m), 6.32-6.40 (1H, m), 6.50 (1H, d, J=9.1 Hz), 7.54-7.68 (2H, m), 7.91 (1H, d, J=7.6 Hz), 8.06 (1H, s).

Example 139

Production of 6-ethyl-5-(2-fluorophenyl)-N-[1-(hydroxyacetyl)piperidin-4-yl]-1-methyl-3-(1-methylethoxy)-1H-pyrrolo[3,2-b]pyridine-2-carboxamide

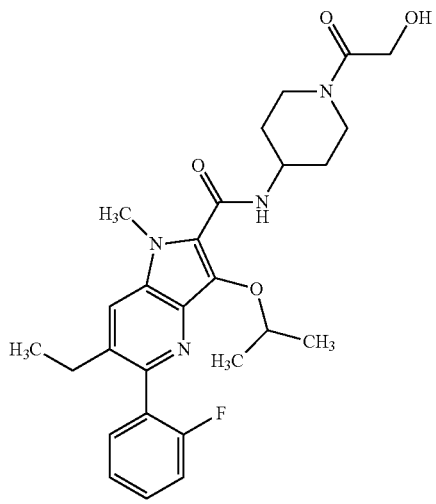 [SMILES: CCc1cc2c(nc1-c1ccccc1F)c(OC(C)C)c(C(=O)NC1CCN(C(=O)CO)CC1)n2C]

By a method similar to that in Example 16, the title compound (119 mg, 80%) was obtained as a white powder from the compound of Reference Example 308 (107 mg, 0.300 mmol), 2-(4-aminopiperidin-1-yl)-2-oxoethanol hydrochloride (70.1 mg, 0.360 mmol), HOBt (60.8 mg, 0.450 mmol), WSCD (86.3 mg, 0.450 mmol), triethylamine (0.125 mL, 0.900 mmol) and DMF (2.1 mL).

$^1$H NMR (300 MHz, DMSO-$d_6$) δ: 1.08 (3H, t, J=7.5 Hz), 1.28 (6H, d, J=6.2 Hz), 1.34-1.60 (2H, m), 1.88-2.00 (2H, m), 2.57 (2H, q, J=7.5 Hz), 2.85-3.00 (1H, m), 3.07-3.23 (1H, m), 3.61-3.74 (1H, m), 4.00 (3H, s), 4.03-4.31 (4H, m), 4.52 (1H, t, J=5.0 Hz), 5.32-5.47 (1H, m), 7.26-7.37 (2H, m), 7.37-7.56 (2H, m), 7.90 (1H, d, J=7.6 Hz), 7.95 (1H, s).

Example 140

Production of 6-ethyl-N-[1-(hydroxyacetyl)piperidin-4-yl]-5-(2-methoxyphenyl)-1-methyl-3-(1-methylethoxy)-1H-pyrrolo[3,2-b]pyridine-2-carboxamide

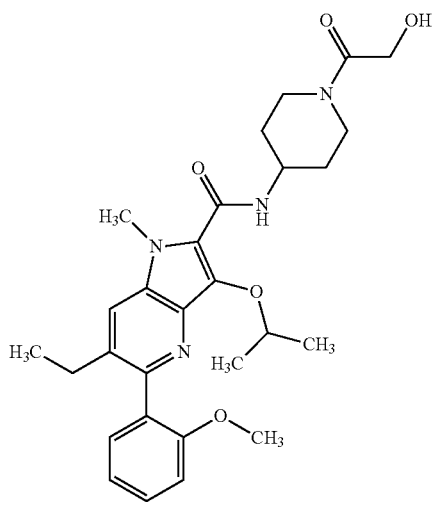 [SMILES: CCc1cc2c(nc1-c1ccccc1OC)c(OC(C)C)c(C(=O)NC1CCN(C(=O)CO)CC1)n2C]

By a method similar to that in Example 16, the title compound (108 mg, 66%) was obtained as a pale-yellow powder from the compound of Reference Example 310 (119 mg, 0.323 mmol), 2-(4-aminopiperidin-1-yl)-2-oxoethanol hydrochloride (75.5 mg, 0.388 mmol), HOBt (78.6 mg, 0.582 mmol), WSCD (112 mg, 0.582 mmol), triethylamine (0.134 mL, 0.969 mmol) and DMF (2.4 mL).

$^1$H NMR (300 MHz, DMSO-$d_6$) δ: 1.04 (3H, t, J=7.5 Hz), 1.28 (6H, d, J=6.0 Hz), 1.33-1.59 (2H, m), 1.87-2.01 (2H, m), 2.36-2.48 (2H, m), 2.84-3.00 (1H, m), 3.06-3.22 (1H, m), 3.60-3.75 (4H, m), 4.00 (3H, s), 4.02-4.17 (3H, m), 4.17-4.30 (1H, m), 4.52 (1H, t, J=5.2 Hz), 5.35-5.49 (1H, m), 6.99-7.14 (2H, m), 7.15-7.23 (1H, m), 7.36-7.48 (1H, m), 7.80-7.93 (2H, m).

Example 141

Production of 6-ethyl-N-[1-(hydroxyacetyl)piperidin-4-yl]-5-(2-hydroxyphenyl)-1-methyl-3-(1-methylethoxy)-1H-pyrrolo[3,2-b]pyridine-2-carboxamide

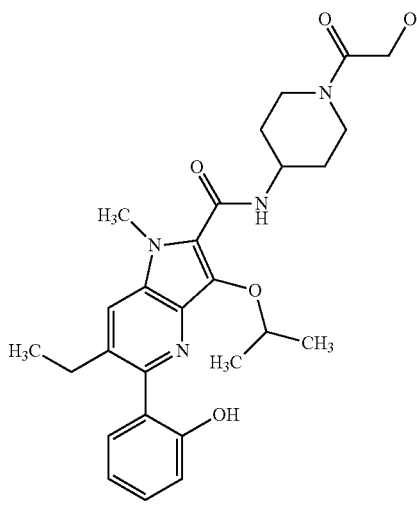

By a method similar to that in Example 16, the title compound (112 mg, 68%) was obtained as a white powder from the compound of Reference Example 312 (118 mg, 0.333 mmol), 2-(4-aminopiperidin-1-yl)-2-oxoethanol hydrochloride (77.8 mg, 0.400 mmol), HOBt (67.6 mg, 0.500 mmol), WSCD (95.9 mg, 0.500 mmol), triethylamine (0.138 mL, 1.00 mmol) and DMF (2.4 mL).

$^1$H NMR (300 MHz, DMSO-$d_6$) δ: 1.06 (3H, t, J=7.5 Hz), 1.28 (6H, d, J=6.2 Hz), 1.33-1.60 (2H, m), 1.88-2.01 (2H, m), 2.60 (2H, q, J=7.5 Hz), 2.86-3.01 (1H, m), 3.07-3.22 (1H, m), 3.60-3.75 (1H, m), 4.00 (3H, s), 4.02-4.16 (3H, m), 4.16-4.30 (1H, m), 4.52 (1H, t, J=5.3 Hz), 5.37-5.50 (1H, m), 6.83-6.96 (2H, m), 7.09-7.16 (1H, m), 7.17-7.27 (1H, m), 7.83 (1H, s), 7.88 (1H, d, J=7.7 Hz), 9.50 (1H, s).

Example 142

Production of 6-ethyl-N-[1-(hydroxyacetyl)piperidin-4-yl]-1-methyl-3-(1-methylethoxy)-5-{2-[(methylsulfonyl)amino]phenyl}-1H-pyrrolo[3,2-b]pyridine-2-carboxamide

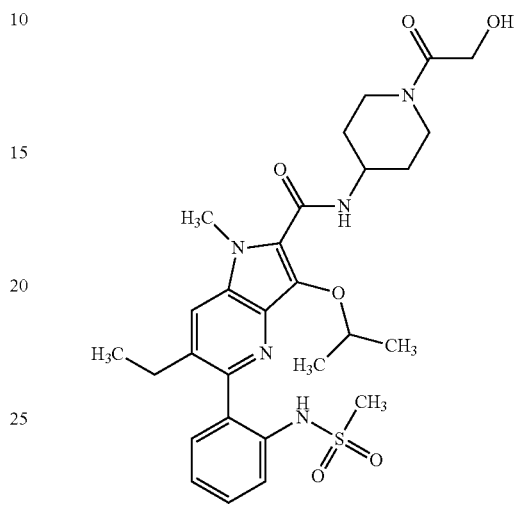

By a method similar to that in Example 16, the title compound (133 mg, 72%) was obtained as a white powder from the compound of Reference Example 314 (140 mg, 0.324 mmol), 2-(4-aminopiperidin-1-yl)-2-oxoethanol hydrochloride (75.7 mg, 0.389 mmol), HOBt (65.7 mg, 0.486 mmol), WSCD (93.2 mg, 0.486 mmol), triethylamine (0.135 mL, 0.972 mmol) and DMF (2.8 mL).

$^1$H NMR (300 MHz, DMSO-$d_6$) δ: 1.10 (3H, t, J=7.5 Hz), 1.27 (6H, d, J=6.2 Hz), 1.32-1.61 (2H, m), 1.86-1.98 (2H, m), 2.58 (2H, q, J=7.5 Hz), 2.80-2.98 (4H, m), 3.07-3.22 (1H, m), 3.60-3.74 (1H, m), 4.01 (3H, s), 4.03-4.16 (3H, m), 4.17-4.31 (1H, m), 4.51 (1H, t, J=5.5 Hz), 5.27-5.41 (1H, m), 7.18-7.36 (2H, m), 7.37-7.48 (1H, m), 7.48-7.58 (1H, m), 7.88-8.01 (2H, m), 8.78 (1H, br s).

Example 143

Production of N-[1-(hydroxyacetyl)piperidin-4-yl]-3,5-dimethyl-7-(1-methylethoxy)-2-phenyl-5H-pyrrolo[2,3-b]pyrazine-6-carboxamide

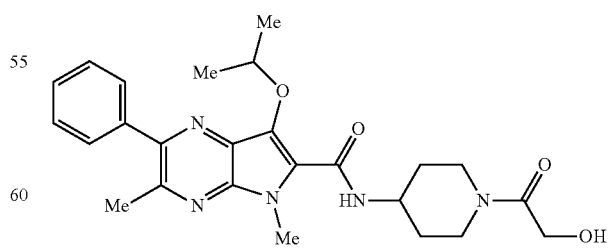

By a method similar to that in Example 1, the title compound (141 mg, 65%) was obtained as yellow crystals from the compound of Reference Example 207 (151 mg, 0.465 mmol), 2-(4-aminopiperidin-1-yl)-2-oxoethanol hydrochloride (115 mg, 0.590 mmol), HOBt (88.8 mg, 0.657 mmol), WSCD (123 mg, 0.644 mmol) and triethylamine (130 μL, 0.933 mmol).

$^1$H NMR (300 MHz, DMSO-d$_6$) δ: 1.34 (6H, d, J=6.2 Hz), 1.37-1.63 (2H, m), 1.87-2.01 (2H, m), 2.63 (3H, s), 2.86-3.01 (1H, m), 3.07-3.23 (1H, m), 3.60-3.75 (1H, m), 4.01 (3H, s), 4.03-4.16 (3H, m), 4.16-4.30 (1H, m), 4.52 (1H, t, J=5.2 Hz), 5.33-5.47 (1H, m), 7.41-7.57 (3H, m), 7.58-7.67 (2H, m), 7.92 (1H, d, J=7.6 Hz).

Example 144

Production of 3-ethyl-N-[1-(hydroxyacetyl)piperidin-4-yl]-5-methyl-2-phenyl-7-(2,2,2-trifluoroethoxy)-5H-pyrrolo[2,3-b]pyrazine-6-carboxamide

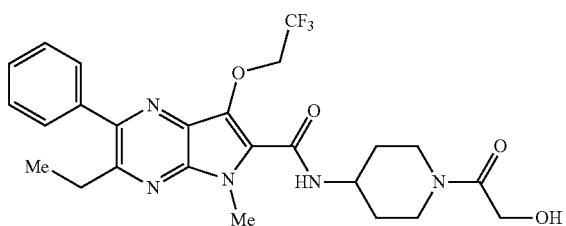 [SMILES: CCc1nc2c(nc1-c1ccccc1)c(OCC(F)(F)F)c(C(=O)NC1CCN(C(=O)CO)CC1)n2C]

By a method similar to that in Example 1, the title compound (51.5 mg, 42%) was obtained as white crystals from the compound of Reference Example 213 (89.0 mg, 0.235 mmol), 2-(4-aminopiperidin-1-yl)-2-oxoethanol hydrochloride (60.0 mg, 0.308 mmol), HOBt (52.2 mg, 0.386 mmol), WSCD (69.2 mg, 0.361 mmol) and triethylamine (65.4 μL, 0.469 mmol).

$^1$H NMR (300 MHz, DMSO-d$_6$) δ: 1.21 (3H, t, J=7.4 Hz), 1.29-1.61 (2H, m), 1.84-2.00 (2H, m), 2.82-3.02 (3H, m), 3.05-3.22 (1H, m), 3.61-3.79 (1H, m), 3.97 (3H, s), 4.02-4.18 (3H, m), 4.18-4.31 (1H, m), 4.54 (1H, t, J=5.4 Hz), 5.28 (2H, q, J=9.0 Hz), 7.43-7.66 (5H, m), 7.92 (1H, d, J=7.6 Hz).

Example 145

Production of N-[1-(hydroxyacetyl)piperidin-4-yl]-3,5-dimethyl-2-[(phenylcarbonyl)amino]-7-(2,2,2-trifluoroethoxy)-5H-pyrrolo[2,3-b]pyrazine-6-carboxamide

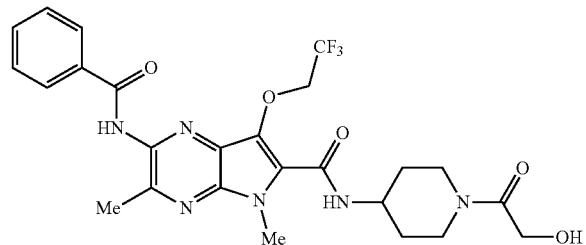 [SMILES: Cc1nc2c(nc1NC(=O)c1ccccc1)c(OCC(F)(F)F)c(C(=O)NC1CCN(C(=O)CO)CC1)n2C]

By a method similar to that in Example 1, the title compound (113 mg, 61%) was obtained as pale-yellow crystals from the compound of Reference Example 221 (137 mg, 0.336 mmol), 2-(4-aminopiperidin-1-yl)-2-oxoethanol hydrochloride (84.9 mg, 0.436 mmol), HOBt (68.9 mg, 0.510 mmol), WSCD (93.2 mg, 0.486 mmol) and triethylamine (93.8 μL, 0.673 mmol).

$^1$H NMR (300 MHz, DMSO-d$_6$) δ: 1.27-1.60 (2H, m), 1.83-1.99 (2H, m), 2.55 (3H, s), 2.81-3.00 (1H, m), 3.04-3.22 (1H, m), 3.61-3.77 (1H, m), 3.95 (3H, s), 4.00-4.19 (3H, m), 4.18-4.33 (1H, m), 4.54 (1H, t, J=5.5 Hz), 5.20 (2H, q, J=9.0 Hz), 7.49-7.69 (3H, m), 7.96 (1H, d, J=7.7 Hz), 8.00-8.09 (2H, m), 10.83 (1H, s).

Example 146

Production of 6-ethyl-N-[1-(hydroxyacetyl)piperidin-4-yl]-1-methyl-5-[(phenylcarbonyl)amino]-3-(2,2,2-trifluoroethoxy)-1H-indole-2-carboxamide

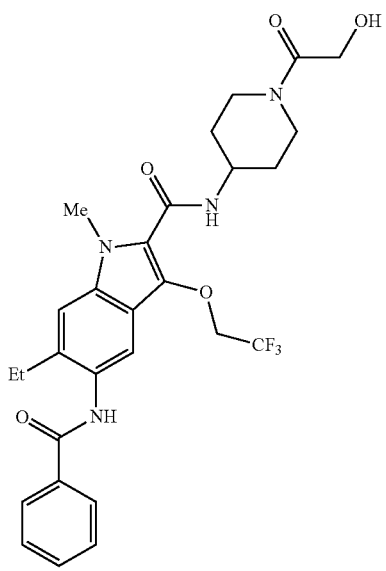 [SMILES: CCc1cc2c(cc1NC(=O)c1ccccc1)c(OCC(F)(F)F)c(C(=O)NC1CCN(C(=O)CO)CC1)n2C]

A mixture of the compound of Reference Example 201 (65 mg, 0.15 mmol), 2-(4-aminopiperidin-1-yl)-2-oxoethanol hydrochloride (36 mg, 0.19 mmol), HOBt (27 mg, 0.20 mmol), WSCD (39 mg, 0.20 mmol) and triethylamine (31 mg, 0.31 mmol) in DMF (2 mL) was stirred at room temperature for 16 hr. The reaction mixture was diluted with saturated aqueous sodium hydrogen carbonate, and extracted twice with ethyl acetate. The extracts were combined and washed with brine, dried over magnesium sulfate, and concentrated under reduced pressure. The residue was purified by amino silica gel column chromatography (eluent, ethyl acetate) and recrystallized from ethyl acetate-hexane to give the title compound (69 mg, 82%) as white crystals.

$^1$H NMR (300 MHz, DMSO-d$_6$) δ: 1.20 (3H, t, J=7.5 Hz), 1.30-1.50 (2H, m), 1.91 (2H, d, J=9.9 Hz), 2.72 (2H, q, J=7.5 Hz), 2.82 (1H, t, J=11.9 Hz), 3.10 (1H, t, J=11.9 Hz), 3.71 (1H, d, J=12.9 Hz), 3.89 (3H, s), 4.04-4.12 (3H, m), 4.30 (1H, d, J=13.8 Hz), 4.54 (1H, t, J=5.4 Hz), 4.85 (2H, q, J=8.9 Hz), 7.44 (1H, s), 7.51-7.62 (4H, m), 7.84 (1H, d, J=7.5 Hz), 8.01 (2H, d, J=6.9 Hz), 9.96 (1H, s).

Example 147

Production of 6-ethyl-N-[1-(hydroxyacetyl)piperidin-4-yl]-1-methyl-5-[(thiophen-3-ylcarbonyl)amino]-3-(2,2,2-trifluoroethoxy)-1H-indole-2-carboxamide

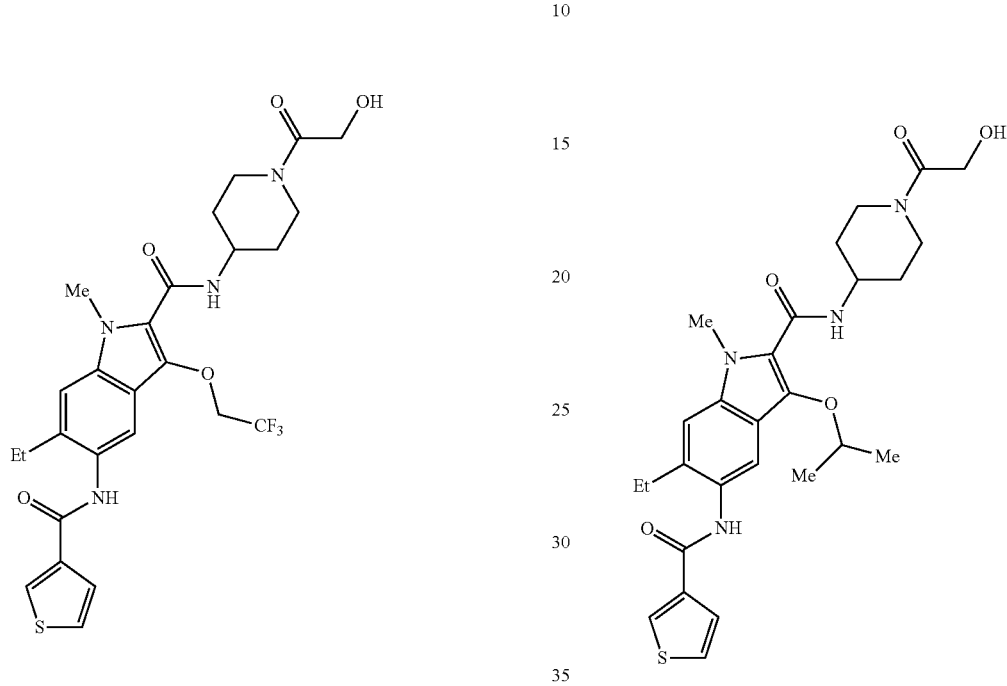

A mixture of the compound of Reference Example 203 (60 mg, 0.14 mmol), 2-(4-aminopiperidin-1-yl)-2-oxoethanol hydrochloride (33 mg, 0.17 mmol), HOBt (25 mg, 0.18 mmol), WSCD (35 mg, 0.18 mmol) and triethylamine (28 mg, 0.28 mmol) in DMF (2 mL) was stirred at room temperature for 16 hr. The reaction mixture was diluted with saturated aqueous sodium hydrogen carbonate, and extracted twice with ethyl acetate. The extracts were combined and washed with brine, dried over magnesium sulfate, and concentrated under reduced pressure. The residue was purified by amino silica gel column chromatography (eluent, ethyl acetate) and recrystallized from ethyl acetate-hexane to give the title compound (51 mg, 64%) as white crystals.

$^1$H NMR (300 MHz, DMSO-$d_6$) δ: 1.19 (3H, t, J=7.5 Hz), 1.25-1.50 (2H, m), 1.91 (2H, d, J=10.8 Hz), 2.71 (2H, q, J=7.5 Hz), 2.82 (1H, t, J=12.0 Hz), 3.10 (1H, t, J=12.0 Hz), 3.71 (1H, d, J=12.3 Hz), 3.89 (3H, s), 4.02-4.12 (3H, m), 4.30 (1H, d, J=12.0 Hz), 4.54 (1H, t, J=5.0 Hz), 4.84 (2H, q, J=9.0 Hz), 7.44 (1H, s), 7.60 (1H, m), 7.66 (2H, s), 7.85 (1H, d, J=7.8 Hz), 8.33 (1H, s), 9.79 (1H, s).

Example 148

Production of 6-ethyl-N-[1-(hydroxyacetyl)piperidin-4-yl]-1-methyl-3-(1-methylethoxy)-5-[(thiophen-3-ylcarbonyl)amino]-1H-indole-2-carboxamide A mixture of the compound of Reference Example 205 (90 mg, 0.23 mmol), 2-(4-aminopiperidin-1-yl)-2-oxoethanol hydrochloride (55 mg, 0.28 mmol), HOBt (41 mg, 0.30 mmol), WSCD (58 mg, 0.30 mmol) and triethylamine (47 mg, 0.47 mmol) in DMF (2 mL) was stirred at room temperature for 20 hr. The reaction mixture was diluted with saturated aqueous sodium hydrogen carbonate, and extracted twice with ethyl acetate. The extracts were combined and washed with brine, dried over magnesium sulfate, and concentrated under reduced pressure. The residue was purified by amino silica gel column chromatography (eluent, ethyl acetate) and recrystallized from ethyl acetate-hexane to give the title compound (91 mg, 75%) as white crystals.

$^1$H NMR (300 MHz, DMSO-$d_6$) δ: 1.19 (3H, t, J=7.5 Hz), 1.30 (6H, d, J=6.0 Hz), 1.36-1.55 (2H, m), 1.93 (2H, d, J=9.9 Hz), 2.70 (2H, q, J=7.5 Hz), 2.85 (1H, t, J=10.8 Hz), 3.12 (1H, t, J=12.2 Hz), 3.70 (1H, d, J=13.8 Hz), 3.94 (3H, s), 4.02-4.17 (3H, m), 4.30 (1H, d, J=13.5 Hz), 4.51 (1H, t, J=5.3 Hz), 4.57-4.65 (1H, m), 7.40 (1H, s), 7.51 (1H, s), 7.64 (2H, s), 7.82 (1H, d, J=7.8 Hz), 8.31 (1H, s), 9.74 (1H, s).

Example 149

Production of 6-ethyl-N-[1-(hydroxyacetyl)piperidin-4-yl]-5-[(phenylcarbonyl)amino]-3-(2,2,2-trifluoroethoxy)-1-benzothiophene-2-carboxamide

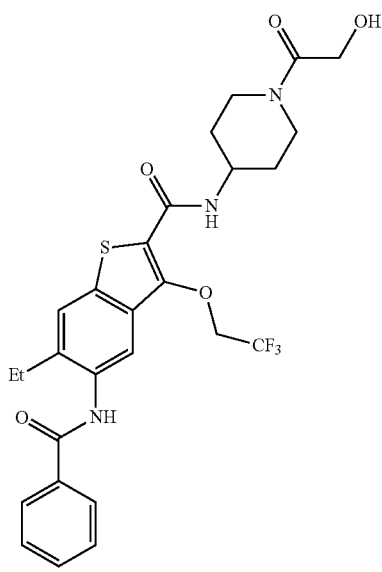 [SMILES: CCc1cc2sc(C(=O)NC3CCN(C(=O)CO)CC3)c(OCC(F)(F)F)c2cc1NC(=O)c1ccccc1]

A mixture of the compound of Reference Example 174 (75 mg, 0.18 mmol), 2-(4-aminopiperidin-1-yl)-2-oxoethanol hydrochloride (41 mg, 0.21 mmol), HOBt (31 mg, 0.23 mmol), WSCD (44 mg, 0.23 mmol) and triethylamine (36 mg, 0.36 mmol) in DMF (2 mL) was stirred at room temperature for 16 hr. The reaction mixture was diluted with saturated aqueous sodium hydrogen carbonate, and extracted twice with ethyl acetate. The extracts were combined and washed with brine, dried over magnesium sulfate, and concentrated under reduced pressure. The residue was purified by amino silica gel column chromatography (eluent, ethyl acetate) and recrystallized from ethyl acetate-hexane to give the title compound (65 mg, 64%) as white crystals.

$^1$H NMR (300 MHz, DMSO-$d_6$) δ: 1.20 (3H, t, J=7.4 Hz), 1.35-1.55 (2H, m), 1.91 (2H, d, J=9.6 Hz), 2.72-2.83 (3H, m), 3.08 (1H, t, J=12.0 Hz), 3.71 (1H, d, J=13.8 Hz), 4.00-4.10 (3H, m), 4.33 (1H, d, J=11.4 Hz), 4.55 (1H, br s), 5.02 (2H, q, J=8.9 Hz), 7.53-7.65 (3H, m), 7.81-7.84 (2H, m), 7.94 (1H, s), 8.02 (2H, d, J=7.2 Hz), 10.11 (1H, s).

Example 150

Production of 6-ethyl-N-[1-(hydroxyacetyl)piperidin-4-yl]-5-[(thiophen-3-ylcarbonyl)amino]-3-(2,2,2-trifluoroethoxy)-1-benzothiophene-2-carboxamide A mixture of the compound of Reference Example 176 (70 mg, 0.16 mmol), 2-(4-aminopiperidin-1-yl)-2-oxoethanol hydrochloride (38 mg, 0.20 mmol), HOBt (29 mg, 0.21 mmol), WSCD (41 mg, 0.21 mmol) and triethylamine (33 mg, 0.33 mmol) in DMF (2 mL) was stirred at room temperature for 16 hr. The reaction mixture was diluted with saturated aqueous sodium hydrogen carbonate, and extracted twice with ethyl acetate. The extracts were combined and washed with brine, dried over magnesium sulfate, and concentrated under reduced pressure. The residue was purified by amino silica gel column chromatography (eluent, ethyl acetate) and recrystallized from ethyl acetate-hexane to give the title compound (70 mg, 77%) as white crystals.

$^1$H NMR (300 MHz, DMSO-$d_6$) δ: 1.19 (3H, t, J=7.5 Hz), 1.30-1.55 (2H, m), 1.91 (2H, d, J=10.2 Hz), 2.71-2.83 (3H, m), 3.08 (1H, t, J=12.0 Hz), 3.71 (1H, d, J=12.9 Hz), 4.00-4.15 (3H, m), 4.33 (1H, d, J=13.2 Hz), 4.54 (1H, t, J=5.4 Hz), 5.01 (2H, q, J=8.9 Hz), 7.65-7.70 (2H, m), 7.82-7.84 (2H, m), 7.93 (1H, s), 8.36 (1H, d, J=0.9 Hz), 9.93 (1H, s).

Example 151

Production of 6-ethyl-N-[1-(hydroxyacetyl)piperidin-4-yl]-3-(1-methylethoxy)-5-[(phenylcarbonyl)amino]-1-benzothiophene-2-carboxamide

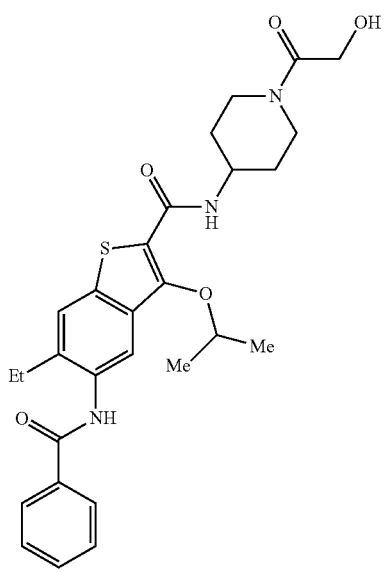 [SMILES: CCc1cc2sc(C(=O)NC3CCN(C(=O)CO)CC3)c(OC(C)C)c2cc1NC(=O)c1ccccc1]

A mixture of the compound of Reference Example 180 (50 mg, 0.13 mmol), 2-(4-aminopiperidin-1-yl)-2-oxoethanol hydrochloride (37 mg, 0.19 mmol), HOBt (27 mg, 0.20 mmol), WSCD (39 mg, 0.20 mmol) and triethylamine (32 mg, 0.32 mmol) in DMF (2 mL) was stirred at room temperature for 16 hr. The reaction mixture was diluted with saturated aqueous sodium hydrogen carbonate, and extracted twice with ethyl acetate. The extracts were combined and washed with brine, dried over magnesium sulfate, and concentrated under reduced pressure. The residue was purified by amino silica gel column chromatography (eluent, ethyl acetate) and recrystallized from ethyl acetate-hexane to give the title compound (52 mg, 76%) as white crystals.

$^1$H NMR (300 MHz, DMSO-$d_6$) δ: 1.20 (3H, t, J=7.5 Hz), 1.36 (6H, d, J=6.3 Hz), 1.40-1.60 (2H, m), 1.92 (2H, d, J=12.0 Hz), 2.72-2.86 (3H, m), 3.11 (1H, t, J=12.0 Hz), 3.71 (1H, d, J=12.0 Hz), 4.00-4.13 (3H, m), 4.33 (1H, d, J=12.0 Hz), 4.51 (1H, t, J=5.4 Hz), 4.72-4.82 (1H, m), 7.53-7.65 (3H, m), 7.77 (1H, d, J=8.1 Hz), 7.81 (1H, s), 7.89 (1H, s), 8.02 (2H, d, J=7.2 Hz), 10.04 (1H, s).

Example 152

Production of 6-ethyl-N-[1-(hydroxyacetyl)piperidin-4-yl]-3-(1-methylethoxy)-5-[(thiophen-3-ylcarbonyl)amino]-1-benzothiophene-2-carboxamide

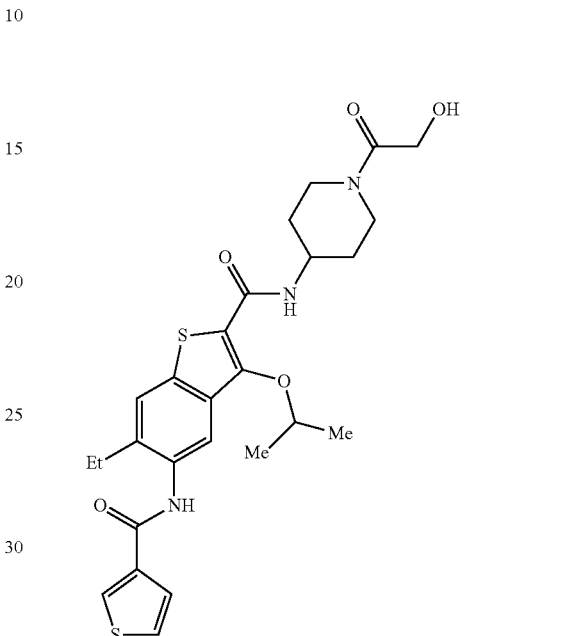

A mixture of the compound of Reference Example 182 (60 mg, 0.15 mmol), 2-(4-aminopiperidin-1-yl)-2-oxoethanol hydrochloride (36 mg, 0.18 mmol), HOBt (27 mg, 0.20 mmol), WSCD (38 mg, 0.20 mmol) and triethylamine (31 mg, 0.31 mmol) in DMF (2 mL) was stirred at room temperature for 16 hr. The reaction mixture was diluted with saturated aqueous sodium hydrogen carbonate, and extracted twice with ethyl acetate. The extracts were combined and washed with brine, dried over magnesium sulfate, and concentrated under reduced pressure. The residue was purified by amino silica gel column chromatography (eluent, ethyl acetate) and recrystallized from ethyl acetate-hexane to give the title compound (63 mg, 79%) as white crystals.

$^1$H NMR (300 MHz, DMSO-$d_6$) δ: 1.20 (3H, t, J=7.5 Hz), 1.35-1.60 (8H, m), 1.93 (2H, d, J=10.5 Hz), 2.70-2.85 (3H, m), 3.10 (1H, t, J=12.0 Hz), 3.71 (1H, d, J=13.5 Hz), 4.02-4.13 (3H, m), 4.33 (1H, d, J=13.5 Hz), 4.51 (1H, t, J=5.4 Hz), 4.73-4.82 (1H, m), 7.64-7.69 (2H, m), 7.75-7.79 (2H, m), 7.89 (1H, s), 8.35 (1H, t, J=1.5 Hz), 9.86 (1H, s).

Example 153

Production of 6-ethyl-N-[1-(hydroxyacetyl)piperidin-4-yl]-3-(1-methylethoxy)-5-[(thiophen-2-ylcarbonyl)amino]-1-benzothiophene-2-carboxamide

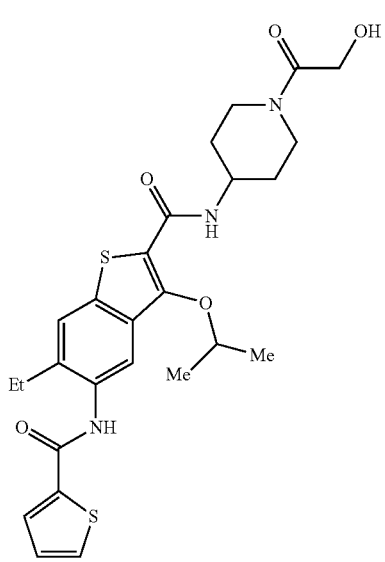 [SMILES: CCc1cc2sc(C(=O)NC3CCN(C(=O)CO)CC3)c(OC(C)C)c2cc1NC(=O)c1cccs1]

A mixture of the compound of Reference Example 184 (140 mg, 0.36 mmol), 2-(4-aminopiperidin-1-yl)-2-oxoethanol hydrochloride (84 mg, 0.43 mmol), HOBt (63 mg, 0.47 mmol), WSCD (90 mg, 0.47 mmol) and triethylamine (73 mg, 0.73 mmol) in DMF (4 mL) was stirred at room temperature for 16 hr. The reaction mixture was diluted with saturated aqueous sodium hydrogen carbonate, and extracted twice with ethyl acetate. The extracts were combined and washed with brine, dried over magnesium sulfate, and concentrated under reduced pressure. The residue was purified by amino silica gel column chromatography (eluent, ethyl acetate) and recrystallized from ethyl acetate-hexane to give the title compound (131 mg, 69%) as beige crystals.

$^1$H NMR (300 MHz, DMSO-$d_6$) δ: 1.19 (3H, t, J=7.5 Hz), 1.35 (6H, d, J=6.0 Hz), 1.40-1.60 (2H, m), 1.92 (2H, d, J=10.5 Hz), 2.70-2.85 (3H, m), 3.10 (1H, t, J=11.9 Hz), 3.70 (1H, d, J=14.1 Hz), 4.00-4.13 (3H, m), 4.32 (1H, d, J=13.2 Hz), 4.51 (1H, t, J=5.4 Hz), 4.73-4.81 (1H, m), 7.23-7.26 (1H, m), 7.76-7.78 (2H, m), 7.86-7.89 (2H, m), 8.01 (1H, d, J=3.0 Hz), 10.06 (1H, s).

Example 154

Production of 6-ethyl-5-{[(4-fluorophenyl)carbonyl]amino}-N-[1-(hydroxyacetyl)piperidin-4-yl]-3-(1-methylethoxy)-1-benzothiophene-2-carboxamide A mixture of the compound of Reference Example 186 (65 mg, 0.16 mmol), 2-(4-aminopiperidin-1-yl)-2-oxoethanol hydrochloride (38 mg, 0.19 mmol), HOBt (28 mg, 0.21 mmol), WSCD (40 mg, 0.21 mmol) and triethylamine (33 mg, 0.33 mmol) in DMF (2 mL) was stirred at room temperature for 16 hr. The reaction mixture was diluted with saturated aqueous sodium hydrogen carbonate, and extracted twice with ethyl acetate. The extracts were combined and washed with brine, dried over magnesium sulfate, and concentrated under reduced pressure. The residue was purified by amino silica gel column chromatography (eluent, ethyl acetate) and recrystallized from ethyl acetate-hexane to give the title compound (64 mg, 74%) as beige crystals.

$^1$H NMR (300 MHz, DMSO-$d_6$) δ: 1.19 (3H, t, J=7.5 Hz), 1.35 (6H, d, J=6.0 Hz), 1.92 (2H, d, J=11.1 Hz), 2.70-2.85 (3H, m), 3.10 (1H, t, J=12.6 Hz), 3.70 (1H, d, J=12.6 Hz), 4.00-4.13 (3H, m), 4.33 (1H, d, J=11.7 Hz), 4.52 (1H, t, J=5.3 Hz), 4.73-4.81 (1H, m), 7.39 (2H, t, J=8.9 Hz), 7.75-7.80 (2H, m), 7.89 (1H, s), 8.09 (2H, dd, J=8.7, 5.7 Hz), 10.07 (1H, s).

Example 155

Production of N-[1-(hydroxyacetyl)piperidin-4-yl]-1,6-dimethyl-3-(1-methylethoxy)-5-[(phenylcarbonyl)amino]-1H-pyrrolo[2,3-b]pyridine-2-carboxamide

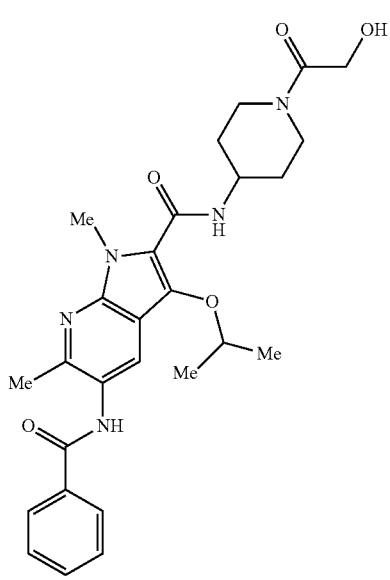 [SMILES: Cc1nc2c(cc1NC(=O)c1ccccc1)c(OC(C)C)c(C(=O)NC1CCN(C(=O)CO)CC1)n2C]

A mixture of the compound of Reference Example 191 (75 mg, 0.20 mmol), 2-(4-aminopiperidin-1-yl)-2-oxoethanol hydrochloride (48 mg, 0.24 mmol), HOBt (41 mg, 0.30 mmol), WSCD (59 mg, 0.30 mmol) and triethylamine (41 mg, 0.41 mmol) in DMF (2 mL) was stirred at room temperature for 16 hr. The reaction mixture was diluted with saturated aqueous sodium hydrogen carbonate, and extracted twice with ethyl acetate. The extracts were combined and washed with brine, dried over magnesium sulfate, and concentrated under reduced pressure. The residue was purified by amino silica gel column chromatography (eluent, ethyl acetate) and recrystallized from ethyl acetate-hexane to give the title compound (81 mg, 80%) as white crystals.

$^1$H NMR (300 MHz, DMSO-$d_6$) δ: 1.30-1.53 (8H, m), 1.93 (2H, d, J=9.6 Hz), 2.50 (3H, s), 2.87 (1H, t, J=11.7 Hz), 3.12 (1H, t, J=11.9 Hz), 3.69 (1H, d, J=13.8 Hz), 3.97 (3H, s), 4.02-4.20 (3H, m), 4.28 (1H, d, J=13.2 Hz), 4.53 (1H, t, J=5.4 Hz), 4.64-4.72 (1H, m), 7.52-7.64 (3H, m), 7.86 (1H, d, J=7.8 Hz), 8.01-8.05 (3H, m), 10.08 (1H, s).

Example 157

Production of 5-{[(4-fluorophenyl)carbonyl]amino}-N-[1-(hydroxyacetyl)piperidin-4-yl]-1,6-dimethyl-3-(1-methylethoxy)-1H-pyrrolo[2,3-b]pyridine-2-carboxamide

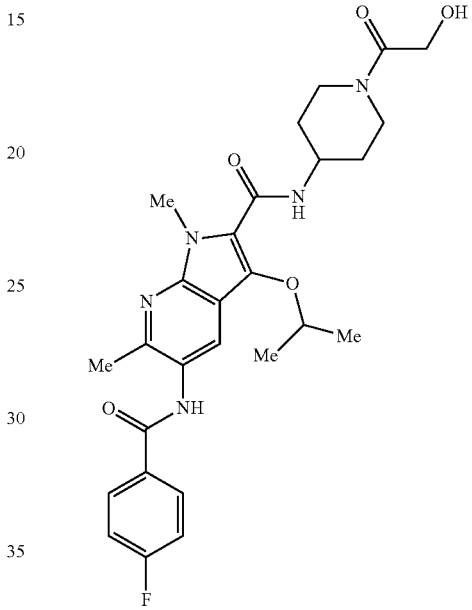

A mixture of the compound of Reference Example 193 (70 mg, 0.18 mmol), 2-(4-aminopiperidin-1-yl)-2-oxoethanol hydrochloride (42 mg, 0.22 mmol), HOBt (37 mg, 0.27 mmol), WSCD (52 mg, 0.27 mmol) and triethylamine (37 mg, 0.36 mmol) in DMF (2 mL) was stirred at room temperature for 16 hr. The reaction mixture was diluted with saturated aqueous sodium hydrogen carbonate, and extracted twice with ethyl acetate. The extracts were combined and washed with brine, dried over magnesium sulfate, and concentrated under reduced pressure. The residue was purified by amino silica gel column chromatography (eluent, ethyl acetate) and recrystallized from ethyl acetate-hexane to give the title compound (72 mg, 76%) as white crystals.

$^1$H NMR (300 MHz, DMSO-$d_6$) δ: 1.31 (6H, d, J=6.0 Hz), 1.37-1.55 (2H, m), 1.93 (2H, d, J=9.6 Hz), 2.50 (3H, s), 2.87 (1H, t, J=12.0 Hz), 3.12 (1H, t, J=12.0 Hz), 3.69 (1H, d, J=14.1 Hz), 3.97 (3H, s), 4.02-4.25 (3H, m), 4.28 (1H, d, J=12.3 Hz), 4.53 (1H, t, J=5.4 Hz), 4.63-4.71 (1H, m), 7.39 (2H, t, J=8.9 Hz), 7.86 (1H, d, J=7.8 Hz), 8.04 (1H, s), 8.07-8.12 (2H, m), 10.11 (1H, s).

Example 158

Production of 3-ethyl-2-(4-fluorophenyl)-N-[1-(hydroxyacetyl)piperidin-4-yl]-5-methyl-7-(2,2,2-trifluoroethoxy)-5H-pyrrolo[2,3-b]pyrazine-6-carboxamide

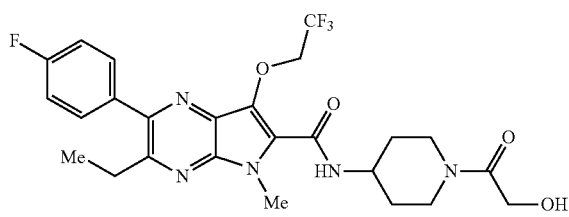 [SMILES: CCc1nc2c(nc1-c1ccc(F)cc1)c(OCC(F)(F)F)c(C(=O)NC1CCN(C(=O)CO)CC1)n2C]

By a method similar to that in Example 1, the title compound (100 mg, 51%) was obtained as pale-yellow crystals from the compound of Reference Example 227 (145 mg, 0.365 mmol), 2-(4-aminopiperidin-1-yl)-2-oxoethanol hydrochloride (91.8 mg, 0.436 mmol), HOBt (75.8 mg, 0.561 mmol), WSCD (102 mg, 0.531 mmol) and triethylamine (102 μL, 0.732 mmol).

$^1$H NMR (300 MHz, DMSO-$d_6$) δ: 1.21 (3H, t, J=7.4 Hz), 1.29-1.58 (2H, m), 1.84-1.98 (2H, m), 2.82-2.99 (3H, m), 3.06-3.21 (1H, m), 3.62-3.77 (1H, m), 3.97 (3H, s), 4.02-4.18 (3H, m), 4.18-4.32 (1H, m), 4.54 (1H, t, J=5.4 Hz), 5.27 (2H, q, J=9.0 Hz), 7.29-7.41 (2H, m), 7.61-7.71 (2H, m), 7.92 (1H, d, J=7.7 Hz).

Example 159

Production of 3-ethyl-2-(4-fluorophenyl)-N-[1-(hydroxyacetyl)piperidin-4-yl]-5-methyl-7-(1-methylethoxy)-5H-pyrrolo[2,3-b]pyrazine-6-carboxamide

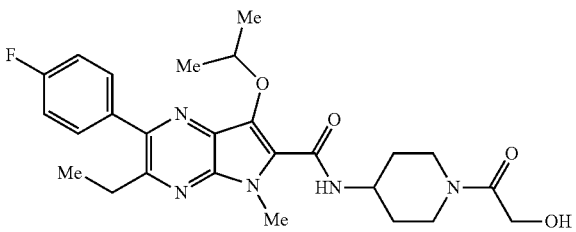 [SMILES: CCc1nc2c(nc1-c1ccc(F)cc1)c(OC(C)C)c(C(=O)NC1CCN(C(=O)CO)CC1)n2C]

By a method similar to that in Example 1, the title compound (127 mg, 66%) was obtained as yellow crystals from the compound of Reference Example 228 (138 mg, 0.386 mmol), 2-(4-aminopiperidin-1-yl)-2-oxoethanol hydrochloride (103 mg, 0.530 mmol), HOBt (79.1 mg, 0.585 mmol), WSCD (111 mg, 0.577 mmol) and triethylamine (108 μL, 0.772 mmol).

$^1$H NMR (300 MHz, DMSO-$d_6$) δ: 1.22 (3H, t, J=7.5 Hz), 1.34 (6H, d, J=6.2 Hz), 1.36-1.63 (2H, m), 1.86-2.02 (2H, m), 2.83-3.01 (3H, m), 3.07-3.24 (1H, m), 3.59-3.75 (1H, m), 4.02 (3H, s), 4.05-4.17 (3H, m), 4.17-4.30 (1H, m), 4.52 (1H, t, J=5.4 Hz), 5.29-5.46 (1H, m), 7.26-7.42 (2H, m), 7.55-7.70 (2H, m), 7.92 (1H, d, J=7.7 Hz).

Example 160

Production of 3-ethyl-N-[1-(hydroxyacetyl)piperidin-4-yl]-5-methyl-2-[(phenylcarbonyl)amino]-7-(2,2,2-trifluoroethoxy)-5H-pyrrolo[2,3-b]pyrazine-6-carboxamide

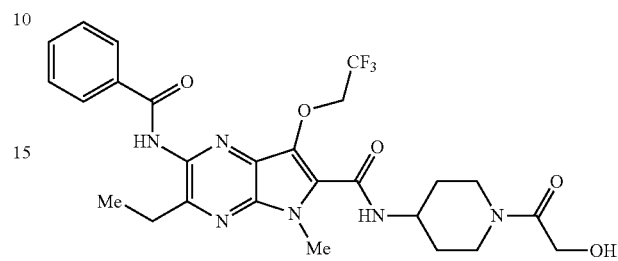

By a method similar to that in Example 1, the title compound (79.4 mg, 61%) was obtained as pale-yellow crystals from the compound of Reference Example 236 (97.0 mg, 0.230 mmol), 2-(4-aminopiperidin-1-yl)-2-oxoethanol hydrochloride (56.4 mg, 0.290 mmol), HOBt (48.1 mg, 0.356 mmol), WSCD (78.5 mg, 0.409 mmol) and triethylamine (64 μL, 0.459 mmol).

$^1$H NMR (300 MHz, DMSO-$d_6$) δ: 1.28 (3H, t, J=7.5 Hz), 1.33-1.58 (2H, m), 1.84-1.99 (2H, m), 2.81-2.98 (3H, m), 3.06-3.21 (1H, m), 3.62-3.76 (1H, m), 3.97 (3H, s), 4.01-4.18 (3H, m), 4.18-4.32 (1H, m), 4.54 (1H, t, J=5.5 Hz), 5.20 (2H, q, J=8.9 Hz), 7.49-7.69 (3H, m), 7.95 (1H, d, J=7.6 Hz), 7.99-8.10 (2H, m), 10.79 (1H, s).

Example 161

Production of 2-(4-chlorophenyl)-3-ethyl-N-[1-(hydroxyacetyl)piperidin-4-yl]-5-methyl-7-(1-methylethoxy)-5H-pyrrolo[2,3-b]pyrazine-6-carboxamide

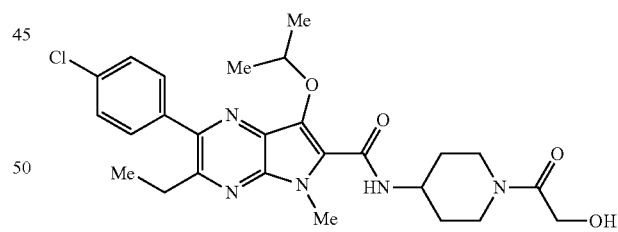

By a method similar to that in Example 1, the title compound (79.5 mg, 71%) was obtained as yellow crystals from the compound of Reference Example 241 (81.0 mg, 0.217 mmol), 2-(4-aminopiperidin-1-yl)-2-oxoethanol hydrochloride (54.2 mg, 0.278 mmol), HOBt (42.8 mg, 0.317 mmol), WSCD (64.0 mg, 0.334 mmol) and triethylamine (60.4 μL, 0.433 mmol).

$^1$H NMR (300 MHz, DMSO-$d_6$) δ: 1.22 (3H, t, J=7.5 Hz), 1.34 (6H, d, J=6.2 Hz), 1.37-1.64 (2H, m), 1.87-2.01 (2H, m), 2.84-3.01 (3H, m), 3.07-3.24 (1H, m), 3.60-3.75 (1H, m), 4.02 (3H, s), 4.05-4.16 (3H, m), 4.16-4.31 (1H, m), 4.47-4.58 (1H, m), 5.30-5.43 (1H, m), 7.52-7.66 (4H, m), 7.92 (1H, d, J=7.6 Hz).

Example 162

Production of 3-ethyl-2-{[(4-fluorophenyl)carbonyl]amino}-N-[1-(hydroxyacetyl)piperidin-4-yl]-5-methyl-7-(1-methylethoxy)-5H-pyrrolo[2,3-b]pyrazine-6-carboxamide

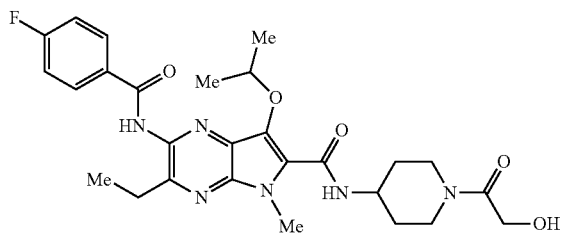 [SMILES: CCc1nc2c(nc1NC(=O)c1ccc(F)cc1)c(OC(C)C)c(C(=O)NC1CCN(C(=O)CO)CC1)n2C]

By a method similar to that in Example 1, the title compound (76.3 mg, 59%) was obtained as pale-yellow crystals from the compound of Reference Example 244 (95.0 mg, 0.237 mmol), 2-(4-aminopiperidin-1-yl)-2-oxoethanol hydrochloride (62.8 mg, 0.323 mmol), HOBt (48.1 mg, 0.356 mmol), WSCD (69.1 mg, 0.360 mmol) and triethylamine (66 µL, 0.474 mmol).

$^1$H NMR (300 MHz, DMSO-$d_6$) δ: 1.27 (3H, t, J=7.5 Hz), 1.32 (6H, d, J=6.2 Hz), 1.36-1.63 (2H, m), 1.87-2.02 (2H, m), 2.77-3.01 (3H, m), 3.06-3.23 (1H, m), 3.59-3.76 (1H, m), 4.02 (3H, s), 4.05-4.18 (3H, m), 4.18-4.32 (1H, m), 4.52 (1H, t, J=5.4 Hz), 5.19-5.36 (1H, m), 7.32-7.47 (2H, m), 7.91 (1H, d, J=7.6 Hz), 8.03-8.17 (2H, m), 10.78 (1H, s).

Example 163

Production of 3-ethyl-N-[1-(hydroxyacetyl)piperidin-4-yl]-5-methyl-7-(1-methylethoxy)-2-[(phenylcarbonyl)amino]-5H-pyrrolo[2,3-b]pyrazine-6-carboxamide

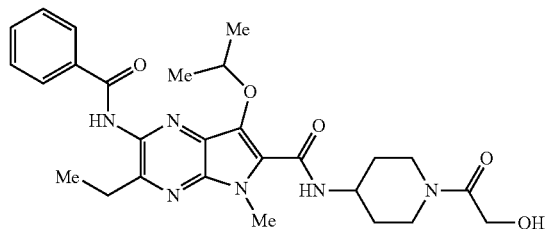 [SMILES: CCc1nc2c(nc1NC(=O)c1ccccc1)c(OC(C)C)c(C(=O)NC1CCN(C(=O)CO)CC1)n2C]

By a method similar to that in Example 1, the title compound (75.5 mg, 61%) was obtained as pale-yellow crystals from the compound of Reference Example 246 (91.0 mg, 0.238 mmol), 2-(4-aminopiperidin-1-yl)-2-oxoethanol hydrochloride (62.4 mg, 0.321 mmol), HOBt (48.7 mg, 0.360 mmol), WSCD (68.0 mg, 0.355 mmol) and triethylamine (66.4 µL, 0.476 mmol).

$^1$H NMR (300 MHz, DMSO-$d_6$) δ: 1.28 (3H, t, J=7.6 Hz), 1.32 (6H, d, J=6.2 Hz), 1.36-1.65 (2H, m), 1.87-2.02 (2H, m), 2.79-3.01 (3H, m), 3.07-3.23 (1H, m), 3.60-3.75 (1H, m), 4.02 (3H, s), 4.05-4.17 (3H, m), 4.18-4.32 (1H, m), 4.52 (1H, t, J=5.4 Hz), 5.22-5.35 (1H, m), 7.50-7.69 (3H, m), 7.91 (1H, d, J=7.7 Hz), 8.03 (2H, d, J=7.2 Hz), 10.74 (1H, s).

Example 164

Production of N-[1-(hydroxyacetyl)piperidin-4-yl]-3,5-dimethyl-7-(1-methylethoxy)-2-[(phenylcarbonyl)amino]-5H-pyrrolo[2,3-b]pyrazine-6-carboxamide

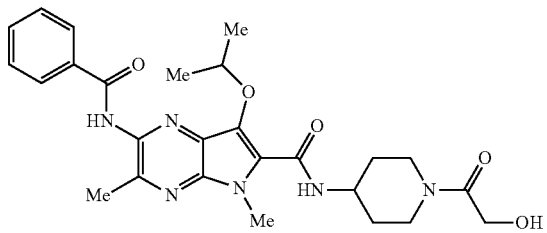 [SMILES: Cc1nc2c(nc1NC(=O)c1ccccc1)c(OC(C)C)c(C(=O)NC1CCN(C(=O)CO)CC1)n2C]

By a method similar to that in Example 1, the title compound (82.3 mg, 70%) was obtained as yellow crystals from the compound of Reference Example 248 (85.0 mg, 0.231 mmol), 2-(4-aminopiperidin-1-yl)-2-oxoethanol hydrochloride (63.3 mg, 0.325 mmol), HOBt (53.5 mg, 0.396 mmol), WSCD (69.2 mg, 0.361 mmol) and triethylamine (64.4 µL, 0.462 mmol).

$^1$H NMR (300 MHz, DMSO-$d_6$) δ: 1.32 (6H, d, J=6.0 Hz), 1.36-1.64 (2H, m), 1.86-1.99 (2H, m), 2.54 (3H, s), 2.84-2.99 (1H, m), 3.06-3.23 (1H, m), 3.59-3.75 (1H, m), 4.00 (3H, s), 4.03-4.18 (3H, m), 4.18-4.31 (1H, m), 4.52 (1H, t, J=5.5 Hz), 5.20-5.35 (1H, m), 7.48-7.69 (3H, m), 7.92 (1H, d, J=7.7 Hz), 8.00-8.09 (2H, m), 10.80 (1H, s).

Example 165

Production of N-[1-(hydroxyacetyl)piperidin-4-yl]-3,5-dimethyl-7-(1-methylethoxy)-2-[methyl(phenylcarbonyl)amino]-5H-pyrrolo[2,3-b]pyrazine-6-carboxamide

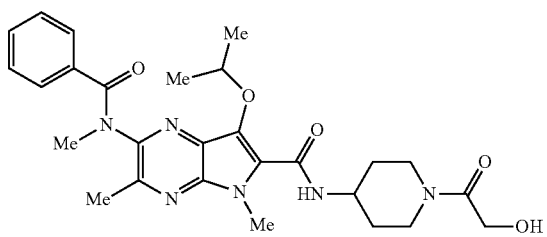 [SMILES: Cc1nc2c(nc1N(C)C(=O)c1ccccc1)c(OC(C)C)c(C(=O)NC1CCN(C(=O)CO)CC1)n2C]

By a method similar to that in Example 1, the title compound (69.8 mg, 76%) was obtained as yellow crystals from the compound of Reference Example 250 (67.4 mg, 0.176 mmol), 2-(4-aminopiperidin-1-yl)-2-oxoethanol hydrochloride (45.3 mg, 0.233 mmol), HOBt (36.7 mg, 0.272 mmol), WSCD (56.9 mg, 0.297 mmol) and triethylamine (49 µL, 0.352 mmol).

$^1$H NMR (300 MHz, DMSO-$d_6$) δ: 0.95-1.61 (8H, m), 1.79-1.97 (2H, m), 2.55 (3H, s), 2.81-2.99 (1H, m), 3.04-3.22 (1H, m), 3.35 (3H, s), 3.57-3.74 (1H, m), 3.90 (3H, s), 3.98-4.14 (3H, m), 4.14-4.30 (1H, m), 4.52 (1H, t, J=5.3 Hz), 4.85-5.05 (1H, m), 7.02-7.37 (5H, m), 7.88 (1H, d, J=7.9 Hz).

Example 166

Production of 6-ethyl-5-[2-fluoro-4-(trifluoromethyl)phenyl]-N-[1-(hydroxyacetyl)piperidin-4-yl]-1-methyl-3-(1-methylethoxy)-1H-pyrrolo[3,2-b]pyridine-2-carboxamide

Example 167

Production of 6-ethyl-5-{[(4-fluorophenyl)carbonyl]amino}-N-[1-(hydroxyacetyl)piperidin-4-yl]-1-methyl-3-(1-methylethoxy)-1H-pyrrolo[3,2-b]pyridine-2-carboxamide

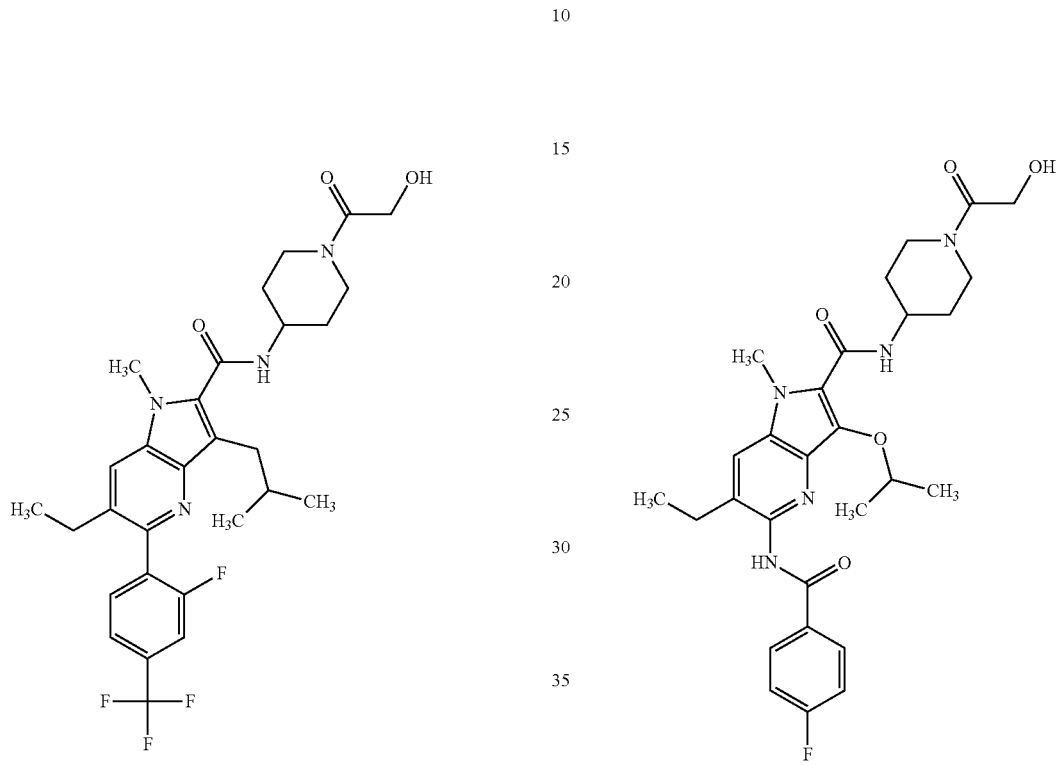

By a method similar to that in Example 16, the title compound (131 mg, 70%) was obtained as a white powder from the compound of Reference Example 316 (140 mg, 0.329 mmol), 2-(4-aminopiperidin-1-yl)-2-oxoethanol hydrochloride (76.9 mg, 0.395 mmol), HOBt (66.8 mg, 0.494 mmol), WSCD (94.6 mg, 0.494 mmol), triethylamine (0.137 mL, 0.987 mmol) and DMF (2.8 mL).

$^1$H NMR (300 MHz, DMSO-$d_6$) δ: 1.10 (3H, t, J=7.5 Hz), 1.28 (6H, d, J=6.2 Hz), 1.35-1.59 (2H, m), 1.88-2.00 (2H, m), 2.57 (2H, q, J=7.5 Hz), 2.85-2.99 (1H, m), 3.08-3.22 (1H, m), 3.61-3.74 (1H, m), 4.01 (3H, s), 4.03-4.16 (3H, m), 4.18-4.30 (1H, m), 4.52 (1H, t, J=5.3 Hz), 5.30-5.42 (1H, m), 7.65-7.76 (2H, m), 7.79-7.87 (1H, m), 7.91 (1H, d, J=7.7 Hz), 8.01 (1H, s).

By a method similar to that in Example 16, the title compound (112 mg, 76%) was obtained as a white powder from the compound of Reference Example 318 (109 mg, 0.273 mmol), 2-(4-aminopiperidin-1-yl)-2-oxoethanol hydrochloride (63.8 mg, 0.328 mmol), HOBt (55.4 mg, 0.410 mmol), WSCD (78.5 mg, 0.410 mmol), triethylamine (0.114 mL, 0.820 mmol) and DMF (2.2 mL).

$^1$H NMR (300 MHz, DMSO-$d_6$) δ: 1.22 (3H, t, J=7.6 Hz), 1.28 (6H, d, J=6.2 Hz), 1.34-1.59 (2H, m), 1.87-1.99 (2H, m), 2.68 (2H, q, J=7.6 Hz), 2.83-2.99 (1H, m), 3.06-3.21 (1H, m), 3.62-3.74 (1H, m), 4.00 (3H, s), 4.03-4.16 (3H, m), 4.18-4.31 (1H, m), 4.52 (1H, t, J=4.9 HZ), 5.29-5.42 (1H, m), 7.31-7.42 (2H, m), 7.88 (1H, d, J=7.7 Hz), 7.94 (1H, s), 8.01-8.13 (2H, m), 10.53 (1H, s).

Example 168

Production of 6-ethyl-5-{[(4-fluorophenyl)carbonyl]amino}-N-[1-(hydroxyacetyl)piperidin-4-yl]-1-methyl-3-(1-methylethoxy)-1H-indole-2-carboxamide

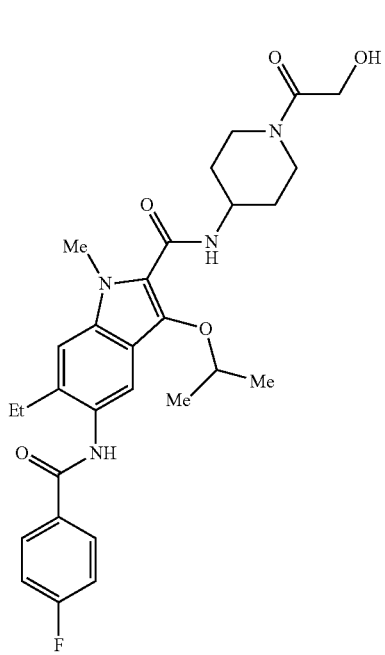

A mixture of the compound of Reference Example 195 (150 mg, 0.38 mmol), 2-(4-aminopiperidin-1-yl)-2-oxoethanol hydrochloride (110 mg, 0.56 mmol), HOBt (61 mg, 0.45 mmol), WSCD (87 mg, 0.45 mmol) and triethylamine (76 mg, 0.75 mmol) in DMF (4 mL) was stirred at room temperature for 16 hr. The reaction mixture was diluted with saturated aqueous sodium hydrogen carbonate, and extracted twice with ethyl acetate. The extracts were combined and washed with brine, dried over magnesium sulfate, and concentrated under reduced pressure. The residue was purified by amino silica gel column chromatography (eluent, ethyl acetate) and recrystallized from ethyl acetate-hexane to give the title compound (165 mg, 81%) as white crystals.

$^1$H NMR (300 MHz, DMSO-$d_6$) δ: 1.19 (3H, t, J=7.5 Hz), 1.30 (6H, d, J=6.0 Hz), 1.37-1.55 (2H, m), 1.93 (2H, d, J=10.8 Hz), 2.72 (2H, q, J=7.5 Hz), 2.84 (1H, t, J=11.4 Hz), 3.12 (1H, t, J=12.5 Hz), 3.70 (1H, d, J=11.7 Hz), 3.95 (3H, s), 4.02-4.18 (3H, m), 4.30 (1H, d, J=13.8 Hz), 4.52 (1H, t, J=5.4 Hz), 4.58-4.66 (1H, m), 7.34-7.41 (3H, m), 7.53 (1H, s), 7.83 (1H, d, J=7.8 Hz), 8.06-8.11 (2H, m), 9.95 (1H, s).

Example 169

Production of 5-{[(4-chlorophenyl)carbonyl]amino}-6-ethyl-N-[1-(hydroxyacetyl)piperidin-4-yl]-1-methyl-3-(1-methylethoxy)-1H-indole-2-carboxamide

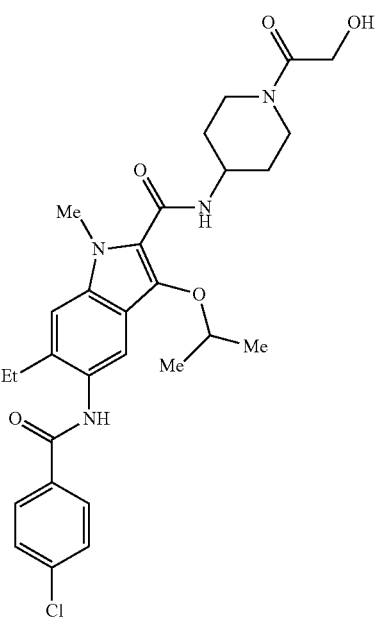 [SMILES: CCc1cc2c(cc1NC(=O)c1ccc(Cl)cc1)c(OC(C)C)c(C(=O)NC1CCN(C(=O)CO)CC1)n2C]

A mixture of the compound of Reference Example 197 (150 mg, 0.36 mmol), 2-(4-aminopiperidin-1-yl)-2-oxoethanol hydrochloride (106 mg, 0.54 mmol), HOBt (59 mg, 0.43 mmol), WSCD (83 mg, 0.43 mmol) and triethylamine (73 mg, 0.72 mmol) in DMF (4 mL) was stirred at room temperature for 16 hr. The reaction mixture was diluted with saturated aqueous sodium hydrogen carbonate, and extracted twice with ethyl acetate. The extracts were combined and washed with brine, dried over magnesium sulfate, and concentrated under reduced pressure. The residue was purified by amino silica gel column chromatography (eluent, ethyl acetate) and recrystallized from ethyl acetate-hexane to give the title compound (142 mg, 71%) as white crystals.

$^1$H NMR (300 MHz, DMSO-$d_6$) δ: 1.19 (3H, t, J=7.5 Hz), 1.29 (6H, d, J=6.0 Hz), 1.36-1.52 (2H, m), 1.93 (2H, d, J=10.5 Hz), 2.70 (2H, q, J=7.5 Hz), 2.84 (1H, t, J=11.6 Hz), 3.11 (1H, t, J=11.9 Hz), 3.69 (1H, d, J=11.4 Hz), 3.95 (3H, s), 4.02-4.18 (3H, m), 4.30 (1H, d, J=13.2 Hz), 4.52 (1H, t, J=5.4 Hz), 4.57-4.65 (1H, m), 7.41 (1H, s), 7.53 (1H, s), 7.61 (2H, d, J=8.7 Hz), 7.82 (1H, d, J=7.5 Hz), 8.02 (2H, d, J=8.4 Hz), 10.00 (1H, s).

Example 172

Production of 6-ethyl-N-(trans-4-hydroxycyclohexyl)-1-methyl-3-(1-methylethoxy)-5-[(phenylcarbonyl)amino]-1H-pyrrolo[2,3-b]pyridine-2-carboxamide

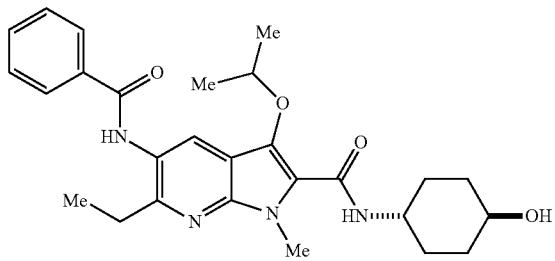

By a method similar to that in Example 1, the title compound (163 mg, 81%) was obtained as white crystals from the compound of Reference Example 89 (160 mg, 0.421 mmol), trans-4-aminocyclohexanol (63.6 mg, 0.552 mmol), HOBt (84.5 mg, 0.625 mmol), WSCD (147 mg, 0.767 mmol) and triethylamine (117 μL, 0.839 mmol).

$^1$H NMR (300 MHz, DMSO-$d_6$) δ: 1.24 (3H, t, J=7.6 Hz), 1.28-1.46 (10H, m), 1.79-2.02 (4H, m), 2.85 (2H, q, J=7.6 Hz), 3.38-3.54 (1H, m), 3.66-3.87 (1H, m), 3.99 (3H, s), 4.58 (1H, d, J=4.3 Hz), 4.62-4.76 (1H, m), 7.48-7.66 (3H, m), 7.71 (1H, d, J=7.7 Hz), 7.95-8.10 (3H, m), 10.06 (1H, s).

Example 173

Production of 6-ethyl-N-(cis-4-hydroxycyclohexyl)-1-methyl-3-(1-methylethoxy)-5-[(phenylcarbonyl)amino]-1H-pyrrolo[2,3-b]pyridine-2-carboxamide

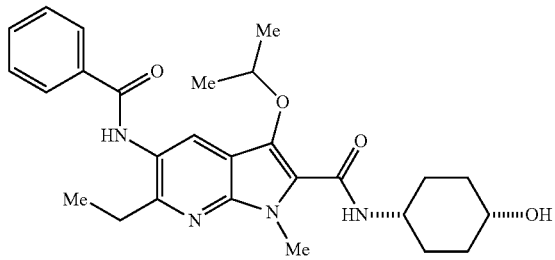

By a method similar to that in Example 1, the title compound (181 mg, 90%) was obtained as white crystals from the compound of Reference Example 89 (161 mg, 0.421 mmol), cis-4-aminocyclohexanol hydrochloride (80.6 mg, 0.532 mmol), HOBt (83.5 mg, 0.618 mmol), WSCD (128 mg, 0.666 mmol) and triethylamine (117 μL, 0.839 mmol).

$^1$H NMR (300 MHz, DMSO-$d_6$) δ: 1.25 (3H, t, J=7.5 Hz), 1.34 (6H, d, J=6.0 Hz), 1.46-1.84 (8H, m), 2.85 (2H, q, J=7.5 Hz), 3.61-3.75 (1H, m), 3.85-3.99 (1H, m), 4.02 (3H, s), 4.52 (1H, d, J=3.4 Hz), 4.71-4.90 (1H, m), 7.46-7.71 (3H, m), 7.82 (1H, d, J=7.6 Hz), 7.96-8.12 (3H, m), 10.07 (1H, s).

Example 174

Production of 3-ethyl-N-[1-(hydroxyacetyl)piperidin-4-yl]-5-methyl-2-phenyl-7-(2,2,2-trifluoroethoxy)-5H-pyrrolo[2,3-b]pyrazine-6-carboxamide

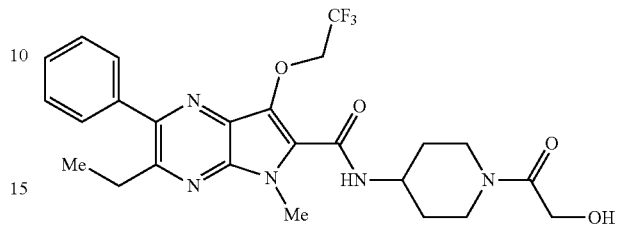

To a solution of the compound of Reference Example 213 (89.0 mg, 0.235 mmol), 2-(4-aminopiperidin-1-yl)-2-oxoethanol hydrochloride (60.0 mg, 0.308 mmol), HOBt (52.2 mg, 0.386 mmol) and triethylamine (65.4 μL, 0.469 mmol) in DMF (1.5 mL) was added WSCD (69.2 mg, 0.361 mmol), and the mixture was stirred at room temperature for 19 hr. To the reaction mixture was added water (5 mL), and the mixture was extracted with ethyl acetate (5 mL×4). The organic layer was dried over anhydrous magnesium sulfate, and concentrated under reduced pressure. The residue was purified by silica gel column chromatography (eluent, hexane:ethyl acetate=2:1→ethyl acetate) and crystallized from hexane/diisopropyl ether to give the title compound (51.5 mg, 42%) as white crystals.

$^1$H NMR (300 MHz, DMSO-$d_6$) δ: 1.21 (3H, t, J=7.4 Hz), 1.29-1.61 (2H, m), 1.84-2.00 (2H, m), 2.82-3.02 (3H, m), 3.05-3.22 (1H, m), 3.61-3.79 (1H, m), 3.97 (3H, s), 4.02-4.18 (3H, m), 4.18-4.31 (1H, m), 4.54 (1H, t, J=5.4 Hz), 5.28 (2H, q, J=9.0 Hz), 7.43-7.66 (5H, m), 7.92 (1H, d, J=7.6 Hz).

Example 175

Production of 6-ethyl-5-(4-fluorophenyl)-N-[1-(hydroxyacetyl)piperidin-4-yl]-1-methyl-3-(1-methylethoxy)-1H-pyrrolo[3,2-b]pyridine-2-carboxamide

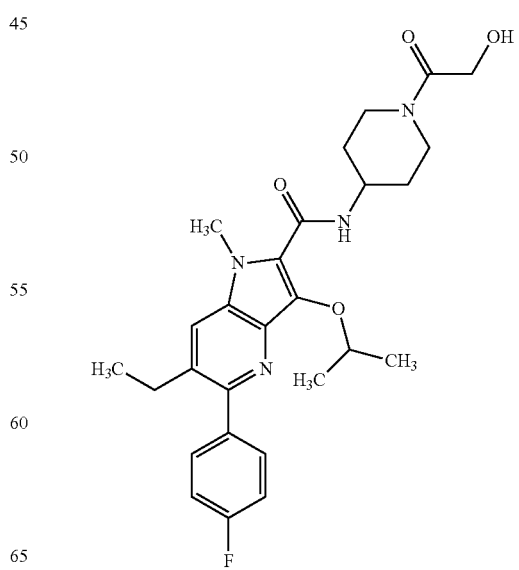

A mixture of the compound of Reference Example 289 (137 mg, 0.384 mmol), 2-(4-aminopiperidin-1-yl)-2-oxoethanol hydrochloride (89.7 mg, 0.461 mmol), HOBt (77.8 mg, 0.576 mmol), WSCD (110 mg, 0.576 mmol), triethylamine (0.159 mL, 1.15 mmol) and DMF (2.7 mL) was stirred at room temperature for 17 hr. The reaction mixture was diluted with water, and extracted twice with ethyl acetate. The extracts were combined, washed with water and brine, dried over sodium sulfate, and concentrated under reduced pressure. The residue was purified by amino silica gel chromatography (eluent; ethyl acetate) and the obtained solid was recrystallized from ethyl acetate to give the title compound (157 mg, 82%) as a white powder.

$^1$H NMR (300 MHz, DMSO-$d_6$) δ: 1.12 (3H, t, J=7.5 Hz), 1.30 (6H, d, J=6.0 Hz), 1.34-1.59 (2H, m), 1.87-1.99 (2H, m), 2.72 (2H, q, J=7.5 Hz), 2.85-3.00 (1H, m), 3.06-3.22 (1H, m), 3.61-3.74 (1H, m), 4.00 (3H, s), 4.02-4.17 (3H, m), 4.16-4.30 (1H, m), 4.53 (1H, t, J=5.4 Hz), 5.38-5.52 (1H, m), 7.24-7.35 (2H, m), 7.48-7.59 (2H, m), 7.85-7.97 (2H, m). δ

Formulation Example 1

A medicament containing the compound of the present invention as an active ingredient can be produced, for example, based on the following composition.

1. Capsule

| (1) the compound obtained in Example 1 | 40 mg |
|---|---|
| (2) lactose | 70 mg |
| (3) crystalline cellulose | 9 mg |
| (4) magnesium stearate | 1 mg |
| 1 capsule | 120 mg |

(1), (2), (3) and ½ of (4) are blended and granulated. Thereto is added the rest of (4) and the total amount is filled in a gelatin capsule.

2. Tablet

| (1) the compound obtained in Example 1 | 40 mg |
|---|---|
| (2) lactose | 58 mg |
| (3) cornstarch | 18 mg |
| (4) crystalline cellulose | 3.5 mg |
| (5) magnesium stearate | 0.5 mg |
| 1 tablet | 120 mg |

(1), (2), (3), ⅔ of (4) and ½ of (5) are blended and granulated. Thereto is added the rest of (4) and (5) and the mixture is compression formed to give a tablet.

Formulation Example 2

The compound obtained in Example 1 (50 mg) is dissolved in the Japanese Pharmacopoeia distilled water for injection (50 ml), and the Japanese Pharmacopoeia distilled water for injection is added to 100 ml. The solution is filtered under sterile conditions, and 1 ml of the solution is filled in an injection vial under sterile conditions, and freeze-dried and sealed.

Genetic operation methods described in Experimental Examples below are based on the methods described in a book (Maniatis et al., Molecular Cloning, Cold Spring Harbor Laboratory, 1989), and the appended protocol of the reagent.

Experimental Example 1

1. Construction of Gli Reporter Plasmid

Gli reporter plasmid was constructed by inserting 8×Gli-binding site and chicken δ-crystalline promoter into the upstream of luc+ of pGL3 (Promega).

δ-Crystalline promoter was cloned by PCR method using, as a primer set, synthetic DNAs (SEQ ID NO: 1)
5'-GAAGATCTGCCAGCCCAGGCTCCGGGGC-3'

(SEQ ID NO: 2)
5'-CCCAAGCTTCTGCCCGCACAGCCCTGCTC-3' prepared in reference to the base sequence described in GenBank accession No.; X02187, and chicken genome DNA (Clontech) as a template. PCR reaction was performed using Pfu Turbo (Stratagene) and following the attached protocol. The obtained 108 bp fragment was digested with restriction enzymes BglII and HindIII, and inserted into BglII-HindIII site of pGL3 to give plasmid pGL3/δ-cry promoter.

As 8× Gli-binding site, a sequence containing eight 9-bp Gli bound consensus sequences (GACCACCCA) described in Yoon et al., J. Biol. Chem., vol. 273, pages 3496-3501 (1998) was prepared from synthetic DNA. That is, two synthetic DNAs, (SEQ ID NO: 3)
5'-GGGGTACCGACCACCCAGACCACCCAGACCACCCAGACCACCCAG

ACCACCCAGACCACCCAGACCACCCAGACCACCCAAGATCTTC-3'

(SEQ ID NO: 4)
5'-GAAGATCTTGGGTGGTCTGGGTGGTCTGGGTGGTCTGGGTGGTCT

GGGTGGTCTGGGTGGTCTGGGTGGTCTGGGTGGTCGGTACCCC-3' were heat treated at 95° C. for 2 minutes, and incubated at 37° C. for 1 hr for annealing to give a double stranded DNA of the above-mentioned two synthetic DNAs. The obtained double stranded DNA was digested with restriction enzymes BglII and KpnI, and the obtained DNA fragment was inserted into BglII-KpnI site of pGL3/δ-cry promoter to construct plasmid pGL3/δ-cry promoter, 8× Gli binding site, i.e., Gli reporter plasmid.

2. Construction of Plasmid for Expression of Mouse Shh-N End Fragment

As a material for construction of plasmid for Shh-N end fragment expression, mouse Shh cDNA was cloned at first.

The mouse Shh cDNA was cloned by Nested PCR method using mouse 11-day fetus cDNA (Clontech) as a template. The primer sequence was prepared in reference to the base sequence described in GenBank accession No.; NM_009170.

As the primer set for $1^{st}$ PCR, 5'-CTGGGTGGGGATCG-GAGACA-3' (SEQ ID NO: 5) 5'-GCGCTTTCCCATCAGT-TCCTTATT-3' (SEQ ID NO: 6) were used, and as the primer set for $2^{nd}$ PCR, 5'-GGGGTACCATGCTGCTGCTGCTG-GCCA-3' (SEQ ID NO: 7) 5'-GCTCTAGATCAGCTG-GACTTGACCGCCA-3' (SEQ ID NO: 8) were used. PCR reaction was performed using Pfu Turbo (Stratagene) and following the attached protocol. The resulting PCR product was cloned by pcDNA3.1 (+) (Invitrogen), and the inserted base sequence was confirmed.

Using the mouse Shh cDNA sequence obtained as mentioned above as a template, a partial cDNA sequence wherein stop codon (TGA) was added to 3'-terminal of cDNA sequence encoding 1st to 198th amino acid sequence of mouse Shh was obtained by PCR method. As the primer set, (SEQ ID NO: 9)
5'-ATGCTGCTGCTGCTGGCCAG-3'

(SEQ ID NO: 10)
5'-TCAGCCGCCGGATTTGGCCG-3' were used.

PCR reaction was performed using Pfu Turbo (Stratagene) and following the attached protocol. The obtained PCR product was cloned by pcDNA3.1 (+) (Invitrogen), and the inserted base sequence was confirmed.

In the manner mentioned above, a plasmid for mouse Shh-N end fragment expression, pcDNA3.1/mShh-N, was constructed.

3. Production of Recombinant Type Mouse Shh-N End Fragment

HEK293 cells were grown in D-MEM medium (Invitrogen) containing 10% fetal bovine serum in a 10 cm dish and pcDNA3.1/mShh-N was introduced into the cells using FuGENE6 (Roche Applied Science). Thereafter, the HEK293 cells were cultured in a carbon dioxide gas incubator at 37° C. for 24 hours, and the medium was exchanged with D-MEM medium (Invitrogen) containing 2% fetal bovine serum. After culturing for 48 hr, culture supernatant containing recombinant type mouse Shh-N end fragment was obtained by filtration using a filter (0.22 μM).

4. Introduction of Plasmid for Gli-1 Expression and Reporter Plasmid into NIH-3T3 Cells and Production of Expressing Cells Using D-MEM (Invitrogen) containing 10% fetal bovine serum, expression plasmid pcDNA3:1 and Gli reporter plasmid (pGL3/δ-cry promoter, 8× Gli binding site) produced by the method of Experimental Example 1 were introduced into NIH-3T3 cells grown in a 10 cm dish by the use of FuGENE6 (Roche Applied Science).

After culture for 24 hr, the cells were recovered, suspended in D-MEM medium containing 10% fetal bovine serum and supplemented with Geneticin (Life Technologies Oriental, Inc.) to a final concentration of 500 μg/ml, diluted to $10^4$ cells/ml, plated on a 96 well plate, and cultured in a carbon dioxide gas incubator at 37° C. to give Geneticin resistant transformed cell line.

The obtained transformed cell line was cultured in a 96 well plate, mouse Shh-N end fragment obtained in Experimental Example 3 was added, and NIH-3T3/Gli reporter cell, which is a cell line capable of induction of luciferase expression, was selected.

5. Evaluation of Compound

NIH-3T3/Gli reporter cells cultured in D-MEM (Invitrogen) containing 10% fetal bovine serum were plated in a 96 well white plate at 1×$10^4$ cells/well, and cultured overnight in a carbon dioxide gas incubator at 37° C. The medium was removed, a compound (50 μl) and culture supernatant of mouse Shh-N end fragment-expressing HEK293 (D-MEM medium containing 2% fetal bovine serum, 50 μl) were added, and the cells were cultured for 48 hr in a carbon dioxide gas incubator at 37° C. Bright-Glo (Promega, 50 μl) was added, and the mixture was stirred, after which luciferase activity was measured by EnVision (PerkinElmer). The inhibition rate was calculated based on the luciferase activity of the control without addition of the compound as 100. The results are shown in Table 3 below.

TABLE 3

| Example | inhibition rate (%) at 1 μM |
| --- | --- |
| 5 | 97 |
| 7 | 96 |
| 9 | 98 |
| 22 | 93 |
| 24 | 90 |
| 29 | 95 |
| 30 | 97 |
| 32 | 98 |
| 33 | 95 |
| 34 | 93 |
| 37 | 87 |
| 39 | 96 |
| 40 | 97 |
| 41 | 96 |
| 42 | 92 |
| 45 | 98 |
| 46 | 98 |
| 47 | 97 |
| 48 | 97 |
| 50 | 94 |
| 51 | 94 |
| 52 | 94 |
| 53 | 95 |
| 54 | 99 |
| 56 | 97 |
| 57 | 99 |
| 58 | 97 |
| 59 | 95 |
| 60 | 95 |
| 61 | 98 |
| 62 | 98 |
| 63 | 96 |
| 67 | 97 |
| 68 | 96 |
| 69 | 99 |
| 70 | 98 |
| 71 | 97 |
| 127 | 96 |
| 128 | 94 |
| 129 | 92 |
| 130 | 84 |
| 131 | 82 |
| 132 | 86 |
| 133 | 90 |
| 136 | 95 |
| 143 | 96 |
| 144 | 98 |
| 145 | 98 |
| 146 | 90 |
| 147 | 91 |
| 148 | 98 |
| 149 | 85 |
| 150 | 89 |
| 151 | 98 |
| 152 | 97 |
| 153 | 97 |
| 154 | 97 |
| 155 | 99 |
| 160 | 99 |
| 162 | 100 |
| 163 | 98 |
| 164 | 99 |
| 167 | 99 |
| 168 | 97 |
| 169 | 99 |
| 173 | 98 |

Experimental Example 2

In Vivo Anti-Tumor Test

According to the description in Sasaki, K. et al., (2006) Cancer Res. 66: 4215-4222, an anti-tumor effect of a compound was evaluated using a mouse medulloblastoma allogeneic transplantation model. To be precise, Patched 1 gene mutant mouse (lineage name: Ptch1tm1Mps/J) was purchased from The Jackson Laboratory and p53 gene mutant mouse (lineage name: P53N4-M, Nomenclature: B6.129-Trp53tm/BrdN4) was purchased from Taconic, and a mouse of Patched 1(+/−), p53(−/−) phenotype was prepared by mating. The tumor tissue of medulloblastoma spontaneously occurred in the cerebellum of 7- to 9-week-old Patched 1(+/−), p53(−/−) mouse was taken and subcutaneously transplanted into a nude mouse (lineage name: CAnN.Cg-Foxn1<nu>/CrlCrlj).

An anti-tumor test was performed using a tumor passaged by subcutaneous transplantation. A tumor mass was isolated by a 40 μm cell strainer (BD Biosciences, Cat. No. 352340), a tumor suspension was prepared with Leibovitz's L-15 medium (GIBCO, Cat. No. 11415-114) in a 2-fold amount relative to the tumor mass weight, mixed with the same amount of matrigel (BD Biosciences, Cat. No. 356237), and subcutaneously transplanted to a mouse at 100 μl per transplantation site. The tumor diameter after transplantation was measured and, when the tumor size reached 150-250 mm$^3$, the anti-tumor test was started using 5 mice per group.

The test compound was prepared to achieve a dose of 1 mg/kg with a 0.5% methylcellulose (Shin-Etsu Chemical Co., Ltd., Cat. No. SM-100) suspension, and orally administered once a day for 2 weeks. The tumor size was calculated based on the longer diameter and shorter diameter of the tumor measured with an electron vernier caliper. After the start of the test, the tumor size was measured every 2 or 3 days and the growth rate of the tumor size was calculated. The growth rate of the tumor size by each test compound at the end of the test is shown in the following Table 4.

The tumor growth rate and the results of a significant difference test by the administration of each test compound are shown in the Table. The growth rate of the tumor size (T/C) was calculated according to:

growth rate(T/C)=((tumor size of compound administration group at the end of administration)−(tumor size of compound administration group at the start of administration))/((tumor size of control group at the end of administration)−(tumor size of control group at the start of administration))×100.

TABLE 4

| Example | T/C (%) | P value (Dunnett's test) |
|---------|---------|--------------------------|
| 46      | 51      | $p < 0.025$              |

From the above-mentioned results, the compound of the present invention was shown to have a superior Smo inhibitory action.

INDUSTRIAL APPLICABILITY

Since the compound of the present invention shows a superior Smo inhibitory action, a clinically useful agent for the prophylaxis or treatment of diseases related to Smo (e.g., cancer etc.) can be provided. In addition, since the compound of the present invention is also superior in the efficacy expression, pharmacokinetics, solubility, interaction with other pharmaceutical products, safety and stability, it is useful as a medicament.

This application is based on patent application Nos. 2009-195754 and 2010-015643 filed in Japan, the contents of which are encompassed in full herein.

The invention claimed is:

1. A compound represented by formula (AI-b):

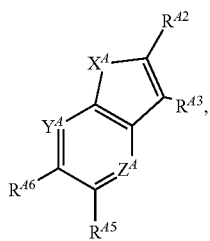

(AI-b)

wherein
$X^A$ is $NR^{A1}$ wherein $R^{A1}$ is hydrogen or a $C_{1-6}$ alkyl group,
$Y^A$ is nitrogen,
$Z^A$ is $CR^{A4}$ wherein $R^{A4}$ is hydrogen, halogen, an amino group optionally having substituent(s) or a mercapto group optionally having a substituent,
$R^{A2}$ is a carbamoyl group optionally having substituent(s),
$R^{A3}$ is a substituted hydroxy group,
$R^{A5}$ is a $C_{1-6}$ alkyl group having substituent(s) selected from Substituent A Group below, an amino group optionally having substituent(s), a cyclic group optionally having substituent(s), or a hydroxy group substituted by a cyclic group optionally having substituent(s), and
$R^{A6}$ is a $C_{1-6}$ alkyl group optionally having substituent(s) selected from the Substituent A Group, or a pharmaceutically acceptable salt thereof,
wherein
(i) the amino group optionally having substituent(s) is an amino group optionally having 1 or 2 substituents selected from the group consisting of
  (1) a $C_{1-6}$ alkyl group optionally having substituent(s) selected from Substituent A Group,
  (2) a $C_{2-6}$ alkenyl group optionally having substituent(s) selected from the Substituent A Group,
  (3) a $C_{2-6}$ alkynyl group optionally having substituent(s) selected from the Substituent A Group,
  (4) a $C_{1-6}$ alkoxy group optionally having substituent(s) selected from the Substituent A Group,
  (5) a $C_{1-6}$ alkyl-carbonyl group optionally having substituent(s) selected from the Substituent A Group,
  (6) a $C_{3-8}$ cycloalkyl group optionally having substituent(s) selected from Substituent C Group below,
  (7) a $C_{6-10}$ aryl group optionally having substituent(s) selected from Substituent B Group below,
  (8) a $C_{6-10}$ aryl-carbonyl group optionally having substituent(s) selected from the Substituent B Group,
  (9) an aromatic heterocyclic group optionally having substituent(s) selected from the Substituent B Group,
  (10) a non-aromatic heterocyclic group optionally having substituent(s) selected from the Substituent C Group,
  (11) an aromatic optionally having substituent(s) selected from the Substituent B Group, and
  (12) a non-aromatic heterocyclyl-carbonyl group optionally having substituent(s) selected from the Substituent C Group,
(ii) the mercapto group optionally having a substituent is a mercapto group optionally substituted by a substituent selected from the group consisting of
  (1) a $C_{1-6}$ alkyl group optionally having substituent(s) selected from the Substituent A Group,
  (2) a $C_{2-6}$ alkenyl group optionally having substituent(s) selected from the Substituent A Group,
  (3) a $C_{2-6}$ alkynyl group optionally having substituent(s) selected from the Substituent A Group,
  (4) a $C_{1-6}$ alkoxy group optionally having substituent(s) selected from the Substituent A Group,
  (5) a $C_{1-6}$ alkyl-carbonyl group optionally having substituent(s) selected from the Substituent A Group,
  (6) a $C_{3-8}$ cycloalkyl group optionally having substituent(s) selected from the Substituent C Group,
  (7) a $C_{6-10}$ aryl optionally having substituent(s) selected from the Substituent B Group,
  (8) a $C_{6-10}$ aryl-carbonyl group optionally having substituent(s) selected from the Substituent B Group,
  (9) an aromatic heterocyclic group optionally having substituent(s) selected from the Substituent B Group,
  (10) a non-aromatic heterocyclic group optionally having substituent(s) selected from the Substituent C Group,
  (11) an aromatic heterocyclyl-carbonyl group optionally having substituent(s) selected from the Substituent B Group, and
  (12) a non-aromatic heterocyclyl-carbonyl group optionally having substituent(s) selected from the Substituent C Group,
(iii) the carbamoyl group optionally having substituent(s) is a carbamoyl group optionally having 1 or 2 substituents selected from the group consisting of
  (1) a $C_{1-6}$ alkyl group optionally having substituent(s) selected from the Substituent A Group,
  (2) a $C_{2-6}$ alkenyl group optionally having substituent(s) selected from the Substituent A Group,
  (3) a $C_{2-6}$ alkenyl group optionally having substituent(s) selected from the Substituent A Group,
  (4) a $C_{1-6}$ alkoxy group optionally having substituent(s) selected from the Substituent A Group,
  (5) a $C_{1-6}$alkyl-carbonyl group optionally having substituent(s) selected from the Substituent A Group,
  (6) a $C_{3-8}$ cycloalkyl group optionally having substituent(s) selected from the Substituent C Group,
  (7) a $C_{6-10}$ aryl group optionally having substituent(s) selected from the Substituent B Group, (8) a $C_{6-10}$ aryl-carbonyl group optionally having substituent(s) selected from the Substituent B Group;
(9) an aromatic heterocyclic group optionally having substituent(s) selected from the Substituent B Group,
(10) a non-aromatic heterocyclic group optionally having substituent(s) selected from the Substituent C Group,
(11) an aromatic heterocycyl-carbonyl group optionally having substituent(s) selected from the Substituent B Group, and
(12) a non-aromatic heterocyclyl-carbonyl group optionally having substituent(s) selected from the Substituent C Group, (iv) the substituted hydroxy group is a hydroxy group substituted by a substituent selected from the group consisting of
(1) a $C_{1-6}$ alkyl group optionally having substituent(s) selected from the Substituent A Group,
(2) a $C_{2-6}$ alkenyl group optionally having substituent(s) selected from the Substituent A Group,
(3) a $C_{2-6}$ alkynyl group optionally having substituent(s) selected from the Substituent A Group,
(4) a $C_{1-6}$ alkoxy group optionally having substituent(s) selected from the Substituent A Group,
(5) a $C_{1-6}$ alkyl-carbonyl group optionally having substituent(s) selected from the Substituent A Group,
(6) a $C_{3-8}$ cycloalkyl group optionally having substituent(s) selected from the Substituent C Group,
(7) a $C_{6-10}$ aryl group optionally having substituent(s) selected from the Substituent B Group,
(8) a $C_{6-10}$ aryl-carbonyl group optionally having substituent(s) selected from the Substituent B Group,
(9) an aromatic heterocyclic group optionally having substituent(s) selected from the Substituent B Group,
(10) a non-aromatic heterocyclic group optionally having substituent(s) selected from the Substituent C Group,
(11) an aromatic heterocyclyl-carbonyl group optionally having substituent(s) selected from the Substituent B Group, and
(12) a non-aromatic heterocyclyl-carbonyl group optionally having substituent(s) selected from the Substituent C Group, and (v) the cyclic group optionally having substituent(s) is selected from the group consisting of
(1) a $C_{3-8}$ cycloalkyl group optionally having substituent(s) selected from the Substituent C Group,
(2) a group derived from a fused ring wherein a $C_{3-8}$ cycloalkane and a benzene ring are condensed, which optionally has substituent(s) selected from the Substituent C Group,
(3) a $C_{6-10}$ aryl group optionally having substituent(s) selected from the Substituent B Group,
(4) an aromatic heterocyclic substituent(s) selected from the Substituent B Group, and
(5) a non-aromatic heterocyclic group optionally having substituent(s) selected from the Substituent C Group, wherein the Substituent A group consists of:
(1) halogen;
(2) a cyano group;
(3) a nitro group;
(4) a hydroxy group;
(5) a carboxy group;
(6) a $C_{3-8}$ cycloalkyl group optionally having 1 to 3 substituents selected from the group consisting of
(a) halogen,
(b) a hydroxy group,
(c) a $C_{1-6}$ alkyl group optionally having 1 to 3 halogen atoms,
(d) a $C_{1-6}$ alkoxy group optionally having 1 to 3 halogen atoms, and
(e) an oxo group;
(7) a $C_{6-10}$ aryl group optionally having 1 to 3 substituents selected from the group consisting of
(a) halogen,
(b) a hydroxy group,
(c) a $C_{1-6}$ alkyl group optionally having 1 to 3 halogen atoms, and
(d) a $C_{1-6}$ alkoxy group optionally having 1 to 3 halogen atoms;
(8) a 5- to 12-membered aromatic heterocyclic group optionally having 1 to 3 substituents selected from the group consisting of
(a) halogen,
(b) a hydroxy group,
(c) a $C_{1-6}$ alkyl group and
(d) a $C_{1-6}$ alkoxy group optionally having 1 to 3 halogen atoms;
(9) a 4- to 12-membered non-aromatic heterocyclic group optionally having 1 to 3 substituents selected from the group consisting of
(a) halogen,
(b) a hydroxy group,
(c) a $C_{1-6}$ alkyl group optionally having 1 to 3 halogen atoms,
(d) a $C_{1-6}$ alkoxy group optionally having 1 to 3 halogen atoms,
(e) a $C_{1-6}$ alkyl-carbonyl group optionally having 1 to 3 hydroxy, and
(f) an oxo group;
(10) an amino group optionally having 1 or 2 substituents selected from the group consisting of
(a) a $C_{1-6}$ alkyl group optionally having 1 to 3 halogen atoms,
(b) a $C_{1-6}$ alkyl-carbonyl group optionally having 1 to 3 substituents selected from the group consisting of
(i) halogen,
(ii) a hydroxy group, and
(iii) a $C_{6-10}$ aryl group,
(c) a $C_{1-6}$ alkoxy-carbonyl group optionally having 1 to 3 substituents selected from the group consisting of
(i) halogen and
(ii) a $C_{6-10}$ aryl group,
(d) a $C_{1-6}$ alkylsulfonyl group optionally having 1 to 3 substituents selected from the group consisting of
(i) halogen and
(ii) a $C_{6-10}$ aryl group,
(e) a $C_{6-10}$ arylsulfonyl group,
(f) a carbamoyl group optionally having 1 or 2 $C_{1-6}$ alkyl groups optionally having 1 to 3 halogen atoms,
(g) a 5- to 12-membered aromatic heterocyclic group optionally having 1 to 3 substituents selected from the group consisting of
(i) a $C_{1-6}$ alkyl group optionally having 1 to 3 halogen atoms,
(ii) a hydroxy group,
(iii) a $C_{1-6}$ alkoxy group optionally having 1 to 3 halogen atoms, and
(iv) halogen, and
(h) a 4- to 12-membered non-aromatic heterocyclic group optionally having 1 to 3 substituents selected from the group consisting of
(i) a $C_{1-6}$ alkyl group optionally to 3 halogen atoms,
(ii) a hydroxy group, (iii) a $C_{1-6}$ alkoxy group optionally having 1 to 3 halogen atoms,
(iv) halogen, and
(v) an oxo group;
(11) an imino group;
(12) a $C_{1-6}$ alkyl-carbonyl group optionally having 1 to 3 halogen atoms;
(13) a $C_{1-6}$ alkoxy-carbonyl group optionally having 1 to 3 substituents selected from the group consisting of
(a) halogen,
(b) a $C_{1-6}$ alkoxy group,
(c) a $C_{6-10}$ aryl group,
(d) a 5- to 12-membered aromatic heterocyclic group optionally having 1 to 3 substituents selected from the group consisting of
(i) a $C_{1-6}$ alkyl group optionally having 1 to 3 halogen atoms,
(ii) a hydroxy group,
(iii) a $C_{1-6}$ alkoxy group optionally having 1 to 3 halogen atoms, and
(iv) halogen, and
(e) a 4- to 12-membered non-aromatic heterocyclic group optionally having 1 to 3 substituents selected from the group consisting of
(i) a $C_{1-6}$ alkyl group optionally en atoms,
(ii) a hydroxy group,
(iii) a $C_{1-6}$ alkoxy group optionally having 1 to 3 halogen atoms,
(iv) halogen, and
(v) an oxo group;
(14) a $C_{1-6}$ alkylsulfonyl group optionally having 1 to 3 substituents selected from the group consisting of
(a) halogen and
(b) a $C_{1-6}$ alkoxy group;
(15) a $C_{6-10}$ arylsulfonyl group;
(16) a carbamoyl group optionally having 1 or 2 substituents selected from the group consisting of
(a) a $C_{1-6}$ alkyl group optionally having 1 to 3 halogen atoms and
(b) $C_{6-10}$ aryl group;
(17) a thiocarbamoyl group optionally having 1 or 2 $C_{1-6}$ alkyl groups optionally having 1 to 3 halogen atoms;
(18) a sulfamoyl group optionally having 1 or 2 $C_{1-6}$ alkyl groups optionally having 1 to 3 halogen atoms;
(19) $C_{1-6}$ alkoxy group optionally having 1 to 3 substituents selected from the group consisting of
(a) halogen,
(b) a carboxy group,
(c) a $C_{1-6}$ alkoxy group,
(d) a $C_{1-6}$ alkoxy-carbonyl group optionally having 1 to 3 $C_{6-10}$ aryl groups,
(e) an amino group optionally having 1 or 2 substituents selected from a $C_{1-6}$ alkyl group and a $C_{1-6}$ alkoxy-carbonyl group,
(f) a $C_{3-8}$ cycloalkyl group,
(g) a 5- to 12-membered aromatic heterocyclic group optionally having 1 to 3 substituents selected from the group consisting of
(i) halogen,
(ii) a hydroxy group,
(iii) a $C_{1-6}$ alkyl group optionally having 1 to 3 halogen atoms, and
(iv) a $C_{1-6}$ alkoxy group optionally having 1 to 3 halogen atoms, and
(h) a 4- to 12-membered non-aromatic heterocyclic group optionally having 1 to 3 substituents selected from the group consisting of
(i) halogen,
(ii) a hydroxy group,
(iii) a $C_{1-6}$ alkyl group optionally having 1 to 3 halogen atoms,
(iv) a $C_{1-6}$ alkoxy group optionally en atoms, and
(v) an oxo group;
(20) a $C_{2-6}$ alkenyloxy group optionally having 1 to 3 halogen atoms;
(21) a $C_{3-8}$ cycloalkyloxy group optionally having 1 to 3 substituents selected from the group consisting of
(a) halogen and
(b) a $C_{1-6}$ alkoxy group;
(22) a $C_{6-10}$ aryloxy group;
(23) a $C_{7-13}$ aralkyloxy group;
(24) a $C_{1-6}$ alkyl-carbonyloxy group;
(25) a $C_{6-10}$ aryl-carbonyl group optionally having 1 to 3 substituents selected from the group consisting of
(a) halogen and
(b) a $C_{1-6}$ alkyl group optionally having 1 to 3 halogen atoms;
(26) a 5- to 12-membered aromatic heterocyclyl-carbonyl group optionally having 1 to 3 substituents selected from a $C_{1-6}$ alkyl group optionally having 1 to 3 halogen atoms;
(27) a 4- to 12-membered non-aromatic heterocyclyl-carbonyl group optionally substituents selected from a $C_{1-6}$ alkyl group optionally having 1 to 3 halogen atoms;
(28) a $C_{3-8}$ cycloalkyl-carbonyl group;
(29) a $C_{7-13}$ aralkyloxy-carbonyl group;
(30) a mercapto group;
(31) a $C_{1-6}$ alkylthio group optionally having 1 to 3 substituents selected from the group consisting of
(a) halogen and
(b) a $C_{1-6}$ alkoxy-carbonyl group;
(32) a $C_{7-13}$ aralkylthio group;
(33) a $C_{6-10}$ arylthio group;
(34) a $C_{1-3}$ alkyleneoxy group; and
(35) a $C_{1-3}$ alkylenedioxy group,
wherein the Substituent B Group consists of:
(1) a substituent selected from the Substituent A Group;
(2) a $C_{1-6}$ alkyl group optionally having 1 to 3 substituents selected from the group consisting of
(a) halogen,
(b) a hydroxy group,
(c) a carboxy group,
(d) a $C_{1-6}$ alkoxy group,
(e) a $C_{1-6}$ alkoxy-carbonyl group,
(f) an amino group optionally having 1 or 2 $C_{1-6}$ alkyl groups, and
(g) a $C_{6-10}$ aryl-carbonyl group;
(3) a $C_{2-6}$ alkenyl group optionally having 1 to 3 substituents selected from the group consisting of
(a) halogen,
(b) a hydroxy group,
(c) a carboxy group,
(d) a $C_{1-6}$ alkoxy group,
(e) a $C_{1-6}$ alkoxy-carbonyl group, and
(f) an amino group optionally having 1 or 2 $C_{1-6}$ alkyl groups; and
(4) a $C_{7-13}$ aralkyl group optionally having 1 to 3 substituents selected from the group consisting of
(a) halogen,
(b) a hydroxy group,
(c) a $C_{1-6}$ alkyl group optionally having 1 to 3 halogen atoms, and
(d) a $C_{1-6}$ alkoxy group, wherein the Substituent C Group consists of:
  (1) a substituent selected from the Substituent A Group;
  (2) a $C_{1-6}$ alkyl group optionally having 1 to 3 substituents selected from the group consisting of
    (a) halogen,
    (b) a hydroxy group,
    (c) a carboxy group,
    (d) a $C_{1-6}$ alkoxy group,
    (e) a $C_{1-6}$ alkoxy-carbonyl group,
    (f) an amino group optionally having 1 or 2 $C_{1-6}$ alkyl groups, and
    (g) a $C_{6-10}$ aryl-carbonyl group,
  (3) a $C_{2-6}$ alkenyl group optionally to 3 substituents selected from the group consisting of
    (a) halogen,
    (b) a hydroxy group,
    (c) a carboxy group,
    (d) a $C_{1-6}$ alkoxy group,
    (e) a $C_{1-6}$ alkoxy-carbonyl group, and
    (f) an amino group optionally having 1 or 2 $C_{1-6}$ alkyl groups;
  (4) a $C_{7-13}$ aralkyl group optionally having 1 to 3 substituents selected from the group consisting of
    (a) halogen,
    (b) a hydroxy group,
    (c) a $C_{1-6}$ alkyl group optionally having 1 to 3 halogen atoms, and
    (d) a $C_{1-6}$ alkoxy group; and
  (5) an oxo group.

2. The compound or the pharmaceutically acceptable salt thereof according to claim 1, wherein
  $X^A$ is $NR^{A1}$, wherein $R^{A1}$ is methyl,
  $Z^A$ is $CR^{A4}$, wherein $R^{A4}$ is hydrogen,
  $R^{A2}$ is a carbamoyl group optionally having 1 or 2 substituents selected from the group consisting of
    (1) the $C_{1-6}$ alkyl group optionally having substituent(s) selected from the Substituent A Group,
    (2) the $C_{3-8}$ cycloalkyl group optionally having substituent(s) selected from the Substituent C Group,
    (3) the aromatic heterocyclic group optionally having substituent(s) selected from the Substituent B Group, and
    (4) the non-aromatic heterocyclic group optionally having substituent(s) selected from the Substituent C Group,
  $R^{A3}$ is the optionally halogenated $C_{1-6}$ alkoxy group,
  $R^{A5}$ is
    (1) the $C_{1-6}$ alkyl group having substituent(s) selected from the Substituent A Group,
    (2) the amino group optionally having substituent(s),
    (3) a $C_{6-10}$ aryl group optionally having substituent(s) selected from the Substituent B Group,
    (4) the aromatic heterocyclic group optionally having substituent(s) selected from the Substituent B group, or
    (5) the non-aromatic heterocyclic group optionally having substituent(s) selected from the Substituent C Group, and
  $R^{A6}$ is a $C_{1-6}$ alkyl group.

3. A pharmaceutical composition comprising the compound according to claim 1, or the pharmaceutically acceptable salt thereof, and a pharmaceutically acceptable carrier.

4. A method of inhibiting smoothened in a mammal, which comprises administering to said mammal an effective amount of the compound according to claim 1, or the pharmaceutically acceptable salt thereof.

5. A compound 6-ethyl-N-[1-(hydroxyacetyl)piperidin-4-yl]-1-methyl-3-(1-methylethoxy)-5-[(phenylcarbonyl)amino]-1H-pyrrolo[2,3-b]pyridine-2-carboxamide or a pharmaceutically acceptable salt thereof.

6. A pharmaceutical composition comprising the compound according to claim 5, or the pharmaceutically acceptable salt thereof, and a pharmaceutically acceptable carrier.

7. A method of inhibiting smoothened in a mammal, which comprises administering to said mammal an effective amount of the compound according to claim 5, or the pharmaceutically acceptable salt thereof.

* * * * *

UNITED STATES PATENT AND TRADEMARK OFFICE
CERTIFICATE OF CORRECTION

PATENT NO. : 8,486,965 B2  Page 1 of 1
APPLICATION NO. : 13/391217
DATED : July 16, 2013
INVENTOR(S) : Ohashi et al.

It is certified that error appears in the above-identified patent and that said Letters Patent is hereby corrected as shown below:

On the Title page, Item [75] Inventors: delete "Zenyu Shiokawa, Kanagawa (JP)".

On the Title page, Item [75] Inventors: delete "Satoshi Sasaki, Kanagawa (JP)".

In the Claim

Claim 1, column 290, line 15: after "aromatic" insert --heterocyclyl - carbonyl group--.

Claim 1, column 291, line 8: after "aromatic" delete "heterocycyl" and insert --heterocyclyl--.

Claim 1, column 292, line 19: after "alkyl group" insert --optionally having 1 to 3 halogen atoms--.

Claim 1, column 293, line 25: delete "en" and insert --having 1 to 3 halogen--.

Claim 1, column 294, line 5: delete "en" and insert --having 1 to 3 halogen--.

Claim 1, column 295, line 13: after "optionally" insert --having 1--.

Signed and Sealed this
Twenty-ninth Day of April, 2014

Michelle K. Lee
*Deputy Director of the United States Patent and Trademark Office*

SEQUENCE LISTING

<160> NUMBER OF SEQ ID NOS: 10

<210> SEQ ID NO 1
<211> LENGTH: 28
<212> TYPE: DNA
<213> ORGANISM: Artificial Sequence
<220> FEATURE:
<223> OTHER INFORMATION: primer

<400> SEQUENCE: 1
gaagatctgc cagcccaggc tccggggc                                      28

<210> SEQ ID NO 2
<211> LENGTH: 29
<212> TYPE: DNA
<213> ORGANISM: Artificial Sequence
<220> FEATURE:
<223> OTHER INFORMATION: primer

<400> SEQUENCE: 2
cccaagcttc tgcccgcaca gccctgctc                                     29

<210> SEQ ID NO 3
<211> LENGTH: 88
<212> TYPE: DNA
<213> ORGANISM: Artificial Sequence
<220> FEATURE:
<223> OTHER INFORMATION: primer

<400> SEQUENCE: 3

```
ggggtaccga ccacccagac cacccagacc acccagacca cccagaccac ccagaccacc    60
cagaccaccc agaccaccca agatcttc                                       88

<210> SEQ ID NO 4
<211> LENGTH: 88
<212> TYPE: DNA
<213> ORGANISM: Artificial Sequence
<220> FEATURE:
<223> OTHER INFORMATION: primer

<400> SEQUENCE: 4
gaagatcttg ggtggtctgg gtggtctggg tggtctgggt ggtctgggtg gtctgggtgg    60
tctgggtggt ctgggtggtc ggtacccc                                       88

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
ctgggtgggg atcggagaca                                                20

<210> SEQ ID NO 6
<211> LENGTH: 24
<212> TYPE: DNA
<213> ORGANISM: Artificial Sequence
<220> FEATURE:
<223> OTHER INFORMATION: primer

<400> SEQUENCE: 6
gcgctttccc atcagttcct tatt                                           24

<210> SEQ ID NO 7
<211> LENGTH: 27
<212> TYPE: DNA
<213> ORGANISM: Artificial Sequence
<220> FEATURE:
<223> OTHER INFORMATION: primer

<400> SEQUENCE: 7
ggggtaccat gctgctgctg ctggcca                                        27

<210> SEQ ID NO 8
<211> LENGTH: 28
<212> TYPE: DNA
<213> ORGANISM: Artificial Sequence
<220> FEATURE:
<223> OTHER INFORMATION: primer

<400> SEQUENCE: 8
gctctagatc agctggactt gaccgcca                                       28

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
atgctgctgc tgctggccag                                                20

<210> SEQ ID NO 10
```

```
<211> LENGTH: 20
<212> TYPE: DNA
<213> ORGANISM: Artificial Sequence
<220> FEATURE:
<223> OTHER INFORMATION: primer

<400> SEQUENCE: 10
tcagccgccg gatttggccg                                              20
```